US012577583B2

(12) United States Patent
Hay et al.

(10) Patent No.: US 12,577,583 B2
(45) Date of Patent: Mar. 17, 2026

(54) DNA SEQUENCE MODIFICATION-BASED GENE DRIVE

(71) Applicant: California Institute of Technology, Pasadena, CA (US)

(72) Inventors: Bruce A. Hay, Encino, CA (US); Georg Oberhofer, Pasadena, CA (US); Tobin William Ivy, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 18/611,182

(22) Filed: Mar. 20, 2024

(65) Prior Publication Data

US 2024/0344081 A1      Oct. 17, 2024

Related U.S. Application Data

(62) Division of application No. 16/673,823, filed on Nov. 4, 2019, now Pat. No. 11,965,172.

(60) Provisional application No. 62/755,763, filed on Nov. 5, 2018.

(51) Int. Cl.
| | |
|---|---|
| *C12N 15/85* | (2006.01) |
| *C12N 9/22* | (2006.01) |
| *C12N 15/90* | (2006.01) |

(52) U.S. Cl.
CPC .............. *C12N 15/85* (2013.01); *C12N 9/22* (2013.01); *C12N 15/907* (2013.01); *C12N 2310/20* (2017.05); *C12N 2800/40* (2013.01); *C12N 2800/50* (2013.01); *C12N 2810/10* (2013.01)

(58) Field of Classification Search
CPC ........ C12N 15/85; C12N 9/22; C12N 15/907; C12N 2310/20; C12N 2800/40; C12N 2800/50; C12N 2810/10; C12N 2800/30; C12N 2800/80; A01K 2217/15; A01K 2217/06; A01K 6/0339
See application file for complete search history.

(56) References Cited

U.S. PATENT DOCUMENTS

| | | | |
|---|---|---|---|
| 4,676,981 | A | 6/1987 | Silversides et al. |
| 4,879,112 | A | 11/1989 | Silversides et al. |
| 4,946,778 | A | 8/1990 | Ladner et al. |
| 4,980,286 | A | 12/1990 | Morgan et al. |
| 5,139,941 | A | 8/1992 | Muzyczka et al. |
| 5,173,414 | A | 12/1992 | Lebkowski et al. |
| 5,354,678 | A | 10/1994 | Lebkowski et al. |
| 5,436,146 | A | 7/1995 | Shenk et al. |
| 5,474,935 | A | 12/1995 | Chatterjee et al. |
| 5,478,745 | A | 12/1995 | Samulski et al. |
| 5,580,859 | A | 12/1996 | Felgner et al. |
| 5,589,377 | A | 12/1996 | Lebkowski et al. |
| 5,589,466 | A | 12/1996 | Felgner et al. |
| 5,593,972 | A | 1/1997 | Weiner et al. |
| 5,641,870 | A | 6/1997 | Rinderknecht et al. |
| 5,652,224 | A | 7/1997 | Wilson et al. |
| 5,753,434 | A | 5/1998 | Ryner et al. |
| 5,801,030 | A | 9/1998 | McVey et al. |
| 6,013,770 | A | 1/2000 | Reeves et al. |
| 6,284,733 | B1 | 9/2001 | Meloen et al. |
| 7,339,031 | B2 | 3/2008 | Baker et al. |
| 7,731,939 | B2 | 6/2010 | Miller et al. |
| 10,570,200 | B2 | 2/2020 | Hay et al. |
| 10,966,414 | B2 | 4/2021 | Hay et al. |
| 11,965,172 | B2 * | 4/2024 | Hay ...................... C12N 15/85 |
| 12,157,883 | B2 * | 12/2024 | Hay .................... C12N 15/907 |
| 12,213,468 | B2 | 2/2025 | Hay et al. |
| 2003/0213005 | A1 | 11/2003 | Alphey et al. |
| 2005/0032171 | A1 | 2/2005 | Saxena et al. |
| 2007/0056051 | A1 | 3/2007 | Alphey |
| 2009/0183269 | A1 | 7/2009 | Alphey |
| 2010/0186103 | A1 | 7/2010 | Gao et al. |
| 2010/0233249 | A1 | 9/2010 | Sutovsky et al. |
| 2011/0113497 | A1 | 5/2011 | Lee |
| 2012/0266264 | A1 | 10/2012 | Lee |
| 2013/0298266 | A1 | 11/2013 | Alphey et al. |
| 2014/0283155 | A1 | 9/2014 | Akbari et al. |
| 2014/0356384 | A1 | 12/2014 | Hubbell et al. |
| 2015/0010578 | A1 | 1/2015 | Balazs et al. |
| 2015/0159175 | A1 | 6/2015 | Frendewey et al. |
| 2015/0230430 | A1 | 8/2015 | Wilson et al. |
| 2015/0237838 | A1 | 8/2015 | Hay et al. |
| 2016/0060358 | A1 | 3/2016 | Hay |
| 2016/0345556 | A1 * | 12/2016 | Hay ...................... A01K 67/68 |
| 2019/0241879 | A1 | 8/2019 | Esvelt et al. |
| 2024/0425845 | A1 * | 12/2024 | Hay .................... C12N 15/905 |

FOREIGN PATENT DOCUMENTS

| | | | |
|---|---|---|---|
| JP | 63-126482 | A | 5/1988 |
| JP | 2544120 | B2 | 10/1996 |
| KR | 10-2017-0041640 | A | 4/2017 |
| WO | 90/11092 | A1 | 10/1990 |

(Continued)

OTHER PUBLICATIONS

Alhakamy, N.A. et al. "Noncovalently associated cell-penetrating peptides for gene delivery applications," Therapeutic delivery 4: 741-757, Jun. 2013.

(Continued)

*Primary Examiner* — Ganapathirama Raghu

(74) *Attorney, Agent, or Firm* — Knobbe Martens Olson & Bear LLP

(57) ABSTRACT

Described herein are embodiments relating to manipulation of populations and sex ratio in populations through DNA sequence modifications.

11 Claims, 136 Drawing Sheets

Specification includes a Sequence Listing.

(56)                References Cited

FOREIGN PATENT DOCUMENTS

| WO | 92/06180 | A1 | 4/1992 |
| WO | 92/20316 | A2 | 11/1992 |
| WO | 92/22635 | A1 | 12/1992 |
| WO | 93/14188 | A1 | 7/1993 |
| WO | 93/20221 | A1 | 10/1993 |
| WO | 94/08598 | A1 | 4/1994 |
| WO | 94/12649 | A2 | 6/1994 |
| WO | 99/65520 | A1 | 12/1999 |
| WO | 01/07083 | A1 | 2/2001 |
| WO | 2005/095458 | A1 | 10/2005 |
| WO | 2008/009960 | A2 | 1/2008 |
| WO | 2010/049777 | A1 | 5/2010 |
| WO | 2012/143401 | A1 | 10/2012 |
| WO | 2013/176722 | A2 | 11/2013 |
| WO | 2013/176772 | A1 | 11/2013 |
| WO | 2014/052693 | A2 | 4/2014 |
| WO | 2014/096428 | A1 | 6/2014 |
| WO | 2014/120975 | A1 | 8/2014 |
| WO | 2016/049230 | A1 | 3/2016 |
| WO | 2018/204722 | A1 | 11/2018 |

OTHER PUBLICATIONS

Aluwe et al. "Effect of surgical castration, immunocastration and chicory-diet on the meat quality and palatability of boars," Meat Science 94: 402-407, Jul. 2013.

Amatayakul-Chantler, S. et al. "Effects on performance and carcass and meat quality attributes following immunocastration with the gonadotropin releasing factor vaccine Bopriva or surgical castration of Bos indicus bulls raised on pasture in Brazil," Meat Science 95: 78-84, Sep. 2013.

Amatayakul-Chantler, S. et al. "Immunocastration of Bos indicus x Brown Swiss bulls in feedlot with gonadotropin-releasing hormone vaccine Bopriva provides improved performance and meat quality," Journal of animal science 90: 3718-3728, 2012.

An, G. et al. "In Vitro and in Vivo Studies Evaluating Recombinant Plasmid Pcxn2-mlzumo as a Potential Immunocontraceptive Antigen," Am J Reprod Immunol 61: 227-235, 2009.

Anderson et al., "Serum-derived protein S binds to phosphatidylserine and stimulates the phagocytosis of apoptotic cells," Nature Immunology, vol. 4, pp. 87-91, 2003.

Arimura, A. et al. "Production of Antiserum to LH-Releasing Hormone (LH-RH) Associated with Gonadal Atrophy in Rabbits: Development of Radioimmunoassays for LH-RH," Endocrinology 93: 1092-1103, 1973.

Asano, K., et al., M. Masking of phosphatIdylserine inhibits apoptotic cell engulfment and induces autoantibody production in mice. J Exp Med 200, pp. 459-467, (2004).

ASPCA. https://www.as12ca.org/about-us/fag/12et-statistics.as12x. This document is not available. It is noted that the document appears to have been publicly available prior to Feb. 1, 2013. ASPCA;https://www.as12ca.org/animal-homelessness/shelter-intake-and-surrender/12etstatistics is submitted herewith in place of this, The original publication date of https://www.as12ca.org/animal-homelessness/shelter-intake-and-surrender/12et-statistics is unknown. The present version was printed on Aug. 5, 2016; 11 pages.

Ausubel et al., eds., Current Protocols in Molecular Biology, John Wiley & Sons, NY, 1998 (in 11 parts).

Avella, M.A. et al. "The molecular basis of gamete recognition in mice and humans," Molecular utei reproduction 19:279-289, Jan. 17, 2013.

Balazs et al., "Antibody-based protection against HIV infection by vectored immunoprophylaxis," Nature, 481:81-84 (2012) and Supplementary Information (Materials and Methods pp. 1-2).

Balazs, A.B. et al. "Broad protection against influenza infection by vectored immunoprophylaxis in mice," Nat Biotechnol 31: 647-652, Jun. 2, 2013.

Barfield, J.P. et al. "Fertility control in wildlife: humans as a model," Contraception 73: 6-22, 2006.

Batorek et al., "Meta-analysis of the effect of immunocastration on production performance, reproductive organs and boar taint compounds in pigs" Animal 6(8):1330-1338, 2012.

Battisto et al., "Dual immunological unresponsiveness induced by cell membrane coupled hapten or antigen," Nature, vol. 212, pp. 156-157, 1966.

Belldegrun et al. "Human Renal Carcinoma Line Transfected With Interleukin-2 and/or Interferon a Gene(s): Implications for Live Cancer Vaccines," J Natl Cancer Inst 85: 207-216, 1993.

Benavides Valades, G. et al. "Non-invasive assessment of the reproductive cycle in free-ranging female African elephants (Loxodonta uteiniz) treated with a gonadotropin-releasing hormone (GnRH) Vaccine for inducing anoestrus," Reproductive biology and endocrinology 10: 63, 2012.

Bird, "Single-chain antigen-binding proteins," Science 242: 423-442, 1988.

Biswajit, P., megaTAL-mediate Gene Editing at the CCR5 locus, PhD Dissertation, University of Washington, pp. 1-113, 2016.

Bleil, J.D. et al., "Identification of a ZP3-binding protein on acrosome-intact mouse sperm by photoaffinity crosslinking," Proc Natl Acad Sci USA 87: 5563-5567, 1990.

Boesen et al. "Circumvention of chemotherapy-induced myelosuppression by transfer of themdr1 gene," Biotherapy 6: 291-302, 1993.

Bondanza, A., et al. Inhibition of phosphatidylserine recognition heightens the immunogenicity of irradiated lymphoma cells in vivo. Journal of Experimental Medicine 200, 1157-1165, (2004).

Bondanza, A., et al., Requirement of dying cells and environmental adjuvants for the induction of autoimmunity. Arthritis Rheum—Us 50, pp. 1549-1560, (2004).

Bonneau et al., "The Effects of Immunization Against Luteinizing Hormone-Releasing Hormone on Performance, Sexual Development, and Levels of Boar Taint-Related Compounds in Intact Male Pigs," Journal of Animal Science 72:14-20, 1994.

Boue, F. et al. "Cases of Human Infertility are Associated with the Absence of P34H, an Epididymal Sperm Antigen'," Biol Reprod 54: 1018-1024, 1996.

Bout et al. "Lung Gene Therapy: In Vivo Adenovirus-Mediated Gene Transfer to Rhesus Monkey Airway Epithelium," Human Gene Therapy 5: 3-10, 1994.

Brevini et al., Theriogeneology, 74: 554-550, 2010.

Buchlis, G. et al. "Factor IX expression in skeletal muscle of a severe hemophilia B patient 10 years after AAV-mediated gene transfer," Blood 119: 3038-3041, 2012.

Burkart, A.D. et al. "Ovastacin, a cortical granule protease, cleaves ZP2 in the zona pellucida to prevent polyspermy" J Cell Biol 197, 37-44, 2012.

Burt A, Trivers R Genes in Conflict: The Biology of Selfish Genetic Elements Belknap Press, Cambridge, MA, 1st Ed. pp. 1-602, only p. 43 (Year: 2008).

Burtea et al., "Peptidic targeting of phosphatidylserine for the MRI detection of apoptosis in atherosclerotic plaques," Molecular pharmaceutics, vol. 6, pp. 1903-1919, 2009.

Calcedo, R. et al. "Adeno-associated virus antibody profiles in newborns, children, and adolescents," Clinical and Vaccine Immunology : CVI 18, 1586-1588, 2011.

Calcedo, R. et al. "Worldwide epidemiology of neutralizing antibodies to adeno-associated viruses," The Journal of Infectious Diseases 199, 381-390, 2009.

Caltech: "Long-Term Contraception in a Single Shot,:" https://www.caltech.edu/news/long-term-contraception-single-shot-48199 Oct. 6, 2015.

Cao et al., J. of Exp. Zoo., 311A: 368-376, 2009.

Carson et al., "Production and biological activity of murine monoclonal antibodies against GnRH," Theriogenology, vol. 48, No. 2, pp. 193-207, 1997.

Chamley, L.W. et al., "Antisperm antibodies and conception," Seminars in Immunopathology, vol. 29, pp. 169-184, 2007.

Chen, S-J., et al. Enhancing the Utility of Adena-Associated Vims Gene Transfer through Inducible Tissue-Specific Expression, Hum Gene Ther Methods. 24: 270-278, Aug. 20, 2013.

Chen, Y. et al. "Construction of sperm-specific lactate dehydrogenase DNA vaccine and experimental study of its immuno-contraceptive

(56)　　　　References Cited

OTHER PUBLICATIONS effect on mice," Science in China Series C, Life sciences / Chinese Academy of Sciences 51: 308-316, 2008.

Chien, W.M. et al., "Genomic DNA recombination with cell-penetrating peptide-tagged ere protein in mouse skeletal and cardiac muscle", Genesis, vol. 52, pp. 695-701, 2014.

Chothia et al. "Structural determinants in the sequences of immunoglobulin variable domain," J Mol Biol 278: 457-479, 1998.

Ciciliot, S. et al. "Regeneration of mammalian skeletal muscle. Basic mechanisms and clinical implications," Curr Pharm Des 16, 906-914, 2010.

Clark et al. Nature Reviews: 4: 825-833, 2003.

Clarke, I.J. "Two decades of measuring GnRH secretion," Reproduction Supplement 59: 1-13, 2002.

Clarke, I.J. "Control of GnRH secretion: one step back," Frontiers in Neuroendocrinology, vol. 32, pp. 367-375, 2011.

Clarke, I.J. "Interface between metabolic balance and reproduction in ruminants: focus on the hypothalamus and pituitary," Hormones and Behavior, vol. 66, pp. 15-40, 2014.

Clarke, I.J. et al. "Active immunization of ewes against luteinizing hormone releasing hormone, and its effects on ovulation and gonadotrophin, prolactin and ovarian steroid secretion," The Journal of endocrinology 78: 39-47, 1978.

Cline "Perspectives for gene therapy: Inserting new genetic information into mammalian cells by physical techniques and viral vectors," Pharmac Ther 29: 69-92, 1985.

Clowes et al. "Long-Term Biological Response of Injured Rat Carotid Artery Seeded with Smooth Muscle Cells Expressing Retrovirally Introduced Human Genes," J Clin Invest 93: 644-651, 1994.

Coffin, J.M., "Retroviridae: The viruses and their replication", Chapter 26, Fundamental Virology, Third Edition, Edited by Fields, B.N, et al., Lippincott—Raven Publishers, Philadelphia, 1996.

Contraceptive Technology, Edited by Robert A. Hatcher, James Trussell and Anita L. Nelson. PDR Network, 19th edition, 2008.

Cooper, D.W. et al. "Immunocontraception of mammalian wildlife: ecological and immunogenetic issues," Reproduction 132: 821-828, 2006.

Cotten et al. "Receptor-mediated transport of DNA into eukaryotic cells," Meth Enzymol 217: 618-644, 1993.

Cox, J. et al. "MaxQuant enables high peptide identification rates, individualized p.p.b.—range mass accuracies and proteome-wide protein quantification," Nat Biotechnol 26, 1367-1372, 2008.

Cox, J. et al. "Andromeda: a peptide search engine integrated into the MaxQuant environment," J Proteome Res 10, 1794-1805, 2011.

Crawford, E.D. et al., "Long-term tolerability and efficacy of degarelix: 5-year results from a phase III extension trial with a 1-arm crossover from leuprolide to degarelix", Urology, vol. 83, No. 5, pp. 1122-1128, 2014.

Cremel et al., "Red blood cells as innovative antigen carrier to induce specific immune tolerance," International journal of pharmaceutics, vol. 443, pp. 39-49, 2013.

D'Occhio et al., "Sustained testicular atrophy in bulls actively immunized against GnRH: potential to control carcase characteristics," Animal Reproduction Science 66: 47-58, 2001.

Darroch, J.E. et al. "Trends in contraceptive need and use in developing countries in 2003, 2008, and 2012: an analysis of national surveys," Lancet 381, 1756-1762, May 2013.

Das, A., et al. Flippase-mediated phospholipid asymmetry promotes fast Cdc42 recycling in dynamic maintenance of cell polarity. Nat Cell Biol 14, pp. 304-310, (2012).

Dasgupta et al., "Role of lactadherin in the clearance of phosphatidylserine-expressing red blood cells," Transfusion, vol. 48, pp. 2370-2376, 2008.

Davies, B. et al. "Targeted Deletion of the Epididymal Receptor HE6 Results in Fluid Dysregulation and Male Infertility," Mol Cell Biol 24: 8642-8648, 2004.

De la Cruz, A. et al. "Effect of Administration of Anti-Serum to Luteinizing Hormone-Releasing Hormone on Gonadal Function During the Estrous Cycle in the Hamster," Endocrinology 98: 490-497, 1976.

De Nys, H.M. et al. "Vaccination against GnRH may suppress aggressive uteiniz and musth in African elephant (Loxodonta uteiniz) bulls-a pilot study," Journal of the South African Veterinary Association 81: 8-15, 2010.

Deehan, M. et al., "Managing unwanted immunogenicity of biologicals", Autoimmunity Reviews, vol. 14, pp. 569-574,2015.

Desjarlais, J.R. et al. "Modulation of antibody effector function," Exp Cell Res 317: 1278-1285, 2011.

Diekman, A.B. et al. "N-linked glycan of a sperm CD52 glycoform associated with human infertility," FASEB J 13: 1303-1313, 1999.

Diekman, A.B. et al. "Evidence for a unique N-linked glycan associated with human infertility on sperm CD52: a candidate contraceptive vaccinogen," Immunological reviews 171: 203-211, 1999.

Dismuke, D.J. et al., "Biosafety of recombinant adeno-associated vims vectors", Current Gene Therapy, vol. 13, pp. 434-452, Dec. 2013.

Dmce, H.C. et al. "How Immunocontraception Can Contribute to Elephant Management in Small, Enclosed Reserves: Munyawana Population as a Case Study," PloS One 6: e27952, 2011.

Dong, Y. et al. "An in vitro approach for production of non-scar minicircle DNA vectors," Journal of biotechnology 166: 84-87, Jul. 10, 2013.

Donovan, C. et al. "Physiologic responses following gonadotropin-releasing hormone immunization in intact male dogs," Reproduction in Domestic Animals = Zuchthygiene 47 (Suppl 6): 403-405, 2012.

Dorman, E. et al. "Demand for male contraception," Expert Review of Pharmacoeconomics & Outcomes Research 12, 605-613, 2012.

Dunshea, F.R. et al. "Vaccination of boars with a GnRH vaccine (Improvac) eliminates boar taint and increases growth performance," Journal of Animal Science 79: 2524-2535, 2001.

East, I.J. et al. "Monoclonal antibodies to the major protein of the murine zona pellucida: Effects on fertilization and early development," Dev Biol 104: 49-56, 1984.

East, I.J. et al. "Monoclonal antibodies to the murine zona pellucida protein with sperm receptor activity: Effects on fertilization and early development," Dev Biol 109: 268-273, 1985.

Elliott, J.I., et al. (2005). Membrane phosphatidylserine distribution as a non-apoptotic signalling mechanism in lymphocytes. Nat Cell Biol 7, pp. 808-816, (2005).

Engelhardt et al. "Adenovims-Mediated Transfer of the CFTR Gene to Lung of Nonhuman Primates: Biological Efficacy Study," Human Genet Ther 4: 759-769, 1993.

Eurogentec, "Gonadotrophin-Releasing Hormone (LHRH) (SMI 41) Monoclonal Antibody" from Eurogentec Price List of Covance Antibodies, 2011.

Ferrantini et al. "IFN-alpha 1 gene expression into a metastatic murine adenocarcinoma (TS/A) results in CD8+ T cell- mediated tumor rejection and development of antitumor immunity. Comparative studies with IFN-gamma-producing TS/A cells," J Immunology 153: 4604-4615, 1994.

Ferrantini et al. "a-Interferon Gene Transfer into Metastatic Friend Leukemia Cells Abrogated Tumorigenicity in Immunocompetent Mice: Antitumor Therapy by Means of Interferon-producing Cells," Cancer Research 53: 1107-1112, 1993.

Ferro, V.A. et al., Reproductive component vaccine developments for contraceptive and noncontraceptive uses, Expert Opin. Ther. Patents, vol. 21, No. 9, 2011.

File History of U.S. Appl. No. 14/206,011, filed Mar. 12, 2014.

File History of U.S. Appl. No. 14/631,171, filed Feb. 25, 2015.

File History of U.S. Appl. No. 15/970,728, filed May 3, 2018.

File History of U.S. Appl. No. 14/170,118.

Found-animals-foundation. http://www.foundanimals.org/pet-spay-neuter/la-lowcost-free-neuter-spay; Original publication date unknown; Version printed on Mar. 22, 2016.

Fraker, M.A. et al. "Long-Lasting, Single-Dose Immunocontraception of Feral Fallow Deer in British Columbia ," Journal of Wildlife Management 66: 1141-1147, 2002.

(56)            References Cited

OTHER PUBLICATIONS

Fraser, "Antifertility effects of GnRH" J. Reprod. Fert. 64:503-515 (1982).

Fraser, H.M. "Effect of active immunization to luteinizing hormone releasing hormone on gonadotrophin levels in ovariectomized rats," The Journal of endocrinology 64: 191-192, 1975.

Fraser, H.M. et al. "Changes in the ovaries of rats after immunization against luteinizing hormone releasing hormone," The Journal of endocrinology 77: 85-93, 1978.

Fraser, H.M. et al. "Gonadotrophin release by a highly active analogue of luteinizing hormone releasing hormone in rats immunized against luteinizing hormone releasing hormone," The Journal of endocrinology 74: 291-296, 1977.

Fraser, H.M. et al. "Effects of Antibodies to Luteinizing Hormone—Releasing Hormone in the Male Rabbit and on the Rat Oestrous Cycle," Nature 244: 160-161, 1973.

Fu, J. et al. "Anti-ACTL7a antibodies: a cause of infertility," Fertility and sterility 97: 1226-1233, 2012.

Gaitonde et al., "Exposure to factor VIII protein in the presence of phosphatidylserine induces hypo-responsiveness toward factor VIII challenge in hemophilia A mice," J. Biol. Chem., vol. 288, pp. 17051-17056, 2013.

Gaitonde et al., "Phosphatidylserine reduces immune response against human recombinant Factor VIII in Hemophilia A mice by regulation of dendritic cell function," Clin. Immunol., vol. 138, pp. 135-145, 2011.

Gaj, T. et al. "ZFN, TALEN, and CRISPR/Cas-based methods for genome engineering," Trends Biotechnol. 3 1: 397-405, Jul. 2013.

Galli, R.A. et al. "Evaluation of the accuracy and ease of use of a rapid HIV-1 Antibody Test performed by untrained operators at the point of care," Journal of Clinical Virology 58 Suppl 1, e65-69, Dec. 2013.

Galluzzi, et al., Consensus guidelines for the definition, detection and interpretation of immunogenic cell death, J Immunother Cancer, 8:e000337, pp. 1-22, 2020.

Geary, T.W. et al."Use of recombinant gonadotropin-releasing hormone antigens for immunosterilization of beef heifers," Journal of animal science 84: 343-350, 2006.

Getts et al., "Exploiting apoptosis for therapeutic tolerance induction," J. Immunol., vol. 191, pp. 5341-5346, 2013.

Getts et al., "Tolerance induced by apoptotic antigen-coupled leukocytes is induced by PD-L1+ and IL-10-producing splenic macrophages and maintained by T regulatory cells", J. Immunol., vol. 187, pp. 2405-2417, 2011.

Gledhill, B. et al. "Effect of passive immunization against LH-RH on gonadotrophin secretion in the ferret," J Reprod Fertil 64: 19-23, 1982.

Gobello, C. "Effects of GnRH antagonists vs agonists in domestic carnivores, a review," Reproduction in Domestic Animals 47 Suppl 6, 373-376, 2012.

Godfrey, S.I. et al. "Immunisation of goat bucks against GnRH to prevent seasonal reproductive and agonistic uteiniz," Animal Reprod. Sci. 44: 41-54, 1996.

Goldberg, E. "Developmental expression of lactate dehydrogenase isozymes during spermatogenesis," Progress in clinical and biological research 344: 49-52, 1990.

Gomez e tal., Theriogeneology, 74: 498-515, 2010.

Gong et al., "Measuring response to therapy by near-infrared imaging of tumors using a phosphatidylserine-targeting antibody fragment," Molecular Imaging, vol. 12, pp. 244-256, 2013.

Goode et al., "Regulatory B cells: the new "it" cell," Transplantation proceedings, vol. 46, pp. 3-8, 2014.

Goodman, R.L. et al. "Kisspeptin neurons from mice to men: similarities and differences," Endocrinology 153, 5105-5118, 2012.

Gracey Maniar, L.E. et al. "Minicircle DNA Vectors Achieve Sustained Expression Reflected by Active Chromatin and Transcriptional Level," Molecular therapy: the journal of the American Society of Gene Therapy 21:131-138, Nov. 27, 2013.

Graham et al., Genome Biology, 16: 260, 2014.

Grandy, J.W. et al. "An animal welfare view of wildlife contraception," Reprod Suppl 60, 1-7, 2002.

Green et al. "Analysis of human tonsil and cancer DNAs and RNAs for DNA sequences of group C (serotypes 1, 2, 5, and 6) human adenovimses,", Proc Natl Acad Sci USA 76: 6606-6610, 1979.

Greenhouse, S. et al. "Antibodies to human ZP3 induce reversible contraception in transgenic mice with 'humanized' zonae pellucidae," Hum Reprod 14: 593-600, 1999.

Griffiths, E.C. et al. "Mechanisms of inactivation of hypothalamic regulatory hormones," Molecular and Cellular Endocrinology 14, 3-17, 1979.

Grossman et al. "Retroviruses: delivery vehicle to the liver," Curr Opin in Genetics and Devel 3: 110-114, 1993.

Guillen et al., "Annexin V-Directed Enzyme Prodrug Therapy Plus Docetaxel for the Targeted Treatment of Pancreatic Cancer," Pancreas, vol. 44, pp. 945-952, 2015.

Gupta et al. "Milestones in contraceptive vaccines development and hurdles in their application," Human Vaccines and immunotherapeutics 10(4): 911-925, 2014; Epub Nov. 21, 2013.

Gupta SK et al. Contraceptive vaccines based on the zone pellucida glycoproteins for dogs and other wildlife population management. Am J Reprod Immunol; 66: 51-62, 2011.

Gupta, S.K. et al. "Vaccines for immunological control of fertility," Reprod Med Biol 9(2): 61-71, 2010.

Gupta, S.K. et al. "Zona pellucida-based contraceptive vaccines for human and animal utility," Journal of reproductive immunology 88: 240-246, 2011.

Hanayama et al., "Identification of a factor that links apoptotic cells to phagocytes," Nature, vol. 417, pp. 182-187, 2002.

Hanayama et al., "MFG-E8-dependent clearance of apoptotic cells, and autoimmunity caused by its failure," Current directions in autoimmunity, vol. 9, pp. 162-172, 2006.

Hanayama, R., et al. Autoimmune disease and impaired uptake of apoptotic cells in MFG-ES-deficient mice. Science 304, pp. 1147-1150, (2004).

Hao, M. et al. "Expression of a recombinant bifunctional protein from a chimera of human lutropin receptor and human chorionic gonadotropin-subunit," Journal of reproductive immunology 63: 123-135, 2004.

Hardy, C.M. et al. "Biological control of vertebrate pests using virally vectored immunocontraception," Journal of Reproductive Immunology 71, 102-111, 2006.

He et al., "Receptor for advanced glycation end products binds to phosphatidylserine and assists in the clearance of apoptotic cells," EMBO Rep., vol. 12, pp. 358-364, 2011.

Hearn , J .P. "Immunization against Pregnancy," Proc R Soc Lond B Biol Sci 195: 149-160, 1976.

Heid and Hamm, "Animal welfare versus food quality: Factors influencing organic consumers' preferences for alternatives to piglet castration without anaesthesia," Meat Science 95: 203-211, Oct. 2013.

Herlyn, H. et al. "The molecular evolution of sperm zonadhesin," The Internationaljournal of developmental biology 52: 781-790, 2008.

Herr, J.C. et al. "Identification of Human Acrosomal Antigen SP-10 in Primates and Pigs," Biol Reprod 42: 377-382, 1990.

Hicks, M.J. et al. "AAV-Directed Persistent Expression of a Gene Encoding Anti-Nicotine Antibody for Smoking Cessation," Sci Transl Med 4: 140ra87, 2012.

Hodges, J.K. et al. "Effects of immunisation against luteinizing hormone releasing hormone on reproduction of the marmoset monkey Callithrixjacchus," Nature 265: 746-748, 1977.

Humane-society. http://www.humanesociety.org/issues/pet_overpopulation/facts/pet_ownership_statistics.html; Original publication date unknown; Version printed on Mar. 22, 2016.

Huston et al. "Protein engineering of antibody binding sites: Recovery of specific activity in an anti-digoxin single-chain Fv analogue produced in *Escherichia coli*," Proc Natl Acad Sci USA 85: 5879-5883, 1988.

Igarashi et al., "A novel phosphatidylserine-binding peptide motif defined by an anti-idiotypic monoclonal antibody. Localization of

(56)         References Cited

OTHER PUBLICATIONS phosphatidylserine-specific binding sites on protein kinase C and phosphatidylserine decarboxylase," J. Biol. Chem., vol. 270, pp. 29075-29078, 1995.

Igarashi, K., et al., Specific binding of a synthetic peptide derived from an antibody complementarity determininQ region to phosphatidylserine, Journal of Biochemistry, vol. 117, pp. 452-457, 1995.

International Search Report and Written Opinion issued on Apr. 25, 2014, in PCT Application PCT/US2014/013943.

Ishimoto et al., "Promotion of the uptake of PS liposomes and apoptotic cells by a product of growth arrest-specific gene, gash," J. Biochem., vol. 127, pp. 411-417, 2000.

Isojima, S. et al. "Establishment and characterization of a human hybridoma secreting monoclonal antibody with high titers of sperm immobilizing and agglutinating activities against human seminal plasma," Journal of reproductive immunology 10: 67-78, 1987.

Isojima, S. et al. "Further studies on sperm-immobilizing antibody found in sera of unexplained cases of sterility in women," Am J Obstet Gynecol 112: 199-207, 1972.

Isojima, S. et al. "Immunologic analysis of sperm-immobilizing factor found in sera of women with unexplained sterility," Am J Obstet Gynecol 101 : 677-683, 1968.

Itoh et al., "Staphylococcal superantigen-like protein 10 binds to phosphatidylserine and apoptotic cells," Microbiology and immunology, vol. 56, pp. 363-371, 2012.

Jackson, R.J. et al. "Infertility in mice induced by a recombinant ectromelia vims expressing mouse zona pellucida glycoprotein 3," Biol Reprod 58, 152-159, 1998.

Jagadish, N. et al. "Characterization of immune response in mice to plasmid DNA encoding human sperm associated antigen 9 (SPAG9)," Vaccine 24: 3695-3703, 2006.

Janett, F. et al. "Effect of vaccination against gonadotropin-releasing factor (GnRF) with Bopriva® in the prepubertal bull calf," Animal reproduction science 131: 72-80, 2012.

Janett, F. et al. "Suppression of testicular function and sexual behavior by vaccination against GnRH (EquityTM) in the adult stallion," Animal reproduction science 115: 88-102, 2009.

Janett. F. et al. "Vaccination against gonadotropin-releasing factor (GnRF) with Bopriva significantly decreases testicular development, serum testosterone levels and physical activity in pubertal bulls," Theriogenology 78: 182-188, 2012.

Jang, Y.C. et al. "Skeletal Muscle Stem Cells: Effects of Aging and Metabolism on Muscle Regenerative Function," Cold Spring harb Symp Quant Biol. 76: 101-111, 2011.

Jean et al. Develop. Growth Differ., (55): 41-51, 2013.

Jeffcoate, I.A. et al. "Effect of active immunisation of ewes against synthetic luteinizing hormone releasing hormone," Theriogenology 10: 323-335, 1978.

Jeffcoate, S.L. et al. "Preparation and specificity of antibodies to the decapeptide, luteinizing hormone-releasing hormone (LH-RH)," Immunochemistry 11: 75-77, 1974.

Jefferis et al., "Human immunoglobulin allotypes: possible implications for immunogenicity," mAbs., vol. 1, pp. 332-338, 2009.

Johnson, P.R. et al. "Vector-mediated gene transfer engenders long-lived neutralizing activity and protection against SIV infection in monkeys," Nat Med 15: 901-906, 2009.

Jones et al., "Improving the safety of cell therapy products by suicide gene transfer," Frontiers in pharmacology, vol. 5, Article 524, pp. 1-8, Nov. 27, 2014.

Jones et al., "Replacing the complementarity-determining regions in a human antibody with those from a mouse," Nature 321:522-525, 1986.

Kaido, T., et al. "IFN-al gene transfection completely abolishes the tumorigenicity of murine B16 melanoma cells in allogeneic DBA/2 mice and decreases their tumorigenicity in syngeneic C57BL/6 mice," Int J Cancer 60: 221-229, 1995.

Kalli, A. et al. "Evaluation and optimization of mass spectrometric settings during data-dependent acquisition mode: focus on LTQ-Orbitrap mass analyzers," J Proteome Res 12, 3071-3086, May 5, 2013.

Kaminska, A. et al. .Lactadherin: An unappreciated haemostasis regulator and potential therapeutic agent. Vascul Pharmacol 101, pp. 21-28, (2018).

Kaneda et al. "Increased expression of DNA cointroduced with nuclear protein in adult rat liver," Science 243: 375, 1989.

Kapty et al., "Evaluation of phosphatidylserine-binding peptides targeting apoptotic cells," Journal of Biomolecular Screening, vol. 17, pp. 1293-1301, 2012.

Kay, "State-of-the-art gene-based therapies: the road ahead," Nat. Rev. Genet., vol. 12, pp. 316-328, 2011.

Kay, M.A. et al. "A robust system for production ofminicircle DNA vectors," Nat Biotechnol 28: 1287-1289, 2010.

Kazama et al., Induction of Immunological Tolerance by Apoptotic Cells Requires Caspase-Dependent Oxidation of High-Mobility Group Box-1 Protein, Immunity, vol. 29, pp. 21-32, 2008.

Keene, J.L. et al. "Recombinant deglycosylated human FSH is an antagonist of human FSH action in cultured granulosa cells," Endocrine Journal 2, 175-180, 1994.

Kiem et al. "Retrovirus-Mediated Gene Transduction Into Canine Peripheral Blood Repopulating Cells," Blood 83: 1467-1473, 1994.

Kim et al., "Advantages of the phosphatidylserine-recognizing peptide PSP1 for molecular imaging of tumor apoptosis compared with annexin V," PLoS One, vol. 10, No. 3, pp. e0121171, 2015.

Kim, Y.H. et al. "Compartmentalization of a Unique ADP/ATP Carrier Protein SFEC (Sperm Flagellar Energy Carrier, AAC4) with Glycolytic Enzymes in the Fibrous Sheath of the Human Sperm Flagellar Principal Piece," Dev Biol 302: 463-476, 2007.

Kirchhoff, C. and Hale, G. "Cell-to-cell transfer of glycosylphosphatidylinositol-anchored membrane proteins during sperm maturation," Molecular human reproduction 2(3): 177-184, 1996.

Kirkpatrick, J.F. et al. "Contraceptive Vaccines for Wildlife: A Review," Am J Reprod Immunol 66: 40-50, 2011.

Kirkpatrick, J.F. et al. "The practical side of immunocontraception: zona proteins and wildlife," Journal of reproductive immunology 83: 151-157, 2009.

Knapp, R.J. et al. "High affinity monoclonal antibodies to luteinizing hormone-releasing hormone. Preparation and binding studies," J Neuroimmunol 6, 361-371, 1984.

Kobayashi et al., "TIM-1 and TIM-4 glycoproteins bind phosphatidylserine and mediate uptake of apoptotic cells", Immunity, vol. 27, pp. 927-940, 2007.

Koch, Y. et al. "Suppression of gonadotropin secretion and prevention of ovulation in the rat by antiserum to synthetic gonadotropin-releasing hormone," Biochem Biophys Res Commun 55: 623-629, 1973.

Koller et al. "Inactivating the β-microglobulin locus in mouse embryonic stem cells by homologous recombination," Proc Natl Acad Sci USA 86: 8932-8935, 1989.

Komori, S. et al. "Production of heavy-chain class-switch variants of human monoclonal antibody by recombinant DNA technology," Clinical and experimental immunology 71: 508-516, 1988.

Kontos et al., "Engineering antigens for in situ erythrocyte binding induces T-cell deletion," Proc. Natl. Acad. Sci. USA., vol. 110, pp. E60-E68, 2013.

Kormann, M.S. et al. "Expression of therapeutic proteins after delivery of chemically modified mRNA in mice," Nat Biotechnol 29, 154-157, 2011.

Kozarsky and Wilson "Gene therapy: adenovims vectors," Current Opinion in Genetics and Development 3: 499-503, 1993.

Krause, W.K.H. and Naz, R.K., eds. in Immune Infertility (Berlin, Germany: Springer-Verlag), 2009.

Krutskikh, A. et al. "Epididymal protein Rnase10 is required for posttesticular sperm maturation and male fertility," FASEB J 26: 4198-4209, 2012.

Kumar, P. et al. "Gonadotropin-releasing hormone analogs: Understanding advantages and limitations," Journal of Human Reproductive Sciences 7, 170-174, 2014.

(56) References Cited

OTHER PUBLICATIONS

Kuriyama et al., "Improvement of peptide vectors for gene delivery with active targeting profiles for phosphatidylserine," Journal of peptide science: an official publication of the European Peptide Society, vol. 15, pp. 114-119, 2009.

Kurosawa, N. et al. "Rapid production of antigen-specific mono-clonal antibodies from a variety of animals," BMC biology 10: 80, 2012.

Kurosawa, N. et al. "Target-selective homologous recombination cloning for high-throughput generation of monoclonal antibodies from single plasma cells," BMC biotechnology 11: 39, 2011.

Kutmeier et al. "Assembly of humanized antibody genes from synthetic oligonucleotides using a single-round PCR," BioTechniques 17: 242, 1994.

Kutzler, M. and Wood, A. "Non-surgical methods of contraception and sterilization," Theriogenology 66: 514-525, 2006.

Lack et al., A Thousand Fly Genomes: An Expanded Drosophila Genome Nexus. Mol Biol Evol33(12):3308-3313. Marshall, J. M. 2009. "The Effect of Gene Drive on Containment of Transaenic Mosquitoes." Journal of Theoretical Biology 258 (2): 250-65, 2016.

Landsteiner et al., "Studies on the Sensitization of Animals with Simple Chemical Compounds", J. Exp. Med., vol. 61, pp. 643-656, 1935.

Laumonier et al., "A new peptidic vector for molecular imaging of apoptosis, identified by phage display technology," Journal of biomolecular screening, vol. 11, pp. 537-545, 2006.

Lea, I.A. et al. "Autoimmunogenicity of the human sperm protein Spl 7 in vasectomized men and identification oflinear B cell epitopes," Fertility and sterility 67: 355-361, 1997.

Lee et al., "Mechanism for phosphatidylserine-dependent erythrophagocytosis in mouse liver," Blood, vol. 117, pp. 5215-5223, 2011.

Lee, E.C. et al. "Complete humanization of the mouse immuno-globulin loci enables efficient therapeutic antibody discovery," Nat Biotechnol 32, 356-363, 2014.

Lefevre, A. et al. "Characterization and isolation of SOB2, a human sperm protein with a potential role in oocyte membrane binding," Molecular human reproduction 3: 507-516, 1997.

Leone, P. et al. "Long-term follow-up after gene therapy for canavan disease," Sci Transl Med 4, 165ral63, 2012.

Levy, J. K. "Contraceptive Vaccines for the Humane Control of Community Cat Populations," Am J Reprod Immunol 66: 63-70, 2011.

Levy, J.K. et al. "Long-term fertility control in female cats with GonaCon™, a GnRH immunocontraceptive," Theriogenology 76: 1517-1525, 2011.

Li, J. et al. "Vectored antibody gene delivery mediates long-term contraception," Current Biology 25: R811-R826, 2015.

Li, L. et al. "Production and characterization of novel recombinant adeno-associated vims replicative-form genomes: a eukaryotic source of DNA for gene transfer," PloS One 8: e69879, Aug. 1, 2013a.

Li, W. et al. "TexIOI is essential for male fertility by affecting sperm migration into the oviduct in mice," Journal of molecular cell biology 5:345-347, Aug. 22, 2013.

Limberis, M.P. et al. "Intranasal Antibody Gene Transfer in Mice and Ferrets Elicits Broad Protection Against Pandemic Influenza," Sci Transl Med 5: 187ra72, May 29, 2013.

Lincoln, G.A. et al. "Blockade of Episodic Secretion of Luteinizing Hormone in the Ram by the Administration of Antibodies to Luteinizing Hormone Releasing Hormone," Biol Reprod 21:1239-1245, 1979.

Lishko, P.V. et al. "The Control of Male Fertility by Spermatozoan Ion Channels," Annual review of physiology 74: 453-475, 2012.

Liu et al., "Immune tolerance after delivery of dying cells to dendritic cells in situ," J. Exp. Med., vol. 196, No. 8, pp. 1091-1097, 2002.

Lloyd, M.L. et al. "Immunocontraception is induced in BALB/c mice inoculated with murine cytomegalovims expressing mouse zona pellucida 3," Biol Reprod 68, 2024-2032, 2003.

Locke. S.L. et al. "Effectiveness of Spayvac® for Reducing White-tailed Deer Fertility," Journal of wildlife diseases 43: 726-730, 2007.

Loeffler and Behr "Gene transfer into primary and established manunalian cell lines with lipopolyamine-coated DNA," Meth Enzymol 217: 599-618, 1993.

Ishino, T. et al. "Engineering a Monomeric Fe Domain Modality by N-Glycosylation for the Half-life Extension of Biotherapeutics," J Biol Chem. 288: 16529-37, Apr. 24, 2013.

Lucas et al., "Phosphatidylserine binding is essential for plasma membrane recruitment and signaling function of 3-phosphoinositide-dependent kinase-1," J. Biol. Chem., vol. 286, pp. 41265-41272, 2011.

Lucas, X. "Clinical use of deslorelin (GnRH agonist) in companion animals: a review," Reproduction in Domestic Animals 49 Suppl 4, 64-71, 2014.

Luo et al., "ECDI-fixed allogeneic splenocytes induce donor-specific tolerance for long-term survival of islet transplants via two distinct mechanisms," Proc. Natl. Acad. Sci. USA., vol. 105, pp. 14527-14532, 2008.

Macdonald, L.E. et al. "Precise and in situ genetic humanization of 6 Mb of mouse immunoglobulin genes," Proc Natl Acad Sci US A 111, 5147-5152, 2014.

Mackenzie, S.M. et al. "Immunocontraceptive effects on female rabbits infected with recombinant myxoma virus expressing rabbit ZP2 or ZP3," Biol Reprod 74, 511-521, 2006.

Magnusson, Kalle et al., Magnusson, K. et al. Demasculinization of the Anopheles gambiae X chromosome. BMC Evol. Biol. 12, 69 (2012)., Aug. 19, 2024.

Majowicz et al. "Mir-142-3p target sequences reduce transgene-directed immunogenicity following intramuscular adeno-associated vims 1 vector-mediated gene delivery," Journal of Gene medicine. 15: 219-232, Jul. 16, 2013.

Majumdar, R. et al. "Docking and free energy simulations to predict conformational domains involved in Hcg-LH receptor interactions using recombinant antibodies," Proteins 79: 3108-3122, 2011.

Marshall, J.M. et al., Samele: a killer-male, rescue-female system for suppression and replacement of insect disease vector popula-tions, Genetics, vol. 187 No. 2, pp. 535-551; 2011.

Mastrangeli et al. "Diversity of airway epithelial cell targets for in vivo recombinant adenovims-mediated gene transfer," J Clinical Invest 91: 225-234, 1993.

Matzuk, M.M. et al. "Site specificity of the chorionic gonadotropin N-linked oligosaccharides in signal transduction," J Biol Chem 264, 2409-2414, 1989.

McCormack, J.T. et al. "The Effect of Luteinizing Hormone Releas-ing Hormone (LHRH) Antiserum Administrationon Gonadotropin Secretion in the Rhesus Monkey," Endocrinology 100: 663-667, 1977.

McGaha et al., "Marginal zone macrophages suppress innate and adaptive immunity to apoptotic cells in the spleen," Blood, vol. 117, No. 20, pp. 5403-5412, 2011.

McLaughlin, E.A. et al. "Cloning and sequence analysis of rat fertilin alpha and beta-developmental expression, processing and immunolocalization," Molecular human reproduction 3: 801-809, 1997.

McLaughlin, E.A. et al. "Is there a role for immunocontraception?," Molecular and cellular endocrinology 335: 78-88, 2011.

Meloen et al., "Efficient immunocastration of male piglets by immunoneutralization of GnRH using a new GnRH-like peptide," Vaccine 12:741-746, 1994.

Midgley Jr. A.R., et al. "Nonclassical secretory dynamics ofLH revealed by hypothalamuseal portal sampling of sheep," Endocrine 6: 133-143, 1997.

Miller et al. "Use of retroviral vectors for gene transfer and expression," Meth Enzymol 217: 581-599, 1993.

Miller et al., "The induction of cell-mediated immunity and toler-ance with protein antigens coupled to syngeneic lymphoid cells," J. Exp. Med., vol. 149, pp. 758-773, 1979.

Miller, A.O., "Retrovirus Packaging Cells," Human Gene Therapy, vol. 1, pp. 5-14, 1990.

(56)                    References Cited

OTHER PUBLICATIONS

Miller, L.A. et al. "The Single-Shot GnRH Immunocontraceptive Vaccine (GonaCon™) in White-Tailed Deer: Comparison of Several GnRH Preparations," Am J Reprod Immunol 60: 214-223, 2008.
Miller, L.A. et al. "Twenty years of immunocontraceptive research: lessons learned," Journal of Zoo and Wildlife Medicine 44, S84-96, Dec. 2013.
Mingozzi, F. "Immune responses to AAV vectors: overcoming barriers to successful gene therapy," Blood 122, 23-36, Jul. 4, 2013.
Mingozzi, F. et al. "Overcoming preexisting humoral immunity to AAVusing capsid decoys," Sci Transl Med 5, 194ral92, Jul. 17, 2013.
Miyake et al., "Critical role of macrophages in the marginal zone in the suppression of immune responses to apoptotic cell-associated antigens", J. Clin. Invest., vol. 117, pp. 2268-2278, 2007.
Miyanishi et al., "Identification of Tim4 as a phosphatidylserine receptor," Nature, vol. 450, pp. 435-439, 2007.
Morizono et al., "The soluble serum protein Gas6 bridges virion envelope phosphatidylserine to the TAM receptor tyrosine kinase Ax1 to mediate viral entry," Cell Host Microbe, vol. 9, pp. 286-298, 2011.
Morrison et al. "Chimeric human antibody molecules: Mouse antigen-binding domains with human constant region domains," Proc Natl Acad Sci 81(21): 6851-6855, 1984.
Morton et al., "Marcks-ED peptide as a curvature and lipid sensor," ACS Chemical Biology, vol. 8, pp. 218-225, 2013.
Munks, M.W. "Progress in Development of Immunocontraceptive Vaccines for Permanent Non-surgical Sterilization of Cats and Dogs," Reproduction in Domestic Animals 47 (Suppl 4): 223-227, 2012.
Munoz et al., Theriogenology, (69): 1159-1164, 2008.
Murphy, A.J. et al. "Mice with megabase humanization of their immunoglobulin genes generate antibodies as efficiently as normal mice," Proc Natl Acad Sci US A 111, 5153-5158, 2014.
Muzyczka "Use of adeno-associated virus as a general transduction vector for mammalian cells," Curr Topics in Microbial Immunol 158: 97, 1992.
Nafissi, N. et al. "Construction and Characterization of an in-vivo Linear Covalently Closed DNA Vector Production System," Microbial cell factories 11: 154, 2012.
Nagata et al., "Autoimmunity and the clearance of dead cells," Cell, vol. 140, pp. 619-630, 2010.
Nagata et al., Sensing and clearance of apoptotic cells, Current Opinion in Immunology, vol. 68, pp. 1-8, 2021.
Nakahashi-Oda et al., "Identification of phosphatidylserine as a ligand for the CD300a immunoreceptor," Biochem Biophys Res Commun., vol. 417, pp. 646-650, 2012.
Nakai et al., "Isolation of a *Drosophila* gene coding for a protein containing a novel phosphatidylserine-binding motif," J. Biochem., vol. 137, pp. 593-599, 2005.
Nathwani, A.C. et al. "Adenovims-Associated Vims Vector-Mediated Gene Transfer in Hemophilia B," The New England journal of medicine 365: 2357-2365, 2011.
Naz et al. "Antibodies to sperm-specific human FA-1 inhibit in vitro fertilization in rhesus monkeys: development of a simian model for testing of anti-FA-1 contraceptive vaccine," Journal of reproductive immunology 27: 111-121, 1994.
Naz et al. "Passive Immunization for Immunocontraception: Lessons Learned from Infections Diseases," Frontiers in Bioscience 9:2457-2465, 2004.
Naz, "Contraceptive Vaccines", Drugs, 65 (5):593-603 (2005).
Naz, "Recent advances in contraceptive vaccine development: a mini-review," Human Reproduction, 20 (12):3271-3283 (2005).
Naz, R.K. "Recent progress toward development of vaccines against conception," Expert Review of Vaccines 13, 145-154, 2014.
Nechansky, A. J. Pharm. Biomed. Anal. 2009;51 :252-254.
Neuberger et al. "Recombinant antibodies possessing novel effector functions," Nature 312: 604-608, 1984.

Neves et al., "Imaging cell death. Journal of nuclear medicine: official publication," Society of Nuclear Medicine, vol. 55, pp. 1-4, 2014.
Niemann, Transgenic Research, 7: 73-75 (1998).
Nimmerjahn, F. "Fcgamma receptors as regulators of immune responses," Nature Rev Immunology 8, 34-47, 2008.
O'Rand, M. G. "Reversible Immunocontraception in Male Monkeys Immunized with Eppin," Science 306: 1189-1190,2004.
Oberhofer et al., "Split versions of Cleave and Rescue selfish genetic elements for measured self limiting gene drive," BA.PLoS Genet., Feb. 18, 2021; 17(2):e1009385. doi: 10.1371/journal.pqen.1009385.
Ogura et al. "Implantation of Genetically Manipulated Fibroblasts into Mice as Antitumor a-Interferon Therapy," Cancer Research 50: 5102-5106, 1990.
Ohlsson et al., BMC Gastroenterology, 10: 48, 2010.
Oi, V.T. et al. "Correlation between segmental flexibility and effector function of antibodies," Nature 307, 136-140, 1984.
Pai, M. et al. "Immunocontraception in Eastern Gray Squirrels (*Sciums carolinensis*): Morphologic Changes in Reproductive Organs," Journal of zoo and wildlife medicine: official publication of the American Association of Zoo Veterinarhms 42: 718-722, 2011.
Paidassi et al., "C1q binds phosphatidylserine and likely acts as a multiligand-bridging molecule in apoptotic cell recognition," J. Immunol., vol. 180, pp. 2329-2338, 2008.
Pandey et al., "The forgotten tale of immunoglobulin allotypes in cancer risk and treatment," Experimental hematology & oncology, vol. 2, p. 6, 2013.
Paris et al., Theriogenology, 74: 516-524, 2010.
Park et al., "BAI1 is an engulfment receptor for apoptotic cells upstream of the ELMO/Dock180/Rac module," Nature, vol. 450, pp. 430-434, 2007.
Park et al., "Epidermal growth factor-like domain repeat of stabilin-2 recognizes phosphatidylserine during cell corpse clearance," Mol. Cell Biol., vol. 28, pp. 5288-5298, 2008a.
Park et al., "Rapid cell corpse clearance by stabilin-2, a membrane phosphatidylserine receptor," Cell Death Differ, vol. 15, pp. 192-201, 2008a.
Pasadena-humane-society. http://www.pasadenahumane.org/site/PageServer?pagename=services_snip_faq; Original publication date unknown; Version printed on Mar. 22, 2016.
Pausch et al. "A Nonsense Mutation in TMEM95 Encoding a Nondescript Transmembrane Protein Causes Idiopathic Male Subfertility in Cattle," PLoS Genet. 10(1):el004044, 2014.
Pickard, A.R. and Holt, W.V. "Contraception in wildlife," The journal of family planning and reproductive health care/ Faculty of Family Planning & Reproductive Health Care, Royal College of Obstetricians & Gvnaecologists 33: 48-52, 2007.
Pittelkow and Scott "New Techniques for the In Vitro Culture of Human Skin Keratinocytes and Perspectives on Their Use for Grafting of Patients With Extensive Bums," Mayo Clinic Proc 61: 771, 1986.
Poulsen et al., Journal ofImmunology, 187: 4229-4235, 2011.
Powers, J.G. et al. "Effects of Gonadotropin-Releasing Hormone Immunization on Reproductive Function and Behavior in Captive Female Rocky Mountain Elk (*Cervus elaphus nelsoni*)," Biol Reprod 85: 1152-1160, 2011.
Presta, L.G. "Engineering of therapeutic antibodies to minimize immunogenicity and optimize function," Advanced Drug Delivery Reviews 58: 640-656, 2006.
Price, E.O. et al. "Aggressive behavior is reduced in bulls actively immunized against gonadotropin-releasing hormone," Journal of animal science 81: 411-415, 2003.
Primakoff, P. et al. "Fully effective contraception in male and female guinea pigs immunized with the sperm protein PH-20," Nature 335: 543-546, 1988.
Purohit et al., "Lower inhibitor development in hemophilia A mice following administration of recombinant factor VIII-O-phospho-L-serine complex," J. Biol. Chem., vol. 280, pp. 17593-17600, 2005.
Qi et al., "Differential membrane interactions of saposins A and C: implications for the functional specificity," J. Biol. Chem., vol. 276, pp. 27010-27017, 2001.

(56) References Cited

OTHER PUBLICATIONS

Qiu et al., "Annexin V-Trail fusion protein is a more sensitive and potent apoptotic inducer for cancer therapy," Scientific reports, vol. 3, p. 3565, 2013.

Ramani et al., "Phosphatidylserine containing liposomes reduce immunogenicity of recombinant human factor VIII (rFVIII) in a murine model of hemophilia A," Journal of pharmaceutical sciences, vol. 97, pp. 1386-1398, 2008.

Rankin, T.L. et al. "Human ZP3 restores fertility in Zp3 null mice without affecting order-specific sperm binding," Development 125 : 2415-2424, 1998.

Ravishankar et al., "Marginal zone CD169+ macrophages coordinate apoptotic cell-driven cellular recruitment and tolerance," Proc. Natl. Acad. Sci. USA, vol. 111, pp. 4215-4220, 2014.

Ravishankar et al., "O death where is thy sting? Immunologic tolerance to apoptotic self," Cell Mol. Life Sci., vol. 70, pp. 3571-3589, 2013.

Reichmann et al., "Reshaping human antibodies for therapy," Nature 332:323-327, 1988.

Reubel, G.H. et al. "Experimental inoculation of European red foxes with recombinant vaccinia vims expressing zona pellucida C proteins," Vaccine 23, 4417-4426, 2005.

Rheinwald "Serial cultivation of normal human epidermal keratinocytes," Meth Cell Bio 2IA: 229-254, 1980.

Robbins, S.C. et al. "Assessment of the immunological and biological efficacy of two different doses of a recombinant GnRH vaccine in domestic male and female cats (*Felis catus*)," Journal of reproductive immunology 64: 107-119, 2004.

Roberts, K.P. et al. "Inhibition of Capacitation-Associated Tyrosine Phosphorylation Signaling in Rat Sperm by Epididymal Protein Crisp-I," Biol Reprod 69: 572-581, 2003.

Robertson, I.S. et al. The Veterinary record 105: 556-557, 1979.

Robertson, I.S. et al. The Veterinary record 108: 381-382, 1981.

Robertson, I.S. et al. The Veterinary record 111: 529-531, 1982.

Rodriguez-Fernandez et al., Phosphatidylserine-liposomes Promote Tolerogenic Features on Dendritic cells in human Type 1 Diabetes by apoptotic Mimicry, Frontiers in Immunology vol. 9, Article 253, 17 pages, 2018.

Ronald, J.A. et al. "Development and Validation of Non-Integrative, Self-Limited, and Replicating Minicircles for Safe Reporter Gene Imaging of Cell-Based Therapies," PLoS One e73138. doi: 10.1 371/journal.pone.0073138, Aug. 28, 2013.

Rosenbaum et al., "Identification of novel binding partners (annexins) for the cell death signal phosphatidylserine and definition of their recognition motif," J. Biol. Chem., vol. 286, pp. 5708-5716, 2011.

Rosenberg, J.B et al. "AAVrh. 10-Mediated Expression of an Anti-Cocaine Antibody Mediates Persistent Passive Immunization That Suppresses Cocaine-Induced Behavior," Hum Gene Ther 23: 451-459, 2012.

Rosenfeld et al. "Adenovirus-mediated transfer of a recombinant alpha 1-antitrypsin gene to the lung epithelium in vivo," Science 252: 431-434, 1991.

Rosenfeld et al. "In vivo transfer of the human cystic fibrosis transmembrane conductance regulator gene to the airway epithelium," Cell 68: 143-155, 1992.

Rudinger, "Characteristics of the amino acids as components of a peptide hormone sequence" Peptide Hormones, Parsons, (ed.), 1976 University Park Press, Baltimore, MD, pp. 1-7.

Rysavy, N.M et al., Beyond apoptosis: the mechanism and function of phosphatidylserine asymmetry in the membrane of activating mast cells. Bioarchitecture 4, pp. 127-137, (2014).

Saint Louis Zoo. http://www.stlzoo.org/animals/scienceresearch/contraceptioncenter/contraceptiomecommendatio/contraceptionmethods/; Original publication date unknown; Version printed on Mar. 22, 2016.

Salmons et al. "Targeting ofRetroviral Vectors for Gene Therapy," Human Gene Therapy 4: 129-141, 1993.

Samoylov, A. et al. Zuchthygiene 47 (Suppl 6):406-411, 2012.

Samuel, A.S. et al. "Isolation of human single chain variable fragment antibodies against specific sperm antigens for immunocontraceptive development," Hum Reprod 23, 1324-1337, 2008.

Samulski, R.J. et al. "AAV-mediated gene therapy for research and therapeutic purposes," Annu. Rev. Virol. 1, 427-451, 2014.

Santiago et al., "TIM-4 structures identify a Metal Ion-dependent Ligand Binding Site where phosphatidylserine binds," Immunity, vol. 27, pp. 941-951, 2007.

Santodonato, et al. "Cure of Mice with Established Metastatic Friend Leukemia Cell Tumors by a Combined Therapy with Tumor Cells Expressing Both Interferon-al and Herpes Simplex Thymidine Kinase Followed by Ganciclovir," Human Gene Therapy 7: 1-10, 1996.

Santodonato, et al. "Local and systemic antitumor response after combined therapy of mouse metastatic tumors with tumor cells expressing IFN-a and HSVtk: perspectives for the generation of cancer vaccines," Gene Therapy 4: 1246- 1255, 1997.

Saunders, A. et al. "Novel recombinant adeno-associated viruses for Cre activated and inactivated transgene expression in neurons," Frontiers in neural circuits 6: 47, 2012.

Sawai, H. et al. "Direct Production of the Fab Fragment Derived From the Sperm Immobilizing Antibody Using Polymerase Chain Reaction and cDNA Expression Vectors," Am J Reprod immunology 34: 26-34, 1995.

Schakowski, F. et al. "Minimal Size Midge Vectors Improve Transgene Expression In Vivo," In Vivo 21: 17-23, 2007.

Schneider, F. et al. "Gonadotropin-releasing hormone (GnRH) and its natural analogues: A review," Theriogenology 66: 691-709, 2006.

Schnepp, B.C. et al. "Vector-mediated antibody gene transfer for infectious diseases," Adv Exp Med Biol 848, 149-167, 2015.

Schulz, M.H. et al. "Oases: robust de novo TNA-seq assembly across the dynamic range of expression levels," Bioinformatics 28, 1086-92, 2012.

Schwartz et al. "Clinical Evaluation of Live, Oral Types 1, 2, and 5 Adenovims Vaccines," Am Rev RespirDis 109: 233-238, 1974.

Schweigert et al., "Soluble T cell immunoglobulin and mucin domain (TIM)-1 and -4 generated by a Disintegrin and Metalloprotease (ADAM)-10 and -17 bind to phosphatidylserine," Biochim Biophys Acta, vol. 1843, pp. 275-287, 2014.

Segawa et al., An Apoptotic 'Eat Me' Signal: Phosphatidylserine Exposure. Trends Cell Biol, vol. 25, pp. 639-650, 2015.

Sen, D. "Improving clinical efficacy of adeno associated vectors by rational capsid bioengineering," Journal of Biomedical Science 21, 103, 2014.

Shao et al., "Crystal structure of lactadherin C2 domain at 1.7A resolution with mutational and computational analyses of its membrane-binding motif," J. Biol. Chem. vol. 283, pp. 7230-7241, 2008.

Shore, N.D. "Experience with degarelix in the treatment of prostate cancer," Therapeutic Advances in Urology 5, 11-24, Jan. 16, 2013.

Short, R.V. et al. "Influence of passive immunization against GnRH on pregnancy and parturition in the tammar wallaby, Macropus eugenii," J Reprod Fertil 75: 567-575, 1985.

Silversides, D.W. et al. "Monoclonal antibodies against LHRH: development and immunoactivity in vivo and in vitro," Journal of reproductive immunology 7: 171-184, 1985.

Simhadri et al., "Human CD300a binds to phosphatidylethanolamine and phosphatidylserine, and modulates the phagocytosis of dead cells," Blood, vol. 119, pp. 2799-2809, 2012.

Simms, M.S. et al. "Anti-GnRH antibodies can induce castrate levels of testosterone in patients with advanced prostate cancer," British Journal of Cancer 83, 443-446, 2000.

Singh, M. et al. "Regain of Fertility and Normality of Progeny Born During Below Protective Threshold Antibody Titers in Women Immunized With the HSD-hCG Vaccine," Am J Reprod Immunology 39: 395-398, 1998.

Singleton et al., Title Page of Dictionary of Microbiology and Molecular Biology, J. Wiley & Sons, New York, N. Y., 1994, Second Edition.

Skerra et al. "Assembly of a functional immunoglobulin Fv fragment in *Escherichia coli*," Science 240: 1038-1041, 1988.

(56)          References Cited

OTHER PUBLICATIONS

Smith, K. "Rapid generation of fully human monoclonal antibodies specific to a vaccinating antigen," Nature protocols 4: 372-384, 2009.

Srivastava et al., "Soluble phosphatidylserine binds to a single identified site in the C2 domain of human factor Va," Biochemistry, vol. 40, pp. 8246-8255, 2001.

Steinman et al., "Avoiding horror autotoxicus: the importance of dendritic cells in peripheral T cell tolerance," Proc. Natl. Acad. Sci. USA, vol. 99, pp. 351-358, 2002.

Steinman et al., "The induction of tolerance by dendritic cells that have captured apoptotic cells," J. Exp. Med., vol. 191, pp. 411-416, 2000.

Stemple et al. "Isolation of a stem cell for neurons and glia from the mammalian neural crest," Cell 71 : 973-985, 1992.

Stevenson, T.J. et al. "Gonadotropin-releasing hormone plasticity: a comparative perspective," Frontiers in Neuroendocrinology 33, 287-300, 2012.

Stribling et al. "Aerosol gene delivery in vivo," Proc Natl Acad Sci USA 189: 11277-11281, 1992.

Strive, T. et al. "Development of canine herpesvims based antifertility vaccines for foxes using bacterial artificial chromosomes," Vaccine 24, 980-988, 2006.

Sun et al., "Allograft tolerance induced by donor apoptotic lymphocytes requires phagocytosis in the recipient," Cell Death Differ, vol. 11, pp. 1258-1264, 2004.

Swann, P.G. et al. "Considerations for the development of therapeutic monoclonal antibodies," Current opinion in immunology 20: 493-499, 2008.

Tada, K, et al. . Tethering of apoptotic cells to phagocytes through binding of CD47 to Src homology 2 domain-bearing protein tyrosine phosphatase substrate-1. J Immunol 171, 5718-5726., (2003).

Takahashi , M. et al. "Active Immunization of Female Rats with Luteinizing Hormone Releasing Hormone (LHRH)," Biol Reprod 18: 754-761, 1978.

Takeda et al. "Construction of chimaeric processed immunoglobulin genes containing mouse variable and human constant region sequences," Nature 314: 452-454, 1985.

Talwar, G.P. "A unique vaccine for control of fertility and therapy of advanced-stage terminal cancers ectopically expressing human chorionic gonadotropin," Ann NY Acad Sci 1283: 50-56, Apr. 2013.

Talwar, G.P. "Fertility regulating and immunotherapeutic vaccines reaching human trials stage," Human reproduction update 3: 301-310, 1997.

Talwar, G.P. et al. "A vaccine that prevents pregnancy in women," Proc Natl Acad Sci USA 91: 8532-8536, 1994.

Talwar, G.P. et al. "Gonadotropin-releasing hormone/human chorionic gonadotropin based recombinant antibodies and vaccines," Journal of reproductive immunology 83: 158-163, 2009.

Talwar, G.P et al. "The HSD-hCG Vaccine Prevents Pregnancy in Women: Feasibility Study of a Reversible Safe Contraceptive Vaccine," Am J Reprod Immunol 37: 153-160, 1997.

Thapa et al., "Discovery of a phosphatidylserine-recognizing peptide and its utility in molecular imaging of tumour apoptosis," J. Cell Mol. Med., vol. 12, pp. 1649-1660, 2008.

Theubet, G. et al. Schweizer Archiv fur Tierheilkunde 152: 459-469, 2010.

Thompson "Immunization against GnRH in male species (comparative aspects)," Animal Reproduction Science 60-61: 459-469, 2000.

Tietjen et al., "Molecular mechanism for differential recognition of membrane phosphatidylserine by the immune regulatory receptor Tim4," Proc. Natl. Acad. Sci. USA, vol. 111, pp. E1463-1472, 2014.

Tiller, T. et al., "Cloning and expression of murine Ig genes from single B cells," J. Immunol. Methods, vol. 350, pp. 183-193, 2009.

Title Page & Table of Contents of Lewin, B., Genes V, Oxford University Press, Oxford and New York, 1994.

Tollner, T.L. et al. "Macaque sperm coating protein DEFB126 facilitates sperm penetration of cervical mucus," HumReprod 23: 2523-2534, 2008.

Tung et al., "Phosphatidylserine recognition and induction of apoptotic cell clearance by Drosophila engulfment receptor Draper," J. Biochem., vol. 153, pp. 483-491, 2013.

Turley et al., "Peripheral tolerance induction using ethylenecarbodiimide-fixed APCs uses both direct and indirect mechanisms of antigen presentation for prevention of experimental autoimmune encephalomyelitis," J. Immunol., vol. 178, pp. 2212-2220, 2007.

Tzioufas, A.G. et al. "Idiotype, anti-idiotype network of autoantibodies: pathogenetic considerations and clinical application," Autoimmunity Reviews 9, 631-633, 2010.

Vafa et al. "An engineered Fc variant of an IgG eliminates all immune effector functions via structural perturbations," Methods 65: 114-26, 2014.

Van Der Lende, T. "Generation and applications of monoclonal antibodies for livestock production," Biotechnology advances 12: 71-87, 1994.

Vargas-Pino, F. et al. "Concomitant administration of GonaConTMand rabies vaccine infemale dogs (Canis familiaris) in Mexico," Vaccine 31: 4442-4447, Jul. 16, 2013.

Verhoeyen et al. "Reshaping human antibodies: grafting an antilysozyme activity," Science, 239: 1534-1536, 1988.

Vidal, A. et al. "A Dynamical Model for the Control of the Gonadotrophin-Releasing Hormone Neurosecretory System," J. Neuroendocrinology 22: 1251-1266, 2010.

Vulin, A. et al. "Muscle Function Recovery in Golden Retriever Muscular Dystrophy After AAVl-U7 Exon Skipping," The journal of the American Society of Gene Therapy 20: 2120-2133, 2012.

Wakchaure et al., IJETAE 5(11), 210-213, 2015.

Walker, J. et al. "Totally synthetic peptide-based immunocontraceptive vaccines show activity in dogs of different breeds," Vaccine 25: 7111-7119, 2007.

Walsh et al. "Gene therapy for human hemoglobinopathies," Proc Soc Exp Biol Med 204: 289-300, 1993.

Walsh, G. "Biopharmaceutical benchmarks 2014," Nat Biotechnol 32, 992-1000, 2014.

Wang D.G. et al. "Investigation of Recombinant Mouse Sperm Protein Izumo as a Potential Immunocontraceptive Antigen," Am J Reprod Immunol 59:225-234, 2008.

Wang et al., "Efficient backsplicing produces translatable circular mRNAs," RNA, vol. 21, pp. 172-179, 2015.

Wang et al., "Regulatory T cells and B cells: implication on autoimmune diseases," International journal of clinical and experimental pathology, vol. 6, pp. 2668-2674, 2013.

Wang, et al. "A packaging cell line for propagation of recombinant adenovims vectors containing two lethal gene-region deletions," Gene Therapy 2: 775-783, 1995.

Wang, M. et al. "Immunocontraceptive potential of the Ig-like domain ofIzumo," Molecular reproduction and development 76: 794-801, 2009.

Ward et al. "Binding activities of a repertoire of single immunoglobulin variable domains secreted from Escherichia coli," Nature 341: 544-54, 1989.

Weiner, G.J. "Building better monoclonal antibody-based therapeutics," Nat Rev Cancer 15, 361-370, 2015.

Wenzinger, B. et al. "The use of a GnRH vaccine in mares and stallions to influence undesirable behavior: a retrospective study of 31 cases," Schweizer Archiv fur Tierheilkunde 152: 373-377, 2010.

Wilkinson, I.C. et al. "Monovalent IgG4 molecules," mAbs 5:406-417, Apr. 8, 2013.

Wilson et al. "Vehicles for gene therapy," Nature 365: 691-692, 1993.

Winter, G. and Harris, W.J. "Humanized antibodies," Immunology today 14: 243-246, 1993.

Wong, S.P. et al. "Genetic modification of dividing cells using episomally maintained Simar DNA vectors," Molecular Therapy-Nucleic Acids 2, ell5; doi: 10.1038/mtna.2013.40, Aug. 13, 2013.

Wu et al. "Receptor-mediated in Vitro Gene Transformation by a Soluble DNA Carrier System," J Biol Chem 262: 4429-4432, 1987.

Wu, X. et al. "Development of combined vaccines for rabies and immunocontraception ," Vaccine 27: 7202-7209, 2009.

Xiong et al., "Peptide-based imaging agents targeting phosphatidylserine for the detection of apoptosis," Journal of medicinal chemistry, vol. 54, pp. 1825-1835, 2011.

(56) References Cited

OTHER PUBLICATIONS

Yamasaki, N. et al. "Complementary DNA for a human subgroup IV immunoglobulin A-chain," Molecular Immunology 24: 981-985, 1987.

Yanagimachi , R. et al., "Immunological block to mammalian fertilization: Survival and organ distribution of immunoglobulin which inhibits fertilization in vivo," Proc Natl Acad Sci USA 73: 2405-2408, 1976.

Yang et al. "Inactivation of E2a in recombinant adenoviruses improves the prospect for gene therapy in cystic fibrosis," Nature Genet 7: 362-369, 1994.

Yang et al., "A lysine-rich motif in the phosphatidylserine receptor PSR-1 mediates recognition and removal of apoptotic cells," Nature communications, vol. 6, pp. 5717, 2015.

Yatim et al., RIPK1 and NF-κB signaling in dying cells determines cross-priming of CD8+ T cells, Science, vol. 350, No. 6258, 2015.

Ye et al., "NMR solution structure of C2 domain of MFG-E8 and insights into its molecular recognition with phosphatidylserine," Biochim Biophys Acta., vol. 1828, pp. 1083-1093, 2013.

Yin et al., "Non-viral vectors for gene-based therapy," Nat. Rev. Genet., vol. 15, pp. 541-555, 2014.

Yin, L. et al. "Therapeutic outcomes, assessments, risk factors and mitigation efforts of immunogenicity of therapeutic protein products," Cellular Immunology 295, 118-126, 2015.

Yoder, C.A. et al. "Effect of GonaConTM vaccine on black-tailed prairie dogs: Immune response and health effects," Vaccine 29: 233-239, 2010.

Yoo, J. et al. "Conversion of lysine 91 to methionine or glutamic acid in human choriogonadotropin alpha results in the loss of cAMP inducibility," J Biol Chem 266, 17741-17743, 1991.

Youn et al., "Modified mRNA as an alternative to plasmid DNA (pDNA) for transcript replacement and vaccination therapy," Expert opinion on biological therapy, vol. 15, pp. 1337-1348, 2015.

Yudin, A.I. et al. "ESP13.2, a Member of the—Defensin Family, is a Macaque Sperm Surface-Coating Protein Involved in the Capacitation Process," Biol Reprod 69: 1118-1128, 2003.

Zeltins, A. "Construction and characterization of virus-like particles: a review," Molecular biotechnology 53: 92-107, Jan. 2013.

Zeng et al., "Molecular imaging of apoptosis: from micro to macro," Theranostics, vol. 5, pp. 559-582, 2015.

Zeng, H. et al. "Lys9 I and His90 of the alpha-subunit are crucial for receptor binding and hormone action of follicle-stimulating hormone (FSH) and play hormone-specific roles in FSH and human chorionic gonadotrooin," Endocrinology 136, 2948-2953, 1995.

Zhang, et al. "Treatment of a human breast cancer xenograft with an adenovirus vector containing an interferon gene results in rapid regression due to viral oncolysis and gene therapy," Cancer Gene Therapy 3: 31-38, 1996.

Zijlstra et al. "Germ-line transmission of a disrupted 2microglobulin gene produced by homologous recombination in embryonic stem cells," Nature 342: 435-438, 1989.

Zuris, J.A. et al. "Cationic lipidmediateddelivery of proteins enables efficient protein-based genome editing in vitro and in vivo," Nat Biotechnol 33, 73-80, 2015.

Advisory Action dated Nov. 21, 2016 in U.S. Appl. No. 14/631,171.

Akbari, O.S. et al., A synthetic gene drive system for local, reversible modification and suppression of insect populations, Curr. Biol., vol. 23 No. 8, pp. 671-677. 2013.

Akbari, O.S. et al., Novel synthetic Medea selfish genetic elements drive population replacement in Drosophila; a theoretical exploration of Medea-dependent population suppression, ACS Synth Biol. vol. 3 No. 12, DD. 915-928; 2014.

Alphey, L. et al., Malaria Control with Genetically Manipulated Insect, Nature vol. 415, 702; 2002.

Alphey, L. Genetic Control of Mosquitoes. Annu. Rev. Entomol, vol. 59, pp. 205-224, (2014).

Altrock, P. M. et al., Stability properties of underdominance in finite subdivided populations, PLoS Comput. Biol., vol. 7 No. 11, e1002260; 2011.

Altrock, P. M. et al., Using underdominance to bi-stably transform local populations, J Theor Biol, vol. 267 No. 1, pp. 62-75; 2010.

Amin et al., "Organization of the Drosophila melanogaster hsp70 heat shock regulation unit," Molecular and Cellular Biology 7:1055-1062 (1987).

Ant et al., "Control of the olive fruit fly using genetics-enhanced sterile insect technique", BMC Biology vol. 10, No. 51, pp. 1-8, 2012.

Arndt, K. M. et al., Helix-stabilized Fv (hsFv) antibody fragments: substituting the constant domains of a Fab fragment for a heterodimeric coiled-coil domain, J Mol Biol, vol. 312 No. 1, pp. 221-228.; 2001.

Asman, S. M. et al., Field studies of genetic control systems for mosquitoes, Annu Rev Entomol., vol. 26 No. 1, pp. 289-318; 1981.

Baker et al., "Genetic sexing for a mosquito sterile-male release", The Journal of Heredity, vol. 7, No. 2, pp. 216-218, 1981.

Baker, R.H., Chromosome Rearrangements in the Control of Mosquitos, Prev Vet Med 2, pp. 529-540; 1984.

Beaghton, A., et al., Gene Drive through a Landscape: Reaction-Diffusion Models of Population Suppression and Elimination by a Sex Ratio Distorter, Theoretical Population Biology, vol. 108, pp. 51-69, (2016).

Beaghton, A., et al., Requirements for Driving Antipathogen Effector Genes into Populations of Disease Vectors by Homing, Genetics, vol. 205 (4), pp. 1587-1596, (2017).

Ben-David, E. et al., A Maternal-Effect Selfish Genetic Element in Caenorhabditis elegans, Science 356 (6342), pp. 1051-1055, (2017).

Bergmann, A. et al., The Drosophila gene hid is a direct molecular target of Ras-dependent survival signaling, Cell, vol. 95 No. 3, pp. 331-341; 1998.

Beumer, K. J. et al., "Induced chromosomal exchange directs the segregation of recombinant chromatids in mitosis of Drosophila. Genetics," Genetics, vol. 150 No. 1, pp. 173-188; (1998).

Bier V.M.G.A.E. et al., The mutagenic chain reaction: A method for converting heterozygous to homozygous mutations, Science, vol. 348 No. 6233, pp. 442-444; 2015.

Billeter, J. C. et al., Specialized cells tag sexual and species identity in Drosophila melanogaster, Nature, vol. 461 No. 7266, pp. 987-991; 2009.

Bischof, J. et al., An Optimized Transgenesis System for Drosophila Using Germ-Line-Specific phiC31 Integrases., Proceedings of the National Academy of Sciences of the United States of America, vol. 104, No. 9, pp. 3312-3317, 2007.

Boerjan et al., Lignin biosynthesis, Annual Review of Plant Biology, vol. 54, pp. 519-546, 2003.

Boete C. et al., A theoretical approach to predicting the success of genetic manipulation of malaria mosquitoes in malaria control, Malar J, vol. 1 No. 3; 2002.

Boete C. et al., Evolutionary ideas about genetically manipulated mosquitoes and malaria control, Trends Parasitol, vol. 19 No. 1, pp. 32-38; 2003.

Bohannon J., Food aid. Zambia rejects GM corn on scientists' advice, Science, vol. 298 No. 5596, pp. 1153-1154; 2002.

Borycz J. et al., ABC transporter mutants white, brown and scarlet have altered contents and distribution of biogenic amines in the brain, J Exp Biol, vol. 211 No. 21, pp. 3454-3466; 2008.

Bossin et al., "Somatic transformation efficiencies and expression patterns using the JcDNV and piggyBac transposon gene factors in insects," Insect Mol. Biol. 16:37-47 (2007).

Braig, H. R. et al., The spread of genetic constructs in natural insect populations. In D. K. Letourneau & B. E. Burrows (Eds.) Genetically Engineered Organisms: Assessing Environmental and Human Health Effects (pp. 251-314). Cleveland, OH/Boca Raton, FL: CRC Press; 2002.

Brelesfoard, et al., Wolbachia-based strategies to control insect pests and disease vectors. Asia-Pacific Journal of Molecular Biology and Biotechnology, vol. 17, pp. 55-63, 2009.

Brunel et al., Cloning and sequencing of pseudomonas genes encoding vaniilate demethylase, Journal of Bacteriology, vol. 170, pp. 4924-4930, 1988.

Buchman et al., Synthetically engineered Medea gene drive system in the worldwide crop pest Drosophila suzukii, PNAS, vol. 115, Mo.18, pp. 4725-4730, 2018.

(56)　　　　　References Cited

OTHER PUBLICATIONS

Buchman, A., et al., Engineered Reciprocal Chromosome Transloca-tions Drive High Threshold, Reversible Population Replacement in *Drosophila*, ACS Synthetic Biology, 2018.

Burt & Trivers, Genes in Conflict, The Belknap Press of Harvard University Press, 613 pages, 2008.

Burt, A. et al Genetic Conflicts in Genomic Imprinting, Proceed-ings. Biological Sciences/ The Royal Society, vol. 265, No. 1413, pp. 2393-2397, 1998.

Burt, A. et al., Homing endonuclease genes: the rise and fall and rise again of a selfish element. Curr. Opin. Genet. Dev. vol. 14, pp. 609-615 (2004).

Burt, A., Site-Specific Selfish Genes as Tools for the Control and Genetic Engineering of Natural Populations, Proceedings. Biologi-cal Sciences/ The Royal Society, vol. 270, No. 1518, pp. 921-928, 2003.

Bushland et al., "Eradication of Screw-Worms through Release of Sterilized Males", Science, vol. 122, No. 3163, pp. 287-288, 1955.

Carvajal-Vallejos, et al. Unprecedented Rates and Efficiencies Revealed for New Natural Split Inteins from Metagenomic Sources, The journal of Biological Chemistry, vol. 287, No. 34, pp. 28686-28696, 2012.

Carvalho D.O. et al., Two step male release strategy using trans-genic mosquito lines to control transmission of vector-borne dis-eases, Acta Trap 132S, S170-S177; 2014.

Carvalho et al., "Mass Production of Genetically Modified Aedes aegypti for Field Releases in Brazil", Journal of Visualized Experi-ments vol. 83, e3579, pp. 1-10, 2014.

Castillo, J. et al., Complex Interaction Between Dengue Virus Replication and Expression of Mirna-133a., BMC Infectious Dis-eases, vol. 16, 2016.

Centers for Disease Control and Prevention (2012). Dengue fact sheet. Retrieved Apr. 30, 2014, from cdc.gov/Dengue/faqFacts/fact.html.

Centers for Disease Control and Prevention (2014). About malaria. Retrieved Apr. 30, 2014, from cdc.gov/malaria/about/facts.html.

Champer, J. et al., Novel CRISPR/Cas9 Gene Drive Constructs Reveal Insights into Mechanisms of Resistance Allele Formation and Drive Efficiency in Genetically Diverse Populations., PLoS Genetics, (2017).

Chan et al., Insect Population Control by Homing Endonuclease-Based Gene Drive: An Evaluation in *Drosophila melanogaster*, Genetics, vol. 188, No. 1, pp. 33-44, 2011.

Chan, Y. et al. Optimising Homing Endonuclease Gene Drive Performance in a Semi-Refractory Species: The *Drosophila melanogaster* Experience, (2013).

Chen C.H. et al., A synthetic maternal-effect selfish genetic element drives population replacement in *Drosophila*, Science, vol. 316 No. 5824, pp. 597-600; 2007.

Chen et al, An Enhanced Gene Targeting Toolkit for *Drosophila*: Golic+, Genetics, vol. 199, pp. 683-694, 2015.

Cheriyan, M. et al., Faster protein splicing with the Nostoc punctiforme DnaE intein using non-native extein residues, J Biol Chem, vol. 288 No. 9, pp. 6202-6211; 2013.

Clark et al., Evolution of Genes and Genomes on the *Drosophila* Phylogeny, Nature, vol. 450, No. 7167, pp. 203-218,2007.

Collins et al., "Effects of irradiation dose rate on quality and sterility of Queensland fruit flies, *Bactrocera tryoni* (Froggatt)," J. Appl. Entomol. 132:398-405 (2008).

Condon et al., Genetic sexing through the use of Y-linked transgenes, Insect Biochemistry and Molecular Biology, vol. 37, pp. 1168-1176, 2007.

Cook, R. K. et al., The generation of chromosomal deletions to provide extensive coverage and subdivision of the *Drosophila melanogaster* genome, Genome Biol, vol. 13 No. 3, R21; 2012.

Corby-Harris, V. et al., Activation of Akt signaling reduces the prevalence and intensity of malaria parasite infection and lifespan in Anopheles stephensi mosquitoes, PLoS Pathog, vol. 6 No. 7, e1001003; 2010.

Crompton, P. D. et al., Malaria immunity in man and mosquito: insights into unsolved mysteries of a deadly infectious disease, Annu Rev of Immunol, vol. 32 No. 1, pp. 157-187; 2014.

Curtis C.F. et al., "Computer simulation of the use of double translocations for pest control," Genetics, vol. 69 No. 1, 97-113; 1971.

Curtis et al., "Genetic sex separation in Anopheles arabiensis and the production of sterile hybrids", Bulletin in the World of Health Organization, vol. 56, No. 3, pp. 453-454, 1978.

Curtis et al., "Genetic Sexing System in *Anopheles-Gambiae* Spe-cies A", Mosquito News, vol. 36, No. 4, pp. 492-498, 1976.

Curtis, C. F., Possible use of translocations to fix desirable genes in insect pest populations, Nature, vol. 218 No. 5139, pp. 368-369; 1968.

Daborn et al., "Evaluating the insecticide resistance potential of eight *Drosophila melanogaster* cytochrome P450 genes by trans-genic over-expression", Insect Biochemistry and Molecular Biol-ogy, vol. 37, DD. 512-519, 2007.

Dang et al. Optimizing sgRNA Structure to Improve CRISPR-Cas9 Knockout Efficiency, Genome Biology, vol. 16, No. 280, 2015.

Dantuma N.P. et al., Short-lived green fluorescent proteins for quantifying ubiquitin/proteasome-dependent proteolysis in living cells, Nat Biotechnol., vol. 18 No. 5, pp. 538-543; 2000.

Davis S. et al., Engineered underdominance allows efficient and economical introgression of traits into pest populations, J Theor Biol., vol. 212 No. 1, pp. 83-98; 2010.

De Jesus C. et al., Use of genetic modified mosquitoes to fight dengue in Brazil, International Journal of Research in Pharmaceu-tical and Nano Sciences, vol. 2 No. 6, pp. 811-816; 2000.

De La Rocque S. et al., A review of trends in the distribution of vector-borne diseases: is international trade contributing to their spread? Rev Sci Tech, vol. 30 No. 1, pp. 119-130; 2011.

De Lara Capurro M. et al., Virus-expressed, recombinant single-chain antibody blocks sporozoite infection of salivary glands in Plasmodium gallinaceum-infected Aedes aegypti, Am J Trop Med Hyg., vol. 62 No. 4, pp. 427-433; 2000.

De N. et al., Highly complementary target RNAs promote release of guide RNAs from human Argonaute2, Mol Cell, vol. 50 No. 3, pp. 344-355; 2013.

Deredec A et al., The population genetics of using homing endonuclease genes in vector and pest management, Genetics, vol. 179 No. 4, pp. 2013-2026; 2008.

Dhar T. et al., Modification of transmembrane and GPI-anchored proteins on living cells by efficient protein trans-splicing using the Npu DnaE intein, Chem Commun (Camb), vol. 47 No. 11, pp. 3063-3065; 2011.

Dhole et al., Invasion and migration of spatially self-limiting gene drives: A comparative analysis, Evolutionary Applications, vol. 11, pp. 794-808, 2017.

Dicarlo, J. E. et al., "Safeguarding CRISPR-Cas9 gene drives in yeast", Nature Biotechnology, vol. 33, No. 12, pp. 1250-1255, (2015).

Doench, J.G. et al., Optimized sgRNA Design to Maximize Activity and Minimize off-Target Effects of CRISPR-Cas9, Nature Biotech-nology, vol. 34, No. 2, pp. 184-191, 2016.

Egli D et al., An efficient method to generate chromosomal rear-rangements by targeted DNA double-strand breaks in *Drosophila melanogaster*, Genome Res., vol. 14 No. 7, pp. 1382-1393; 2004.

Enayati A. et al., Malaria management: past, present, and future, Annu Rev Entomol., vol. 55, pp. 569-591; 2010.

Engler, C. et al., A one pot, one step, precision cloning method with high throughput capability, PLoS one, vol. 3 No. 11, e3647; 2008.

Engler, C. et al., Golden gate shuffling: a one-pot DNA shuffling method based on type IIs restriction enzymes, PLoS one, vol. 4 No. 5, e5553; 2009.

Eppstein, M. J., Payne, J. L., & Goodnight, C. J. (2009). Underdominance, multiscale interactions, and self-organizing bar-riers to gene flow. Journal of Artificial Evolution and Applications 5, 1-13.

Esvelt, K.M. et al., Concerning RNA-guided gene drives for the alteration of wild populations, Elife, e03401; 2014.

(56) References Cited

OTHER PUBLICATIONS

Farasat et al., A Biophysical Model of CRISPR/Cas9 Activity for Rational Design of Genome Editing and Gene Regulation. PLoS Comput Biol 12(1):e1004724, 2016.

Feng, et al. "Vanillic acid derivatives from the green algae *Cladophora socialis* as potent protein tyrosine phosphatase 1B inhibitors." Journal of natural products 70.11 (2007): 1790-1792.

Fields, S. et al., A novel genetic system to detect protein-protein interactions, Nature, vol. 340 No. 6230, pp. 245-246; 1989.

File History of U.S. Appl. No. 14/837,941, filed Aug. 27, 2015.

File History of U.S. Appl. No. 15/164,452, filed May 25, 2016.

Filipowicz, W. et al., Post-transcriptional gene silencing by siRNAs and miRNAs, Curr Opin Struct Biol., vol. 15 No. 3, pp. 331-341; 2005.

Focks et al., "An improved separator for the developmental stages, sexes, and species of mosquitoes (Diptera: Culicidae)", Journal of Medical Entomology, vol. 17, No. 6, pp. 567-568, 1980.

Forster, A. et al., Chromosomal translocation engineering to recapitulate primary events of human cancer, Cold Spring Harb Symp Quant Biol, vol. 70, pp. 275-282; 2005.

Foster, G.et al., Chromosome rearrangements for the control of insect pests, Science, vol. 176 No. 4037, pp. 875-880; 1972.

Franz, A. W. et al., Engineering RNA interference-based resistance to dengue virus type 2 in genetically modified Aedes aegypti, Proc Natl Acad Sci U S A, vol. 103 No. 11, pp. 4198-4203; 2006.

Fu et al., "Female-specific flightless phenotype for mosquito control," Proc. Natl. Acad. Sci. USA 107:4550-4554 (2010).

Galizi et al., A CRISPR-Cas9 Sex-Ratio Distortion System for Genetic Control, Scientific Reports, vol. 6, No. 31139, 2016.

Galizi, R. et al., A synthetic sex ratio distortion system for the control of the human malaria mosquito. Nat. Commun. vol. 5, (2014).

Gallup, J.L. et al., The economic burden of malaria, Am J Trop Med Hyg, vol. 64 No. 1-2 Suppl, pp. 85-96; 2001.

Gantz et al., Highly efficient Cas9-mediated gene drive for population modification of the malaria vector mosquito *Anopheles stephensi*, PNAS, vol. 112, No. 49, pp. E6736-E6743, 2015.

Gdula, D.A. et al., Genetic and molecular analysis of the gypsy chromatin insulator of *Drosophila*, Proc Natl Acad Sci USA, vol. 93 No. 18, pp. 9378-9383; 1996.

Gibson, D. G. et al., Enzymatic assembly of DNA molecules up to several hundred kilobases, Nat Methods, vol. 6 No. 5, pp. 343-345; 2009.

Gimble, F. Invasion of a multitude of genetic niches by mobile endonuclease genes, FEMS Microbiology Letters, vol. 185, pp. 99-107, 2000.

Githeko, A. K. et al., Climate change and vector-borne diseases: a regional analysis, Bulletin of the World Health Organization, vol. 78, No. 9, pp. 1136-1147, 2000.

Gitzinger et al., "The food additive vanillic acid controls transgene expression in mammalian cells and mice," Nucleic Acids Research 40 (2012).

Gloor et al., Targeted Gene Replacement in *Drosophila* via p. Element-induced Gap Repair, Science, vol. 253, No. 5024, pp. 1110-1117, 1991.

Godfray et al., How Driving Endonuclease Genes can be Used to Combat Pests and Disease Vectors. BMC Biology, vol. 15, No. 1, pp. 81, 2017.

Gokhale, Chaitanya S., Richard Guy Reeves, and Floyd A. Reed. 2014. "Dynamics of a Combined Medea-Underdominant Population Transformation System." BMC Evolutionary Biology 14: 98.

Gong et al., "A dominant lethal genetic system for autocidal control of the Mediterranean fruitfly", Nature Biotechnology, vol. 23, No. 4, pp. 453-456, 2005.

Gong, W. J. et al., Ends-out, or replacement, gene targeting in *Drosophila*, Proceedings of the National Academy of Sciences, vol. 100, No. 5, pp. 2556-2561, 2003.

Gossen et al., "Tight control of gene expression in mammalian cells by tetracycline-responsive promoters," Proc Natl Acad Sci USA 89:5547-5551 (1992).

Gould, F. et al., A Killer-Rescue system for selflimiting gene drive of anti-pathogen constructs, Proceedings of the Royal Society B: Biological Sciences, vol. 275, No. 1653, pp. 2823-2829, 2008.

Gould, F. et al., Genetic strategies for controlling mosquitoborne diseases: engineered genes that block the transmission of malaria and dengue can hitch a ride on selfish DNA and spread into wild populations, American scientist, pp. 238-246, 2006.

Gould, F. et al., Population genetics of autocidal control and strain replacement, Annu Rev Entomol, vol. 49, pp. 193-217, 2004.

Gould, F., et al., Pest Management by Genetic Addiction, Proceedings of the National Academy of Sciences of the United States of America, vol. 116, No. 13, pp. 5849-5851, 2019.

Gratz et al., CRISPR-Cas9 Genome Editing in Unit 31.2 *Drosophila*, Current Protocols in Molecular Biology 31.2.1-31.2.20, 2015.

Greisman et al., "A general Stategy for Selecting High-Affinity Zinc Finger Proteins for Diverse DNA Target Sites," 1997, Science, vol. 275:657-661.

Groth, A. C. et al., Construction of transgenic *Drosophila* by using the site-specific integrase from phage ?C31, Genetics, vol. 166, No. 4, pp. 1775-1782, 2004.

Gubler, D. J. et al., Climate variability and change in the United States: potential impacts on vector and rodent-borne diseases, Environmental health perspectives, vol. 109, Suppl 2, pp. 223, 2001.

Gubler, D. J., Resurgent vector-borne diseases as a global health problem, Emerging infectious diseases, vol. 4, No. 3, pp. 442, 1998.

Guilinger et al., "Fusion of catalytically inactive Cas9 to FokI nuclease improves the specificity of genome modification," Jun. 2014, Nature iotehcnology, vol. 32, No. 6, pp. 577-589.

Gutierrez, E. et al., Specialized hepatocytelike cells regulate *Drosophila* lipid metabolism, Nature, vol. 445, No. 7125, pp. 275-280, 2007.

Hagmann et al., "The VP16 paradox: Herpes simplex virus VP16 contains a long-range activation domain but within the natural multiprotein complex activates only from promoter-proximal positions," J Viral 71 :5952-5962 ( 1997).

Hammond et al., The creation and selection ofm utations resistant to a gene drive over multiple generations in the malaria mosquito, PLOS Genetics, vol. 13(10), pp. 1-16, 2017.

Hammond, A., R. Galizi, K. Kyrou, A. Simoni, C. Siniscalchi, D. Katsanos, M. Gribble, et al. 2016. "A CRISPR-Cas9 Gene Drive System Targeting Female Reproduction in the Malaria Mosquito Vector Anopheles Gambiae." Nature Biotechnology 34 (1): 78-83.

Hamza et al., Complementation of Yeast Genes With Human Genes as an Experimental Platform for Functional Testing or Human Genetic Variants, genetics, vol. 201, pp. 1263-1274, 2015.

Han, Z. et al., Hand is a direct target of Tinman and GATA factors during *Drosophila cardiogenesis* and hematopoiesis, Development, vol. 132, No. 15, pp. 3525-3536, 2005.

Handler et al., "Use of the piggyBac transposon for germ-line transformation of insects", Insect Biochemistry and Molecular Biology, vol. 32, pp. 1211-1220, 2002.

Harris et al., "Successful suppression of a field mosquito population by sustained release of engineered male mosquitoes", Nature Biotechnology, vol. 30, No. 9, pp. 828-830, 2012.

Harris, A. F. et al., Field performance of engineered male mosquitoes, Nature biotechnology, vol. 29, No. 11, pp. 1034-1037, 2011.

Hartl, D.L. et al., Principles of Population Genetics, Sunderland, MA: Sinauer Associates, Inc., 1997.

Harwood et al., "The beta-ketoadipate pathway and the biology of self-identity," Ann Rev Microbial 50:553-590 (1996).

Hay, B. A. et al., Engineering the genomes of wild insect populations: challenges, and opportunities provided by synthetic Medea selfish genetic elements, J Insect Physiol, vol. 56, No. 10, pp. 1402-1413, 2010.

Hendrichs et al., "Medfly area wide sterile insect technique programmes for prevention, suppression or eradication: The importance of mating behavior studies", Florida Entomologist, vol. 85, No. 1, pp. 1-13, 2002.

Heravi, et al. "Transcriptional regulation of the vanillate utilization genes (vanABK operon) of Corynebacterium glutamicum by VanR, a PadR-like repressor", Journal of Bacteriology, JB.02431-14, pp. 1-60., (2014).

(56)              References Cited

OTHER PUBLICATIONS

Hoffmann, A. A. et al., Successful establishment of Wolbachia in Aedes populations to suppress dengue transmission, Nature, vol. 476, No. 7361, pp. 454-457, 2011.

Hollingdale, M., et al., Nussenzweig, R. S. Inhibition of entry of Plasmodium falciparum and p. vivax sporozoites into cultured cells; an in vitro assay of protective antibodies. J. Immunol. 132, pp. 909-913, (1984).

Hongenboom, Melissa, "Genetically modified flies 'could save crops'", BBC News, Science and Environment, Aug. 12, 2014. 4 pages.

Hu et al., A Large Gene Family in Fission Yeast Encodes Spore Killers That Subvert Mendel's Law, 2017, elife, pp. 1-19.

Huang, Y. et al. Introducing Desirable Transgnes into Insect Populations Using Y-Linked Meiotic Drive? A Tehoretical Assesement, Evolution vol. 61, pp. 717-726.

International Preliminary Report on Patentability, re PCT Application No. PCT/US18/30990 dated Nov. 14, 2019.

Issacs, A., et al. Engineered Resistance to Plasmodium falciparum Development in Transgenic Anopheles stephensi. PLOS Pathog. 7, e1002017 (2011 ).

Ito, J. et al. Transgenic anopheline mosquitoes impaired in transmission of a malaria parasite, Nature, vol. 417, No. 6887, pp. 452-455, 2002.

Iwaki et al., "Rapid selection of Drosophila S2 cells with the puromycin resistance gene", Biotechniques, vol. 35, pp. 482-486, 2003.

Jacobs-Lorena, M. Genetic approached for malaria control. In Bogers, R.J. (ed.), Bridging Laboratory and Field Research for Genetic Control of Disease Vectors, pp. 52-65, Retrieved from http://library.wur.nl/frontis/, 2004.

James, A. A, Gene drive systems in mosquitoes: rules of the road, Trends Parasitol, vol. 21, No. 2, pp. 64-67, 2005.

Jansen V.A. et al., Stochastic spread of Wolbachia, Proc Biol Sci, vol. 275 No. 1652, pp. 2769-2776; 2008.

Jinek et al., Structures of Cas9 Endonucleases Reeal RNA-Mediated Conformational Activation, Science, vol. 343, 1247997, 2014, 13 pgs.

Kaiser, P.E. et al., Radiation induced reciprocal translocations and inversions in Anopheles albimanus, Can J Genet Cytol, vol. 24 No. 2, pp. 177-188; 1982.

Kakkar, et al., "A review on protocatechuic acid and its pharmacological potential." ISRN pharmacology 2014 (2014).

Kerremans et al., "Use of a Temperature-Sensitive Lethal Mutation Strain of Medfly (Ceratitis-Capitata) for the Suppression of Pest Populations", Theoretical and Applied Genetics, vol. 90, pp. 511-518, 1995.

Kim et al., "A genetic sexing strain of Anopheles quadrimaculatus, species A", Journal of the American Mosquito Control Association, vol. 3, No. 1, pp. 50-53, 1987.

Kim, et al., "Vanillic acid glycoside and quinic acid derivatives from Gardeniae Fructus." Journal of natural products 69.4 (2006): 600-603.

Kim, W. et al., Ectopic expression of a cecropin transgene in the human malaria vector mosquito Anopheles gambiae (Diptera: Culicidae): effects on susceptibility to Plasmodium, Journal of medical entomology, vol. 41, No. 3, pp. 447-455, 2004.

Knols, B. G. et al., Transgenic mosquitoes and the fight against malaria: managing technology push in a turbulent GMO world, Am J Trap Med Hyg., vol. 77, 6 Suppl, pp. 232-242, 2007.

Knott et al., CRISPR-Cas guides the future of genetic engineering. Science, 2018, vol. 361: 866-869. (Year: 2018).

Koon In, E., et al. Evolutionary Genomics of Defense Systems in Archaea and Bacteria. Annu. Rev. Microbiol. 71, 233-261 (2017).

Koon In, E., et al., Diversity, classification and evolution of CRISPR-Cas systems. Curr. Opin. Microbiol. 37, pp. 67-78, (2017).

Krafsur et al., "Screwworm eradication in North and Central America", Parasitology today, vol. 3, No. 5, pp. 131-137, 1987.

Krafsur et al., "Screwworm eradication is what it seems", Nature, vol. 323, No. 9, pp. 495-496, 1986.

Krafsur, E. S. et al., Sterile insect technique for suppressing and eradicating insect populations: 55 years and counting, J, Agr. Entomol., vol. 15, 303-317, 1998.

Krstic, D. et al., Influence of the White Locus on the Courtship Behavior of Drosophila Males, PLoS one, vol. 8, No. 10, e77904, 2013.

Kuhlman, et al. Combinatorial transcriptional control of the lactose operon of Escherichia coli, Procedings of the National Academy of Sciences, USA, 104(14): 6043-48., (2007).

Kwit, C. et al., Transgene introgression in crop relatives: molecular evidence and mitigation strategies. Trends Biotechnol, vol. 29, No. 6, pp. 284-293, 2011.

Kyrchanova, O., et al., Orientation-dependent interaction between Drosophila insulators is a property of this class of regulatory elements, Nucleic acids research, vol. 36, No. 22, pp. 7019-7028, 2008.

Labbe et al., "Female-specific flightless (fsRIDL) phenotype for control of Aedes albopictus", PLoS Neglected Tropical Diseases, vol. 6, No. 7, e1724, 2012.

Lack JB, Lange JD, Tang AD, Corbett-Detig RB, Pool JE (2016) A Thousand Fly Genomes: An Expanded Drosophila Genome Nexus. Mol Biol Evol33(12):3308-3313.Marshall, J. M. 2009. "The Effect of Gene Drive on Containment of Transgenic Mosquitoes." Journal of Theoretical Biology 258 (2): 250-65.

Lambrechts, L. et al., Can transgenic mosquitoes afford the fitness cost? Trends Parasitol, vol. 24 No. 1, pp. 4-7; 2008.

Leftwich et al., "Genetic elimination of field-cage populations of Mediterranean fruit flies", Proc. R. Soc., vol. 281, No. 1792, 21 pages, 2014.

Lemon, S. M. et al., Vector-Borne Diseases: Understanding the Environmental, Human Health, and Ecological Connections, Workshop Summary (Forum on Microbial Threats), National Academies Press, 2008.

Lewin, Genes V, Oxford University Press, Oxford, pp. 847-873, Fifth Edition.

Li, F. et al. An Anti-Chitinase Malaria Transmission-Blocking Single-Chain Antibody as an Effector Molecule for Creating a Plasmodium falciparum-Refractory Mosquito. J. Infect. Dis. 192, pp. 878-887 (2005).

Lin, H. et al., Cellular toxicity induced by SRFmediated transcriptional squelching, Toxicological sciences, vol. 96, No. 1, pp. 83-91, 2007.

Lines et al., "Genetic sexing systems in Anopheles arabiensis Patton (Diptera: Culicidae)", Journal of Economic Entomology, vol. 78, pp. 848-851, 1985.

Lo, P. C. et al., A role for the COUP-TF-related gene seven-up in the diversification of cardioblast identities in the dorsal vessel of Drosophila, Mech Dev, vol. 104, pp. 49-60, 2001.

Lockless, S. W. et al., Traceless protein splicing utilizing evolved split inteins, Proc Natl Acad Sci U S A, vol. 106, No. 27, p. 10999-11004, 2009.

Luan, H. et al., Refined spatial manipulation of neuronal function by combinatorial restriction of transgene expression, Neuron, vol. 52, No. 3, pp. 425-436, 2006.

Lyon, M. F. et al., Mutagenic effects of repeated small radiation doses to mouse spermatogonia I. Specific-locus mutation rates, Mutation Research/Fundamental and Molecular Mechanisms of Mutagenesis, vol. 15, No. 2, pp. 185-190, 1972.

Lyttle, T. Experimental population genetics of meiotic drive systems I. Pseudo-Y chromosomal drive as a means of eliminating cage populations of Drosophila melanogaster, Genetics, vol. 86, DD. 413-445, (1977).

Magnusson et al., "Transcription regulation of sex-biased genes during ontogeny in the malaria vector Anopheles gambiae", PLoS One, vol. 6, No. 6, e21572, 2011.

Magori, K. et al., Genetically engineered underdominance for manipulation of pest populations: a deterministic model. Genetics, vol. 172, No. 4, pp. 2613-2620, 2006.

Malavasi, A. Project Aedes transgenic population control in Juazeiro and, Jacobina Bahia, Brazil. BMC Proc. 8, 011 (2014).

Marois et al. High-throughput sorting of mosquito larvae for laboratory studies and for future vector control interventions, Malaria Journal, vol. 11, No. 1, pp. 302-308, 2012.

(56) References Cited

OTHER PUBLICATIONS

Marris, E., Transgenic fish go large, Nature, vol. 467, No. 7313, pp. 259, 2010.

Marshall, J. et al.The Impact of Dissociation on Transposon-Mediated Disease Control Strategies. Genetics vol. 178, pp. 1673-1682 (2008).

Marshall, J. M. et al., Confinement of gene drive systems to local populations: a comparative analysis, J Theor Biol, vol. 294, pp. 153-171, 2012.

Marshall, J. M. et al., Inverse Medea as a novel gene drive system for local population replacement: a theoretical analysis, J Hered, vol. 102, No. 3, pp. 336-341, 2011.

Marshall, J. M. et al., Perspectives of people in Mali toward genetically-modified mosquitoes for malaria control, Malar J, vol. 9, No. 128, 2010a.

Marshall, J. M. et al., Towards a quantitative assessment of public attitudes to transgenic mosquitoes: Questions based on a qualitative survey in Mali, Asia Pacific J. Mol. Biol. Biotechnol, vol. 18, pp. 251-273, 2010b.

Marshall, J. M., The Cartagena Protocol and genetically modified mosquitoes, Nat. Biotechnol., vol. 28, No. 9, pp. 896-897, 2010.

Marshall, J. M., The effect of gene drive on containment of transgenic mosquitoes, J. of Theor. Biol., vol. 258, No. 2, pp. 250-265, 2009.

Marshall, J.M. et al., General principles of single-construct chromosomal gene drive, Evolution; vol. 66 No. 7, pp. 2150-2166; 2012b.

Marshall, J.M. et al., Semele: a killer-male, rescue-female system for suppression and replacement of insect disease vector populations, Genetics, vol. 187 No. 2, pp. 535-551; 2011.

Martinez et al., Biodegradation of lignocellulosics: microbial, chemical, and enzymatic aspects of the fungal attack of lignin, Int Microbiol 8:195-204 (2005).

Marygold, S. J. et al., The ribosomal protein genes and Minute loci of *Drosophila melanogaster*, Genome Biol, vol. 8, No. 10, R216, 2007.

Mathur, G. et al., Transgene-mediated suppression of dengue viruses in the salivary glands of the yellow fever mosquito, *Aedes aegypti*. Insect Mol. Biol. 19, pp. 753-763 (2010).

Matzen, K.J. Engineering of Dengue virus refractoriness in Aedes aegypti and development of an underdominant gene drive system (Doctoral dissertation), California Institute of Technology, Pasadena, CA, 2012.

McCauley, et al., Analysis of a Human Sperm CD52 Glycoform in Primates: Identification 1-30 of an Animal Model for Immunocontraceptive Vaccine. Development, Biology of Reproduction, vol. 66, pp. 1681-1688, (2002).

McDonald et al., "A Genetic-Sexing Strain Based on Malathion Resistance for Culex-Tarsalis", Mosquito News, vol. 42, No. 4, pp. 531-536, 1982.

McManus, M. T. et al., Gene silencing using micro-RNA designed hairpins, RNA, vol. 8, No. 6, 842-850, 2002.

Medici et al., "Studies on Aedes albopictus larval mass-rearing optimization", Journal of Economic Entomology, vol. 104, No. 1, pp. 266-273, 2011.

Merkens et al., Vanillate metabolism in Corynebacterium glutamicum, Curr Microbiol 51:59-65 (2005).

Miller, L. H. et al., Perspective on malaria eradication: is eradication possible without modifying the mosquito? Journal of Infectious Diseases, vol. 200, No. 11, pp. 1644-1645, 2009.

Miller, T. A., Let high-tech genetically modified insects counter dengue, BioScience, vol. 61, No. 8, pp. 586-587, 2011.

Moreira, L.A. et al., Bee venom phospholipase inhibits malaria parasite development in transgenic mosquitoes, J Biol Chem, vol. 277, No. 43, pp. 40839-40843, 2002.

Moreno, E., Design and construction of "synthetic species," PLoS One, vol. 7, No. 7, e39054, 2012.

Morrison et al., "Engineered repressible lethality for controlling the pink bollworm, a lepidopteran pest of cotton", PLoS One, vol. 7, No. 12, pp. e50922, 2012.

Morrison, N. I. et al., Genetic improvements to the sterile insect technique for agricultural pests, Asia-Pacific Journal of Molecular Biology and Biotechnology, vol. 18, No. 2, pp. 275-295, 2010.

Mumford, J. D. Science, regulation, and precedent for genetically modified insects, PLoS neglected tropical diseases, vol. 6, No. 1, e1504, 2012.

Murray, C. J. et al., Global malaria mortality between 1980 and 201 0: a systematic analysis, The Lancet, vol. 379, No. 9814, pp. 413-431, 2012.

Nath, R., Generation and characterisation of plant produced recombinant antibodies specific to LHRH for treatment of sex hormone dependent diseases. (MS thesis), Fachhochschule Aachen, Aachen, Germany, 2003.

Naveira et al., The Theoretical Distribution of Lengths of Intact Chromosome Segments Around a Locus Held Heterozygous With Backcrossing in a Diploid Species, Genetics, vol. 130:205-209, 1992.

Ndiath, M. O., et al., Resistance to DDT and pyrethroids and increased kdr mutation frequency in An. gambiae after the implementation of permethrin-treated nets in Senegal, PloS one, vol. 7, No. 2, e31943, 2012.

Neely, G. G. et al., A Global In Vivo *Drosophila* RNAi Screen Identifies NOT3 as a Conserved Regulator of Heart Function, Cell, vol. 141, No. 1, pp. 142-153, 2010.

Nern, A. et al., Multiple new site-specific recombinases for use in manipulating animal genomes, Proceedings of the National Academy of Sciences, vol. 108, No. 34, pp. 14198-14203, 2011.

Ngo et al., Computational Complexity Protein Structure Prediction, and the Levinthal Paradox, The Protein Folding and Tertiary Structure Protein, 1994.

Ni, J. Q. et al., A genome-scale shRNA resource for transgenic RNAi in *Drosophila*, Nat Methods, vol. 8, No. 5, pp. 405-407, 2011.

Nicholson, G.M. et al., Fighting the global pest problem: preface to the special Toxicon issue on insecticidal toxins and their potential for insect pest control, Toxicon, vol. 49 No, 4, pp. 413-422; 2007.

Nishimasu et al., Crystal Strucutre of Cas9 in Complex with Guide RNA and Target DNA Cell 156(5), 935-949, 2014.

Nishimura et al., "Molecular cloning of *Streptomyces* genes encoding vaniilate demethylase," Biosci Biotech Bioch 70:2316-2319 (2006).

Noble, C. et al., "Evolutionary dynamics of CRISPR gene drives", Science Advances, 5, vol. 3, e1601964, (2017.

Nowak, C.M., et al., Guide RNA Engineering for Versatile Cas9 functionality, Nucleic Acids Research, vol. 44, No. 20, pp. 9555-9564, 2016.

Nuckolls, N. L., M. A. Bravo Nunez, M. T. Eickbush, J. M. Young, J. J. Lange, J. S. Yu, G. R. Smith, S. L. Jaspersen, H. S. Malik, and S. E. Zanders. 2017. "Wtf Genes are Prolific Dual Poison-Antidote Meiotic Drivers." elife 6. https://doi.org/10.7554/elife.26033.

Oberhofer, et al. : "Cleave and Rescue, a novel selfish genetic element and general strategy for gene drive," PNAS, vol. 116, No. 13, pp. 6250-6259 (Year: 2019).

Oberhofer, et al.: "Behavior of homing endonuclease gene drives targeting genes required for viability or female fertility with multiplexed guide RNAs," PNAS, vol. 115, No. 40, pp. E9343-E9352 (Year: 2018).

Oberhofer, G., et al., Gene Drive and Resilience Through Renewal With Next Generation Cleave and Rescue Selfish Genetic Elements, Proceedings of the National Academy of Sciences of the United States of America, vol. 117, No. 16, DD. 9013-9021, 2020.

Oye, K.A et al., Biotechnology. Regulating gene drives, Science vol. 345 No. 6197, pp. 626-628; 2014.

Pacher et al., Two Unlinked Double-Strand Breaks can Induce Reciprocal Exchanges in Plant Genomes via Homologous Recombination and Nonhomologous End Joining, Genetics 175: 21-29, 2007.

Papathanos et al., "Sex Ratio Manipulation for Insect Population Control", Transgenic Insects: Techniques and Applications, pp. 83-100, Publication date Oct. 29, 2014.

Papathanos, et al., "Sex Separation Strategies: past experience and new approaches", Malaria Journal, vol. 8, Suppl 2, No. S5, 2009.

(56)                    References Cited

OTHER PUBLICATIONS

Pardo, R. et al., The role of means and goals in technology acceptance, A differentiated landscape of public perceptions of pharming, EMBO Rep, vol. 10, No. 10, pp. 1069-1075, 2009.

Parvy, J. P. et al., *Drosophila melanogaster* Acetyl-CoA-Carboxylase Sustains a Fatty Acid-Dependent Remote Signal to Waterproof the Respiratory System, PLoS genetics, vol. 8, No. 8, e1002925, 2012.

Paul B., megaTAL-mediated Gene Editing at the CCR5 locus. PhD Dissertation, Univ. of Washington., USA, 2016, pp. 1-113. (Year: 2016).

Peng, J., et al., High-throughput screens in mammalian cells using the CRISPR-Cas9 system, The FEBS Journal, vol. 282, DD. 2089-2096, 2015.

Perri Mon, N. et al., In vivo RNAi: today and tomorrow, Cold Spring Harbor perspectives in biology, vol. 2, No. 8, a003640, 2010.

Pfeiffer, B. D. et al., Refinement of tools for targeted gene expression in *Drosophila*, Genetics, vol. 186, No. 2, pp. 735-755, 2010.

Pfeiffer, B. D. et al., Using translational enhancers to increase transgene expression in *Drosophila*. Proc Natl Acad Sci USA, vol. 109, No. 17, pp. 6626-6631, 2012.

Poindexter, "Biological properties and classification of the Caulobacter group," Bacterial Rev 28:231-295 (1964).

Pomiankowski et al., "The evolution of the *Drosophila* sex-determination pathway", Genetics, vol. 166, pp. 1761-1773, 2004.

Popovic!, J. et al., Assessing key safety concerns of a Wolbachia-based strategy to control dengue transmission by Aedes mosquitoes. Mem. Inst. Oswaldo Cruz 105, pp. 957-964, (2010).

Port, F. et al., Optimized CRISPR/Cas Tools for Efficient Germline and Somatic Genome Engineering in *Drosophila*. Proceedings of the National Academy of Sciences of the United States of America 111 (29), pp. E2967-E2976. (2014).

Preston, Christine R., Carlos C. Flores, and William R. Engels. 2006. "Differential Usage of Alternative Pathways of Double-Strand Break Repair in *Drosophila*." Genetics 172 (2): 1055-68.

R?rth, P, Gal4 in the *Drosophila* female germline, Mechanisms of development, vol. 78, No. 1, pp. 113-118, 1998.

Ran, F. A. et al., Genome engineering using the CRISPR-Cas9 system, Nature protocols, vol. 8, No. 11, pp. 2281-2308, 2013.

Randolph, S.E. et al., "The arrival, establishment and spread of exotic diseases: patterns and predictions," Nat Rev Microbial., vol. 8 No. 5, pp. 361-371; (2010).

Reeves, R. G., J. Bryk, P. M. Altrock, J. A. Denton, and F. A. Reed. 2014. "First Steps towards Underdominant Genetic Transformation of Insect Populations." PloS One 9 (5): e97557.

Rendon et al., "Medfly *(Diptera: Tephritidae)* genetic sexing: large-scale field comparison of males-only and bisexual sterile fly releases in Guatemala", Journal of Economic Entomology, vol. 97, No. 5, DD. 1544-1553, 2004.

Resnik, D., Ethical Issues in Field Trials of Genetically Modified Disease-Resistant Mosquitoes, Dev. World Bioeth, vol. 14, pp. 37-46, (2014).

Riehle, M. M. et al., Anopheles gambiae APL1 is a family of variable LRR proteins required for Rel1-mediated protection from the malaria parasite, Plasmodium berghei, PLoS One, vol. 3, No. 11, e3672, 2008.

Ringrose, L., et al., Quantitative comparison of DNA looping in vitro and in vivo: chromatin increases effective DNA flexibility at short distances, The EMBO Journal, vol. 18, No. 23, 6630-6641, 1999.

Robinson A.S., A reassessment of the use of chromosome inversions for insect control, Journal of Heredity, vol. 66, pp. 35-37, 1975.

Robinson et al., "Cytological, linkage and insecticide studies on a genetic sexing line in Anopheles stephensi Liston", Heredity, vol. 58, pp. 95-101, 1987.

Robinson, A. S. et al., Insect transgenesis and its potential role in agriculture and human health, Insect biochemistry and molecular biology, vol. 34, No. 2, pp. 113-120, 2004.

Robinson, A.S. et al., Controlled Crosses and Cage Experiments with a Translocation in *Drosophila*, Genetica, vol. 44, pp. 591-601; 1973.

Robinson, A.S., Progress in the use of chromosomal translocations for the control of insect pests. Biological Reviews, vol. 51, No. 1, pp. 1-24, 1976.

Rong, Y. S. et al., The homologous chromosome is an effective template for the repair of mitotic DNA double-strand breaks in *Drosophila*, Genetics, vol. 165, No. 4, pp. 1831-1842, 2003.

Royden, C., et al., The Tko Locus, Site of a Behavioral Mutation in *D. melanogaster*, Codes for a Protein Homologous to Prokaryotic Ribosomal Protein S12. Cell 51 (2), pp. 165-173, (2004).

Rudinger, et al., Peptide Hormones, Parsons, (ed.), 1976 University Park Press, Baltimore, MD, pp. 1-7.

Sambrook et al., Molecular Cloning, A Laboratory Manual, Cold Springs Harbor Press, Cold Springs Harbor, N. Y. 1989, Second Edition.

Schmid-Hempel, P., Evolutionary ecology of insect immune defenses, Annu Rev Entomol, vol. 50, pp. 529-551, 2005.

Schnutgen, F. et al., Adopting the good reFLEXes when generating conditional alterations in the mouse genome, Transgenic research, vol. 16, No. 4, pp. 405-413, 2007.

Schwartz, E. C. et al., Post-translational enzyme activation in an animal via optimized conditional protein splicing, Nat Chem Biol, vol. 3, No. 1., pp. 50-54, 2007.

Seawright et al., "Genetic method for the preferential elimination of females of anopheles albimanus", Science, vol. 200, No. 4347, pp. 1303-1304, 1978.

Sebrovskii, A. et al. A New Possible Method of Pest Control. Zool Zh, vol. 19, pp. 618-630, (1940).

Segura et al., "Genetic analysis of a chromosomal region containing vanA and vanB, genes required for conversion of either ferulate or vanillate to protocatechuate in Acinetobacter," J Bacterial 181 :3494-3504 (1999).

Seidel, H. S., M. Ailion, J. Li, A. van Oudenaarden, M. V. Rockman, and L. Kruglyak. 2011. "A Novel Sperm-Delivered Toxin Causes Late-Stage Embryo Lethality and Transmission Ratio Distortion in C. Elegans." PLoS Biology 9 (7): e1001115.

Sellin, J. et al., Dynamics of heart differentiation, visualized utilizing heart enhancer elements of the *Drosophila melanogaster* bHLH transcription factor Hand, Gene Expr Patterns, vol. 6, No. 4, pp. 360-375, 2006.

Serebrovsky, A.S., On the possibility of a new method for the control of insect pests. Zool. Zh. 19,4, pp. 123-137, 1940.

Shaner, N. et al., Improved Monomeric Red, Orange and Yellow Fluorescent Proteins Derived from *Discosoma* Sp. Red Fluorescent Protein, Nature Biotechnology, 22 (12), pp. 1567-1572, (2004).

Sherizen, D. et al., Meiotic recombination in *Drosophila* females depends on chromosome continuity between genetically defined boundaries, Genetics, vol. 169, No. 2, pp. 767-781, 2005.

Shetty, "Genetic sexing system for the preferential elimination of females in Culex quinquefasciatus", Journal of the American Mosquito Control Association, vol. 3, No. 1, pp. 84-86, 1987.

Shmakov, S. et al., Discovery and Functional Characterization of Diverse Class 2 CRISPR-Cas Systems. Mol. Cell 60, 385-397 (2015).

Shmakov, S. et al., Diversity and evolution of class 2 CRISPR-Cas systems. Nat. Rev. Microbial. 15, pp. 169-182 (2017).

Simoni, A. et al., Development of synthetic selfish elements based on modular nucleases in *Drosophila melanogaster*. Nucleic Acids Res. vol. 42, pp. 7461-7472 (2014).

Singleton et al., "Dictionary of Microbiology and Molecular Biology," 2nd ed., J. Wiley & Sons, New York, N. Y., 1994.

Sinkins, S. P. et al., Gene drive systems for insect disease vectors, Nat Rev Genet, vol. 7, No. 6, pp. 427-435, 2006.

Spradling, A. C. et al., Transposition of cloned P elements into *Drosophila* germ line chromosomes. Science, vol. 218, No. 4570, pp. 341-347, 1982.

Steller et al., "A Transposable P Vector That Confers Selectable G418 Resistance to *Drosophila* Larvae", EMBO Journal, vol. 4, No. 1, pp. 167-171, 1985.

Sternberg et al., DNA interrogation by the CRISPR RNA-guided endonuclease Cas9, Nature, vol. 507, (7490), 62-67, 17 pgs., 2014.

(56) References Cited

OTHER PUBLICATIONS

Sun, N., and H. Zhao. 2014. "A Single-Chain TALEN Architecture for Genome Engineering." Molecular bioSystems 10 (3): 446-53.

Szymczak, A. L. et al., Correction of multi-gene deficiency in vivo using a single'self-cleaving' 2A peptide-based retroviral vector, Nature biotechnology, vol. 22, No. 5, pp. 589-594, 2004.

Tan et al., "Zinc-finger protein-targeted gene regulatio: Genomewide single-gene specificity," 2003, PNAS, vol. 100, No. 21, pp. 11997-12002.

Tatem, A.J. et al., Global transport networks and infectious disease spread, Adv Parasitol, vol. 62, pp. 293-343; 2006.

Tham et al., Mismatch Repair and Homoeologous Recombination, DNA Repair, vol. 38, pp. 75-83, 2016.

Thanbichler et al., "A comprehensive set of plasmids for vanillate- and xylose-inducible gene expression in Caulobacter crescentus," Nucleic Acids Res 35:e137 (2007).

Theilmann et al., "Molecular analysis of the trans-activating IE-2 gene of Orgyia pseudotsugata multicapsid nuclear polyhedrosis virus", Virology, vol. 187, pp. 84-96, 1992.

Thomas et al., "Insect population control using a dominant, repressible, lethal genetic system," Science 287:2474-2476 (2000).

Thorpe, H. M. et al., Control of directionality in the sitespecific recombination system of the *Streptomyces* phage cpC31, Molecular microbiology, vol. 38, No. 2, pp. 232-241, 2000.

Tolle, M. A., Mosquito-borne diseases. Current problems in pediatric and adolescent health care, vol. 39, No. 4, pp. 97-140, 2009.

Travanty, E., et al., Using RNA interference to develop dengue virus resistance in genetically modified Aedes aegypti. Insect Biochem. Mol. Biol. 34, pp. 607-613, (2004).

Tripet, F. et al., Ecological immunology of mosquito-malaria interactions, Trends Parasitol vol. 24 No. 5-3, pp. 219-227; 2008.

Uemura, M. et al., Chromosomal manipulation by site-specific recombinases and fluorescent protein based vectors, PioS one vol. 5 No. 3, e9846; 2010.

Van Dyke, D. L. et al., The frequency and mutation rate of balanced autosomal rearrangements in man estimated from prenatal genetic studies for advanced maternal age, American journal of human aenetics, vol. 35, No. 2, DD. 301-308, 1983.

Wade, M. J., and R. W. Beeman. 1994. "The Population Dynamics of Maternal-Effect Selfish Genes." Genetics 138 (4): 1309-14.

Walker, T. et al., The wMel Wolbachia strain blocks dengue and invades caged Aedes aegypti populations, Nature, vol. 476, No. 7361, pp. 450-453, 2011.

Wang, S. et al., Genetic approaches to interfere with malaria transmission by vector mosquitoes, Trends in biotechnology, vol. 31, No. 3, pp. 185-193, 2013.

Ward, Catherine M., Jessica T. Su, Yunxin Huang, Alun L. Lloyd, Fred Gould, and Bruce A. Hay. 2011. "Medea Selfish Genetic Elements as Tools for Altering Traits of Wild Populations: A Theoretical Analysis." Evolution; International Journal of Organic Evolution 65 (4): 1149-62.

Weber, E. et al., A modular cloning system for standardized assembly of multigene constructs, PLoS one, vol. 6, No. 2, e16765, 2011.

Whitten, M. J., Insect control by genetic manipulation of natural populations, Science, vol. 171, No. 3972, pp. 682-684, 1971.

WHO World Malaria Report dated 2014, accessed on the world wide web at <Who. int/malaria/publications/world_malaria_report_2014/en/>.

Willis, N.L. et al., Reciprocal translocations and partial correlation of chromosomes in the stable fly, J Hered vol. 72 No. 2, pp. 104-106; 1981.

Windbichler, N. et al., A synthetic homing endonuclease-based gene drive system in the human malaria mosquito, Nature, vol. 473, No. 7346, pp. 212-215, 2011.

Windbichler, N., P. A. Papathanos, and A. Crisanti. 2008. "Targeting the X Chromosome during Spermatogenesis Induces Y Chromosome Transmission Ratio Distortion and Early Dominant Embryo Lethality in Anopheles Gambiae." PLoS Genetics.

Windbichler, Nikolai, Philippos Aris Papathanos, Flaminia Catteruccia, Hilary Ranson, Austin Burt, and Andrea Crisanti. 2007. "Homing Endonuclease Mediated Gene Targeting in Anopheles Gambiae Cells and Embrvos." Nucleic Acids Research 35 (17): 5922-33.

World Health Organization (2014b). Dengue factsheet. Retrieved Apr. 30, 2014, from who.int/mediacentre/factsheets/fs117/en/index.html.

Xie, et al., "Antagonistic control of a dual-input mammalian gene switch by food additives." Nucleic acids research (2014): gku545.

Yamada et al., "Genetic sex separation of the malaria vector, Anopheles arabiensis, by exposing eggs to dieldrin", Malaria Journal, vol. 11, No. 1, pp. 208-219, 2012.

Yen, P. et al. Synthetic miRNAs induce dual arboviral-resistance phenotypes in the vector mosquito *Aedes aegypti*. Commun. Biol. 1, p. 11 (2018).

Yu, Y et al., Engineering chromosomal rearrangements in mice, Nat Rev Genet, vol. 2, No. 10, pp. 780-790, 2001.

Zeh et al., "From father to son: transgenerational effect of tetracycline on sperm viability", Scientific Reports vol. 2, No. 375, pp. 15, 2012.

Zettler, J. et al., The naturally split Npu DnaE intein exhibits an extraordinarily high rate in the protein trans-splicing reaction, FEBS Lett, vol. 583, No. 5, pp. 909-914, 2009.

Zhou, X. et al., Optimization of the Tet-On system for regulated gene expression through viral evolution, Gene therapy, vol. 13, No. 19, pp. 1382-1390, 2006.

Zhu, X. D. et al., Cleavage-dependent ligation by the FLP recombinase; characterization of a mutant flp protein with an alteration in a catalytic amino acid, Journal of Biological Chemistry, vol. 270, No. 39, DD, 23044-23054, 1995.

* cited by examiner

Figure 10:
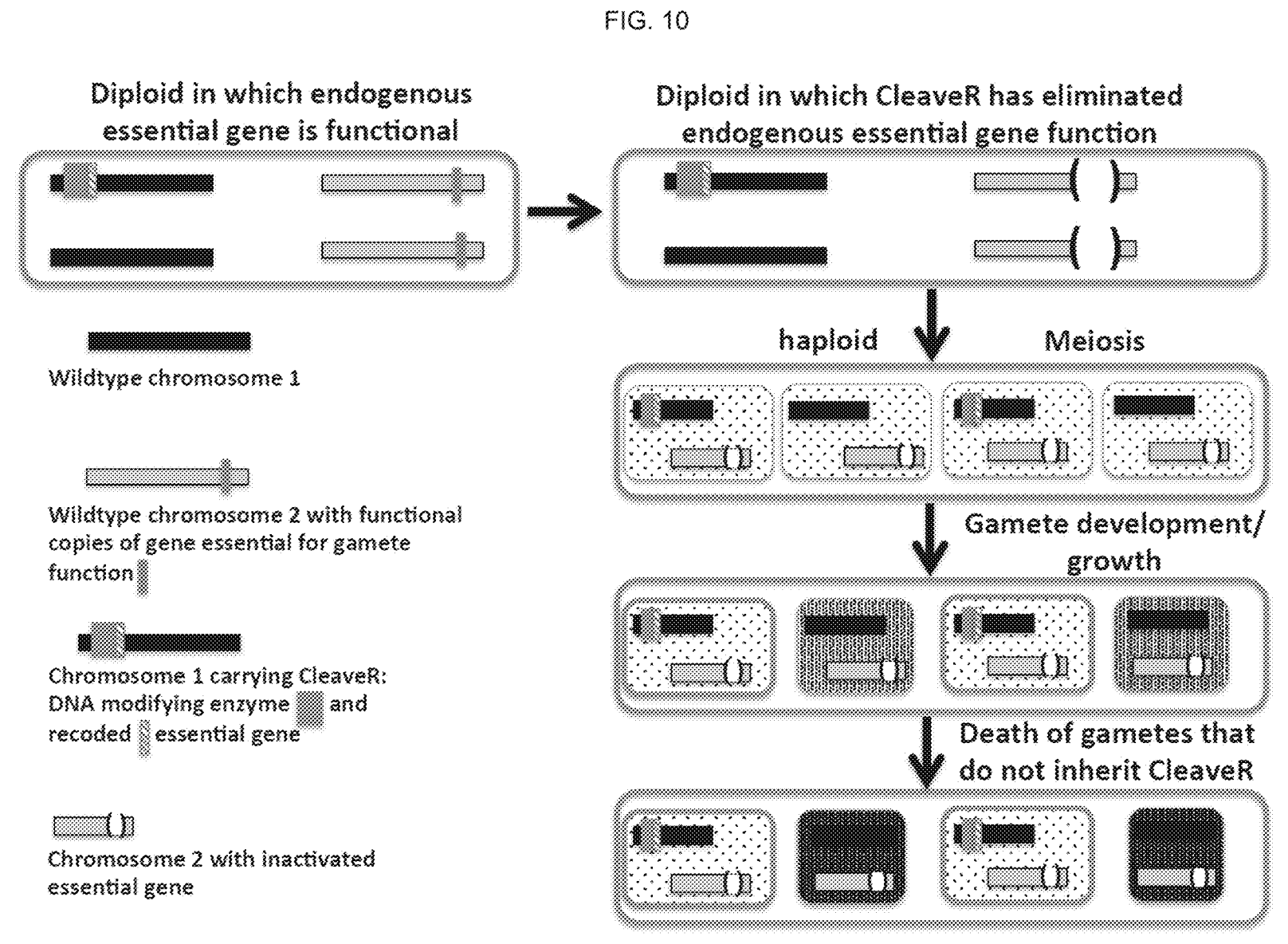

Diploid in which endogenous essential gene is functional

Diploid in which CleaveR has eliminated endogenous essential gene function

Meiosis haploid

Gamete development/ growth

Death of gametes that do not inherit CleaveR

Wildtype chromosome 1

Wildtype chromosome 2 with functional copies of gene essential for gamete function Chromosome 1 carrying CleaveR: DNA modifying enzyme and recoded essential gene Chromosome 2 with inactivated essential gene

FIG. 17

SEQ ID NO: 44
SEQ ID NO: 45

FIG. 18A
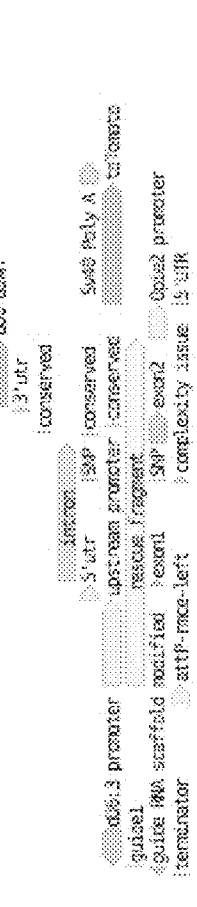
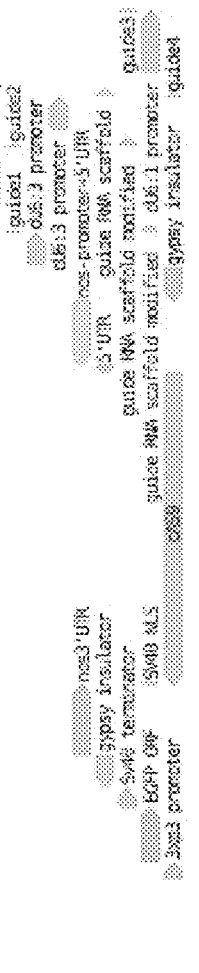
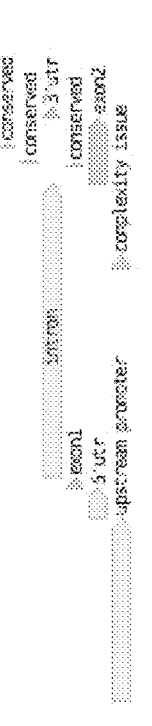
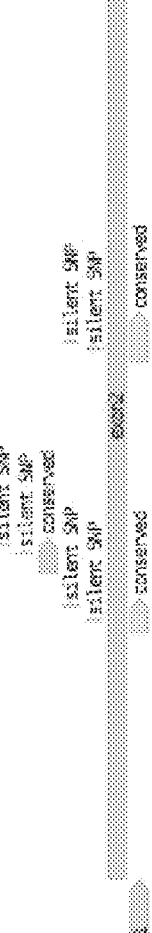

FIG. 19 gRNA1  SEQ ID NO: 47  aatggcatcgatcgctgcagc

SEQ ID NO: 46  PAM  CCGTGG

| | | SEQ ID NO: |
|---|---|---|
| reference | accgcgtccgtgg - - - - - - : aatggcatcgctgcagcagatgcaccgcagcggaccgcacataaagacgcgt | |
| w[118] control | ACCGCGTCCGTGG - - - - : - AATGGCATCGCTGCAGCAGATGCACCGCACCGGACCGCACATAAAGACGCGT | 48 |
| | ACCGCGTCCGTGG - - - - : - - CATCGCTGCAGCAGATGCACCGGACCGCAGCCGCACATAAAGACGCGT | 49 |
| | ACCGCGTCCGTGG - - - - : A - - CATCGCTGCAGCAGATGCACCGGACCGCAGCCGCACATAAAGACGCGT | 50 |
| | ACCGCGTCCGT - - - - - : - - - - - - - - - ACCGTCCGTACATAAAGACGCGT | 51 |
| | ACCGCGTCCGT - - - - - : - - - - - - - - - ACGGTCCGTACATAAAGACGCGT | 52 |
| | ACCGCGTCCGT - - - - - : - - - - - - - - - ACCGTCCGTACATAAAGACGCGT | 53 |
| | ACCGCGTCCGTGG - - - : - ATCGGCTGCAGCAGATGCACCGCAGCGGACCGCACATAAAGACGCGT | 54 |
| | ACCGCGTCCGT - - - - - : - - - - - - - - - ACCGTCCGTACATAAAGACGCGT | 55 |
| | ACCGCGTCCGT - - - - - : - CGGCATCGCTGCAGCAGATGCACCGCAGCGGACCGCACATAAAGACGCGT | 56 |
| | ACCGCGTCCGT - - - - - : - CGGCATCGCTGCAGCAGATGCACCGCAGCGGACCGCACATAAAGACGCGT | 57 |
| | ACCGCGTCCGTGG - - - : A - GGCATCGCTGCAGCAGATGCACCGGACCGCAGCGGACCGCACATAAAGACGCGT | 58 |
| | ACCGCGTCCGTGG - - - : A - GGCATCGCTGCAGCAGATGCACCGGACCGCAGCGGACCGCACATAAAGACGCGT | 59 |
| | ACCGCGCGT - - - - - - : - - - - - - - - - CCGGCACATAAAGACGCGT | 60 |
| | ACCGCGCGT - - - - - - : - - - - - - - - - CCGGCACATAAAGACGCGT | 61 |
| | ACCGC - - - - - - - - : - - - - - - - - - - - - CGT | 62 |
| | ACCGC - - - - - - - - : - - - - - - - - - - - - CGT | 63 |
| | ACCGCGTCCGTGGACC : GGCATCGCAGCGGATGCAGCGGCATCGCTGCAGCAGATGCACCGCAGCGGACCGCACATAAAGACGCGT | 64 |
| | ACCGCGTCCGTGGACC : GGCATCGCAGCGGATGCAGCGGCATCGCTGCAGCAGATGCACCGCAGCGGACCGCACATAAAGACGCGT | 65 |
| | ACCGCGTCCGTG - - : - ACCGCAGATGCACCGCAGCGGACCGCACATAAAGACGCGT | 66 |
| | ACCGCGTCCGTG - - : - ACCGCAGATGCACCGGACCGGACCGCACATAAAGACGCGT | 67 |

♀X/Y;;Clvr^per offspring from ♀Clvr^per/+ XX ♀;w[118]

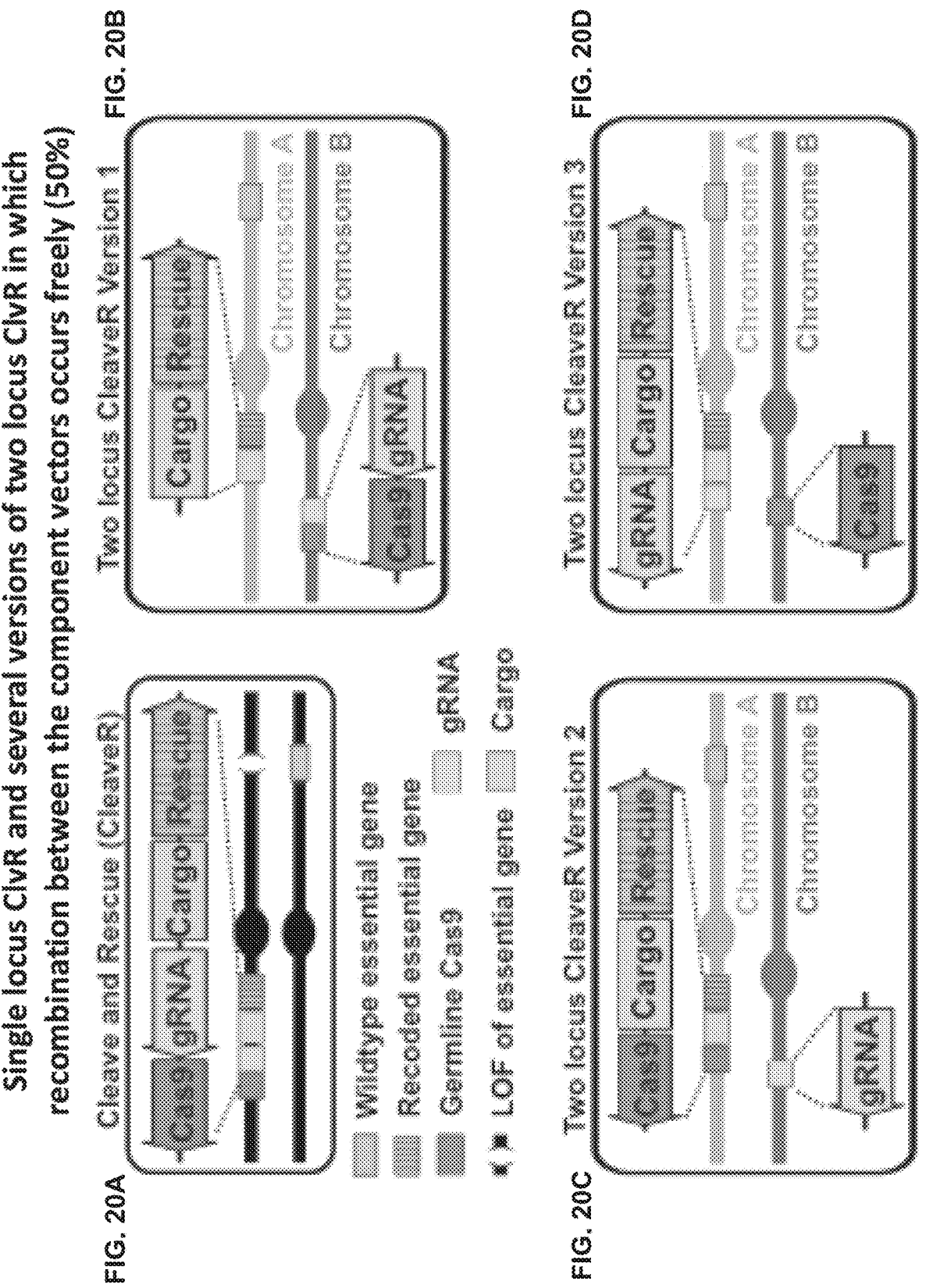
Single locus ClvR and several versions of two locus ClvR in which recombination between the component vectors occurs freely (50%)

When the two components of ClvR are placed on the same chromosome at some distance from each other (recombination distance less than 50%), the linkage between the elements decays overtime.
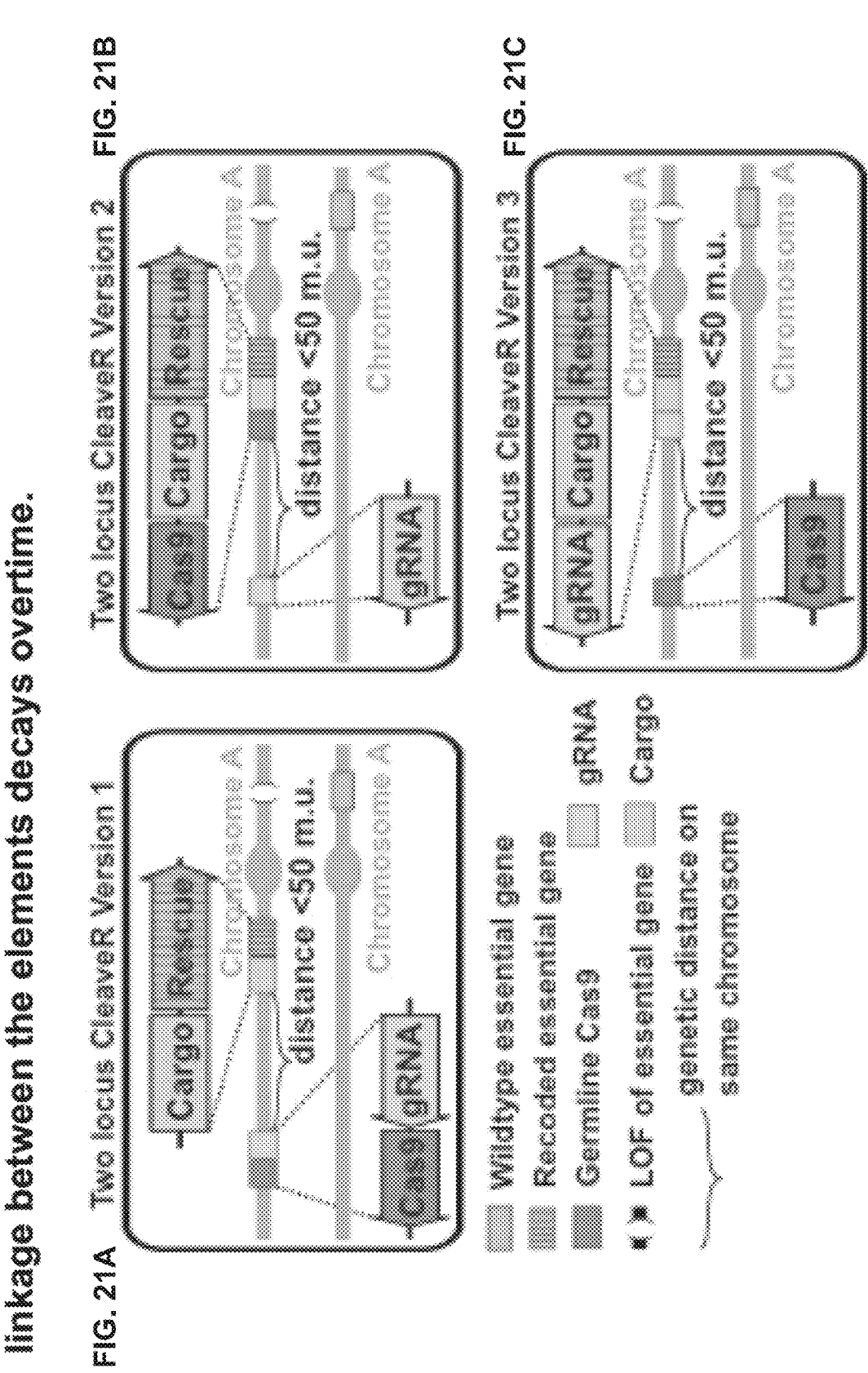
FIG. 21A    Two locus CleaveR Version 1
FIG. 21B    Two locus CleaveR Version 2
FIG. 21C    Two locus CleaveR Version 3

ClvR can create LOF alleles directly, through cleavage followed by error-prone repair (left). Alternatively, cleavage can be followed by repair though HR, using an existing uncleavable LOF allele as the repair template (right).

Fig. 26

ClvR can spread within a population if the site-specific DNA modifying enzyme can move between cells, killing those that lack ClvR Light shaded cells outlined with dashed lines are wildtype, and dying in response to uptake and activity of the DNA sequence modifying enzyme Medium shaded cells are wildtype and not yet exposed to the DNA sequence modifying enzyme Small dots = site-specific DNA sequence modifying enzyme Dark shaded cells carry ClvR, which is secreted into the environment

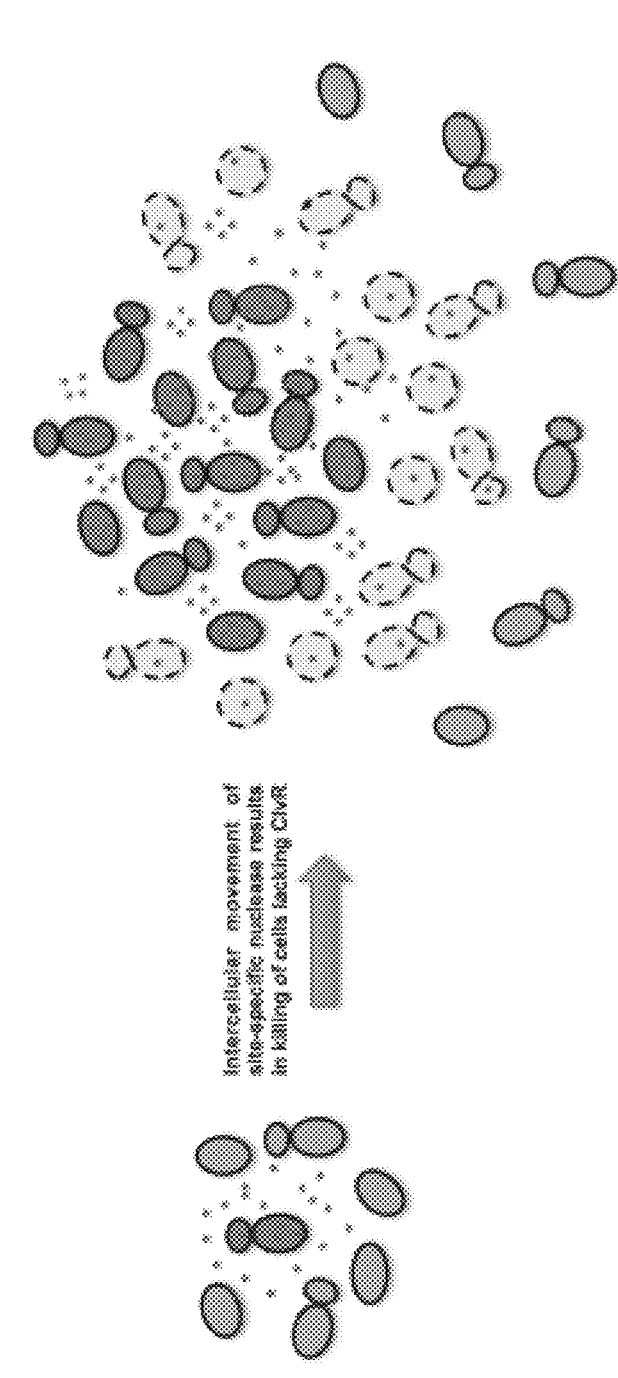

Intercellular movement of site-specific nuclease results in killing of cells lacking ClvR tf2a-step2 (14152 bp)

dribblev2 s2 (14153 bp)

ClvR$^{tko}$ drives population replacement/alteration to genotype fixation in Drosophila

Single locus ClvR is able to drive population alteration/replacement even when the gene being targeted for LOF allele formation is haploinsufficient or haplolethal Cas9-VPR and gRNAs drive expression of the recoded rescue in addition to bringing about cleavage of the wildtype copy of the essential gene

FIG. 33

Cycles of population replacement can be carried out with second generation elements that site at the same position as a first generation element, carry a new cargo, Cas9/gRNA and Rescue, as well as the Rescue associated with the first generation element

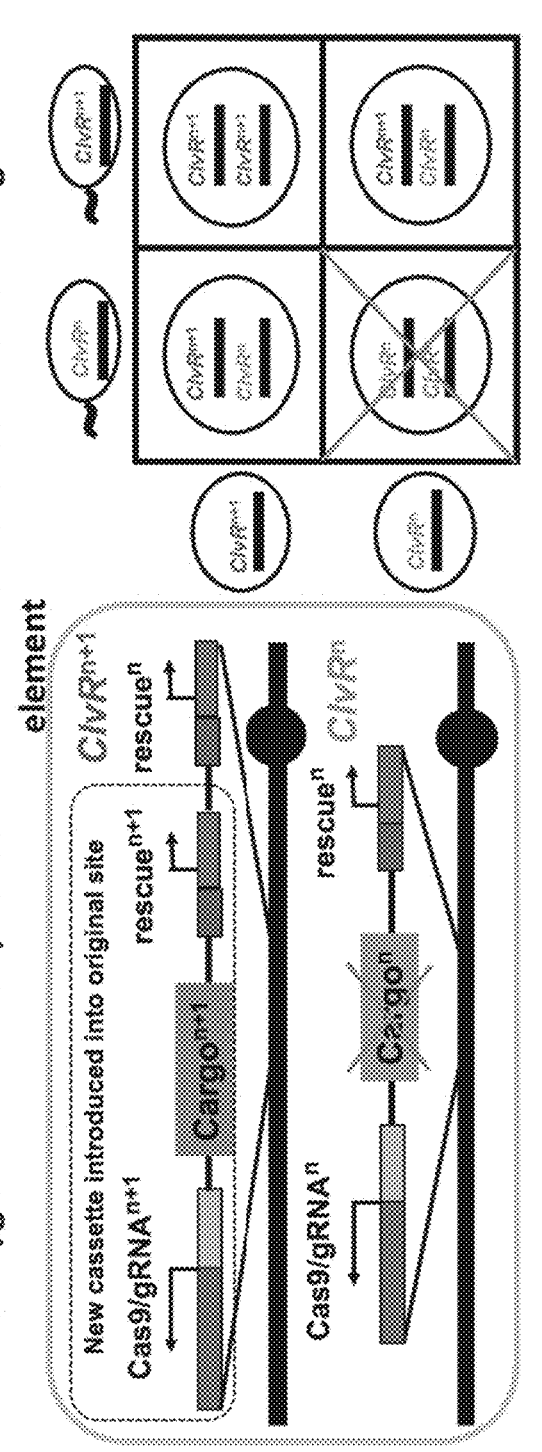

An example of an implementation of a second generation element in which ClvR^dbe (2^nd generation element) also carries the tko Rescue transgene, allowing it to drive into populations carrying ClvR^tko

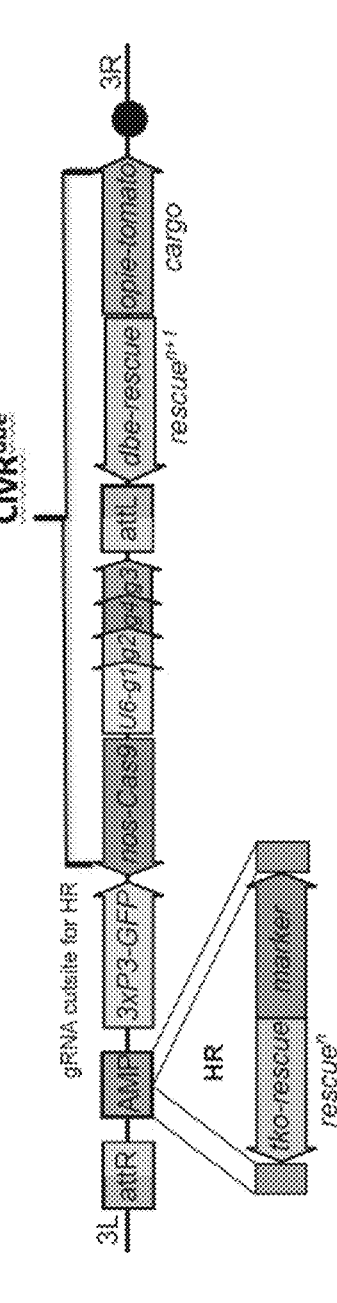

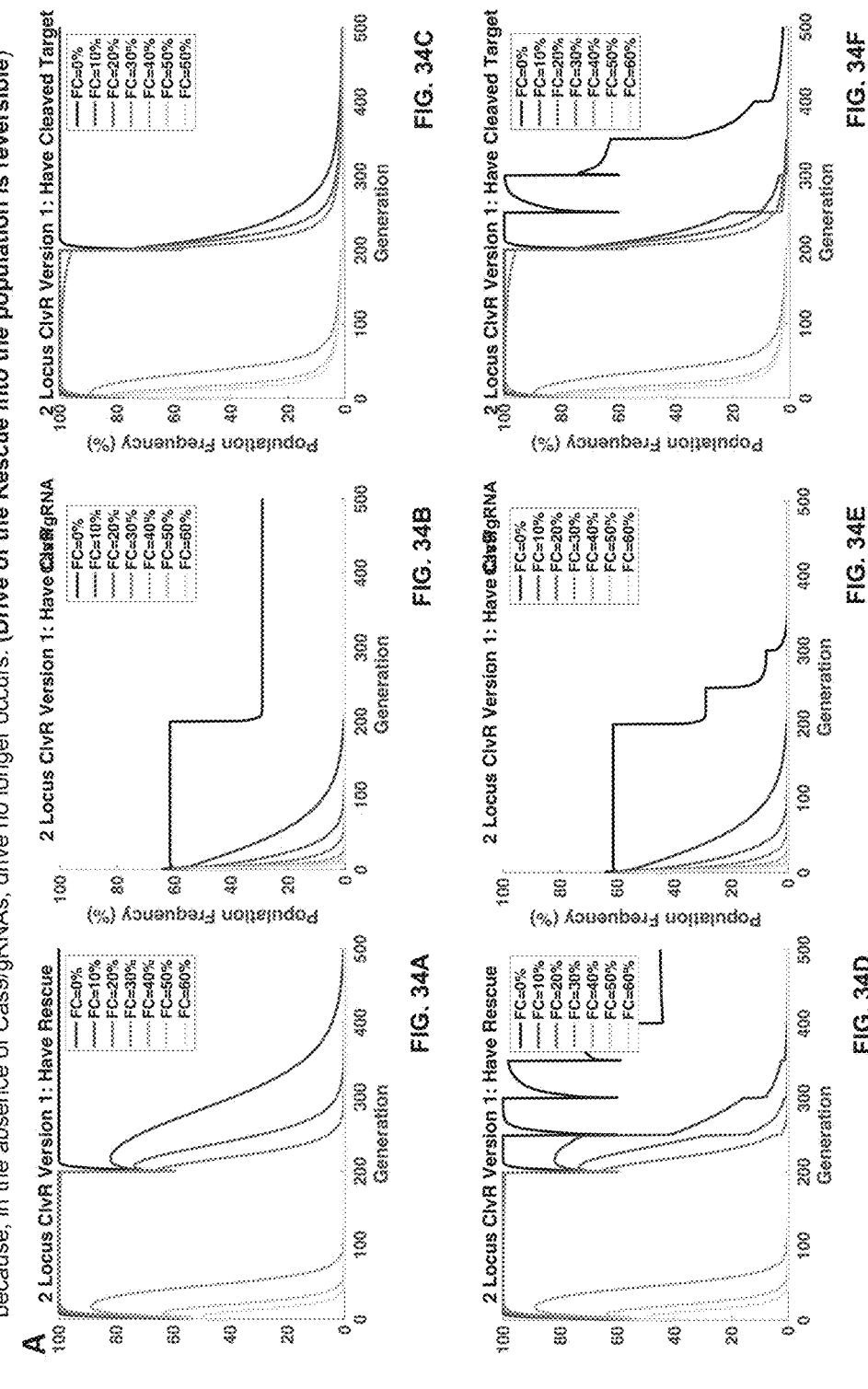

Behavior of two locus Clvr version 1, with maternal carryover, a single introduction frequency of 40%, followed by introduction of wildtypes 1 or 5 times, beginning at generation 200

1. The Rescue spreads to genotype fixation even for high fitness costs. (Drive occurs and is strong)
2. Cas9/gRNAs are eliminated over time. (Drive is transient and thus limited in space as well as time)
3. Introduction of wildtypes results in loss of the Rescue (when it has a fitness cost) and the cleaved target locus over time because, in the absence of Cas9/gRNAs, drive no longer occurs. (Drive of the Rescue into the population is reversible)

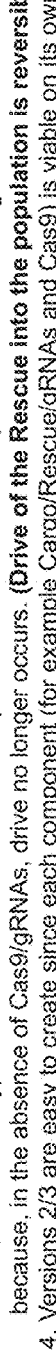

Behavior of two locus ClvR versions 2/3, with maternal carryover, a single introduction frequency of 40%, followed by introduction of wildtypes 1 or 5 times, beginning at generation 200

1. The Rescue spreads to genotype fixation even for high fitness costs. (Drive occurs and is strong)
2. Cas9/gRNAs are eliminated over time. (Drive is transient and thus limited in space as well as time)
3. Introduction of wildtypes results in loss of the Rescue (when it has a fitness cost) and the cleaved target locus over time because, in the absence of Cas9/gRNAs, drive no longer occurs. (Drive of the Rescue into the population is reversible)
4. Versions 2/3 are easy to create since each component (for example Cargo/Rescue/gRNAs and Cas9) is viable on its own.

Behavior of single locus Clvr, with maternal carryover, a single introduction frequency of 40%, followed by introduction of wildtypes every 50 generations, beginning at generation 200

FIG. 37

```
Dvir-TKO-33     MNFLRQTFNYTKQLTAQALQSNYLCAALRGMASLHQMHRTGPHIKK
Dm-TKO-33-C     MIMIAISNLEQLILLYWFSLSDISNSFTSLPAIQCSYE-TAVRGMASLQQMHRSGPHIKT
Dm-TKO-33-B     MNFLRQSFGITKQLASQAIQCSYE-TAVRGMASLQQMHRSGPHIKT
                  :      :                       *
                  :      :                       :  :
                  :      :
```

```
Dvir-TKO-33     RPPRQPLDGKPFAKGVVLKTLIKKPKKPNSAHRKCAALVRLSTGKEMVAYIPGIGHMLQEH
Dm-TKO-33-C     RPPRQPLDGKPFAKGVVLKTLIKKPKKPNSAHRKCVLVRLSTGKEMVAYIPGIGHMLQEH
Dm-TKO-33-B     RPPRQPLDGKPFAKGVVLKTLIKKPKKPNSAHRKCVLVRLSTGKEMVAYIPGIGHMLQEH
                  *                                                       *
                  :                                                       *
                  .                                                       *
```

```
Dvir-TKO-33     NIVLCRVGRLQDVPGVKLKAVRGVYDLAHVIKKGQ*     SEQ ID NO: 68
Dm-TKO-33-C     NIVLCRVGRLQDVPGVKLKAVRGVYDLAHVVKKSQ-     SEQ ID NO: 69
Dm-TKO-33-B     NIVLCRVGRLQDVPGVKLKAVRGVYDLAHVVKKSQ-     SEQ ID NO: 70
                  *                               *  :
                  *                               *  .
```

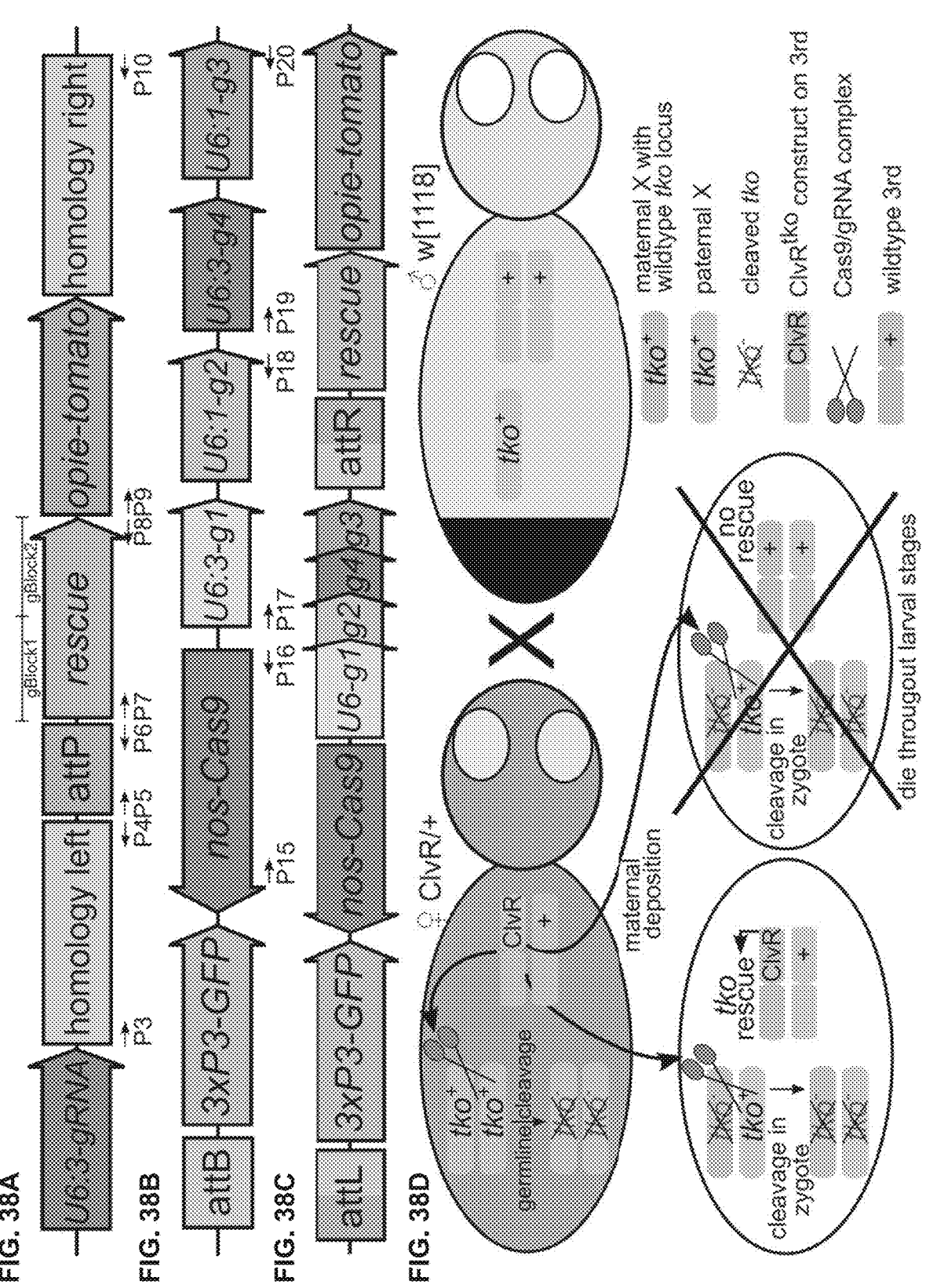

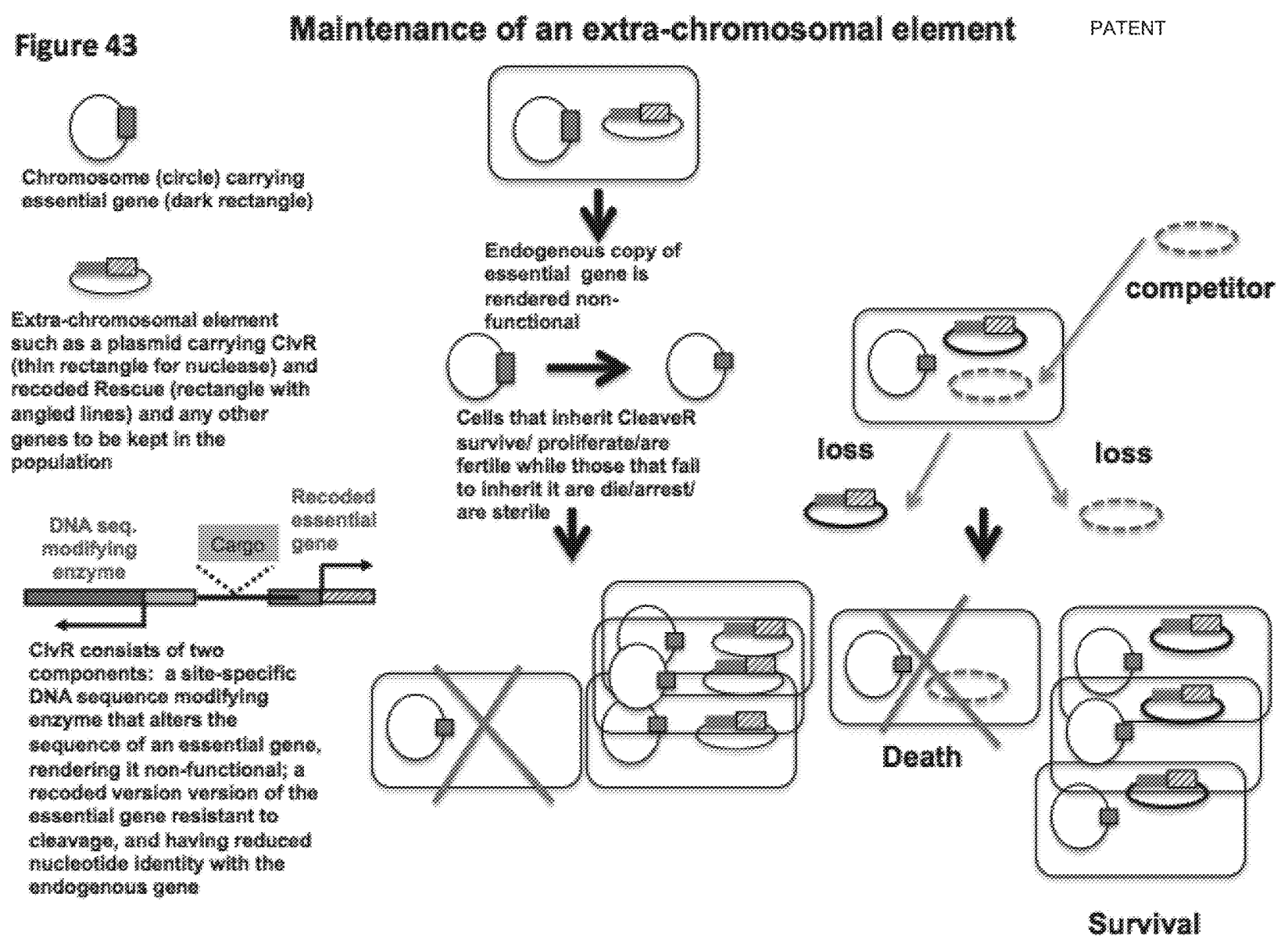

PATENT

Maintenance of an extra-chromosomal element

Figure 43

Chromosome (circle) carrying essential gene (dark rectangle)

Extra-chromosomal element such as a plasmid carrying ClvR (thin rectangle carrying nuclease) and recoded Rescue (rectangle with angled lines) and any other genes to be kept in the population Endogenous copy of essential gene is rendered non-functional Cells that inherit ClvR survive/ proliferate/are fertile while those that fail to inherit it are die/arrest/ are sterile DNA seq- modifying enzyme Recoded essential gene ClvR consists of two components: a site-specific DNA sequence modifying enzyme that alters the sequence of an essential gene, rendering it non-functional; a recoded version version of the essential gene resistant to cleavage, and having reduced nucleotide identity with the endogenous gene competitor loss loss Survival Death (from 1-749 bp)

dribblev2 s2 (14153 bp)

agcagaactttaaaagtgctcatcattggaaaacgttcttcggggcgaaaactctcaaggatcttaccgctgttgagatccagttcgatgtaacccactcgtgcacc
tcgtcttgaaattttcacgagtagtaacctttttgcaagaagccccgcttttgagagttcctagaatggcgacaactctaggtcaagctacattgggtgagcacgtgg 20          40          60          80          100 caactgatcttcagcatcttttactttcaccagcgtttctgggtgagcaaaaacaggaaggcaaaatgccgcaaaaaagggaataagggcgacacggaaatgttgaa
gttgactagaagtcgtagaaaatgaaagtggtcgcaaagacccactcgtttttgtccttccgtttttacggcgtttttttcccttattcccgctgtgcctttacaactt 120         140         160         180         200 tactcatactcttccttttttcaatattattgaagcatttatcagggttattgtctcatgagcggatacatatttgaatgtatttagaaaaatasacaaataggggtt
atgagtatgagaaggaaaaagttataataacttcgtasaatagtcccaataacagagtactcgcctatgtatasacttacataaatcttttttatttgtttatccccaa 220         240         260         280         300         320 ccgcgcacatttcccgaaaagtgccacctgacgtcgacggatcgggagatcggcgcgggatctaattcaattagagactaattcaattagagctaattcaattagg
ggcgcgtgtaaaggggctttcacggtggactgcagctgcctagccctctagccgcgccctagattaagttaatctctgattaagttaatctcgattaagttaatcc 340         360         380         400         420 atccaagcttatcgatttcgaaccctcgaccgccggagtataaatagaggcgcttcgtctacggagcgacaattcaattcaaacaagcaaagtgaacacgtcgctaa
taggttcgaatagctaaagcttgggagctggcggcctcatatttatctccgcgaagcagatgcctcgctgttaagttaagtttgttcgtttcacttgtgcagcgatt 440         460         480         500         520

NcoI gcgaaagctaagcaaataaacaagcgcagctgaacaagctaaacaatcggctcgagaccggtcgccaccatggtgagcaagggcgaggagctgttcaccggggtggt
cgctttcgattcgtttatttgttcgcgtcgacttgttcgatttgttagccgagctctggccagcggtggtaccactcgttcccgctcctcgacaagtggcccccacca 540         560         580         600         620         640 gcccatcctggtcgagctggacggcgacgtaaacggccacaagttcagcgtgtccggcgagggcgagggcgatgccacctacggcaagctgaccctgaagttcatct
cgggtaggaccagctcgacctgccgctgcatttgccggtgttcaagtcgcacaggccgctcccgctcccgctacggtggatgccgttcgactgggacttcaagtaga 660         680         700         720         740

FIG. 44 dribblev2 s2 (14153 bp) (from 750-1498 bp)

gcaccaccggcaagctgcccgtgccctggcccaccctcgtgaccaccctgacctacggcgtgcagtgcttcagccgctaccccgaccacatgaagcagcacgacttc
cgtggtggccgttcgacgggcacgggaccgggtgggagcactggtggactggatgccgcacgtcacgaagtcggcgatggggctggtgtacttcgtcgtgctgaag source
EGFP ORF 760          780          800          820          840 ttcaagtccgccatgcccgaaggctacgtccaggagcgcaccatcttcttcaaggacgacggcaactacaagacccgcgccgaggtgaagttcgagggcgacaccct
aagttcaggcggtacgggcttccgatgcaggtcctcgcgtggtagaagaagttcctgctgccgttgatgttctgggcgcggctccacttcaagctcccgctgtggga source
EGFP ORF 860          880          900          920          940          960 ggtgaaccgcatcgagctgaagggcatcgacttcaaggaggacggcaacatcctggggcacaagctggagtacaactacaacagccacaacgtctatatcatggccg
ccacttggcgtagctcgacttcccgtagctgaagttcctcctgccgttgtaggaccccgtgttcgacctcatgttgatgttgtcggtgttgcagatatagtaccggc source
EGFP ORF 980          1,000          1,020          1,040          1,060 acaagcagaagaacggcatcaaggtgaacttcaagatccgccacaacatcgaggacggcagcgtgcagctcgccgaccactaccagcagaacacccccatcggcgac
tgttcgtcttcttgccgtagttccacttgaagttctaggcggtgttgtagctcctgccgtcgcacgtcgagcggctggtgatggtcgtcttgtggggggtagccgctg source
EGFP ORF 1,080          1,100          1,120          1,140          1,160 ggccccgtgctgctgcccgacaaccactacctgagcacccagtccgccctgagcaaagaccccaacgagaagcgcgatcacatggtcctgctggagttcgtgaccgc
ccggggcacgacgacgggctgttggtgatggactcgtgggtcaggcgggactcgtttctggggttgctcttcgcgctagtgtaccaggacgacctcaagcactggcg source
EGFP ORF 1,180          1,200          1,220          1,240          1,260          1,280 cgccgggatcactctcggcatggacgagctgtacaagtaaagcggccgcgactctagatcataatcagccataccacatttgtagaggttttacttgctttaaaaaa
gcggccctagtgagagccgtacctgctcgacatgttcatttcgccggcgctgagatctagtattagtcggtatggtgtaaacatctccaaaatgaacgaaatttttt source
EGFP ORF          SV40 terminator 1,300          1,320          1,340          1,360          1,380

BsaI cctcccacacctcccctgaacctgaaacataaaatgaatgcaattgttgttgttaacttgtttattgcagcttataatggttacaaataaagcaatagcatcacaa
ggagggtgtggaggggacttggactttgtattttacttacgttaacaacaacaattgaacaaataacgtcgaatattaccaatgtttatttcgttatcgtagtgtt source
SV40 terminator 1,400          1,420          1,440          1,460          1,480

FIG. 44 CONTINUED dribblev2 s2 (14153 bp) (from 1499-2354 bp)

```
atttcacaaataaagcattttttttcactgcattctagttgtggtttgtccaaactcatcaatgtatcttagttgttggttggcacaccacaaatatactgttgccga
taaagtgtttatttcgtaaaaaaagtgacgtaagatcaacaccaaacaggtttgagtagttacatagaatcaacaaccaaccgtgtggtgtttatatgacaacggct
```
source
SV40 terminator                                                    Gypsy Insulator (1)

```
1,500          1,520          1,540          1,560          1,580          1,600
```

```
gcacaattgatcggctaaatggtatggcaagaaaaggtatgcaatataataatcttttattgggtatgcaacgaaaatttgtttcgtcaacgtatgcaatattcttt
cgtgttaactagccgatttaccataccgttcttttccatacgttatattattagaaaataacccatacgttgcttttaaacaaagcagttgcatacgttataagaaa
```
Gypsy Insulator (1)

```
1,620          1,640          1,660          1,680          1,700
```

```
attaaaagagggtatgcaatgtattttattaaaaacgggtatgcaatataataatcttttattgggtatgcaacgaaatttgtttcgtcaaagtatgcaatatttt
taatttctcccatacgttacataaaataattttttgcccatacgttatattattagaaaataacccatacgttgcttttaaacaaagcagtttcatacgttataaaa
```
Gypsy Insulator (1)

```
1,720          1,740          1,760          1,780          1,800
```

```
ttattaaaagagggtatgcaatgtattttattaaaaacgggtatgcaataaaaaattatttggtttctctaaaaagtatgcagcacttatttttttgataaggtatgc
aataattttctcccatacgttacataaaataattttttgcccatacgttattttttaataaaccaaagagattttttcatacgtcgtgaataaaaaaactattccatacg
```
Gypsy Insulator

```
1,820          1,840          1,860          1,880          1,900          1,920
```

```
aacaaaattttactttgccgaaaatatgcaatgtttttgcgaataaaattcaacgcacacttattacgtggccaacgcgcctagTGGATCCTTCCTGGCCCTTTTCGA
ttgtttttaaaatgaaacggctttttatacgttacaaaaacgcttattaagttgcgtgtgaataatgcaccggttgcgcggatcACCTAGGAAGGACCGGGAAAAGCT
```
Gypsy Insulator                                                    nos3'UTR

```
1,940          1,960          1,980          2,000          2,020
```

```
GAAACGCCGCGAGGGCGAAAAGGATTAGTTGTTTCAAACGCAAGAAGGACATTTGTTTCCTTAAATTGTAACCATTTCTTTATTTGGCACTCGAGCCATTGAATTTT
CTTTGCGGCGCTCCCGCTTTTCCTAATCAACAAAGTTTGCGTTCTTCCTGTAAACAAAGGAATTTAACATTGGTAAAGAAATAAACCGTGAGCTCGGTAACTTAAAA
```
nos3'UTR

```
2,040          2,060          2,080          2,100          2,120          2,140
```

```
TCATTTTCAGAATATGTGTACACATTTTTTAAAAAAAATAAAAAAATTATATAATGCTGGCGGTTGTTTCATGTGTGAAAAATTGATCAATGGTAAACAAAATTGAAT
AGTAAAAGTCTTATACACATGTGTAAAAAAATTTTTTTATTTTTTTTAATATATTACGACCGCCAACAAAGTACACACTTTTTAACTAGTTACCATTTGTTTTAACTTA
```
nos3'UTR

```
2,160          2,180          2,200          2,220          2,240
```

```
AAATATATAACATATATATATAGATATGTGTGTTGAAATGAATACTTGCGATACATGTAATAAAAATACTCTTCGCTTATCTATCAAAAAGTGCGGAATGTCAAAAT
TTTATATATTGTATATATATATCTATACACACAACTTTACTTATGAACGCTATGTACATTATTTTTATGAGAAGCGAATAGATAGTTTTTCACGCCTTACAGTTTTA
```
nos3'UTR

```
2,260          2,280          2,300          2,320          2,340
```

FIG. 44 CONTINUED dribblev2 s2 (14153 bp) (from 2355-2996 bp)

TTAAAATTTTACAATGAATGCGTAGCCGACGACGAAAGTGTTCCTTGCTATTTCCTTTAGCAAGATTTAAATTTAGATTAAATTCTAATGATACGATTGACAGTTCG
AATTTTAAAATGTTACTTACGCATCGGCTGCTGCTTTCACAAGGAACGATAAAGGAAATCGTTCTAAATTTAAATCTAATTTAAGATTACTATGCTAACTGTCAAGC nos3'UTR 2,360          2,380          2,400          2,420          2,440          2,460

AAATTCAAAGTGTTCCTTTTTCAAAATTTAGTAAAGATTGTATATCAATTGTAGATATATCGAAATTTTTCGGCCGCAAGCGAACATTTTACAAAATGAAGGCGACC
TTTAAGTTTCACAAGGAAAAAGTTTTAAATCATTTCTAACATATAGTTAACATCTATATAGCTTTAAAAAGCCGGCGTTCGCTTGTAAAATGTTTTACTTCCGCTGG nos3'UTR 2,480          2,500          2,520          2,540          2,560

Csp/I

AGTTGCAGACCAATTCCATTCATCAACTTTCGGATTGTAAGATATTTCTATCGGCCACGACGATTGAACAAGTATTACGATATTGTAAGTCTTCTTTAACAAAATTA
TCAACGTCTGGTTAAGGTAAGTAGTTGAAAGCCTAACATTCTATAAAGATAGCCGGTGCTGCTAACTTGTTCATAATGCTATAACATTCAGAAGAAATTGTTTTAAT nos3'UTR 2,580          2,600          2,620          2,640          2,660

GTTGTCTATACTATAAGATCTATAGGCACGGGATAACGCT

GTTTCCCTTTCACAGAAACAGACATAAATTCTTGAATTATTGACTTGGATTTGAGTGATCGTTCGTTGTCTATACTATAAGATCTATAGGCACGGGATAACGCTCTA
CAAAGGGAAAGTGTCTTTGTCTGTATTTAAGAACTTAATAACTGAACCTAAACTCACTAGCAAGCAACAGATATGATATTCTAGATATCCGTGCCCTATTGCGAGAT sibs frag nos3'UTR                                                        nos3'UTR 2,680          2,700          2,720          2,740          2,760          2,780

Hpal

AATCTCTTTAAAATCGAACGCGCCAGGCGCTAGTTAAACGTTACTATCTATCTGGTTAACCCAGCTTTGATCGGAATGCGTATATATATTTCATGTTATATAAACGC
TTAGAGAAATTTTAGCTTGCGCGGTCCGCGATCAATTTGCAATGATAGATAGACCAATTGGGTCGAAACTAGCCTTACGCATATATATAAAGTACAATATATTTGCG frag
nos3'UTR 2,800          2,820          2,840          2,860          2,880

BstAPI

TGCAAAAGCTGCCAGAGCCTCTGCTCcAGAGCTGGATTCGCTCACACCTTCCTCTTCTTCTTGGGGTCAGCCCTGCTGTCTCCACCGAGCTGAGAGAGGTCGATTCT
ACGTTTTCGACGGTCTCGGAGACGAGgTCTCGACCTAAGCGAGTGTGGAAGGAGAAGAAGAACCCCAGTCGGGACGACAGAGGTGGCTCGACTCTCTCCAGCTAAGA

SV40 NLS

NLS frag nos3'UTR                                                     cAS9

2,900          2,920          2,940          2,960          2,980

FIG. 44 CONTINUED dribblev2 s2 (14153 bp) (from 2997-3638 bp)

TGTTTCATAGAGCCCCGTAATTGACTGATGAATCAGTGTGGCGTCCAGGACCTCCTTTGTAGAGGTGTACCGCTTTCTGTCTATGGTGGTGTCGAAGTACTTGAAGG
ACAAAGTATCTCGGGGCATTAACTGACTACTTAGTCACACCGCAGGTCCTGGAGGAAACATCTCCACATGGCGAAAGACAGATACCACCACAGCTTCATGAACTTCC

```
                                            ORF frame 2
                                      Frag
                                      cAS9
```
3,000        3,020        3,040        3,060        3,080        3,100

EcoNI

CTGCAGGCGCGCCCAAGTTGGTCAGAGTAAACAAGTGGATAATGTTTTCTGCCTGCTCCCTGATGGGCTTATCCCTGTGCTTATTGTAAGCAGAAAGCACCTTATCG
GACGTCCGCGCGGGTTCAACCAGTCTCATTTGTTCACCTATTACAAAAGACGGACGAGGGACTACCCGAATAGGGACACGAATAACATTCGTCTTTCGTGGAATAGC

```
                                            ORF frame 2
                                      Frag
                                      cAS9
```
3,120        3,140        3,160        3,180        3,200

AGGTTAGCGTCGGCGAGGATCACTCTTTTGGAGAATTCGCTTATTTGCTCGATGATCTCATCAAGGTAGTGTTTGTGTTGTTCCACGAACAGCTGCTTCTGCTCATT
TCCAATCGCAGCCGCTCCTAGTGAGAAAACCTCTTAAGCGAATAAACGAGCTACTAGAGTAGTTCCATCACAAACACAACAAGGTGCTTGTCGACGAAGACGAGTAA

```
                                            ORF frame 2
                                      Frag
                                      cAS9
```
3,220        3,240        3,260        3,280        3,300

ATCTTCGGGAGACCCTTTGAGCTTTTCATAGTGGCTGGCCAGATACAAGAAATTAACGTATTTAGAGGGCAGTGCCAGCTCGTTACCTTTCTGCAGCTCGCCCGCAC
TAGAAGCCCTCTGGGAAACTCGAAAAGTATCACCGACCGGTCTATGTTCTTTAATTGCATAAATCTCCCGTCACGGTCGAGCAATGGAAAGACGTCGAGCGGGCGTG

```
                                            ORF frame 2
                                      Frag
                                      cAS9
```
3,320        3,340        3,360        3,380        3,400        3,420

TAGCGAGCATTCGTTTCCGGCCGTTTTCAAGCTCAAAGAGAGAGTACTTGGGAAGCTTAATGATGAGGTCTTTTTTGACCTCTTTATATCCTTTCGCCTCGAGAAAG
ATCGCTCGTAAGCAAAGGCCGGCAAAAGTTCGAGTTTCTCTCTCATGAACCCTTCGAATTACTACTCCAGAAAAAACTGGAGAAATATAGGAAAGCGGAGCTCTTTC

```
                                            ORF frame 2
                                      Frag
                                      cAS9
```
3,440        3,460        3,480        3,500        3,520

TCGATGGGGTTTTTTTCGAAGCTTGATCGCTCCATGATTGTGATGCCCAGCAGTTCCTTGACGCTTTTGAGTTTTTTAGACTTCCCTTTCTCCACTTTGGCCACAAC
AGCTACCCCAAAAAAAGCTTCGAACTAGCGAGGTACTAACACTACGGGTCGTCAAGGAACTGCGAAAACTCAAAAAATCTGAAGGGAAAGAGGTGAAACCGGTGTTG

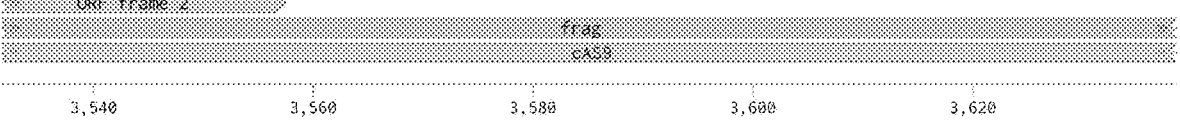

```
  ORF frame 2
                                      Frag
                                      cAS9
```
3,540        3,560        3,580        3,600        3,620

FIG. 44 CONTINUED dribblev2 s2 (14153 bp) (from 3- 3964387 bp)

dribblev2 s2 (14153 bp) (from 4388-5029 bp)

GTTGTGTGATCAGTTTGGCGTTCAGCAGCTGCCGCCAATAATTTTTCATTTTCTTGACAACTTCTTCTGAGGGGACGTTATCACTCTTCCCTCTATTTTTATCGGAT
CAACACACTAGTCAAACCGCAAGTCGTCGACGGCGGTTATTAAAAAGTAAAAGAACTGTTGAAGAAGACTCCCCTGCAATAGTGAGAAGGGAGATAAAAATAGCCTA

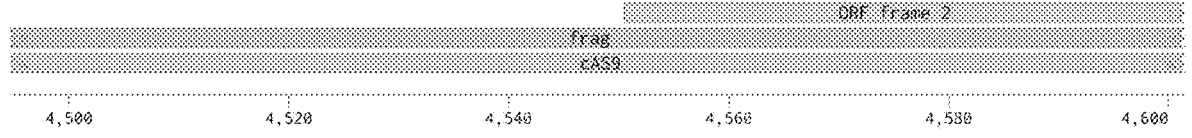

4,400          4,420          4,440          4,460          4,480

CTTGTCAACACTTTATTATCAATAGAATCATCTTTGAGAAAAGACTGGGGCACGATATGATCCACGTCGTAGTCGGAGAGCCGATTGATGTCCAGTTCCTGATCCAC
GAACAGTTGTGAAATAATAGTTATCTTAGTAGAAACTCTTTTCTGACCCCGTGCTATACTAGGTGCAGCATCAGCCTCTCGGCTAACTACAGGTCAAGGACTAGGTG

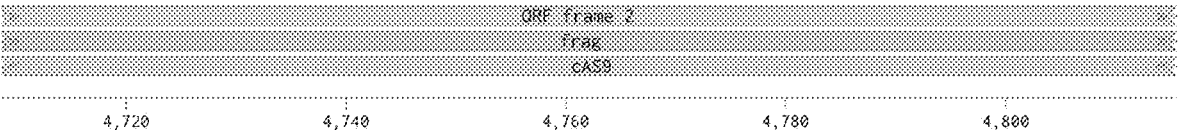

4,500          4,520          4,540          4,560          4,580          4,600

AflII

GTACATGTCCCTGCCGTTCTGCAGGTAGTACAGGTAGAGCTTCTCATTCTGAAGCTGGGTGTTTTCAACTGGGTGTTCCTTAAGGATTTGGGACCCCAGTTCTTTTA
CATGTACAGGGACGGCAAGACGTCCATCATGTCCATCTCGAAGAGTAAGACTTCGACCCACAAAAGTTGACCCACAAGGAATTCCTAAACCCTGGGGTCAAGAAAAT

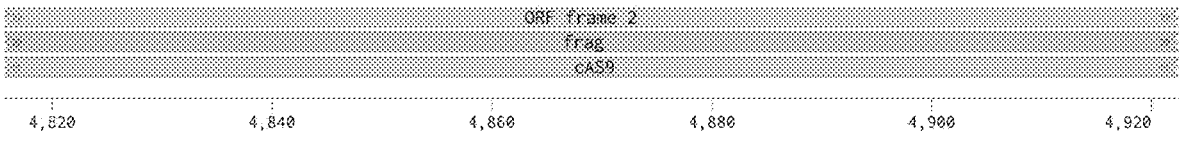

4,620          4,640          4,660          4,680          4,700

TACCCTCTTCAATCCTCTTCATCCTTTCCCTACTGTTCTTCTGTCCCTTCTGGGTAGTTTGGTTCTCTCGGGCCATCTCGATAACGATATTCTCGGGCTTATGCCTT
ATGGGAGAAGTTAGGAGAAGTAGGAAAGGGATGACAAGAAGACAGGGAAGACCCATCAAACCAAGAGAGCCCGGTAGAGCTATTGCTATAAGAGCCCGAATACGGAA 4,720          4,740          4,760          4,780          4,800

CCCATTACTTTGACGAGTTCATCCACGACCTTAACGGTCTGCAGTATTCCCTTTTTGATAGCTGGGCTACCTGCAAGATTAGCGATGTGCTCGTGAAGACTGTCCCC
GGGTAATGAAACTGCTCAAGTAGGTGCTGGAATTGCCAGACGTCATAAGGGAAAAACTATCGACCCGATGGACGTTCTAATCGCTACACGAGCACTTCTGACAGGGG

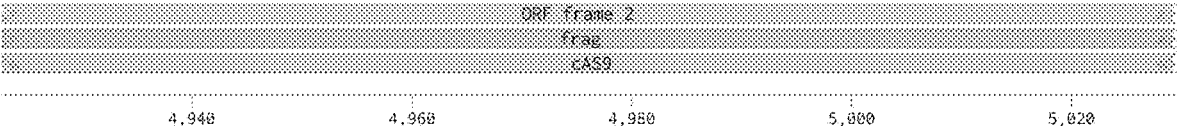

4,820          4,840          4,860          4,880          4,900          4,920

AflII

CTGGCCAGAAACTTGTGCTTTCTGGATGTCCTCCTTAAAGGTGAGAGAGTCATCATGGATCAACTGCATGAAGTTCCGGTTGGCAAATCCATCGGACTTAAGAAAAT
GACCGGTCTTTGAACACGAAAGACCTACAGGAGGAATTTCCACTCTCTCAGTAGTACCTAGTTGACGTACTTCAAGGCCAACCGTTTAGGTAGCCTGAATTCTTTTA 4,940          4,960          4,980          5,000          5,020

FIG. 44 CONTINUED dribblev2 s2 (14153 bp) (from 5030-5671 bp)

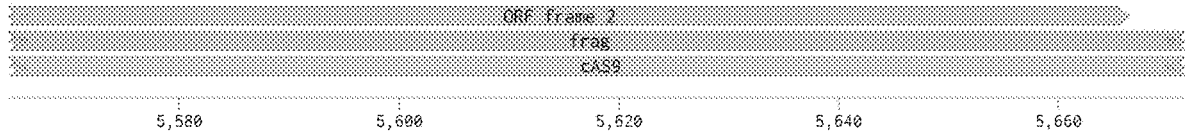

CspCI

CCAGGATTGTCTTTCCACTCTGCTTGTCTCGGATCCCATTGATCAGTTTTCTTGACAGCCGCCCCCATCCTGTATATCGGCGCCTCTTGAGCTGTTTCATGACTTTG
GGTCCTAACAGAAAGGTGAGACGAACAGAGCCTAGGGTAACTAGTCAAAAGAACTGTCGGCGGGGGTAGGACATATAGCCGCGGAGAACTCGACAAAGTACTGAAAC

ORF frame 2
frag
cAS9

5,040　　　5,060　　　5,080　　　5,100　　　5,120

DrdI

TCGTCGAAGAGATGAGCGTAAGTTTTCAAGCGTTCTTCAATCATCTCCCTATCTTCAAACAACGTAAGGGTGAGGACAATGTCCTCAAGAATGTCCTCGTTCTCCTC
AGCAGCTTCTCTACTCGCATTCAAAAGTTCGCAAGAAGTTAGTAGAGGGATAGAAGTTTGTTGCATTCCCACTCCTGTTACAGGAGTTCTTACAGGAGCAAGAGGAG

ORF frame 2
frag
cAS9

5,140　　　5,160　　　5,180　　　5,200　　　5,220　　　5,240

ATTGTCCAGGAAGTCCTTGTCTTTAATGATTTTCAGGAGATCGTGATACGTTCCCAGGGATGCGTTGAAGCGATCCTCCACTCCGCTGATTTCAACAGAGTCGAAAC
TAACAGGTCCTTCAGGAACAGAAATTACTAAAAGTCCTCTAGCACTATGCAAGGGTCCCTACGCAACTTCGCTAGGAGGTGAGGCGACTAAAGTTGTCTCAGCTTTG

ORF frame 2
frag
cAS9

5,260　　　5,280　　　5,300　　　5,320　　　5,340

ATTCAATCTTTTTGAAATAGTCTTCTTTGAGCTGTTTCACGGTAACTTTCCGGTTCGTCTTGAAGAGGAGGTCCACGATAGCTTTCTTCTGCTCTCCAGACAGGAAT
TAAGTTAGAAAAACTTTATCAGAAGAAACTCGACAAAGTGCCATTGAAAGGCCAAGCAGAACTTCTCCTCCAGGTGCTATCGAAAGAAGACGAGAGGTCTGTCCTTA

ORF frame 2
frag
cAS9

5,360　　　5,380　　　5,400　　　5,420　　　5,440

GCTGGCTTTCTCATCCCTTCTGTGACGTATTTGACCTTGGTGAGCTCGTTATAAACTGTGAAGTACTCGTACAGCAGAGAGTGTTTAGGAAGCACCTTTTCGTTAGG
CGACCGAAAGAGTAGGGAAGACACTGCATAAACTGGAACCACTCGAGCAATATTTGACACTTCATGAGCATGTCGTCTCTCACAAATCCTTCGTGGAAAAGCAATCC

ORF frame 2
frag
cAS9

5,460　　　5,480　　　5,500　　　5,520　　　5,540　　　5,560

CAGATTTTTATCAAAGTTAGTCATCCTTTCGATGAAGGACTGGGCAGAGGCCCCCTTATCCACGACTTCCTCGAAGTTCCAGGGAGTGATGGTCTCTTCTGATTTGC
GTCTAAAAATAGTTTCAATCAGTAGGAAAGCTACTTCCTGACCCGTCTCCGGGGGAATAGGTGCTGAAGGAGCTTCAAGGTCCCTCACTACCAGAGAAGACTAAACG

ORF frame 2
frag
cAS9

5,580　　　5,600　　　5,620　　　5,640　　　5,660

FIG. 44 CONTINUED dribblev2 s2 (14153 bp) (from 5- 726 420 bp)

Smal
TspMI
Smal

GAGTCATCCACGCGAATCTGGAATTTCCCCGGGCGAGGGGGCCTACATAGTAGGGTATCCGAAATGTGAGGATTTTCTCAATCTTTTCCCTGTTATCTTTCAAAAAG
CTCAGTAGGTGCGCTTAGACCTTAAAGGGGCCCGCTCCCCCGGATGTATCATCCCATAGGCTTTACACTCCTAAAAGAGTTAGAAAAGGGACAATAGAAAGTTTTTC frag
CAS9

5,680          5,700          5,720          5,740          5,760

GGGTAGAAATCCTCTTGCCGCCTGAGGATAGCGTGCAGTTCGCCCAGGTGAATCTGGTGGGGGATGCTTCCATTGTCGAAAGTGCGCTGTTTGCGCAACAGATCTTC
CCCATCTTTAGGAGAACGGCGGACTCCTATCGCACGTCAAGCGGGTCCACTTAGACCACCCCCTACGAAGGTAACAGCTTTCACGCGACAAACGCGTTGTCTAGAAG frag
CAS9

5,780          5,800          5,820          5,840          5,860          5,880

TCTGTTAAGCTTTACCAGCAGCTCCTCGGTGCCGTCCATTTTTTCCAAGATGGGCTTAATAAATTTGTAAAATTCCTCCTGGCTTGCTCCGCCGTCAATGTATCCGG
AGACAATTCGAAATGGTCGTCGAGGAGCCACGGCAGGTAAAAAAGGTTCTACCCGAATTATTTAAACATTTTAAGGAGGACCGAACGAGGCGGCAGTTACATAGGCC frag
CAS9

5,900          5,920          5,940          5,960          5,980

CGTAGCCATTTTTAGACTGATCGAAGAAAATTTCCTTGTACTTCTCAGGCAGTTGCTGTGTCTGACAAGGGCCTTCAGCAAAGTCAAGTCTTGGTGGTGCTCATCATAG
GCATCGGTAAAAATCTGACTAGCTTCTTTTTAAAGGAACATGAAGAGTCCGTCAACGACAGACTGTTCCCGGAAGTCGTTTCAGTTCAGAACCACCACGAGTAGTATC frag
CAS9

6,000          6,020          6,040          6,060          6,080

CGCTTGATCATACTAGCGCTCAGCGGAGCTTTGGTGATCTCCGTGTTCACTCGCAGAATATCACTCAGCAGAATGGCGTCTGACAGGTTCTTTGCCGCCAAAAAAAG
GCGAACTAGTATGATCGCGAGTCGCCTCGAAACCACTAGAGGCACAAGTGAGCGTCTTATAGTGAGTCGTCTTACCGCAGACTGTCCAAGAAACGGCGGTTTTTTTC frag
CAS9

6,100          6,120          6,140          6,160          6,180          6,200

GTCTGCGTACTGGTCGCCGATCTGGGCCAGCAGATTGTCGAGATCATCATCGTAGGTGTCTTTGCTCAGTTGAAGCTTGGCATCTTCGGCCAGGTCGAAGTTAGATT
CAGACGCATGACCAGCGGCTAGACCCGGTCGTCTAACAGCTCTAGTAGTAGCATCCACAGAAACGAGTCAACTTCGAACCGTAGAAGCCGGTCCAGCTTCAATCTAA frag
CAS9

6,220          6,240          6,260          6,280          6,300

TAAAGTTGGGGGTCAGCCCGAGTGACAGGGCGATAAGATTACCAAACAGGCCGTTCTTCTTCTCCCCAGGGAGCTGTGCGATGAGGTTTTCGAGCCGCCGGGATTTG
ATTTCAACCCCCAGTCGGGCTCACTGTCCCGCTATTCTAATGGTTTGTCCGGCAAGAAGAAGAGGGGTCCCTCGACACGCTACTCCAAAAGCTCGGCGGCCCTAAAC frag
CAS9

6,320          6,340          6,360          6,380          6,400          6,420

FIG. 44 CONTINUED dribblev2 s2 (14153 bp) (from - 42167 0- 2 bp)

GACAGCCTAGCGCTCAGGATTGCTTTGGCGTCAACTCCGGATGCGTTGATCGGGTTCTCTTCGAAAAGCTGATTGTAAGTCTGAACCAGTTGGATAAAGAGTTTGTC
CTGTCGGATCGCGAGTCCTAACGAAACCGCAGTTGAGGCCTACGCAACTAGCCCAAGAGAAGCTTTTCGACTAACATTCAGACTTGGTCAACCTATTTCTCAAACAG

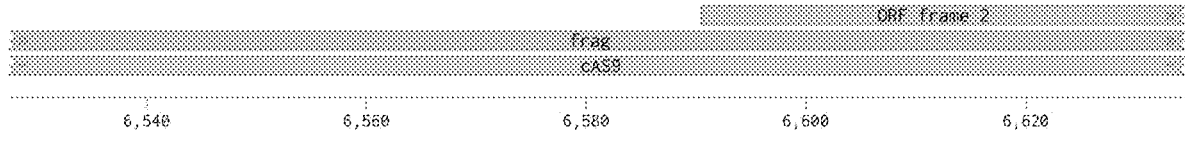

6,440     6,460     6,480     6,500     6,520

GACATCGCTGTTGTCTGGGTTCAGGTCCCCCTCGATGAGGAAGTGTCCCCGAAATTTGATCATATGCGCCAGCGCGAGATAGATCAACCGCAAGTCAGCCTTATCAG
CTGTAGCGACAACAGACCCAAGTCCAGGGGGAGCTACTCCTTCACAGGGGCTTTAAACTAGTATACGCGGTCGCGCTCTATCTAGTTGGCGTTCAGTCGGAATAGTC

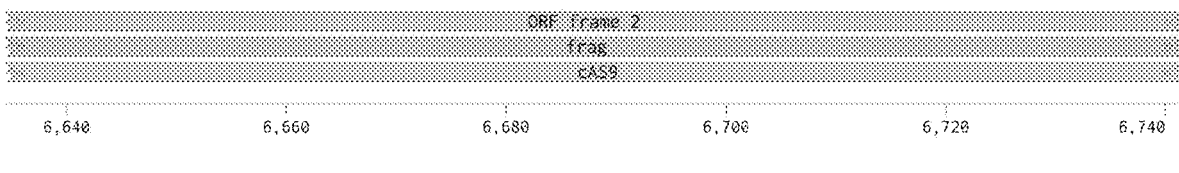

6,540     6,560     6,580     6,600     6,620

TACTGTCTACAAGCTTCTTCCTCAGATGATATATGGTTGGGTACTTTTCATGGTACGCCACCTCGTCCACGATATTGCCAAAGATTGGGTGGCGCTCGTGCTTTTTA
ATGACAGATGTTCGAAGAAGGAGTCTACTATATACCAACCCATGAAAAGTACCATGCGGTGGAGCAGGTGCTATAACGGTTTCTAACCCACCGCGAGCACGAAAAAT

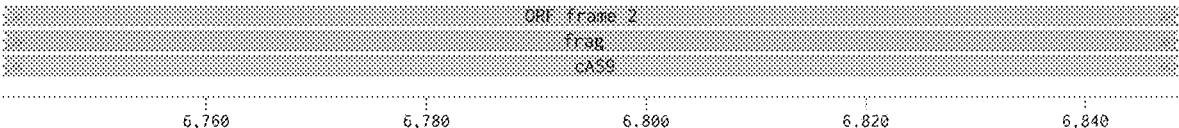

6,640     6,660     6,680     6,700     6,720     6,740

TCCTCCTCCACCAAAAAGGACTCCTCCAGCCTATGGAAGAAAGAGTCATCCACCTTAGCCATCTCATTACTAAAGATCTCCTGCAGGTAGCAGATCCGATTCTTTCT
AGGAGGAGGTGGTTTTTCCTGAGGAGGTCGGATACCTTCTTTCTCAGTAGGTGGAATCGGTAGAGTAATGATTTCTAGAGGACGTCCATCGTCTAGGCTAAGAAAGA

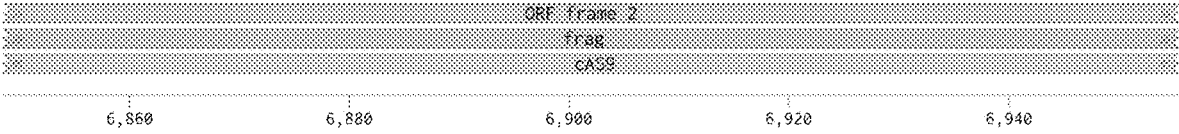

6,760     6,780     6,800     6,820     6,840

GCGGGTATATCTGCGCCGTGCTGTTCTTTTGAGCCGCGTGGCTTCGGCCGTCTCCCCGGAGTCGAACAGGAGGGCGCCAATGAGGTTCTTCTTTATGCTGTGGCGAT
CGCCCATATAGACGCGGCACGACAAGAAAACTCGGCGCACCGAAGCCGGCAGAGGGGCCTCAGCTTGTCCTCCCGCGGTTACTCCAAGAAGAAATACGACACCGCTA 6,860     6,880     6,900     6,920     6,940

CGGTATTGCCCAGAACTTTGAATTTTTTTGCTCGGCACCTTGTACTCGTCCGTAATGACGGCCCAGCCGACGCTGTTTGTGCCGATATCGAGCCCAATGGAGTACTTC
GCCATAACGGGTCTTGAAACTTAAAAAACGAGCCGTGGAACATGAGCAGGCATTACTGCCGGGTCGGCTGCGACAAACACGGCTATAGCTCGGGTTACCTCATGAAG

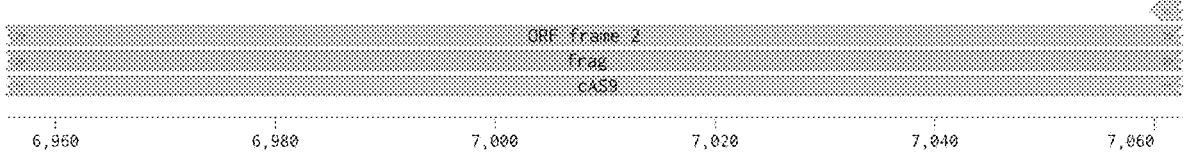

6,960     6,980     7,000     7,020     7,040     7,060

FIG. 44 CONTINUED dribblev2 s2 (14153 bp) (from 70- 3@704 bp)

Ncol

```
TTGTCCATGGCGAAAATCCGGGTCGAAAGTTACGGTTATCGCGCACTCTACTTTCCACAAATCCTCACCCAAAAACCAAGCACAGTTTATTCAACTGAAGTATTCGC
AACAGGTACCGCTTTTAGGCCCAGCTTTCAATGCCAATAGCGCGTGAGATGAAAGGTGTTTAGGAGTGGGTTTTTGGTTCGTGTCAAATAAGTTGACTTCATAAGCG
```

ORF frame 2 frag

```
        7,080              7,100              7,120              7,140              7,160
```

```
GATACTTCTTTATCTAATAATAATGTACATGTAACTAAACTCGCTTTTGGGTTAAAATCGTGACGCAGAGGCAAAAAAAATCGTATGTCCCTTAGACAACTTGAAAC
CTATGAAGAAATAGATTATTATTACATGTACATTGATTTGAGCGAAAACCCAATTTTAGCACTGCGTCTCCGTTTTTTTTTAGCATACAGGGAATCTGTTGAACTTTG
``` frag nos-promoter+5'UTR

```
    7,180          7,200          7,220          7,240          7,260
```

```
AACTGCGAAGCGTACGGCAATTCCAGGAATTTTGTGGTAAAGCTACGCGCCAACTAACGGTTCTTGCTTAGAGGTGGAATAATGTAGTTTTCCAGCGATAATAAATA
TTGACGCTTCGCATGCCGTTAAGGTCCTTAAAACACCATTTCGATGCGCGGTTGATTGCCAAGAACGAATCTCCACCTTATTACATCAAAAGGTCGCTATTATTTAT
``` frag nos-promoter+5'UTR

```
7,280          7,300          7,320          7,340          7,360          7,380
```

```
TATCGATATTTTTAGTAAAATTGAAAAGGTAAACTTAATTTTAGAAAATAATTTATAAGAAATTTAATAGTATGCAAAATAATTTTTACTTGCTAAGAATATGTGCC
ATAGCTATAAAAATCATTTTAACTTTTCCATTTGAATTAAAATCTTTTATTAAATATTCTTTAAATTATCATACGTTTTATTAAAAATGAACGATTCTTATACACGG
``` frag nos-promoter+5'UTR

```
        7,400              7,420              7,440              7,460              7,480
```

```
ACTAATTAAAAGCTGGACACCGCGCAATGGAAAATAGTACTACAACACAGCAACAAAGCCTGAGTTATCAACAAAAAAATACGAAAACATCTCCCAAAACTAAGCAC
TGATTAATTTTCGACCTGTGGCGCGTTACCTTTTATCATGATGTTGTGTCGTTGTTTCGGACTCAATAGTTGTTTTTTTTATGCTTTTGTAGAGGGTTTTGATTCGTG
``` frag nos-promoter+5'UTR

```
    7,500          7,520          7,540          7,560          7,580
```

```
CCACACGCGCCACTCGCCGTCACAACACAATCACTGCACACCACCATTCGAATTTCGCGCACTGTGACAACATCACATGATATCGGCGCGGCAACATCGGATTACCG
GGTGTGCGCGGTGAGCGGCAGTGTTGTGTTAGTGACGTGTGGTGGTAAGCTTAAAGCGCGTGACACTGTTGTAGTGTACTATAGCCGCGCCGTTGTAGCCTAATGGC
``` frag nos-promoter+5'UTR

```
7,600          7,620          7,640          7,660          7,680          7,700
```

FIG. 44 CONTINUED dribblev2 s2 (14153 bp) (from 7705-8346 bp)

NaeI
NgoMIV
SgrAI                                              SgrAI

ACAAAACGAACTATCGCACGAGCCACCGCCGGCGAAGAGCGCTCGTTTTGCAACACCGGCGCGCGCTGAACGAAGAGAACAGCTGACTGCTTGATACGTGCGTGTTT
TGTTTTGCTTGATAGCGTGCTCGGTGGCGGCCGCTTCTCGCGAGCAAAACGTTGTGGCCGCGCGCGACTTGCTTCTCTTGTCGACTGACGAACTATGCACGCACAAA frag
nos-promoter+5'UTR 7,720          7,740          7,760          7,780          7,800

PstEII

CGCGGCAGGAATTACATAAAGTTTAGAGCCTCTGACGCCAGACCCCCCGAACATTCGCTCCGATCAAACTACCTGCGAACGGTCACCTAATCCCCACCATGCATGGT
GCGCCGTCCTTAATGTATTTCAAATCTCGGAGACTGCGGTCTGGGGGGCTTGTAAGCGAGGCTAGTTTGATGGACGCTTGCCAGTGGATTAGGGGTGGTACGTACCA frag
nos-promoter+5'UTR 7,820          7,840          7,860          7,880          7,900

PstEII

AGGTTACCTCTGATCCCGGTCATCACTGGCGTTCGCTCACATCCGTCCTTACATGTGCATATTTCGAGGTTAAAACGGTCGAAGCTTGGATCCGCTAGCgttgttgg
TCCAATGGAGACTAGGGCCAGTAGTGACCGCAAGCGAGTGTAGGCAGGAATGTACACGTATAAAGCTCCAATTTTGCCAGCTTCGAACCTAGGCGATCGcaacaacc frag
nos-promoter+5'UTR 7,920          7,940          7,960          7,980          8,000          8,020 ttggcacaccacaaatatactgttgccgagcacaattgatcggctaaatggtatggcaagaaaaggtatgcaatataataatctttattgggtatgcaacgaaaat
aaccgtgtggtgtttatatgacaacggctcgtgttaactagccgatttaccataccgttcttttccatacgttatattattagaaaataacccatacgttgctttta frag
Gypsy Insulator(1)

8,040          8,060          8,080          8,100          8,120 ttgtttcgtcaacgtatgcaatattctttattaaaagagggtatgcaatgtattttattaaaaacgggtatgcaatataataatctttattgggtatgcaacgaaa
aacaaagcagttgcatacgttataagaaataattttctcccatacgttacataaaataatttttgcccatacgttatattattagaaaataacccatacgttgcttt frag
Gypsy Insulator(1)                    Gypsy Insulator(1)

8,140          8,160          8,180          8,200          8,220 atttgtttcgtcaaagtatgcaatattttttattaaaagagggtatgcaatgtatttattaaaaacgggtatgcaataaaaaattatttggtttctctaaaaagta
taaacaaagcagtttcatacgttataaaaaataattttctcccatacgttacataaaataattttttgcccatacgttattttttaataaaccaaagagattttttcat frag
Gypsy Insulator(1)                    Gypsy Insulator 8,240          8,260          8,280          8,300          8,320          8,340

FIG. 44 CONTINUED dribblev2 s2 (14153 bp) (from 8347-9095 bp)

```
tgcagcacttattttttgataaggtatgcaacaaaattttactttgccgaaaatatgcaatgttttttgcgaataaattcaacgcacacttattacgtggccaaCTAG
acgtcgtgaataaaaaactattccatacgttgttttaaaatgaaacggcttttatacgttacaaaaacgcttatttaagttgcgtgtgaataatgcaccggttGATC
```
                                              frag
                                        Gypsy Insulator

```
         8,360              8,380              8,400              8,420              8,440
```

```
     AGTTCCAGTGAAATCCAAGCaagcacttaggtcagcgtct
CCTAGTTCCAGTGAAATCCAAGCaagcacttaggtcagcgtctgatgaattctttttttgctcacctgtgattgctcctactcaaatacaaaaacatcaaatttttctg
GGATCAAGGTCACTTTAGGTTCGttcgtgaatccagtcgcagactacttaagaaaaaacgagtggacactaacgaggatgagtttatgttttttgtagtttaaaagac
     TCAAGGTCACTTTAGGTTCGttcgtgaatccagtcgcaga
```

```
         frag
        source                                        dU6-3 promoter
```

```
       8,460              8,480              8,500              8,520              8,540              8,560
```

```
tcaataaagcatatttatttatatttattttacaggaaagaattcctttttaaagtgtattttaacctataatgaaaaacgattaaaaaaaaatacataaaataattcg
agttatttcgtataaataaatataaataaaatgtcctttcttaaggaaaatttcacataaaattggatattacttttttgctaattttttttatgtattttattaagc
```
                                            dU6-3 promoter

```
         8,580              8,600              8,620              8,640              8,660
```

```
aaaattttttgaatagcccaggttgataaaaattcatttcatacgtttttataacttatgcccctaagtattttttgaccatagtgtttcaattctacattaattttac
ttttaaaaacttatcgggtccaactattttttaagtaaagtatgcaaaatattgaatacggggattcataaaaaactggtatcacaaagttaagatgtaattaaaatg
```
                                            dU6-3 promoter

```
         8,680              8,700              8,720              8,740              8,760
```

```
agagtagaatgaaacgccacctactcagccaagaggcgaaaaggttagctcgccaagcagagagggcgccagtgctcactactttttataattctcaacttcttttt
tctcatcttactttgcggtggatgagtcggttctccgcttttccaatcgagcggttcgtctctcccgcggtcacgagtgatgaaaaatattaagagttgaagaaaaa
```
                                            dU6-3 promoter

```
         8,780              8,800              8,820              8,840              8,860              8,880
```

```
ccagactcagttcgtatatatagacctattttcaatttaacgtcgTCAAGTCGGAAGAAGGAGGAGTTTCagagctaTGCTGgaaaCAGCAtagcaagttGaaataa
ggtctgagtcaagcatatatatctggataaaagttaaattgcagcAGTTCAGCCTTCTTCCTCCTCAAAGtctcgatACGACctttGTCGTatcgttcaaCttttatt
```
                                                                    ▷
                                                           ▓▓▓▓ ▷▶ ▷           ◁▓▓
```
              dU6-3 promoter                         M2-dbe G1
```

```
         8,900              8,920              8,940              8,960              8,980
```

```
ggctagtccgttatcaacttgaaaaagtggcaccgagtcggtgcttttttgcctacctggagcctgagagttgttcaataaaataaaaatgtttcgtttttttgctt
ccgatcaggcaatagttgaacttttttcaccgtggctcagccacgaaaaaacggatggaccatcggactctcaacaagttattttattttttacaaagcaaaaaaacgaa
```
     priming site ▷
                                                 repeated after u6.1 ▷

```
         9,000              9,020              9,040              9,060              9,080
```

FIG. 44 CONTINUED dribblev2 s2 (14153 bp) (from 909- 69844 bp)

tcgccagtatttattattttttcatcaatatgtattcaatttggtatgtatttagtaattgtaatatatagacaatggttttccgttgacgtacatacatctgacgtg
agcggtcataaataataaaaagtagttatacataagttaaaccatacataaatcattaacattatatatctgttaccaaaaggcaactgcatgtatgtagactgcac 9,100          9,120          9,140          9,160          9,180          9,200 tgtttatttagacataatagttatgttttcacatctttttaatgttcgcttaatgcgtatgcattctagattttcaacgtcctcgatagtatagtggttagtatccc
acaaataaatctgtattatcaatacaaaagtgtagaaaaaattacaagcgaattacgcatacgtaagatctaaaagttgcaggagctatcatatcaccaatcataggg
                                                                          source 9,220          9,240          9,260          9,280          9,300 cgcctgtcacgcgggagaccgggggttcaattccccgtcggggagaatctgtgattcttttttttttttcttttactttgttatataaacaattttgttttaattgaa
gcggacagtgcgccctctggccccaagttaaggggcagcccctcttagacactaagaaaaaaaaaaagaaaatgaaacaatatatttgttaaaaacaaaattaactt
                    RNA polymerase III promoter for Drosophila U6-1 snRNA (Port et al., 2014)
                                             source 9,320          9,340          9,360          9,380          9,400 tctaatttgccattgcttttaggaatctcaggcatccagcaagcgtttgtccgccgaatcgcccatcagtgaagaagatcctgtggcggctacgaaaatctccccgg
agattaaacggtaacgaaaatccttagagtccgtaggtcgttcgcaaacaggcggcttagcggggtagtcacttcttctaggacaccgccgatgctttagagggggcc
                    RNA polymerase III promoter for Drosophila U6-1 snRNA (Port et al., 2014)
                                             source 9,420          9,440          9,460          9,480          9,500          9,520

SRT
ccatgtcggcctccacctccagcgaaaaacccatcagcgagctggccacctctgtgctgacccaccgctttccagactccacctcctcacccggcgaacatggcctt
ggtacagccggaggtggaggtcgcttttttgggtagtcgctcgaccggtggagacacgactgggtggcgaaaggtctgaggtggaggagtgggccgcttgtaccggaa
                    RNA polymerase III promoter for Drosophila U6-1 snRNA (Port et al., 2014)
                                             source 9,540          9,560          9,580          9,600          9,620 ggacgaatgcagttgtcgatccgctacagcgcccagcgtcaaaaactagacgtgaccatacacaaaatccagaagataccacttcgcgatcccagcaatatccccga
cctgcttacgtcaacagctaggcgatgtcgcgggtcgcagtttttgatctgcactggtatgtgtttaggtcttctatggtgaagcgctagggtcgttataggggct
                    RNA polymerase III promoter for Drosophila U6-1 snRNA (Port et al., 2014)
                                             source 9,640          9,660          9,680          9,700          9,720 tccgtatgttaagctgtatctgttgcctggacgcaccaaggagtcgaaacgcaagacgagcgtgatcaaggacaactgcaaccccgtctacgatgcatcctttgagt
aggcatacaattcgacatagacaacggacctgcgtggttcctcagctttgcgttctgctcgcactagttcctgttgacgttggggcagatgctacgtaggaaactca
                    RNA polymerase III promoter for Drosophila U6-1 snRNA (Port et al., 2014)
                                             source 9,740          9,760          9,780          9,800          9,820          9,840

FIG. 44 CONTINUED dribblev2 s2 (14153 bp) (from 9845-10593 bp)

```
acctgatttccattgccgaactcaggcagacggaactggaggtgacggtgtgcacccaaaagggattcctatccggcggtagtcccatcattggcatggtaggtacc
tggactaaaggtaacggcttgagtccgtctgccttgacctccactgccacacgtgggtttccctaaggataggccgccatcagggtagtaaccgtaccatccatgg
```

RNA polymerase III promoter for Drosophila U6-1 snRNA (Port et al., 2014)
source

```
      9,860              9,880              9,900              9,920              9,940
```

```
cgaaagcaacccctttagttacagacacagcgcgtacgtccttcgcatccttatgattcccaagtacatattctgcaagagtacagtatatataggaaagatatccgg
gctttcgttggggaatcaatgtctgtgtcgcgcatgcaggaagcgtaggaatactaagggttcatgtataagacgttctcatgtcatatatatcctttctataggcc
```

RNA polymerase III promoter for Drosophila U6-1 snRNA (Port et al., 2014)
source

```
      9,960              9,980              10,000             10,020             10,040
```

```
gtgaacttcGTTAAGGCTCTGATGATCAAGGTTTCagagctaTGCTGgaaaCAGCAtagcaagttGaaataaggctagtccgttatcaacttgaaaaagtggcaccg
cacttgaagCAATTCCGAGACTACTAGTTCCAAAGtctcgatACGACcttttGTCGTatcgttcaaCtttattccgatcaggcaatagttgaacttttttcaccgtggc
```

M2-dbe G2        priming site

```
10,060        10,080        10,100        10,120        10,140        10,160
```

SbfI

```
agtcggtgctttttttgcctacctggagcctgagagttgttcaatctagacaattgtgctcggcaacagtatatttgtggtgtgccaaccaacaacctgcaggagctc
tcagccacgaaaaaacggatggacctcggactctcaacaagttagatctgttaacacgagccgttgtcatataaacaccacacggttggttgttggacgtcctcgag
``` repeated after U6-3    20bp!

```
10,180        10,200        10,220        10,240        10,260
```

```
cagcttttgttccctttagtgagggttaatttttttttgctcacctgtgattgctcctactcaaatacaaaaacatcaaattttctgtcaataaagcatatttattta
gtcgaaaacaagggaaatcactcccaattaaaaaaaacgagtggacactaacgaggatgagtttatgtttttgtagtttaaaagacagttatttcgtataaataaat
```

T3 promoter
priming site
T3           dU6-3 promoter

```
10,280        10,300        10,320        10,340        10,360
```

```
tatttattttacaggaaagaattccttttaaagtgtattttaacctataatgaaaaacgattaaaaaaaatacataaaataattcgaaaattttttgaatagcccagg
ataaataaaatgtcctttcttaaggaaaatttcacataaaattggatattacttttttgctaattttttttatgtattttattaagctttttaaaaacttatcgggtcc
``` dU6-3 promoter

```
        10,400             10,420             10,440             10,460             10,480
```

```
ttgataaaaattcatttcatacgtttttataacttatgcccctaagtattttttgaccatagtgtttcaattctacattaattttacagagtagaatgaaacgccacc
aactattttttaagtaaagtatgcaaaatattgaatacggggattcataaaaaactggtatcacaaagttaagatgtaattaaaatgtctcatcttactttgcggtgg
``` dU6-3 promoter

```
        10,500             10,520             10,540             10,560             10,580
```

FIG. 44 CONTINUED dribblev2 s2 (14153 bp) (from 10594-11449 bp)

```
tactcagccaagaggcgaaaaggttagctcgccaagcagagagggcgccagtgctcactacttttttataattctcaacttcttttttccagactcagttcgtatatat
atgagtcggttctccgcttttccaatcgagcggttcgtctctcccgcggtcacgagtgatgaaaaatattaagagttgaagaaaaaggtctgagtcaagcatatata
```
                                              dU6.3 promoter 10,600        10,620        10,640        10,660        10,680        10,700

```
agacctattttcaatttaacgtcgcggagctagatttgatggagGTTTCagagctaTGCTGgaaaCAGCAtagcaagttGaaataaggctagtccgttatcaacttg
tctggataaaagttaaattgcagcgcctcgatctaaactacctcCAAAGtctcgatACGACctttGTCGTatcgttcaaCtttattccgatcaggcaatagttgaac
```
                                                                                          priming site
   dU6.3 promoter       M2-dbe_G3

10,720        10,740        10,760        10,780        10,800

```
aaaaagtggcaccgagtcggtgcttttttgcctacctggagcctgagagttgttcaataaaataaaaatgtttcgttttttttgctttcgccagtatttattattttt
tttttcaccgtggctcagccacgaaaaaacggatggacctcggactctcaacaagttatttattttttacaaagcaaaaaaacgaaagcggtcataaataataaaaa
```
                                      repeated after U6-1

10,820        10,840        10,860        10,880        10,900

```
catcaatatgtattcaatttggtatgtatttagtaattgtaatatatagacaatggttttccgttgacgtacatacatctgacgtgtgtttatttagacataatagt
gtagttatacataagttaaaccatacataaatcattaacattatatatctgttaccaaaaggcaactgcatgtatgtagactgcacacaaatacatctgtattatca
```

10,920        10,940        10,960        10,980        11,000        11,020

```
tatgttttcacatcttttttaatgttcgcttaatgcgtatgcattctagattttcaacgtcctcgatagtatagtggttagtatccccgcctgtcacgcgggagaccg
atacaaaagtgtagaaaaattacaagcgaattacgcatacgtaagatctaaaagttgcaggagctatcatatcaccaatcataggggcggacagtgcgccctctggc
```
                                                                                source 11,040        11,060        11,080        11,100        11,120

```
gggttcaattccccgtcggggagaatctgtgattcttttttttttttcttttactttgttatataaacaatttttgttttaattgaatctaatttgccattgcttttta
cccaagttaaggggcagcccctcttagacactaagaaaaaaaaaaagaaaatgaaacaatatatttgttaaaaacaaaattaacttagattaaacggtaacgaaaat
```
     RNA polymerase III promoter for Drosophila U6-1 snRNA (Port et al., 2014)
                       source 11,140        11,160        11,180        11,200        11,220

SfiI

```
ggaatctcaggcatccagcaagcgtttgtccgccgaatcgcccatcagtgaagaagatcctgtggcggctacgaaaatctccccggccatgtcggcctccacctcca
ccttagagtccgtaggtcgttcgcaaacaggcggcttagcgggtagtcacttcttctaggacaccgccgatgctttagagggggccggtacagccggaggtggaggt
```
     RNA polymerase III promoter for Drosophila U6-1 snRNA (Port et al., 2014)
                       source 11,240        11,260        11,280        11,300        11,320        11,340

```
gcgaaaaacccatcagcgagctggccacctctgtgctgacccaccgctttccagactccacctcctcacccggcgaacatggccttggacgaatgcagttgtcgatc
cgcttttt gggtagtcgctcgaccggtggagacacgactgggtggcgaaaggtctgaggtggaggagtgggccgcttgtaccggaacctgcttacgtcaacagctag
```
     RNA polymerase III promoter for Drosophila U6-1 snRNA (Port et al., 2014)
                       source 11,360        11,380        11,400        11,420        11,440

FIG. 44 CONTINUED dribblev2 s2 (14153 bp) (from 11450-12198 bp)

cgctacagcgcccagcgtcaaaaactagacgtgaccatacacaaaatccagaagataccacttcgcgatcccagcaatatccccgatccgtatgttaagctgtatct
gcgatgtcgcgggtcgcagtttttgatctgcactggtatgtgtttttaggtcttctatggtgaagcgctagggtcgttatagggggctaggcatacaattcgacataga RNA polymerase III promoter for Drosophila U6-1 snRNA (Port et al., 2014)
source 11,460          11,480          11,500          11,520          11,540 gttgcctggacgcaccaaggagtcgaaacgcaagacgagcgtgatcaaggacaactgcaaccccgtctacgatgcatcctttgagtacctgatttccattgccgaac
caacggacctgcgtggttcctcagctttgcgttctgctcgcactagttcctgttgacgttggggcagatgctacgtaggaaactcatggactaaaggtaacggcttg RNA polymerase III promoter for Drosophila U6-1 snRNA (Port et al., 2014)
source 11,560          11,580          11,600          11,620          11,640          11,660 tcaggcagacggaactggaggtgacggtgtgcacccaaaagggattcctatccggcggtagtcccatcattggcatggtaggtacccgaaagcaaccccttagttac
agtccgtctgccttgacctccactgccacacgtgggtttttccctaaggataggccgccatcagggtagtaaccgtaccatccatgggctttcgttggggaatcaatg RNA polymerase III promoter for Drosophila U6-1 snRNA (Port et al., 2014)
source 11,680          11,700          11,720          11,740          11,760 agacacagcgcgtacgtccttcgcatccttatgattcccaagtacatattctgcaagagtacagtatatataggaaagatatccgggtgaacttcGgcaggaggac
tctgtgtcgcgcatgcaggaagcgtaggaatactaagggttcatgtataagacgttctcatgtcatatatatcctttctataggcccacttgaagCcgtcctcctg RNA polymerase III promoter for Drosophila U6-1 snRNA (Port et al., 2014)
source 11,780          11,800          11,820          11,840          11,860 aacccgcatGTTTCagagctaTGCTGgaaaCAGCAtagcaagttGaaataaggctagtccgttatcaacttgaaaaagtggcaccgagtcggtgctttttttgcctac
ttgggcgtaCAAAGtctcgatACGACcctttGTCGTatcgttcaaCtttattccgatcaggcaatagttgaacttttttcaccgtggctcagccacgaaaaaacggatg priming site 11,880          11,900          11,920          11,940          11,960          11,980 ctggagcctgagagttgttcaatctagacaattgtgctcggcaacagtatatttgtggtgtgccGTACCGGGCCAATTCGAGCTatcatcgatctcgaggctgcatc
gacctcggactctcaacaagttagatctgttaacacgagccgttgtcatataaacaccacacggCATGGCCCGGTTAAGCTCGAtagtagctagagctccgacgtag CATGGCCCGGTTAAGCTCGAtagtagctagagctccgacg 20bp1

12,000          12,020          12,040          12,060          12,080 caacgcgcgcgttgggagctctccggatcaattcggcttcaggtaccgtcgacgatgtaggtcacggtctcgaagccgcggtgcgggtgccagggcgtgcccttggg
gttgcgcgcgcaaccctcgagaggcctagttaagccgaagtccatggcagctgctacatccagtgccagagcttcggcgccacgcccacggtcccgcacgggaaccc attb 12,100          12,120          12,140          12,160          12,180

FIG. 44 CONTINUED dribblev2 s2 (14153 bp) (from 12199-12947 bp)

Smal
TspMI
XmaI ctccccgggcgcgtactccacctcacccatctggtccatcatgatgaacgggtcgaggtggcggtagttgatcccggcgaacgcgcggcgcaccgggaagccctcgc
gaggggcccgcgcatgaggtggagtgggtagaccaggtagtactacttgcccagctccaccgccatcaactagggccgcttgcgcgccgcgtggcccttcgggagcg attb 12,200            12,220            12,240            12,260            12,280            12,300 cctcgaaaccgctgggcgcggtggtcacggtgagcacgggacgtgcgacggcgtcggctgggtgcggatacgcggggcagcgtcagcgggttctcgacggtcacggc
ggagctttggcgacccgcgccaccagtgccactcgtgccctgcacgctgccgcagccgacccacgcctatgcgccccgtcgcagtcgcccaagagctgccagtgccg attb 12,320            12,340            12,360            12,380            12,400 gggcatgtcgacgacatgttcgcctcatttgtgttcgtttatgtattcgatgttatgtgtatgctcatgtgatgtttagcttgtaagcgcgagatgtgggtagcagg
cccgtacagctgctgtacaagcggagtaaacacaagcaaatacataagctacaatacacatacgagtacactacaaatcgaacattcgcgctctacacccatcgtcc attb            dhd-3'UTR 12,420            12,440            12,460            12,480            12,500

BstAPI agatgcagtgcagccaacagcagtgaccagatgatatatgctatgctactactactacttatatgctatgatttgtggcgcggaggcgtgtctgcgacacataatcc
tctacgtcacgtcggttgtcgtcactggtctactatatacgatacgatgatgatgatgaatatacgatactaaacaccgcgcctccgcacagacgctgtgtattagg dhd-3'UTR 12,540            12,560            12,580            12,600            12,620 cgcccatttagctttaagattcaggcactaagaagcaattcgatcaataaattattgtaaccactctgcatgtgagcaaaaggccagcaaaaggccaggaaccgtaa
gcgggtaaatcgaaattctaagtccgtgattcttcgttaagctagttatttaataacattggtgagacgtacactcgtttttccggtcgtttttccggtccttggcatt dhd-3'UTR                                                    source 12,640            12,660            12,680            12,700            12,720

OraI aaaggccgcgttgctggcgtttttccataggctccgcccccctgacgagcatcacaaaaatcgacgctcaagtcagaggtggcgaaacccgacaggactataaagat
tttccggcgcaacgaccgcaaaaaggtatccgaggcgggggggactgctcgtagtgtttttagctgcgagttcagtctccaccgctttgggctgtcctgatatttcta high-copy-number ColE1/pMB1/pBR322/pUC origin of replication
source 12,740            12,760            12,780            12,800            12,820            12,840 accaggcgtttcccctggaagctccctcgtgcgctctcctgttccgaccctgccgcttaccggatacctgtccgcctttctcccttcggaagcgtggcgctttct
tggtccgcaaaggggggaccttcgaggagcacgcgagaggacaaggctgggacggcgaatggcctatggacaggcggaaagagggaagcccttcgcaccgcgaaaga high-copy-number ColE1/pMB1/pBR322/pUC origin of replication
source 12,860            12,880            12,900            12,920            12,940

FIG. 44 CONTINUED dribblev2 s2 (14153 bp) (from 12948-13696 bp)

```
catagctcacgctgtaggtatctcagttcggtgtaggtcgttcgctccaagctgggctgtgtgcacgaaccccccgttcagcccgaccgctgcgccttatccggtaa
gtatcgagtgcgacatccatagagtcaagccacatccagcaagcgaggttcgacccgacacacgtgcttggggggcaagtcgggctggcgacgcggaataggccatt
         high-copy-number ColE1/pMB1/pBR322/pUC origin of replication
                              source
           12,960           12,980           13,000           13,020           13,040
```

```
ctatcgtcttgagtccaacccggtaagacacgacttatcgccactggcagcagccactggtaacaggattagcagagcgaggtatgtaggcggtgctacagagttct
gatagcagaactcaggttgggccattctgtgctgaatagcggtgaccgtcgtcggtgaccattgtcctaatcgtctcgctccatacatccgccacgatgtctcaaga
         high-copy-number ColE1/pMB1/pBR322/pUC origin of replication
                              source
       13,060           13,080           13,100           13,120           13,140           13,160
```

```
tgaagtggtggcctaactacggctacactagaagaacagtatttggtatctgcgctctgctgaagccagttaccttcggaaaaagagttggtagctcttgatccggc
acttcaccaccggattgatgccgatgtgatcttcttgtcataaaccatagacgcgagacgacttcggtcaatggaagcctttttctcaaccatcgagaactaggccg
         high-copy-number ColE1/pMB1/pBR322/pUC origin of replication
                              source
           13,180           13,200           13,220           13,240           13,260
```

```
aaacaaaccaccgctggtagcggtggtttttttgtttgcaagcagcagattacgcgcagaaaaaaaggatctcaagaagatcctttgatcttttctacggggtctga
tttgtttggtggcgaccatcgccaccaaaaaaacaaacgttcgtcgtctaatgcgcgtctttttttcctagagttcttctaggaaactagaaaagatgccccagact
    high-copy-number ColE1/pMB1/pBR322/pUC origin of replication
                              source
           13,280           13,300           13,320           13,340           13,360
```

```
cgctcagtggaacgaaaactcacgttaagggattttggtcatgagattatcaaaaaggatcttcacctagatcctttttaaattaaaaatgaagttttaaatcaatct
gcgagtcaccttgctttttgagtgcaattccctaaaaccagtactctaatagtttttttcctagaagtggatctaggaaaatttaattttttacttcaaaatttagttaga
                              source
      13,380           13,400           13,420           13,440           13,460           13,480
```

```
aaagtatatatgagtaaacttggtctgacagttaccaatgcttaatcagtgaggcacctatctcagcgatctgtctatttcgttcatccatagttgcctgactcccc
tttcatatatactcatttgaaccagactgtcaatggttacgaattagtcactccgtggatagagtcgctagacagataaagcaagtaggtatcaacggactgaggg g
                              source
                                            bla CDS
            13,500           13,520           13,540           13,560           13,580
```

```
gtcgtgtagataactacgatacgggagggcttaccatctggccccagtgctgcaatgataccgcgagacccacgctcaccggctccagatttatcagcaataaacca
cagcacatctattgatgctatgccctcccgaatggtagaccggggtcacgacgttactatggcgctctgggtgcgagtggccgaggtctaaatagtcgttatttggt
                              source
                              bla CDS
           13,600           13,620           13,640           13,660           13,680
```

FIG. 44 CONTINUED dribblev2 s2 (14153 bp) (from 13- 9761 4153 bp)

gccagccggaagggccgagcgcagaagtggtcctgcaactttatccgcctccatccagtctattaattgttgccgggaagctagagtaagtagttcgccagttaata
cggtcggccttcccggctcgcgtcttcaccaggacgttgaaataggcggaggtaggtcagataattaacaacggcccttcgatctcattcatcaagcggtcaattat

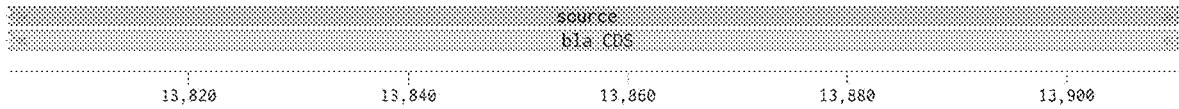

13,700        13,720        13,740        13,760        13,780        13,800 gtttgcgcaacgttgttgccattgctacaggcatcgtggtgtcacgctcgtcgtttggtatggcttcattcagctccggttcccaacgatcaaggcgagttacatga
caaacgcgttgcaacaacggtaacgatgtccgtagcaccacagtgcgagcagcaaaccataccgaagtaagtcgaggccaagggttgctagttccgctcaatgtact source
bla CDS 13,820        13,840        13,860        13,880        13,900

PvuI tccccatgttgtgcaaaaaagcggttagctccttcggtcctccgatcgttgtcagaagtaagttggccgcagtgttatcactcatggttatggcagcactgcataa
aggggggtacaacacgttttttcgccaatcgaggaagccaggaggctagcaacagtcttcattcaaccggcgtcacaatagtgagtaccaataccgtcgtgacgtatt source
bla CDS 13,920        13,940        13,960        13,980        14,000 ttctcttactgtcatgccatccgtaagatgctttttctgtgactggtgagtactcaaccaagtcattctgagaatagtgtatgcggcgaccgagttgctcttgcccgg
aagagaatgacagtacggtaggcattctacgaaaagacactgaccactcatgagttggttcagtaagactcttatcacatacgccgctggctcaacgagaacgggcc source
bla CDS 14,020        14,040        14,060        14,080        14,100        14,120 cgtcaatacgggataataccgcgccacat     SEQ ID NO: 177
gcagttatgccctattatggcgcggtgta     SEQ ID NO: 178 source
bla CDS 14,130    14,140    14,150

FIG. 44 CONTINUED

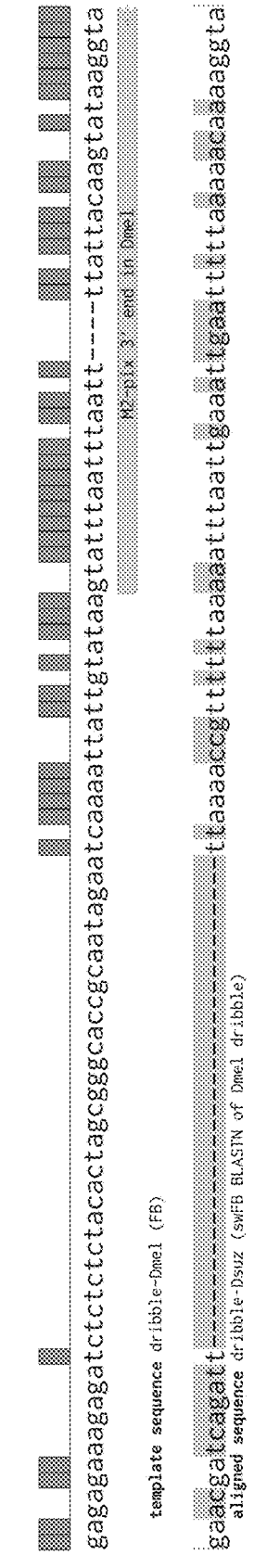
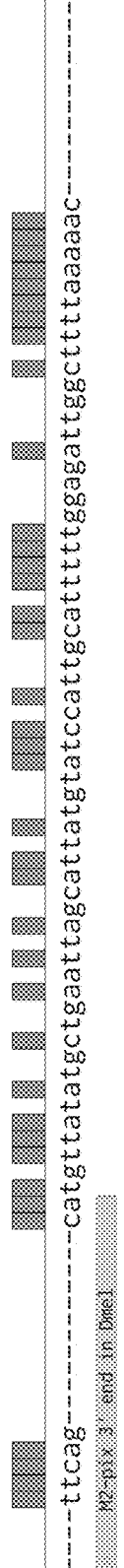
FIG. 45

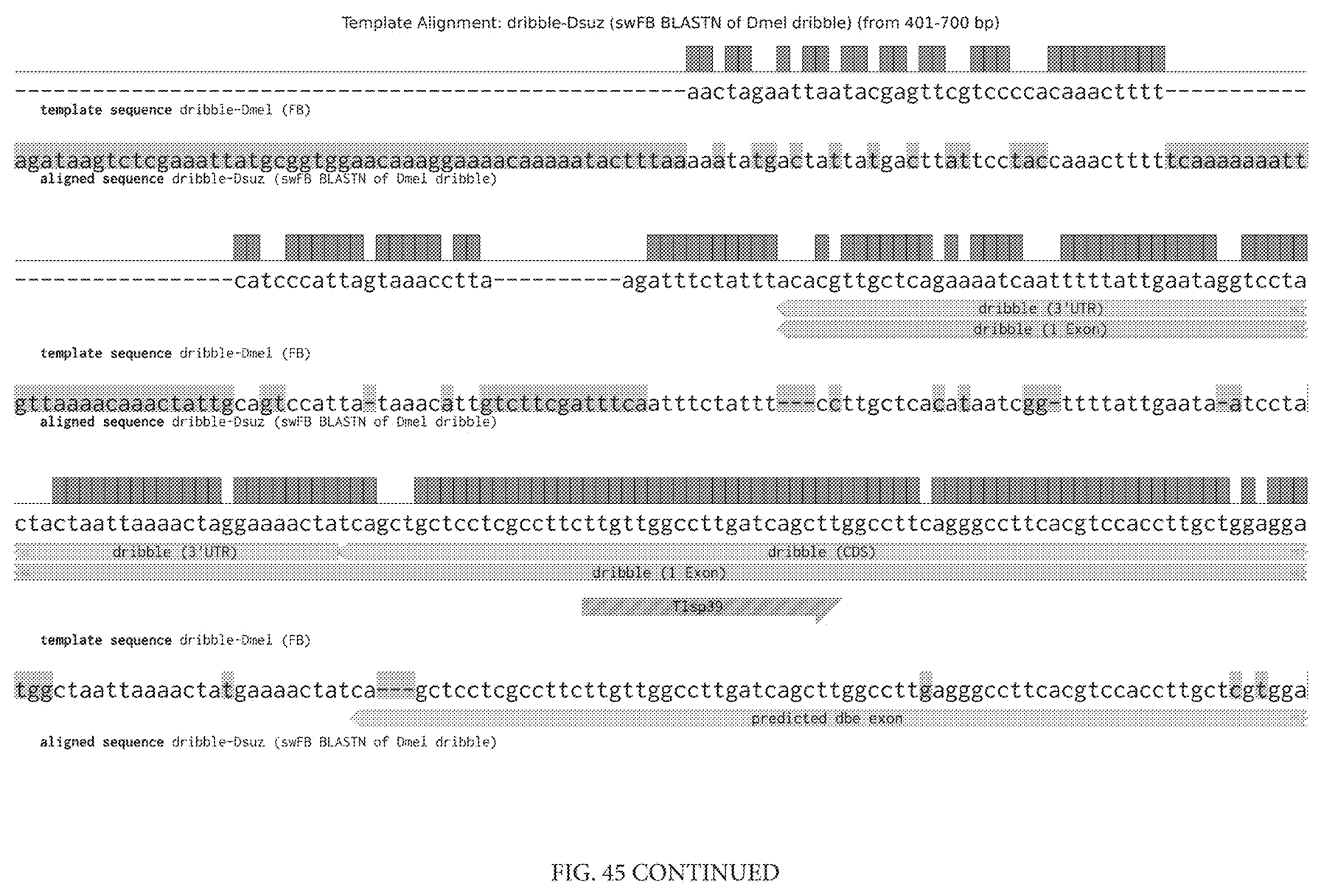

Template Alignment: dribble-Dsuz (swFB BLASTN of Dmel dribble) (from 401-700 bp)

------------------------------------------------------aactagaattaatacgagttcgtcccacaaacttt-------------
template sequence dribbie-Dmel (FB)

agataagtcttcgaaattatgccggtggaacaaaggaaacaaaaaactttaaaaatatgactattatgtgactatttattcctaccaaacttttttcaaaaaaatt
aligned sequence dribble-Dsuz (swFB BLASTN of Dmel dribble)

-----------catcccattagtaaacctta------------agatttctattacacgttgctcagaaatcaatttttattgaataggtccta
                                                    dribble (3'UTR)
                                                    dribble (1 Exon)
template sequence dribbie-Dmel (FB)

gttaaaacaaactattgcagtccatta-taaacattgtcttcgatttcaatttctattt---ccttgctcacataatcgg-ttttattgaata-atccta
aligned sequence dribble-Dsuz (swFB BLASTN of Dmel dribble)

ctactaattaaaactaggaaaactatcagctgctcctcgcctcttcttgttggccttctcgttggccttggccttcagggccttcacgtccacttgctggagga
                                                 dribble (CDS)
dribble (3'UTR)                            dribble (1 Exon)
                                      Tlsp39
template sequence dribbie-Dmel (FB)

tggctaattaaaactatgaaaactatca--gctcctcgcctcttgttggccttgatcagctggcccttgagggccttcacgtccacttgctcgtgga
                                          predicted dbe exon
aligned sequence dribble-Dsuz (swFB BLASTN of Dmel dribble)

FIG. 45 CONTINUED

Template Alignment: dribble-Dsuz (swFB BLASTN of Dmel dribble) (from 701-1000 bp)

ggagccatcctccttcttccgacttgaagcagctgactcctccgtgggcgggacaaagtccttgttcggcgttcgttcctggcgttcgttcctggcgcctccttc dribble (CDS)

dribble (1 Exon)

template sequence dribble-Dmel (FB)

ggaggcatcctccttccgattcgaagatgcagactcctccgtgggcgggcacaaagtccttgttgcggcggtcgccctggccgttgccgcctccttc predicted dbe exon aligned sequence dribble-Dsuz (swFB BLASTN of Dmel dribble)

tgcttttcggtgcgctcctggttgcgcttcgctcctggttgaggaagtactctccgctggccagctgcttgtccacctgctctccggct dribble (CDS)

dribble (1 Exon)

TSS39 template sequence dribble-Dmel (FB)

tgcttttcggtgcgctcctggttcgcttgcctgcttctgctcctggttgaggaagtactctccgctggccaactgcttgtccacctgctctccggct predicted dbe exon aligned sequence dribble-Dsuz (swFB BLASTN of Dmel dribble)

ggctgggcgcggaatggggtgtactccttcttttgcttcttgaccttcggctgcttgcgttgctaatgtttttgttcttgaacttgggcaggaatcggga dribble (CDS)

dribble (1 Exon)

template sequence dribble-Dmel (FB)

ggctgggcgcggaatggagtgtactccttcttttgcttcttcacttcggctgcttgcgttgctgatgttcttgttcttgaacttggcaggaacctaga predicted dbe exon aligned sequence dribble-Dsuz (swFB BLASTN of Dmel dribble)

FIG. 45 CONTINUED

Template Alignment: dribble-Dsuz (swFB BLASTN of Dmel dribble) (from 1001-1300 bp)

ccagtcctcgttggccagagacgcggatccttcatcagctcccgcttgatcatcagagccttaatgttgtatatggggtgcacattgttcatggtctccagg g1 (1 bp of PAM mutated)

dribble (CDS)

dribble (1 Exon)

template sequence dribble-Dmel (FB)

ccaatcctcgttggccaggcggggatccttcatcagctcggcgcttgatcatcagggcttgatgttgtatatgggatgcacattgttcatgtttccagg predicted dbe exon aligned sequence dribble-Dsuz (swFB BLASTN of Dmel dribble)

actatatcccgcacctgctgaaggcccttgtaaggaccaaggcggagactgtgttcttccttgaaccaaaacgtagcaatcggtgagcagttcaatggact dribble (CDS)

dribble (1 Exon)

template sequence dribble-Dmel (FB)

acaatatcccgcacctgctgaggccctgtatggacccaaggcggagacggtgtttccttgtaccagaacatagcagtcggtaagcagttcgatggact predicted dbe exon aligned sequence dribble-Dsuz (swFB BLASTN of Dmel dribble)

taagggtggcgcgttaggtccgatcaaacgctgtcgccgcttcacgaacttctcctcttcttgtgcacaaggtttccgatttgatgatgtcacacccaat dribble (CDS)

dribble (1 Exon)

template sequence dribble-Dmel (FB)

tcaggggtggcctccgttgggccatcaaacgctggcgccgcttcacgaacttctcctcttcttgtggactagattgccgatttgatgatgtcgcacccaat predicted dbe exon aligned sequence dribble-Dsuz (swFB BLASTN of Dmel dribble)

FIG. 45 CONTINUED

Template Alignment: dribble-Dsuz (swF    N of Dmel dribble) (from 1301-1600 bp)

gtcgtcctgcaggaccgcttggcctgctcgaagggaacacttctggccatcagcttgatcatatcccgcgccttgatgatgtaggatcccaggtc dribble (CDS)
dribble (1 Exon)

template  esqeune dribble-Dmel (FB)

gtcatcctgcaggaccgcttggcctgctcaagggcacactcctggccatcagcttgatcatgtccctcgccttgataatgatgtagggtcccaggtc predicted dbe exon alciuegd esqeune dribble-Dsuz (swFB BLASTN of Dmel dribble)

ttgcgactggtcttcaccaccatgctcccctccatcaaatctagctccgccttcaggtggtccgccaagcactgctccaccagagggccaaacctcct dribble (CDS)
dribble (1 Exon)

templated esqeune dribble-Dmel (FB)

ttacgactggtcttcaccaccatgctgccctccatcaggtccagttccgccttaggtggtgctcctccaggcactgctccaccagggggccagacctcct predicted dbe exon alciuegd esqeune dribble-Dsuz (swFB BLASTN of Dmel dribble)

taagatagcgctccgatatttgggaaacagcgtggcgaaggagctctcctcctccaccatccatgcggttgtctcctgcctgaaggccagggatcttcat dribble (CDS)
dribble (1 Exon)

templated esqeune dribble-Dmel (FB)

ttagatatcgctccggtatttgggaacagcgtggcgaaggagctcttccaccatccgtgcgggttgtctcctgcttgaaagccgggatcttcat predicted dbe exon alciuegd esqeune dribble-Dsuz (swFB BLASTN of Dmel dribble)

FIG. 45 CONTINUED

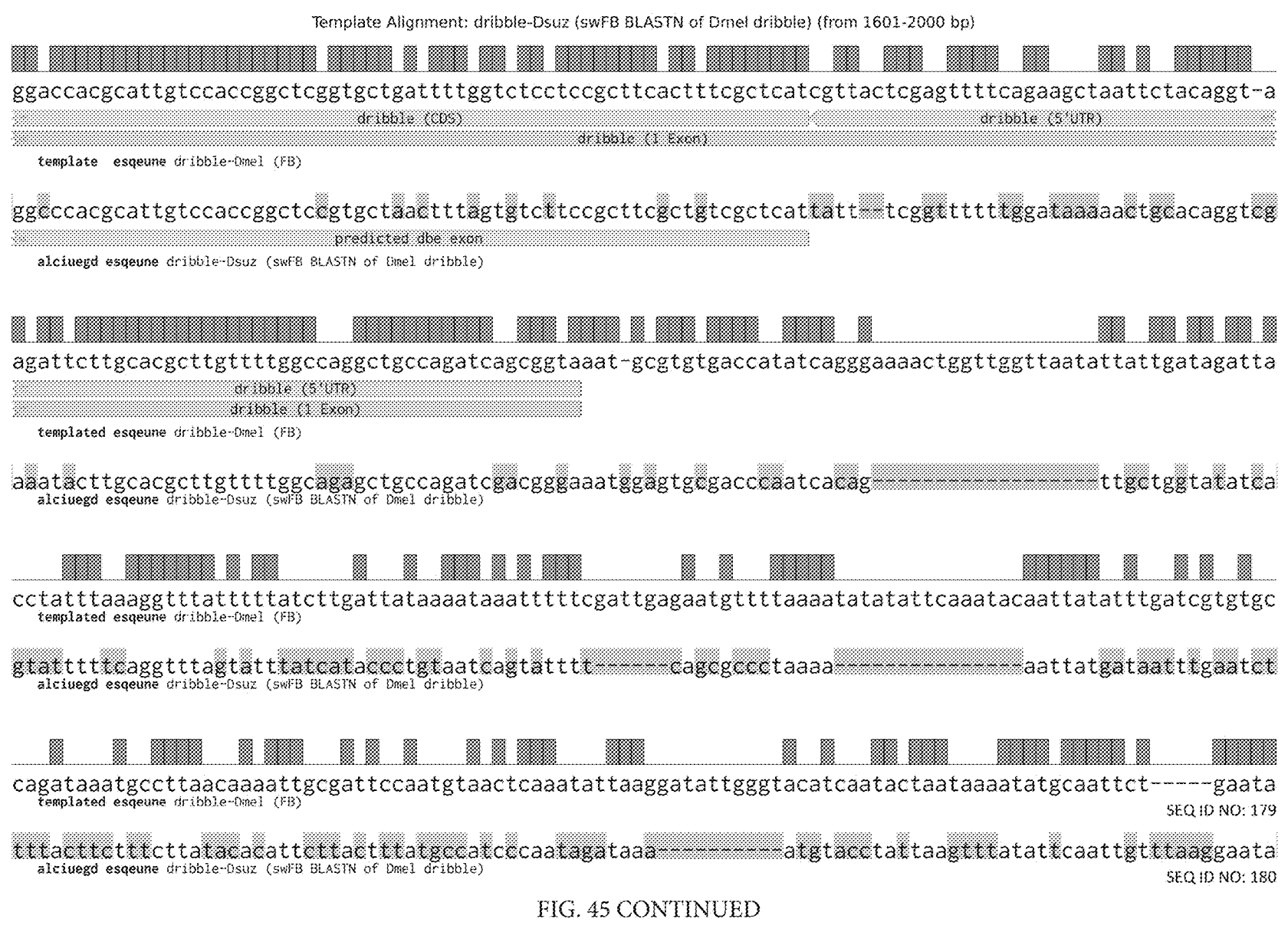

Template Alignment: dribble-Dsuz (swFB BLASTN of Dmel dribble) (from 1601-2000 bp)

ggaccacgcattgtccaccggctcggtgctgattttggtctcctccgctcactttcgctcatcgttactcgagtttcagaagctaattctacaggt-a
dribble (CDS)
dribble (5'UTR)
template   esqeune dribble-Dmel (FB)

ggccacgcattgtccaccggctccgtgctaactttagtgtcttccgcttcgcttcgctcattatt---tcggttttttggataaaaactgcacaggtcg
predicted dbe exon
alciuegd esqeune dribble-Dsuz (swFB BLASTN of Dmel dribble)

agattcttgcacgcttgtttggccaggctgccagatcagcggtaaat-gcgtgtgaccatatcagggaaaactggtggttaatattattgatagatta
dribble (5'UTR)
dribble (1 Exon)
templated esqeune dribble-Dmel (FB)

aaatacttgcacgcttgtttggcagagctgccagatcgacgggaaatggagtgtggacccaatcacag----------ttgctggtatatca
alciuegd esqeune dribble-Dsuz (swFB BLASTN of Dmel dribble)

cctatttaaaggtttattttttatcttgattataaaataaattttcgattgagaatgtttaaaatatatatcaaatacaattatatttgatcgtgtgc
templated esqeune dribble-Dmel (FB)

gtattttttcaggtttagtattttatcatcaccctgtaatcagtattt----cagcgcctaaaa----------aattatgatataattgaatct
alciuegd esqeune dribble-Dsuz (swFB BLASTN of Dmel dribble)

cagataaatgccttaacaaaattgcgattccaatgtaactcaatattaaggatattggtacatcaatactaataaaatatgcaattct----gaata
templated esqeune dribble-Dmel (FB)
SEQ ID NO: 179 tttacttcttttcttatacacacattcttacttttatgccatcccaatagataaa----------atgtacctattaagtttatatticaattgtttaaggaata
alciuegd esqeune dribble-Dsuz (swFB BLASTN of Dmel dribble)
SEQ ID NO: 180

FIG. 45 CONTINUED

Template Alignment: dribble-Dsuz (swFB BLASTN of Dmel dribble) (from 2001-2393 bp)

SEQ ID NO: 181

SEQ ID NO: 182

FIG. 45 CONTINUED (from 1-500 bp)

Template Alignment: D-suzukii rescue

```
                                                                          -acatagqcttgactgata-
------------------------------------------------------------------------
template sequence tfIIA-D genomic tctctgacggacacatagacccgttaattgagctgtcaaaatgggttaacgacatcgccagatatcggggaatacaacatccacacatagqtctgactgatag
aligned sequence D-suzukii rescue ---aaactgaaatgcattacgattattggacgattacttaccgttcaccatttgttggttaccccgagttgtttcctgctgagtgccaatatca
template sequence tfIIA-D genomic taccgatctgaaatgcattacgattactagatgataacttaccgttcaccatttgttggttaccccgagttgtttcctgctgagtgccaatatca
aligned sequence D-suzukii rescue acggatctgttataatccagtttgatgtaaagattttaatgcgacggaattaatttgccgatctttagtcaaacctttaaataatcgatacggata
template sequence tfIIA-D genomic acggatctgttataatccagtttgatgtaaagattttaatgcgacggaattaatttgccgatcttttgtaaaacctttaaataatcgatacggata
aligned sequence D-suzukii rescue ttatggattaatttgctattcaacgcaactttacttcctagaaggcgagaagtatttttaaa-gtgatggagacgcagcaggagtccaattg
template sequence tfIIA-D genomic ttatggattaatttgcttttgcaacgcgactttttacttcctagaaggcagaagtagtattttaaaggcatggggcgcagcaggagtccaattg
aligned sequence D-suzukii rescue gaaacatacaaaactagaaggga------------aggggggtacataaattattatattcacagggcggctgctcaa---tttgtttccattttctg
template sequence tfIIA-D genomic ggaaaacaaagaaagaaataacaacagagaagaaattcggggggtagataatttatttatattt-------ctgcttgggtttttttctgctgctgctt
aligned sequence D-suzukii rescue
```

FIG. 46

Template Alignment: D.suzukii rescue (from 501-1100 bp)

-ac-ac-ct-c---tt--c--ttccaaaataaaa--ttaaaaaaaaaa-aaaa-a-caact-ac--t--ctttgggggggggtaacta---c-aaa-c---cattaa
template sequence aflIAgD genomil-ac-ac-ct-c---tt--c--ttccaaaataaaattggggggggggggggaaataccc-ac--t--cttttta-t-aaataacta---c-aaa-c---cattaa
aligned sequence Dgsuzukii res-ue tataa-t-caaaggg-ac--tcaccttttt-cc-cctctaatc-t-c--ttatatttac-t-aaatctaaaaa---aac---t-aa-a-c--a-----tt---t-
template sequence aflIAgD genomitataa-t-caaa-ac-ac-tcaccttttt-cc-cctctaatc-t-c--ttatacttac-t-aaatctaaaaa---aaa---t-aaaa-ctt-c--gggggggg
aligned sequence Dgsuzukii res-ue -c-atc-a--c-aaaa--c-aaaa---t-aaa-aaac-cc-c-aatca-t-aa-c-tc-t-t-atcgggc-t-t-a-aa-tttta-t-t-aa-caaaac
template sequence aflIAgD genomiggggggg-t---c-aaaa--c-aaaa---t-aaa-aaac-cc-c-aatca-t-aa-c-gggggg-t-t-att-t-t-t-a-a-attttta-t-t-at-ctaaac
aligned sequence Dgsuzukii res-ue -taaaaat--a-a-cttac-ctaaataa-tc-tta-ac-aaccctataataactataac-aaa-c-t-acc-a-ta--c-t-tttctta-attccctaaa
template sequence aflIAgD genomil-taaaaat--a-a-cttac-ctaaatta-tc-tta-ac-aalccaataataaacataac-aaa-c-t-acc-a-ta--c-t-ttctta-aatccctaaa
aligned sequence Dgsuzukii res-ue a-aatacaataaaa--ctat-t-tatt-tttc-a-c-cc-caaacc-aaaa--c-ta-a-c-c-caaaa-ctaaatttta-c--a-ct-aa-cta--c
template sequence aflIAgD genomia-lacacaataaaa--ctat-t-tatt-tttc-a-c-cc-caaacc-aaaa--c-ta-a-c-c-caaaa-ccaaatttaa-c-aa-ctaaa-cta--c
aligned sequence Dgsuzukii res-ue --acc-tcaaa-gctaa-c-ccc-aa-a-aatttcacttcc-tcac--ac--caa--acaataacaaaaacaacaattaaca-tc-ctaatttt-cc-catc
template sequence aflIAgD genomil-acc--c-aaacctca-c-tggg-a-aaatttta-cttcc-tcaca-ac--aaa--aaaacaaaacaacaatgttaaca-tc-ctactttt-cc-catc
aligned sequence Dgsuzukii res-ue

FIG. 46 CONTINUED

Template Alignment: D-suzukii rescue (from 1101-1700 bp)

-a---a---a---c---at-ctatcttcc-ctatttattcttccccctggggggggccatcctt-ta--tctct-acta-ttcatat-ttac-tat-taaaggg
template sequence cfIIAgD tenomia -a---a---a---c---at-ctatctact-ctatttattcttccccattccatcccatcccctt---tctct-acta-ctcat---taa-t--t-taaat
aligned sequence Dgsuzukii resaue gggggggggggggggggggggggggggggggggggggggggggggggggggggggggggggggggggggggggggggggggggggggggggggggggg
template sequence cfIIAgD tenomia tat-ttctt--acattttttcttttctaccccccaattata-tat--at-a-atcatcac-ttc--a-tttttta-tcccccaccc--aatcat-ct
aligned sequence Dgsuzukii resaue gggggggggggggggggggggggggggggggggggggggggggggggggggggggggggggggggggggggggggggggggggggggggggggggggg
template sequence cfIIAgD tenomia tca-a-ac-acactcc--ac--at-ttt-t-aaacactcc-ctac--ctatactc--atc-tc--atc--t--ttc--t--ttt-tca--a-aa--atc
aligned sequence Dgsuzukii resaue gggggggggggggggggggggggggggggggggggggggggggggggggggggggggg-acat---cttac-a-aa------tcgggggggggggggggggg
template sequence cfIIAgD tenomia tttcta-tc--t--t-t-t-a---c-tct-t-t-aatc-ccc-tccttcatt--caa-at-atca-a-aa-----tcc-ttc-cccc--a-cct
aligned sequence Dgsuzukii resaue gggggggggggggggggggggggggtct-ac------ggggggggggggggggggggg-c-aa---c--a--c-cgggggggggggggggggga-actac
template sequence cfIIAgD tenomia tccacttcc--ac--atc-tca--ca--t--t-a---c-t-a-ttcatcc--acc---ca-a--c-c--ccc-cttaca--tccaatcc-t
aligned sequence Dgsuzukii resaue -cac-tat-ttca-aca-aa-ccgg-tact-ac--a-t-tacactc---tctaca--ac--ct--ac-a--ccgggggggggggggggggggggggg
template sequence cfIIAgD tenomia tcc-tc-ttt-ac-t--aa-cc-ttct-ac--a-gggcactcc--tcc-aa-t-catct---c-c--aca-c-caa-ctt-t-tt--t-ata
aligned sequence Dgsuzukii resaue

FIG. 46 CONTINUED

Template Alignment: D-suzukii rescue (from 1701-2200 bp)

```
--------accatgaaacaacaaac------------------------------------------------aaactcccgagagtcaga------
        template sequence cfIIA-D tenomig acttatggcctaccgaaaaactcctaacatatttgtacacatatattctgattatacaaaatttaaacggttcgttgaatgacaatcccac
        aligned sequence D-suzukii resgue ----------------------------------gacacccctgaccagcacccttcaacttgaccaa--------------------------
        template sequence cfIIA-D tenomig gcacgcatatgggcgaccggggacctgaagagccgagagacgacgaccaaaatagaattgcatatagagcccccaaaaacggctaaaacatatcgacaaccc
        aligned sequence D-suzukii resgue -----------------------------------------------------------------------------------------------
        template sequence cfIIA-D tenomig aaaaatggccagagaagaaggaagtcaaccccctgccgtgccgtagccgtcatcggcgtatcgagcgtagccgtataaaggcgcaggaaaaatatgaagaacggttacggaat
        aligned sequence D-suzukii resgue -----------------------------ataagggcccctctgggcagatacc-------------------------------------cctcaa------
        template sequence cfIIA-D tenomig atcattacagtccacgtgcgaaaagagtggtgggacgcatagatacgtgacccagtgcgcacatagcctagagcaaagactcccacctcaaagacagcga
        aligned sequence D-suzukii resgue --gtgaaccacccctgacaggga---------ggcgactcccggaataag--------------------------cgggccc------
        template sequence cfIIA-D tenomig accaaaaagcaaccaatgaccgaatacctccgccgaaaacagaagacgggaaagtcccggcaaaacagaagaaacccactgaagaaaccgagcgggcgaggact
        aligned sequence D-suzukii resgue
```

FIG. 46 CONTINUED

Template Alignment: D-suzukii rescue (from 2201-2600 bp)

----------------------------------ttttaacggaataacataacaaacatactcgactcggtgaactgtgaattaacagtgtatttcttgcaatgcctg
                                                                                                3'UTR
                                                                                                transcript
template sequence tfIIA-D genomic actatgaattctatatcaaagtagtttttcacggaataaataacaaaaatcctcgacttgttgaattaacagtatatttcttgcaatgccta
aligned sequence D-suzukii rescue ctgcatcgcacggtcgg-ttttcgtgtttttccaacccagcttatcgcctacgaatcttacagctatttgtaatggtgtgtttttgtggggttac
                                                                                3'UTR
                                                                                transcript
template sequence tfIIA-D genomic ctgcatcacacggtcggtttttggtggcccaacccagcttatcgactattgatcttaaactatttgttatgattataatggtgtatacgg-------
aligned sequence D-suzukii rescue atggtgtgtttagtggggttacattgggtgttcagatcggtcggtgtgttcagaactcgccgctcttgccgtcgcaggccacgatcttcaccttgtcc
                                                                                                exon2
                                                                                                transcript
template sequence tfIIA-D genomic ------------gtatatggggctcagatcggttggtgctcagaactcgccgctcttgccgtcgcaggccacgatcttgaccttgtcc
aligned sequence D-suzukii rescue acccttgacgatctcgtgcacttcgcggaactccacatcgttaagcatgagagtccagacattgtcgcagaagcggtaggtgtttagttttccagccttga
                                                                                                guide2
                                                                                                exon2
                                                                                                transcript
template sequence tfIIA-D genomic accttgacgaactcgtgcacctcgcggaactccacatcgttgagcatgagggtccagacattatcgcagaagcggtatgtgttcagttttccagccttga
aligned sequence D-suzukii rescue

FIG. 46 CONTINUED

Template Alignment: D-suzukii rescue (from 2601-3000 bp)

aggtgacgcgggccttgacccgctggtttagggcattgttgatgctctcttgtgtcgaattgcagcagaaccttgaaagccagtccggcgtaatctggccgta
template sequence tfIIA-D genomic aggttacgcgcgggccttgacccgctggtttgagggcattgttgatgctctcttgtgtcgaattgcagcagcaccttgaaagccaatccggcgtgtgatctgaccgta
aligned sequence D-suzukii rescue exon2 / transcript / guide3 ctgcaatatggaa--gcccaaaattacaatgcgtttcacttcgccagc----------gcg---aactcacctgaatcagctcgtcgaggctctcctgca
template sequence tfIIA-D genomic ctacaatatggaatccgtggaaaaattacaatacgttctgtttggacagccaatatgtgggcgcatagctcacctgaatcagctcatcgaggctctcctgca
aligned sequence D-suzukii rescue guide4 / exon4 / transcript gggtgttgccgagcgtgtggttgcggtacagttgatacgacatagtggc----tgccttaattccgacggaacagcttttcttctgcgacttttctacg
template sequence tfIIA-D genomic gtgtgttgccgagcgtggttgcggtattcggtaaagttgatataggacatggctgctctcgtgtttttttaatgccta------------tttcgactttcctgg
aligned sequence D-suzukii rescue 5UTR / transcript aacct-----gtcaagtcaagcaaaaatttttaatgcgaagcaacagattagtgttggttagcacgcgatagcgtgacactttggaacacttctgttatag
template sequence tfIIA-D genomic aattttccgatctagtcgagtataaaatttttaatgcgaagcaacagattagtgttggtaaggccgttgacgggctggcagtctgtcaacactgc---ttttgg
aligned sequence D-suzukii rescue 5UTR / transcript

FIG. 46 CONTINUED

Template Alignment: D-suzukii rescue (from 3001-3600 bp)

--ac--aat-tcc-att--ta-tac--cataacct-acac-a-ct-cc-attc-cattaa-t--c--ataacc--c-acc-tac-ccctcccc-ttccc
template sequence cgffIAD -enomia t--tc--aa--tc--c--c-tat-ac--cataaacttaAAAAAAAt-ac-a-aaaaaaaaaaaaaaaAAAAAAAAacatttcccaccttttcaattccc
aligned sequence DAsuzukii resaue tttttattct--ttttc--ctct-ca-t-ccaaaa-tactcat-tctaaa-cctacat-act-c---ttc-aattt---ttatcccatcatccccac---
template sequence cgffIAD -enomia c--tcaactaccc-tttt--tatatccctttccAAAAAAAAAAAAAAAAAAAAAAAAAacttttc-cttcccaattcc-attc-ccatcc--tt
aligned sequence DAsuzukii resaue tctca-tct-tctac-----ttcttttct-ca-c-taa-cccc-----a-CAAAAAAAAAAtcc-ct-atttt---t--a-AAAAAAa-c--act-c-ccccAA
template sequence cgffIAD -enomia tttCAAAAAAAAAAAAAAAAtct-a-cttcc--cttc-ctc-ct--t-acat-ct-tttctctaatact-t---a-aataaccacattaat-ctctccctt
aligned sequence DAsuzukii resaue AAAAAAAAAAAAAAAAAAAAAAAACCCC-ata-tt-tttttcactt-atccccattt-c-c---a-c--atttc-t-tAAAAAAAAAAAAAAAAAcattcta
template sequence cgffIAD -enomia tatcct-ttccctc-cta-cttcctctc-a-tt-attat-acct-c-ccAAAAAAA--ctt----a-c-ta--ac--at-cac-attatac-acccc--ttc
aligned sequence DAsuzukii resaue t-ta--tatc--aat-tca-taca--actcc-tcaac-tAAAAAAAAAAAAAAAAAAAAAAAAAAAAAcattttc-ctct-tattc-ctctc-tca-a
template sequence cgffIAD -enomia c-aa--tc-ct-c-tAAAAAAAat-ac--cataaacttat-ac-acatttccccccccttctaa-ccccctcctcccc-ttt-tctatcctttcccc
aligned sequence DAsuzukii resaue ttca-accaaccac-aac-ccaatctaccccatta-atcact-cttctataAAAA--ctcttcctttactc-t-ttc-ca--ct-aca-cttcct-Attca
template sequence cgffIAD -enomia tttc-AAAAAAAAAAAAAAAAActtcccctcttcatccccacttcattcatctttccctttcc-cttctc--ctttt-ctc-ct-t-ccatt-cat-ttttc
aligned sequence DAsuzukii resaue

FIG. 46 CONTINUED

Template Alignment: D-suzukii rescue (from 3601-4074 bp)

```
-a--aaaa--ccta--a--t--aataaa--ac--a--a--a--aa--a--a--aaact--aaaat--aaaaaaaat--aaattcacca--c--aata--t--t--taaa--atc
template sequence agfFlAD cenomit -a--ttt--ccccctt--taataAAAt--tt--ca--a-aaa--t--aaac--aa-ac-AAAAA-at--ttcaacaa-a--t--a-t--aa-t-AAAA
aligned sequence DAsuzukii restue ta-at-a--caaaccat-att--ctcctattca--tt--ccac----aataaca-t-attaccccatt-aaaaacaAAAAAAAA-t-tatctacaataact-
template sequence agfFlAD cenomit AAAAAAAAAAAAAAAAAAAAAAAAAAAAAAAAAAAAC----Ca-aaaca-AAAAAAA-c-tt-t-a-aaacaaa--tca--a-aaac-a--aa-aaa-
aligned sequence DAsuzukii restue t---t-ccc-tattcaaaa--a--a---accCAAAAAAAtaaacc---ttt-attaaac---aataa-aa-ctcaaaataacAAAaaa--ac-ct-ccaaaa
template sequence agfFlAD cenomit ta-cc--aattcat-a-aaata--atcc--atcat-a-a-c-cctcct-aaaac---c-cctaAaacctcaaaattt--taaacctaaaaaccatata
aligned sequence DAsuzukii restue cac-cat-tc---ataacaattactacctt--tt-caac-tctttaaaaattaaccttcacct--aa--tattaca-taaccct-cttaaaatat---
template sequence agfFlAD cenomit ctc-aattAa---ataataaattactacctt--tt--ctatc-taaaattaaccttcacct-ctt-caattaca-taacct-cttatttatc---
aligned sequence DAsuzukii restue CAAAAAAAAAAAAAAAAAAAAAAAAAAAAAAAAAAAAAAAAAAAAAAAAAAAA          SEQ ID NO: 187
template sequence agfFlAD cenomit ccatatt-acc-taataat-ttc-t-ataaccat--att-ataatacc--ct-ctct-act-aa-acc--t          SEQ ID NO: 188
aligned sequence DAsuzukii restue
```

FIG. 46 CONTINUED (from 1-749 bp)

tf2a-step2 (14152 bp)

SacII atcatcgatctcgaggctgcatccaacgcgcgcgttgggagctctccggatcaattcggcttcaggtaccgtcgacgatgtaggtcacggtctcgaagccgcggtgc
tagtagctagagctccgacgtaggttgcgcgcgcaaccctcgagaggcctagttaagccgaagtccatggcagctgctacatccagtgccagagcttcggcgccacg attb 20          40          60          80          100 gggtgccagggcgtgcccttgggctccccgggcgcgtactccacctcacccatctggtccatcatgatgaacgggtcgaggtggcggtagttgatcccggcgaacgc
cccacggtcccgcacgggaacccgaggggcccgcgcatgaggtggagtgggtagaccaggtagtactacttgcccagctccaccgccatcaactagggccgcttgcg attb 120          140          160          180          200 gcggcgcaccgggaagccctcgccctcgaaaccgctgggcgcggtggtcacggtgagcacgggacgtgcgacggcgtcggctgggtgcggatacgcggggcagcgtc
cgccgcgtggcccttcgggagcgggagctttggcgacccgcgccaccagtgccactcgtgccctgcacgctgccgcagccgacccacgcctatgcgccccgtcgcag attb 220          240          260          280          300          320 agcgggttctcgacggtcacggcgggcatgtcgacgacatgttcgcctcatttgtgttcgtttatgtattcgatgttatgtgtatgctcatgtgatgtttagcttgt
tcgcccaagagctgccagtgccgcccgtacagctgctgtacaagcggagtaaacacaagcaaatacataagctacaatacacatacgagtacactacaaatcgaaca attb          dhd-3'UTR 340          360          380          400          420 aagcgcgagatgtgggtagcaggagatgcagtgcagccaacagcagtgaccagatgatatatgctatgctactactactacttatatgctatgatttgtggcgcgga
ttcgcgctctacacccatcgtcctctacgtcacgtcggttgtcgtcactggtctactatatacgatacgatgatgatgatgaatatacgatactaaacaccgcgcct dhd-3'UTR 440          460          480          500          520 ggcgtgtctgcgacacataatcccgcccatttagctttaagattcaggcactaagaagcaattcgatcaataaattattgtaaccactctgcatgtgagcaaaaggc
ccgcacagacgctgtgtattagggcgggtaaatcgaaattctaagtccgtgattcttcgttaagctagttatttaataacattggtgagacgtacactcgttttccg dhd-3'UTR          source 540          560          580          600          620          640 cagcaaaaggccaggaaccgtaaaaaggccgcgttgctggcgttttttccataggctccgcccccctgacgagcatcacaaaaatcgacgctcaagtcagaggtggcg
gtcgtttttccggtccttggcattttttccggcgcaacgaccgcaaaaaggtatccgaggcggggggggactgctcgtagtgttttttagctgcgagttcagtctccaccgc source

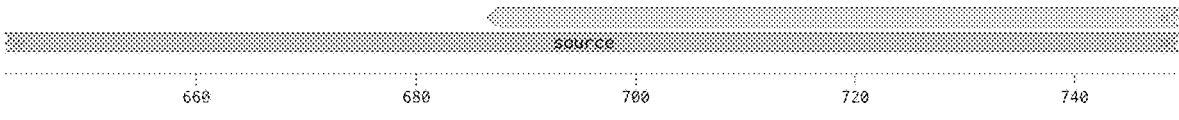

660          680          700          720          740

FIG. 47 tf2a-step2 (14152 bp) (from 750-1498 bp)

```
aaacccgacaggactataaagataccaggcgtttccccctggaagctccctcgtgcgctctcctgttccgaccctgccgcttaccggatacctgtccgcctttctcc
tttgggctgtcctgatatttctatggtccgcaaaggggggaccttcgaggagcacgcgagaggacaaggctggacggcgaatggcctatggacaggcggaaagagg
```
high-copy-number ColE1/pMB1/pBR322/pUC origin of replication
source
```
             760           780           800           820           840
```

```
cttcgggaagcgtggcgctttctcatagctcacgctgtaggtatctcagttcggtgtaggtcgttcgctccaagctgggctgtgtgcacgaaccccccgttcagccc
gaagcccttcgcaccgcgaaagagtatcgagtgcgacatccatagagtcaagccacatccagcaagcgaggttcgacccgacacacgtgcttggggggcaagtcggg
```
high-copy-number ColE1/pMB1/pBR322/pUC origin of replication
source
```
  860           880           900           920           940           960
```

```
gaccgctgcgccttatccggtaactatcgtcttgagtccaacccggtaagacacgacttatcgccactggcagcagccactggtaacaggattagcagagcgaggta
ctggcgacgcggaataggccattgatagcagaactcaggttgggccattctgtgctgaatagcggtgaccgtcgtcggtgaccattgtcctaatcgtctcgctccat
```
high-copy-number ColE1/pMB1/pBR322/pUC origin of replication
source
```
             980         1,000         1,020         1,040         1,060
```

```
tgtaggcggtgctacagagttcttgaagtggtggcctaactacggctacactagaagaacagtatttggtatctgcgctctgctgaagccagttaccttcggaaaaa
acatccgccacgatgtctcaagaacttcaccaccggattgatgccgatgtgatcttcttgtcataaaccatagacgcgagacgacttcggtcaatggaagcctttt
```
high-copy-number ColE1/pMB1/pBR322/pUC origin of replication
source
```
  1,080         1,100         1,120         1,140         1,160
```

```
gagttggtagctcttgatccggcaaacaaaccaccgctggtagcggtggtttttttgtttgcaagcagcagattacgcgcagaaaaaaaggatctcaagaagatcct
ctcaaccatcgagaactaggccgtttgtttggtggcgaccatcgccaccaaaaaaacaaacgttcgtcgtctaatgcgcgtcttttttttcctagagttcttctagga
```
high-copy-number ColE1/pMB1/pBR322/pUC origin of replication
source
```
1,180       1,200         1,220         1,240         1,260         1,280
```

```
ttgatctttttctacggggtctgacgctcagtggaacgaaaactcacgttaagggattttggtcatgagattatcaaaaaggatcttcacctagatcctttttaaatta
aactagaaaagatgccccagactgcgagtcaccttgcttttgagtgcaattccctaaaaccagtactctaatagtttttcctagaagtggatctaggaaaatttaat
```
source
```
     1,300         1,320         1,340         1,360         1,380
```

```
aaaatgaagtttttaaatcaatctaaagtatatatgagtaaacttggtctgacagttaccaatgcttaatcagtgaggcacctatctcagcgatctgtctatttcgtt
ttttacttcaaaaatttagttagatttcatatatactcatttgaaccagactgtcaatggttacgaattagtcactccgtggatagagtcgctagacagataaagcaa
```
bla CDS
source
```
     1,400         1,420         1,440         1,460         1,480
```

FIG. 47 CONTINUED

AfdT tf2a-step2 (14152 bp) (from 1477-2249 bp)

catccatagttgcctgactccccgtcgtgtagataactacgatacgggagggcttaccatctggccccagtgctgcaatgataccgcgagacccacgctcaccggct
gtaggtatcaacggactgaggggcagcacatctattgatgctatgccctcccgaatggtagaccggggtcacgacgttactatggcgctctgggtgcgagtggccga bia CDS
source 1,500       1,520       1,540       1,560       1,580       1,600 ccagatttatcagcaataaaccagccagccggaagggccgagcgcagaagtggtcctgcaactttatccgcctccatccagtctattaattgttgccgggaagctag
ggtctaaatagtcgttatttggtcggtcggccttcccggctcgcgtcttcaccaggacgttgaaataggcggaggtaggtcagataattaacaacggcccttcgatc bia CDS
source 1,620       1,640       1,660       1,680       1,700 agtaagtagttcgccagttaatagtttgcgcaacgttgttgccattgctacaggcatcgtggtgtcacgctcgtcgtttggtatggcttcattcagctccggttccc
tcattcatcaagcggtcaattatcaaacgcgttgcaacaacggtaacgatgtccgtagcaccacagtgcgagcagcaaaccataccgaagtaagtcgaggccaaggg bia CDS
source 1,720       1,740       1,760       1,780       1,800 aacgatcaaggcgagttacatgatcccccatgttgtgcaaaaaagcggttagctccttcggtcctccgatcgttgtcagaagtaagttggccgcagtgttatcactc
ttgctagttccgctcaatgtactaggggggtacaacacgttttttcgccaatcgaggaagccaggaggctagcaacagtcttcattcaaccggcgtcacaatagtgag bia CDS
source 1,820       1,840       1,860       1,880       1,900       1,920 atggttatggcagcactgcataattctcttactgtcatgccatccgtaagatgcttttctgtgactggtgagtactcaaccaagtcattctgagaatagtgtatgcg
taccaataccgtcgtgacgtattaagagaatgacagtacggtaggcattctacgaaaagacactgaccactcatgagttggttcagtaagactcttatcacatacgc bia CDS
source 1,940       1,960       1,980       2,000       2,020 gcgaccgagttgctcttgcccggcgtcaatacgggataataccgcgccacatagcagaactttaaaagtgctcatcattggaaaacgttcttcggggcgaaaactct
cgctggctcaacgagaacgggccgcagttatgccctattatggcgcggtgtatcgtcttgaaattttcacgagtagtaaccttttgcaagaagccccgctttggaga bia CDS
source 2,040       2,060       2,080       2,100       2,120       2,140 caaggatcttaccgctgttgagatccagttcgatgtaacccactcgtgcacccaactgatcttcagcatcttttactttcaccagcgtttctgggtgagcaaaaaca
gttcctagaatggcgacaactctaggtcaagctacattgggtgagcacgtgggttgactagaagtcgtagaaaatgaaagtggtcgcaaagacccactcgttttgt bia CDS
source 2,160       2,180       2,200       2,220       2,240

FIG. 47 CONTINUED tf2a-step2 (14152 bp) (from 2248-2889 bp)

ggaaggcaaaatgccgcaaaaaagggaataagggcgacacggaaatgttgaatactcatactcttccttttcaatattattgaagcatttatcagggttattgtct ccttccgttttacggcgtttttcccttattcccgctgtgcctttacaacttatgagtatgagaaggaaaaagttataataacttcgtaaatagtcccaataacaga catgagcggatacatatttgaatgtatttagaaaaataaacaaatagggggttccgcgcacatttccccgaaaagtgccacctgacgtcgacggatcgggagatcggc gtactcgcctatgtataaacttacataaatctttttatttgtttatccccaaggcgcgtgtaaaggggctttcacggtggactgcagctgcctagccctctagccg gcgggatctaattcaattagagactaattcaattagagctaattcaattaggatccaagcttatcgatttcgaaccctcgaccgccggagtataaatagaggcgctt cgccctagattaagttaatctctgattaagttaatcctaggttcgaatagctaaagcttgggagctggcggcctcatatttatctccgcgaa cgtctacggagcgacaattcaattcaaacaagcaaagtgaacacgtcgctaagcgaaagctaagcaaataaacaagcgcagctgaacaagctaaacaatcggctcga gcagatgcctcgctgttaagttaagtttgttcgtttcacttgtgcagcgattcgctttcgattcgtttatttgttcgcgtcgacttgttcgatttgttagccgagct gaccggtcgccaccatggtgagcaagggcgaggagctgttcaccggggtggtgcccatcctggtcgagctggacggcgacgtaaacggccacaagttcagcgtgtcc ctggccagcgcggtggtaccactcgttcccgctcctcgacaagtggccccaccacgggtaggaccagctcgacctgccgctgcatttgccggtgttcaagtcgcacagg ggcgagggcgagggcgatgccacctacggcaagctgaccctgaagttcatctgcaccaccggcaagctgcccgtgccctggcccaccctcgtgaccaccctgaccta ccgctcccgctcccgctacggtggatgccgttcgactgggacttcaagtagacgtggtggccgttcgacgggcacgggaccgggtgggagcactggtgggactggat

FIG. 47 CONTINUED tf2a-step2 (14152 bp) (from 2890-3638 bp)

cggcgtgcagtgcttcagccgctaccccgaccacatgaagcagcacgacttcttcaagtccgccatgcccgaaggctacgtccaggagcgcaccatcttcttcaagg
gccgcacgtcacgaagtcggcgatggggctggtgtacttcgtcgtgctgaagaagttcaggcggtacgggcttccgatgcaggtcctcgcgtggtagaagaagttcc source
EGFP ORF 2,900      2,920      2,940      2,960      2,980 acgacggcaactacaagacccgcgccgaggtgaagttcgagggcgacaccctggtgaaccgcatcgagctgaagggcatcgacttcaaggaggacggcaacatcctg
tgctgccgttgatgttctgggcgcggctccacttcaagctcccgctgtgggaccacttggcgtagctcgacttcccgtagctgaagttcctcctgccgttgtaggac source
EGFP ORF 3,000      3,020      3,040      3,060      3,080      3,100 gggcacaagctggagtacaactacaacagccacaacgtctatatcatggccgacaagcagaagaacggcatcaaggtgaacttcaagatccgccacaacatcgagga
cccgtgttcgacctcatgttgatgttgtcggtgttgcagatatagtaccggctgttcgtcttcttgccgtagttccacttgaagttctaggcggtgttgtagctcct source
EGFP ORF 3,120      3,140      3,160      3,180      3,200 cggcagcgtgcagctcgccgaccactaccagcagaacacccccatcggcgacgacgccccgtgctgctgcccgacaaccactacctgagcacccagtccgccctgagca
gccgtcgcacgtcgagcggctggtgatggtcgtcttgtggggggtagccgctgccggggcacgacgacgggctgttggtgatggactcgtgggtcaggcgggactcgt source
EGFP ORF 3,220      3,240      3,260      3,280      3,300

NotI aagaccccaacgagaagcgcgatcacatggtcctgctggagttcgtgaccgccgccgggatcactctcggcatggacgagctgtacaagtaaagcggccgcgactct
ttctggggttgctcttcgcgctagtgtaccaggacgacctcaagcactggcggcggcccctagtgagagccgtacctgctcgacatgttcatttcgccggcgctgaga source
EGFP ORF 3,320      3,340      3,360      3,380      3,400      3,420 agatcataatcagccataccacatttgtagaggtttttacttgctttaaaaaaacctcccacacctccccctgaacctgaaacataaaatgaatgcaattgttgttgtt
tctagtattagtcggtatggtgtaaacatctccaaaatgaacgaaattttttggagggtgtggaggggggacttggactttgtattttacttacgttaacaacaacaa source
SV40 terminator 3,440      3,460      3,480      3,500      3,520 aacttgtttattgcagcttataatggttacaaataaagcaatagcatcacaaatttcacaaataaagcattttttttcactgcattctagttgtggtttgtccaaact
ttgaacaaataacgtcgaatattaccaatgtttatttcgttatcgtagtgtttaaagtgtttatttcgtaaaaaaagtgacgtaagatcaacaccaaacaggtttga source
SV40 terminator 3,540      3,560      3,580      3,600      3,620

FIG. 47 CONTINUED tf2a-step2 (14152 bp) (from 3936-4464 bp)

catcaatgtatcttagttgttggttggcacaccacaaatatactgttgccgagcacaattgatcggctaaatggtatggcaagaaaaggtatgcaatataataatct
gtagttacatagaatcaacaaccaaccgtgtggtgtttatatgacaacggctcgtgttaactagccgatttaccataccgttcttttccatacgttatattattaga gfp REV source
Gypsy Insulator (1)

3,640          3,660          3,680          3,700          3,720          3,740 tttattgggtatgcaacgaaaatttgtttcgtcaacgtatgcaatattctttattaaaagagggtatgcaatgtattttattaaaaacgggtatgcaatataataat
aaataaacccatacgttgcttttaaacaaagcagttgcatacgttataagaaataattttctcccatacgttacataaaataattttttgcccatacgttatattatta Gypsy Insulator (1)          Gypsy Insulator (1)

3,760          3,780          3,800          3,820          3,840 ctttttattgggtatgcaacgaaaatttgtttcgtcaaagtatgcaatattttttattaaaagagggtatgcaatgtattttattaaaaacgggtatgcaataaaaaa
gaaaataacccatacgttgcttttaaacaaagcagtttcatacgttataaaaaataattttctcccatacgttacataaaataatttttgcccatacgttattttttt Gypsy Insulator (1)          Gypsy Insulator 3,860          3,880          3,900          3,920          3,940 ttatttggtttctctaaaaagtatgcagcacttattttttgataaggtatgcaacaaaattttactttgccgaaaatatgcaatgttttttgcgaataaattcaacgc
aataaaccaaagagattttttcatacgtcgtgaataaaaaactattccatacgttgttttaaaatgaaacggctttttatacgttacaaaaacgcttatttaagttgcg Gypsy Insulator 3,960          3,980          4,000          4,020          4,040          4,060 acacttattacgtggccaacgcgcctagTGGATCCTTCCTGGCCCTTTTCGAGAAACGCCGCGAGGGCGAAAAGGATTAGTTGTTTCAAACGCAAGAAGGACATTTG
tgtgaataatgcaccggttgcgcggatcACCTAGGAAGGACCGGGAAAAGCTCTTTGCGGCGCTCCCGCTTTTCCTAATCAACAAAGTTTGCGTTCTTCCTGTAAAC nos3'UTR 4,080          4,100          4,120          4,140          4,160

PspXI
TTTCCTTAAATTGTAACCATTTCTTTATTTGGCACTCGAGCCATTGAATTTTTCATTTTCAGAATATGTGTACACATTTTTTAAAAAAATAAAAAAATTATATAATG
AAAGGAATTTAACATTGGTAAAGAAATAAACCGTGAGCTCGGTAACTTAAAAAGTAAAAGTCTTATACACATGTGTAAAAAATTTTTTTATTTTTTTAATATATTAC nos3'UTR 4,180          4,200          4,220          4,240          4,260          4,280

CTGGCCGGTTGTTTCATGTGTGTGAAAAATTGATCAATGGTAAACAAAATTGAATAAATATATAACATATATATATAGATATGTGTGTTGAAATGAATACTTGCGATACA
GACCGCCAACAAAGTACACACTTTTTAACTAGTTACCATTTGTTTTAACTTATTTATATATTGTATATATATATCTATACACACAACTTTACTTATGAACGCTATGT nos3'UTR 4,300          4,320          4,340          4,360          4,380

TGTAATAAAAATACTCTTCGCTTATCTATCAAAAAGTGCGGAATGTCAAAATTTAAAATTTTACAATGAATGCGTAGCCGACGACGAAAGTGTTCCTTGCTATTTCC
ACATTATTTTTATGAGAAGCGAATAGATAGTTTTTCACGCCTTACAGTTTTAAATTTTAAAATGTTACTTACGCATCGGCTGCTGCTTTCACAAGGAACGATAAAGG nos3'UTR 4,400          4,420          4,440          4,460          4,480

FIG. 47 CONTINUED tf2a-step2 (14152 bp) (from 5137-5778 bp)

AscI

```
TTTGTAGAGGTGTACCGCTTTCTGTCTATGGTGGTGTCGAAGTACTTGAAGGCTGCAGGCGCGCCCAAGTTGGTCAGAGTAAACAAGTGGATAATGTTTTCTGCCTG
AAACATCTCCACATGGCGAAAGACAGATACCACCACAGCTTCATGAACTTCCGACGTCCGCGCGGGTTCAACCAGTCTCATTTGTTCACCTATTACAAAAGACGGAC
```

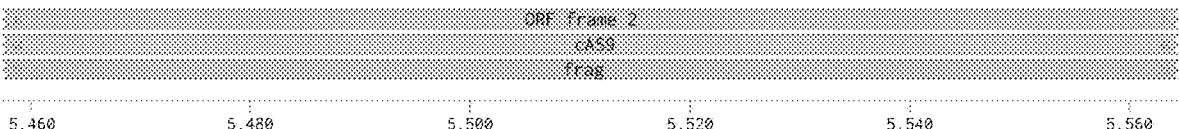

```
5,140              5,160              5,180              5,200              5,220              5,240
```

```
CTCCCTGATGGGCTTATCCCTGTGCTTATTGTAAGCAGAAAGCACCTTATCGAGGTTAGCGTCGGCGAGGATCACTCTTTTGGAGAATTCGCTTATTTGCTCGATGA
GAGGGACTACCCGAATAGGGACACGAATAACATTCGTCTTTCGTGGAATAGCTCCAATCGCAGCCGCTCCTAGTGAGAAAACCTCTTAAGCGAATAAACGAGCTACT
```

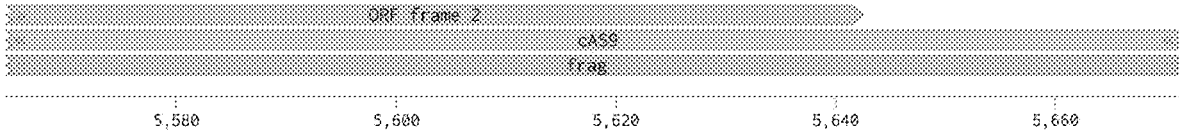

```
          5,260              5,280              5,300              5,320              5,340
```

```
TCTCATCAAGGTAGTGTTTGTGTTGTTCCACGAACAGCTGCTTCTGCTCATTATCTTCGGGAGACCCTTTGAGCTTTTCATAGTGGCTGGCCAGATACAAGAAATTA
AGAGTAGTTCCATCACAAACACAACAAGGTGCTTGTCGACGAAGACGAGTAATAGAAGCCCTCTGGGAAACTCGAAAAGTATCACCGACCGGTCTATGTTCTTTAAT
```

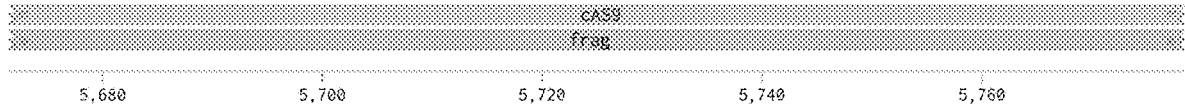

```
          5,360              5,380              5,400              5,420              5,440
```

```
ACGTATTTAGAGGGCAGTGCCAGCTCGTTACCTTTCTGCAGCTCGCCCGCACTAGCGAGCATTCGTTTCCGGCCGTTTTCAAGCTCAAAGAGAGAGTACTTGGGAAG
TGCATAAATCTCCCGTCACGGTCGAGCAATGGAAAGACGTCGAGCGGGCGTGATCGCTCGTAAGCAAAGGCCGGCAAAAGTTCGAGTTTCTCTCTCATGAACCCTTC
```

ORF Frame 2
cAS9
frag

```
5,460              5,480              5,500              5,520              5,540              5,560
```

```
CTTAATGATGAGGTCTTTTTTGACCTCTTTATATCCTTTCGCCTCGAGAAAGTCGATGGGGTTTTTTTCGAAGCTTGATCGCTCCATGATTGTGATGCCCAGCAGTT
GAATTACTACTCCAGAAAAAACTGGAGAAATATAGGAAAGCGGAGCTCTTTCAGCTACCCCAAAAAAAGCTTCGAACTAGCGAGGTACTAACACTACGGGTCGTCAA
```

ORF Frame 2
cAS9
frag

```
          5,580              5,600              5,620              5,640              5,660
```

```
CCTTGACGCTTTTGAGTTTTTTAGACTTCCCTTTCTCCACTTTGGCCACAACCAGTACACTGTAAGCGACTGTAGGAGAATCGAATCCGCCGTATTTCTTGGGGTCC
GGAACTGCGAAAACTCAAAAAATCTGAAGGGAAAGAGGTGAAACCGGTGTTGGTCATGTGACATTCGCTGACATCCTCTTAGCTTAGGCGGCATAAAGAACCCCAGG
``` cAS9
frag

```
          5,680              5,700              5,720              5,740              5,760
```

FIG. 47 CONTINUED tf2a-step2 (14152 bp) (from 5996-h529 bp)

CAATCTTTTTTGCGTGCGATCAGCTTGTCGCTGTTCCTTTTCGGGAGGATACTTTCCTTGGAGAAGCCTCCGGTCTGTACTTCGGTCTTTTTAACGATGTTCACCTG
GTTAGAAAAAACGCACGCTAGTCGAACAGCGACAAGGAAAAGCCCTCCTATGAAAGGAACCTCTTCGGAGGCCAGACATGAAGCCAGAAAAATTGCTACAAGTGGAC cAS9
frag 5,780        5,800        5,820        5,840        5,860        5,880

CGGCATGGACAGGACCTTCCGGACTGTCGCGAAATCCCTACCCTTGTCCCACACGATTTCTCCTGTTTCTCCGTTTGTTTCGATAAGTGGTCGCTTCCGAATCTCTC
GCCGTACCTGTCCTGGAAGGCCTGACAGCGCTTTAGGGATGGGAACAGGGTGTGCTAAAGAGGACAAAGAGGCAAACAAAGCTATTCACCAGCGAAGGCTTAGAGAG cAS9
frag 5,900        5,920        5,940        5,960        5,980

CATTGGCCAGTGTAATCTCGGTCTTGAAAAAATTCATAATATTGCTGTAAAAGAAGTACTTAGCGGTGGCCTTGCCTATTTCCTGCTCAGACTTTGCGATCATTTTC
GTAACCGGTCACATTAGAGCCAGAACTTTTTTAAGTATTATAACGACATTTTCTTCATGAATCGCCACCGGAACGGATAAAGGACGAGTCTGAAACGCTAGTAAAAG cAS9
frag 6,000        6,020        6,040        6,060        6,080

CTAACATCGTACACTTTATAGTCTCCGTAAACAAATTCAGATTCAAGCTTGGGATATTTTTTGATAAGTGCAGTGCCTACCACTGCATTCAGGTAGGCATCATGCGC
GATTGTAGCATGTGAAATATCAGAGGCATTTGTTTAAGTCTAAGTTCGAACCCTATAAAAAACTATTCACGTCACGGATGGTGACGTAAGTCCATCCGTAGTACGCG cAS9
frag 6,100        6,120        6,140        6,160        6,180        6,200

ATGGTGGTAATTGTTGATCTCTCTCACCTTATAAAACTGAAAGTCCTTTCTGAAATCTGAGACCAGCTTAGACTTCAGAGTAATAACTTTCACCTCTCGAATCAGTT
TACCACCATTAACAACTAGAGAGAGTGGAATATTTTGACTTTCAGGAAAGACTTTAGACTCTGGTCGAATCTGAAGTCTCATTATTGAAAGTGGAGAGCTTAGTCAA cAS9
frag 6,220        6,240        6,260        6,280        6,300

BstXI
PstI

TGTCATTTTCATCGTACTTGGTGTTCATGCGTGAATCGAGAATTTGGGCCACGTGCTTGGTGATCTGGCGTGTCTCAACAAGCTGCCTTTTGATGAAGCCGGCTTTA
ACAGTAAAAGTAGCATGAACCACAAGTACGCACTTAGCTCTTAAACCCGGTGCACGAACCACTAGACCGCACAGAGTTGTTCGACGGAAAACTACTTCGGCCGAAAT cAS9
frag 6,320        6,340        6,360        6,380        6,400        6,420

TCCAACTCAGACAGGCCACCTCGTTCAGCCTTAGTCAGATTATCGAACTTCCGTTGTGTGATCAGTTTGGCGTTCAGCAGCTGCCGCCAATAATTTTTCATTTTCTT
AGGTTGAGTCTGTCCGGTGGAGCAAGTCGGAATCAGTCTAATAGCTTGAAGGCAACACACTAGTCAAACCGCAAGTCGTCGACGGCGGTTATTAAAAAGTAAAAGAA cAS9
frag 6,440        6,460        6,480        6,500        6,520

FIG. 47 CONTINUED tf2a-step2 (14152 bp) (from 9528-619h bp)

GACAACTTCTTCTGAGGGGACGTTATCACTCTTCCCTCTATTTTTATCGGATCTTGTCAACACTTTATTATCAATAGAATCATCTTTGAGAAAAGACTGGGGCACGA
CTGTTGAAGAAGACTCCCCTGCAATAGTGAGAAGGGAGATAAAAATAGCCTAGAACAGTTGTGAAATAATAGTTATCTTAGTAGAAACTCTTTTCTGACCCCGTGCT

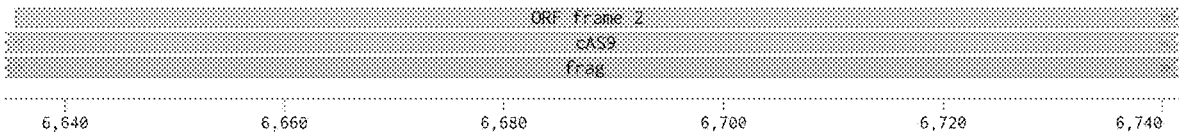

6,540　　　　　6,560　　　　　6,580　　　　　6,600　　　　　6,620

TATGATCCACGTCGTAGTCGGAGAGCCGATTGATGTCCAGTTCCTGATCCACGTACATGTCCCTGCCGTTCTGCAGGTAGTACAGGTAGAGCTTCTCATTCTGAAGC
ATACTAGGTGCAGCATCAGCCTCTCGGCTAACTACAGGTCAAGGACTAGGTGCATGTACAGGGACGGCAAGACGTCCATCATGTCCATCTCGAAGAGTAAGACTTCG

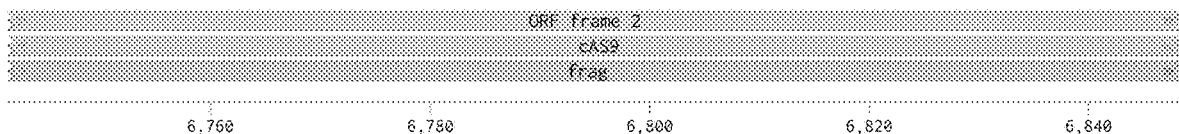

6,640　　　　　6,660　　　　　6,680　　　　　6,700　　　　　6,720　　　　　6,740

TGGGTGTTTTCAACTGGGTGTTCCTTAAGGATTTGGGACCCCAGTTCTTTTATACCCTCTTCAATCCTCTTCATCCTTTCCCTACTGTTCTTCTGTCCCTTCTGGGT
ACCCACAAAAGTTGACCCACAAGGAATTCCTAAACCCTGGGGTCAAGAAAATATGGGAGAAGTTAGGAGAAGTAGGAAAGGGATGACAAGAAGACAGGGAAGACCCA

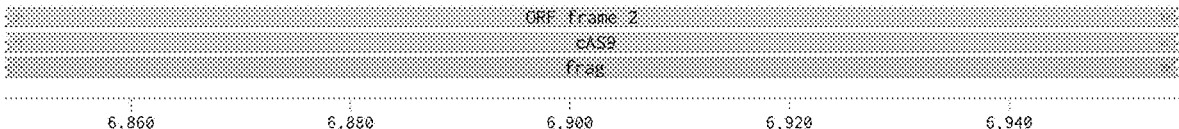

6,760　　　　　6,780　　　　　6,800　　　　　6,820　　　　　6,840

AGTTTGGTTCTCTCGGGCCATCTCGATAACGATATTCTCGGGCTTATGCCTTCCCATTACTTTGACGAGTTCATCCACGACCTTAACGGTCTGCAGTATTCCCTTTT
TCAAACCAAGAGAGCCCGGTAGAGCTATTGCTATAAGAGCCCGAATACGGAAGGGTAATGAAACTGCTCAAGTAGGTGCTGGAATTGCCAGACGTCATAAGGGAAAA

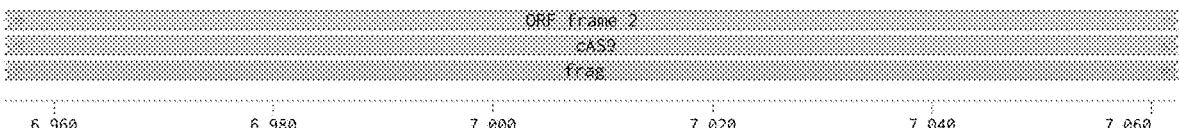

6,860　　　　　6,880　　　　　6,900　　　　　6,920　　　　　6,940

TGATAGCTGGGCTACCTGCAAGATTAGCGATGTGCTCGTGAAGACTGTCCCCCTGGCCAGAAACTTGTGCTTTCTGGATGTCCTCCTTAAAGGTGAGAGAGTCATCA
ACTATCGACCCGATGGACGTTCTAATCGCTACACGAGCACTTCTGACAGGGGGACCGGTCTTTGAACACGAAAGACCTACAGGAGGAATTTCCACTCTCTCAGTAGT

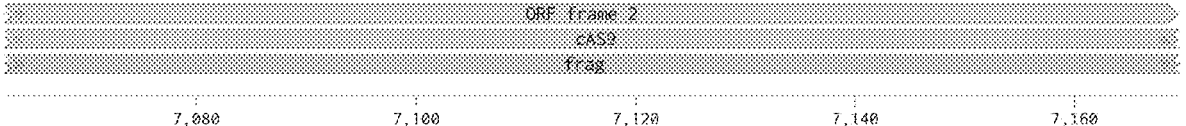

6,960　　　　　6,980　　　　　7,000　　　　　7,020　　　　　7,040　　　　　7,060

TGGATCAACTGCATGAAGTTCCGGTTGGCAAATCCATCGGACTTAAGAAAATCCAGGATTGTCTTTCCACTCTGCTTGTCTCGGATCCCATTGATCAGTTTTCTTGA
ACCTAGTTGACGTACTTCAAGGCCAACCGTTTAGGTAGCCTGAATTCTTTTAGGTCCTAACAGAAAGGTGAGACGAACAGAGCCTAGGGTAACTAGTCAAAAGAACT 7,080　　　　　7,100　　　　　7,120　　　　　7,140　　　　　7,160

FIG. 47 CONTINUED tf2a-step2 (14152 bp) (from 7170-7811 bp)

CAGCCGCCCCCATCCTGTATATCGGCGCCTCTTGAGCTGTTTCATGACTTTGTCGTCGAAGAGATGAGCGTAAGTTTTCAAGCGTTCTTCAATCATCTCCCTATCTT
GTCGGCGGGGGTAGGACATATAGCCGCGGAGAACTCGACAAAGTACTGAAACAGCAGCTTCTCTACTCGCATTCAAAAGTTCGCAAGAAGTTAGTAGAGGGATAGAA

ORF frame 2
cAS9
frag 7,180          7,200          7,220          7,240          7,260

CAAACAACGTAAGGGTGAGGACAATGTCCTCAAGAATGTCCTCGTTCTCCTCATTGTCCAGGAAGTCCTTGTCTTTAATGATTTTCAGGAGATCGTGATACGTTCCC
GTTTGTTGCATTCCCACTCCTGTTACAGGAGTTCTTACAGGAGCAAGAGGAGTAACAGGTCCTTCAGGAACAGAAATTACTAAAAGTCCTCTAGCACTATGCAAGGG

ORF frame 2
cAS9
frag 7,280          7,300          7,320          7,340          7,360          7,380

AGGGATGCGTTGAAGCGATCCTCCACTCCGCTGATTTCAACAGAGTCGAAACATTCAATCTTTTTGAAATAGTCTTCTTTGAGCTGTTTCACGGTAACTTTCCGGTT
TCCCTACGCAACTTCGCTAGGAGGTGAGGCGACTAAAGTTGTCTCAGCTTTGTAAGTTAGAAAAACTTTATCAGAAGAAACTCGACAAAGTGCCATTGAAAGGCCAA

ORF frame 2
cAS9
frag 7,400          7,420          7,440          7,460          7,480

CGTCTTGAAGAGGAGGTCCACGATAGCTTTCTTCTGCTCTCCAGACAGGAATGCTGGCTTTCTCATCCCTTCTGTGACGTATTTGACCTTGGTGAGCTCGTTATAAA
GCAGAACTTCTCCTCCAGGTGCTATCGAAAGAAGACGAGAGGTCTGTCCTTACGACCGAAAGAGTAGGGAAGACACTGCATAAACTGGAACCACTCGAGCAATATTT

ORF frame 2
cAS9
frag 7,500          7,520          7,540          7,560          7,580

CTGTGAAGTACTCGTACAGCAGAGAGTGTTTAGGAAGCACCTTTTCGTTAGGCAGATTTTTATCAAAGTTAGTCATCCTTTCGATGAAGGACTGGGCAGAGGCCCCC
GACACTTCATGAGCATGTCGTCTCTCACAAATCCTTCGTGGAAAAGCAATCCGTCTAAAAATAGTTTCAATCAGTAGGAAAGCTACTTCCTGACCCGTCTCCGGGGG

ORF frame 2
cAS9
frag 7,600          7,620          7,640          7,660          7,680          7,700

TTATCCACGACTTCCTCGAAGTTCCAGGGAGTGATGGTCTCTTCTGATTTGCGAGTCATCCACGCGAATCTGGAATTTCCCCGGGCGAGGGGGCCTACATAGTAGGG
AATAGGTGCTGAAGGAGCTTCAAGGTCCCTCACTACCAGAGAAGACTAAACGCTCAGTAGGTGCGCTTAGACCTTAAAGGGGCCCGCTCCCCCGGATGTATCATCCC

ORF frame 2
cAS9
frag 7,720          7,740          7,760          7,780          7,800

FIG. 47 CONTINUED tf2a-step2 (14152 bp) (from 7812-8560 bp)

Bsu36I

TATCCGAAATGTGAGGATTTTCTCAATCTTTTCCCTGTTATCTTTCAAAAAGGGGTAGAAATCCTCTTGCCGCCTGAGGATAGCGTGCAGTTCGCCCAGGTGAATCT
ATAGGCTTTACACTCCTAAAAGAGTTAGAAAAGGGACAATAGAAAGTTTTTCCCCATCTTTAGGAGAACGGCGGACTCCTATCGCACGTCAAGCGGGTCCACTTAGA cAS9
frag 7,820          7,840          7,860          7,880          7,900

GGTGGGGGATGCTTCCATTGTCGAAAGTGCGCTGTTTGCGCAACAGATCTTCTCTCTGTTAAGCTTTACCAGCAGCTCCTCGGTGCCGTCCATTTTTTCCAAGATGGGC
CCACCCCCTACGAAGGTAACAGCTTTCACGCGACAAACGCGTTGTCTAGAAGAGACAATTCGAAATGGTCGTCGAGGAGCCACGGCAGGTAAAAAAGGTTCTACCCG cAS9
frag 7,920          7,940          7,960          7,980          8,000          8,020

TTAATAAATTTGTAAAATTCCTCCTGGCTTGCTCCGCCGTCAATGTATCCGGCGTAGCCATTTTTAGACTGATCGAAGAAAATTTCCTTGTACTTCTCAGGCAGTTG
AATTATTTAAACATTTTAAGGAGGACCGAACGAGGCGGCAGTTACATAGGCCGCATCGGTAAAAATCTGACTAGCTTCTTTTAAAGGAACATGAAGAGTCCGTCAAC cAS9
frag 8,040          8,060          8,080          8,100          8,120

CTGTCTGACAAGGGCCTTCAGCAAAGTCAAGTCTTGGTGGTGCTCATCATAGCGCTTGATCATACTAGCGCTCAGCGGAGCTTTGGTGATCTCCGTGTTCACTCGCA
GACAGACTGTTCCCGGAAGTCGTTTCAGTTCAGAACCACCACGAGTAGTATCGCGAACTAGTATGATCGCGAGTCGCCTCGAAACCACTAGAGGCACAAGTGAGCGT cAS9
frag 8,140          8,160          8,180          8,200          8,220

GAATATCACTCAGCAGAATGGCGTCTGACAGGTTCTTTGCCGCCAAAAAAAGGTCTGCGTACTGGTCGCCGATCTGGGCCAGCAGATTGTCGAGATCATCATCGTAG
CTTATAGTGAGTCGTCTTACCGCAGACTGTCCAAGAAACGGCGGTTTTTTTTCCAGACGCATGACCAGCGGCTAGACCCGGTCGTCTAACAGCTCTAGTAGTAGCATC cAS9
frag 8,240          8,260          8,280          8,300          8,320          8,340

GTGTCTTTGCTCAGTTGAAGCTTGGCATCTTCGGCCAGGTCGAAGTTAGATTTAAAGTTGGGGGTCAGCCCGAGTGACAGGGCGATAAGATTACCAAACAGGCCGTT
CACAGAAACGAGTCAACTTCGAACCGTAGAAGCCGGTCCAGCTTCAATCTAAATTTCAACCCCCAGTCGGGCTCACTGTCCCGCTATTCTAATGGTTTGTCCGGCAA cAS9
frag 8,360          8,380          8,400          8,420          8,440

CTTCTTCTCCCCAGGGAGCTGTGCGATGAGGTTTTCGAGCCGCCGGGATTTGGACAGCCTAGCGCTCAGGATTGCTTTGGCGTCAACTCCGGATGCGTTGATCGGGT
GAAGAAGAGGGGTCCCTCGACACGCTACTCCAAAAGCTCGGCGGCCCTAAACCTGTCGGATCGCGAGTCCTAACGAAACCGCAGTTGAGGCCTACGCAACTAGCCCA cAS9
frag 8,460          8,480          8,500          8,520          8,540          8,560

FIG. 47 CONTINUED tf2a-step2 (14152 bp) (from 8591-6202 bp)

TCTCTTCGAAAAGCTGATTGTAAGTCTGAACCAGTTGGATAAAGAGTTTGTCGACATCGCTGTTGTCTGGGTTCAGGTCCCCCTCGATGAGGAAGTGTCCCCGAAAT
AGAGAAGCTTTTCGACTAACATTCAGACTTGGTCAACCTATTTCTCAAACAGCTGTAGCGACAACAGACCCAAGTCCAGGGGGAGCTACTCCTTCACAGGGGCTTTA 8,580          8,600          8,620          8,640          8,660

NdeI

TTGATCATATGCGCCAGCGCGAGATAGATCAACCGCAAGTCAGCCTTATCAGTACTGTCTACAAGCTTCTTCCTCAGATGATATATGGTTGGGTACTTTTCATGGTA
AACTAGTATACGCGGTCGCGCTCTATCTAGTTGGCGTTCAGTCGGAATAGTCATGACAGATGTTCGAAGAAGGAGTCTACTATATACCAACCCATGAAAAGTACCAT 8,680          8,700          8,720          8,740          8,760

CGCCACCTCGTCCACGATATTGCCAAAGATTGGGTGGCGCTCGTGCTTTTTATCCTCCTCCACCAAAAAGGACTCCTCCAGCCTATGGAAGAAAGAGTCATCCACCT
GCGGTGGAGCAGGTGCTATAACGGTTTCTAACCCACCGCGAGCACGAAAAATAGGAGGAGGTGGTTTTTCCTGAGGAGGTCGGATACCTTCTTTCTCAGTAGGTGGA 8,780          8,800          8,820          8,840          8,860          8,880

TAGCCATCTCATTACTAAAGATCTCCTGCAGGTAGCAGATCCGATTCTTTCTGCGGGTATATCTGCGCCGTGCTGTTCTTTTGAGCCGCGTGGCTTCGGCCGTCTCC
ATCGGTAGAGTAATGATTTCTAGAGGACGTCCATCGTCTAGGCTAAGAAAGACGCCCATATAGACGCGGCACGACAAGAAAACTCGGCGCACCGAAGCCGGCAGAGG 8,900          8,920          8,940          8,960          8,980

BamHI

CCGGAGTCGAACAGGAGGGCGCCAATGAGGTTCTTCTTTATGCTGTGGCGATCGGTATTGCCCAGAACTTTGAATTTTTTGCTCGGCACCTTGTACTCGTCCGTAAT
GGCCTCAGCTTGTCCTCCCGCGGTTACTCCAAGAAGAAATACGACACCGCTAGCCATAACGGGTCTTGAAACTTAAAAAACGAGCCGTGGAACATGAGCAGGCATTA 9,000          9,020          9,040          9,060          9,080

GACGGCCCAGCCGACGCTGTTTGTGCCGATATCGAGCCCAATGGAGTACTTCTTGTCCATGGCGAAAATCCGGGTCGAAAGTTACGGTTATCGCGCACTCTACTTTC
CTGCCGGGTCGGCTGCGACAAACACGGCTATAGCTCGGGTTACCTCATGAAGAACAGGTACCGCTTTTAGGCCCAGCTTTCAATGCCAATAGCGCGTGAGATGAAAG 9,100          9,120          9,140          9,160          9,180          9,200

FIG. 47 CONTINUED tf2a-step2 (14152 bp) (from 9203-9951 bp)

CACAAATCCTCACCCAAAAACCAAGCACAGTTTATTCAACTGAAGTATTCGCGATACTTCTTTATCTAATAATAATGTACATGTAACTAAACTCGCTTTTGGGTTAA
GTGTTTAGGAGTGGGTTTTTGGTTCGTGTCAAATAAGTTGACTTCATAAGCGCTATGAAGAAATAGATTATTATTACATGTACATTGATTTGAGCGAAAACCCAATT

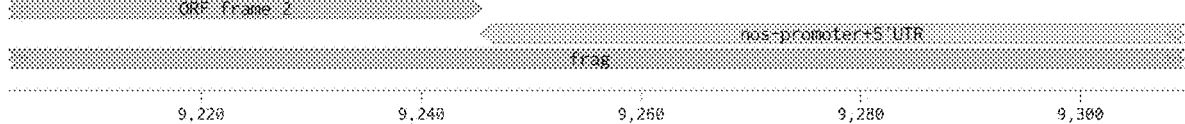

AATCGTGACGCAGAGGCAAAAAAAATCGTATGTCCCTTAGACAACTTGAAACAACTGCGAAGCGTACGGCAATTCCAGGAATTTTGTGGTAAAGCTACGCGCCAACT
TTAGCACTGCGTCTCCGTTTTTTTTAGCATACAGGGAATCTGTTGAACTTTGTTGACGCTTCGCATGCCGTTAAGGTCCTTAAAACACCATTTCGATGCGCGGTTGA

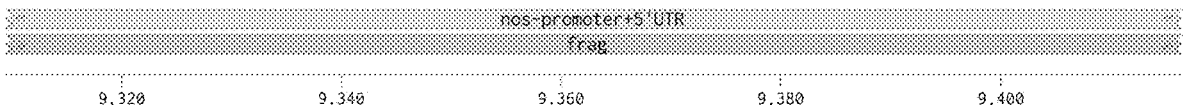

AACGGTTCTTGCTTAGAGGTGGAATAATGTAGTTTTTCCAGCGATAATAAATATATCGATATTTTTAGTAAAATTGAAAAGGTAAACTTAATTTTTAGAAAATAATTTA
TTGCCAAGAACGAATCTCCACCTTATTACATCAAAAGGTCGCTATTATTTATATAGCTATAAAAATCATTTTAACTTTTCCATTTGAATTAAAATCTTTTATTAAAT

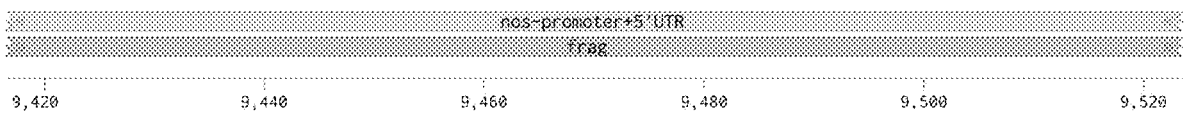

TAAGAAATTTAATAGTATGCAAAATAATTTTTTACTTGCTAAGAATATGTGCCACTAATTAAAAGCTGGACACCGCGCAATGGAAAATAGTACTACAACACAGCAACA
ATTCTTTAAATTATCATACGTTTTATTAAAAATGAACGATTCTTATACACGGTGATTAATTTTCGACCTGTGGCGCGTTACCTTTTATCATGATGTTGTGTCGTTGT

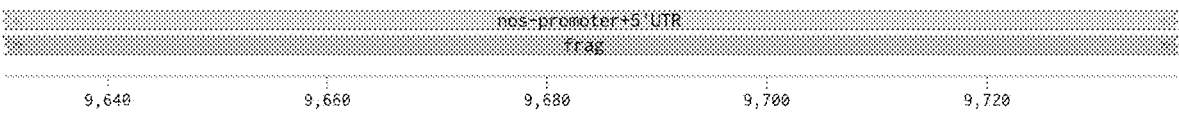

AAGCCTGAGTTATCAACAAAAAAAATACGAAAACATCTCCCAAAACTAAGCACCCACACGCGCCACTCGCCGTCACAACACAATCACTGCACACCACCATTCGAATTT
TTCGGACTCAATAGTTGTTTTTTTTATGCTTTTGTAGAGGGTTTTTGATTCGTGGGTGTGCGCGGTGAGCGGCAGTGTTGTGTTAGTGACGTGTGGTGGTAAGCTTAAA

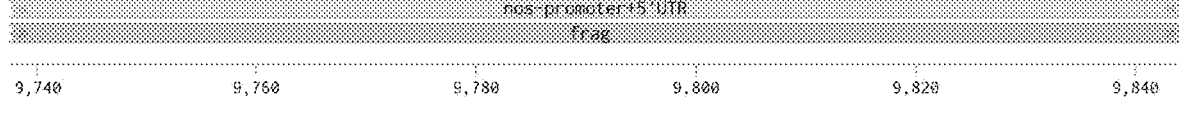

BspQI
SapI

CGCGCACTGTGACAACATCACATGATATCGGCGCGGCAACATCGGATTACCGACAAAACGAACTATCGCACGAGCCACCGCCGGCGAAGAGCGCTCGTTTTGCAACA
GCGCGTGACACTGTTGTAGTGTACTATAGCCGCGCCGGTTGTAGCCTAATGGCTGTTTTGCTTGATAGCGTGCTCGGTGGCGGCCGCTTCTCGCGAGCAAAACGTTGT

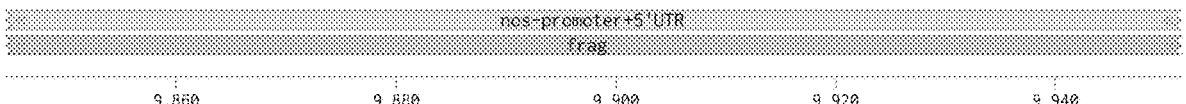

BaeI

CCGGCGCGCGCTGAACGAAGAGAACAGCTGACTGCTTGATACGTGCGTGTTTCGCGGCAGGAATTACATAAAGTTTAGAGCCTCTGACGCCAGACCCCCCGAACATT
GGCCGCGCGCGACTTGCTTCTCTTGTCGACTGACGAACTATGCACGCACAAAGCGCCGTCCTTAATGTATTTCAAATCTCGGAGACTGCGGTCTGGGGGGCTTGTAA

FIG. 47 CONTINUED tf2a-step2 (14152 bp) (from 9952-10593 bp)

CGCTCCGATCAAACTACCTGCGAACGGTCACCTAATCCCCACCATGCATGGTAGGTTACCTCTGATCCCGGTCATCACTGGCGTTCGCTCACATCCGTCCTTACATG
GCGAGGCTAGTTTGATGGACGCTTGCCAGTGGATTAGGGGTGGTACGTACCATCCAATGGAGACTAGGGCCAGTAGTGACCGCAAGCGAGTGTAGGCAGGAATGTAC

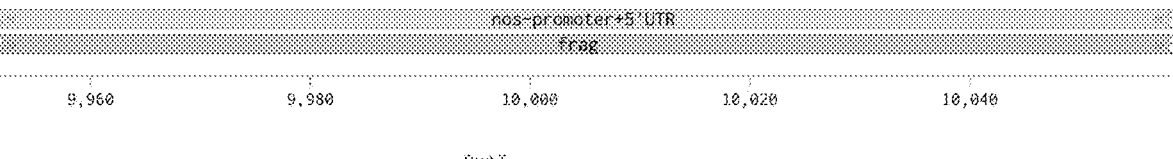

```
        9,960              9,980             10,000             10,020             10,040
```

BstI
                                                 NheI

TGCATATTTCGAGGTTAAAACGGTCGAAGCTTGGATCCGCTAGCgttgttggttggcacaccacaaatatactgttgccgagcacaattgatcggctaaatggtatg
ACGTATAAAGCTCCAATTTTGCCAGCTTCGAACCTAGGCGATCGcaacaaccaaccgtgtggtgtttatatgacaacggctcgtgttaactagccgatttaccatac

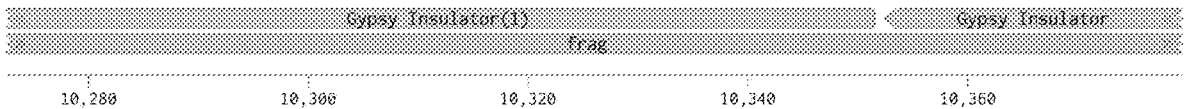

```
      10,060            10,080            10,100            10,120            10,140            10,160
``` gcaagaaaaggtatgcaatataataatctttattgggtatgcaacgaaaatttgtttcgtcaacgtatgcaatattctttattaaaagagggtatgcaatgtattt
cgttcttttccatacgttatattattagaaaataacccatacgttgcttttaaacaaagcagttgcatacgttataagaaataatttttctcccatacgttacataaa

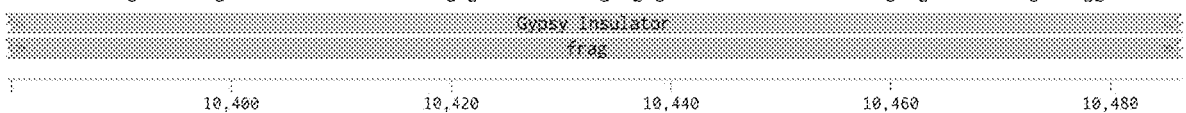

```
        10,180            10,200            10,220            10,240            10,260
``` tattaaaaacgggtatgcaatataataatctttattgggtatgcaacgaaaatttgtttcgtcaaagtatgcaatatttttattaaaagagggtatgcaatgtat
ataattttttgcccatacgttatattattagaaaataacccatacgttgcttttaaacaaagcagtttcatacgttatasaaaataattttctcccatacgttacata

```
        10,280            10,300            10,320            10,340            10,360
``` tttattaaaaacgggtatgcaataaaaaattatttggtttctctaaaaagtatgcagcacttattttttgataaggtatgcaacaaaattttactttgccgaaaata
aaataattttgcccatacgttatttttttaataaaccaaagagattttttcatacgtcgtgaataaaaaaactattccatacgttgtttttaaaatgaaacggcttttat

```
        10,400            10,420            10,440            10,460            10,480
```

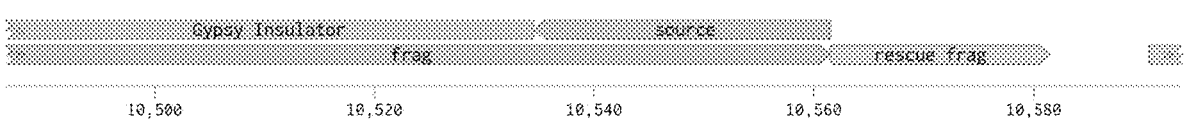

tgcaatgtttttgcgaataaaattcaacgcacacttattacgtggccaaCTAGCCTAGTTCCAGTGAAATCCAAGCgcgcaatgcattatggaacagatgaattcttt
acgttacaaaaacgcttatttaagttgcgtgtgaataatgcaccggttGATCGGATCAAGGTCACTTTAGGTTCGcgcgttacgtaataccttgtctacttaagaaa

```
        10,500            10,520            10,540            10,560            10,580
```

FIG. 47 CONTINUED tf2a-step2 (14152 bp) (from 10594-11449 bp)

```
tttgctcacctgtgattgctcctactcaaatacaaaaacatcaaattttctgtcaataaagcatatttatttatatttattttacaggaaagaattccttttaaagt
aaacgagtggacactaacgaggatgagtttatgtttttgtagtttaaaagacagttatttcgtataaataaatataaataaaatgtcctttcttaaggaaaatttca
``` dU6.3 promoter

```
    10,600          10,620          10,640          10,660          10,680          10,700
```

```
gtattttaacctataatgaaaaacgattaaaaaaaatacataaaataattcgaaaattttttgaatagcccaggttgataaaaattcatttcatacgttttataactt
cataaaattggatattacttttttgctaatttttttttatgtattttattaagctttttaaaaacttatcgggtccaactattttttaagtaaagtatgcaaaatattgaa
``` dU6.3 promoter

```
        10,720          10,740          10,760          10,780          10,800
```

```
atgcccctaagtattttttgaccatagtgtttcaattctacattaattttacagagtagaatgaaacgccacctactcagccaagaggcgaaaaggttagctcgcca
tacggggattcataaaaaaactggtatcacaaagttaagatgtaattaaaatgtctcatcttactttgcggtggatgagtcggttctccgcttttccaatcgagcggt
``` dU6.3 promoter

```
        10,820          10,840          10,860          10,880          10,900
```

```
agcagagagggcgccagtgctcactactttttataattctcaacttcttttttccagactcagttcgtatatatagacctattttcaatttaacgtcgcgaagtgcac
tcgtctctcccgcggtcacgagtgatgaaaaatattaagagttgaagaaaaaggtctgagtcaagcatatatatctggataaaagttaaattgcagcgcttcacgtg
``` dU6.3 promoter

```
    10,920          10,940          10,960          10,980          11,000          11,020
```

```
gagatcgtcaGTTTCagagctaTGCTGgaaaCAGCAtagcaagttGaaataaggctagtccgttatcaacttgaaaaagtggcaccgagtcggtgcttttttgccta
ctctagcagtCAAAGtctcgatACGACcttttGTCGTatcgttcaaCtttattccgatcaggcaatagttgaactttttcaccgtggctcagccacgaaaaaacggat
``` priming site

```
    11,040          11,060          11,080          11,100          11,120
```

```
cctggagcctgagagttgttcaataaaataaaaatgtttcgttttttttgctttcgccagtatttattattttttcatcaatatgtattcaatttggtatgtatttagt
ggacctcggactctcaacaagttatttttattttttacaaagcaaaaaaacgaaagcggtcataaataataaaaagtagttatacataagttaaaccatacaaaatca
``` repeated after U6.1

```
    11,140          11,160          11,180          11,200          11,220
```

```
aattgtaatatatagacaatggttttccgttgacgtacatacatctgacgtgtgtttatttagacataatagttatgttttcacatcttttttaatgttcgcttaatg
ttaacattatatatctcgttaccaaaaggcaactgcatgtatgtagactgcacacaaatataatctgtattatcaatacaaaagtgtagaaaaattacaagcgaattac
```

```
11,240          11,260          11,280          11,300          11,320          11,340
```

```
cgtatgcattctagattttcaacgtcctcgatagtatagtggttagtatccccgcctgtcacgcgggagaccggggttcaattccccgtcggggagaatctgtgatt
gcatacgtaagatctaaaagttgcaggagctatcatatcaccaatcataggggcggacagtgcgccctctggccccaagttaaggggcagcccctcttagacactaa
``` source
RNA polymerase III promoter for Drosophila U6-1 snRNA (Port et al., 2014)

```
    11,360          11,380          11,400          11,420          11,440
```

FIG. 47 CONTINUED tf2a-step2 (14152 bp) (from 11450-12178 bp)

cttttttttttttctttttactttgttatataaacaatttttgtttttaattgaatctaatttgccattgcttttaggaatctcaggcatccagcaagcgtttgtccgcc gaaaaaaaaaaagaaaatgaaacaatatatttgttaaaaacaaaattaacttagattaaacggtaacgaaaatccttagagtccgtaggtcgttcgcaaacaggcgg source
RNA polymerase III promoter for Drosophila U6-1 snRNA (Port et al., 2014)

11,460          11,480          11,500          11,520          11,540 gaatcgcccatcagtgaagaagatcctgtggcggctacgaaaatctccccggccatgtcggcctccacctccagcgaaaaacccatcagcgagctggccacctctgt cttagcgggtagtcacttcttctaggacaccgccgatgctttagaggggccggtacagccggaggtggaggtcgcttttttgggtagtcgctcgaccggtggagaca source
RNA polymerase III promoter for Drosophila U6-1 snRNA (Port et al., 2014)

11,560          11,580          11,600          11,620          11,640          11,660 gctgacccaccgctttccagactccacctcctcacccggcgaacatggccttggacgaatgcagttgtcgatccgctacagcgcccagcgtcaaaaactagacgtga cgactgggtggcgaaaggtctgaggtggaggagtgggccgcttgtaccggaacctgcttacgtcaacagctaggcgatgtcgcgggtcgcagttttttgatctgcact source
RNA polymerase III promoter for Drosophila U6-1 snRNA (Port et al., 2014)

11,680          11,700          11,720          11,740          11,760 ccatacacaaaatccagaagataccacttcgcgatcccagcaatatccccgatccgtatgttaagctgtatctgttgcctggacgcaccaaggagtcgaaacgcaag ggtatgtgttttaggtcttctatggtgaagcgctagggtcgttatagggcaggcatacaattcgacatagacaacggacctgcgtggttcctcagctttgcgttc source
RNA polymerase III promoter for Drosophila U6-1 snRNA (Port et al., 2014)

11,780          11,800          11,820          11,840          11,860 acgagcgtgatcaaggacaactgcaaccccgtctacgatgcatcctttgagtacctgatttccattgccgaactcaggcagacggaactggaggtgacggtgtgcac tgctcgcactagttcctgttgacgttgggggcagatgctacgtaggaaactcatggactaaaggtaacggcttgagtccgtctgccttgacctccactgccacacgtg source
RNA polymerase III promoter for Drosophila U6-1 snRNA (Port et al., 2014)

11,880     11,900          11,920          11,940          11,960          11,980 ccaaaagggattcctatccggcggtagtcccatcattggcatggtaggtacccgaaagcaacccccttagttacagacacagcgcgtacgtccttcgcatccttatga ggttttccctaaggataggccgccatcagggtagtaaccgtaccatccatgggctttcgttggggaatcaatgtctgtgtcgcgcatgcaggaagcgtaggaatact source
RNA polymerase III promoter for Drosophila U6-1 snRNA (Port et al., 2014)

12,000          12,020          12,040          12,060          12,080 ttcccaagtacatattctgcaagagtacagtatatataggaaagatatccgggtgaacttcGacattgtcgcagaagcggtGTTTCagagctaTGCTGgaaaCAGCA aagggttcatgtataagacgttctcatgtcatatatatcctttctataggcccacttgaagCtgtaacagcgtcttcgccaCAAAGtctcgatACGACctttGTCGT source 12,100          12,120          12,140          12,160          12,180

FIG. 47 CONTINUED tf2a-step2 (14152 bp) (from 12177-12749 bp)

tagcaagttGaaataaggctagtccgttatcaacttgaaaaagtggcaccgagtcggtgcttttttgcctacctggagcctgagagttgttcaatctagacaattgt
atcgttcaaCtttattccgatcaggcaatagttgaacttttttcaccgtggctcagccacgaaaaaacggatggacctcggactctcaacaagttagatctgttaaca

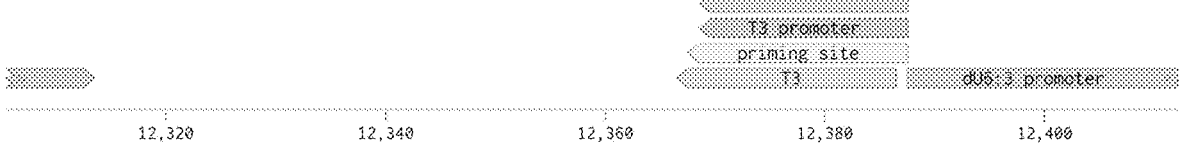

```
12,200          12,220          12,240          12,260          12,280          12,300
``` gctcggcaacagtatatttgtggtgtgccaaccaacaacctgcaggagctccagcttttgttccctttagtgagggttaatttttttttgctcacctgtgattgctcc
cgagccgttgtcatataaacaccacacggttggttgttggacgtcctcgaggtcgaaaacaagggaaatcactcccaattaaaaaaaaacgagtggacactaacgagg

```
12,320          12,340          12,360          12,380          12,400
``` tactcaaatacaaaaacatcaaattttctgtcaataaagcatatttatttatatttattttacaggaaagaattcctttaaagtgtattttaacctataatgaaaa
atgagtttatgttttttgtagtttaaaagacagttatttcgtataaataaatataaataaaatgtcctttcttaaggaaaatttcacataaaattggatattacttttt

```
12,420          12,440          12,460          12,480          12,500
``` acgattaaaaaaaatacataaaataattcgaaaattttttgaatagcccaggttgataaaaattcatttcatacgtttttataacttatgcccctaagtattttttgac
tgctaattttttttttatgtattttattaagcttttaaaaaacttatcgggtccaactattttttaagtaaagtatgcaaaatattgaatacggggattcataaaaaactg

```
12,540          12,560          12,580          12,600          12,620
``` catagtgtttcaattctacattaattttacagagtagaatgaaacgccacctactcagccaagagggcgaaaaggttagctcgccaagcagagagggcgccagtgctc
gtatcacaaagttaagatgtaattaaaatgtctcatcttacttgcggtggatgagtcggttctccgcttttccaatcgagcggttcgtctctcccgcggtcacgag

```
12,640          12,660          12,680          12,700          12,720
``` actacttttttataattctcaacttcttttttccagactcagttcgtatatatagacctattttcaatttaacgtcgaagccagtccgggcgtaatcGTTTCagagcta
tgatgaaaaatattaagagttgaagaaaaaggtctgagtcaagcatatatatctggataaaagttaaattgcagcttcggtcaggcccgcattagCAAAGtctcgat

```
12,740          12,760          12,780          12,800          12,820          12,840
```

TGCTGgaaaCAGCAtagcaagttGaaataaggctagtccgttatcaacttgaaaaagtggcaccgagtcggtgcttttttgcctacctggagcctgagagttgttca
ACGACctttGTCGTatcgttcaaCtttattccgatcaggcaatagttgaacttttttcaccgtggctcagccacgaaaaaacggatggacctcggactctcaacaagt

```
12,860          12,880          12,900          12,920          12,940
```

FIG. 47 CONTINUED tf2a-step2 (14152 bp) (from 12948-13696 bp)

ataaaataaaaatgtttcgtttttttgctttcgccagtatttattattttttcatcaatatgtattcaatttggtatgtatttagtaattgtaatatatagacaatgg
tattttattttttacaaagcaaaaaaacgaaagcggtcataaataataaaaagtagttatacataagttaaaccatacataaatcattaacattatatatctgttacc

```
         12,960          12,980          13,000          13,020          13,040
``` ttttccgttgacgtacatacatctgacgtgtgtttatttagacataatagttatgttttcacatctttttaatgttcgcttaatgcgtatgcattctagattttcaa
aaaaggcaactgcatgtatgtagactgcacacaaataaatctgtattatcaatacaaaagtgtagaaaaattacaagcgaattacgcatacgtaagatctaaaagtt

```
  13,060          13,080          13,100          13,120          13,140          13,160
``` cgtcctcgatagtatagtggttagtatccccgcctgtcacgcgggagaccggggttcaattccccgtcggggagaatctgtgattctttttttttttctttttacttt
gcaggagctatcatatcaccaatcatagggggcggacagtgcgccctctggccccaagttaaggggcagcccctcttagacactaagaaaaaaaaaaagaaaatgaaa
RNA polymerase III promoter for Drosophila U6-1 snRNA (Port et al., 2014)
source

```
         13,180          13,200          13,220          13,240          13,260
``` gttatataaacaattttttgtttttaattgaatctaatttgccattgctttttaggaatctcaggcatccagcaagcgtttgtccgccgaatcgcccatcagtgaagaag
caatatatttgttaaaaacaaaattaacttagattaaacggtaacgaaaatccttagagtccgtaggtcgttcgcaaacaggcggcttagcgggtagtcacttcttc
RNA polymerase III promoter for Drosophila U6-1 snRNA (Port et al., 2014)
source

```
  13,280          13,300          13,320          13,340          13,360
``` atcctgtggcggctacgaaaatctccccggccatgtcggcctccacctccagcgaaaaacccatcagcgagctggccaccctctgtgctgacccaccgctttccagac
taggacaccgccgatgctttttagaggggccggtacagccggaggtggaggtcgcttttttgggtagtcgctcgaccggtggagacacgactgggtggcgaaaggtctg
RNA polymerase III promoter for Drosophila U6-1 snRNA (Port et al., 2014)
source

```
  13,380          13,400          13,420          13,440          13,460          13,480
``` tccacctcctcacccggcgaacatggccttggacgaatgcagttgtcgatccgctacagcgcccagcgtcaaaaactagacgtgaccatacacaaaatccagaagat
aggtggaggagtgggccgcttgtaccggaacctgcttacgtcaacagctaggcgatgtcgcgggtcgcagtttttgatctgcactggtatgtgttttaggtcttcta
RNA polymerase III promoter for Drosophila U6-1 snRNA (Port et al., 2014)
source

```
         13,500          13,520          13,540          13,560          13,580
``` accacttcgcgatcccagcaatatccccgatccgtatgttaagctgtatctgttgcctggacgcaccaaggagtcgaaacgcaagacgagcgtgatcaaggacaact
tggtgaagcgctagggtcgttatagggggctaggcatacaattcgacatagacaacggacctgcgtggttcctcagctttgcgttctgctcgcactagttcctgttga
RNA polymerase III promoter for Drosophila U6-1 snRNA (Port et al., 2014)
source

```
  13,600          13,620          13,640          13,660          13,680
```

FIG. 47 CONTINUED tf2a-step2 (14152 bp) (from 1396h-14152 bp)

gcaaccccgtctacgatgcatcctttgagtacctgatttccattgccgaactcaggcagacggaactggaggtgacggtgtgcacccaaaagggattcctatccggc cgttggggcagatgctacgtaggaaaactcatggactaaaggtaacggcttgagtccgtctgccttgacctccactgccacacgtgggtttttccctaaggataggccg RNA polymerase III promoter for Drosophila U6-1 snRNA (Port et al., 2014)

source 13,700     13,720     13,740     13,760     13,780     13,800 ggtagtcccatcattggcatggtaggtacccgaaagcaaccccttagttacagacacagcgcgtacgtccttcgcatccttatgattcccaagtacatattctgcaa ccatcagggtagtaaccgtaccatccatgggctttcgttggggaatcaatgtctgtgtcgcgcatgcaggaagcgtaggaatactaagggttcatgtataagacgtt RNA polymerase III promoter for Drosophila U6-1 snRNA (Port et al., 2014)

source 13,820     13,840     13,860     13,880     13,900 gagtacagtatatataggaaagatatccgggtgaacttcGctcgtcgaggctctcctgcaGTTTCagagctaTGCTGgaaaCAGCAtagcaagttGaaataaggcta ctcatgtcatatatatcctttctataggcccacttgaagCgagcagctccgagaggacgtCAAAGtctcgatACGACcttttGTCGTatcgttcaaCtttattccgat source 13,920     13,940     13,960     13,980     14,000 gtccgttatcaacttgaaaaagtggcaccgagtcggtgcttttttgcctacctggagcctgagagttgttcaatctagacaattgtgctcggcaacagtatatttgt caggcaatagttgaacttttttcaccgtggctcagccacgaaaaaacggatggacctcggactctcaacaagttagatctgttaacacgagccgttgtcatataaaca repeated after u6.3     200bp 14,020     14,040     14,060     14,080     14,100     14,120 ggtgtgccGTACCGGGCCAATTCGAGCT     SEQ ID NO: 183 ccacacggCATGGCCCGGTTAAGCTCGA     SEQ ID NO: 184

14,130     14,140     14,150

FIG. 47 CONTINUED tko-step2 (14148 bp) (from 857-1712 bp)

cttcgggaagcgtggcgctttctcatagctcacgctgtaggtatctcagttcggtgtaggtcgttcgctccaagctgggctgtgtgcacgaaccccccgttcagccc
gaagcccttcgcaccgcgaaagagtatcgagtgcgacatccatagagtcaagccacatccagcaagcgaggttcgacccgacacacgtgcttggggggcaagtcggg high-copy-number ColE1/pMB1/pBR322/pUC origin of replication 860       880       900       920       940       960 gaccgctgcgccttatccggtaactatcgtcttgagtccaacccggtaagacacgacttatcgccactggcagcagccactggtaacaggattagcagagcgaggta
ctggcgacgcggaataggccattgatagcagaactcaggttgggccattctgtgctgaatagcggtgaccgtcgtcggtgaccattgtcctaatcgtctcgctccat high-copy-number ColE1/pMB1/pBR322/pUC origin of replication 980       1,000       1,020       1,040       1,060 tgtaggcggtgctacagagttcttgaagtggtggcctaactacggctacactagaagaacagtatttggtatctgcgctctgctgaagccagttaccttcggaaaaa
acatccgccacgatgtctcaagaacttcaccaccggattgatgccgatgtgatcttcttgtcataaaccatagacgcgagacgacttcggtcaatggaagccttttt high-copy-number ColE1/pMB1/pBR322/pUC origin of replication 1,080       1,100       1,120       1,140       1,160 gagttggtagctcttgatccggcaaacaaaccaccgctggtagcggtggtttttttgtttgcaagcagcagattacgcgcagaaaaaaaggatctcaagaagatcct
ctcaaccatcgagaactaggccgtttgtttggtggcgaccatcgccaccaaaaaaacaaacgttcgtcgtctaatgcgcgtctttttttcctagagttcttctagga high-copy-number ColE1/pMB1/pBR322/pUC origin of replication 1,180       1,200       1,220       1,240       1,260       1,280 ttgatcttttctacggggtctgacgctcagtggaacgaaaactcacgttaagggattttggtcatgagattatcaaaaaggatcttcacctagatccttttaaatta
aactagaaaagatgccccagactgcgagtcaccttgcttttgagtgcaattccctaaaaccagtactctaatagtttttcctagaagtggatctaggaaaatttaat 1,300       1,320       1,340       1,360       1,380 aaaatgaagttttaaatcaatctaaagtatatatgagtaaacttggtctgacagttaccaatgcttaatcagtgaggcacctatctcagcgatctgtctatttcgtt
ttttacttcaaaatttagttagatttcatatatactcatttgaaccagactgtcaatggttacgaattagtcactccgtggatagagtcgctagacagataaagcaa bla CDS 1,400       1,420       1,440       1,460       1,480

AhdI catccatagttgcctgactccccgtcgtgtagataactacgatacgggagggcttaccatctggccccagtgctgcaatgataccgcgagacccacgctcaccggct
gtaggtatcaacggactgaggggcagcacatctattgatgctatgccctcccgaatggtagaccggggtcacgacgttactatggcgctctgggtgcgagtggccga bla CDS 1,500       1,520       1,540       1,560       1,580       1,600 ccagatttatcagcaataaaccagccagccggaagggccgagcgcagaagtggtcctgcaactttatccgcctccatccagtctattaattgttgccgggaagctag
ggtctaaatagtcgttatttggtcggtcggccttcccggctcgcgtcttcaccaggacgttgaaataggcggaggtaggtcagataattaacaacggcccttcgatc bla CDS 1,620       1,640       1,660       1,680       1,700

FIG. 48 CONTINUED tko-step2 (14148 bp) (from 171h-2568 bp)

agtaagtagttcgccagttaatagtttgcgcaacgttgttgccattgctacaggcatcgtggtgtcacgctcgtcgtttggtatggcttcattcagctccggttccc
tcattcatcaagcggtcaattatcaaacgcgttgcaacaacggtaacgatgtccgtagcaccacagtgcgagcagcaaaccataccgaagtaagtcgaggccaaggg bla CDS 1,720          1,740          1,760          1,780          1,800 aacgatcaaggcgagttacatgatcccccatgttgtgcaaaaaagcggttagctccttcggtcctccgatcgttgtcagaagtaagttggccgcagtgttatcactc
ttgctagttccgctcaatgtactaggggggtacaacacgttttttcgccaatcgaggaagccaggaggctagcaacagtcttcattcaaccggcgtcacaatagtgag bla CDS 1,820         1,840          1,860          1,880          1,900          1,920 atggttatggcagcactgcataattctcttactgtcatgccatccgtaagatgcttttctgtgactggtgagtactcaaccaagtcattctgagaatagtgtatgcg
taccaataccgtcgtgacgtattaagagaatgacagtacggtaggcattctacgaaaagacactgaccactcatgagttggttcagtaagactcttatcacatacgc bla CDS 1,940          1,960          1,980          2,000          2,020 gcgaccgagttgctcttgcccggcgtcaatacgggataataccgcgccacatagcagaactttaaaagtgctcatcattggaaaacgttcttcggggcgaaaactct
cgctggctcaacgagaacgggccgcagttatgccctattatggcgcggtgtatcgtcttgaaattttcacgagtagtaaccttttgcaagaagccccgcttttgaga bla CDS 2,040          2,060          2,080          2,100          2,120          2,140 caaggatcttaccgctgttgagatccagttcgatgtaacccactcgtgcacccaactgatcttcagcatctttttactttcaccagcgtttctgggtgagcaaaaaca
gttcctagaatggcgacaactctaggtcaagctacattgggtgagcacgtgggttgactagaagtcgtagaaaatgaaagtggtcgcaaagacccactcgttttgt bla CDS 2,160          2,180          2,200          2,220          2,240 ggaaggcaaaatgccgcaaaaaagggaataagggcgacacggaaatgttgaatactcatactcttcctttttcaatattattgaagcatttatcagggttattgtct
ccttccgtttacggcgttttttcccttattcccgctgtgccttacaacttatgagtatgagaaggaaaaagttataataacttcgtaaatagtcccataacaga bla CDS                                  bla promoter 2,260          2,280          2,300          2,320          2,340

AatII
 BsrBI                                                       ZraI catgagcggatacatatttgaatgtatttagaaaaataaacaaatagggggttccgcgcacatttccccgaaaagtgccacctgacgtcgacggatcgggagatcggc
gtactcgcctatgtataaacttacataaatcttttttatttgtttatccccaaggcgcgtgtaaaggggcttttcacggtggactgcagctgcctagccctctagccg bla promoter 2,360          2,380          2,400          2,420          2,440          2,460 gcgggatctaattcaattagagactaattcaattagagctaattcaattaggatccaagcttatcgatttcgaaccctcgaccgccggagtataaatagaggcgctt
cgccctagattaagttaatctctgattaagttaatctctgattaagttaatcctaggttcgaatagctaaagcttgggagctggcggcctcatatttatctccgcgaa 3xp3 promoter 2,480          2,500          2,520          2,540          2,560

FIG. 48 CONTINUED tko-step2 (14148 bp) (from 2569-3424 bp)

```
cgtctacggagcgacaattcaattcaaacaagcaaagtgaacacgtcgctaagcgaaagctaagcaaataaacaagcgcagctgaacaagctaaacaatcggctcga
gcagatgcctcgctgttaagttaagtttgttcgtttcacttgtgcagcgattcgctttcgattcgtttatttgttcgcgtcgacttgttcgatttgttagccgagct
```

3xp3 promoter 2,580          2,600          2,620          2,640          2,660

Agel

```
gaccggtcgccaccatggtgagcaagggcgaggagctgttcaccggggtggtgcccatcctggtcgagctggacggcgacgtaaacggccacaagttcagcgtgtcc
ctggccagcggtggtaccactcgttcccgctcctcgacaagtggcccaccacgggtaggaccagctcgacctgccgctgcatttgccggtgttcaagtcgcacagg
```

EGFP ORF 2,680          2,700          2,720          2,740          2,760          2,780

```
ggcgagggcgagggcgatgccacctacggcaagctgaccctgaagttcatctgcaccaccggcaagctgcccgtgccctggcccaccctcgtgaccaccctgacccta
ccgctcccgctcccgctacggtggatgccgttcgactgggacttcaagtagacgtggtggccgttcgacgggcacgggaccgggtgggagcactggtgggactggat
```

EGFP ORF 2,800          2,820          2,840          2,860          2,880

```
cggcgtgcagtgcttcagccgctaccccgaccacatgaagcagcacgacttcttcaagtccgccatgcccgaaggctacgtccaggagcgcaccatcttcttcaagg
gccgcacgtcacgaagtcggcgatggggctggtgtacttcgtcgtgctgaagaagttcaggcggtacgggcttccgatgcaggtcctcgcgtggtagaagaagttcc
```

EGFP ORF 2,900          2,920          2,940          2,960          2,980

```
acgacggcaactacaagacccgcgccgaggtgaagttcgagggcgacaccctggtgaaccgcatcgagctgaagggcatcgacttcaaggaggacggcaacatcctg
tgctgccgttgatgttctgggcgcggctccacttcaagctcccgctgtgggaccacttggcgtagctcgacttcccgtagctgaagttcctcctgccgttgtaggac
```

EGFP ORF 3,000          3,020          3,040          3,060          3,080          3,100

```
gggcacaagctggagtacaactacaacagccacaacgtctatatcatggccgacaagcagaagaacggcatcaaggtgaacttcaagatccgccacaacatcgagga
cccgtgttcgacctcatgttgatgttgtcggtgttgcagatatagtaccggctgttcgtcttcttgccgtagttccacttgaagttctaggcggtgttgtagctcct
```

EGFP ORF 3,120          3,140          3,160          3,180          3,200

```
cggcagcgtgcagctcgccgaccactaccagcagaacacccccatcggcgacggccccgtgctgctgcccgacaaccactacctgagcacccagtccgccctgagca
gccgtcgcacgtcgagcggctggtgatggtcgtcttgtggggtagccgctgccggggcacgacgacgggctgttggtgatggactcgtgggtcaggcgggactcgt
```

EGFP ORF 3,220          3,240          3,260          3,280          3,300

NotI

```
aagaccccaacgagaagcgcgatcacatggtcctgctggagttcgtgaccgccgcgggatcactctcggcatggacgagctgtacaagtaaagcggccgcgactct
ttctggggttgctcttcgcgctagtgtaccaggacgacctcaagcactggcggcggccctagtgagagccgtacctgctcgacatgttcatttcgccggcgctgaga
```

EGFP ORF 3,320          3,340          3,360          3,380          3,400          3,420

FIG. 48 CONTINUED tko-step2 (14148 bp) (from 3425-4280 bp)

agatcataatcagccataccacatttgtagaggttttacttgctttaaaaaacctcccacacctcccctgaacctgaaacataaaatgaatgcaattgttgttgtt
tctagtattagtcggtatggtgtaaacatctccaaaatgaacgaaattttttggagggtgtggagggggacttggactttgtattttacttacgttaacaacaacaa Sv40 terminator 3,440          3,460          3,480          3,500          3,520 aacttgtttattgcagcttataatggttacaaataaagcaatagcatcacaaatttcacaaataaagcattttttttcactgcattctagttgtgggtttgtccaaact
ttgaacaaataacgtcgaatattaccaatgtttatttcgttatcgtagtgtttaaagtgtttatttcgtaaaaaaagtgacgtaagatcaacaccaaacaggtttga Sv40 terminator 3,540          3,560          3,580          3,600          3,620 catcaatgtatcttagttgttggttggcacaccacaaatatactgttgccgagcacaattgatcggctaaatggtatggcaagaaaaggtatgcaatataataatct
gtagttacatagaatcaacaaccaaccgtgtggtgtttatatgacaacggctcgtgttaactagccgatttaccataccgttcttttccatacgttatattattaga gypsy insulator 3,640      3,660      3,680      3,700      3,720      3,740 tttattgggtatgcaacgaaaatttgtttcgtcaacgtatgcaatattctttattaaaagagggtatgcaatgtattttattaaaaacgggtatgcaatataataat
aaataacccatacgttgcttttaaacaaagcagttgcatacgttataagaaataattttctcccatacgttacataaaataattttgcccatacgttatattatta gypsy insulator 3,760          3,780          3,800          3,820          3,840 cttttattgggtatgcaacgaaaatttgtttcgtcaaagtatgcaatatttttattaaaagagggtatgcaatgtattttattaaaaacgggtatgcaataaaaaa
gaaataacccatacgttgcttttaaacaaagcagtttcatacgttataaaaaataattttctcccatacgttacataaaataattttgcccatacgttattttttt gypsy insulator 3,860          3,880          3,900          3,920          3,940 ttatttggtttctctaaaaagtatgcagcacttatttttttgataaggtatgcaacaaaattttactttgccgaaaatatgcaatgtttttgcgaataaattcaacgc
aataaaccaaagagattttttcatacgtcgtgaataaaaaaactattccatacgttgtttttaaaatgaaacggctttttatacgttacaaaaacgcttatttaagttgcg gypsy insulator 3,960      3,980      4,000      4,020      4,040      4,060 acacttattacgtggccaacgcgcctagTGGATCCTTCCTGGCCCTTTTCGAGAAACGCCGCGAGGGCGAAAAGGATTAGTTGTTTCAAACGCAAGAAGGACATTTG
tgtgaataatgcaccggttgcgcggatcACCTAGGAAGGACCGGGAAAAGCTCTTTGCGGCGCTCCCGCTTTTCCTAATCAACAAAGTTTGCGTTCTTCCTGTAAAC nos3 UTR 4,080          4,100          4,120          4,140          4,160

PspXI

TTTCCTTAAATTGTAACCATTTCTTTATTTGGCACTCGAGCCATTGAATTTTTCATTTTCAGAATATGTGTACACATTTTTTAAAAAAATAAAAAAATTATATAATG
AAAGGAATTTAACATTGGTAAAGAAATAAACCGTGAGCTCGGTAACTTAAAAAGTAAAAGTCTTATACACATGTGTAAAAAATTTTTTTATTTTTTTAATATATTAC nos3 UTR 4,180          4,200          4,220          4,240          4,260          4,280

FIG. 48 CONTINUED tko-step2 (14148 bp) (from 5070-56h1 bp)

TCTTCTTGGGGTCAGCCCTGCTGTCTCCACCGAGCTGAGAGAGGTCGATTCTTGTTTCATAGAGCCCCGTAATTGACTGATGAATCAGTGTGGCGTCCAGGACCTCC
AGAAGAACCCCAGTCGGGACGACAGAGGTGGCTCGACTCTCTCCAGCTAAGAACAAAGTATCTCGGGGCATTAACTGACTACTTAGTCACACCGCAGGTCCTGGAGG

ORF frame 2
CAS9

5,040　　　5,060　　　5,080　　　5,100　　　5,120

TTTGTAGAGGTGTACCGCTTTCTGTCTATGGTGGTGTCGAAGTACTTGAAGGCTGCAGGCGCGCCCAAGTTGGTCAGAGTAAACAAGTGGATAATGTTTTCTGCCTG
AAACATCTCCACATGGCGAAAGACAGATACCACCACAGCTTCATGAACTTCCGACGTCCGCGCGGGTTCAACCAGTCTCATTTGTTCACCTATTACAAAAGACGGAC

ORF frame 2
CAS9

5,140　　　5,160　　　5,180　　　5,200　　　5,220　　　5,240

CTCCCTGATGGGCTTATCCCTGTGCTTATTGTAAGCAGAAAGCACCTTATCGAGGTTAGCGTCGGCGAGGATCACTCTTTTGGAGAATTCGCTTATTTGCTCGATGA
GAGGGACTACCCGAATAGGGACACGAATAACATTCGTCTTTCGTGGAATAGCTCCAATCGCAGCCGCTCCTAGTGAGAAAACCTCTTAAGCGAATAAACGAGCTACT

ORF frame 2
CAS9

5,260　　　5,280　　　5,300　　　5,320　　　5,340

TCTCATCAAGGTAGTGTTTGTGTTGTTCCACGAACAGCTGCTTCTGCTCATTATCTTCGGGAGACCCTTTGAGCTTTTCATAGTGGCTGGCCAGATACAAGAAATTA
AGAGTAGTTCCATCACAAACACAACAAGGTGCTTGTCGACGAAGACGAGTAATAGAAGCCCTCTGGGAAACTCGAAAAGTATCACCGACCGGTCTATGTTCTTTAAT

ORF frame 2
CAS9

5,360　　　5,380　　　5,400　　　5,420　　　5,440

ACGTATTTAGAGGGCAGTGCCAGCTCGTTACCTTTCTGCAGCTCGCCCGCACTAGCGAGCATTCGTTTCCGGCCGTTTTCAAGCTCAAAGAGAGTACTTGGGAAG
TGCATAAATCTCCCGTCACGGTCGAGCAATGGAAAGACGTCGAGCGGGCGTGATCGCTCGTAAGCAAAGGCCGGCAAAAGTTCGAGTTTCTCTCTCATGAACCCTTC

ORF frame 2
CAS9

5,460　　　5,480　　　5,500　　　5,520　　　5,540　　　5,560

CTTAATGATGAGGTCTTTTTTTGACCTCTTTATATCCTTTCGCCTCGAGAAAGTCGATGGGGTTTTTTTCGAAGCTTGATCGCTCCATGATTGTGATGCCCAGCAGTT
GAATTACTACTCCAGAAAAAACTGGAGAAATATAGGAAAGCGGAGCTCTTTCAGCTACCCCAAAAAAAGCTTCGAACTAGCGAGGTACTAACACTACGGGTCGTCAA

ORF frame 2
CAS9

5,580　　　5,600　　　5,620　　　5,640　　　5,660

FIG. 48 CONTINUED tko-step2 (14148 bp) (from 5672-6527 bp)

```
CCTTGACGCTTTTGAGTTTTTTAGACTTCCCTTTCTCCACTTTGGCCACAACCAGTACACTGTAAGCGACTGTAGGAGAATCGAATCCGCCGTATTTCTTGGGGTCC
GGAACTGCGAAAACTCAAAAAATCTGAAGGGAAAGAGGTGAAACCGGTGTTGGTCATGTGACATTCGCTGACATCCTCTTAGCTTAGGCGGCATAAAGAACCCCAGG
                                                    CAS9
       5,680            5,700            5,720            5,740            5,760
```

```
CAATCTTTTTTGCGTGCGATCAGCTTGTCGCTGTTCCTTTTCGGGAGGATACTTTCCTTGGAGAAGCCTCCGGTCTGTACTTCGGTCTTTTTAACGATGTTCACCTG
GTTAGAAAAAACGCACGCTAGTCGAACAGCGACAAGGAAAAGCCCTCCTATGAAAGGAACCTCTTCGGAGGCCAGACATGAAGCCAGAAAAATTGCTACAAGTGGAC
                                                    CAS9
  5,780          5,800            5,820          5,840            5,860            5,880
```

```
CGGCATGGACAGGACCTTCCGGACTGTCGCGAAATCCCTACCCTTGTCCCACACGATTTCTCCTGTTTCTCCGTTTGTTTCGATAAGTGGTCGCTTCCGAATCTCTC
GCCGTACCTGTCCTGGAAGGCCTGACAGCGCTTTAGGGATGGGAACAGGGTGTGCTAAAGAGGACAAAGAGGCAAACAAAGCTATTCACCAGCGAAGGCTTAGAGAG
                                                    CAS9
       5,900            5,920            5,940            5,960            5,980
```

```
CATTGGCCAGTGTAATCTCGGTCTTGAAAAAATTCATAATATTGCTGTAAAAGAAGTACTTAGCGGTGGCCTTGCCTATTTCCTGCTCAGACTTTGCGATCATTTTC
GTAACCGGTCACATTAGAGCCAGAACTTTTTTAAGTATTATAACGACATTTTCTTCATGAATCGCCACCGGAACGGATAAAGGACGAGTCTGAAACGCTAGTAAAAG
                                                    CAS9
       6,000            6,020            6,040            6,060            6,080
```

```
CTAACATCGTACACTTTATAGTCTCCGTAAACAAATTCAGATTCAAGCTTGGGATATTTTTTGATAAGTGCAGTGCCTACCACTGCATTCAGGTAGGCATCATGCGC
GATTGTAGCATGTGAAATATCAGAGGCATTTGTTTAAGTCTAAGTTCGAACCCTATAAAAAACTATTCACGTCACGGATGGTGACGTAAGTCCATCCGTAGTACGCG
                                                    CAS9
  6,100          6,120            6,140            6,160            6,180            6,200
```

```
ATGGTGGTAATTGTTGATCTCTCTCACCTTATAAAACTGAAAGTCCTTTCTGAAATCTGAGACCAGCTTAGACTTCAGAGTAATAACTTTCACCTCTCGAATCAGTT
TACCACCATTAACAACTAGAGAGAGTGGAATATTTTGACTTTCAGGAAAGACTTTAGACTCTGGTCGAATCTGAAGTCTCATTATTGAAAGTGGAGAGCTTAGTCAA
                                                    CAS9
       6,220            6,240            6,260            6,280            6,300
```

```
                                                    BstXI
                                                    PaII
TGTCATTTTCATCGTACTTGGTGTTCATGCGTGAATCGAGAATTTGGGCCACGTGCTTGGTGATCTGGCGTGTCTCAACAAGCTGCCTTTTGATGAAGCCGGCTTTA
ACAGTAAAAGTAGCATGAACCACAAGTACGCACTTAGCTCTTAAACCCGGTGCACGAACCACTAGACCGCACAGAGTTGTTCGACGGAAAACTACTTCGGCCGAAAT
                                                    CAS9
  6,320          6,340            6,360            6,380            6,400            6,420
```

```
TCCAACTCAGACAGGCCACCTCGTTCAGCCTTAGTCAGATTATCGAACTTCCGTTGTGTGATCAGTTTGGCGTTCAGCAGCTGCCGCCAATAATTTTTCATTTTCTT
AGGTTGAGTCTGTCCGGTGGAGCAAGTCGGAATCAGTCTAATAGCTTGAAGGCAACACACTAGTCAAACCGCAAGTCGTCGACGGCGGTTATTAAAAAGTAAAAGAA
                                                                        CAS9
                                                    CAS9
            6,440            6,460            6,480            6,500            6,520
```

FIG. 48 CONTINUED tko-step2 (14148 bp) (from 6528-7383 bp)

GACAACTTCTTCTGAGGGGACGTTATCACTCTTCCCTCTATTTTTATCGGATCTTGTCAACACTTTATTATCAATAGAATCATCTTTGAGAAAAGACTGGGGCACGA
CTGTTGAAGAAGACTCCCCTGCAATAGTGAGAAGGGAGATAAAAATAGCCTAGAACAGTTGTGAAATAATAGTTATCTTAGTAGAAACTCTTTTCTGACCCCGTGCT

CAS9

6,540          6,560          6,580          6,600          6,620

TATGATCCACGTCGTAGTCGGAGAGCCGATTGATGTCCAGTTCCTGATCCACGTACATGTCCCTGCCGTTCTGCAGGTAGTACAGGTAGAGCTTCTCATTCTGAAGC
ATACTAGGTGCAGCATCAGCCTCTCGGCTAACTACAGGTCAAGGACTAGGTGCATGTACAGGGACGGCAAGACGTCCATCATGTCCATCTCGAAGAGTAAGACTTCG

CAS9

6,640          6,660          6,680          6,700          6,720          6,740

TGGGTGTTTTCAACTGGGTGTTCCTTAAGGATTTGGGACCCCAGTTCTTTTATACCCTCTTCAATCCTCTTCATCCTTTCCCTACTGTTCTTCTGTCCCTTCTGGGT
ACCCACAAAAGTTGACCCACAAGGAATTCCTAAACCCTGGGGTCAAGAAAATATGGGAGAAGTTAGGAGAAGTAGGAAAGGGATGACAAGAAGACAGGGAAGACCCA

CAS9

6,760          6,780          6,800          6,820          6,840

AGTTTGGTTCTCTCGGGCCATCTCGATAACGATATTCTCGGGCTTATGCCTTCCCATTACTTTGACGAGTTCATCCACGACCTTAACGGTCTGCAGTATTCCCTTTT
TCAAACCAAGAGAGCCCGGTAGAGCTATTGCTATAAGAGCCCGAATACGGAAGGGTAATGAAACTGCTCAAGTAGGTGCTGGAATTGCCAGACGTCATAAGGGAAAA

CAS9

6,860          6,880          6,900          6,920          6,940

TGATAGCTGGGCTACCTGCAAGATTAGCGATGTGCTCGTGAAGACTGTCCCCCTGGCCAGAAACTTGTGCTTTCTGGATGTCCTCCTTAAAGGTGAGAGAGTCATCA
ACTATCGACCCGATGGACGTTCTAATCGCTACACGAGCACTTCTGACAGGGGGACCGGTCTTTGAACACGAAAGACCTACAGGAGGAATTTCCACTCTCTCAGTAGT

CAS9

6,960          6,980          7,000          7,020          7,040          7,060

TGGATCAACTGCATGAAGTTCCGGTTGGCAAATCCATCGGACTTAAGAAAATCCAGGATTGTCTTTCCACTCTGCTTGTCTCGGATCCCATTGATCAGTTTTCTTGA
ACCTAGTTGACGTACTTCAAGGCCAACCGTTTAGGTAGCCTGAATTCTTTTAGGTCCTAACAGAAAGGTGAGACGAACAGAGCCTAGGGTAACTAGTCAAAAGAACT

CAS9/FS

CAS9

7,080          7,100          7,120          7,140          7,160

CAGCCGCCCCCATCCTGTATATCGGCGCCTCTTGAGCTGTTTCATGACTTTGTCGTCGAAGAGATGAGCGTAAGTTTTCAAGCGTTCTTCAATCATCTCCCTATCTT
GTCGGCGGGGGTAGGACATATAGCCGCGGAGAACTCGACAAAGTACTGAAACAGCAGCTTCTCTACTCGCATTCAAAAGTTCGCAAGAAGTTAGTAGAGGGATAGAA

CAS9

7,180          7,200          7,220          7,240          7,260

CAAACAACGTAAGGGTGAGGACAATGTCCTCAAGAATGTCCTCGTTCTCCTCATTGTCCAGGAAGTCCTTGTCTTTAATGATTTTCAGGAGATCGTGATACGTTCCC
GTTTGTTGCATTCCCACTCCTGTTACAGGAGTTCTTACAGGAGCAAGAGGAGTAACAGGTCCTTCAGGAACAGAAATTACTAAAAGTCCTCTAGCACTATGCAAGGG

CAS9

7,280          7,300          7,320          7,340          7,360          7,380

FIG. 48 CONTINUED tko-step2 (14148 bp) (from 7384-823h bp)

```
AGGGATGCGTTGAAGCGATCCTCCACTCCGCTGATTTCAACAGAGTCGAAACATTCAATCTTTTTGAAATAGTCTTCTTTGAGCTGTTTCACGGTAACTTTCCGGTT
TCCCTACGCAACTTCGCTAGGAGGTGAGGCGACTAAAGTTGTCTCAGCTTTGTAAGTTAGAAAAACTTTATCAGAAGAAACTCGACAAAGTGCCATTGAAAGGCCAA
```
CAS9
```
        7,400            7,420            7,440            7,460            7,480
```

```
CGTCTTGAAGAGGAGGTCCACGATAGCTTTCTTCTGCTCTCCAGACAGGAATGCTGGCTTTCTCATCCCTTCTGTGACGTATTTGACCTTGGTGAGCTCGTTATAAA
GCAGAACTTCTCCTCCAGGTGCTATCGAAAGAAGACGAGAGGTCTGTCCTTACGACCGAAAGAGTAGGGAAGACACTGCATAAACTGGAACCACTCGAGCAATATTT
```
CAS9
```
        7,500            7,520            7,540            7,560            7,580
```

```
CTGTGAAGTACTCGTACAGCAGAGAGTGTTTAGGAAGCACCTTTTCGTTAGGCAGATTTTTATCAAAGTTAGTCATCCTTTCGATGAAGGACTGGGCAGAGGCCCCC
GACACTTCATGAGCATGTCGTCTCTCACAAATCCTTCGTGGAAAGCAATCCGTCTAAAAATAGTTTCAATCAGTAGGAAAGCTACTTCCTGACCCGTCTCCGGGGG
```
CAS9
```
    7,600            7,620            7,640            7,660            7,680            7,700
```

```
TTATCCACGACTTCCTCGAAGTTCCAGGGAGTGATGGTCTCTTCTGATTTGCGAGTCATCCACGCGAATCTGGAATTTCCCCGGGCGAGGGGGCCTACATAGTAGGG
AATAGGTGCTGAAGGAGCTTCAAGGTCCCTCACTACCAGAGAAGACTAAACGCTCAGTAGGTGCGCTTAGACCTTAAAGGGGCCCGCTCCCCCGGATGTATCATCCC
```
CAS9
```
        7,720            7,740            7,760            7,780            7,800
```

Bsu36I
```
TATCCGAAATGTGAGGATTTTCTCAATCTTTTCCCTGTTATCTTTCAAAAAGGGGTAGAAATCCTCTTGCCGCCTGAGGATAGCGTGCAGTTCGCCCAGGTGAATCT
ATAGGCTTTACACTCCTAAAAGAGTTAGAAAAGGGACAATAGAAAGTTTTTCCCCATCTTTAGGAGAACGGCGGACTCCTATCGCACGTCAAGCGGGTCCACTTAGA
```
CAS9R
CAS9
```
    7,820            7,840            7,860            7,880            7,900
```

```
GGTGGGGGATGCTTCCATTGTCGAAAGTGCGCTGTTTGCGCAACAGATCTTCTCTGTTAAGCTTTACCAGCAGCTCCTCGGTGCCGTCCATTTTTTCCAAGATGGGC
CCACCCCCTACGAAGGTAACAGCTTTCACGCGACAAACGCGTTGTCTAGAAGAGACAATTCGAAATGGTCGTCGAGGAGCCACGGCAGGTAAAAAAGGTTCTACCCG
```
CAS9
```
7,920            7,940            7,960            7,980            8,000            8,020
```

```
TTAATAAATTTGTAAAATTCCTCCTGGCTTGCTCCGCCGTCAATGTATCCGGCGTAGCCATTTTTAGACTGATCGAAGAAAATTTCCTTGTACTTCTCAGGCAGTTG
AATTATTTAAACATTTTAAGGAGGACCGAACGAGGCGGCAGTTACATAGGCCGCATCGGTAAAAATCTGACTAGCTTCTTTTAAAGGAACATGAAGAGTCCGTCAAC
```
CAS9
```
        8,040            8,060            8,080            8,100            8,120
```

```
CTGTCTGACAAGGGCCTTCAGCAAAGTCAAGTCTTGGTGGTGCTCATCATAGCGCTTGATCATACTAGCGCTCAGCGGAGCTTTGGTGATCTCCGTGTTCACTCGCA
GACAGACTGTTCCCGGAAGTCGTTTCAGTTCAGAACCACCACGAGTAGTATCGCGAACTAGTATGATCGCGAGTCGCCTCGAAACCACTAGAGGCACAAGTGAGCGT
```
CAS9
```
    8,140            8,160            8,180            8,200            8,220
```

FIG. 48 CONTINUED tko-step2 (14148 bp) (from 8787-73h3 bp)

BamHI

CCGGAGTCGAACAGGAGGGCGCCAATGAGGTTCTTCTTTATGCTGTGGCGATCGGTATTGCCCAGAACTTTGAATTTTTTGCTCGGCACCTTGTACTCGTCCGTAAT
GGCCTCAGCTTGTCCTCCCGCGGTTACTCCAAGAAGAAATACGACACCGCTAGCCATAACGGGTCTTGAAACTTAAAAAACGAGCCGTGGAACATGAGCAGGCATTA

CAS9

9,000          9,020          9,040          9,060          9,080

GACGGCCCAGCCGACGCTGTTTGTGCCGATATCGAGCCCAATGGAGTACTTCTTGTCCATGGCGAAAATCCGGGTCGAAAGTTACGGTTATCGCGCACTCTACTTTC
CTGCCGGGTCGGCTGCGACAAACACGGCTATAGCTCGGGTTACCTCATGAAGAACAGGTACCGCTTTTAGGCCCAGCTTTCAATGCCAATAGCGCGTGAGATGAAAG

CAS9                    5'UTR 9,100          9,120          9,140          9,160          9,180          9,200

CACAAATCCTCACCCAAAAACCAAGCACAGTTTATTCAACTGAAGTATTCGCGATACTTCTTTATCTAATAATAATGTACATGTAACTAAACTCGCTTTTGGGTTAA
GTGTTTAGGAGTGGGTTTTTGGTTCGTGTCAAATAAGTTGACTTCATAAGCGCTATGAAGAAATAGATTATTATTACATGTACATTGATTTGAGCGAAAACCCAATT

5'UTR                    nos-promoter+5'UTR 9,220          9,240          9,260          9,280          9,300

AATCGTGACGCAGAGGCAAAAAAAATCGTATGTCCCTTAGACAACTTGAAACAACTGCGAAGCGTACGGCAATTCCAGGAATTTTGTGGTAAAGCTACGCGCCAACT
TTAGCACTGCGTCTCCGTTTTTTTTTAGCATACAGGGAATCTGTTGAACTTTGTTGACGCTTCGCATGCCGTTAAGGTCCTTAAAACACCATTTCGATGCGCGGTTGA nos-promoter+5'UTR 9,320          9,340          9,360          9,380          9,400

AACGGTTCTTGCTTAGAGGTGGAATAATGTAGTTTTCCAGCGATAATAAATATATCGATATTTTTAGTAAAATTGAAAAGGTAAACTTAATTTTAGAAAATAATTTA
TTGCCAAGAACGAATCTCCACCTTATTACATCAAAAGGTCGCTATTATTTATATAGCTATAAAAATCATTTTAACTTTTCCATTTGAATTAAAATCTTTTATTAAAT nos-promoter+5'UTR 9,420          9,440          9,460          9,480          9,500          9,520

TAAGAAATTTAATAGTATGCAAAATAATTTTTACTTGCTAAGAATATGTGCCACTAATTAAAAGCTGGACACCGCGCAATGGAAAATAGTACTACAACACAGCAACA
ATTCTTTAAATTATCATACGTTTTATTAAAAAATGAACGATTCTTATACACGGTGATTAATTTTCGACCTGTGGCGCGTTACCTTTTATCATGATGTTGTGTCGTTGT nos-promoter+5'UTR 9,540          9,560          9,580          9,600          9,620

AAGCCTGAGTTATCAACAAAAAAAATACGAAAACATCTCCCAAAACTAAGCACCCACACGCGCCACTCGCCGTCACAACACAATCACTGCACACCACCATTCGAATTT
TTCGGACTCAATAGTTGTTTTTTTTATGCTTTTGTAGAGGGTTTTGATTCGTGGGTGTGCGCGGTGAGCGGCAGTGTTGTGTTAGTGACGTGTGGTGGTAAGCTTAAA nos-promoter+5'UTR 9,640          9,660          9,680          9,700          9,720

FIG. 48 CONTINUED tko-step2 (14148 bp) (from 73h8-10486 bp)

BspQI
SapI

CGCGCACTGTGACAACATCACATGATATCGGCGCGGCAACATCGGATTACCGACAAAACGAACTATCGCACGAGCCACCGCCGGCGAAGAGCGCTCGTTTTGCAACA
GCGCGTGACACTGTTGTAGTGTACTATAGCCGCGCCGTTGTAGCCTAATGGCTGTTTTGCTTGATAGCGTGCTCGGTGGCGGCCGCTTCTCGCGAGCAAAACGTTGT nos-promoter+5'UTR 9,740          9,760          9,780          9,800          9,820          9,840

BaeI

CCGGCGCGCGCTGAACGAAGAGAACAGCTGACTGCTTGATACGTGCGTGTTTCGCGGCAGGAATTACATAAAGTTTAGAGCCTCTGACGCCAGACCCCCCGAACATT
GGCCGCGCGCGACTTGCTTCTCTTGTCGACTGACGAACTATGCACGCACAAAGCGCCGTCCTTAATGTATTTCAAATCTCGGAGACTGCGGTCTGGGGGGCTTGTAA nos-promoter+5'UTR 9,860          9,880          9,900          9,920          9,940

CGCTCCGATCAAACTACCTGCGAACGGTCACCTAATCCCCACCATGCATGGTAGGTTACCTCTGATCCCGGTCATCACTGGCGTTCGCTCACATCCGTCCTTACATG
GCGAGGCTAGTTTGATGGACGCTTGCCAGTGGATTAGGGGTGGTACGTACCATCCAATGGAGACTAGGGCCAGTAGTGACCGCAAGCGAGTGTAGGCAGGAATGTAC nos-promoter+5'UTR 9,960          9,980          10,000          10,020          10,040

PstI
NheI

TGCATATTTCGAGGTTAAAACGGTCGAAGCTTGGATCCGCTAGCgttgttggttggcacaccacaaatatactgttgccgagcacaattgatcggctaaatggtatg
ACGTATAAAGCTCCAATTTTGCCAGCTTCGAACCTAGGCGATCGcaacaaccaaccgtgtggtgtttatatgacaacggctcgtgttaactagccgatttaccatac nos-promoter+5'UTR                              gypsy insulator 10,060          10,080          10,100          10,120          10,140          10,160 gcaagaaaaggtatgcaatataataatctttttattgggtatgcaacgaaaatttgtttcgtcaacgtatgcaatattctttattaaaagagggtatgcaatgtattt
cgttcttttccatacgttatattattagaaaataacccatacgttgcttttaaacaaagcagttgcatacgttataagaaataattttctcccatacgttacataaa gypsy insulator 10,180          10,200          10,220          10,240          10,260 tattaaaaacgggtatgcaatataataatctttttattgggtatgcaacgaaaatttgtttcgtcaaagtatgcaatatttttttattaaaagagggtatgcaatgtat
ataattttttgcccatacgttatattattagaaaataacccatacgttgcttttaaacaaagcagtttcatacgttataaaaaataattttctcccatacgttacata gypsy insulator 10,280          10,300          10,320          10,340          10,360 tttattaaaaacgggtatgcaataaaaaattatttggtttctctaaaaagtatgcagcacttatttttttgataaggtatgcaacaaaattttactttgccgaaaata
aaataattttttgcccatacgttattttttaataaaccaaagagattttttcatacgtcgtgaataaaaaactattccatacgttgttttaaaatgaaacggctttat gypsy insulator 10,400          10,420          10,440          10,460          10,480

FIG. 48 CONTINUED tko-step2 (14148 bp) (from 11296-12031 bp)

taatatatagacaatggtttttccgttgacgtacatacatctgacgtgtgtttatttagacataatagttatgttttcacatcttttaatgttcgcttaatgcgtat
attatatatctgttaccaaaaggcaactgcatgtatgtagactgcacacaaataaatctgtattatcaatacaaaagtgtagaaaaattacaagcgaattacgcata 11,240          11,260          11,280          11,300          11,320          11,340 gcattctagattttcaacgtcctcgatagtatagtggttagtatccccgcctgtcacgcgggagaccggggttcaattccccgtcggggagaatctgtgattctttt
cgtaagatctaaaagttgcaggagctatcatatcaccaatcataggggcggacagtgcgccctctggccccaagttaaggggcagcccctcttagacactaagaaaa
                                        dU6-1 promoter 11,360          11,380          11,400          11,420          11,440 tttttttctttactttgttatataaacaattttttgtttttaattgaatctaatttgccattgcttttaggaatctcaggcatccagcaagcgtttgtccgccgaatc
aaaaaaagaaaatgaaacaatatatttgttaaaaacaaaattaacttagattaaacggtaacgaaaatccttagagtccgtaggtcgttcgcaaacaggcggcttag
                                        dU6-1 promoter 11,460          11,480          11,500          11,520          11,540 gcccatcagtgaagaagatcctgtggcggctacgaaaatctccccggccatgtcggcctccacctccagcgaaaaacccatcagcgagctggccacctctgtgctga
cgggtagtcacttcttctaggacaccgccgatgctttttagagggggccggtacagccggaggtggaggtcgctttttgggtagtcgctcgaccggtggagacacgact
                                        dU6-1 promoter 11,560          11,580          11,600          11,620          11,640          11,660 cccaccgctttccagactccacctcctcacccggcgaacatggccttggacgaatgcagttgtcgatccgctacagcgcccagcgtcaaaaactagacgtgaccata
gggtggcgaaaggtctgaggtggaggagtgggccgcttgtaccggaacctgcttacgtcaacagctaggcgatgtcgcgggtcgcagttttttgatctgcactggtat
                                        dU6-1 promoter 11,680          11,700          11,720          11,740          11,760 cacaaaatccagaagataccacttcgcgatcccagcaatatccccgatccgtatgttaagctgtatctgttgcctggacgcaccaaggagtcgaaacgcaagacgag
gtgttttaggtcttctatggtgaagcgctagggtcgttataggggctaggcatacaattcgacatagacaacggacctgcgtggttcctcagctttgcgttctgctc
                                        dU6-1 promoter 11,780          11,800          11,820          11,840          11,860 cgtgatcaaggacaactgcaacccgtctacgatgcatcctttgagtacctgatttccattgccgaactcaggcagacggaactggaggtgacggtgtgcacccaaa
gcactagttcctgttgacgttggggcagatgctacgtaggaaactcatggactaaaggtaacggcttgagtccgtctgccttgacctccactgccacacgtgggttt
                                        dU6-1 promoter 11,880          11,900          11,920          11,940          11,960          11,980 agggattcctatccggcggtagtcccatcattggcatggtaggtacccgaaagcaacccctttagttacagacacagcgcgtacgtccttcgcatccttatgattccc
tccctaaggataggccgccatcagggtagtaaccgtaccatccatgggctttcgttggggaatcaatgtctgtgtcgcgcatgcaggaagcgtaggaatactaaggg
                                        dU6-1 promoter 12,000          12,020          12,040          12,060          12,080

FIG. 48 CONTINUED tko-step2 (14148 bp) (from 12072-123hh bp)

aagtacatattctgcaagagtacagtatatataggaaagatatccgggtgaacttcGcaggacaacgcccttggcgaGTTTCagagctaTGCTGgaaaCAGCAtagc
ttcatgtataagacgttctcatgtcatatatatcctttctataggcccacttgaagCgtcctgttgcgggaaccgctCAAAGtctcgatACGACctttGTCGTatcg dJ6.1 promoter                 guide2

12,100          12,120          12,140          12,160          12,180 aagttGaaataaggctagtccgttatcaacttgaaaaagtggcaccgagtcggtgcttttttgcctacctggagcctgagagttgttcaatctagacaattgtgctc
ttcaaCtttattccgatcaggcaatagttgaactttttcaccgtggctcagccacgaaaaaacggatggacctcggactctcaacaagttagatctgttaacacgag guide RNA scaffold modified
              priming site                  repeated after U6.3        20bp1

12,200         12,220         12,240         12,260         12,280         12,300 ggcaacagtatatttgtggtgtgccaaccaacaacctgcaggagctccagctttgttccctttagtgagggttaatttttttttgctcacctgtgattgctcctact
ccgttgtcatataaacaccacacggttggttgttggacgtcctcgaggtcgaaaacaagggaaatcactcccaattaaaaaaaacgagtggacactaacgaggatga T3 seq REV
                            20.T3

T3 promoter
                           priming site
                             T3          dU6.3 promoter 12,320         12,340         12,360         12,380         12,400 caaatacaaaaacatcaaattttctgtcaataaagcatatttatttatatttatttttacaggaaagaattccttttaaagtgtattttaacctataatgaaaaacga
gtttatgtttttgtagtttaaaagacagttatttcgtataaataaatataaataaaatgtcctttcttaaggaaaatttcacataaaattggatattacttttttgct

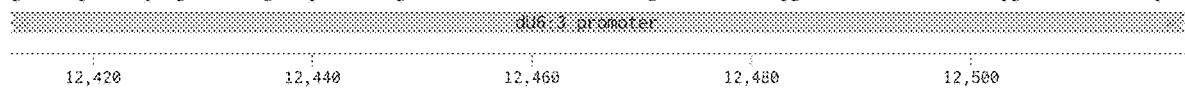

dU6.3 promoter 12,420         12,440         12,460         12,480         12,500 ttaaaaaaaatacataaaataattcgaaaatttttgaatagcccaggttgataaaaattcatttcatacgtttttataacttatgcccctaagtattttttgaccata
aatttttttttatgtatttattaagctttaaaaaacttatcgggtccaactattttttaagtaaagtatgcaaaatattgaatacggggattcataaaaaactggtat

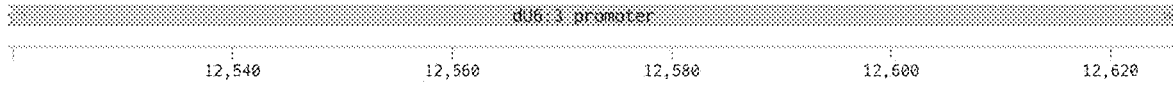

dU6.3 promoter 12,540         12,560         12,580         12,600         12,620 gtgtttcaattctacattaattttacagagtagaatgaaacgccacctactcagccaagaggcgaaaaggttagctcgccaagcagagagggcgccagtgctcacta
cacaaagttaagatgtaattaaaatgtctcatcttactttgcggtggatgagtcggttctccgctttccaatcgagcggttcgtctctcccgcggtcacgagtgat dU6.3 promoter 12,640         12,660         12,680         12,700         12,720

FIG. 48 CONTINUED tko-step2 (14148 bp) (from 12734-1358h bp)

```
cttttttataattctcaacttcttttttccagactcagttcgtatatatagacctattttcaatttaacgtcgcaacattgtactgtgccgcgGTTTCagagctaTGCT
gaaaaatattaagagttgaagaaaaaggtctgagtcaagcatatatatctggataaaagttaaattgcagcgttgtaacatgacacggcgcCAAAGtctcgatACGA
``` duU6.3 promoter                                        guide4

```
12,740        12,760        12,780        12,800        12,820        12,840
```

```
GgaaaCAGCAtagcaagttGaaataaggctagtccgttatcaacttgaaaaagtggcaccgagtcggtgcttttttgcctacctggagcctgagagttgttcaataa
CctttGTCGTatcgttcaaCtttattccgatcaggcaatagttgaacttttttcaccgtggctcagccacgaaaaaacggatggacctcggactctcaacaagttatt
``` priming site
guide RNA scaffold                                    repeated after u6.1

```
12,860        12,880        12,900        12,920        12,940
```

```
aataaaaatgtttcgttttttttgctttcgccagtatttattatttttcatcaatatgtattcaatttggtatgtatttagtaattgtaatatatagacaatggtttt
ttattttttacaaagcaaaaaaacgaaagcggtcataaataataaaaagtagttatacataagttaaaccatacataaatcattaacattatatatctgttaccaaaa
```

```
12,960        12,980        13,000        13,020        13,040
```

```
ccgttgacgtacatacatctgacgtgtgtttatttagacataatagttatgttttcacatctttttaatgttcgcttaatgcgtatgcattctagattttcaacgtc
ggcaactgcatgtatgtagactgcacacaaataaatctgtattatcaatacaaaagtgtagaaaaattacaagcgaattacgcatacgtaagatctaaaagttgcag
```

```
13,060        13,080        13,100        13,120        13,140        13,160
```

```
ctcgatagtatagtggttagtatccccgcctgtcacgcgggagaccggggttcaattccccgtcggggagaatctgtgattcttttttttttttcttttactttgtta
gagctatcatatcaccaatcatagggggcggacagtgcgccctctggccccaagttaaggggcagcccctcttagacactaagaaaaaaaaaaagaaaatgaaacaat
``` duU6.1 promoter

```
13,180        13,200        13,220        13,240        13,260
```

```
tataaacaattttttgttttaattgaatctaatttgccattgcttttaggaatctcaggcatccagcaagcgtttgtccgccgaatcgcccatcagtgaagaagatcc
atatttgttaaaaacaaaattaacttagattaaacggtaacgaaaatccttagagtccgtaggtcgttcgcaaacaggcggcttagcgggtagtcacttcttctagg
``` duU6.1 promoter

```
13,280        13,300        13,320        13,340        13,360
```

```
tgtggcggctacgaaaatctccccggccatgtcggcctccacctccagcgaaaaacccatcagcgagctggccacctctgtgctgacccaccgctttccagactcca
acaccgccgatgcttttagaggggccggtacagccggaggtggaggtcgcttttgggtagtcgctcgaccggtggagacacgactggtggcgaaaggtctgaggt
``` duU6.1 promoter

```
13,380        13,400        13,420        13,440        13,460        13,480
```

```
cctcctcacccggcgaacatggccttggacgaatgcagttgtcgatccgctacagcgcccagcgtcaaaaactagacgtgaccatacacaaaatccagaagatacca
ggaggagtgggccgcttgtaccggaacctgcttacgtcaacagctaggcgatgtcgcgggtcgcagtttttgatctgcactggtatgtgtttaggtcttctatggt
``` duU6.1 promoter

```
13,500        13,520        13,540        13,560        13,580
```

FIG. 48 CONTINUED tko-step2 (14148 bp) (from 19530-14148 bp)

cttcgcgatcccagcaatatccccgatccgtatgttaagctgtatctgttgcctggacgcaccaaggagtcgaaacgcaagacgagcgtgatcaaggacaactgcaa
gaagcgctagggtcgttataggggctaggcatacaattcgacatagacaacggacctgcgtggttcctcagctttgcgttctgctcgcactagttcctgttgacgtt

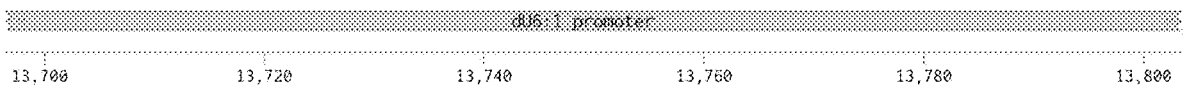

13,600          13,620          13,640          13,660          13,680 ccccgtctacgatgcatcctttgagtacctgatttccattgccgaactcaggcagacggaactggaggtgacggtgtgcacccaaaagggattcctatccggcggta
gggcagatgctacgtaggaaactcatggactaaaggtaacggcttgagtccgtctgccttgacctccactgccacacgtgggttttccctaaggataggccgccat

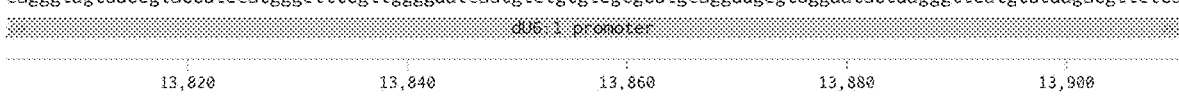

13,700          13,720          13,740          13,760          13,780          13,800 gtcccatcattggcatggtaggtacccgaaagcaacccgttagttacagacacagcgcgtacgtccttcgcatccttatgattcccaagtacatattctgcaagagt
cagggtagtaaccgtaccatccatgggctttcgttgggggaatcaatgtctgtgtcgcgcatgcaggaagcgtaggaatactaagggttcatgtataagacgttctca

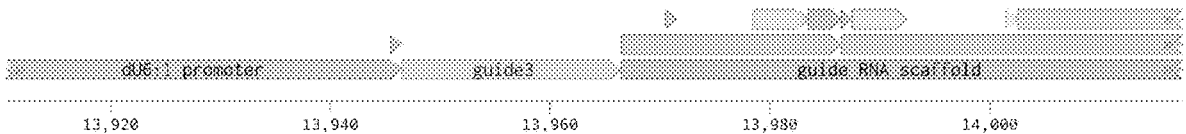

13,820          13,840          13,860          13,880          13,900 acagtatatataggaaagatatccgggtgaacttcGcaccagcacgcactttcgatGTTTCagagctaTGCTGgaaaCAGCAtagcaagttGaaataaggctagtcc
tgtcatatatatcctttctataggcccacttgaagCgtggtcgtgcgtgaaagctaCAAAGtctcgatACGACcttt GTCGTatcgttcaaCtttattccgatcagg

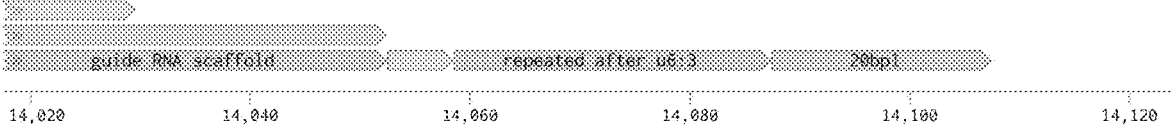

13,920          13,940          13,960          13,980          14,000 gttatcaacttgaaaaagtggcaccgagtcggtgctttttttgcctacctggagcctgagagttgttcaatctagacaattgtgctcggcaacagtatatttgtggtg
caatagttgaactttttcaccgtggctcagccacgaaaaaacggatggaacctcggactctcaacaagttagatctgttaacacgagccgttgtcatataaacaccac 14,020          14,040          14,060          14,080          14,100          14,120 tgccGTACCGGGCCAATTCGAGCT     SEQ ID NO: 185
acggCATGGCCCGGTTAAGCTCGA     SEQ ID NO: 186

Data from an example of two locus ClvR, version 3
(see Figure 20)

Rescue/Cargo/gRNA and no Cas9

Rescue/Cargo/gRNA + Cas9

Wildtype    Cas9 alone generation frequency

Data from an example of two locus ClvR, version 3
(see Figure 20)

FIG. 49D

Two locus Cleaver (ClvR) with genetic linkage between one locus (Cas9) and a second locus (Rescue, gRNAs and Cargo).

Fitness costs for this example are 5% for each allele of the Cas9 construct and each allele of the Rescue, gRNAs + Cargo construct.

m.u. = map units. 0 map units = completely linked, as in single locus ClvR. 50+ map units = freely recombining

DNA SEQUENCE MODIFICATION-BASED GENE DRIVE

CROSS-REFERENCE TO RELATED APPLICATIONS

This application is a divisional application of U.S. application Ser. No. 16/673,823, filed Nov. 4, 2019, which claims the benefit of U.S. Provisional Application 62/755,763 filed on Nov. 5, 2018. All of the foregoing applications are hereby incorporated by reference in their entireties.

REFERENCE TO ELECTRONIC SEQUENCE LISTING

The present application is being filed along with an Electronic Sequence Listing. The Electronic Sequence Listing is provided as a file entitled CALTE.135D1_ST26.XML which is 113,436 bytes in size, created on Mar. 19, 2024. The information in the Electronic Sequence Listing is incorporated herein by reference in its entirety.

BACKGROUND

Field

The disclosure is generally related to DNA sequence modification-based modification of a population.

Description of the Related Art

Gene drive occurs when genetic elements—including genes, gene complexes, entire chromosomes and endosymbiotic bacteria—are transmitted to viable, fertile progeny at rates greater than those due to Mendelian transmission, resulting in an increase in their frequency in the population over time, even if their presence results in a fitness cost to carriers.

SUMMARY

In some embodiments, a two-vector system is provided. The two-vector system comprises a first vector comprising a DNA sequence modifying enzyme; a first promoter operably linked to the DNA sequence modifying enzyme, wherein the DNA modifying enzyme modifies an endogenous copy of an essential gene; and a second vector comprising a rescue transgene sequence; a rescue transgene promoter operably linked to the rescue transgene sequence; and optionally, one or more cargo sequences.

In some embodiments, a two-vector system is provided. The two-vector system comprises a first vector comprising a first sequence encoding a first component of a DNA sequence modifying complex; a second sequence encoding a second component of the DNA sequence modifying complex; a first promoter operably linked to the first sequence encoding the first component; a second promoter operably linked to the second sequence encoding the second component, wherein the DNA modifying enzyme complex modifies an endogenous copy of an essential gene; and a second vector comprising a rescue transgene sequence; a rescue transgene promoter operably linked to the rescue transgene sequence; and optionally, one or more cargo sequences.

In some embodiments, the two-vector system comprises a first vector comprising a first sequence encoding a first component of a DNA sequence modifying complex, a first promoter operably linked to the first sequence encoding the first component of the DNA sequence modifying complex a rescue transgene sequence; a rescue transgene promoter operably linked to the rescue transgene sequence; and optionally, one or more cargo sequences; and a second vector comprising a second sequence encoding a second component of the DNA sequence modifying complex; a second promoter operably linked to the second component of the DNA sequence modifying complex, wherein the DNA modifying enzyme complex modifies an endogenous copy of an essential gene. In some embodiments of the two-vector system, the first vector comprises the second sequence encoding the second component of the DNA sequence modifying complex, and the second vector comprises the first sequence encoding the first component of a DNA sequence modifying complex.

In some embodiments of the two-vector system, the two vectors are configured to be positioned on a single chromosome or a single extrachromosomal element at a distance from each other, two different chromosomes, a chromosome and an extrachromosomal element, or two different extrachromosomal elements. In some embodiments of the two-vector system, the distance is less than 50 map units.

in some embodiments of the two vector system, the DNA sequence modifying enzyme comprises a nuclease, a base editor, or a Search and Replace Prime editor.

In some embodiments of the two-vector system, the two components of the DNA sequence modifying complex comprise a nuclease, a base editor, or a Search and Replace Prime editor.

In some embodiments of the two-vector system, the nuclease cleaves and generates one or more double strand breaks in the endogenous copy of the essential gene.

In some embodiments of the two-vector system, the one or more double strand breaks are repaired to create an altered sequence of the essential gene.

In some embodiments of the two-vector system, the base editor creates one or more base changes in endogenous copy of the essential gene to create an altered sequence of the essential gene.

In some embodiments of the two-vector system, the one or more base changes comprise one or more point mutations in the endogenous copy of the essential gene.

In some embodiments of the two-vector system the Search and Replace Prime editor creates base changes, insertions or deletions in the endogenous copy of the essential gene to create an altered sequence of the essential gene.

In some embodiments of the two-vector system, the rescue transgene is either a recoded copy of the essential gene or is a gene of unrelated sequence, wherein the rescue transgene encodes a protein that is functionally equivalent to a protein encoded by the essential gene, and wherein the DNA sequence modifying enzyme does not modify the rescue transgene.

In some embodiments of the two-vector system, the chromosome is an autosome, X chromosome, Y chromosome, Z chromosome, W chromosome, a prokaryotic genome, or supernumerary chromosome.

In some embodiments of the two-vector system, the extra-chromosomal element is a plasmid or a virus.

In some embodiments of the two-vector system, the one or more cargo sequences comprise a one or more foreign gene sequences, or one or more alleles of an endogenous chromosomal or extra-chromosomal gene to which one of the vectors has been linked through nearby insertion on the chromosome or extra-chromosomal element that carries the endogenous allele of interest.

In some embodiments of the two-vector system, the first, second and rescue transgene promoters are selected from the group consisting of a germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, a viral promoter or prokaryotic promoter.

In some embodiments, a method of reversibly modifying a population is described. In some embodiments, the method comprises obtaining a wild type organism, positioning a two-vector system in the wild type organism thereby generating an altered organism, generating a further altered organism by inducing one or more sequence modifications in an essential gene by a DNA sequence modifying complex in the two-vector system that result in a defect in survival, growth control, fertility, or differentiation in one or more cells in the organism, and rescuing the defect in survival, growth control, fertility, or differentiation by a rescue transgene in the two-vector system, introducing the altered organism in an environment wherein an increase in a frequency of the altered organism is desired relative to a frequency of the wild type organism in a population; replacing the wild type organism with the altered organism in the population in the environment, thereby obtaining a modified population, reintroducing the wild type organism in an environment wherein an increase in a frequency of the wild type organism is desired relative to a frequency of the modified organism in the modified population; replacing the modified organism with the wild type organism in the modified population in the environment, thereby reversibly modifying the population.

In some embodiments of the method, the one or more cells comprise somatic cells, germline cells, gametes, or a combination thereof.

In some embodiments of the method, the altered organism is heterozygous or homozygous for one or both of the vectors.

In some embodiments of the method, the organism is haploid, diploid, or polyploid.

In some embodiments of the method, the reversible modification of the population occurs at a rapid rate, high frequency, or both. In some embodiments of the method, the rapid rate is defined as replacement of at least 90% of the wild type organism by the altered organism or vice versa in the population after at most 100 generations. In some embodiments of the method, the high frequency is defined as replacement of at least 90% of the wild type organism by the altered organism or vice versa after 100 generations in the population.

In some embodiments, a two-vector system is provided. The two-vector system comprises a first vector comprising a DNA sequence modifying enzyme; a first promoter operably linked to the DNA sequence modifying enzyme, wherein the DNA modifying enzyme modifies an endogenous copy of an essential gene; and a second vector comprising a rescue transgene sequence; a rescue transgene promoter operably linked to the rescue transgene sequence; and optionally, one or more cargo sequences.

In some embodiments, a two-vector system is described. In some embodiments the two-vectors system comprises a first vector comprising a first sequence encoding a first component of a DNA sequence modifying complex; a first promoter operably linked to the first sequence encoding the first component of the DNA sequence modifying complex, wherein the DNA modifying enzyme complex modifies an endogenous copy of an essential gene; and a second sequence encoding a second component of a DNA sequence modifying complex; a second promoter operably linked to the second sequence encoding the second component of the DNA sequence modifying complex; and a second vector comprising: a rescue transgene sequence and; a rescue transgene promoter operably linked to the rescue transgene sequence; and optionally, one or more cargo sequences.

In some embodiments, a two-vector system is described. In some embodiments, the two-vector system comprises a first vector comprising a first sequence encoding a first component of a DNA sequence modifying complex, a first promoter operably linked to the first sequence encoding the first component of the DNA sequence modifying complex; and a second vector comprising a second sequence encoding a second component of a DNA sequence modifying complex; a second promoter operably linked to the second sequence encoding the second component of the DNA sequence modifying complex, a rescue transgene sequence; a rescue transgene promoter operably linked to the rescue transgene sequence; and optionally, one or more cargo sequences, wherein the DNA active modifying enzyme complex modifies an endogenous copy of an essential gene.

In some embodiments, a vector is provided. The vector comprises: a first sequence encoding a first component of a DNA sequence modifying complex; a first promoter operably linked to the first sequence encoding the first component of the DNA sequence modifying complex; a second sequence encoding a second component of a DNA sequence modifying complex; a second promoter operably linked to the second sequence encoding complex; a rescue transgene; a promoter operably linked to the rescue transgene that requires binding by the DNA sequence modifying complex for transcription of the rescue transgene; and optionally one or more cargo sequences.

In some embodiments, a two-vector system is provided that comprises: a first vector. The first vector comprises: a first sequence encoding a first component of a DNA sequence modifying complex; a second sequence encoding a second component of the DNA sequence modifying complex; a first promoter operably linked to the first sequence encoding the first component of the DNA sequence modifying complex, a second promoter operably linked to the second sequence encoding the second component of the DNA sequence modifying complex. The DNA modifying enzyme complex modifies an endogenous copy of an essential gene. The system comprises a second vector that comprises a rescue transgene sequence; a promoter operably linked to the rescue transgene that requires binding by the DNA sequence modifying complex for transcription of the rescue transgene; and optionally, one or more cargo sequences.

In some embodiments a two-vector system is provided that comprises a first vector that comprises a first sequence encoding a first component of a DNA sequence modifying complex, a first promoter operably linked to the first sequence encoding the first component of the DNA sequence modifying complex, a rescue transgene sequence; a promoter operably linked to the rescue transgene that requires binding by the DNA sequence modifying complex for transcription of the rescue transgene; and optionally, one or more cargo sequences. The two-vector system further comprises a second vector that comprises a second sequence encoding a second component of the DNA sequence modifying complex; and a second promoter operably linked to the second component of the DNA sequence modifying complex. The DNA modifying enzyme complex modifies an endogenous copy of an essential gene. In some embodiments, the first vector comprises the second sequence encoding the second component of the DNA sequence modifying complex, and the second vector comprises the first sequence encoding the first component of a DNA sequence modifying complex.

BRIEF DESCRIPTION OF THE DRAWINGS

FIG. 1A shows a schematic of the mechanism of action an embodiment of a vector (transgenic construct) that brings about drive of a vector-bearing Y chromosome through cleavage of an essential gene on the X chromosome.

FIG. 1B shows a schematic of an embodiment of inheritance, and viable or non-viable progeny, of an X chromosome cleavage mediated Y chromosome drive process. X (linear) and Y (kinked) chromosomes are indicated.

FIG. 1C shows a graph of an embodiment of a population frequency modeling of X cleavage mediated Y drive for different fitness costs and introduction frequencies. The heat map to the right indicates the number of generations required for the vector to reach a population frequency of >99%.

FIG. 2A shows a schematic of the mechanism of action an embodiment of a vector (transgenic construct) for cleavage mediated X drive with the vector located on the X.

FIG. 2B shows a schematic of inheritance, and viable or non-viable progeny, of a cleavage mediated X drive process with the vector located on the X.

FIG. 2C shows a graph of an embodiment of a population frequency modeling of cleavage mediated X drive with the vector located on the X.

FIG. 3A shows a schematic of the mechanism of action an embodiment of a vector (transgenic construct) for cleavage mediated autosomal drive.

FIG. 3B shows a schematic of inheritance and viable or non-viable progeny of a cleavage mediated autosomal drive process.

FIG. 3C shows a graph of an embodiment of a population frequency modeling of cleavage mediated autosomal drive.

FIG. 4A shows a schematic of the mechanism of action an embodiment of a vector (transgenic construct) for cleavage mediated 2-locus autosomal drive.

FIG. 4B shows a schematic of inheritance, and viable or non-viable progeny, of a cleavage mediated 2-locus autosomal drive process.

FIG. 4C shows a graph of an embodiment of a population frequency modeling of cleavage mediated 2-locus autosomal drive.

FIG. 5A shows a schematic of the mechanism of action an embodiment of a vector (transgenic construct) for cleavage mediated haplolethal drive.

FIG. 5B shows a schematic of inheritance and viable or non-viable progeny of a cleavage mediated haplolethal drive process.

FIG. 5C shows a graph of an embodiment of a population frequency modeling of cleavage mediated haplolethal drive.

FIG. 9A shows a schematic of an embodiment the results of a cross when there is maternal transfer of DNA cleavage/alteration activity from germline into embryo.

FIG. 10 shows a schematic of an embodiment of a meiotic gene drive. Spores that fail to inherit a functional copy of the essential gene die.

FIG. 17 shows an embodiment of an alignment of the target gene (*Drosophila melanogaster* tko—Examples 15 and 16) with the recoded rescue based on *Drosophila virilis* tko. PAM in bold letters, additional silent point mutations introduced into the rescue copy to reduce homology also indicated by shading.

FIG. 18A show a schematic of an embodiment of the components of the DNA sequence modification-based gene drive (Example 17).

FIG. 19 shows an embodiment of the results of Sanger sequencing from the endogenous tko locus following cleavage by ClvR$^{tko}$, demonstrating LOF allele creation, from Example 17.

FIGS. 20A-D show schematics of embodiments of single locus ClvR, and two locus ClvR involving components located on two separate chromosomes.

FIG. 20A shows schematics of embodiments of single locus ClvR.

FIG. 20B shows schematics of embodiments of two locus ClvR, version 1.

FIG. 20C shows schematics of embodiments of two locus ClvR, version 2.

FIG. 20D shows schematics of embodiments of two locus ClvR, version 3.

FIGS. 21A-C show schematics of embodiments of two locus ClvR involving components located on the same chromosome at a distance of less than 50 map units.

FIG. 21A shows schematics of embodiments of two locus ClvR, version 1, involving components located on the same chromosome at a distance of less than 50 map units.

FIG. 21B shows schematics of embodiments of two locus ClvR, version 2, involving components located on the same chromosome at a distance of less than 50 map units.

FIG. 21C shows schematics of embodiments of two locus ClvR, version 2, involving components located on the same chromosome at a distance of less than 50 map units.

FIG. 22 shows a schematic of an embodiment of ClvR in which the Cargo transgene is located in an intron of the Rescue transgene. Similar considerations apply to two locus versions also.

FIG. 24 shows a schematic of an embodiment of ClvR in which the Rescue and the Cargo transgenes are arranged such that the Cargo is located between two transgenes, the presence of both of which is required for expression of a functional Rescue transgene. Similar considerations apply to two locus versions also.

FIG. 26 shows a schematic illustrating how movement of the site-specific DNA modifying enzyme between cells can result in selection for ClvR-bearing genotypes.

FIGS. 29A-D show data from example 17 illustrating drive to genotype fixation in *Drosophila* for ClvR$^{tko}$.

FIG. 29A shows data from 5 drive experiments in which heterozygous ClvR-bearing males were crossed with wild-type females in generation zero.

FIG. 29B shows data from 4 drive experiments in which equal numbers of homozygous ClvR-bearing males and wildtype males were crossed with wildtype females in generation zero.

FIG. 29C shows data from 4 control drive experiments in which males heterozygous for the step 1 construct, which carries only the Rescue transgene, were crossed with wild-type females in generation zero.

FIG. 29D shows data from the 5 drive experiments from FIG. 29A showing the fraction of individuals who are homozygous for ClvR$^{tko}$.

FIG. 31A shows a graph of an embodiment of a population frequency modeling of single locus ClvR drive targeting a haplosufficient locus without maternal carryover for different fitness costs.

FIG. 31B shows a graph of an embodiment of a population frequency modeling of single locus ClvR drive targeting a haplosufficient locus with maternal carryover for different fitness costs FIG. 31C shows a graph of an embodiment of a population frequency modeling of single locus ClvR drive targeting a haploinsufficient locus with maternal carryover for different degrees of haploinsufficiency FIG. 31D shows a graph of an embodiment of a population frequency model of single locus ClvR targeting a haplolethal locus for different introduction frequencies.

FIG. 33 shows schematics illustrating how second generation ClvR elements can be used to replace first generation elements when both are located at the same position in the genome. Upper panel shows general strategy. Lower panel shows schematics illustrating how a specific implementation is created using components from Example 17 and Example 24.

FIGS. 34A-34F show graphs of an embodiment of a population frequency modeling of two locus ClvR, version 1, including reversibility through dilution of an altered population with wildtpes.

FIGS. 35A-35F show graphs of an embodiment of a population frequency modeling of two locus ClvR, versions 2 and 3, including reversibility through dilution of an altered population with wildtypes.

FIG. 37 shows an embodiment of an alignment of amino acid sequence of *D. virilis* tko (Dvir-Tko-aa) and the two annotated protein isoforms from *D. melanogaster* (Dm-Tko-aa-B and Dm-Tko-aa-C).

FIG. 38A-FIG. 38D show another embodiment of the ClvR construct design and principle from Example 17.

FIG. 38A shows Construct A with a U6:3-gRNA, an attP site, the tko rescue copy based on *Drosophila virilis* tko and a ubiquitous opie2-td-tomato marker. Only elements between the homology arms were inserted into a neutral site (68E) on the 3rd chromosome via Cas9 mediated HR. Cloning primers for Gibson assembly are indicated as arrows.

FIG. 38B shows Construct B with an attB site, a 3xP3-GFP marker, Cas9 driven by nanos regulatory elements, and a set of four U6 driven gRNAs. Construct B was integrated into the attP landing site of construct A via phiC31 integrase.

FIG. 38C shows final construct after B was integrated into A.

FIG. 38D shows principle by which ClvR acts. Females heterozygous for the ClvR construct create cleaved and LOF tko alleles in the germline. Additionally, active Cas9/gRNA complex is deposited maternally to all embryos, where subsequently paternal alleles are cleaved rendered LOF. Offspring without the Rescue copy from the ClvR element die.

FIG. 42A-FIG. 42C show an embodiment from Example 17 of components of ClvR and its behavior in females and males.

FIG. 42A shows component genes and their arrangement in ClvR$^{tko}$.

FIG. 42B shows an embodiment of the behavior of ClvR$^{tko}$ when present in a ClvR$^{tko}$/+ adult female. Female progeny inherit an X from their mother and one from their father. Male progeny inherit an X from their mother. One non-ClvR$^{tko}$-bearing male survived. 3735 surviving progeny inherited ClvR$^{tko}$, for a cleavage rate of >99.9%.

FIG. 42C shows an embodiment of the behavior of ClvR$^{tko}$ when present in a ClvR$^{tko}$/+ male. When ClvR$^{tko}$/+ males are crossed to tko$^3$/FM7,B$^1$ females, non-FM7,B$^1$ female progeny carry tko$^3$ and an X chromosome from their father. 907 of these carry ClvR$^{tko}$, while only 8 (which may not represent independent events; FIGS. 39A-E and TABLE 5) do not, for a cleavage rate of >99%. Individuals carrying the FM7,B$^1$ balancer, particularly males, are much less fit than others, and were not considered in the calculations. ClvR$^{tko}$-dependent rescue of the tko$^3$ mutant phenotype is indicated by the large numbers of tko$^3$/Y; ClvR$^{tko}$/+ progeny (880), as compared with none for tko$^3$/Y; +/+.

FIG. 43 illustrates some embodiments in which cells that acquire a competitor plasmid are eliminated if this results in the loss of the ClvR-bearing plasmid.

FIG. 45 depicts a sequence of some embodiments.

FIG. 46 depicts a sequence of some embodiments.

FIG. 49D shows an embodiment of dynamics of components of a two-locus ClvR system in *Drosophila*, in four replicates. Version 3, as illustrated in FIG. 20D, is implemented. Data is from FIG. 49A and FIG. 49B. Rescue, gRNAs and Cargo are present on the third chromosome. Cas9 is on the second chromosome, and the target locus, tko, is on the X.

DETAILED DESCRIPTION

Figure 1A:
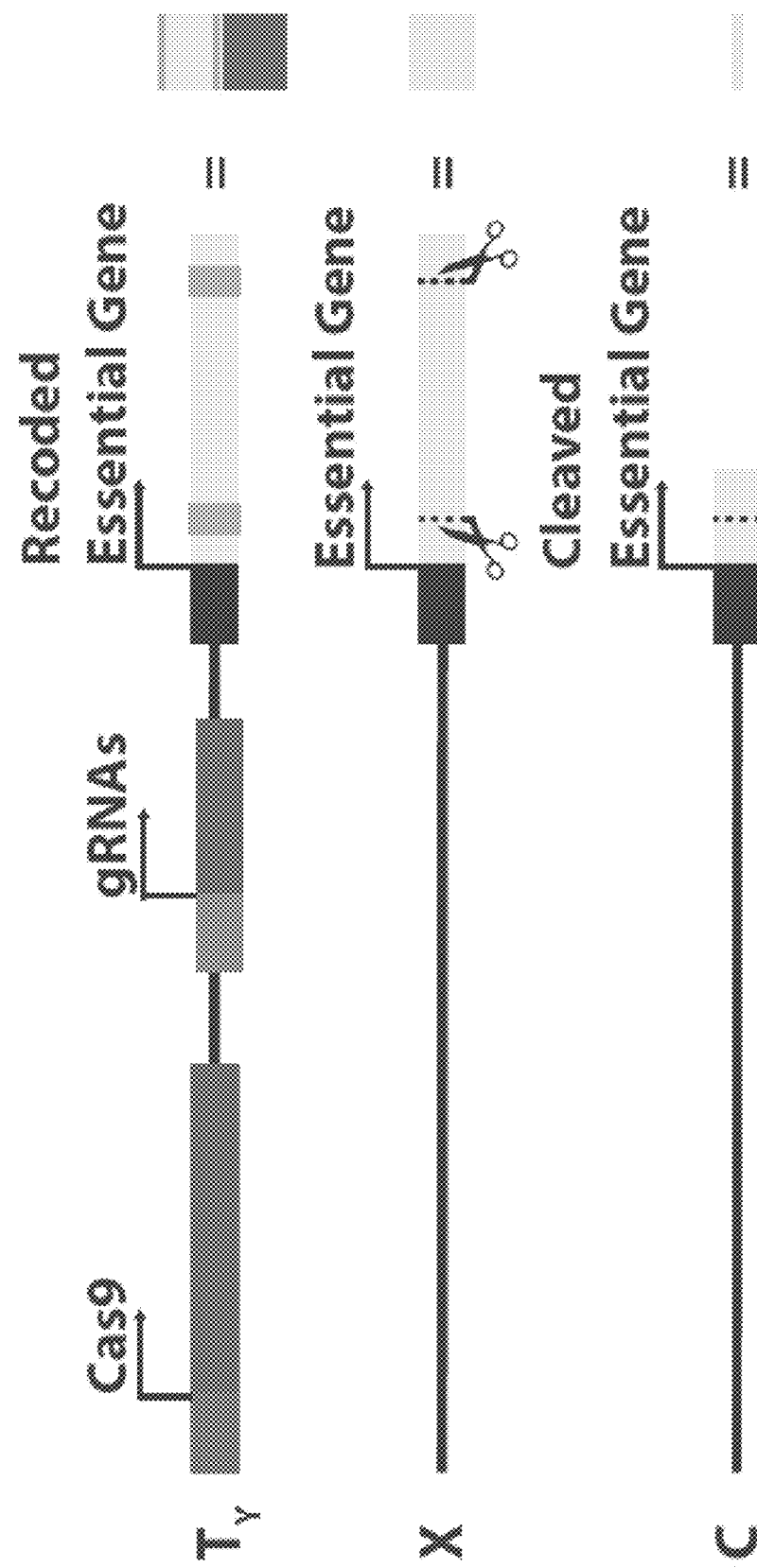
FIG. 1A-FIG. 1C show an embodiment of an X cleavage mediated Y drive. The vector is present on the Y chromosome. Cleavage of an essential gene located on the X chromosome is brought about by Cas9 and associated gRNAs. The Y chromosome also carries a recoded version of the essential gene that is resistant to cleavage by Cas9.

In nature gene drive is brought about by a number of mechanisms, in a number of contexts (Ben-David et al. 2017; Burt and Trivers 1998; Seidel et al. 2011; Nuckolls et al. 2017; Hu et al. 2017). A number of novel methods of engineering gene drive have also been proposed, and in several cases implemented.

There are two general contexts in which gene drive is considered as a technological tool. In one, the goal is population replacement: to spread a trait throughout an extant population. This is sometimes also referred to as population alteration. Herein these terms are used interchangeably. For organisms such as beneficial insects such traits include insecticide, natural pathogen resistance or resistance to other stresses. For a pest/disease vector traits of interest include insecticide sensitivity, the inability to carry or transmit specific pathogens, or a change in life history that preclude pathogen transmission. Genes that confer conditional lethality in response to an environmental cue, so as to ultimately bring about population suppression, are also of interest. A second goal is population suppression or elimination. Targets of interest include invasive species of plants and animals, pests that cause damage directly to plants or animals, and vectors of plant or animal disease. Finally, gene drive is also of interest as a tool for maintaining the presence of a trait in a population in which the genetic element (plasmid, chromosome, virus) in which the gene drive element and any associated cargo genes are sometimes lost, for example during cell division. This is related to population replacement.

A number of methods have been considered for bringing about self-sustaining population replacement. Many of these take as their starting point naturally occurring selfish genetic elements to which cargo genes could be linked (Braig and Yan 2001; Burt and Trivers 1998; Chen et al. 2007). Others involve the use of novel, engineered systems, many of which utilize, in one way or another, the phenomenon of underdominance (heterozygote disadvantage) (Gould and Schliekelman 2004; Marshall and Hay 2011; Marshall and Hay 2012; Marshall et al. 2011; Akbari et al. 2013; Altrock et al. 2010; Altrock et al. 2011; Davis et al. 2001; Gokhale et al. 2014; Reeves et al. 2014). An important characteristic of any gene drive mechanism is its level of invasiveness: its ability to increase in frequency both at the point of release and in surrounding areas linked to the release site by various levels of migration, when introduced at various population frequencies. Here, gene drive mechanisms are divided somewhat arbitrarily into low and high threshold variants, with the understanding that these distinctions lie along a continuum. Low threshold gene drive mechanisms require that only a small fraction of individuals in the population carry the drive element in order for spread to occur locally (Marshall 2009; Marshall and Hay 2012). Examples include transposons, engineered *Medea* chromosomal elements (Chen et al. 2007; Wade and Beeman 1994; Ward et al. 2011), several other possible single locus chromosomal elements (Marshall and Hay 2012), site-specific nucleases that home into their target site (Burt 2003; Gantz and Bier 2015; Gantz et al. 2015; Hammond et al. 2016; Simoni et al. 2014; Windbichler et al. 2011), and site-specific nucleases located on the Y chromosome that cleave and thereby (somehow) block development of X-bearing sperm, resulting in sex ratio distortion (Galizi et al. 2014). These mechanisms are predicted to be invasive because low levels of migration of drive element-bearing individuals into areas outside the release area may, depending on the threshold and the migration rate (Beaghton et al. 2016; Beaghton et al. 2017; Godfray et al. 2017; Marshall 2009; Marshall and Hay 2012), result in these areas being seeded with enough transgene-bearing individuals that drive is likely to occur. Low threshold, invasive gene drive mechanisms are attractive when the goal is to spread transgenes over a large area, and migration rates between the release site and surrounding areas of interest are low. However, for these same reasons, it is likely to be challenging to restore the population to the pre-transgenic state if desired. High (or higher) threshold gene drive mechanisms require, as their name implies, that transgenes make up a much larger fraction of the total insect population (important examples range from ~15-70%) before gene drive occurs. Below this frequency transgenes are instead actively eliminated from the population. These drive mechanisms thus behave as frequency-dependent bistable switches. High transgene frequencies are needed to initiate drive at the release site, limiting the possibility that unintended release of a few individuals could initiate replacement (Marshall 2009). Furthermore, once replacement has occurred at the release site, spread to high frequency in areas connected to the release site by low levels of migration is prevented because the transgene never reaches the threshold frequency needed for drive (Altrock et al. 2010; Altrock et al. 2011; Marshall and Hay 2012). Finally, transgenes can be eliminated from the population if the release of wildtypes results in the frequency of transgenics being driven below the threshold required for drive. A number of gene drive mechanisms that could in principal bring about high threshold gene drive have been proposed. Examples include a number of single locus toxin-antidote gene drive mechanisms (Marshall and Hay 2011; Marshall and Hay 2012; Marshall et al. 2011), reciprocal chromosome translocations, inversions and compound chromosomes (Gould and Schliekelman 2004), and several forms of engineered underdominance (Akbari et al. 2013; Altrock et al. 2010; Altrock et al. 2011; Davis et al. 2001; Gokhale et al. 2014; Marshall and Hay 2012; Reeves et al. 2014). Two of these, UD$^{MEL}$ (double *Medea*), and engineered reciprocal translocations, have recently been shown to drive reversible population replacement into populations of wildtype *Drosophila* (Akbari et al. 2013; Buchman et al. 2018). A third system has been shown to drive high threshold population replacement in *Drosophila* in a split configuration (Reeves et al. 2014). In each of these systems gene drive occurs when transgene-bearing chromosomes experience frequency-dependent changes in fitness with respect to non-transgene-bearing counterparts, with the former having high fitness at high frequency and lower fitness at low frequency. These systems all rely, in one way or another, on the phenomena of underdominance, in which transgene-bearing heterozygotes (or some fraction of them or their progeny) have a lower fitness than either homozygous wildtypes or homozygous transgenics (or transgene-bearing trans-heterozygote in some three allele cases). If the frequency of one allele or pair of alleles or chromosome type is above a critical threshold it spreads to genotype, and in some cases allele fixation. Conversely, if it falls below the critical threshold it is lost in favor of the other allele or chromosome type, usually wildtype. In broad outline, this behavior occurs because when transgene-bearing individuals are common they mate mostly with each other, producing transgene-bearing offspring of high fitness (high survival and/or fecundity), while wildtypes mate mostly with transgene-bearing individuals, producing a preponderance of heterozygous offspring of low fitness (inviable and/or with reduced fecundity). However, when the frequency of wildtypes is high the tables are turned, with transgene-bearing individuals producing high frequencies of unfit heterozygous progeny, and wildtypes producing a high frequency of fit homozygous progeny.

The only gene drive mechanisms shown to drive population replacement in otherwise wildtype organisms are *Medea* (Akbari et al. 2012; Buchman et al. 2018; Chen et al. 2007), UDMEL (double *Medea*) (Akbari et al. 2013), and reciprocal chromosome translocations (Buchman et al. 2018), all in *Drosophila melanogaster* or *Drosophila suzukii*. Several other methods, including engineered under-dominance (Reeves et al. 2014) and homing endonucleases (Windbichler et al. 2011; Windbichler et al. 2007; Simoni et al. 2014; Gantz and Bier 2015; Gantz et al. 2015; Hammond et al. 2016; Champer et al. 2017; Chan et al. 2011; Chan et al. 2013), have seen important progress, though population replacement has not been demonstrated.

There is a need for robust mechanisms of gene drive that can easily be developed for diverse species, and that are robust to mechanisms that can cause failure of gene drive to occur. Thus, while *Medea* elements have been generated in *Drosophila*, it has not yet been possible to develop them in other insects. In addition, *Medea* is inherently challenging because it requires that early zygotic promoters be available, along with antidotes, which together are capable of rescuing maternal lethality. These reagents, as well as specific mechanisms for bringing about toxicity in embryos but not oocytes, are challenging to identify and create, and their implementation requires that one have detailed biological knowledge of the species under consideration (Hay et al. 2010). UDMEL (double *Medea*) represents a more complicated version of *Medea*, and therefore suffers from the same problems (Akbari et al. 2013). Homing-based population replacement is challenging for several reasons. First, it requires that DNA cleavage be followed by DNA repair using homologous recombination, and that homologous recombination proceed through the entire gene drive element that must be copied. Since the cell utilizes multiple repair pathways, and HR is inefficient, complete copying through HR often does not happen. Second, because homing requires the targeting and cleavage of a specific sequence, its efficacy is sensitive to genomic sequence variation. Variation can occur as pre existing sequence polymorphisms in a population. It can also arise from mutation, and as a result of break repair through non-homologous end joining, which is error prone (Preston et al. 2006; Windbichler et al. 2011). Regardless of the mechanism, sequence variants that are not cleaved are resistant to homing, and may retain some or complete wildtype gene function. The presence of such resistant alleles can block HEG spread and thereby prevent population replacement. Thus, the question of how to bring about high frequency homing that is gene specific, but insensitive to some level of sequence variation within the gene, is central to the development of HEG-based population replacement technologies, and remains to be solved. Translocations can only provide high threshold population replacement. They also require a significant amount of chromosomal engineering, in that two large chromosome fragments must become linked to each other, while maintaining high levels of organism fitness (Buchman et al. 2018; Marshall and Hay 2012). Finally, shredding of the X chromosome through the use of a Y-linked transgene that thereby causes the loss of X-bearing sperm has also been proposed (Burt 2003), and significant progress has been made (Galizi et al. 2014; Galizi et al. 2016; Windbichler et al. 2008). However, this approach is limited to population suppression and species that have clear X and Y chromosomes in which males are Y. Many species of interest lack this configuration. In summary, gene drive for population replacement is an important technological goal, but methods for easily engineering it in diverse species are lacking.

As a specific example of the need for population replacement gene drive, despite a myriad of approaches to controlling mosquito-borne infections, ranging from insecticide treated bed nets, new anti-malarial drugs such as artemisinin, and suppression attempts using sterile males, there are still over 600,000 deaths from malaria each year [WHO World Malaria Report 2014]. This stems from a combination of lack of human compliance, emerging drug resistance, and selection for mosquitoes preferring to bite outdoors. These failures show the need for novel molecular approaches to combating insect-borne disease [Alphey, 2014].

However, the approaches proposed face substantial barriers to their development. In toxin-antidote systems, the toxin has to be strong enough to suppress one or both copies of the target gene and the recoded 'antidote' version of this gene has to have strong enough and timely zygotic expression to compensate for the loss of the maternal product Chen et al 2007, [Akbari, 2013; Akbari, 2014]. These are already difficult requirements for the development of a first generation gene drive, let alone successive drives (second and third generation versions) in case the original mutates to inactivity. Additionally, what works in one species, such as the *Medea^{myd88}* in *Drosophila melanogaster*, does not necessarily work in other species, such as *Aedes aegypti*, despite sharing the molecular components involved in the drive.

HEG approaches are elegant in that they increase their frequency not through the destruction of competing alleles as in toxin-antidote drives but by copying themselves onto non HEG containing homologs, thus forcing heterozygotes for the HEG to become homozygous. However, they suffer from the being limited in what they can target due to their inherent base specificity and from potential replication errors every time they are copied.

HEG based approaches to gene drive are predicted to be very powerful, driving from low frequency and in relatively few generations. The emergence of TALENs and ZFNs have vastly expanded the number of possible target sites while maintaining specificity, but their multiple repeats make them prone to mutation due to recombination [Simoni, 2014; Esvelt, 2014]. An alternative now being very actively explored utilizes the CRISPR nuclease Cas9 and gRNAs that target Cas9 to specific sequences for cleavage based on Watson-Crick base pairing interactions. While HEGs based on Cas9 can target virtually any sequence, a Cas9 drive construct is likely to be quite large, making homing more difficult and the construct much more prone to copying errors.

While drives like *Medea* can incorporate new toxins in addition to old ones to perform additional stages of replacement, adding additional gRNAs will buffer a Cas9 HEG against NHEJ resistant alleles but will only make the construct even larger and thus more prone to other problems, such as abortive gap repair.

Cas9 and other RNA-guided DNA nucleases can be used at the heart of any of the gene drives previously proposed for use as HEGs, with a substantially larger pool of potential targets while maintaining specificity. However, these strategies have the major drawback of susceptibility to DNA loss or drive dysfunction due to the imperfect copying of Cas9 and any associated cargo during homology directed repair.

As detailed in PCT Application No. PCT/US2018/030990 (the entirety of which is incorporated by reference here), various gene drive systems are known. Some involve a first and second component. The first component is a gene (or genes) expressing an enzyme (or the two essential components of an enzyme) that bring about DNA sequence modification, and thus inactivation (creation of loss of function [LOF] alleles), of an essential gene. The second component is a transgene (the rescue transgene) that is able to rescue the loss of function phenotype due to inactivation of the endogenous copies of the essential gene, and is insensitive to enzyme-mediated DNA sequence modification. This method requires only two components: a site-specific DNA modifying enzyme that targets a gene required for viability or fertility in any way (an essential gene), and a second, functional version of the essential gene that includes sequences that are resistant to modification by the site-specific DNA modifying enzyme (the rescue transgene). When these two elements are linked together, for example, in a vector (e.g., plasmid, chromosome, extrachromosomal element, virus), organisms that carry the vector always survive because they always carry the rescue transgene. In contrast, organisms that do not carry the rescue transgene will die or be sterile if they only carry inactive copies of the essential gene that are inherited from vector-bearing parents or created de novo through site-specific DNA modifying enzyme activity that is brought into these cells through diffusion, transport, or cell-cell movement. The above is taken a step further herein, and involves two or more loci for the embodiments presented in PCT Application No. PCT/US2018/030990. In some embodiments, two locus gene drive is provided herein, and can be applied to any of the single locus embodiments described herein, as outlined herein. That is, any of the embodiments provided herein can be modified such that there are effectively two or more loci in the system. In some embodiments, two vectors ("a two-vector system") are provided for the implementation of the various embodiments provided herein. Without being limited by any particular theory, the fact that two locus gene drive wanes over generations provides two locus systems (such as ClvR) with three important new, unique features not exhibited by single locus systems (e.g., ClvR embodiments provided herein). As a short hand, embodiments are provided herein with respect to CLvR, however, these embodiments can be employed in the other embodiments provided herein as well (as appropriate).

First, gene drive for a given population introduction frequency is limited in time. This is illustrated, for example in FIGS. 34A-F and FIGS. 35A-F, and FIG. 49A-E, FIG. 50, and illustrated in Example 41 and Example 42, and occurs because the frequency of one or both Cas9/gRNA components decreases over time. Once these alleles are at low frequency or are eliminated, drive can no longer occur. However, even though drive is eliminated, the Rescue/Cargo can remain at genotype fixation. Without being limited by any particular theory, this occurs because all (or nearly all) wildtype alleles of the essential gene have been eliminated, locking the population into a Cargo/Rescue-bearing state.

Figure 50:
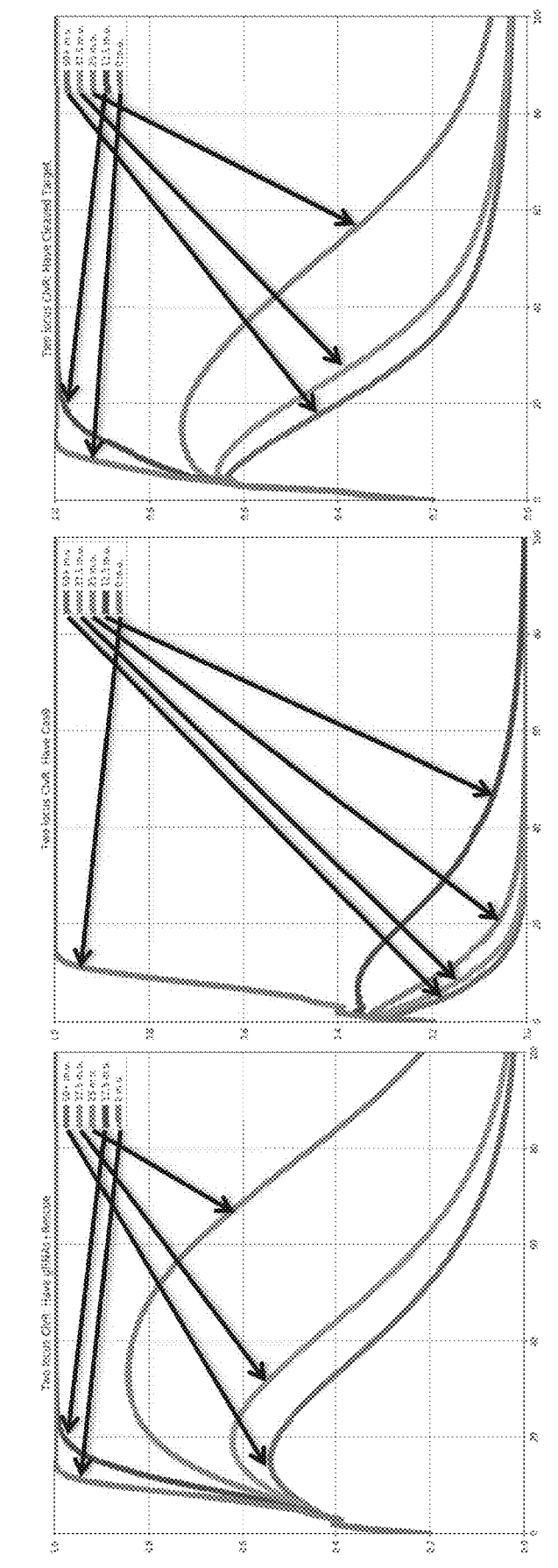
FIG. 50 shows an embodiment of modeling of two locus ClvR with linkage and different levels of recombination between the two loci.

The second new and unique feature of two locus ClvR is that drive is limited in space. It is local rather than global, as with single locus ClvR. This is because as the transgene-bearing organisms distribute in space from a source through migration, the frequency of the Cas9/gRNA components will decrease. Drive of the Cargo/Rescue only occurs in which the frequency of Cas9/gRNA (or that of other RNA-guided DNA sequence modifying enzymes such as base editors or Prime editors) is high enough to bring about high frequency creation of LOF alleles of the essential gene. In particular, when two locus ClvR individuals are migrating into a neighboring population composed mostly of wild-types, the independent segregation of the two chromosomes means that Cas9/gRNA-bearing individuals will often find themselves without a copy of the Rescue, and therefore die. In the absence of levels of LOF allele creation sufficient to create many LOF homozygotes, drive of the Cargo/Rescue into the population will not occur. These points are illustrated in FIG. 50, which shows that for a constant introduction frequency the degree of linkage determines the extent of drive, and whether the Rescue and Cargo spread to high frequency.

The third new and unique feature of two locus ClvR is that with it, unlike with single locus ClvR, reversibility to a population that lacks the Cargo/Rescue and the cleaved allele can be achieved by dilution of a transgene-bearing population with wildtype individuals. Whenever the presence of the Cargo/Rescue results in some fitness cost, dilution can lead to elimination of drive, Cargo and LOF alleles of the essential gene, from the population. In contrast, with single locus ClvR, reversibility cannot easily be achieved through dilution because the drive is so powerful. See, for example, FIGS. 34A-F and FIGS. 35A-F. A similar result is implied by the modeling presented in FIG. 50 and the data from Example 40 presented in FIGS. 49A-E.

The above three features are useful to implement in order to have the gene drive mechanisms function within regulatory frameworks. Central to these developments are aspects of confinement and reversibility: can the spread of transgenes to high frequency be limited to locations in which their presence is sought, and can the population be restored to the pre-transgenic state. Two locus versions of ClvR, described herein provide a method for addressing these concerns, while also bringing about population alteration to a high frequency of transgene-bearing individuals under a variety of conditions of fitness cost and introduction frequency.

In some embodiments of the two vector system, the first vector comprises a DNA sequence modifying enzyme, wherein the DNA sequence modifying enzyme modifies an endogenous copy of an essential gene, and a promoter is operably linked to the DNA sequence modifying enzyme, and second vector comprising a rescue transgene sequence and a rescue transgene promoter operably linked to the rescue transgene sequence. In some embodiments, the two vectors are positioned on a single chromosome at a distance from each other. In some embodiments, the two vectors are positioned on a single extrachromosomal element at a distance from each other. In some embodiments, the two vectors are positioned on two different chromosomes. In some embodiments, the first vector is positioned on a chromosome and the second vector is positioned on an extrachromosomal element. In some embodiments, the second vector is positioned on a chromosome and the first vector is positioned on an extrachromosomal element. In some embodiments, the second vector optionally comprises one or more cargo sequences.

In some embodiments of the two-vector system, the first vector comprises a first sequence encoding a first component of a DNA sequence modifying complex, and a second sequence encoding the second component of the DNA sequence modifying complex wherein the DNA sequence modifying complex modifies an endogenous copy of an essential gene, and a first promoter that is operably linked to the first sequence encoding the first component and a second promoter is operably linked to the second sequence encoding the second component of the DNA sequence modifying complex, and a second vector comprising a rescue transgene sequence and a rescue transgene promoter operably linked to the rescue transgene sequence. In some embodiments, the two vectors are positioned on a single chromosome at a distance from each other. In some embodiments, the two vectors are positioned on a single extrachromosomal element at a distance from each other. In some embodiments, the two vectors are positioned on two different chromosomes. In some embodiments, the first vector is positioned on a chromosome and the second vector is positioned on an extrachromosomal element. In some embodiments, the second vector is positioned on a chromosome and the first vector is positioned on an extrachromosomal element. In some embodiments, the second vector optionally comprises one or more cargo sequences.

In some embodiments of the two-vector system, the first vector comprises a first sequence encoding a first component of a DNA sequence modifying complex, wherein the DNA sequence modifying complex modifies an endogenous copy of an essential gene, and a first promoter that is operably linked to the first sequence encoding the first component of the DNA sequence modifying complex, a rescue transgene, and rescue transgene promoter operably linked to the rescue transgene, and optionally one or more cargo transgenes, and a second vector comprising a second sequence encoding a second component of the DNA sequence modifying complex, and a second promoter operably linked to the second component of the DNA sequence modifying complex. In some embodiments, the two vectors are positioned on a single chromosome at a distance from each other. In some embodiments, the two vectors are positioned on a single extrachromosomal element at a distance from each other. In some embodiments, the two vectors are positioned on two different chromosomes. In some embodiments, the first vector is positioned on a chromosome and the second vector is positioned on an extrachromosomal element. In some embodiments, the second vector is positioned on a chromosome and the first vector is positioned on an extrachromosomal element. In some embodiments, the first vector optionally comprises one or more cargo sequences.

In some embodiments, a two-vector system is provided that comprises a first vector. The first vector comprises a first sequence encoding a first component of a DNA sequence modifying complex. The first vector also comprises a second sequence encoding a second component of the DNA sequence modifying complex. There is also a first promoter operably linked to the first sequence encoding the first component of the DNA sequence modifying complex. There is also a second promoter operably linked to the second sequence encoding the second component of the DNA sequence modifying complex, wherein the DNA modifying enzyme complex modifies an endogenous copy of an essential gene. The two-vector system also comprises a second vector that comprises a rescue transgene sequence; a rescue transgene promoter operably linked to the rescue transgene sequence; and optionally, one or more cargo sequences.

In some embodiments, a two-vector system is provided that comprises a first vector comprising: a first sequence encoding a first component of a DNA sequence modifying complex, a first promoter operably linked to the first sequence encoding the first component of the DNA sequence modifying complex a rescue transgene sequence; a rescue transgene promoter operably linked to the rescue transgene sequence; and optionally, one or more cargo sequences. The two-vector system also comprises a second vector that comprises a second sequence encoding a second component of the DNA sequence modifying complex; a second promoter operably linked to the second component of the DNA sequence modifying complex, wherein the DNA modifying enzyme complex modifies an endogenous copy of an essential gene.

In some embodiments, a two-vector system comprises a first vector that comprises a DNA sequence modifying enzyme; and a first promoter operably linked to the DNA sequence modifying enzyme, wherein the DNA modifying enzyme complex modifies an endogenous copy of an essential gene. The two-vector system also comprises a second vector that comprises a rescue transgene sequence; a rescue transgene promoter operably linked to the rescue transgene sequence; and optionally, one or more cargo sequences.

In some embodiments, the "distance" is defined in terms of probability of recombination between the two vectors during each replication cycle. Without being limited by any particular theory, a 50% probability of recombination is equivalent to 50 map units or greater i.e., being equivalent to independent segregation. In some embodiments, the distance ranges from about 50 map units to about 100 map units. In some embodiments, the distance is about 50, 55, 60, 65, 70, 75, 80, 85, 90, 95, or 100 map units, or a value within a range defined by any two of the aforementioned values. In some embodiments the distance is less than 50 map units. In some embodiments the distance ranges from about 0 map unit to about 50 map units. In some embodiments, the distance is about 0, 1, 5, 10, 15, 20, 25, 30, 35, 40, 45, or 50 map units, or a value within a range defined by any two of the aforementioned values.

Figure 36:
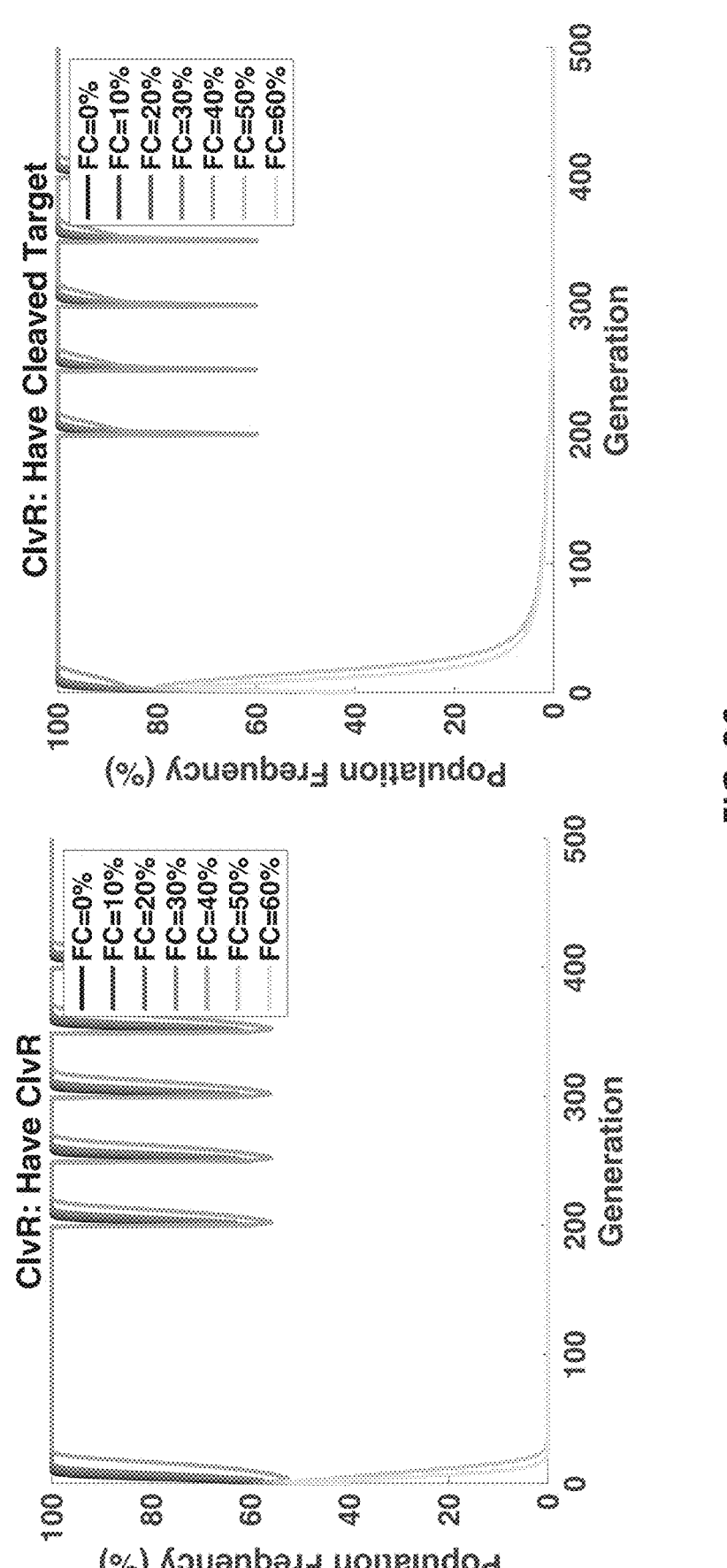
FIG. 36 shows graphs of an embodiment of a population frequency modeling of single locus ClvR, including lack of reversibility through dilution of an altered population with wildtypes under conditions present in FIGS. 34A-F and FIGS. 35A-F.

In some embodiments, the DNA sequence modifying enzyme is encoded by a single gene, and the Cargo/Rescue transgenes can also be located at some distance from this gene on the same chromosome, or on different chromosomes. In some embodiments, the DNA sequence modifying enzyme is encoded by two tightly linked genes, and the Cargo/Rescue transgenes can also be located at some distance from these genes either on the same chromosome, or on different chromosomes (FIGS. 20A-D, FIGS. 21A-C). In some embodiments a first component of a DNA sequence modifying complex, and the Cargo/Rescue transgenes can also be located together, but at some distance from a second gene encoding a second component of the DNA sequence modifying enzyme on the same chromosome, or on different chromosomes (FIGS. 20B-D, FIGS. 21A-C). These embodiments create gene drive elements known as two locus ClvR. These are distinguished from those discussed above in which all components are tightly linked at a single locus (FIG. 20A). Behavior of single locus ClvR for several introduction frequencies and fitness costs is illustrated in FIG. 36. This figure also illustrates the effects of introducing wildtype individuals at timepoints after ClvR has spread to genotype fixation, such that wildtypes constitute 30% of the population following each introduction. The population rapidly rebounds to a state in which all individuals are Rescue-and thus cargo-bearing. These results are important because they illustrate that for many conditions single locus ClvR-dependent population replacement is not easily reversed through dilution of the population with wildtpes. In the case of two locus ClvR (e.g., involving a two-vector system), ClvR components are on two different chromosomes, and segregate independently at meiosis (FIGS. 20B-D), or they are located on the same chromosome at some distance from each other, such that recombination separates them at some frequency less than 50% of the time (FIGS. 21A-C and FIG. 50). This results in some gametes carrying the Cargo/Rescue but not Cas9/gRNA, others carrying Cas9/gRNA alone, and others carrying both transgene cassettes. The fate of these gametes in progeny (dead or alive) depends on when sequence modification occurs (in the germline alone or in somatic cells as well), and the presence or absence of the Cargo/Rescue. In short, the fates of the Cargo/Rescue and Cas9/gRNA components are dissociated because they do not always travel together through meiosis.

Without being limited by any particular theory, an implication of this behavior is that while with each two locus scenario the frequency of the Cargo/Rescue can increase in the population as compared to the non Cargo/Rescue bearing homologous chromosome (notwithstanding any limitations imposed by fitness costs associated with carrying the Cargo/Rescue cassette), the frequency of Cas9/gRNA (two locus version 1) (FIG. 20B or the Cas9/gRNA component not linked to the Cargo/Rescue (two locus version 2 and 3) (FIGS. 20C, D) will decrease over time since they sometimes find themselves in individuals who carry no functional copies of the essential gene, and are therefore dead (FIGS. 34A-F, FIGS. 35A-F and FIG. 50. Also see example 40 and 41, and associated figures, FIG. 49A-E and FIG. 50). Since it is the presence of both Cas9 and gRNAs that leads to selection (indirectly, through the creation of LOF alleles of the essential gene) for the presence of the Cargo/Rescue, this means that in two locus ClvR the strength of drive (the ability create LOF alleles which select for Cargo/Rescue-bearing chromosomes and against their wildtype counterparts) wanes over time. Thus, two locus ClvR results in drive that is ultimately self-limiting, rather than self-sustaining, as is the case with single locus ClvR. Importantly, all the components of two locus ClvR already exist. They are exactly the same components as those used to implement ClvR$^{tko}$ (FIGS. 29A-D, FIG. 30, FIGS. 42A-C) and ClvRs targeting other essential genes (dbe FIG. 26, FIG. 30) and (tf2As FIG. 27, FIG. 30). It is just that the components have been rearranged in terms of their chromosomal location. The behavior of two locus ClvR, version 1, is illustrated in FIGS. 34A-F. ClvR is introduced into the wildtype population at a fixed frequency of 40%, for illustrative purposes. Cas9/gRNAs cut in the male and female germline, and in embryos that derive from Cas9/gRNA-bearing mothers, due to maternal carryover of Cas9/gRNA. (left panel) Cargo/Rescue spreads to genotype fixation for a number of different fitness costs (up to and including 30%), but fails to spread when costs are higher (40-60%). Upper panels show the consequences of making a single introduction of wildtypes into the replaced/altered population at generation 200, such that wildtypes now make up 30% of the population. Lower panels show the consequences of five such introductions, one each 50 generations. More frequent introductions would result in more dramatic effects, since 50 generations provides an opportunity for some genotypes to rebound towards pre-introduction frequencies. Here, the 50 generation scenario is used to provide a conservative estimate picture of reversibility. Note that 30% introduction of wildtypes at generation 200 results in loss of Rescue from the population for all fitness costs except the zero fitness cost scenario, which is unlikely to exist in the wild. (middle panel) Frequency of Cas9/gRNAs over time. Note that the frequency decreases rapidly under all conditions when there is a fitness cost to carrying Cas9. In the case of no fitness cost (horizontal line with a square wave drop at generation 200) the frequency does not decrease because the Cargo/Rescue has gone to allele fixation and therefore there are no individuals lacking Rescue activity. This condition is unlikely to obtain in the real world. Introduction of wildtypes results in a decrease in the frequency of the cas9/gRNA under all conditions. In the case Cas9 does not result in a fitness cost to carriers, Cas9 is not eliminated. It simply undergoes the square wave transition as their numbers are diluted following the introduction of wildtypes. (right panel) Frequency of cleaved, LOF alleles of the essential gene for the conditions described in the left panel. Note that whenever ClvR spreads the frequency of the cleaved LOF allele goes to fixation. This occurs because the continuous presence of Cas9/gRNA ensures complete cleavage. Addition of wildtypes at a frequency of 30% results in loss of the cleaved allele over time when there is a fitness cost. This is because there is no further cleavage (Cas9/gRNAs have already been eliminated), and therefore no creation of new LOF alleles. In addition, because there is no drive, and therefore no selection for the presence of the Rescue, which also often carries a fitness cost, the Rescue is also lost from the population. Finally, with decreasing levels of Rescue, wildtype alleles of the essential gene are more fit than LOF alleles (because they allow survival in the absence of the Rescue), and therefore spread. In sum, while drive with two locus ClvR version 1 is strong (able to spread rapidly to high frequency while carrying a fitness cost), it is also transient, and therefore reversible through dilution with wildtypes (FIGS. 34A-F).

Similar qualitative points apply to the case of two locus ClvR, versions 2 and 3, which behave in an identical manner to each other with the given parameters (FIGS. 35A-F). These are illustrated in FIGS. 35A-F, FIGS. 49A-49E, and discussed in Example 40. They provide an example of an implementation of two-locus ClvR. Conditions are as in FIGS. 34A-F, with the exception that Cas9 and gRNA are split, with one linked to the Rescue/Cargo and the other located on a distinct chromosome. The behavior of these elements is qualitatively similar to that of two locus ClvR (version 1) (FIGS. 34A-F). In addition, versions 2/3 are particularly easy to create since they can be created simply by crossing two simple strains to each other: one strain carries germline-expressed Cas9; the other carries gRNA/Cargo/Rescue. Both are homozygous viable and populations heterozygous for two locus Clvr (version2/3) are created when the strains are crossed to each other. Note that for all two locus versions of ClvR this modeling assumes that maternally deposited Cas9 decays rapidly and therefore does not interact with zygotically expressed gRNAs in the early embryo. Other assumptions of the model are 90% cleavage, and 90% maternal carryover. In addition, fitness costs are additive and distributed across the components. Thus, for a 30% total homozygous fitness cost (homozygous at both loci) there is a 7.5 fitness cost for each allele of the Cargo/Rescue/Cas9 or gRNA, and the Cas9/gRNA component present on the other chromosome. Changing these variables does not qualitatively alter the outcome. All versions of two locus ClvR drive population replacement for some time, but then drive fades as components of the Cas9/gRNA decrrease in frequency. In consequence of this decrease, population replacement becomes reversible through dilution with wildtypes.

In some embodiments, the two-vector versions of Clvr, using the components described herein, and the arrangements of components described herein, can also be implemented in formats in which ClvR components are located on the same chromosome, at some distance less than 50 map units from each other. In single locus ClvR the components are tightly linked, with very little or no recombination occurring between Cargo/Rescue and Cas9/gRNA. This makes drive strong and constant, since cleavage activity is always linked to the Cargo/Rescue. In the two locus versions of ClvR described above, Cargo/Rescue and Cas9/gRNA recombine freely with each other since they are on separate chromosomes. This is equivalent to a map distance of 50 map units or greater for two loci on the same chromosome (effectively unlinked). In considering these two extremes it is important to note that versions of two locus ClvR can also be created using the same procedures, with Cargo/Rescue and Cas9 components (either together or being separated such that one is linked to the Cargo/Rescue and one is not) being located on the same chromosome at something less than 50 map units distance. In this scenario, when individuals carrying both constructs on the same chromosome are released into a population, drive will initially be strong, reflecting linkage between the two sets of components (they travel together on the same chromosome more often than not). However, as recombination between the components occurs over subsequent generations, the loci will separate, with the rate of separation being dependent on the distance between the loci. Ultimately, recombination will create a situation identical to that observed with unlinked two locus ClvR, in which the two loci are in what is referred to as linkage equilibrium. The important point is that the smaller the recombination distance is between the two transgene cassette-bearing loci is, the longer the components will remain linked. In consequence, the strength of drive will decay more slowly than with unlinked two locus ClvR. It will start as strong as that of single locus Clvr. Recombination will slowly (depending on the distance between the loci) break up this association, resulting in drive with the self-limiting characteristics of unlinked two locus ClvR. Examples of ClvR with varying degrees of linkage are shown in Example 41, FIG. 50.

Without being limited by any particular theory, versions of two locus ClvR with linkage (FIGS. 21A-C and FIG. 50) are unique because they provide a method for titrating the strength of what is ultimately a self-limiting drive simply by changing the location of the two components on the same chromosome, with the strength and duration of drive being direct function of the degree of linkage: two locus ClvR with closely linked loci will have stronger drive (be able to spread more quickly and in the face of greater fitness costs), and drive for more generations, than will happen for two locus ClvRs with linkage in which the key genes are located farther apart. However, drive will ultimately be limited, as recombination occurs and the alleles approach linkage equilibrium.

In some embodiments, a two-vector system comprises a first vector comprising a DNA sequence modifying enzyme; a first promoter operably linked to the DNA sequence modifying enzyme, wherein the DNA modifying enzyme modifies an endogenous copy of an essential gene; and a second vector comprising a rescue transgene sequence; a rescue transgene promoter operably linked to the rescue transgene sequence; and optionally, one or more cargo sequences. Without being limited by any particular theory, the situation applies when the DNA sequence modifying complex is a base editor or an enzyme that does not require, for example, a guide RNA to modify an endogenous copy of an essential gene.

In some embodiments, a two-vector system comprises a first vector comprising a first sequence encoding a first component of a DNA sequence modifying complex; a second sequence encoding a second component of the DNA sequence modifying complex; a first promoter operably linked to the first sequence encoding the first component and a second sequence encoding the second component of the DNA sequence modifying complex, a second promoter operably linked to the second sequence encoding the second component, wherein the DNA modifying enzyme complex modifies an endogenous copy of an essential gene; and a second vector comprising a rescue transgene sequence; a rescue transgene promoter operably linked to the rescue transgene sequence; and optionally, one or more cargo sequences.

In some embodiments, a two-vector system comprises a first vector comprising a first sequence encoding a first component of a DNA sequence modifying complex, a first promoter operably linked to the first sequence encoding the first component of the DNA sequence modifying complex, a rescue transgene sequence; a rescue transgene promoter operably linked to the rescue transgene sequence; and optionally, one or more cargo sequences; and a second vector comprising a second sequence encoding a second component of the DNA sequence modifying complex; a second promoter operably linked to the second component of the DNA sequence modifying complex, wherein the DNA modifying enzyme complex modifies an endogenous copy of an essential gene. In some embodiments of the two-vector system, the first vector comprises the second sequence encoding the second component of the DNA sequence modifying complex, and the second vector comprises the first sequence encoding the first component of a DNA sequence modifying complex.

Figure 25:
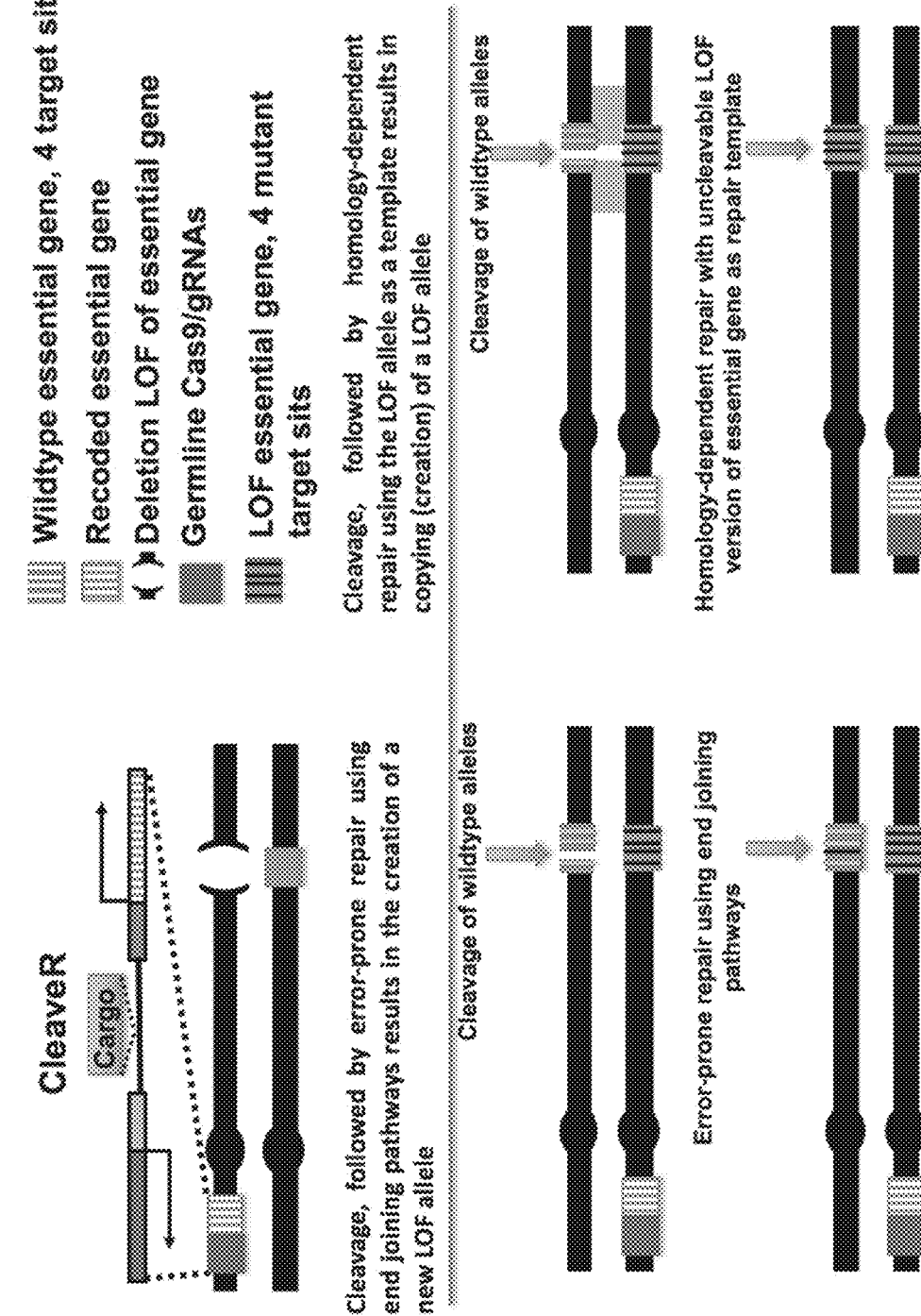
FIG. 25 shows a schematic illustrating how ClvR can create loss of function (LOF) alleles using homologous recombination.

In some embodiments, the gene drive disclosed herein is an alternative form of gene drive that utilizes Cas9 or other nucleases to bring about cleavage and repair of an essential gene that does not involve or require homing, though homing can potentially contribute to drive (FIG. 25). This form of gene drive can also make use of base editing enzymes such as adenosine or cytosine deaminase to modify specific bases to create non-functional versions of an essential gene. It can also use Search and Replace Prime editing, which uses a Cas9 nickase linked to a reverse transcriptase, and a modified gRNA to introduce base changes or insertions or deletions. Without being limited by any particular theory, the mechanism simply involves a DNA sequence modifying enzyme such as Cas9, a set of gRNAs targeting an essential gene for cleavage, base editing, or Search and Replace Prime editing and a recoded version of the target essential gene that is immune to modification, linked as a single construct (by linked it is meant that they are not separated from each other during meiotic or other forms of recombination). This gene drive method is known as single locus ClvR (FIG. 20A). In some embodiments, individuals carrying one or more copies of this construct bring about modification of the sequence of one or more copies of the endogenous version of the essential gene such that it is no longer functional. Individuals who end up inheriting only non-functional versions of the essential gene die or are sterile, while those that carry one or more copies of the construct, which includes a rescue transgene, will survive and/or be fertile. Over multiple generations this behavior is predicted to result in the spread of the construct/vector into the population at the expense of the wild types version of the same chromosome (FIG. 1-5; FIGS. 31A-D; FIG. 36).

In some embodiments the gene drive disclosed herein is an alternative form of gene drive that utilizes Cas9 or other nucleases to bring about cleavage and repair of an essential gene that does not involve or require homing, though homing can potentially contribute to drive (FIG. 25). This form of gene drive can also make use of base editing enzymes such as adenosine or cytosine deaminase to modify specific bases to create non-functional versions of an essential gene. It can also use Search and Replace Prime editing, which uses a Cas9 nickase linked to a reverse transcriptase, and one or more modified gRNAs to introduce base changes or insertions or deletions. Without being limited by any particular theory, the mechanism involves the DNA sequence modifying enzyme such as Cas9 and a set of gRNAs targeting an essential gene for cleavage, (or a sequence targeted base editor) located at one position in the genome, with a recoded version of the target essential gene that is immune to modification, along with any associated cargo transgenes, located at another position in the genome. This gene drive method is known as two locus ClvR, version 1 (FIG. 20B). In some embodiments, individuals carrying one or both of these vectors bring about modification of the sequence of one or more copies of the endogenous version of the essential gene such that it is no longer functional. Individuals who end up inheriting only non-functional versions of the essential gene die or are sterile, while those that carry one or more copies of the rescue transgene and cargo, will survive and/or be fertile. Over multiple generations this behavior is predicted to result in the spread of the construct/vector into the population at the expense of the wild types version of the same chromosome. However, drive is ultimately limited in time (generations), and thus space (drive over generations in the presence of migration), and therefore allows for the possibility of reversal through dilution with wild types (FIGS. 34A-F).

In some embodiments the gene drive disclosed herein is an alternative form of gene drive that utilizes Cas9 or other nucleases to bring about cleavage and repair of an essential gene that does not involve or require homing, though homing can potentially contribute to drive (FIG. 25). This form of gene drive can also make use of base editing enzymes such as adenosine or cytosine deaminase to modify specific bases to create non-functional versions of an essential gene. It can also use Search and Replace Prime editing, which uses a Cas9 nickase linked to a reverse transcriptase, and a modified gRNA to introduce base changes or insertions or deletions. Without being limited by any particular theory, the mechanism involves a first component of the DNA sequence modifying enzyme such as Cas9 and a set of gRNAs targeting an essential gene for cleavage, (or a sequence targeted base editor) located at one position in the genome, with a recoded version of the target essential gene that is immune to modification, along with any associated cargo transgenes, and a second component of the DNA sequence modifying enzyme, located at another position in the genome. This gene drive method is known as two locus ClvR, version 2 and version 3 (FIGS. 20C,D). In some embodiments, individuals carrying one or both of these vectors bring about modification of the sequence of one or more copies of the endogenous version of the essential gene such that it is no longer functional. Individuals who end up inheriting only non-functional versions of the essential gene die or are sterile, while those that carry one or more copies of the rescue transgene and cargo, will survive and/or be fertile. Over multiple generations this behavior is predicted to result in the spread of the construct/vector into the population at the expense of the wild types version of the same chromosome. However, drive is ultimately limited in time (generations), and thus space (drive over generations in the presence of migration), and therefore allows for the possibility of reversal through dilution with wild types (FIGS. 35A-F).

In some embodiments, characterized and disclosed herein are multiple forms of this DNA sequence modification mediated drive. A discrete generation, deterministic population frequency model is used to demonstrate that there are a variety of conditions, that include various fitness costs, DNA sequence modification frequencies, and introduction frequencies, under which population replacement is predicted to occur.

Definitions

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below. It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, "regulatory element" refers to nucleic acid elements that can influence the expression of a coding sequence (for example, a gene) in a particular host organism. These terms are used broadly and encompass all elements that promote or regulate transcription, including promoters, core elements required for basic interaction of RNA polymerase and transcription factors, upstream elements, enhancers, and response elements (see, for example, Lewin, "Genes V" (Oxford University Press, Oxford) pages 847-873).

As used herein, the term "insertion site" refers a nucleic acid sequence that allows for insertion of the constructs as provided herein into a genome of a multicellular organism (for example, an insect genome). In some embodiments, a construct as provided herein can comprise a "insertion sequence" that allows for insertion of the construct into a genome of the host organism. Some embodiments that can be employed include the piggybac transposable element, mariner type transposable elements, and the P-element. Also, plasmids can be site specifically integrated into the genome using attb/attp or even by using CRISPR/Cas9, TALEN, MegaTAL and homologous recombination.

As used herein, a "vector," interchangeably referred to as a transgenic construct, a targeting construct, or simply a construct, is a nucleic acid. As used herein, "nucleic acid" refers to deoxyribonucleic acid (DNA). In some embodiments, nucleic acid may refer to ribonucleic acid (RNA). In some embodiments, the construct as provided herein comprise one or more regulatory elements. Exemplary regulatory elements in prokaryotes include promoters, operators and ribosome binding sites. Regulatory elements that are used in eukaryotic cells can include, without limitation, transcriptional and translational control sequences, such as promoters, terminators, enhancers, insulators, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell. For example, a promoter is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions (for example, a change in temperature).

As used herein, "homologous recombination" refers to exchange of nucleotide sequences between two identical nucleic acid sequences. Homologous recombination also refers to exchange of nucleotide sequences between two similar nucleic acid sequences. In some embodiments, when the two nucleic acid sequences are similar, a similarity between the two nucleic acid sequences can be about 90% to about 99.9%. In some embodiments, the similarity between the two nucleic acid sequences can be about 90, 91, 92, 93, 94, 95, 96, 97, 98, 99, 99.1, 99.2, 99.3, 99.4, 99.5, 99.6, 99.7, 99.8 or 99.9%.

As used herein, "gene drive" refers to a situation in which genetic elements—including alleles of specific genes, gene complexes, entire chromosomes or endosymbiotic bacteria—are transmitted to viable, fertile progeny at rates greater than those due to Mendelian transmission, resulting in an increase in their frequency in the population over time, even if their presence results in a fitness cost to carriers. Without being limited by any particular theory, gene drive can occur by a number of mechanisms. In some embodiments gene drive has evolved in wild populations of various organisms, through a variety of mechanisms that are still under study (Burt and Trivers, 2006). In some embodiments, the gene drive is engineered. In some embodiments, the gene drive represents a naturally occurring mechanism or is engineered depending on the context and environment in which it occurs. A number of novel methods of engineering gene drive have also been proposed, and in several cases implemented.

In some embodiments, the present disclosure is related to vectors and methods for DNA sequence modification-based modification of populations, and beneficial and commercial applications of the vectors and methods.

In one implementation of this system, detailed below in the examples and sometimes referred to as CleaveR (also referred to herein as ClvR), the nuclease includes a member of the RNA-guided nucleases, such as Cas9. In this implementation Cas9 is expressed in the germline of male, females, or both sexes. Multiple gRNAs are also expressed, preferably three or four of them. They are designed to engage in Watson-Crick base pairing with, and therefore target for cleavage, distinct sequences within a target gene, so as to bring about its cleavage at multiple sites. These multiple breakages are expected to result in the creation of repair products—deletions, base changes, small additions—that create a non-functional version of the targeted gene. In summary, the purpose of the nuclease is to bring about loss-of-function (LOF) mutants of the targeted gene. As detailed in FIG. 25, DNA breaks in the target sequence can also be used to create LOF mutations in the target sequence when a cleavage-resistant LOF allele is used as a template for repair. There are two important characteristics of the system described thus far. First, the cassette encoding the nuclease can sit at any position in the genome. Second, the gene being targeted for inactivation is in some sense an essential gene: required for organism survival or fertility, broadly defined as fitness.

The second component of the CleaveR gene drive system is the existence of a version of the targeted essential gene that can rescue the lethality or infertility of those individuals in which both copies (for a diploid) of the essential gene have been inactivated, but that is itself resistant to cleavage by the RNA-guided Cas9 component of the construct. Resistance to cleavage is brought about by recoding the transgene so that it no longer productively interacts with the guide RNA Cas9 complex, according to rules that are well known in the field. Further recoding of the rescue transgene, in both the coding region and non-coding and regulatory regions, is also carried out. This recoding is done so as to minimize homology between the wildtype, endogenous version of the gene and the rescue version of the gene. This recoding is also done so as to minimize/eliminate the possibility that the cleaved version of the wildtype endogenous essential gene can be repaired and restored to functionality through ectopic homologous recombination, using the rescue transgene as a template for repair based on existing homology at the broken ends of the former. The literature provides guidance on the level of homology needed to prevent or promote homologous recombination. Without being limited by any particular theory, recoding can successfully achieved even when the rescue transgene has essentially no nucleotide homology to the endogenous copy of the gene. Demonstration that this can be achieved comes from multiple reports showing that bacterial and/or human versions of a large number of essential genes can successfully replace their yeast counterparts, resulting in yeast with high fitness.

Single Locus

In the single locus CleaveR construct, also often referred to as the vector or the construct, when these two genes are located near each other (tightly linked), they behave, as illustrated below, as a novel selfish genetic element, able to spread itself into a population and/or maintain itself in a population (bring about population replacement) under a variety of conditions that include varying levels of fitness cost associated with carrying the vector and any associated cargo genes, and introduction frequencies (FIG. 1-5; FIGS. 31A-D; FIG. 36). The details of these characters are described in more detail below.

Overview of CleaveR-Based Gene Drive

Without being limited by any particular theory, when the CleaveR construct is present in an organism, wildtype copies of the essential are at risk for cleavage and inactivation. The individuals carrying CleaveR themselves do not experience any cost from this cleavage, which happens in the germline and also in some cases in somatic cells, because they also carry a tightly linked copy of the rescue transgene. However, the gametes they pass on will in many cases not carry a functional copy of the endogenous essential gene, and they may also lack the CleaveR construct. In some cases the Cas9/gRNA complexes will also be deposited into oocytes/eggs, resulting in cleavage of the endogenous copy of the essential gene in early embryos that do not carry the CleaveR construct. In all of these cases, which arise through normal Mendelian segregation of chromosomes during meiosis in males and females, and in some cases diffusion or transport of Cas9/gRNA into daughter cells or products of cell-cell fusion (fertilization), progeny are often created that carry no functional copies of the essential gene. These individuals are of low fitness (dead, sterile or otherwise dysfunctional [flightless]) and do not contribute further to the population. Similar considerations apply with versions of two locus ClvR: whenever Cas9/gRNAs or other site-specific nucleases are present, they have the opportunity to cleave endogenous versions of the essential gene, creating LOF alleles.

The above behavior results in some loss in each generation of chromosomes and individuals that do not carry the CleaveR. This results, over multiple generations, in a progressive increase in the frequency of CleaveR-bearing individuals. Modeling, discussed further below, shows that under a variety of conditions CleaveR is predicted to spread to high frequency such that most or all individuals in the population bear at least one copy of the CleaveR chromosome (FIG. 1-5; FIGS. 31A-D; FIG. 36). The CleaveR chromosome is in some sense "held" in the population because as it has been spread (and the mechanism by which it has been spreading), it has necessarily caused inactivation of most or all of the wildtype copies of the essential gene. Thus the population has become "locked" into a configuration in which it now depends on the presence of CleaveR in order to maintain viability or fertility. In the case of two locus ClvR similar considerations apply, with the exception that what is driven into the population is the Rescue transgene and any other tightly linked transgenes. In addition, with versions of two locus ClvR reversal to a pre-transgenic (or low frequency transgenic) state is possible through dilution of the population with wildtypes, once the frequency of Cas9 and gRNAs (or some other site-specific nuclease that brings about cleavage of the essential gene) needed to cleave endogenous copies of the essential gene drops to low frequency. It should be understood that by low frequency it is meant lower than the initial frequency, with the number of wild types needed to bring about reversal being dependent on the frequency of Cas9 and gRNAs remaining in the population.

A similar principle, cleavage associated with rescue of those who carry the CleaveR vector, allows CleaveR to act as a gamete killer (known as spore killers in yeast), and to be able to force its inheritance in conditions in which it is episomal (as in a plasmid). In both cases the presence of the CleaveR element selects for those who carry it, and against those who fail to inherit it. Similar considerations apply in contexts in which the DNA sequence modifying enzyme makes it way into neighboring cells, through direct contact-mediated mechanisms or through release by a donor cell and uptake by a recipient cell: Cells that acquire the DNA sequence modifying enzyme but not the Rescue transgene are at risk of death through the creation of LOF alleles of an essential gene (FIG. 26).

In some embodiments, the method of gene drive described herein is agnostic as to the mechanism by which sequence modification-dependent inactivation of the essential gene is brought about. It can involve cleavage and error-prone repair, as discussed above. It can also involve the use of base editing enzymes known from the literature. It can also utilize other DNA modifying enzymes such as sequence targeted transposases, recombinases, integrases, topoisomerases, or other enzymes that can be targeted to specific sequences in DNA to bring about sequence changes. It can also use Search and Replace Prime editing, which uses a Cas9 nickase linked to a reverse transcriptase, and a modified gRNA to introduce base changes or insertions or deletions. Finally, it can also utilize homologous recombination when the template for repair of a wildtype cleaved allele is a previously cleaved, altered to LOF, and now cleavage insensitive allele, as a template for repair (FIG. 25). Importantly, the exact nature of the sequence changes brought about is not critical since there are many ways of rendering nonfunctional any particular gene through sequence modification.

In some embodiments, a vector is provided. The vector comprises: a first sequence encoding a first component of a DNA sequence modifying complex; a first promoter operably linked to the first sequence encoding the first component of the DNA sequence modifying complex; a second sequence encoding a second component of a DNA sequence modifying complex; a second promoter operably linked to the second sequence encoding complex; a rescue transgene; a promoter operably linked to the rescue transgene that requires binding by the DNA sequence modifying complex for transcription of the rescue transgene; and optionally one or more cargo sequences.

In some embodiments, a two-vector system is provided that comprises: a first vector. The first vector comprises: a first sequence encoding a first component of a DNA sequence modifying complex; a second sequence encoding a second component of the DNA sequence modifying complex; a first promoter operably linked to the first sequence encoding the first component of the DNA sequence modifying complex, a second promoter operably linked to the second sequence encoding the second component of the DNA sequence modifying complex. The DNA modifying enzyme complex modifies an endogenous copy of an essential gene. The system comprises a second vector that comprises a rescue transgene sequence; a promoter operably linked to the rescue transgene that requires binding by the DNA sequence modifying complex for transcription of the rescue transgene; and optionally, one or more cargo sequences.

In some embodiments a two-vector system is provided that comprises a first vector that comprises a first sequence encoding a first component of a DNA sequence modifying complex, a first promoter operably linked to the first sequence encoding the first component of the DNA sequence modifying complex, a rescue transgene sequence; a promoter operably linked to the rescue transgene that requires binding by the DNA sequence modifying complex for transcription of the rescue transgene; and optionally, one or more cargo sequences. The two-vector system further comprises a second vector that comprises a second sequence encoding a second component of the DNA sequence modifying complex; and a second promoter operably linked to the second component of the DNA sequence modifying complex. The DNA modifying enzyme complex modifies an endogenous copy of an essential gene. In some embodiments, the first vector comprises the second sequence encoding the second component of the DNA sequence modifying complex, and the second vector comprises the first sequence encoding the first component of a DNA sequence modifying complex.

Vectors

FIG. 15A-FIG. 15C, FIG. 38A-FIG. 38C, FIG. 42A show embodiment of single locus ClvR construct design and principle according to the present disclosure (Example 15, Example 17). In some embodiments, the disclosure is related to a vector. In some embodiments, the vector comprises a first gene encoding a DNA sequence modifying enzyme. In some embodiments, the DNA modifying enzyme modifies the sequence of an endogenous copy of an essential gene. As used herein, an "essential gene" is defined as a gene that is critical for survival, growth or fertility, and whose loss of function is either lethal, prevents growth or is sterilizing. Some essential genes are critical for survival under all circumstances. Some essential genes are critical for survival only under particular circumstances and/or particular environmental conditions (e.g., in the presence of toxic drugs, toxins, etc., or in the absence of nutrients, vitamins, etc.). In some embodiments, more than one or more endogenous copies of the essential gene are present. In some embodiments, when one or more endogenous copies of the essential gene are present they are alleles or allelic variants of the essential gene. As used herein, the "endogenous copy" refers to the wild type version of the essential gene.

Figures 42A, 42B, 42C:
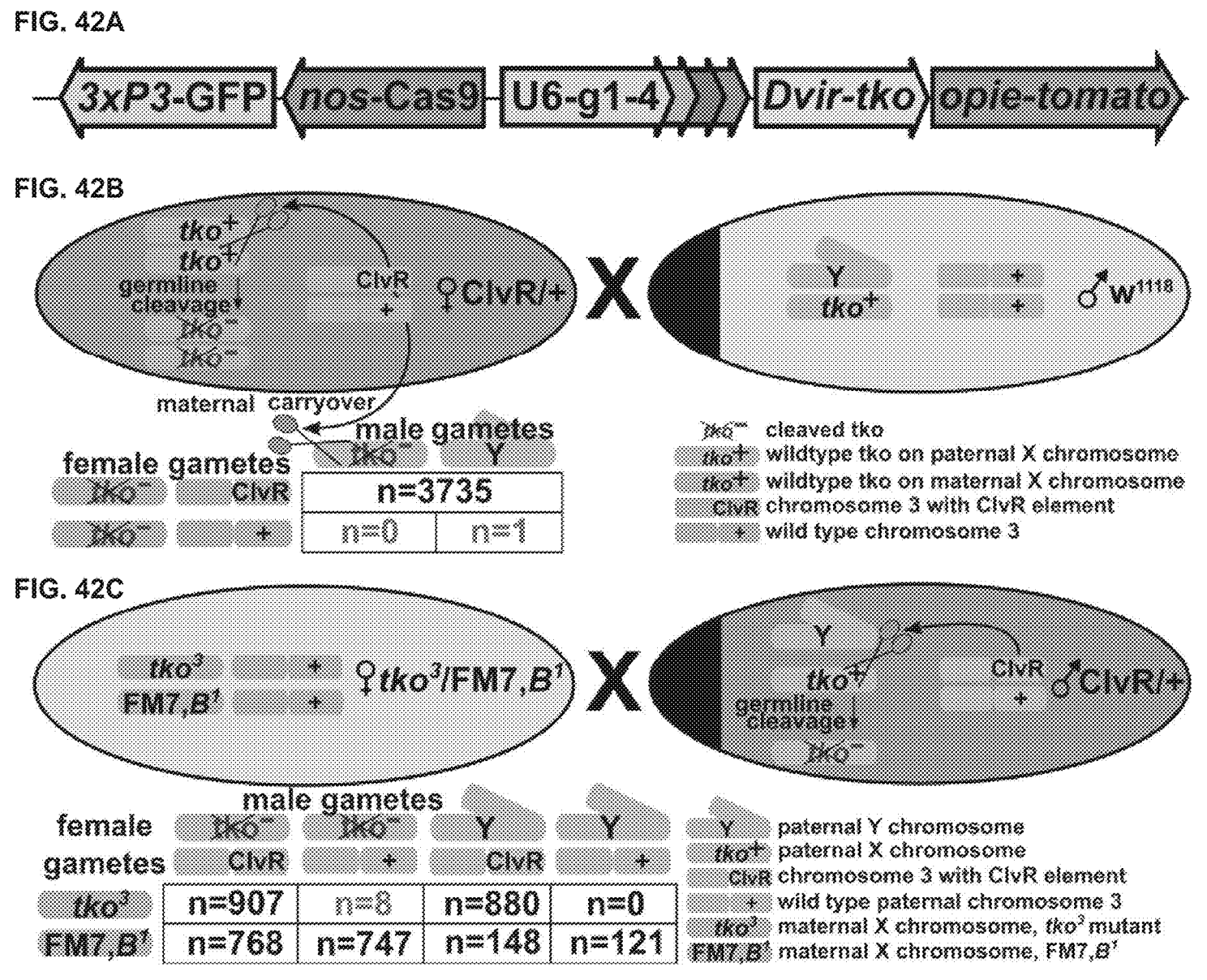

In some embodiments, a vector comprises a first promoter operably linked to the first gene encoding the DNA sequence modifying enzyme. In some embodiments, the first gene is operably linked to one or more additional regulatory elements. In some embodiments, the vector further comprises a second gene encoding a rescue transgene. In some embodiments of the vector, a second promoter is operably linked to the rescue transgene. In some embodiments, the second gene is operably linked to one or more additional regulatory elements. In some embodiments a third and fourth gene (cargo genes/dominant markers), including promoters linked to these genes are also present (c.f. FIGS. 42A-C).

In some embodiments multiple vectors are created. FIGS. 20A-D-FIGS. 21A-C show embodiments of two locus ClvR construct design and principle according to the present disclosure (Examples 28-30).

In some embodiments, the vector or one of the vectors in the case of a two locus configuration optionally comprises one or more cargo sequences. In some embodiments, a cargo sequence is a nucleic acid. In some embodiments, the vector is configured to be positioned in a chromosome. In some embodiments, the vector is configured to be positioned in an extra-chromosomal element. Non-limiting examples of cargo genes include are sequences encoding antibodies against *Plasmodium*, the causal agent of malaria (Isaacs et. al. 2011, Hollingdale et. al. 1984, and Li et. al. 2005), or non-coding RNAs to bring about cleavage of the dengue virus RNA genome (Yen et. al. 2018, Franz et. al. 2006, Mathur et. al. 2010, Travanty et. al. 2004, and Castillo et. al. 2016). In some embodiments, the vector or vectors are configured to be positioned in a chromosome and an extra chromosomal element. In some embodiments, the vector or vectors are configured to be positioned in a chromosome but not in an extra chromosomal element. In some embodiments, the vector or vectors are configured to be positioned in an extra chromosomal element but not in a chromosome.

In some embodiments, the DNA sequence modifying enzyme is a nuclease. Non-limiting examples of nucleases include Flap endonucleases, restriction endonucleases (e.g., F-EcoT5I, F-EcoT5II, F-EcoT5IV, F-SceI, F-TevI, F-TevII, I-AchMI, I-AniI, I-BasI, I-BmoI, I-Bth0305I, I-BthII, I-BthORFAP, I-CeuI, I-*ChuI*, I-CpaI, I-CpaII, I-CreI, I-CsmI, I-CvuI, I-DdiI, I-DmoI, I-GpiI, I-GzeI, I-HjeMI, I-HmuI, I-HmuII, I-LlaI, I-LtrI, I-LtrWI, I-MpeMI, I-MsoI, I-NanI, I-NitI, I-NjaI, I-OnuI, I-PakI, I-PanMI, I-PnoMI, I-PogTE7I, I-PorI, I-PpoI, I-ScaI, I-SceI, I-SceII, I-SceIII, I-SceVI, I-SpomI, I-SscMI, I-Ssp6803I, I-TevI, I-TevII, I-TevIII, I-TslI, I-TslWI.AY76, I-Vdil41I, PI-AvaI, PI-BciPI, PI-HvoWI, PI-MleSI, PI-MtuI, PI-PkoI, PI-PkoII, PI-PspI, PI-SceI, PI-TfuI, PI-TfuII, PI-TliI, PI-TliII, PI-TmaI, PI-TmaKI), Cas9, and Cas9-like enzymes (including but not limited to CPf1, C2c1, C2c2, and C2c3 (Shmakov et. al. 2015, Shmakov et. al. 2017, Koonin et. al. 2017-1, Koonin et. al. 2017-2), ZFNs, MegaTALs, TALENs, HEGs, meganucleases, and Search and Replace Prime editors, which use a Cas9 nickase linked to a reverse transcriptase, and a modified gRNA to introduce base changes or insertions or deletions.

In some embodiments, DNA modifications are achieved through cleavage by site-specific nucleases. Without being limited by any particular theory, it should be understood that equivalent effects can be obtained through the use of any enzyme that brings about modification of a target DNA sequence. Non-limiting examples include cytosine and adenine base changes brought about through the targeted use of deaminases and site-specific integrases. It can also use Search and Replace Prime editing, which uses a Cas9 nickase linked to a reverse transcriptase, and a modified gRNA to introduce base changes or insertions or deletions.

In some embodiments, the nuclease cleaves the endogenous copy of the essential gene. In some embodiments, the nuclease generates one or more double strand breaks in the endogenous copy of the essential gene. In some embodiments, the nuclease cleaves and generates one or more double strand breaks in the endogenous copy of the essential gene. In some embodiments, the one or more double strand breaks in the endogenous copy of the essential gene are staggered. In some embodiments, the one or more double strand breaks in the endogenous copy of the essential gene are not staggered. In some embodiments, the nuclease cleaves and generates one or more single strand breaks in the endogenous copy of the essential gene.

In some embodiments, the one or more double strand breaks (DSBs) are repaired. In some embodiments, the one or more DSBs are repaired to create an altered sequence of the essential gene. In some embodiments, the one or more DSBs are repaired by one or more of non-homologous end joining (NHEJ), microhomology-mediated end joining (MMEJ), homologous recombination (HR), complete HR, and incomplete HR. nicking, followed by reverse transcription and ligation, and incomplete HR In some embodiments, the altered sequence comprises substitutions, insertions, deletions, frame-shifts, or a combination thereof.

In some embodiments, the DNA sequence modifying enzyme is a base editor. Non-limiting examples of a base editor include cytosine deaminase, and adenine deaminases.

In some embodiments, the base editor creates one or more base changes in endogenous copy of the essential gene. In some embodiments, the one or more base changes comprise transitions, transversions, or both. In some embodiments, the one or more base changes occur due to tautomerism, depurination, deamidation, or a combination thereof. In some embodiments, the one or more base changes create an altered sequence of the essential gene. In some embodiments, the one or more base changes comprise one or more point mutations in the endogenous copy of the essential gene. In some embodiments, the one or more point mutations comprise frameshift mutation, nonsense mutation, missense mutation, small deletions or additions, neutral mutation, silent mutation, or a combination thereof.

In some embodiments, the DNA sequence modifying enzyme is a Search and Replace Prime editor, which uses a Cas9 nickase linked to a reverse transcriptase, and a modified gRNA to introduce base changes or insertions or deletions.

In some embodiments, the Search and Replace Prime editor creates one or more base changes in endogenous copy of the essential gene. In some embodiments, the one or more base changes comprise transitions, transversions, or both. In some embodiments, the one or more base changes occur due to tautomerism, depurination, deamidation, or a combination thereof. In some embodiments, the one or more base changes create an altered sequence of the essential gene. In some embodiments, the one or more base changes comprise one or more point mutations in the endogenous copy of the essential gene. In some embodiments, the one or mutations comprise frameshift mutation, nonsense mutation, missense mutation, small deletions or additions, neutral mutation, silent mutation, or a combination thereof.

In some embodiments, the promoter of the first gene expresses within females such that the DNA-modifying enzyme produced by the first gene is deposited into eggs and can modify target sequences inherited from a father who lacks the vector. This activity, while unnecessary for the majority of cases wherein this drive method successfully replaces a population, results in more rapid population replacement than without, for a given fitness cost and/or introduction frequency. Where the DNA-modifying enzyme is a version of Cas9 or a Cas9-related enzyme (guided to a target sequence by a guide RNA), both Cas9 and any and all associated gRNAs are deposited into the eggs of such females together to enable modification of alleles inherited from a non-vector bearing male (Example 17, FIG. 42B).

In some embodiments, there is paternal carryover of the DNA modifying enzyme, allowing for modification of alleles inherited from the mother, even in those who have not inherited the vector.

In some embodiments, the rescue transgene is a recoded copy of the essential gene. In some embodiments, when the rescue transgene is a recoded copy of the essential gene, the protein encoded by the recoded copy of the essential gene (recoded protein) is about 90% to about 99.9% identical to protein encoded by the endogenous copy of the essential gene (endogenous protein). In some embodiments, the recoded protein is about 50, 52.5, 55, 57.5, 60, 62.5, 65, 67.5, 70, 72.5, 75, 77.5, 80, 82.5, 85, 87.5, 90, 91, 92, 93, 94, 95, 96, 97, 98, 99, 99.1, 99.2, 99.3, 99.4, 99.5, 99.6, 99.7, 99.8, or 99.9% to the endogenous protein. In some embodiments, the rescue transgene is a gene of unrelated sequence. In some embodiments, when the rescue transgene is a gene of unrelated sequence, the protein encoded by the recoded copy of the essential gene (recoded protein) is functionally equivalent to the protein encoded by the endogenous copy of the essential gene (endogenous protein). In some embodiments, the DNA sequence modifying enzyme does not modify the rescue transgene.

In some embodiments, the chromosome in which the vector or vectors are positioned is one or more of an autosome, X chromosome, Y chromosome, Z chromosome, W chromosome, or supernumerary chromosome. In some embodiments, the vector or vectors are positioned in one or more combinations of an autosome, X chromosome, Y chromosome, Z chromosome, W chromosome, or supernumerary chromosome. For example, in some embodiments, the vector or vectors are positioned in an autosome and an X chromosome, in some embodiments, the vector or vectors are positioned in an autosome and a Y chromosome, in some embodiments, the vector or vectors are positioned in an autosome and a supernumerary chromosome, in some embodiments, the vector or vectors are positioned in an X chromosome and a Y chromosome, in some embodiments, the vector or vectors are positioned in an X chromosome and a supernumerary chromosome, in some embodiments, the vector or vectors are positioned in an Y chromosome and a supernumerary chromosome, in some embodiments the vector or vectors are positioned on some combination of chromosomes that include either the Z chromosome or the W chromosome, and in some embodiments, the vector is positioned in an autosome, X chromosome, Y chromosome, and supernumerary chromosome.

In some embodiments, the vector or vectors are positioned in an extra-chromosomal element. In some embodiments, the extra-chromosomal element is a plasmid. In some embodiments, the extra-chromosomal element is a virus. In some embodiments, the extra-chromosomal element is a plasmid and a virus. In some embodiments, the vector or vectors are positioned in combinations of one or more chromosomes and one or more extra-chromosomal elements.

In some embodiments, the vector or vectors optionally comprises one or more cargo sequences. In some embodiments, the one or more cargo comprise foreign gene sequences, or one or more alleles of an endogenous chromosomal or extra-chromosomal gene.

In some embodiments the cargo comprises one or more alleles of an endogenous chromosomal or extra-chromosomal gene to which the vector or one of the vectors has been linked through nearby insertion on the chromosome or extra-chromosomal element that carries the endogenous allele of interest.

In some embodiments, the cargo can be physically part of the vector or one of the vectors prior to its insertion in a chromosomal or an extra-chromosomal element. In some embodiments, the cargo can be a chromosomal/extra-chromosomal allele of a gene that becomes linked to the vector or vectors after the insertion of the vector near that allele. In some embodiments, a fraction of the cargo can be physically part of the vector or one or more of multiple vectors prior to its insertion in a chromosomal or an extra-chromosomal element, and a remainder of the cargo can be a chromosomal/extra-chromosomal allele of a gene that becomes linked to the vector after the insertion of the vector near that allele. In some embodiments, the cargo does not have to be a part of the vector or vectors, i.e., in some embodiments, the cargo is optional and can be physically part of the vector prior to its insertion in a chromosomal or an extra chromosomal element. In some embodiments, the cargo does not have to be a part of the vector, i.e., in some embodiments, a fraction of the cargo can optionally be physically part of the vector prior to its insertion in a chromosomal or an extra chromosomal element, and a remainder of the cargo can be a chromosomal/extra-chromosomal allele of a gene that becomes linked to the vector after the insertion of the vector near that allele.

In some embodiments herein, the vector comprising the first gene encoding the DNA sequence modifying enzyme and the second gene encoding the rescue transgene is referred to as CleaveR (e.g., FIG. 6; FIG. 7; FIG. 10; FIG. 20A; FIG. 42A), which comprises and/or consists of two components: (1) a site-specific DNA modifying enzyme designed to alter the sequence of an endogenous gene required for survival, proliferation, fertility, or differentiation so as to render it non-functional; (2) a recoded version of the essential gene resistant to cleavage, and having reduced nucleotide identity with the endogenous gene. Optionally, one or more cargo sequences are present.

In some embodiments herein, two vectors are present (the components of which can be used for any of the single vector or single locus arrangements provided herein). The first comprises the first gene encoding the DNA sequence modifying enzyme or a first fragment of the DNA sequence modifying enzyme. The second gene encodes the rescue transgene, any cargo transgenes, and optionally a second fragment of the DNA sequence modifying enzyme. These variants are referred to as two locus CleaveR (e.g., FIGS. 20B-D; FIGS. 21A-C), which comprises and/or consists of two vectors that incorporate the following: (vector 1) a site-specific DNA modifying enzyme or first fragment thereof, designed to alter the sequence of an endogenous gene required for survival, proliferation, fertility, or differentiation so as to render it non-functional; (vector 2) a recoded version of the essential gene resistant to cleavage, and having reduced nucleotide identity with the endogenous gene (right). Optionally, one or more cargo sequences are present; optionally a second fragment of the DNA sequence modifying enzyme is present.

In some embodiments, DNA sequence modifying enzyme is, without limitation, Cas9, Cas-9-related RNA-guided nucleases, ZFNs, TALENs, homing endonucleases, restriction enzymes, natural site-specific nucleases, engineered site-specific nucleases, base editing enzymes, cytidine deaminase, and adenine deaminase.

In some embodiments, the vector or the vectors further comprises one or more additional sequences. In some embodiments, the one or more additional sequences allow the vector or vectors to be positioned in the chromosome. In some embodiments, the one or more additional sequences allow the vector or vectors to be positioned in the extra-chromosomal element. In some embodiments, the one or more additional sequences allow the vector or vectors to be positioned in the chromosome and the extra-chromosomal element. In some embodiments, the one or more additional sequences allow the vector or vectors to be positioned in the chromosome but not the extra-chromosomal element. In some embodiments, the one or more additional sequences allow the vector or vectors to be positioned in the extra-chromosomal element but not the chromosome.

In some embodiments, the one or more additional sequences is, without limitations, transposase binding site, LTRs, recombinase binding site, a sequence with homology to a desired location on the chromosome or a sequence with homology to a desired location on the extra-chromosomal element, or combinations thereof.

In some embodiments, the vector or vectors further comprises one or more additional sequences, wherein the one or more additional sequences serve as dominant marker genes that allow individuals carrying the vector to be easily identified either visually, as with expression of a fluorescent protein, or by virtue of surviving a negative selection procedure, as with expression of a gene that encodes resistance to a toxin (such as an antibiotic, insecticide, herbicide), in the presence of the toxin. In some embodiments, the vector or vector comprises one or more sequences that encode marker proteins that can be expressed under the control of suitable regulatory elements. Non-limiting examples of marker proteins include dsRed, GFP, EGFP, CFP, ECFP, BFP, EBFP, mHoneydew, mBanana, mOrange, tdTomato, mTangering, mStrawberry, mCherry, mGrape1, mGrape2, mRaspberry, mPlum, YFP or EYFP, and can be chosen by one of skilled in the art according to need. Fluorescent marker protein can be visualized by illuminating with a suitable excitatory wavelength and observing the fluorescence (e.g., by fluorescence microscopy). In some embodiments, a marker protein would allow for easy identification of organisms carrying the vector.

In some embodiments, the first promoter is, without limitations, a germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, or combinations thereof.

In some embodiments, the size of the one or more cargo sequences ranges from about is about 0.5 kb to about 500 kb. In some embodiments, the size ranges from about 1 kb to about 1000 kb. In some embodiments, the size ranges from about 5 kb to about 5000 kb. In some embodiments, the size ranges from about 10 kb to about 10000 kb. In some embodiments, the size is about 0.1, 0.5, 1, 5, 10, 25, 50, 75, 100, 250 500, 750 1000, 2500, 5000, 7500, or 10000 kb.

In some embodiments, the nuclease comprises at least one nuclease domain. In some embodiments, the nuclease comprises one or more DNA binding domains. In some embodiments, the nuclease comprises at least one nuclease domain and one or more DNA binding domains.

In some embodiments, when the nuclease is Cas9 or a Cas9-related enzyme, the vector further comprises one or more genes encoding one or more guide RNAs. In some embodiments, involving two locus ClvR, the two vectors will each comprise either Cas9 or gRNAs, such that cleavage only occurs when both are present. In some embodiments, the guide RNA enables the nuclease to target specific DNA sequences through Watson-Crick base pairing, thereby allowing targeting of very many positions in any genome. In some embodiments, the guide RNA enables the nuclease to target specific sequences within the endogenous copy of the essential gene. In some embodiments, the guide RNA enables the nuclease to target specific sequences within the protein coding region of endogenous copy of the essential gene. In some embodiments, the guide RNA allows the nuclease to target specific sequences within the non-coding region of endogenous copy of the essential gene. In some embodiments, the guide RNA allows the nuclease to target specific sequences outside the endogenous copy of the essential gene.

In some embodiments, when the nuclease is Cas9, the nuclease domain of Cas9 is deliberately inactivated through one or more mutations and the vector comprises a different nuclease domain. In some embodiments, the different nuclease domain is single chain variant of FokI. In some embodiments, when the DNA binding domain is a TALE, the nuclease domain is provided as a single active nuclease domain. In some embodiments, the single active nuclease domain is a single chain variants of FokI. In some embodiments of the vector, when the DNA binding domain is a TALE, the nuclease domain is provided as a single active nuclease domain, such as single chain variants of FokI (Sun and Zhao 2014).

Figure 22:
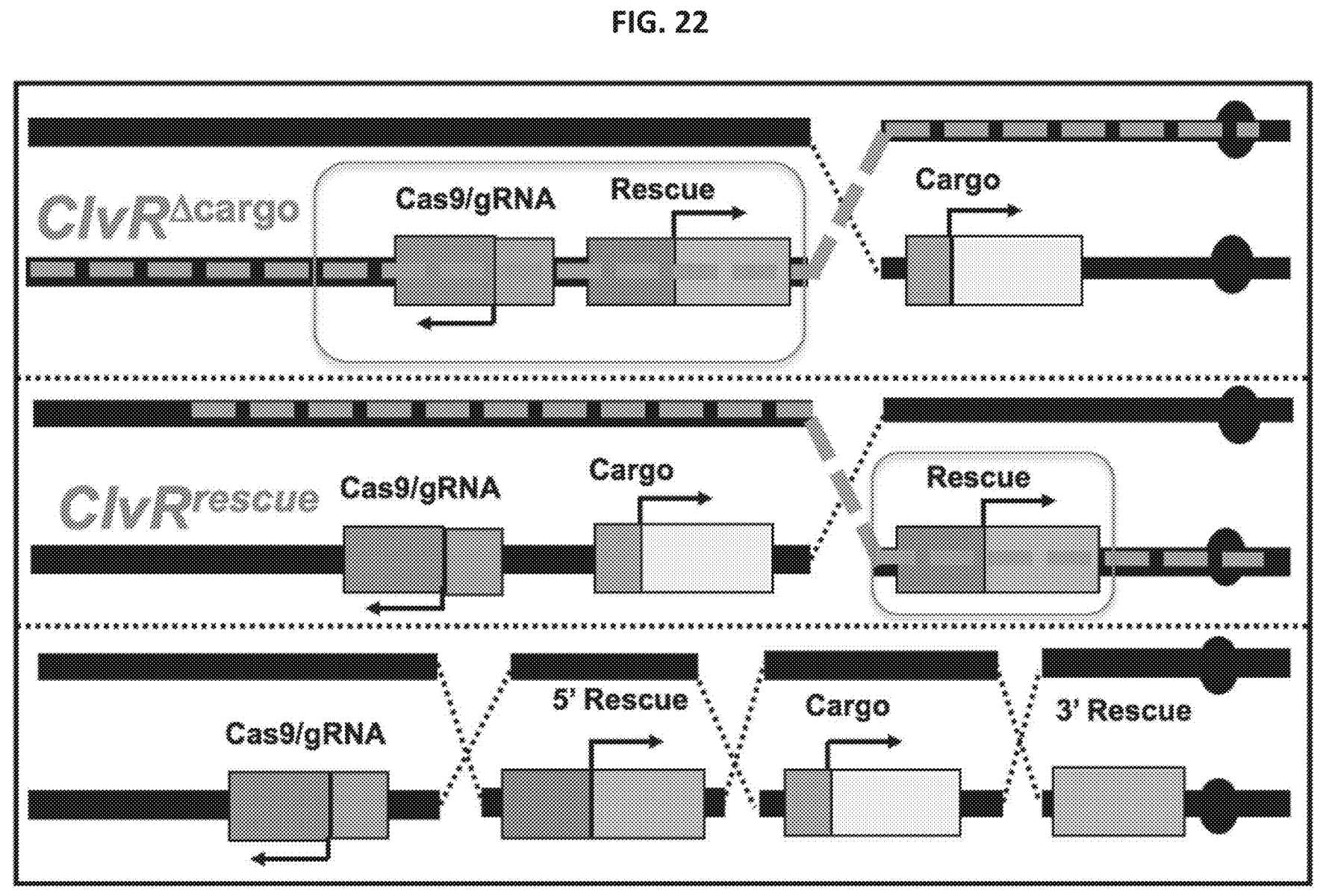

In some embodiments of single locus and two locus ClvR the separation of a functional Rescue from the Cargo can be prevented by locating the Cargo in an intron of the Rescue (FIG. 22). A break between the two genes followed by reciprocal end joining with the same region on the homologous chromosome could separate them. Locating the ClvR cargo in an intron of the Rescue transgene (bottom panel) reduces breakage and end joining-mediated separation of a functional Rescue (the component driven into the population by ClvR) from the Cargo. Separation could otherwise generate empty ClvR elements (ClvR$^{\Delta cargo}$, top panel), or Rescue only elements (ClvR$^{rescue}$, middle panel), the spread of which provide no beneficial function. Crossed lines indicate sites of chromosome breakage and end joining with a similar position on a homologous chromosome. Recombinant products of interest are indicated by the dotted lines.

Figure 23:
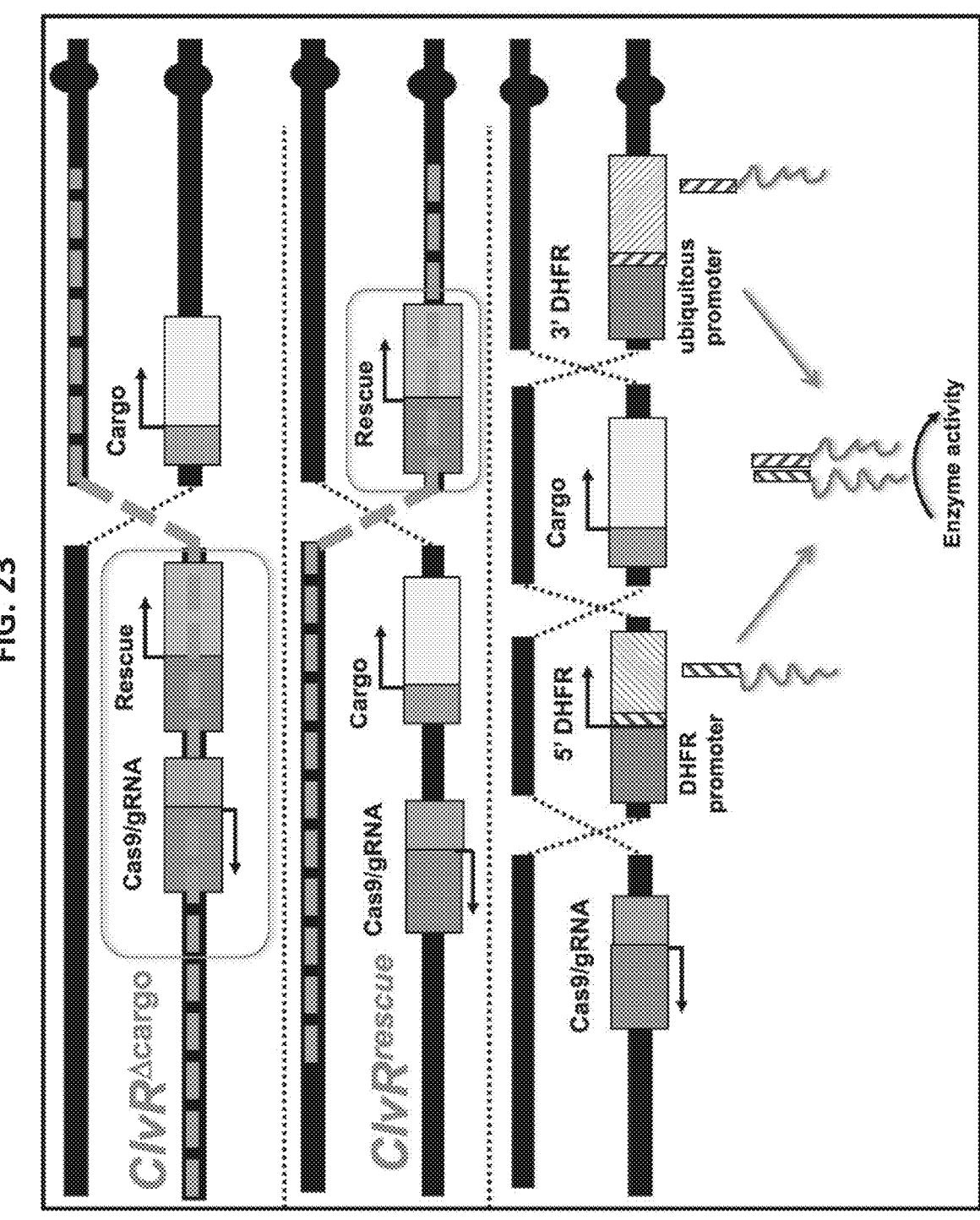
FIG. 23 shows a schematic of an embodiment of ClvR in which the cargo is located between two transgenes whose co-expression is required to create a functional Rescue protein. Similar considerations apply to two locus versions also.

In some embodiments of single and two locus ClvR separation of a functional Rescue from the Cargo can be reduced by locating the Cargo between two transgenes whose co-expression is required to produce a functional Rescue essential enzyme, such as dihydrofolate reducatse (FIG. 23). The 5' half of DHFR is driven by its own promoter. The 3' half is driven by a strong ubiquitous promoter. The two domains are brought together to form an active enzyme through heterodimerization, mediated by specific domains at the N-terminus of each protein (boxes with diagonal lines).

Figure 24:
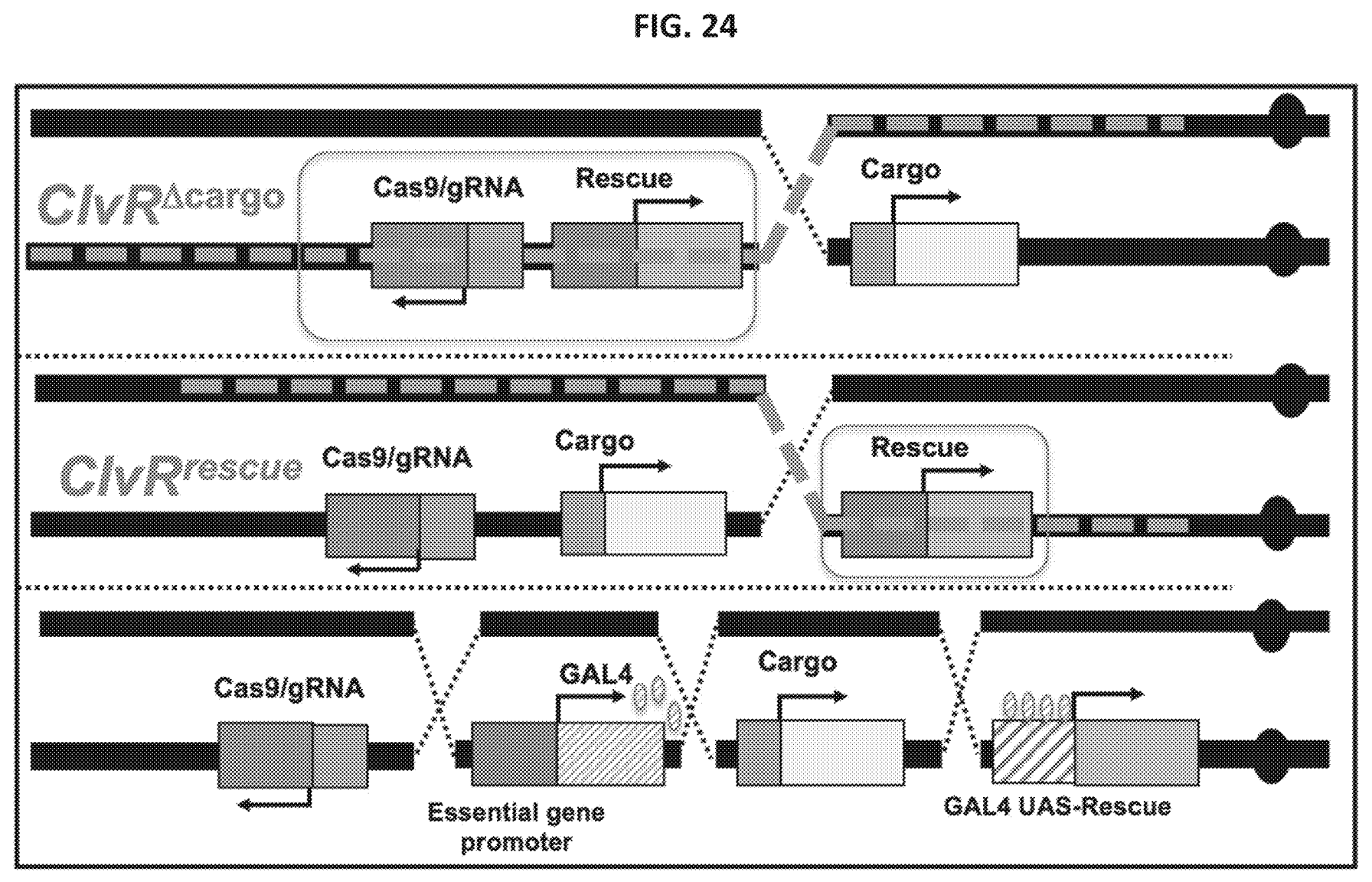

In some embodiments of single and two locus ClvR separation of a functional Rescue from the Cargo can be reduced by locating the Cargo between two transgenes whose co-expression is required to produce a functional Rescue protein (FIG. 24). Here this is achieved using a two-component transcription-based system. The essential gene promoter drives the expression of a heterologous transcriptional activator such as GAL4. The Rescue transgene contains GAL4 UAS binding sites sufficient to drive GAL4-dependent expression, upstream of an otherwise promoterless, recoded Rescue transgene.

Figure 32:
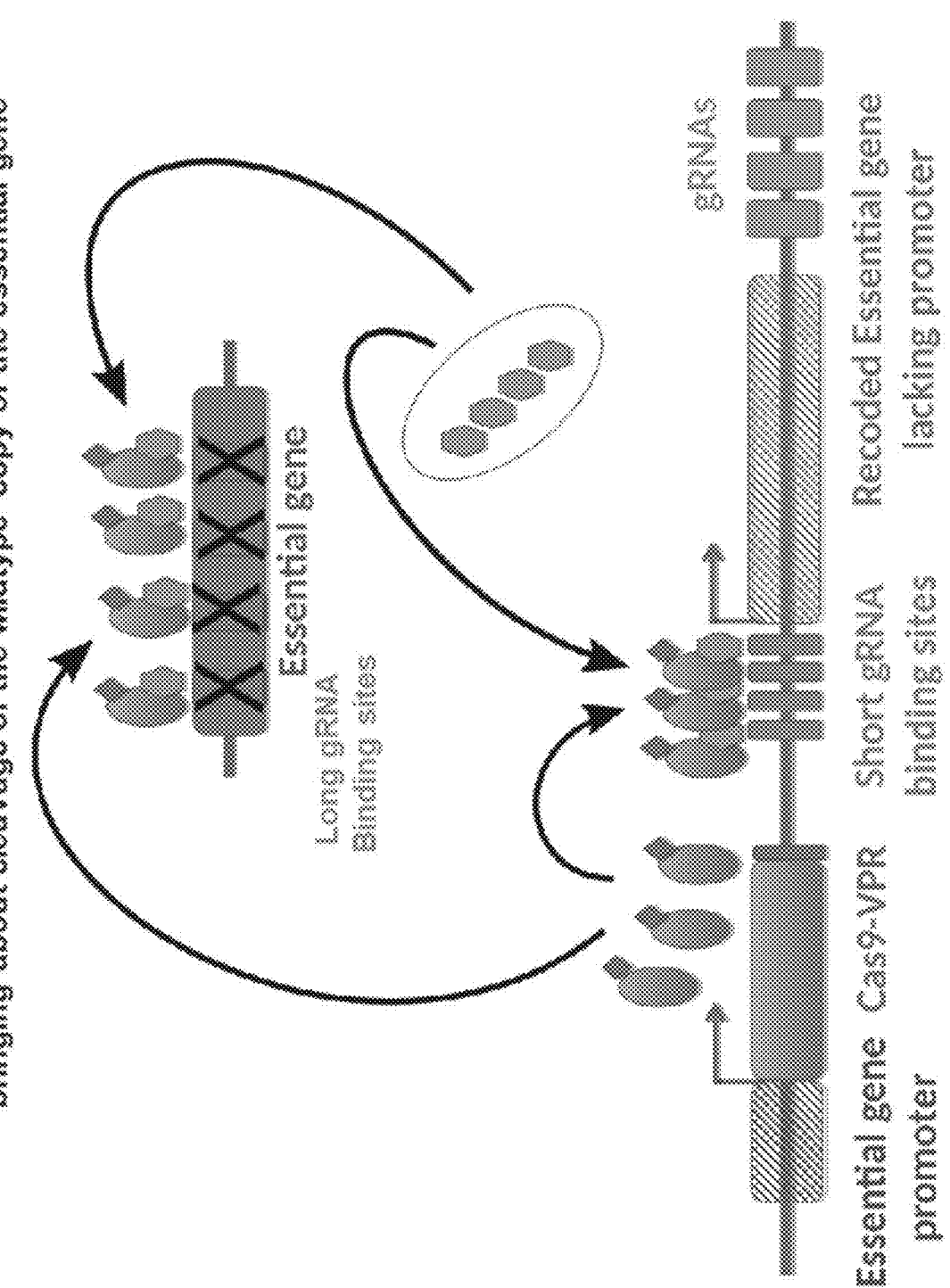
FIG. 32 shows a schematic illustrating a strategy by which Cas9, gRNAs and Rescue transgene can be implemented such that Cas9 and gRNAs are required for Rescue expression in addition to cleavage of an essential gene.

In some embodiments of single and two locus ClvR Cas9 can be made essential for Rescue function. A circuit that selects against mutation of Cas9/gRNAs to inactivity is illustrated in FIG. 32. In this implementation a variant of Cas9 known as Cas9-VPR includes a domain that can activate transcription following DNA binding. Cas9-VPR can also bring about cleavage of full length target sites. Importantly, however, Cas9-VPR can also bind truncated gRNA target sites and drive transcription of a nearby gene, without cleaving these sites. In this way the exact same gRNAs and Cas9 are used for cleavage and transcriptional activation. The figure illustrates an implementation in which Cas9 expression is driven by the promoter of the essential gene. The gRNAs are expressed ubiquitously under U6 promoter control, as usual. Cas9 and gRNAs will cleave the wildtype copy of the essential gene in all tissues in which the essential gene is expressed. Cas9 and gRNAs will also drive expression of a promoterless, recoded version of the essential gene (the Rescue) in these same tissues. The system thus creates tight linkage between components required for cleavage and those required for rescue. It can fail due to point mutations in Cas9 that allow target site DNA binding and transcriptional activation but that prevent cleavage, as with dead Cas9 variants used for transcriptional regulation or visualization of specific genomic loci. These will happen, but are very specific mutations, and thus any spread of dead Cas9 within the population should be delayed. An important requirement for this approach is that the essential gene be expressed in the germline at levels sufficient to bring about Cas9-dependent germline cleavage of the wildtype essential gene. Also note that unless the essential gene is only required in the germline, Cas9 will be expressed and active in some somatic tissues.

Methods

One of ordinary skill in the art would appreciate that any of the methods disclosed herein can be performed by any of the vectors provided herein.

In some embodiments, a method of modifying a population by a vector or vectors is provided. In some embodiments, the method comprises obtaining an organism of the population. In some embodiments, the organism is, without limitations, bacteria, archaea, fungi, plants and animals, including rodents, amphibians, mammals, reptiles, insects, mosquitoes, fish, etc.

In some embodiments, the method comprises positioning the vector or vectors in at least one chromosome or extra-chromosomal element in the organism. In some embodiments, the vector or vectors is any of the embodiments of the vectors provided herein.

In some embodiments, the DNA sequence modifying enzyme is expressed in the organism. In some embodiments, the organism is unicellular or multicellular. In some embodiments, when the organism is multicellular, the DNA sequence modifying enzyme is expressed in all cells of the organism. In some embodiments, the DNA sequence modifying enzyme is not expressed in all cells of the multicellular organism. In some embodiments, the DNA sequence modifying enzyme is expressed in a fraction of cells of the multicellular organism. In some embodiments, the DNA sequence modifying enzyme is expressed only in the male or female germline, or in the germline of both sexes.

In some embodiments, the expression of the DNA sequence modifying enzyme induces one or more sequence modifications. In some embodiments, the expression of the DNA sequence modifying enzyme induces one or more sequence modifications in an essential gene. In some embodiments, the expression of the DNA sequence modifying enzyme induces one or more sequence modifications in an essential gene in one or more cells in the organism. In some embodiments, the one or more sequence modifications result in the essential gene being rendered partially non-functional. In some embodiments, the one or more sequence modifications result in the essential gene being rendered wholly non-functional. In some embodiments, the one or more sequence modifications result in the essential gene being rendered partially non-functional in some circumstances and wholly non-functional in other circumstances. In some embodiments, the result of the essential gene being rendered partially or wholly non-functional is in a defect in the organism. In some embodiments, the defect is, without limitations, a defect in survival, growth control, fertility, differentiation, or combinations thereof.

In some embodiments, the defect occurs when the one or more cells in which the essential gene being rendered partially or wholly non-functional lack a rescue transgene. In some embodiments, the rescue transgene expresses a recoded protein that rescues the defects in survival, growth control, differentiation, or combinations thereof.

In some embodiments, the expression of the recoded protein by the rescue transgene results in the generations of an altered organism. In some embodiments, the altered organism expresses the recoded protein in the one or more cells in which the essential gene has been rendered partially non-functional. In some embodiments, the altered organism expresses the recoded protein in the one or more cells in which the essential gene has been rendered wholly non-functional. In some embodiments, the altered organism expresses the recoded protein in the one or more cells in which the essential gene has been rendered partially non-functional in some circumstances and wholly non-functional in other circumstances.

In some embodiments, the altered organism carries one or more copies of the vector or vectors, and wherein the defects in survival, growth control, or differentiation of the one or more cells in which the essential gene has been rendered partially non-functional have been rescued the rescue transgene expressed from the one or more copies of the vector or vectors. In some embodiments, the altered organism carries one or more copies of the vector or vectors, and wherein the defects in survival, growth control, or differentiation of the one or more cells in which the essential gene has been rendered wholly non-functional have been rescued the rescue transgene expressed from the one or more copies of the vector or vectors. In some embodiments, the altered organism carries one or more copies of the vector or vectors, and wherein the defects in survival, growth control, or differentiation of the one or more cells in which the essential gene has been rendered partially non-functional in some circumstances and wholly non-functional in other circumstances have been rescued the rescue transgene expressed from the one or more copies of the vector or vectors.

In some embodiments, the altered organism is introduced in a population. In some embodiments, the altered organism is introduced in a population in which an increase in a frequency of the altered organism is desired relative to a frequency of a wild type organism. In some embodiments, the altered organism is introduced in a population in a particular environment. In some embodiments, the altered organism is introduced in a population in a particular environment in which an increase in a frequency of the altered organism is desired relative to a frequency of a wild type organism in the population in the particular environment. In some embodiments, the altered organisms is introduced in the population such that the percent of the altered organism in the population ranges from about 0.0001% to about 50%. In some embodiments, the percent is about 0.00001, 0.0005, 0.0001, 0.0005, 0.001, 0.005, 0.01, 0.05, 0.1, 0.5, 1, 5, 10, 20, 30, 40, or 50%. In some embodiments, the percent is greater than 100%, so as to achieve a more rapid change in the population.

In some embodiments, introducing the altered organism in the population results in replacement of the wild type organism with the altered organism in the population. In some embodiments, introducing the altered organism in the population results in replacement of the wild type organism with the altered organism in the population in the particular environment.

In some embodiments, the altered organism exhibits one or more altered traits. In some embodiments, the altered organism introduces and spreads one or more traits of interest in the population. In some embodiments, the one or more traits of interest is a novel trait not previously prevalent in the population, a trait that is a modified version of a trait previously present in the population (e.g., an enhance or a suppressed version of a trait previously present in the population) or a combination thereof. In some embodiments, the population is modified by the introduction of the altered organism in the population. In some embodiments, the population is modified by the introduction of the altered organism in the population in the particular environment. In Non-limiting examples of traits of interest to enhance or decrease include but are not limited to pathogen resistance, insecticide resistance, environmentally triggered death or sterility, herbicide resistance, fungicide resistance, phage resistance, resistance to viral infection, resistance to abiotic environmental factors, such as cold, heat, and stress.

In some embodiments, the population is modified by the introduction of the altered organism in the population. In some embodiments, the population is modified by the introduction of the altered organism in the population in the particular environment. Non-limiting examples of traits of interest include but are not limited to pathogen resistance, insecticide resistance, environmentally triggered death or sterility, herbicide resistance, fungicide resistance, phage resistance, resistance to viral infection, resistance to abiotic environmental factors, such as cold, heat, and stress. In some embodiments the population is modified such that gene drive is limited in time and space by segregation of the vectors that make up versions of two locus ClvR.

In some embodiments, the population is modified by the introduction of the altered organism in the population. In some embodiments, the population is modified by the introduction of the altered organism in the population in the particular environment. In non-limiting examples of traits of interest include but are not limited to pathogen resistance, insecticide resistance, environmentally triggered death or sterility, herbicide resistance, fungicide resistance, phage resistance, resistance to viral infection, resistance to abiotic environmental factors, such as cold, heat, and stress. In some embodiments the modified population is eliminated or greatly decreased with respect to one or more component transgenes through dilution of the population with wild-types.

In some embodiments, a method of reversibly modifying a population is provided. In some embodiments, the method comprises obtaining a wild type organism, positioning a two-vector system in the wild type organism generating an altered organism by inducing one or more sequence modifications in an essential gene by a DNA sequence modifying enzyme/complex in the two-vector system that result in a defect in survival, growth control, fertility, or differentiation in one or more cells in the organism, and rescuing the defect in survival, growth control, fertility, or differentiation by a rescue transgene in the two-vector system, introducing the altered organism in an environment wherein an increase in a frequency of the altered organism is desired relative to a frequency of the wild type organism in a population; replacing the wild type organism with the altered organism in the population in the environment, thereby obtaining a modified population. In some embodiments one can then reintroduce the wild type organism in an environment wherein an increase in a frequency of the wild type organism is desired relative to a frequency of the modified organism in the modified population. This will result in replacing the modified organism with the wild type organism in the modified population in the environment, thereby reversibly modifying the population.

In some embodiments of the method, the one or more cells comprise somatic cells, germline cells, gametes, or a combination thereof.

In some embodiments of the method, the altered organism is heterozygous or homozygous for one or both of the vectors.

In some embodiments of the method, the organism is haploid, diploid, or polyploid.

In some embodiments of the method, the reversible modification of the population occurs at a rapid rate, high frequency, or both. In some embodiments of the method, the rapid rate is defined as replacement of at least 90% of the wild type organism by the altered organism or vice versa in the population after at most 100 generations. In some embodiments of the method, the high frequency is defined as replacement of at least 90% of the wild type organism by the altered organism or vice versa after 100 generations in the population.

In some embodiments, an organism with the defect in survival, growth control, fertility, or differentiation of the one or more cells is eliminated if the one or more cells of the organism lack the rescue transgene.

In some embodiments, the DNA sequence modifying enzyme does not modify the rescue transgene.

In some embodiments, rescuing the defects in one or more of survival, growth control, or differentiation is achieved by restoring one or more of normal survival, growth control, fertility, or differentiation of the one or more cells by the rescue transgene.

In some embodiments, the one or more cells comprise somatic cells, germline cells, gametes, or a combination thereof.

In some embodiments, the DNA sequence modifying enzyme is a nuclease, a base editor, or a Search and Replace Prime editor according to the embodiments herein.

In some embodiments, the nuclease cleaves and generates one or more double strand breaks in the endogenous copy of the essential gene as described herein.

In some embodiments, the one or more double strand breaks are repaired to create an altered sequence comprising insertions, deletions, base alterations, or a combination thereof.

In some embodiments, the base editor creates one or more base changes or small insertions/deletions in the endogenous copy of the essential gene.

In some embodiments, the one or more base changes comprise one or more point mutations, or deamidated bases that are replaced with nucleotides of a different sequence.

In some embodiments the Search and Replace Prime editor creates one or more base changes or insertion/deletions in the endogenous copy of the essential gene.

In some embodiments, the altered organism is heterozygous or homozygous for the vector or vectors.

In some embodiments, the organism is haploid. Non-limiting example of haploid organisms include prokaryotes. In some embodiments, the organism is diploid. Non-limiting example of diploid organisms include insects, fungi, many plants and animals. In some embodiments, the organism is polyploidy. Non-limiting examples of polyploid organisms include some fungi and animals and many plants.

In some embodiments, the organism is selected from the group consisting of prokaryotes, fungi, plants, and animals. In some embodiments, the organism is, without limitations, a prokaryote (bacteria, archaea), fungi, insect, mammal, rodent, fish, amphibian, reptile or plant. In some embodiments, any of the embodiments of the vectors and and/or methods can be one or more of the following: *Autographa gamma* Silver Y moth *Chilo suppressalis* Asiatic rice borer *Diabrotica speciosa* Cucurbit beetle *Harpophora maydis* Late wilt of corn *Helicoverpa armigera* Old world bollworm *Heteronychus arator* Black maize beetle *Peronosclerospora maydis* Java downy mildew *Peronosclerospora philippinensis* Philippine downy mildew *Punctodera chalcoensis* Mexican corn cyst nematode *Sclerophthora rayssiae* var. *zeae* Brown stripe downy mildew *Spodoptera littoralis*

Egyptian cottonworm *Spodoptera litura* Cotton cutworm *Thaumatotibia leucotreta* False codling moth *Anthonomus grandis* Boll weevil *Autographa gamma* Silver Y moth *Eutetranychus orientalis* Citrus brown mite *Helicoverpa armigera* Old World bollworm *Oxycarenus hyalinipennis* Cotton seed bug *Pectinophora gossypiella* Pink bollworm *Spodoptera littoralis* Egyptian cottonworm *Spodoptera litura* Cotton cutworm *Thaumatotibia leucotreta* False codling moth *Adoxophyes orana* Summer fruit *tortrix* moth *Aeolesthes sarta* City longhorned beetle *Agrilus biguttatus* Oak splendour beetle *Archips xylosteanus* Variegated golden *tortrix Epiphyas postvittana* Light brown apple moth *Lymantria dispar asiatica* Asian gypsy moth *Lymantria mathura* Rosy moth *Massicus raddei* Mountain oak longhorned beetle *Phytophthora quercina* Oak decline *Platypus quercivorus* Oak ambrosia beetle *Raffaelea quercivora* Japanese oak wilt *Scolytus intricatus* European oak bark beetle *Spodoptera littoralis* Egyptian cottonworm *Thaumatotibia leucotreta* False codling moth *Thaumetopoea processionea* Oak processionary moth *Tortrix viridana* Green oak *tortrix* Tremex *fuscicornis* Tremex woodwasp *Candidatus Phytoplasma pini* Pine witches' broom *Cronartium flaccidum* Scots pine blister rust *Dendroctonus micans* Great spruce bark beetle *Dendrolimus pini* Pine-tree lappet *Dendrolimus punctatus* Masson pine moth *Dendrolimus sibiricus* Siberian silk moth *Diprion pini* Pine sawfly *Hylobius abietis* Large pine weevil *Lymantria mathura* Rosy moth *Monochamus saltuarius* Japanese pine sawyer *Monochamus sutor* Small white-marmorated longhorned beetle *Mycosphaerella gibsonii* Needle blight of pine *Panolis flammea* Pine beauty moth *Tomicus destruens* No common name, a pine shoot beetle *Autographa gamma* Silver Y moth *Cernuella virgate* Maritime garden snail *Cochlicella* spp. Exotic species *Diabrotica speciosa* Cucurbit beetle *Helicoverpa armigera* Old world bollworm *Heterodera filipjevi* Cereal cyst nematode *Heterodera latipons* Mediterranean cereal cyst nematode *Heteronychus arator* Black maize beetle *Lobesia botrana* European grape vine moth *Meloidogyne artiellia* British root-knot nematode *Nysius huttoni* Wheat bug *Peronosclerospora philippinensis* Philippine downy mildew *Spodoptera littoralis* Egyptian cottonworm *Spodoptera litura* Cotton cutworm *Adoxophyes orana* Summer fruit *tortrix* moth *Alectra vogelii* Yellow witchweed *Autographa gamma* Silver Y moth *Cernuella virgata* Maritime garden snail *Chrysodeixis chalcites* Golden twin spot moth *Crocidosema aporema* Bud borer *Diabrotica speciosa* Cucurbit beetle *Eutetranychus orientalis* Citrus brown mite *Helicoverpa armigera* Old world bollworm *Spodoptera littoralis* Egyptian cottonworm *Adoxophyes orana* Summer fruit *tortrix* moth *Autographa gamma* Silver Y moth *Candidatus Phytoplasma australiense* Australian grapevine yellows *Cryptoblabes gnidiella Epiphyas* Honeydew moth *postvittana Eupoecilia ambiguella Candidatus Phytoplasma vitis* 1 Light brown apple moth *Heteronychus arator Lobesia botrana Pseudopezicula tracheiphila Spodoptera* European grape berry moth *littoralis Spodoptera litura Thaumatotibia leucotreta* Flavescence doree Black maize beetle European grape vine *Bursaphelenchus cocophilus* Red ring nematode *Candidatus Phytoplasma palmae* Palm lethal yellowing Cocadviroid Coconut cadang cadang Coconut cadang cadang viroid *Darna pallivitta* Nettle caterpillar *Haplaxius crudus* American palm cixiid *Metamasius hemipterus* West Indian cane weevil *Oryctes rhinoceros* Coconut rhinoceros beetle *Paysandisia archon* No common name, a palm borer *Raoiella indica* Red palm mite *Rhabdoscelus obscurus* New Guinea sugarcane weevil *Rhynchophorus ferrugineus* Red palm weevil *Rhynchophorus palmarum* South American palm weevil *Autographa gamma* Silver-Y moth *Candidatus Phytoplasma australiense* Australian grapevine yellows *Chrysodeixis chalcites* Golden twin spot moth *Globodera pallida* Pale cyst nematode *Globodera rostochiensis* Golden nematode *Helicoverpa armigera* Old world bollworm *Meloidogyne fallax* False Columbia root-knot nematode *Meloidogyne minor* Root-knot nematode *Neoleucinodes elegantalis* Tomato fruit borer *Ralstonia solanacearum* race 3 Bacterial wilt/Southern biovar 2 bacterial Wilt *Spodoptera littoralis* Egyptian cottonworm *Spodoptera litura* Cotton cutworm *Synchytrium endobioticum* Potato wart *Tecia solanivora* Guatemalan potato tuber moth *Thaumatotibia leucotreta* False codling moth *Tuta absoluta* Tomato leaf miner *Adoxophyes orana* Summer fruit *tortrix Argyresthia pruniella* Cherry blossom moth *Bactrocera zonata* Peach fruit fly *Candidatus Phytoplasma prunorum* European stone fruit yellows *Enarmonia formosana* Cherry bark *tortrix Epiphyas postvittana* Light brown apple moth *Grapholita funebrana* (Syn.: Plum fruit moth *Cydia funebrana*) *Leucoptera malifoliella* Pear leaf blister moth *Lobesia botrana* European grape vine moth *Monilia polystroma* Asiatic brown rot *Monilinia fructigena* Brown rot, Apple brown rot Potyvirus Plum Pox Virus Plum pox *Rhagoletis cerasi* European cherry fruit fly *Thaumatotibia leucotreta* False codling moth *Globodera pallida* Pale cyst nematode *Globodera rostochiensis* Golden nematode *Heterodera cajani* Pigeonpea cyst nematode *Heterodera ciceri* Chickpea cyst nematode *Heterodera filipjevi* Cereal cyst nematode *Heterodera latipons* Mediterranean cereal cyst nematode *Heterodera sacchari* Sugarcane cyst nematode *Punctodera chalcoensis* Mexican corn cyst nematode *Agrilus auroguttatus* Goldspotted oak borer *Agrilus biguttatus* Oak splendour beetle *Agrilus planipennis* Emerald ash borer *Anoplophora chinensis* Citrus longhorned beetle *Anoplophora glabripennis* Asian longhorned beetle *Chlorophorus annularis* Bamboo borer *Chlorophorus strobilicola* Slender-banded pine cone longhorn beetle *Dendroctonus micans* Great spruce bark beetle *Ips sexdentatus* Six-toothed bark beetle *Ips typographus* European spruce bark beetle *Megaplatypus mutatus* No common name, an *ambrosia* beetle *Monochamus alternatus* Japanese pine sawyer *Monochamus saltuarius* Japanese pine sawyer *Monochamus sutor* Small white-marmorated longhorned beetle *Orthotomicus erosus* Mediterraneran pine engraver *Pityogenes chalcographus* Sixtoothed spruce bark beetle *Platypus quercivorus* Oak ambrosia beetle *Scolytus intricatus* European oak bark beetle *Tetropium castaneum* Black spruce beetle *Tetropium fuscum* Brown spruce longhorned beetle *Tomicus destruens* No common name, a pine shoot beetle *Tomicus minor* Lesser pine shoot beetle *Tomicus piniperda* Pine shoot beetle *Trichoferus campestris* Velvet longhorned beetle *Trypodendron* European hardwood *ambrosia* beetle *domesticum* Redbay *ambrosia* beetle *Belocaulus* spp. No common name, leatherleaf slugs *Cernuella* spp. No common name, hygromiid snails *Cochlicella* spp. No common name, cochlicellid snails *Colosius* spp. No common name, leatherleaf slugs *Laevicaulis* spp. No common name, leatherleaf slugs *Lissachatina fulica* Giant African snail *Meghimatium pictum* Chinese slug *Monacha* spp. No common name, hygromiid snails *Sarasinula* spp. No common name, leatherleaf slugs *Semperula* spp. No common name, leatherleaf slugs *Veronicella* spp. No common name, leatherleaf slugs *Dendrolimus pini* Pine-tree lappet *Dendrolimus punctatus* Masson pine moth *Dendrolimus sibiricus* Siberian silk moth *Lymantria albescens* Okinawa gypsy moth *Lymantria dispar asiatica* Asian gypsy moth *Lymantria dispar japonica* Japanese gypsy moth *Lymantria mathura* Rosy moth *Lymantria monacha* Nun moth *Lyman-*

*tria postalba* White-winged gypsy moth *Lymantria umbrosa* Hokkaido gypsy moth *Lymantria xylina Casuarina* tussock moth.

In some embodiments, an insect can be a direct pest or indirect pest. A "direct pest" refers to insects that can cause damage at one or more stage of their life cycle by, for example, eating crops or damaging animals. The New World screw-worm fly *Cochliomyia hominivorax*, for example, is a direct pest of cattle, and the spotted wing *Drosophila, Drosophila suzukii* is pest of many fruit crops. An "indirect pest" refers to insects that transmit human diseases, for example, mosquitoes which carry malaria. Indirect pests of organisms other than humans, such as livestock or plants are also known.

In some embodiments, insect refers to, without limitations, one or more of *Drosophila*, mosquitoes, bumblebees, hoverflies, grasshoppers, dragonfly, dancefly, weevil, cricket, wasp, moth, beetles, honey bee, robberfly or butterfly. Additional examples of insects include, but are not limited to, Asian citrus psyllid (diaphorini citrii, Australian sheep blowfly (*Lucilia cuprina*, Asian tiger mosquito (*Aedes albopictus*); Japanese beetle (*Popilla japonica*), White-fringed beetle (*Graphognatus* spp.), Citrus blackfly (*Aleurocanthus woglumi*), Oriental fruit fly (*Dacus dorsalis*), Olive fruit fly (*Dacus oleae*), tropical fruit fly (*Dacus cucurbitae, Dacus zonatus*), Mediterranean fruit fly (*Ceratitis capitata*), Natal fruit fly (*Ceratitis rosa*), Chemy fruit fly (*Rhagoletis cerasi*), Queensland fruit fly (*Bactrocera tryoni*), Caribbean fruit fly (*Anastrepha suspensa*), imported fire ants (*Solenopis richteri, Solenopis invictai*, Gypsy moth (*Lyman tria dispar*), Codling moth (*Cydia pomonella*), Brown tail moth (*Euproctis chrysorrhoea*), yellow fever mosquito (*Aedes aegypti*), malaria mosquitoes (*Anopheles gambiae, Anopheles stephensi*), New world screwworm (*Cochliomyia hominivorax*), Old World Screwworm (*Chrysomya bezziana*), Tsetse fly (*Glossina* spp), Boll weevil (*Anthonomous grandis*), Damsel fly (*Enallagma hageni*), Dragonfly (*Libellula luctuosa*), and rice stem borer (*Tryporyza incertulas*). In some embodiments, the insect either transmits human disease or are agricultural pests. In some embodiments, the insects are wild insect populations.

In some embodiments, the insects are mosquitoes or flies (for example fruit flies, tsetse flies, sand flies). The mosquitoes can be, for example, *Aedes* sp. or *Anopheles* sp. In some embodiments, the mosquito is yellow fever mosquito (*Aedes aegypti*), malaria mosquito (*Anopheles gambiae, Anopheles stephensi*), Asian tiger mosquito (*Aedes albopictus*) or *Culex* mosquitoes. In some embodiments, the insect is one that transmits a disease of a mammal. The disease can be any disease, for example, malaria and/or yellow fever. In some embodiments, the insect is a Spotted wing *Drosophila* (*Drosophila Suzukii*).

In some embodiments, insect refers to an insect that spreads a disease of humans. In some embodiments, insect refers to an insect that spreads a disease of economically important animals. In some embodiments, insect refers to an insect that spreads a disease of companion animals. In some embodiments, insect refers to an insect that spreads a disease of plants.

In some embodiments, mosquitoes can be, without limitations, of *Aedes, Anopheles, Culex, Coquillettidia, Haemagogus, Mansonia, Ochlerotatus, Psorophora* or other genera that transmit diseases. In some embodiments, the diseases transmitted by mosquitoes can be one or more of Malaria, Chikungunya, Dog Heartworm, Dengue, Yellow Fever, Eastern Equine Encephalitis, St. Louis Encephalitis, LaCrosse Encephalitis, Western Equine Encephalitis, West Nile Virus, or Zika Virus, lymphatic filariasis.

In some embodiments, the population has about 10,000 to about 100,000,000,000 organisms. In some embodiments, the population has about 500, 1000, 1500, 2000, 2500, 3000, 3500, 4000, 4500, 5000, 5500, 6000, 6500, 7000, 7500, 8000, 8500, 9000, 9500, 10,000, 100,000, 500,000, 1,000, 000, 100,000,000, 1,000,000,000, 100,000,000,000 or 1,000,000,000,000 organisms, or a number within a range defined by any two of the aforementioned values.

In some embodiments, the environment comprises an open environment, a bioreactor, or a multicellular body, a closed container, or combinations thereof. In some embodiments, the environment is a combination of an open environment, a bioreactor, or a multicellular body, a closed container, and the environment changes sequentially from one to the other In some embodiments, the wild type organism is replaced at a high frequency with the altered organism in the population wherein the wild type organism is present. In some embodiments, the wild type organism is replaced at a high frequency with the altered organism in the population in a particular environment wherein the wild type organism is present. In some embodiments, high frequency is defined as replacement of at least 90% of the wild type organism with the altered organism after 50 generations. In some embodiments, high frequency is defined as replacement of at least 80% of the wild type organism with the altered organism after 50 generations. In some embodiments, high frequency is defined as replacement of at least 70% of the wild type organism with the altered organism after 50 generations. In some embodiments, high frequency is defined as replacement of at least 60% of the wild type organism with the altered organism after 50 generations. In some embodiments, high frequency is defined as replacement of at least 50% of the wild type organism with the altered organism after 50 generations.

In some embodiments, the wild type organism is replaced at a rapid rate with the altered organism in the population wherein the wild type organism is present. In some embodiments, the wild type organism is replaced at a rapid rate with the altered organism in the population in a particular environment wherein the wild type organism is present. In some embodiments, rapid rate is defined as replacement of at least 90% of the wild type organism with the altered organism after 50 generations. In some embodiments, rapid rate is defined as replacement of at least 80% of the wild type organism with the altered organism after 50 generations. In some embodiments, rapid rate is defined as replacement of at least 70% of the wild type organism with the altered organism after 50 generations. In some embodiments, rapid rate is defined as replacement of at least 60% of the wild type organism with the altered organism after 50 generations. In some embodiments, rapid rate is defined as replacement of at least 50% of the wild type organism with the altered organism after 50 generations.

In some embodiments, at least 90% of the wild type organism is replaced with the altered organism after 50 generations. In some embodiments, at least 90% of the wild type organism is replaced with the altered organism after 50 generations. In some embodiments, at least 80% of the wild type organism is replaced with the altered organism after 50 generations. In some embodiments, at least 70% of the wild type organism is replaced with the altered organism after 50 generations. In some embodiments, at least 60% of the wild type organism is replaced with the altered organism after 50 generations. In some embodiments, at least 50% of the wild type organism is replaced with the altered organism after 50 generations.

In some embodiments, the one or more sequence modifications in the one or more cells is a result of the one or more cells carrying the first gene encoding the DNA sequence modifying enzyme. In some embodiments, the one or more sequence modifications in the one or more cells is a result of the DNA sequence modifying enzyme being transmitted to the one or more cells from one or more cells expressing the DNA sequence modifying enzyme through diffusion following cell fusion. In some embodiments, the one or more sequence modifications in the one or more cells is a result of the DNA sequence modifying enzyme being transmitted to the one or more cells from one or more cells expressing the DNA sequence modifying enzyme through active transport. In some embodiments, the one or more sequence modifications in the one or more cells is a result of the one or more cells carrying the first gene encoding the DNA sequence modifying enzyme or a combination of genes that together encode the essential components of the DNA sequence modifying enzyme, and is a result of the DNA sequence modifying enzyme or its component parts being transmitted to the one or more cells from one or more cells expressing the DNA sequence modifying enzyme through diffusion following cell fusion, mating, or conjugation. In some embodiments, the one or more sequence modifications in the one or more cells is a result of the one or more cells carrying the first gene encoding the DNA sequence modifying enzyme and is a result of the DNA sequence modifying enzyme being transmitted to the one or more cells from one or more cells expressing the DNA sequence modifying enzyme through active transport. In some embodiments, the one or more sequence modifications in the one or more cells is a result of the DNA sequence modifying enzyme being transmitted to the one or more cells from one or more cells expressing the DNA sequence modifying enzyme or a combination of genes that together encode the essential components of the DNA sequence modifying enzyme through active transport and is a result of the DNA sequence modifying enzyme or its component parts being transmitted to the one or more cells from one or more cells expressing the DNA sequence modifying enzyme through active transport. In some embodiments, the one or more sequence modifications in the one or more cells is a result of the DNA sequence modifying enzyme being transmitted to the one or more cells from one or more cells expressing the DNA sequence modifying enzyme through intercellular movement which may occur through multiple mechanisms including conjugation, vesicle uptake, uptake of free enzyme, uptake of cell synthesized nanoparticles, uptake through tunneling nanotubes.

In some embodiments, the vector or vectors are positioned in one or more chromosomes or extra-chromosomal elements by a homologous recombination-dependent integration, random integration, integration using transposition, integration using a recombinase, or combinations thereof.

In some embodiments, the one or more cargo sequences comprise a one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments, when the vector is positioned on the chromosome or the extra-chromosomal element, the first gene operably linked to the first promoter, the second gene operably linked to the second promoter, and the one or more cargo transgenes are genetically linked.

In some embodiments, when two vectors are utilized, these are positioned on distinct chromosomes or on the same chromosome at some distance with respect to each other, the first gene is operably linked to the first promoter, the second gene operably linked to the second promoter, the third gene operably linked to the third promoter, and the fourth gene operably linked to the fourth promoter, and the one or more cargo transgenes are in some cases genetically linked.

In some embodiments of single locus and two locus ClvR the separation of a functional Rescue from the Cargo can be prevented by locating the Cargo in an intron of the Rescue (FIG. 22). A break between the two genes followed by reciprocal end joining with the same region on the homologous chromosome could potentially separate them, though the frequency of this kind of event is unclear. Locating the ClvR cargo in an intron of the Rescue transgene (bottom panel) prevents breakage and end joining-mediated separation of a functional Rescue (the key component driven into the population by ClvR) from the Cargo. Separation could otherwise generate empty ClvR elements (ClvR$^{\Delta cargo}$, top panel), or Rescue only elements (ClvR$^{rescue}$, middle panel), the spread of which provide no beneficial function. Crossed lines indicate sites of chromosome breakage and end joining with a similar position on a homologous chromosome. Recombinant products of interest are indicated by the dotted lines.

In some embodiments of single and two locus ClvR separation of a functional Rescue from the Cargo can be prevented by locating the Cargo between two transgenes whose co-expression is required to produce a functional Rescue essential enzyme, such as dihydrofolate reducatse (FIG. 23). The 5' half of DHFR is driven by its own promoter. The 3' half is driven by a strong ubiquitous promoter. The two domains are brought together to form an active enzyme through heterodimerization, mediated by specific domains at the N-terminus of each protein (boxes with diagonal lines).

In some embodiments of single and two locus ClvR separation of a functional Rescue from the Cargo can be prevented by locating the Cargo between two transgenes whose co-expression is required to produce a functional Rescue protein (FIG. 24). Here this is achieved using a two-component transcription-based system. The essential gene promoter drives the expression of a heterologous transcriptional activator such as GAL4. The Rescue transgene contains GAL4 UAS binding sites sufficient to drive GAL4-dependent expression, upstream of an otherwise promoterless, recoded Rescue transgene.

In some embodiments of single and two locus ClvR Cas9 can be made essential for Rescue function. A circuit that selects against mutation of Cas9/gRNAs to inactivity is illustrated in FIG. 32. In this implementation a variant of Cas9 known as Cas9-VPR includes a domain that can activate transcription following DNA binding. Cas9-VPR can also bring about cleavage of full length target sites. Importantly, however, Cas9-VPR can also bind truncated gRNA target sites and drive transcription of a nearby gene, without cleaving these sites. In this way the exact same gRNAs and Cas9 are used for cleavage and transcriptional activation. The figure illustrates an implementation in which Cas9 expression is driven by the promoter of the essential gene. The gRNAs are expressed ubiquitously under U6 promoter control, as usual. Cas9 and gRNAs will cleave the wildtype copy of the essential gene in all tissues in which the essential gene is expressed. Cas9 and gRNAs will also drive expression of a promoterless, recoded version of the essential gene (the Rescue) in these same tissues. The system thus creates tight linkage between components required for cleavage and those required for rescue. It can fail due to point mutations in Cas9 that allow target site DNA binding and transcriptional activation but that prevent cleavage, as with dead Cas9 variants used for transcriptional regulation or visualization of specific genomic loci. These will happen, but are very specific mutations, and thus any spread of dead Cas9 within the population should be delayed. An important requirement for this approach is that the essential gene be expressed in the germline at levels sufficient to bring about Cas9-dependent germline cleavage of the wildtype essential gene. Also note that unless the essential gene is only required in the germline, Cas9 will be expressed and active in some somatic tissues.

In some embodiments of the method, the vector and cargo are located in a small chromosomal inversion. In some embodiments of the method, the vector and cargo are located in a small chromosomal inversion further limiting the possibility that the vector and cargo can separate from each other during any stage of DNA replication, mitosis, and/or or meiosis.

In some embodiments, the nuclease cleaves and generates one or more double strand breaks in the endogenous copy of the essential gene with a high cleavage efficiency. In some embodiments, the high cleavage frequency is defined as at least 30% of individuals carrying the nuclease cleave the endogenous copy of the essential gene in each generation. In some embodiments, the high cleavage frequency is defined as at least 40% of individuals carrying the nuclease cleave the endogenous copy of the essential gene being cleaved in each generation. In some embodiments, the high cleavage frequency is defined as at least 50% of individuals carrying the nuclease cleave the endogenous copy of the essential gene being cleaved in each generation. In some embodiments, the high cleavage frequency is defined as at least 60% of individuals carrying the nuclease cleave the endogenous copy of the essential gene being cleaved in each generation.

In some embodiments, the high cleavage frequency is defined as the nuclease cleaving one or more alleles of the endogenous copy of the essential gene in at least 30% of organisms carrying the vector or vectors and the one or more alleles of the endogenous copy of the essential gene in each generation. In some embodiments, the high cleavage frequency is defined as the nuclease cleaving one or more alleles of the endogenous copy of the essential gene in at least 40% of organisms carrying the vector or vectors and the one or more alleles of the endogenous copy of the essential gene in each generation. In some embodiments, the high cleavage frequency is defined as the nuclease cleaving one or more alleles of the endogenous copy of the essential gene in at least 50% of organisms carrying the vector and the one or more alleles of the endogenous copy of the essential gene in each generation. In some embodiments, the high cleavage frequency is defined as the nuclease cleaving one or more alleles of the endogenous copy of the essential gene in at least 60% of organisms carrying the vector or vectors and the one or more alleles of the endogenous copy of the essential gene in each generation.

In some embodiments, the base editor creates one or more base changes in endogenous copy of the essential gene with a high base editing frequency. In some embodiments, the high base editing frequency is defined as base editing in at least 20% of organisms that carry the vector or vectors in each generation. In some embodiments, the high base editing frequency is defined as base editing in at least 30% of organisms that carry the vector in each generation. In some embodiments, the high base editing frequency is defined as base editing in at least 40% of organisms that carry the vector or vectors in each generation. In some embodiments, the high base editing frequency is defined as base editing in at least 50% of organisms that carry the vector or vectors in each generation.

In some embodiments, the high base editing frequency is defined as the base editor modifying one or more alleles of the endogenous copy of the essential gene in at least 20% of the organisms carrying the vector or vectors and the one or more alleles of the endogenous copy of the essential gene in each generation. In some embodiments, the high base editing frequency is defined as the base editor modifying one or more alleles of the endogenous copy of the essential gene in at least 30% of the organisms carrying the vector or vectors and the one or more alleles of the endogenous copy of the essential gene in each generation. In some embodiments, the high base editing frequency is defined as the base editor modifying one or more alleles of the endogenous copy of the essential gene in at least 40% of the organisms carrying the vector or vectors and the one or more alleles of the endogenous copy of the essential gene in each generation. In some embodiments, the high base editing frequency is defined as the base editor modifying one or more alleles of the endogenous copy of the essential gene in at least 50% of the organisms carrying the vector or vectors and the one or more alleles of the endogenous copy of the essential gene in each generation.

In some embodiments of the method, the nuclease cleaves and generates one or more double strand breaks in the endogenous copy of the essential gene with a high cleavage efficiency. In some embodiments of the method, the high cleavage frequency is defined as the nuclease cleaving the endogenous copy of the essential gene in at least 30% of the organisms carrying the vector or vectors in each generation. In some embodiments of the method, the base editor creates one or more base changes in the endogenous copy of the essential gene with a high base editing frequency. In some embodiments of the method, the high base editing frequency is defined as the base editor modifying the endogenous copy of the essential gene in at least 20% of the organisms carrying the vector or vectors in each generation. In some embodiments of the method, the Search and Replace Prime editor nicks the target DNA in the endogenous copy of the essential gene, and reverse transcriptase, in conjunction with a modified gRNA, creates base changes, insertions or deletions, with high efficiency. In some embodiments of the method, the high frequency of modification is defined as modification of the endogenous copy of the essential gene at a frequency of at least 20% per gRNA of organisms carrying the vector, or progeny of these organisms, in each generation.

In some embodiments, the promoter of the first gene is a female-specific promoter such that the first gene encoding the DNA sequence modifying enzyme is expressed within females only. In some embodiments, female-specific expression of the DNA sequence modifying enzyme results in the DNA-modifying enzyme being present in the eggs. In some embodiments, when an egg expressing the DNA sequence modifying enzyme is fertilized by a male gamete, the DNA sequence modifying enzyme from the egg can modify target sequence in the paternal copy provided by the father. In some embodiments, there is paternal carryover wherein sperm contribute DNA modifying activity to eggs, resulting in modification of the copy of the target sequence provided by the mother. In some embodiments, there is potential for carryover. In some embodiments, modification of an allele in a fertilized egg is achieved even when the allele is inherited from a parent that did not carry the vector.

In some embodiments, the promoter of the first gene is a germline-specific promoter such that the first gene encoding the DNA sequence modifying enzyme or an essential component of this enzyme is expressed within the germline only. In some embodiments the promoter of the second gene, which drives expression of gRNAs, results in ubiquitous gRNA expression. In some embodiments, germline-specific expression of the DNA sequence modifying enzyme and the ubiquitously expressed gRNAs results in the DNA-modifying enzyme being present in the eggs through maternal carryover from oogenesis. In some embodiments, when an egg carrying the DNA sequence modifying enzyme deposited during oogenesis is fertilized by a male gamete, the DNA sequence modifying enzyme from the egg can modify target sequence in the paternal copy provided by the father. This is known as maternal carryover. In some embodiments, there is paternal carryover wherein sperm contribute DNA modifying activity to eggs, resulting in modification of the copy of the target sequence provided by the mother. In some embodiments, there is potential for carryover. In consequence, in some embodiments, modification of an allele in a fertilized egg is achieved even when the allele is inherited from a parent that did not carry the vector.

In some embodiments, as used herein, "fitness cost" is defined as a relative reduction in the number of offspring produced by, or survival of, individuals carrying the transgenic construct, as compared with wild type individuals. In some embodiments fitness cost is defined as a relative reduction in the number of offspring produced by, or survival of, individuals not carrying the transgenic construct, as compared with those who do. In some embodiments, fitness benefit is defined as a relative increase in the number of offspring produced by, or survival of, individuals carrying the transgenic construct as compared with wild type individuals.

In some embodiments, the first gene expresses within females (the female germline or cells that contribute components to the female germline), such that the DNA-modifying enzyme and any associated cofactors such as guide RNAs, whose expression may be driven by an independent promoter, are deposited into all oocytes/eggs, including those that do not inherit one or more of the vectors, and modify target sequences in the version of the essential gene provided by the father. This represents maternal carryover of DNA sequence modifying activity.

In some embodiments, paternal carryover of the DNA modifying enzyme results in modification of the maternal copy of the essential locus in eggs, including those that do not inherit the vector or vectors.

Applications

In some embodiments, the methods provided herein can be applied for modification of populations for beneficial outcomes. For example, in some embodiments, to prevent mosquito-borne diseases (e.g., malaria, dengue, etc.), mosquitoes can be engineered based on the embodiments of the vectors and methods disclosed herein to resist infection. The engineered mosquito can be used to replace wild mosquito population in order to achieve less transmission and less disease. Such a trait (e.g., refractoriness of the engineered mosquito to disease transmission) is unlikely to spread into a population in the absence of gene drive because the trait results in a fitness cost to carriers. A gene drive solution to this problem described herein is to increase the fitness cost associated with not carrying the gene of interest through DNA sequence modification-based gene drive.

In comparison to other low threshold gene drive systems (Example, 12-14), the single locus Cas9 based gene drive mechanisms in Examples 1-11, Examples 15-17, Example 24, Examples 30-39 do not require any homing to occur (homing is known to vary in its relative rate compared to other forms of DNA repair in different species), and they are predicted to rapidly take over wild type populations even when the associated cargo results in significant fitness costs. The presently proposed DNA sequence modification-based drives, including two locus versions of ClvR in Examples 15-19 (FIGS. 34A-F, FIGS. 35A-F), are all predicted to replace wild type populations quickly while bearing substantial fitness costs, and each of the these drives displays characteristics that qualify them for different scenarios.

While all of these single and two locus ClvR drive mechanisms have been considered in the context of Cas9, these drive results could apply to any endonuclease or base editor used or Search and Replace Prime editor or other method of bringing about site-specific modification of DNA, used to disrupt the function of an endogenous gene. For some embodiments, one of the biggest advantages of these drives is their adaptability to new species. This is because the primary requirements are the identification of an essential gene (thousands in each organism), a recoded or sequence unrelated version of the gene (including associated regulatory sequences) that has wildtype or close to wildtype function, and a promoter and DNA sequence-modifying enzyme capable of bringing about sequence alteration of the endogenous copy of the essential gene in the germline, or germline and early embryo cells exposed to the enzyme.

Additional Embodiments

Without being limited by any particular theory, one implementation of a DNA sequence-based modification-based gene drive is as follows: a cell expresses a DNA sequence modifying enzyme that alters the sequence of an essential gene, inactivating it. The DNA sequence modifying enzyme is transmitted through cytoplasm to offspring (either maternally, paternally, or both), where it modifies the target gene, regardless of whether the gene encoding the DNA sequence modifying enzyme is transmitted to these progeny. Progeny that inherit the DNA sequence modifying enzyme-encoding gene also inherit a rescue copy of the wildtype gene that has been cleaved. This rescue copy is both functional and uncleavable. In this way key features required for gene drive are brought about in both single and two locus configurations.

Without being limited by any particular theory, some embodiments of a DNA sequence-based modification-based gene drive are as follows: a cell expresses a DNA sequence modifying enzyme—or a first component of this enzyme such that when a first and second components are both present—that alters the sequence of an essential gene, inactivating it. The DNA sequence modifying enzyme is transmitted through cytoplasm to offspring (either maternally, paternally, or both), where it modifies the target gene, regardless of whether the gene or genes encoding the DNA sequence modifying enzyme is transmitted to these progeny. Progeny that inherit the DNA sequence modifying enzyme-encoding gene or a first component of it have some probability, depending on the degree of linkage with the Rescue and any associated transgenes, to also inherit a Rescue copy of the wildtype gene that has been cleaved. This Rescue copy is both functional and uncleavable. Since one or more components of the gene or gene encoding the DNA sequence modifying enzyme have a non-zero frequency of recombination (up to 50%) with the rescue, the genes encoding one or more components of the DNA sequence modifying enzyme will sometimes find themselves in individuals who lack the rescue and any other functional copies of the essential gene. These individuals die. Since drive requires the creation of LOF alleles by the DNA sequence modifying enzyme, drive in the presence of recombination will decrease over generations, and ultimately cease. In this way, key features required for transient gene drive are brought about. If the rescue and/or any associated transgenes, or components of the DNA sequence modifying enzyme result in a fitness cost to carriers, dilution of the population with wildtypes, in the absence of drive, or in the presence of low levels of drive, can lead to loss of transgenes from the population. In this way key features required for reversible gene drive are brought about.

Figures 31A, 31B, 31C, 31D:
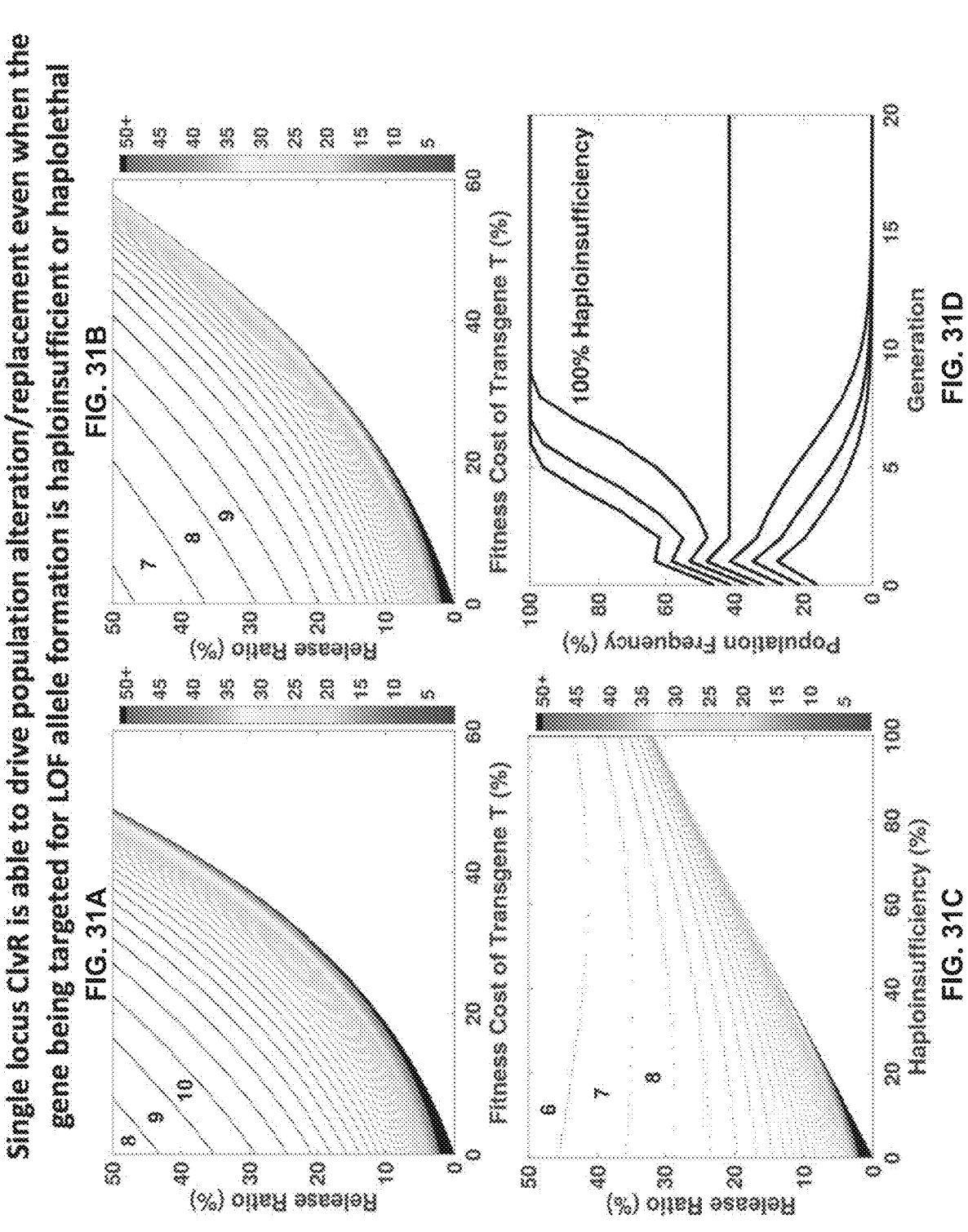
FIGS. 31A-D show graphs of an embodiment of a population frequency modeling of cleavage mediated drive for genes that are haploinsufficient or haplolethal.

In some embodiments, the above system is applicable to insects. A DNA sequence modifying enzyme is expressed under the control of a germline promoter. The promoter may be expressed in both the male and female germline. However, let us also consider a case in which the nuclease is expressed under the control of a late female germline specific promoter. In this case the DNA sequence modifying enzyme is transmitted from the oocyte, where its mRNA (and any associated co-factors such as gRNAs) is synthesized, to the mature oocyte/fertilized egg. In the zygote (fertilized egg) the DNA sequence modifying enzyme alters wildtype copies of the gene, resulting in their inactivation. This inactivation can occur in the nuclei that will ultimately give rise to cells of various somatic tissues of the animal. It can also occur in the cells that will give rise to the embryonic germline. Without being limited by any particular theory, provided that endogenous copies of the essential gene are altered in a sufficient number of nuclei, and are inactivated in both copies (for diploid organisms), which can happen early in embryogenesis (at the single diploid nucleus stage) or later, after some number of nuclei have been generated, then development will be disrupted, resulting in animal death. However, if the zygote inherits along with the DNA sequence modifying enzyme-encoded gene a tightly linked copy of the rescue transgene that cannot be modified, or copy of the rescue transgene that is not tightly linked to that of the DNA sequence modifying enzyme, progeny will survive if they inherit the rescue transgene, even if both copies of the wildtype copy of the gene have been modified. This occurs because for most genes in diploids heterozygosity for one wildtype copy of the gene is sufficient to provide enough function to allow the organisms to survive and thrive. Good evidence for this conclusion comes from several sources: the many examples of phenotypically normal heterozygotes in many species; and the ability to create and maintain healthy stocks for deletions that eliminate, one at a time, one copy of most regions of the *drosophila* genome (flybase.org). If there is a modest fitness cost associated with heterozygosity this will be decreased over time as the construct spreads. This is because as spread occurs the frequency of homozygotes for the construct rises, in which case individuals now carry two copies of the rescue gene of interest and are therefore have increased fitness. Importantly, there is no requirement that the essential gene being targeted is haplosufficient or even haploviable. This is illustrated in FIGS. 31C and D, which show predicted drive behavior when a haplolethal (heterozygotes are dead) gene is targeted.

Without being limited by any particular theory, the model can be generalized and extrapolated to prokaryotes or other haploids carrying a plasmid that encodes a DNA sequence modifying enzyme and a recoded or sequence unrelated version of an essential gene. In this case progeny that fail to inherit the plasmid will still inherit the chromosomal mutation that results in loss of function of the wildtype copy of the gene. They may also inherit the DNA sequence modifying enzyme, in which case the sequence of any wildtype copies of the essential gene (incorporated through horizontal gene transfer, transduction, transformation, or conjugation) will be altered and the cell will die. However, those cells that inherit the plasmid inherit a functional copy of the gene, even though the chromosomal version of the gene has been altered (FIG. 6; FIG. 43).

Without being limited by any particular theory, the model can be generalized and extrapolated to organisms such as yeast, other fungi and some plants that go from a haploid to diploid phase and back to haploid through sporulation or have a prolonged gametophyte stage in which transcription of the essential gene is required for haploid stage or gamete viability. A chromosomal copy of the DNA sequence modifying enzyme and a recoded or sequence unrelated version of the rescue will be transmitted to only some progeny during sporulation. Those haploids that fail to inherit the rescue copy of the gene will die because the DNA sequence modifying enzyme, which is transmitted through cytoplasm, will cause alteration of the wildtype copy. The wildtype copy of the gene will likely also have been cleaved during the diploid stage in which case cytoplasmic inheritance of the nuclease is not essential. In any case, only haploids that inherit the tightly linked rescue construct, or rescue construct separated by some degree of linkage from that encoding the DNA sequence modifying enzyme, will survive. This constitutes a kind of gamete killing (FIG. 10). Most generally, the system described applies to any biological situation in which a DNA sequence modifying enzyme alters the sequence of an essential gene so as to disrupt essential functions in haploid, diploid or polyploid cells. This modification can occur in the parental cell, which can be haploid, diploid, tetraploid, or polyploid. Alternatively the DNA sequence modifying enzyme, the transcript and/or protein for which is produced in the parental cell, can alter the sequence of the essential gene in the progeny cells in which it becomes located through cytoplasmic diffusion or active transport. The operative principle in all cases is that in the relevant cell type, or in a multicellular organism, in some fraction of these cells, all or most copies of the endogenous copies of the essential gene are altered so as to produce non-functional copies of the gene. This results in death of all cells that fail to inherit one or more copies of the rescue transgene. The DNA sequence modifying enzyme and the rescue transgene are tightly linked and behave as a single genetic unit. As described herein, this same set of principles applies to two locus versions of ClvR. In such systems those cells inheriting the Rescue and any other associated cargo will survive, while those that do not (including those who inherit some or all components of the DNA sequence modifying enzyme) will die.

In some embodiments, the model is extrapolated to a diploid animal such as a rodent, mosquito, fish, amphibian, a plant or other organism in which spermatogenesis (pollen formation and/or function) utilizes haploid-specific promoters to drive the expression of genes essential for spermatogenesis (pollen formation/function). In some embodiments, the DNA sequence modifying enzyme is expressed in the germline at some point. It is not critical when, or in which sex. What matters is that ultimately one will end up with post-meiotic cells that carry a copy of the rescue transgene, while their post-meiotic brothers do not. To the extent that it is true that the product of the rescue transgene, which will have all the endogenous regulatory sequences of the endogenous gene, does not diffuse into the meiotic brothers to which they are still connected by cytoplasmic bridges, those sperm will die, be resorbed, or be ejaculated in a state that is non-functional. This will result in nuclease and rescue transgene-bearing meiotic products being preferentially represented in the next generation, a form of population replacement.

Figure 11:
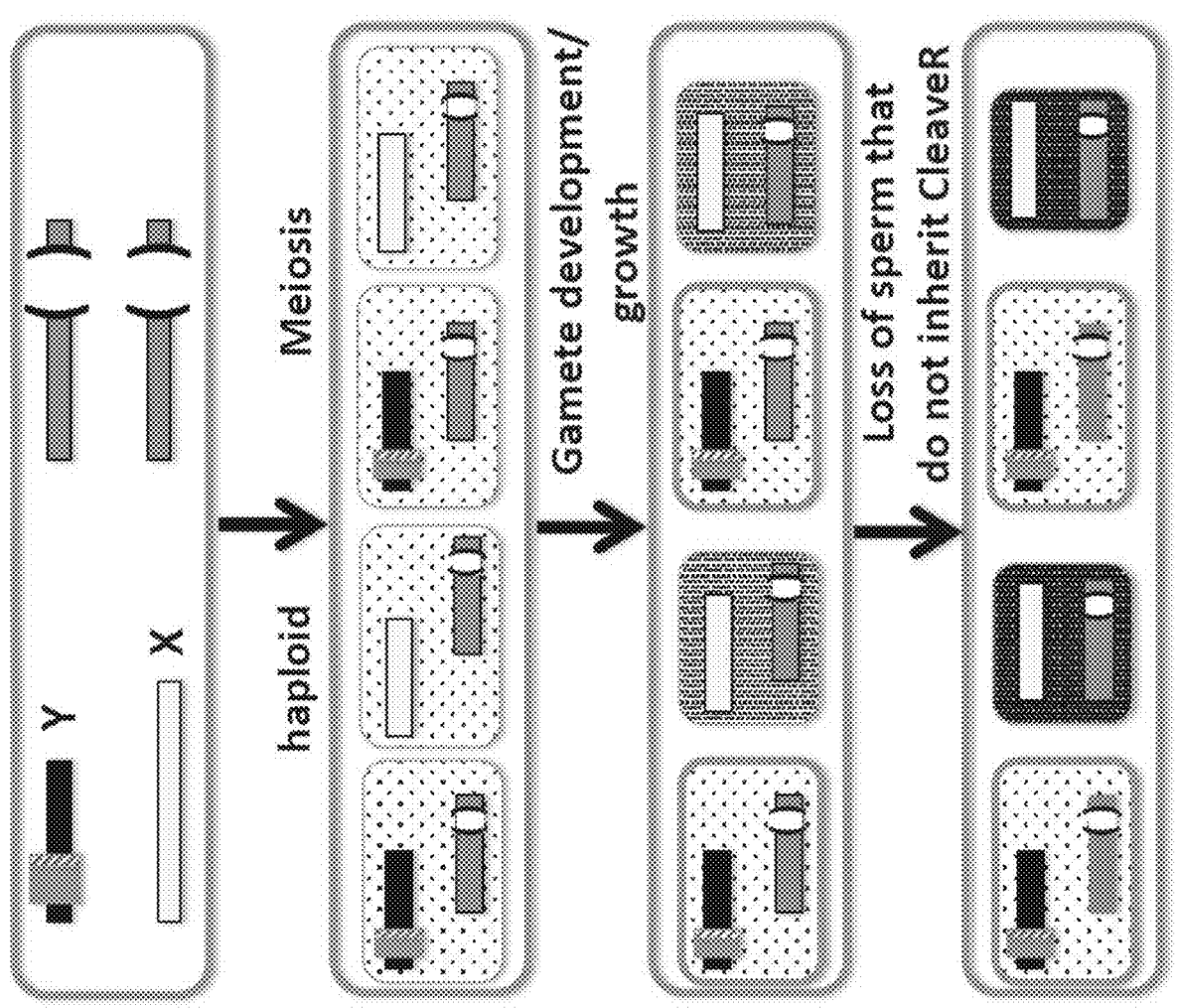
FIG. 11 shows a schematic of an embodiment of vector-mediated sex ratio distortion.

In some embodiments, a rescue version of a post-meiotic expressed gene that is normally present on an autosome can be expressed from the Y chromosome along with the DNA sequence modifying enzyme. Provided the DNA sequence modifying enzyme alters the wildtype endogenous copy of the gene in the germline then only Y-bearing sperm will generate this product. This holds even if the haplo-expressed gene is on the autosome (FIG. 11). In early generations there may be some reduced sex ratio bias if some wildtype copies are not cleaved, and depending on when in germline development the nuclease acts (before or after this generations post-meiotic expression). However, the bottom line is the same. Eventually, wildtype copies of the haplo-expressed gene are lost and the only remaining functional copies are those on the Y chromosome. This can result in sex ratio distortion if the sperm in which the gene has been inactivated are unable to carry out fertilization.

In some embodiments, the model is applicable to species with ZW sex chromosomes. W is the sex chromosome. Males are ZZ. A W chromosome that carries a rescue cassette and a nuclease. It is inherited only into females. Males that inherit the Z chromosome inherit a cleaved copy of an essential Z gene, or cleaved copies of an autosomal essential gene. In any case, ultimately a population in which there are only females is obtained because males do not inherit a rescue construct. Eggs that are genotypically male simply do not develop. A big male egg is still obtained because the actual embryo is quite small. However, viable individuals are not obtained. Ultimately females carrying the rescue construct and no wildtype copies of the gene are mated with wildtype males. Female progeny survive. Male progeny do not survive if there is maternal carryover that causes killing of the wildtype loci inherited from the male. If W-bearing females are mated with to wildtype males, which is what is done in a breeding or hybrid generation situation, the males will all die if the gene that is essential is normal on the Z and there is enough maternal carryover of the DNA sequence modifying enzyme to cause the wildtype copy of whatever chromosome carries the wildtype copy of the gene from males to undergo sequence modification such that males inherit no good copies of the essential gene.

In some embodiments, a vector is provided. In some embodiments, the vector comprises a first gene encoding a DNA sequence modifying enzyme, wherein the DNA modifying enzyme modifies an endogenous copy of an essential gene, a first promoter operably linked to the first gene encoding the DNA sequence modifying enzyme, a second gene encoding a rescue transgene, a second promoter operably linked to the rescue transgene, and optionally, one or more cargo sequences, wherein the vector is configured to be positioned in a chromosome or an extra-chromosomal element.

Figure 49A:
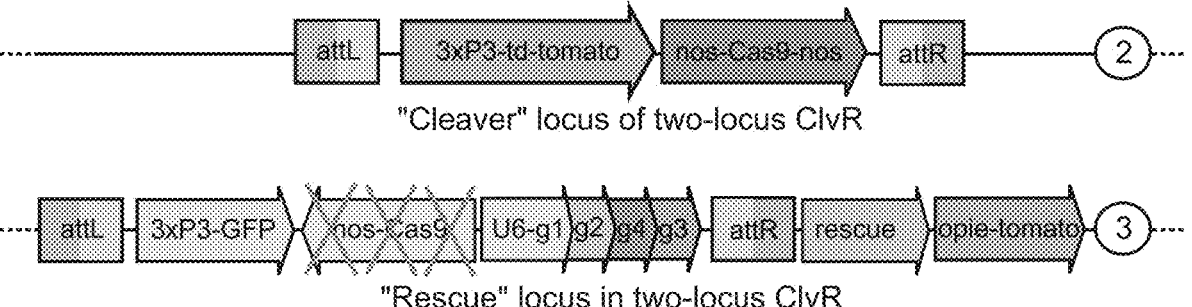
FIG. 49A shows schematic showing embodiments of the genetic constructs used to create two locus ClvR in *Drosophila*. On chromosome 2 (identified by the 2 in a circle), the Cleaver locus contains Cas9, whose expression is driven by the nanos promoter and the dominant marker td-tomato, all integrated using a site-specific recombination system (attL and attR). On chromosome 3 (identified by the 3 in a circle) the Rescue+ Cargo+gRNAs and their insertion site are derived from the single locus ClvR system described by Oberhofer et al., (2019). However, Cas9 activity has been eliminated (Xs).

In some embodiments two vectors are provided, with each vector containing distinct parts of the vector described in FIG. 20A and illustrated in FIG. 49A, in Example 40. In some embodiments the first vector comprises a first gene encoding a DNA sequence modifying enzyme, wherein the DNA sequence modifying enzyme modifies an endogenous copy of an essential gene, and a promoter is operably linked to the first gene encoding the DNA sequence modifying enzyme, wherein the vector is configured to be positioned in a chromosome or extra chromosomal element. In one embodiment the second vector encodes a rescue transgene, a second promoter operably linked to the rescue transgene, and optionally, one or more cargo sequences, wherein the vector is configured to be positioned in a chromosome or an extra-chromosomal element at some distance from the first vector encoding the DNA sequence modifying enzyme on the same chromosome or extra chromosomal element, or on a distinct chromosome or extra chromosomal element. Distance is defined in terms of probability of recombination between the two vectors during each replication cycle or generation, with 50 map units or greater (50% probability of recombination) being equivalent independent segregation.

In some embodiments two vectors are provided, with each vector containing distinct parts of the vector described in FIG. 20A. In some embodiments the first vector comprises a first gene encoding a first component of a DNA sequence modifying enzyme, wherein the complete DNA sequence modifying enzyme modifies an endogenous copy of an essential gene, and a promoter is operably linked to the first gene encoding first component of a DNA sequence modifying enzyme, wherein the vector is configured to be positioned in a chromosome or extra chromosomal element. In some embodiments the second vector encodes a second component of a DNA sequence modifying enzyme, a promoter operably linked to the second component, a rescue transgene, a second promoter operably linked to the rescue transgene, and optionally, one or more cargo sequences, wherein the vector is configured to be positioned in a chromosome or an extra-chromosomal element at some distance from the first vector encoding the first component of the DNA sequence modifying enzyme on the same chromosome or extra chromosomal element, or on a distinct chromosome or extra chromosomal element. Distance is defined in terms of probability of recombination between the two vectors during each replication cycle or generation, with 50 map units or greater (50% probability of recombination) being equivalent independent segregation. See FIGS. 20A-D and FIGS. 21A-C.

In some embodiments of the vector, the DNA sequence modifying enzyme is a nuclease, a base editor, or a Search and Replace Prime editor. In some embodiments of the vector, the nuclease cleaves and generates one or more double strand breaks in the endogenous copy of the essential gene. In some embodiments of the vector, the one or more double strand breaks are repaired to create an altered sequence of the essential gene. In some embodiments of the vector, the base editor creates one or more base changes in the endogenous copy of the essential gene to create an altered sequence of the essential gene. In some embodiments of the vector, the one or more base changes comprise one or more point mutations in the endogenous copy of the essential gene. In some embodiments of the vector, the Search and Replace Prime editor creates one or more base changes, or insertions, or deletions, in the endogenous copy of the essential gene to create an altered sequence of the essential gene.

In some embodiments of the vector, the rescue transgene is either a recoded copy of the essential gene or is a gene of unrelated sequence, wherein the rescue transgene encodes a protein that is functionally equivalent to a protein encoded by the essential gene, and wherein the DNA sequence modifying enzyme does not modify the rescue transgene.

In some embodiments of the vector, the chromosome is an autosome, X chromosome, Y chromosome, Z chromosome, W chromosome, or supernumerary chromosome. In some embodiments of the vector, the extra-chromosomal element is a plasmid or a virus.

In some embodiments of the vector, the one or more cargo sequences comprise one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments of the vector, the vector is positioned within a gene required for fertility or viability.

In some embodiments of the vector, the DNA sequence modifying enzyme is selected from the group consisting of Cas9, Cas-9-related RNA-guided nucleases, ZFN, TALEN, homing endonuclease, restriction enzymes, natural site-specific nucleases, engineered site-specific nucleases, base editing enzymes, transposase, Search and Replace Prime editing enzyme complex cytidine deaminase, and adenine deaminase.

In some embodiments, the vector further comprises one or more additional sequences, wherein the one or more additional sequences allow the vector to be positioned in the chromosome or the extra-chromosomal element. In some embodiments of the vector, the one or more additional sequences is selected from the group consisting of transposase binding site, LTRs, recombinase binding site, a sequence with homology to a desired location on the chromosome or the extra-chromosomal element.

In some embodiments of the vector, the first promoter is selected from the group consisting of a germline promoter, a male specific germline promoter, a female specific germline promoter, a cell-type specific promoter, a tissue-specific promoter, a ubiquitous promoter, a promoter activated at a specific stage of mitosis, and a promoter activated at a specific stage of meiosis.

In some embodiments of the vector, the double strand break is repaired by a mechanism selected from the group consisting of non-homologous end joining, microhomology-mediated end joining, and incomplete homologous recombination.

In some embodiments of the vector, the size of the one or more cargo sequences ranges from about 0.5 kb to about 500 kb.

In some embodiments of the vector, the nuclease comprises at least one nuclease domain and one or more DNA binding domains. In some embodiments of the vector, when the nuclease is Cas9 or a Cas9-related enzyme, the vector further comprise one or more genes encoding a guide RNA, wherein the guide RNA enables the nuclease to target specific sequences within the essential gene through Watson-Crick base pairing. In some embodiments of the vector, when the nuclease is Cas9, the nuclease domain of Cas9 is inactivated through one or more mutations, and the vector comprises a different nuclease domain. In some embodiments of the vector, the different nuclease domains is a single chain variant of FokI. In some embodiments of the vector, when the DNA binding domain is a TALE, the nuclease domain is provided as a single active nuclease domain, such as single chain variants of FokI.

In some embodiments of the vector, the Rescue and the Cargo transgenes are arranged such that the Cargo is located in an intron of the Rescue transgene (FIG. 22).

In some embodiments of the vector the cargo is located between two transgenes whose co-expression is required to create a functional Rescue protein (FIG. 23).

In some embodiments of the vector, the Rescue and the Cargo transgenes are arranged such that the Cargo is located between two transgenes, the presence of both of which is required for expression of a functional Rescue transgene (FIG. 24).

In some embodiments, a method of modifying a population by a vector is provided. In some embodiments, the method comprises obtaining an organism of the population, positioning one or more vectors, configured to be positioned in at least one chromosome or extra-chromosomal element in the organism, comprising a first gene encoding a DNA sequence modifying enzyme or first component thereof, wherein the DNA modifying enzyme modifies an endogenous copy of an essential gene, a first promoter operably linked to the first gene encoding the DNA sequence modifying enzyme or first component thereof, a second gene encoding a rescue transgene, a second promoter operably linked to the rescue transgene, optionally a third promoter operably linked to second component of the DNA sequence modifying enzyme, and optionally, one or more cargo sequences, expressing the DNA sequence modifying enzyme in the organism, inducing one or more sequence modifications in the essential gene in one or more cells in the organism, such that the one or more sequence modifications result in the essential gene being rendered partially or wholly non-functional and result in a defect in survival, growth control, fertility, or differentiation of the one or more cells if the one or more cells lack the rescue transgene, rescuing the defects in survival, growth control, or differentiation of the one or more cells in which the essential gene has been rendered partially or wholly non-functional, by the rescue transgene, generating an altered organism, wherein the altered organism carries one or more copies of the vector, and wherein the defects in survival, growth control, or differentiation of the one or more cells in which the essential gene has been rendered partially or wholly non-functional have been rescued by the rescue transgene, introducing the altered organism in an environment wherein an increase in a frequency of the altered organism is desired relative to a frequency of a wild type organism in the population; replacing the wild type organism with the altered organism in the population in the environment wherein the altered organism is introduced, thereby modifying the population.

In some embodiments of the method, an organism with the defect in survival, growth control, fertility, or differentiation of the one or more cells is eliminated if the one or more cells of the organism lack the rescue transgene.

In some embodiments of the method, the DNA sequence modifying enzyme does not modify the rescue transgene.

In some embodiments of the method, rescuing the defects in survival, growth control, or differentiation is achieved by restoring normal survival, growth control, fertility, or differentiation of the one or more cells by the rescue transgene.

In some embodiments of the method, the one or more cells comprise prokaryotic cells, somatic cells, germline cells, gametes, or a combination thereof.

In some embodiments of the method, the DNA sequence modifying enzyme is a nuclease, a base editor, or a Search and Replace Prime editor. In some embodiments of the method, the nuclease cleaves and generates one or more double strand breaks in the endogenous copy of the essential gene.

In some embodiments of the method, the one or more double strand breaks are repaired to create an altered sequence comprising insertions, deletions, base alterations, or a combination thereof.

In some embodiments of the method, the one or more double strand breaks are repaired to create an altered sequence using a previously cleaved and altered uncleavable sequence on a homologous chromosome as a template for repair mediated by homologous recombination (FIG. 6).

In some embodiments of the method, the base editor creates one or more base changes or small insertions/ deletions in the endogenous copy of the essential gene. In some embodiments of the method, the one or more base changes comprise one or more point mutations, or deaminated bases that are replaced with nucleotides of a different sequence.

In some embodiments of the vector, the Search and Replace Prime editor creates one or more base changes, or insertions, or deletions, in the endogenous copy of the essential gene to create an altered sequence of the essential gene.

In some embodiments of the method, the altered organism is heterozygous or homozygous for one or more of the vectors. In some embodiments of the method, the organism is haploid, diploid, or polyploid. In some embodiments of the method, the organism is selected from the group consisting of prokaryotes, fungi, plants, and animals, In some embodiments of the method, the environment comprises an open environment, a bioreactor, a multicellular body, or a colony of individual cells.

In some embodiments of the method, the wild type organism is replaced at a high frequency with the altered organism carrying one or more of the vectors in the environment wherein the wild type organism is present. In some embodiments of the method, the high frequency is defined as replacement of at least 90% of the wild type organism with the altered organism after 100 generations in the population. In some embodiments of the method, the wild type organism is replaced at a rapid rate with the altered organism in the environment wherein the wild type organism is present. In some embodiments of the method, the rapid rate is defined as replacement of at least 90% of the wild type organisms by organisms carrying the vector in the population after at most 100 generations.

Figure 9A:
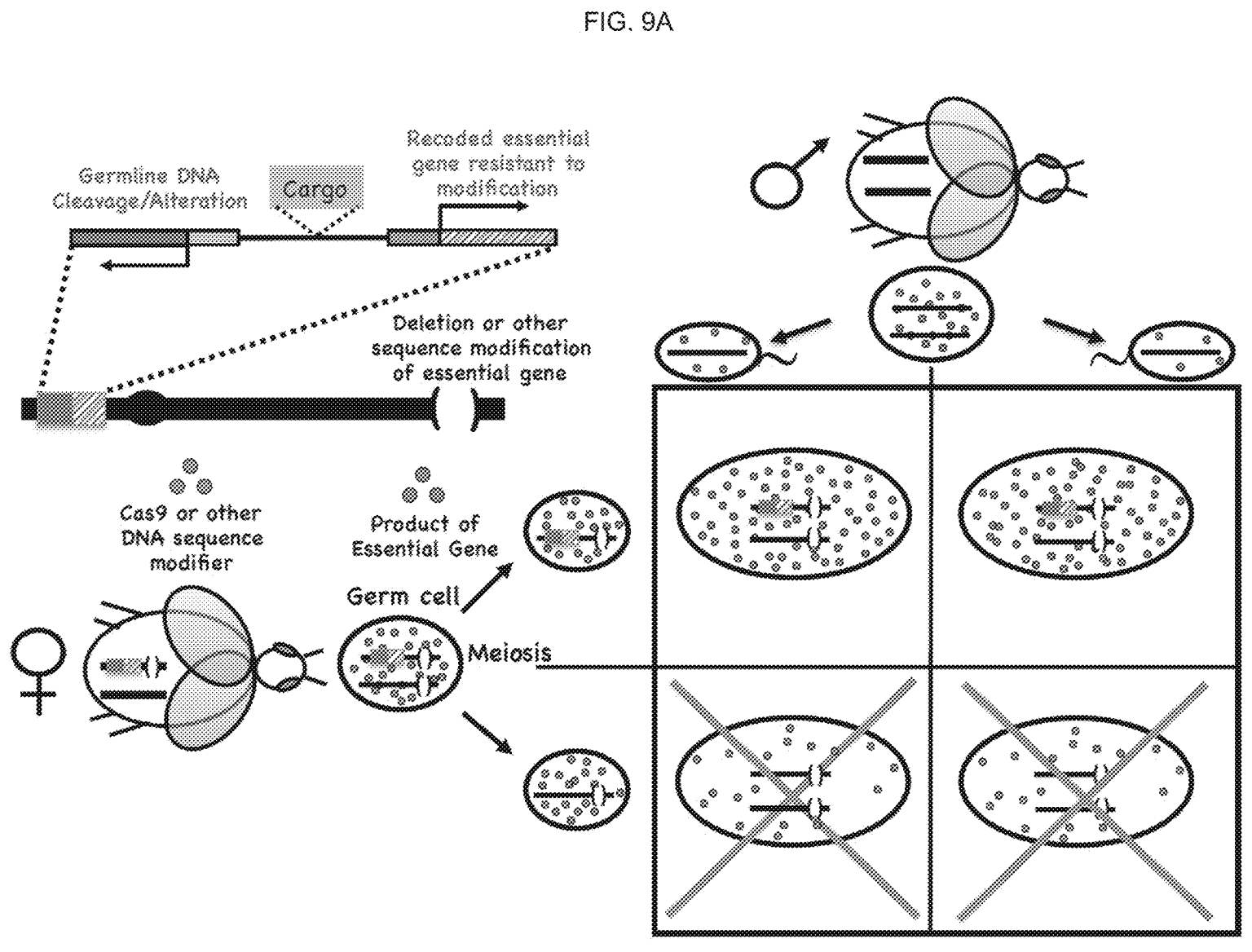

In some embodiments of the method, the one or more sequence modifications in the one or more cells is a result of the one or more cells carrying the first gene encoding the DNA sequence modifying enzyme or is a result of the DNA sequence modifying enzyme being transmitted to the one or more cells from one or more cells expressing the DNA sequence modifying enzyme through diffusion, active transport, or movement of the DNA sequence modifying enzyme from a cell that expresses the DNA sequence modifying enzyme to a cell that does not express the DNA sequence modifying enzyme. (FIG. 6, 7; FIG. 9A; FIG. 10, 11; FIG. 26, FIG. 43.

In some embodiments of the method, one or more of the vectors is positioned on the chromosome or the extra-chromosomal element by a homologous recombination-dependent integration. In some embodiments of the method, one or more of the vectors is positioned on the chromosome or extra-chromosomal element by random integration, integration using transposition, integration using a recombinase, or a combination thereof.

In some embodiments of the method, the one or more cargo sequences comprise one or more foreign gene sequences, or one or more alleles of an endogenous chromosomal or extra-chromosomal gene to which the vector has been linked through nearby insertion on the chromosome or extra-chromosomal element that carries the endogenous allele of interest.

In some embodiments of the method, the vector is positioned on the chromosome or the extra-chromosomal element, the first gene operably linked to the first promoter, the second gene operably linked to the second promoter, and the one or more cargo transgenes are genetically linked.

In some embodiments of the method, the nuclease cleaves and generates one or more double strand breaks in the endogenous copy of the essential gene with high cleavage efficiency. In some embodiments of the method, the high cleavage frequency is defined as the nuclease cleaving the endogenous copy of the essential gene in at least 30% of the organisms carrying the vector and the endogenous copy of the essential gene in each generation. In some embodiments of the method, the base editor creates one or more base changes in the endogenous copy of the essential gene with a high base editing frequency. In some embodiments of the method, the high base editing frequency is defined as the base editor modifying the endogenous copy of the essential gene in at least 20% of the organisms carrying the vector and the endogenous copy of the essential gene in each generation.

Additional Embodiments

In some embodiments of a two locus ClvR wherein the Rescue, Cargo and gRNAs are located on the third chromosome, Cas9 is located on the second chromosome, and the locus being targeted by Cas9 and gRNAs for cleavage is the tko locus, located on the X chromosome (Example 40; FIG. 20D; FIGS. 35A-35F).

In some embodiments, the construct for the "Cleaver" element comprises Cas9 under the control of nanos regulatory elements (promoter and UTRs), a 3xP3-td-tomato dominant marker gene, and an attB site to facilitate site-specific integration into the fly genome. This construct along with a phiC31 integrase helper plasmid can be injected into a fly stock that has an attP site at 59D3 on chromosome 2. Successful integration of Cas9 into the second chromosome can be identified by the expression of tdTomato in the eyes of the flies (Example 40).

In some embodiments, the "Rescue" element of two-locus ClvR (Cargo, Rescue and gRNAs) can be created by modifying the single-locus version of ClvR$^{tko}$ from Oberhofer et al., 2019. This can be achieved by injecting Cas9/gRNA RNP-complexes into ClvR$^{tko}$ flies. The Cas9/gRNA RNP-complexes targeted the Cas9 reading frame of ClvR$^{tko}$ to create mutations within and abolish Cas9 function at that site. Flies carrying both the second and third chromosome constructs can be made doubly homozygous and kept as a stock (Example 40; FIG. 49A).

In some embodiments of gene drive experiments (Example 40), males homozygous for the second and third chromosome constructs can be mated with wildtype females (Example 40). At the same time wildtype males can be mated with wildtype females. Mated females at a ratio of 2:1 (mated with transgenic: mated with wildtype) can be then introduced into four bottles and allowed to lay eggs for several days. Adults can be then removed and progeny allowed to develop to adulthood. After three days of mating among this adult population, adults can be scored for the presence or absence of markers that identify the transgene-bearing third chromosome and the transgene-bearing second chromosome, using a fluorescence microscope. Adults can be then transferred to fresh bottles for three days, removed and the process repeated for a number of generations.

In some embodiments, counts of the proportion of individuals carrying the two transgenic components (Cas9 and/or Rescue+ Cargo) can be plotted for each generation. A subset of the different transgene-bearing and non-transgene-bearing genotypes can be observed over time. In some embodiments, the frequency of Rescue+ Cargo+gRNA-bearing genotypes increases over time, while the frequency of Cas9-bearing genotypes decreases. Whenever Cas9 and Rescue+ Cargo+gRNA are found in the same individual, cleavage at the tko locus occurs. Progeny that inherit the Rescue+ Cargo+gRNAs always survive because they carry at least one copy of the Rescue transgene. Individuals that inherit Cas9 but not the Rescue transgene may die if the transgene is in an individual that lack a functional copy of tko, resulting in a decrease in Cas9 frequency in the population over the generations.

In some embodiments, linkage is important in terms of thinking about the ability of ClvR to spread beyond a target area. In some embodiments, by titrating the degree of linkage between the two locus components one can titrate the extent of ClvR spread in space. In some embodiments, this can be appreciated by considering first the case of completely linked loci, single locus ClvR. In this case drive is always present. However, in some embodiments, when different degrees of linkage are present the two components of the system dissociate from each other specific kinetics. The important point is that regardless of the degree of linkage, as two locus ClvR spreads in space, drive will decrease as Cas9 segregates away from the Rescue-bearing components. In some embodiments, it will segregate slowly when recombination distances are low (e.g., 12.5 m.u.), and more rapidly when recombination distances are higher. In any case other than complete linkage, in some embodiments, segregation of Cas9 from Rescue-bearing constructs will ultimately result in loss of drive. In this way, in some embodiments, any degree of linkage makes two locus ClvR ultimately a self-limiting drive system with respect to spread in space. In some embodiments, two locus Clvr can spread to genotype fixation in a constrained area in which all the wildtype copies of the essential gene have been lost (genetic addiction) (as in FIG. 50, 12.5% recombination). But, in some embodiments, when spread in space is not constrained, the ultimate loss of Cas9 through segregation and loss in dead individuals who lack functional copies of the essential gene results in loss of drive potential.

TABLE 0.1

| Sequence description | Origin/Source | SEQ ID NO: |
|---|---|---|
| rescue (FIG. 17)) | artifiicial | 44 |
| Dm-tko (FIG. 17)) | drosophila and artificial | 45 |
| PAM (FIG. 19) | artificial | 46 |
| gRNA1 (FIG. 19) | artificial | 47 |
| reference (FIG. 19) | wildtype sequence database | 48 |
| w[1118] control (FIG. 19) | widltype sequence for this strain | 49 |
| ♂X/Y;;ClvR$^{tko}$ offspring from ♀ClvRtko/+ XX ♂w[1118] | mutant sequence after cleavage | 50 |
| | mutant sequence after cleavage | 51 |
| | mutant sequence after cleavage | 52 |
| | mutant sequence after cleavage | 53 |
| | mutant sequence after cleavage | 54 |

TABLE 0.1-continued

Figures 39A, 39B, 39C, 39D, 39E:
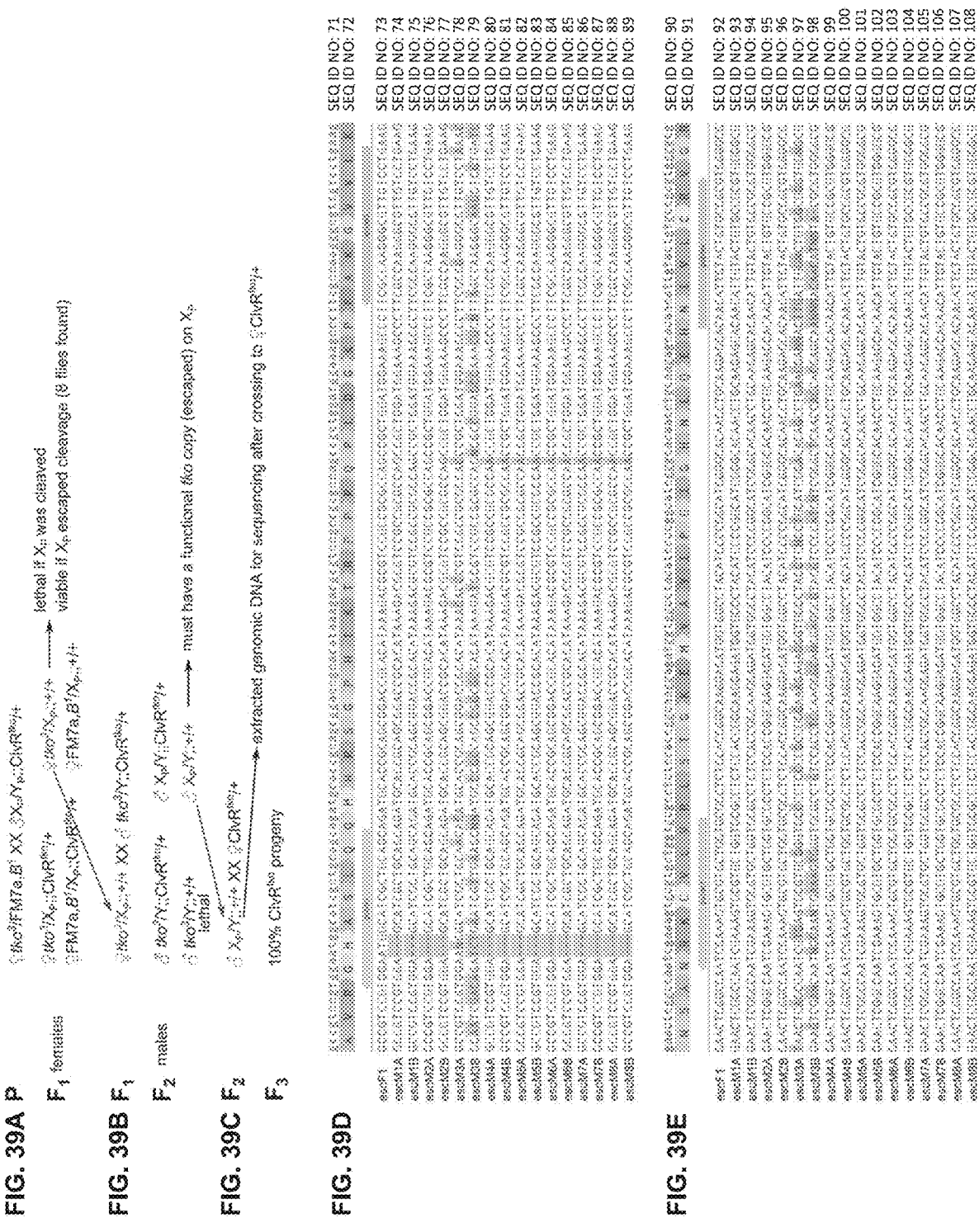
FIG. 39A-FIG. 39C show embodiments of Mating scheme to isolate X chromosomes in which the *D. melanogaster* tko locus was not rendered non-functional (escapers) in the germline of male parents heterozygous for ClvR$^{tko}$.
FIG. 39D-FIG. 39E shows embodiments of sequencing alignments to target sites 1,2 (FIG. 39D) and 3,4 (FIG. 39E). Escaper "escF1" from bottle 2 of female ClvR$^{tko}$/+XX w$^{1118}$ (see TABLE 4). Escapers M1-M3 from bottle 1, M4-M8 from bottle 2 of male ClvR$^{tko}$ XX tko$^3$/FM7,B$^1$ (see TABLE 5). Male escapers from bottle 2 have a common SNP (G to A between gRNA1 and gRNA2) not present in escapers from bottle 1. Thus, it is possible that the 8 isolates from males represent multiple isolates of two or more germline events. Note that the large number of sequence polymorphisms in escM3A and escM3B reflects ambiguous sequencing signal at a variety of positions. The basis for this remains unclear. Without being limited by any particular theory, it is speculated that this reflects nuclear mosaicism, which could occur if the F1 ClvR$^{tko}$-bearing males provided some level of paternal carryover that altered the tko locus from the Xp chromosome in some nuclei of the F2 males used for sequencing and crosses to the ClvR$^{tko}$-bearing female.

| Sequence description | Origin/Source | SEQ ID NO: |
|---|---|---|
| | mutant sequence after cleavage | 55 |
| | mutant sequence after cleavage | 56 |
| | mutant sequence after cleavage | 57 |
| | mutant sequence after cleavage | 58 |
| | mutant sequence after cleavage | 59 |
| | mutant sequence after cleavage | 60 |
| | mutant sequence after cleavage | 61 |
| | mutant sequence after cleavage | 62 |
| | mutant sequence after cleavage | 63 |
| | mutant sequence after cleavage | 64 |
| | mutant sequence after cleavage | 65 |
| | mutant sequence after cleavage | 66 |
| | mutant sequence after cleavage | 67 |
| Dvir-Tko-aa (FIG. 37) | virilis tko sequence | 68 |
| Dm-Tko-aa-C (FIG. 37) | melanog aster tko sequence variant | 69 |
| Dm-Tko-aa-B (FIG. 37) | melanog aster tko seuqence variant | 70 |
| FIG. 39D | mutant sequences in tko after cleavage | 71 |
| FIG. 39D | mutant sequences in tko after cleavage | 72 |
| escF1 (FIG. 39D) | mutant sequences in tko after cleavage | 73 |
| escM1A (FIG. 39D) | mutant sequences in tko after cleavage | 74 |
| escM1B (FIG. 39D) | mutant sequences in tko after cleavage | 75 |
| escM2A (FIG. 39D) | mutant sequences in tko after cleavage | 76 |
| escM2B (FIG. 39D) | mutant sequences in tko after cleavage | 77 |
| escM3A (FIG. 39D) | mutant sequences in tko after cleavage | 78 |
| escM3B (FIG. 39D) | mutant sequences in tko after cleavage | 79 |
| escM4A (FIG. 39D) | mutant sequences in tko after cleavage | 80 |
| escM4B (FIG. 39D) | mutant sequences in tko after cleavage | 81 |
| escM5A (FIG. 39D) | mutant sequences in tko after cleavage | 82 |
| escM5B (FIG. 39D) | mutant sequences in tko after cleavage | 83 |
| escM6A (FIG. 39D) | mutant sequences in tko after cleavage | 84 |
| escM6B (FIG. 39D) | mutant sequences in tko after cleavage | 85 |
| escM7A (FIG. 39D) | mutant sequences in tko after cleavage | 86 |
| escM7B (FIG. 39D) | mutant sequences in tko after cleavage | 87 |
| escM8A (FIG. 39D) | mutant sequences in tko after cleavage | 88 |
| escM8B (FIG. 39D) | mutant sequences in tko after cleavage | 89 |
| FIG. 39E | mutant sequences in tko after cleavage | 90 |
| FIG. 39E | mutant sequences in tko after cleavage | 91 |
| escF1 (FIG. 39E) | mutant sequences in tko after cleavage | 92 |
| escM1A (FIG. 39E) | mutant sequences in tko after cleavage | 93 |
| escM1B (FIG. 39E) | mutant sequences in tko after cleavage | 94 |
| escM2A (FIG. 39E) | mutant sequences in tko after cleavage | 95 |
| escM2B (FIG. 39E) | mutant sequences in tko after cleavage | 96 |
| escM3A (FIG. 39E) | mutant sequences in tko after cleavage | 97 |
| escM3B (FIG. 39E) | mutant sequences in tko after cleavage | 98 |
| escM4A (FIG. 39E) | mutant sequences in tko after cleavage | 99 |

TABLE 0.1-continued

Figures 40A, 40B, 40C, 40D:
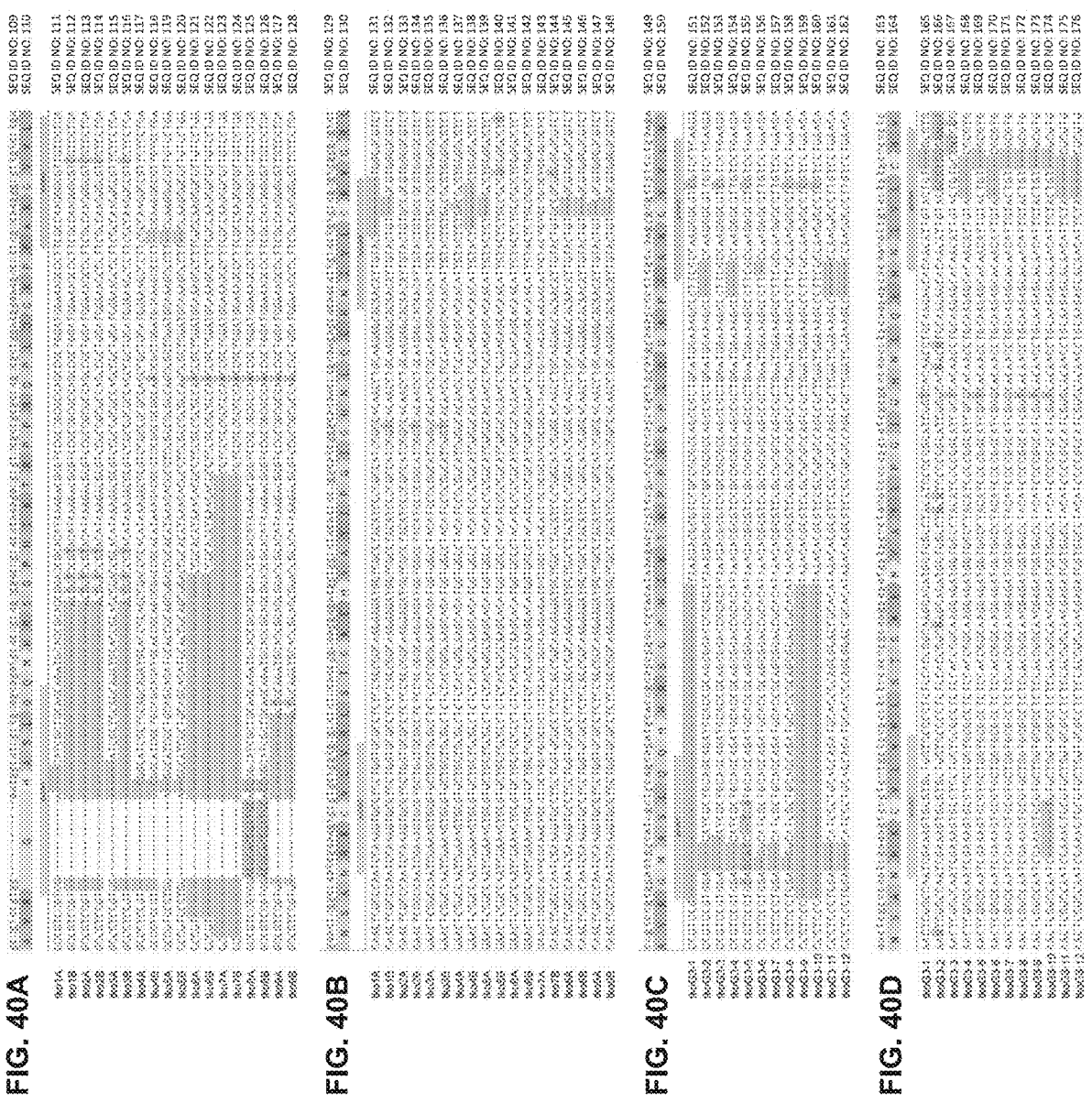
FIG. 40A-FIG. 40D show embodiments of molecular analysis of cleavage events that result in LOF of *Drosophila melanogaster* tko. Shown are the alignments of the tko locus of male progeny coming from ClvR$^{tko}$/+ mothers (two flies selected from 9 crosses, tko1A, tko1B, . . . tko9B) (FIG. 40A & FIG. 40B) or from a homozygous stock inbred for 3 generations (12 flies selected from bottles, tkoG3-1 to tkoG3-12) (FIG. 40C & FIG. 40D). Alignments were split for ease of visibility. gRNA1 and gRNA2 target sites are show in FIG. 40A and FIG. 40C, and gRNA3 and gRNA4 target sites in FIG. 40B and FIG. 40D. Top row shows the template with annotated gRNA target sites and amino acid sequence. Mismatches in the alignments are shown.

| Sequence description | Origin/Source | SEQ ID NO: |
|---|---|---|
| escM4B (FIG. 39E) | mutant sequences in tko after cleavage | 100 |
| escM5A (FIG. 39E) | mutant sequences in tko after cleavage | 101 |
| escM5B (FIG. 39E) | mutant sequences in tko after cleavage | 102 |
| escM6A (FIG. 39E) | mutant sequences in tko after cleavage | 103 |
| escM6B (FIG. 39E) | mutant sequences in tko after cleavage | 104 |
| escM7A (FIG. 39E) | mutant sequences in tko after cleavage | 105 |
| escM7B (FIG. 39E) | mutant sequences in tko after cleavage | 106 |
| escM8A (FIG. 39E) | mutant sequences in tko after cleavage | 107 |
| escM8B (FIG. 39E) | mutant sequences in tko after cleavage | 108 |
| FIG. 40A | mutant sequences in tko after cleavage | 109 |
| FIG. 40A | mutant sequences in tko after cleavage | 110 |
| tko1A (FIG. 40A) | mutant sequences in tko after cleavage | 111 |
| tko1B (FIG. 40A) | mutant sequences in tko after cleavage | 112 |
| tko2A (FIG. 40A) | mutant sequences in tko after cleavage | 113 |
| tko2B (FIG. 40A) | mutant sequences in tko after cleavage | 114 |
| tko3A (FIG. 40A) | mutant sequences in tko after cleavage | 115 |
| tko3B (FIG. 40A) | mutant sequences in tko after cleavage | 116 |
| tko4A (FIG. 40A) | mutant sequences in tko after cleavage | 117 |
| tko4B (FIG. 40A) | mutant sequences in tko after cleavage | 118 |
| tko5A (FIG. 40A) | mutant sequences in tko after cleavage | 119 |
| tko5B (FIG. 40A) | mutant sequences in tko after cleavage | 120 |
| tko6A (FIG. 40A) | mutant sequences in tko after cleavage | 121 |
| tko6B (FIG. 40A) | mutant sequences in tko after cleavage | 122 |
| tko7A (FIG. 40A) | mutant sequences in tko after cleavage | 123 |
| tko7B (FIG. 40A) | mutant sequences in tko after cleavage | 124 |
| tko8A (FIG. 40A) | mutant sequences in tko after cleavage | 125 |
| tko8B (FIG. 40A) | mutant sequences in tko after cleavage | 126 |
| tko9A (FIG. 40A) | mutant sequences in tko after cleavage | 127 |
| tko9B (FIG. 40A) | mutant sequences in tko after cleavage | 128 |
| FIG. 40B | mutant sequences in tko after cleavage | 129 |
| FIG. 40B | mutant sequences in tko after cleavage | 130 |
| tko1A (FIG. 40B) | mutant sequences in tko after cleavage | 131 |
| tko1B (FIG. 40B) | mutant sequences in tko after cleavage | 132 |
| tko2A (FIG. 40B) | mutant sequences in tko after cleavage | 133 |
| tko2B (FIG. 40B) | mutant sequences in tko after cleavage | 134 |
| tko3A (FIG. 40B) | mutant sequences in tko after cleavage | 135 |
| tko3B (FIG. 40B) | mutant sequences in tko after cleavage | 136 |
| tko4A (FIG. 40B) | mutant sequences in tko after cleavage | 137 |

TABLE 0.1-continued

| Sequence description | Origin/Source | SEQ ID NO: |
|---|---|---|
| tko4B (FIG. 40B) | mutant sequences in tko after cleavage | 138 |
| tko5A (FIG. 40B) | mutant sequences in tko after cleavage | 139 |
| tko5B (FIG. 40B) | mutant sequences in tko after cleavage | 140 |
| tko6A (FIG. 40B) | mutant sequences in tko after cleavage | 141 |
| tko6B (FIG. 40B) | mutant sequences in tko after cleavage | 142 |
| tko7A (FIG. 40B) | mutant sequences in tko after cleavage | 143 |
| tko7B (FIG. 40B) | mutant sequences in tko after cleavage | 144 |
| tko8A (FIG. 40B) | mutant sequences in tko after cleavage | 145 |
| tko8B (FIG. 40B) | mutant sequences in tko after cleavage | 146 |
| tko9A (FIG. 40B) | mutant sequences in tko after cleavage | 147 |
| tko9B (FIG. 40B) | mutant sequences in tko after cleavage | 148 |
| FIG. 40C | mutant sequences in tko after cleavage | 149 |
| FIG. 40C | mutant sequences in tko after cleavage | 150 |
| tkoG3-1 (FIG. 40C) | mutant sequences in tko after cleavage | 151 |
| tkoG3-2 (FIG. 40C) | mutant sequences in tko after cleavage | 152 |
| tkoG3-3 (FIG. 40C) | mutant sequences in tko after cleavage | 153 |
| tkoG3-4 (FIG. 40C) | mutant sequences in tko after cleavage | 154 |
| tkoG3-5 (FIG. 40C) | mutant sequences in tko after cleavage | 155 |
| tkoG3-6 (FIG. 40C) | mutant sequences in tko after cleavage | 156 |
| tkoG3-7 (FIG. 40C) | mutant sequences in tko after cleavage | 157 |
| tkoG3-8 (FIG. 40C) | mutant sequences in tko after cleavage | 158 |
| tkoG3-9 (FIG. 40C) | mutant sequences in tko after cleavage | 159 |
| tkoG3-10 (FIG. 40C) | mutant sequences in tko after cleavage | 160 |
| tkoG3-11 (FIG. 40C) | mutant sequences in tko after cleavage | 161 |
| tkoG3-12 (FIG. 40C) | mutant sequences in tko after cleavage | 162 |
| FIG. 40D | mutant sequences in tko after cleavage | 163 |
| FIG. 40D | mutant sequences in tko after cleavage | 164 |
| tkoG3-1 (FIG. 40D) | mutant sequences in tko after cleavage | 165 |
| tkoG3-2 (FIG. 40D) | mutant sequences in tko after cleavage | 166 |
| tkoG3-3 (FIG. 40D) | mutant sequences in tko after cleavage | 167 |
| tkoG3-4 (FIG. 40D) | mutant sequences in tko after cleavage | 168 |
| tkoG3-5 (FIG. 40D) | mutant sequences in tko after cleavage | 169 |
| tkoG3-6 (FIG. 40D) | mutant sequences in tko after cleavage | 170 |
| tkoG3-7 (FIG. 40D) | mutant sequences in tko after cleavage | 171 |
| tkoG3-8 (FIG. 40D) | mutant sequences in tko after cleavage | 172 |
| tkoG3-9 (FIG. 40D) | mutant sequences in tko after cleavage | 173 |
| tkoG3-10 (FIG. 40D) | mutant sequences in tko after cleavage | 174 |
| tkoG3-11 (FIG. 40D) | mutant sequences in tko after cleavage | 175 |

TABLE 0.1-continued

| Sequence description | Origin/Source | SEQ ID NO: |
|---|---|---|
| tkoG3-12 (FIG. 40D) | mutant sequences in tko after cleavage | 176 |
| dribblev2 s2 (FIG. 44) | artificial sequence | 177 |
| dribblev2 s2 (FIG. 44) | articifial sequence | 178 |
| template sequence dribble-Dmel (FB) (FIG. 45) | D. melanogaster sequence | 179 |
| Aligned sequence dribble-Dsuz (swFB BLASTN of Dmel dribble) (FIG. 45) | D. suzukii sequence | 180 |
| template sequence aNeiihbornbh 5'U (FIG. 45) | D. melanogaster sequence | 181 |
| aligned sequence aNeiihborTRd1 TD5'1'm(FB)lsulrnbhlaNeiihbU (FIG. 45) | D. suzukii sequence | 182 |
| tf2a-step2 (FIG. 47) | artificial sequence | 183 |
| tf2a-step2 (FIG. 47) | artificial sequence | 184 |
| tko-step2 (FIG. 48) | artificial sequence | 185 |
| tko-step2 (FIG. 48) | artificial sequence | 186 |
| template sequence tfIIA-D genomic (FIG. 46) | D. melanogaster sequence | 187 |
| template sequence D-suzukii rescue (FIG. 46) | D. suzukii sequence | 188 |

EXAMPLES

Outlined in Examples 1-5 are the designs of five proposed single locus cleavage mediated gene drives. Discrete generation, deterministic population frequency models were developed for each of the five drive mechanisms that demonstrate the range of fitness costs and Cas9 cleavage efficiencies for which they will take over a wildtype population.

Example 1—X Chromosome Cleavage Mediated Y Chromosome Drive

X chromosome cleavage mediated Y chromosome Drive (also referred to herein as X cleavage mediated Y drive) consists of Cas9, gRNAs which target an essential (i.e. recessive lethal) gene on the X chromosome, and a recoded copy of this target X gene which is immune to gRNA targeting, which are situated together at the same locus on the Y chromosome (FIG. 1A). The transgenic construct (TY) is situated on the Y chromosome and consists of Cas9 (long rectangle), gRNAs (short rectangle) targeting an essential gene on the X chromosome, and a recoded version of the target gene (light rectangle with recoded gRNA target sites indicated as darker squares) (FIG. 1A). Potential cleavage sites on the target essential gene (X) are indicated by dashed lines and scissors, and the cleaved locus (C) is a null form of the target gene made of what remains of the gene from the outer ends of the cleavage sites (FIG. 1A).

Figure 1B:
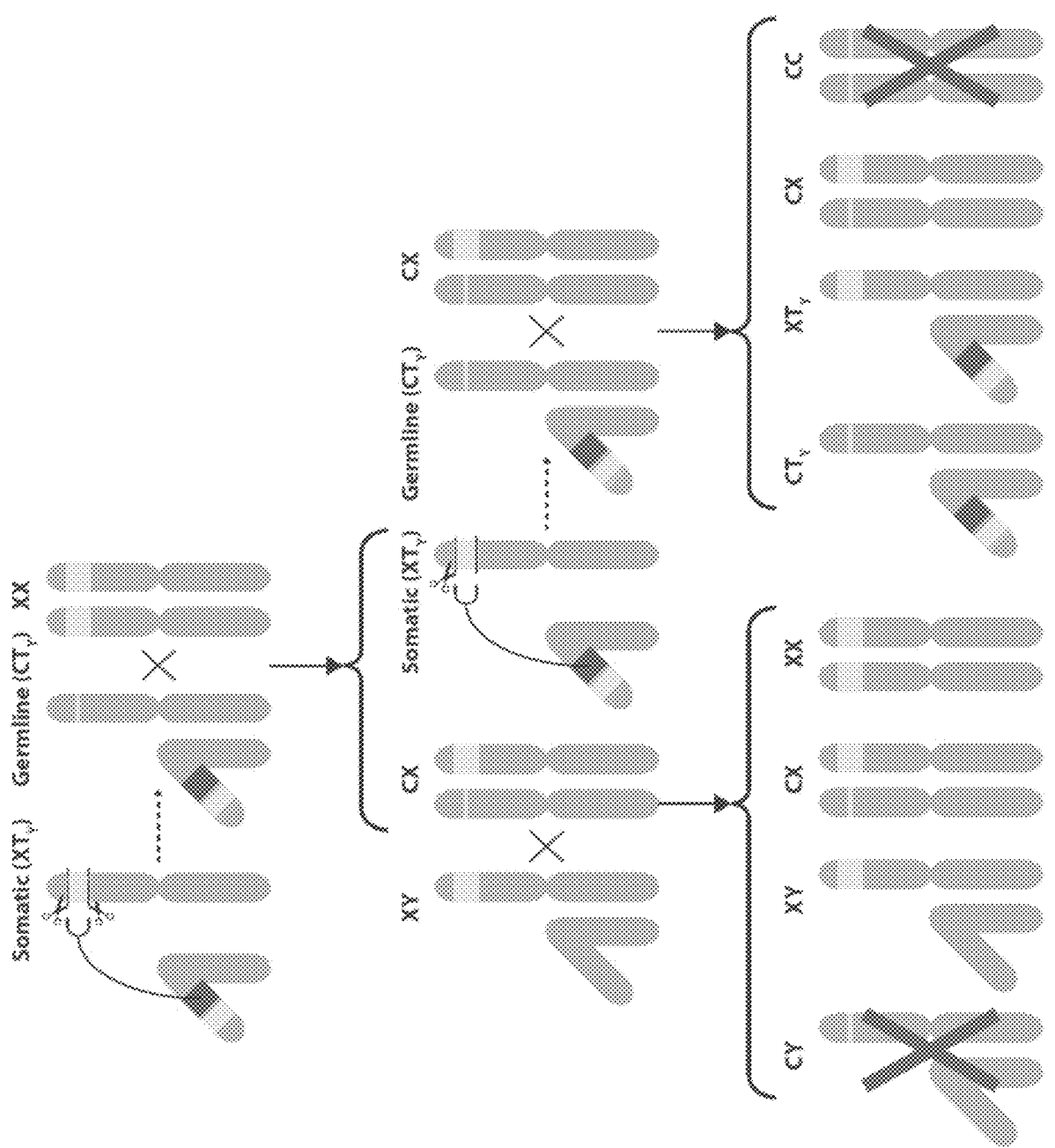

In males who carry this construct (TY) and a normal X chromosome (X), the target gene is cleaved multiple times during spermatogenesis, destroying the wild type copy of the gene on the X chromosome (C) and resulting in either TY or C bearing sperm (FIG. 1B). In transgenic males that bear wild type X chromosomes, Cas9 and Rescue (dark square and and light square with thin dark lines[representing recoding to gRNA resistance], respectively) can find and cleave a copy of the target gene (light square). The resulting cleaved locus (light thin bar) is passed on instead of the original target wildtype locus. When two individuals bearing a cleaved locus mate and the cleaved X loci are paired together (CC) or when the cleaved locus is passed on to a male (CY), the resulting offspring is unviable, removing wild type alleles are from the population (FIG. 1B) As TY males mate with wild type females, C's will begin to accumulate in heterozygotes (CX). All CY males and all CC females will die from the absence of a functional copy of the target essential X gene, leaving the viable genotypes CTY, XTY, XY, CX, and XX (FIG. 1B). Events proceed from left to right. The vector on the Y expresses a site-specific nuclease (dark square) and a rescue transgene (light square). The nuclease has the ability to cleave a wildtype version of the essential gene on the X at multiple positions (scissors). Cleavage does not necessarily happen in somatic cells. The left-most panel (X,Ty) simply indicates where cleavage occurs. Cleavage occurs in germline cells (CTy), resulting in the creation of an X chromosome that lacks a functional copy of the essential gene (thin light line). When a male carrying these chromosomes mates with a wildtype female new opportunities for cleavage of a wildtype X are created (second line). In the third generation matings are shown that result in the death of several genotypes.

Figure 1C:
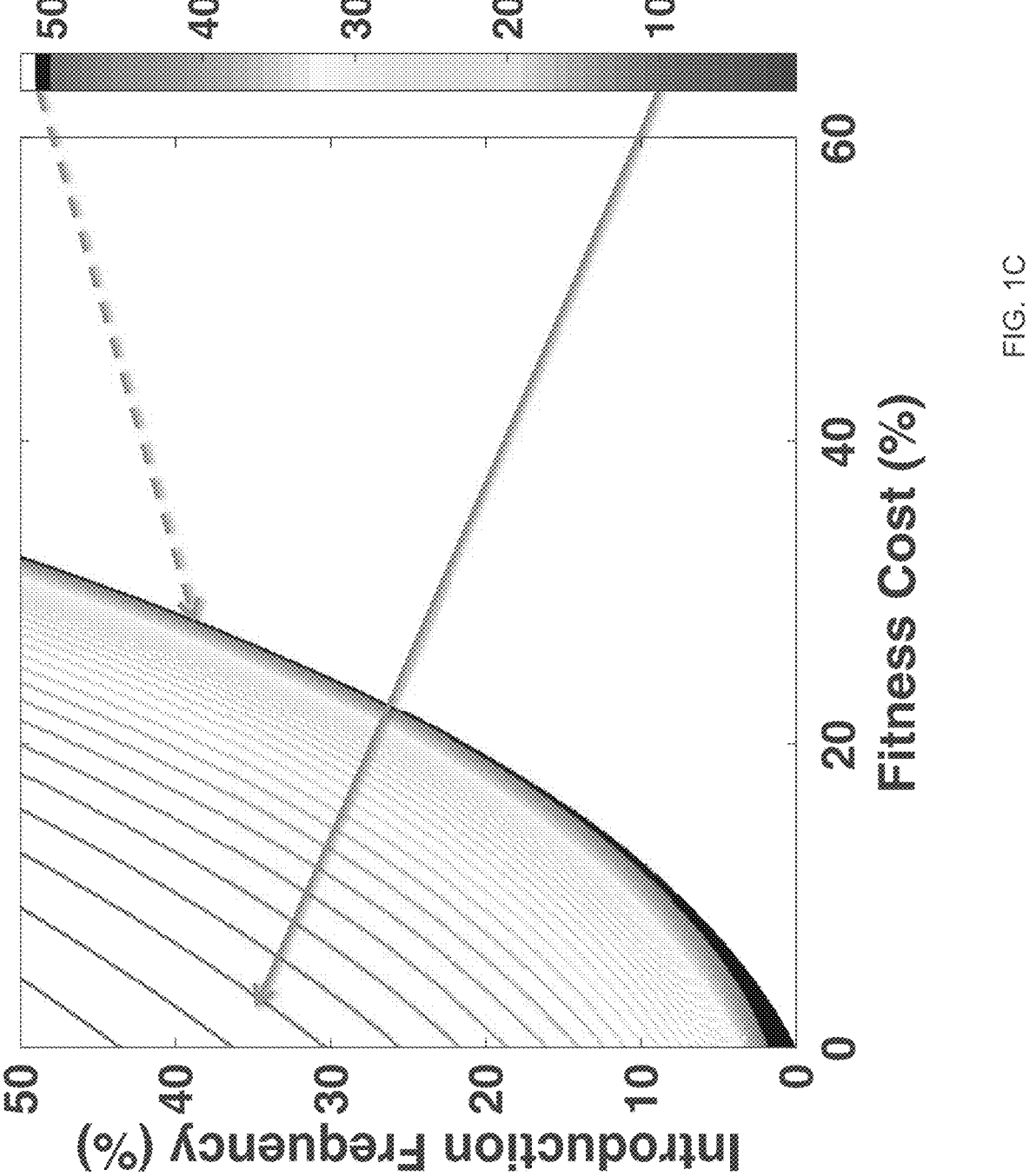

The discrete generation, deterministic population frequency model for this drive mechanism demonstrates that if Cas9 cleaves the target gene with 100% efficiency, TY can drive to fixation amongst Y chromosomes with just a few moderate releases of CTY males while bearing a fitness cost of up to approximately 45% (FIG. 1C). TY can still drive male replacement when Cas9 is cleaving at non-optimal rates, but it can only tolerate correspondingly reduced fitness costs as a result (FIG. 1C). Discrete generation, deterministic population frequency modeling of X cleavage mediated Y drive is shown in FIG. 1C. Each data point uses a few moderate releases of transgenic mosquitoes (three releases of CTY males at 50% of the population) with the specified fitness cost and Cas9 cleavage efficiency. The shade of each data point indicates the number of generations (as indicated by the bar on the right) before TY bearing individuals make up >99% of all males. White indicates the inability of TY to take over under the specified conditions or failure to do so within 70 generations (FIG. 1C).

The X CM Y drive is capable of quickly driving a transgene to fixation on the Y chromosome while bearing ~40% fitness costs at high cleavage efficiency. As males are the only transgenics, it cannot be used as a replacement mechanism for attacking mosquitoes because only the females are vectors. However, it can still be useful in the context of suppression if the cargo is a lethal gene under an environmentally triggered promoter. In this way, the transgene can spread to fixation in males, killing all males once the environmental trigger activates and resulting in a population crash. Alternatively, this construct can be used in ZW species where the female is the heterogametic sex, such as the pink bollworm.

Example 2—Cleavage Mediated X Drive

Figure 2A:
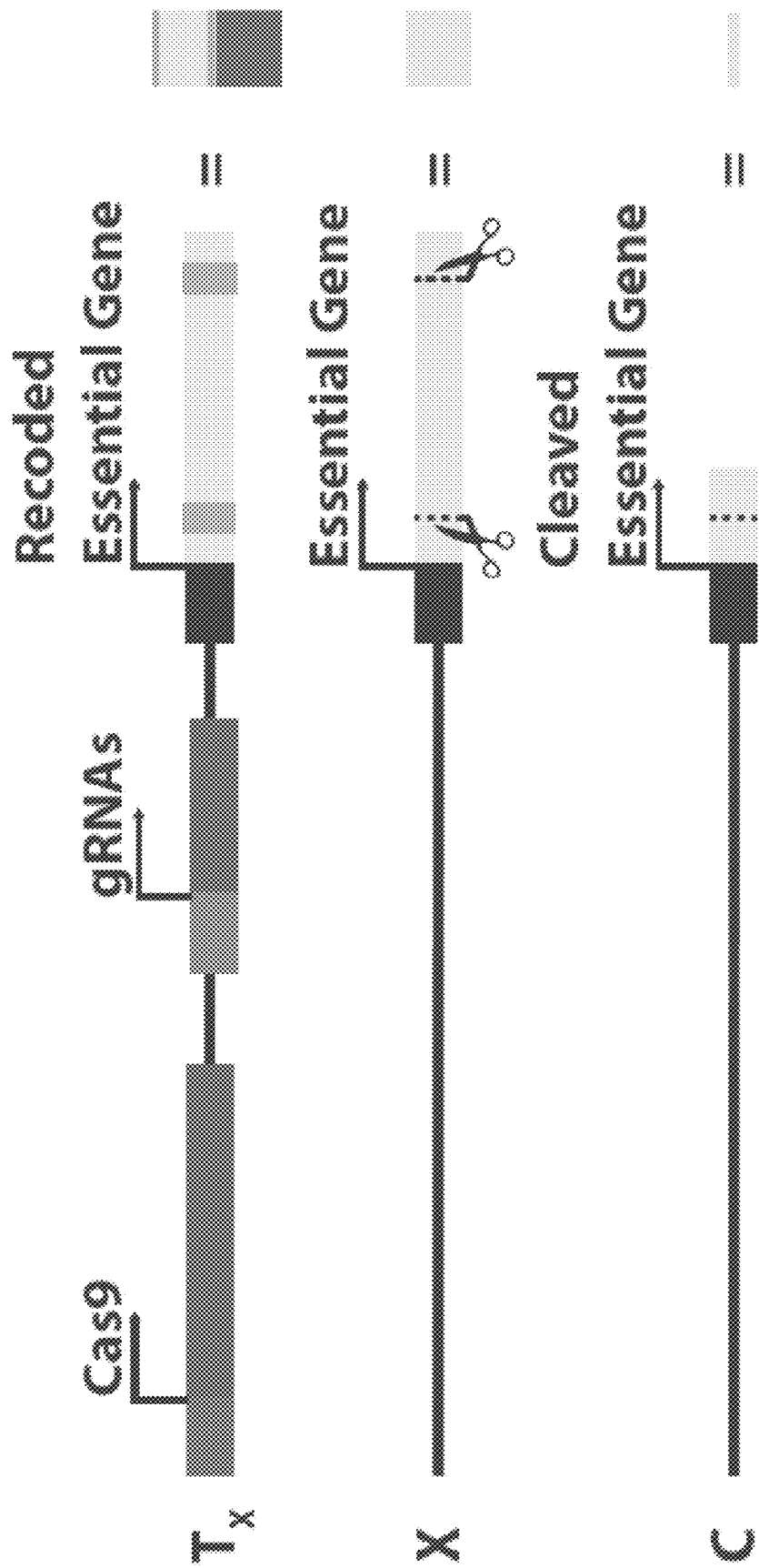
FIG. 2A-FIG. 2C show an embodiment of a cleavage mediated X drive with the vector also located on the X.

Cleavage mediated X drive consists of Cas9, gRNAs which target an essential gene on the X chromosome, and a recoded or sequence unrelated copy of this target X gene which is immune to gRNA targeting, which are situated together at the same locus as the target gene (FIG. 2A). Figure component labeling is as in Example 1. The transgenic construct (TX) is situated on the X chromosome and consists of Cas9, gRNAs targeting an essential gene on the X chromosome (at the same locus as TX), and a recoded version of the target gene (FIG. 2A). Potential cleavage sites on the target essential gene (X) are indicated by dashed lines and scissors, and the cleaved locus (C) is a null form of the target gene made of what remains of the gene from the outer ends of the cleavage sites (FIG. 2A).

Figure 2B:
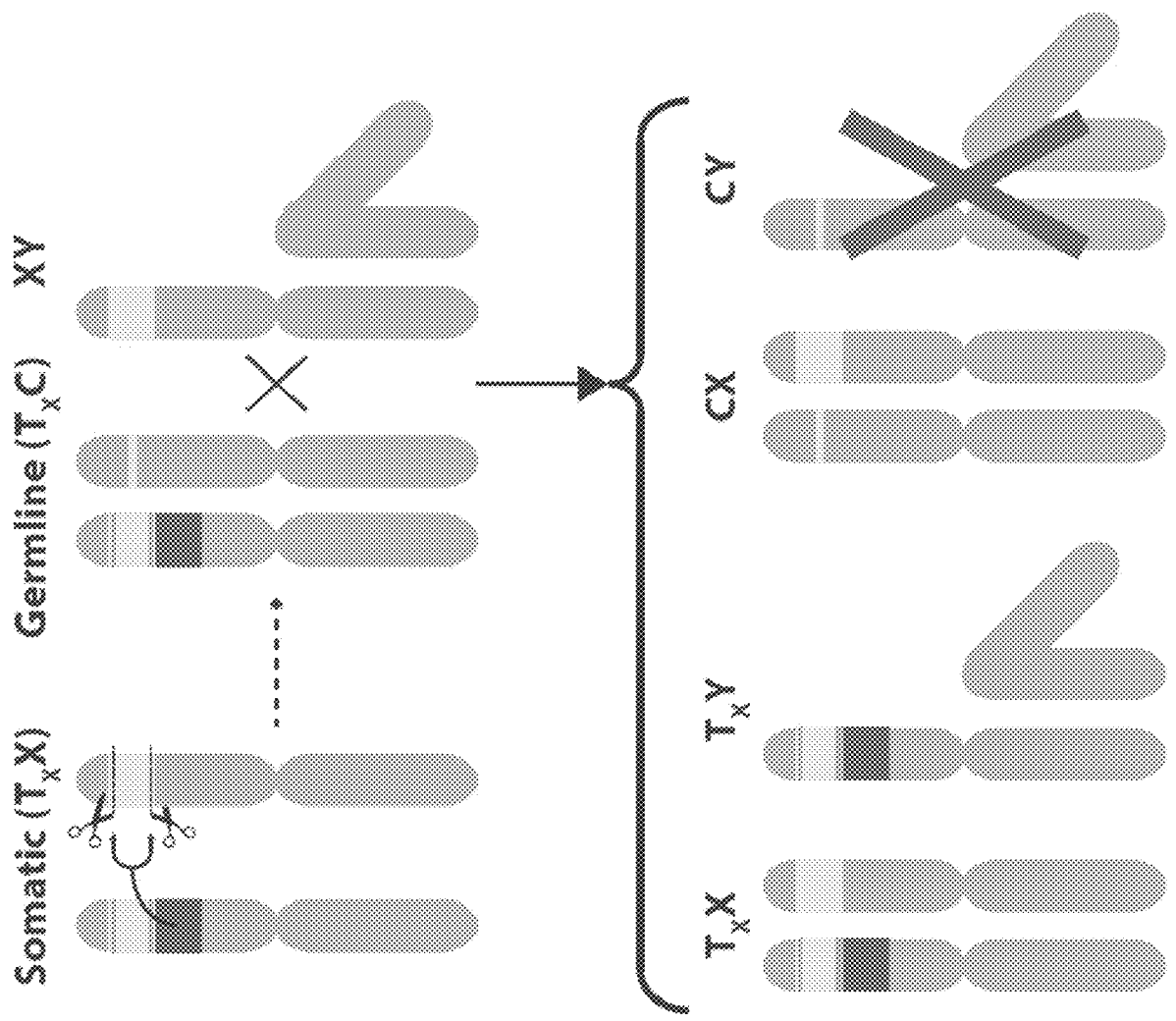

In females who carry this construct (TX) and a normal X chromosome (X), the target gene is cleaved multiple times during oogenesis, destroying the wild type copy of the gene on the X chromosome (C) and resulting in either TX or C bearing eggs (FIG. 2B). In transgenic females that bear wild type X chromosomes (TX X) Cas9 can find and cleave a copy of the target gene. The resulting cleaved locus is passed on instead of the original target wildtype locus. When the cleaved locus is passed on to a male (CY), the resulting offspring is unviable, removing a wild type allele are from the population (FIG. 2B). As transgenic individuals mate with wild types, cleaved copies of the essential X gene will begin to accumulate in females (CX). All males that receive a cleaved X chromosome (CY) will die from the absence of a functional copy of the target essential X, leaving the viable genotypes TXY, XY, TXTX, TXC, TXX, CX, and XX (FIG. 2B).

Figure 2C:
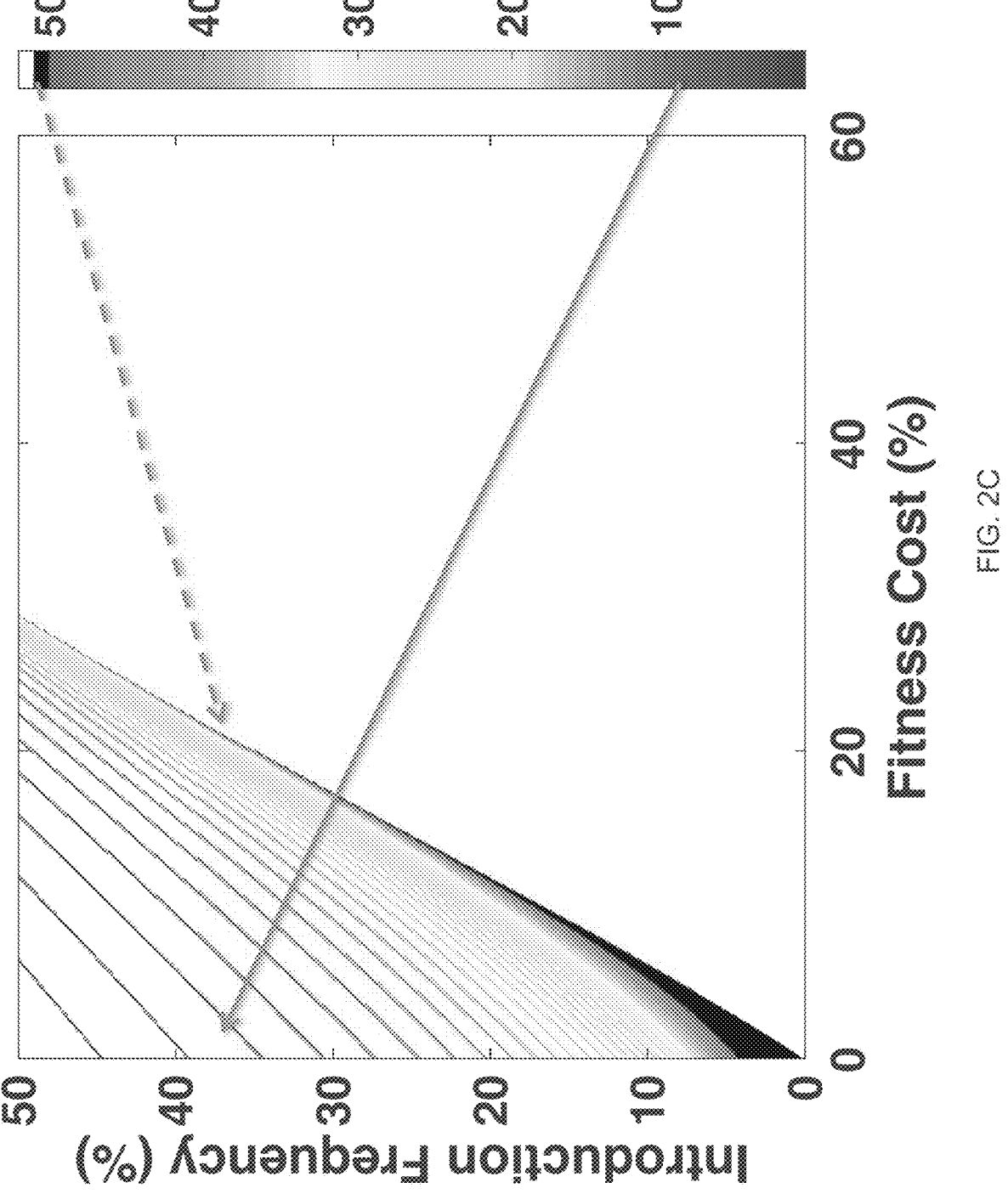

The discrete generation, deterministic population frequency model for this drive mechanism demonstrates that if Cas9 cleaves the target gene with 100% efficiency, TX can drive to fixation with just a few moderate releases of TXY males while bearing a fitness cost of up to approximately 35% (FIG. 2C). TX can still drive population replacement when Cas9 is cleaving at non-optimal rates, but it can only tolerate correspondingly reduced fitness costs as a result (FIG. 2C). Discrete generation, deterministic population frequency modeling of cleavage mediated X drive is shown in FIG. 2C. Each data point uses a few moderate releases of transgenic mosquitoes (three releases of TXY males at 50% of the population) with the specified fitness cost and Cas9 cleavage efficiency. The shade of each data point indicates the number of generations (as indicated by the bar on the right) before TX bearing individuals make up >99% of the population. White indicates the inability of TX to take over under the specified conditions or failure to do so within 70 generations (FIG. 2C).

The X drive can tolerate ~35% fitness costs at high cleavage efficiency. This drive is well suited to replacement in XY species of mosquitoes such as *Anopheles gambiae*.

Example 3—Autosomal Cleavage Mediated Autosomal Drive

Figure 3A:
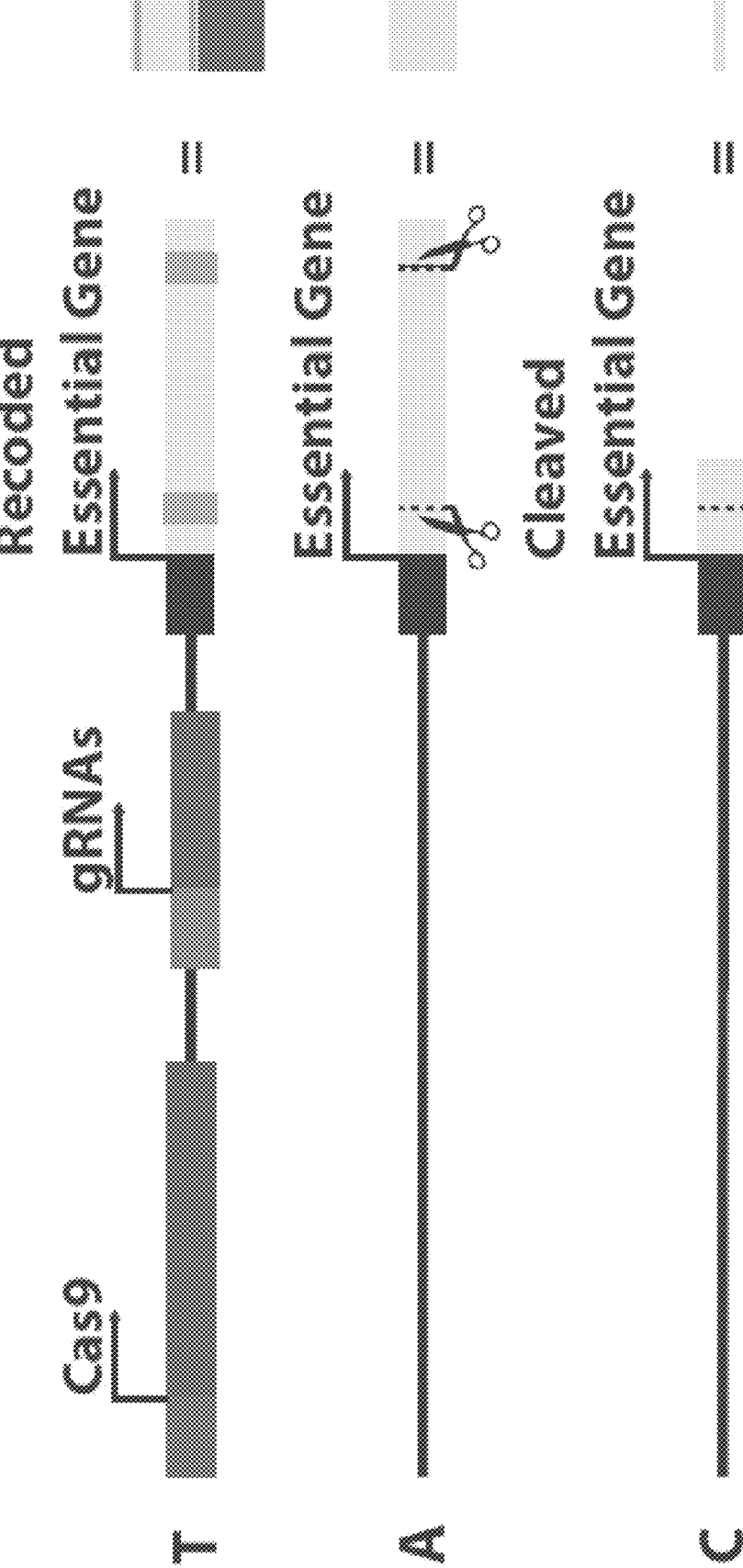
FIG. 3A-FIG. 3C show an embodiment of a cleavage mediated autosomal drive.

Cleavage mediated autosomal drive consists of Cas9, gRNAs which target an essential autosomal gene, and a recoded or sequence unrelated copy of this target gene which is immune to gRNA targeting, which are situated together at the same locus as the target gene (FIG. 3A). The transgenic construct (T) is situated on an autosome and consists of Cas9, gRNAs targeting an essential gene (at the same autosomal locus as T), and a recoded version of the target gene (FIG. 3A). Potential cleavage sites on the target essential gene (A) are indicated by dashed lines and scissors, and the cleaved locus (C) is a null form of the target gene made of what remains of the gene from the outer ends of the cleavage sites (FIG. 3A).

Figure 3B:
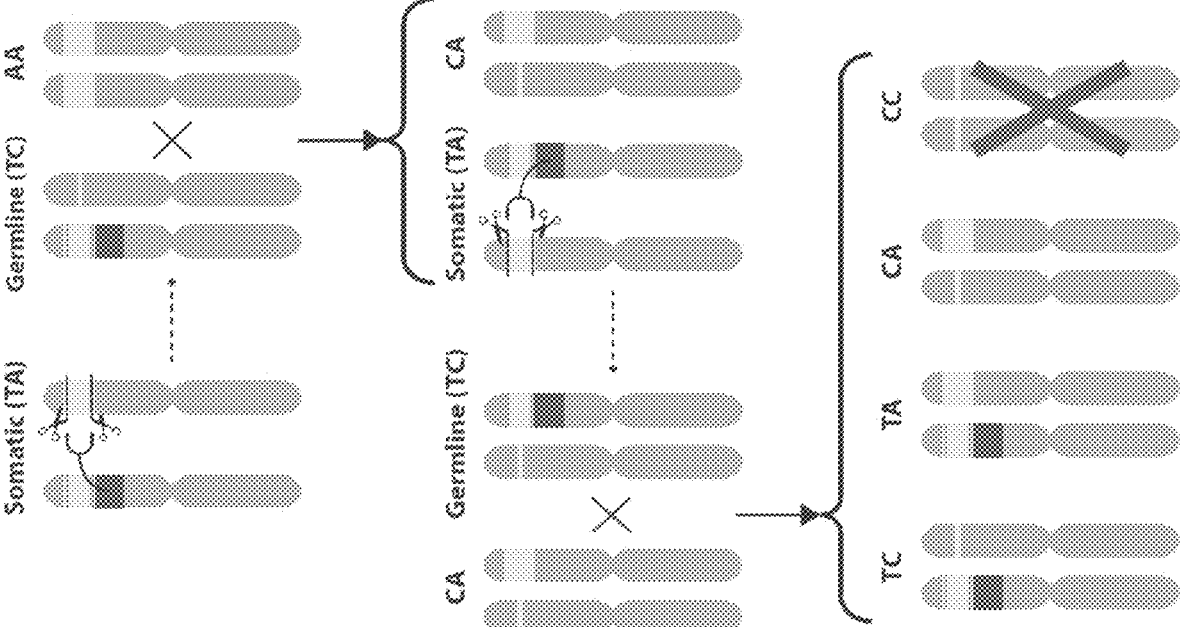

In males and females who carry the construct (T) and a wild type copy of the its target (A), the target gene is cleaved multiple times during gametogenesis, destroying the wild type copy of the gene (C) and resulting in either T or C bearing gametes (FIG. 3B). As transgenic individuals mate with wild types, cleaved copies of the essential gene will begin to accumulate in heterozygotes (CA individuals). All individuals that receive two cleaved autosomes (CC) will die from the absence of a functional copy of the target essential autosomal gene, leaving the viable genotypes TT, TC, TA, CA, and AA (FIG. 3B). In heterozygotes (TA) Cas9 can find and cleave a copy of the target gene. The resulting cleaved locus is passed on instead of the original target wildtype locus. When two individuals bearing cleaved locus mate and the cleaved loci are paired together (CC), the resulting offspring is unviable, removing two wild type alleles are from the population (FIG. 3B).

Figure 3C:
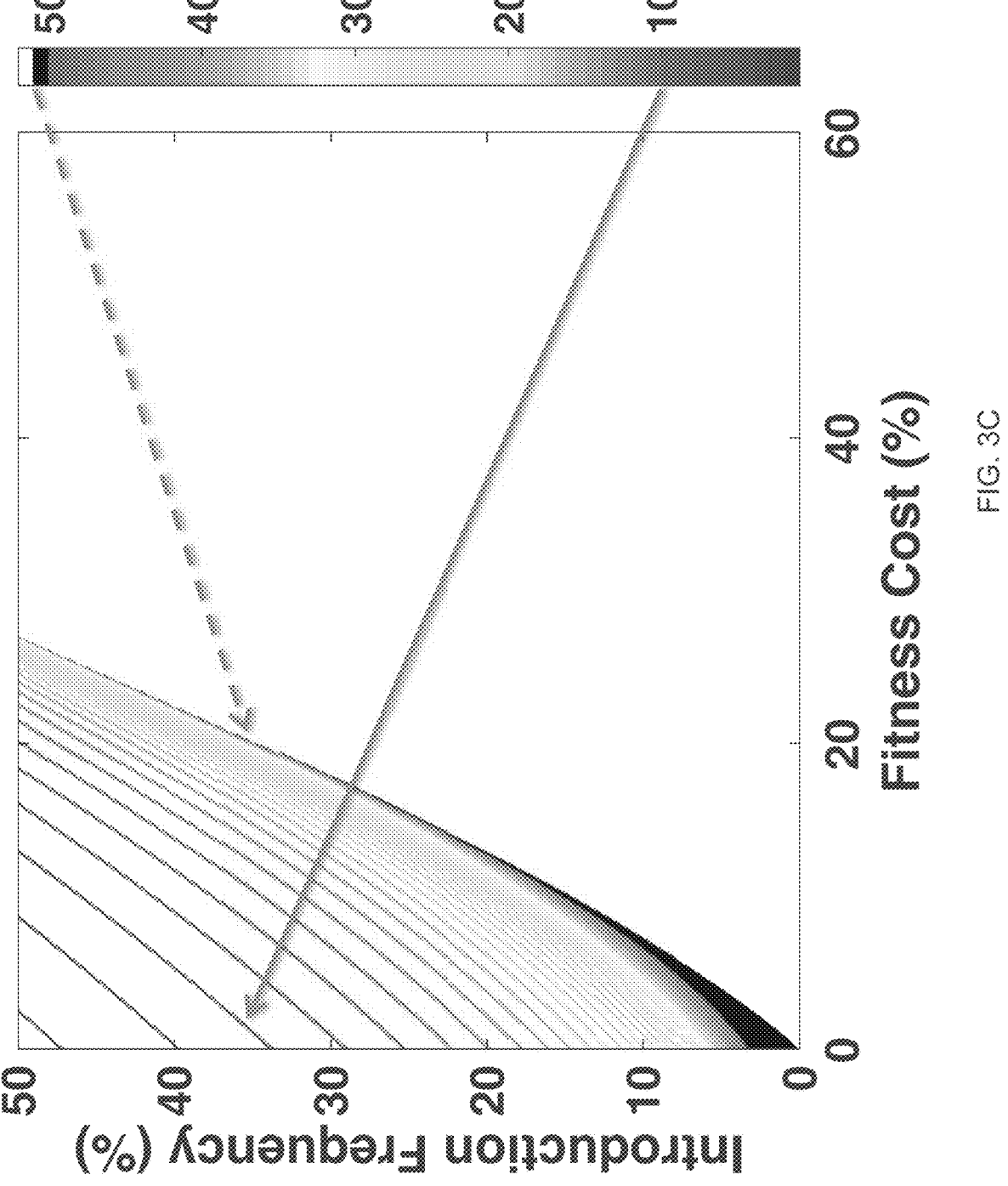

The discrete generation, deterministic population frequency model for this drive mechanism demonstrates that if Cas9 cleaves the target gene with 100% efficiency, T can drive to fixation with just a few moderate releases of TT males while bearing a fitness cost of up to approximately 55% (FIG. 3C). T can still drive population replacement when Cas9 is cleaving at non-optimal rates, but it can only tolerate correspondingly reduced fitness costs as a result (FIG. 3C). Discrete generation, deterministic population frequency modeling of cleavage mediated autosomal drive is shown in FIG. 3C. Each data point uses a few moderate releases of transgenic mosquitoes (three releases of TT males at 50% of the population) with the specified fitness cost and Cas9 cleavage efficiency. The shade of each data point indicates the number of generations (as indicated by the bar on the right) before T bearing individuals make up >99% of the population. White indicates the inability of T to take over under the specified conditions or failure to do so within 70 generations (FIG. 3C).

The autosomal drive is very potent, capable of driving even with ~55% fitness costs at high cleavage efficiency. Because the construct is autosomal, it can be used to drive replacement in any species, importantly covering both *Anopheles gambiae* and *Aedes aegypti*. It is also perhaps the easiest to implement, as the only knowledge it requires about the target species are an essential gene on an autosome and an appropriate promoter to drive expression of the DNA sequence modifying enzyme (either pre-meiotic or gameto-genic).

Example 4—Cleavage Mediated 2-Locus Autosomal Drive

Figure 4A:
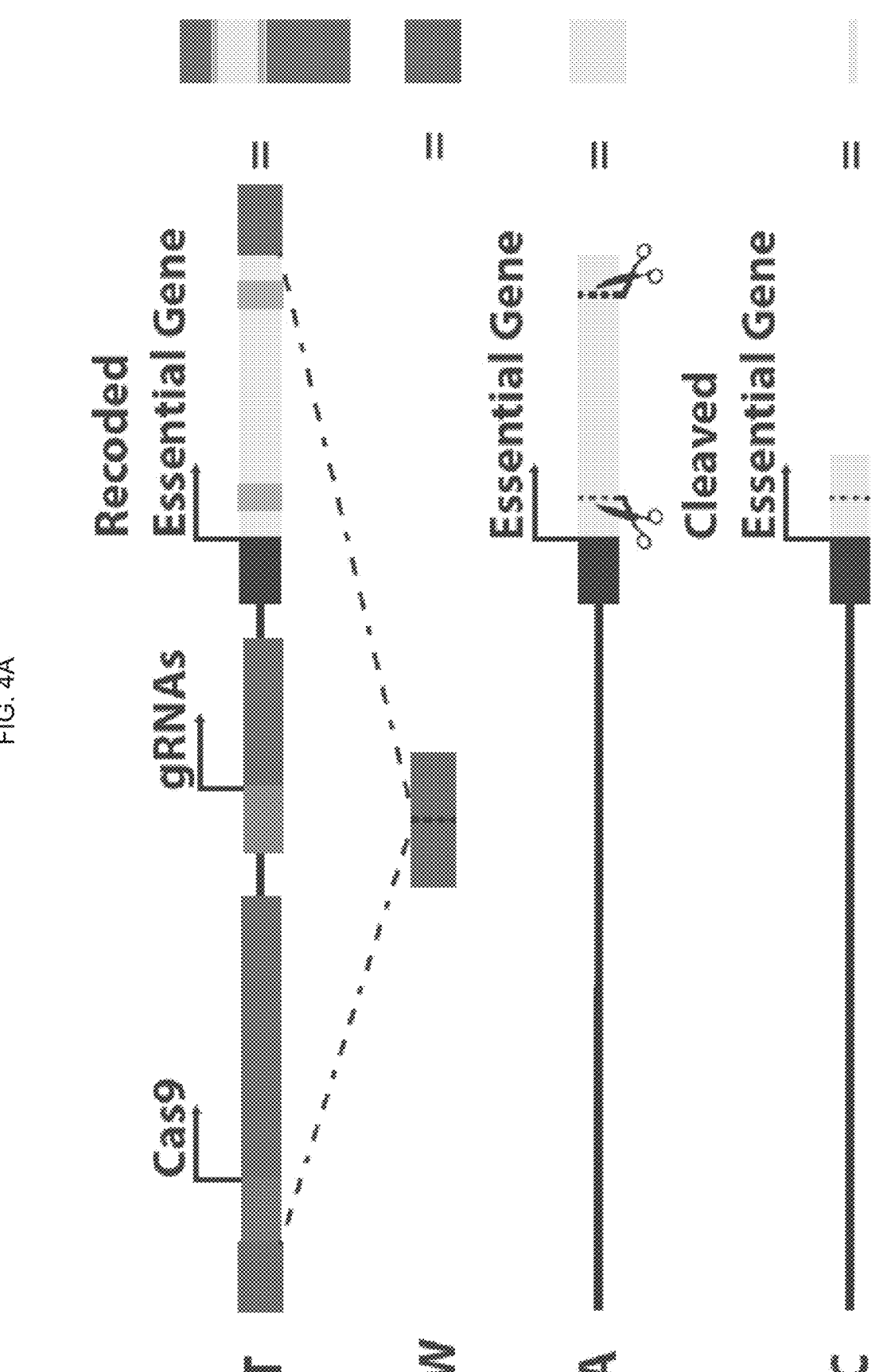
FIG. 4A-FIG. 4C show an embodiment of a cleavage mediated 2-locus autosomal drive.

Cleavage mediated 2-locus autosomal drive consists of Cas9, gRNAs which target an essential autosomal gene, and a recoded or sequence unrelated copy of this target gene which is immune to gRNA targeting, which are situated together on a different autosome (wild type W) than the target gene (FIG. 4A). The transgenic construct (T) is situated on an autosome and consists of Cas9, gRNAs targeting an essential gene (at a different autosomal locus than T), and a recoded version of the target gene. The transgenic construct T is generated by targeted insertion at a wild type locus indicated by the rectangle (W). Potential cleavage sites on the target essential gene (A) are indicated by dashed lines and scissors, and the cleaved locus (C) is a null form of the target gene made of what remains of the gene from the outer ends of the cleavage sites (FIG. 4A).

Figure 4B:
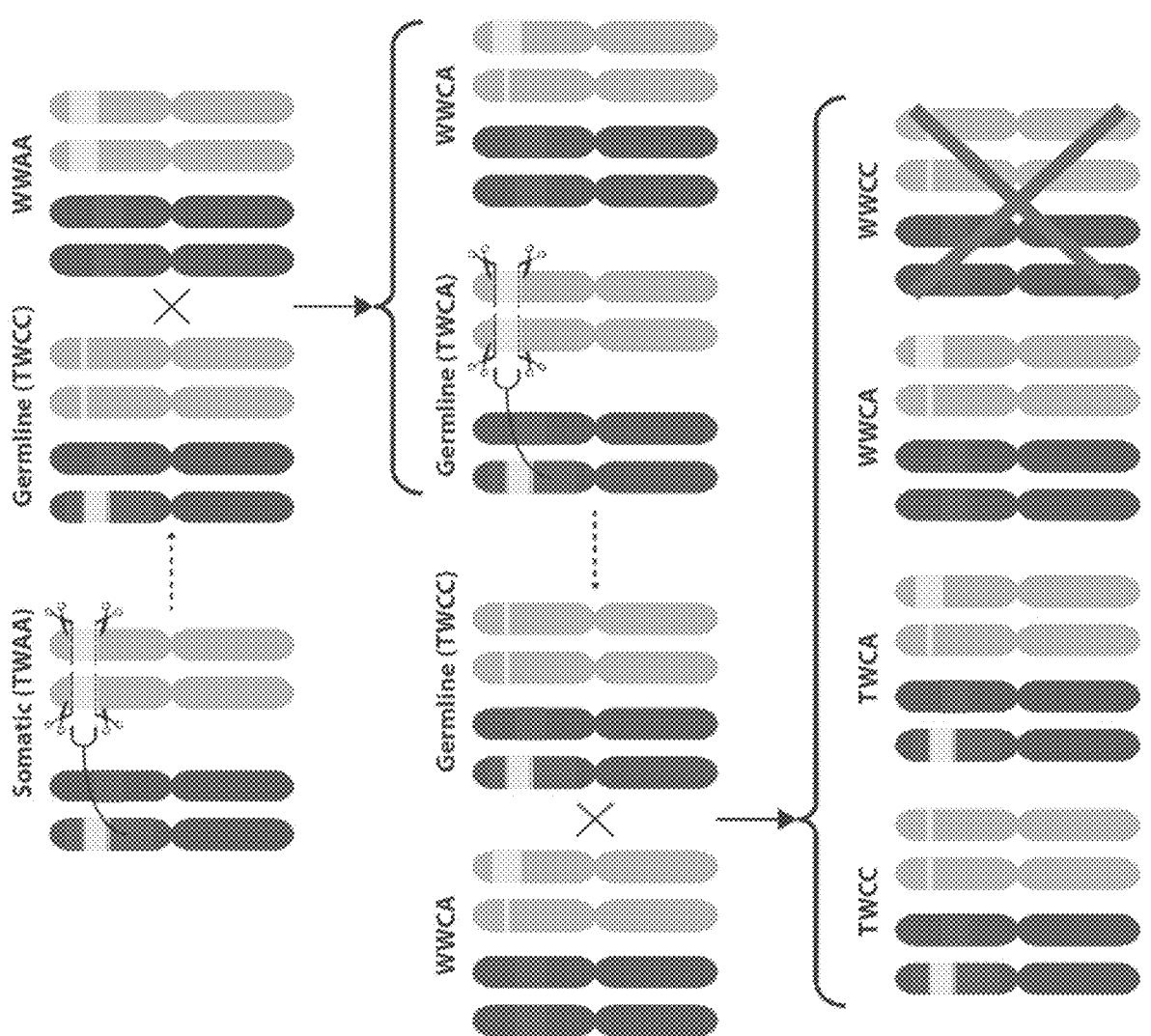

In males and females who carry at least one copy of the construct (T) and at least one copy of the wild type target (A), the target gene is cleaved multiple times during game-togenesis, destroying the wild type copy of the gene (C) and resulting in C bearing gametes (FIG. 4B). As transgenic individuals mate with wild types, cleaved copies of the essential gene will begin to accumulate in heterozygotes (—CA individuals). Only individuals who do not bear a T and receive two cleaved genes (WWCC) will die from the absence of a functional copy of the target essential auto-somal gene, leaving the viable genotypes TTCC, TTCA, TTAA, TWCC, TWCA, TWAA, WWCA, and WWAA (FIG. 4B). In individuals which possess at least one T and at least one A, Cas9 can find and cleave a copy of the target gene. The resulting cleaved locus is passed on instead of the original target wildtype locus. When two individuals bearing the cleaved locus mate and the cleaved loci are paired together in the absence of the transgene (WWCC), the resulting offspring is unviable, removing two wild type alleles are from the population (FIG. 4B).

Figure 4C:
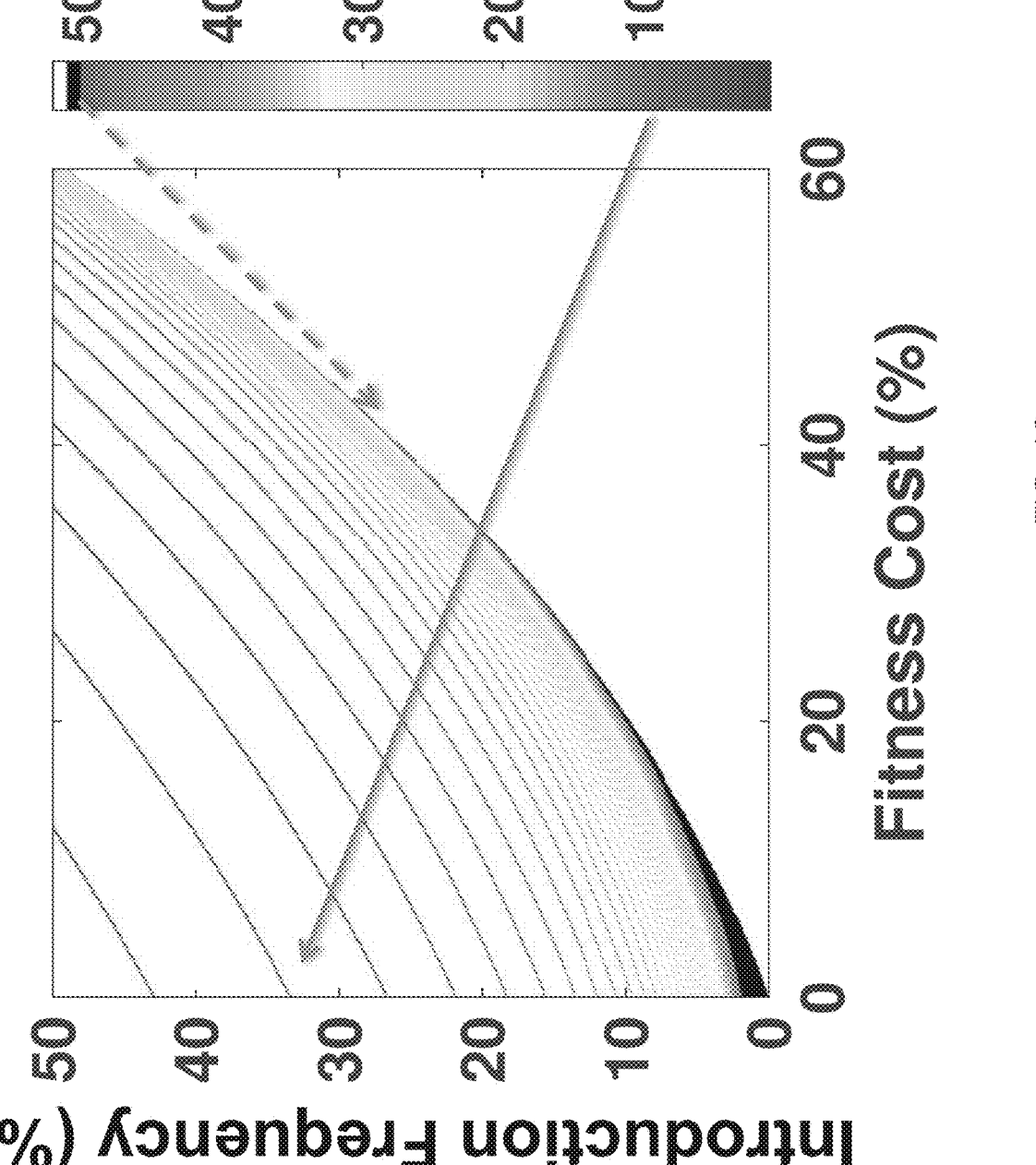

The discrete generation, deterministic population frequency model for this drive mechanism demonstrates that if Cas9 cleaves the target gene with 100% efficiency, this drive mechanism is identical to the single locus cleavage based autosomal drive mechanism. However, if Cas9 cleavage efficiency is imperfect, then this 2-locus cleavage based drive can tolerate larger fitness costs than the single locus version (FIG. 4C, as compared to FIG. 3C). Discrete generation, deterministic population frequency modeling of cleavage mediated 2-locus autosomal drive is shown in FIG. 4C. Each data point uses a few moderate releases of transgenic mosquitoes (three releases of TTCC males at 50% of the population) with the specified fitness cost and Cas9 cleavage efficiency. The shade of each data point indicates the number of generations (as indicated by the bar on the right) before T bearing individuals make up >99% of the population. White indicates the inability of T to take over under the specified conditions or failure to do so within 70 generations (FIG. 4C).

The dynamics of the 2-locus autosomal drive makes it identical to the autosomal drive when the cleavage efficiency of Cas9 is perfect, but when that cleavage efficiency is reduced 2-locus drive becomes the stronger drive. As a result, it can maintain higher fitness costs at reduced cleav-age efficiencies while sharing the same applicability to species and ease of creation as with single locus versions.

Example 5—Cleavage Mediated Haplolethal Drive

Figure 5A:
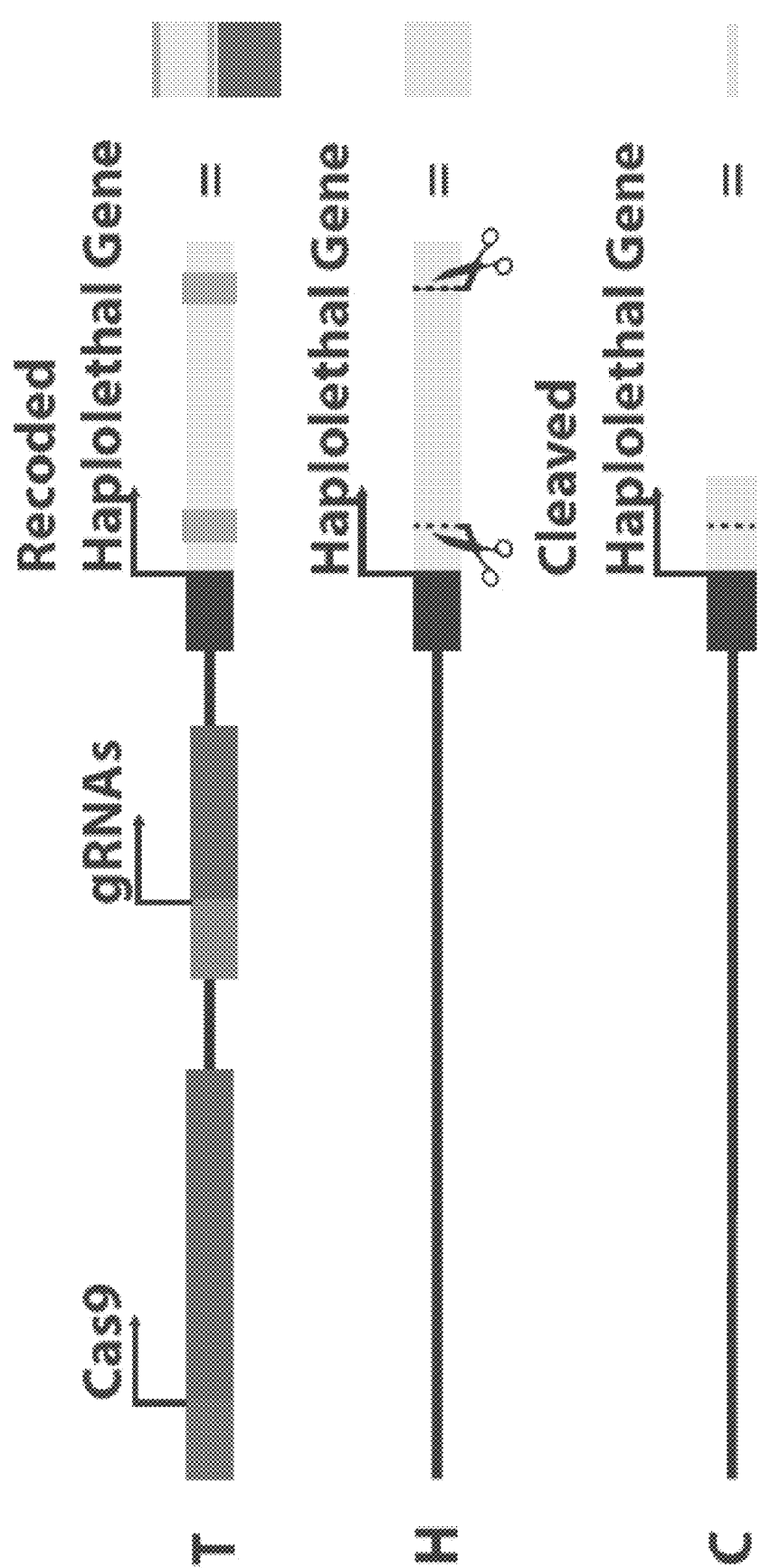
FIG. 5A-FIG. 5C show an embodiment of a cleavage mediated haplolethal drive.

Cleavage mediated haplolethal drive is slightly different from the other four cleavage based mechanisms. It consists of Cas9, gRNAs which target an autosomal haplolethal gene (instead of a recessive lethal gene), and a recoded or sequence unrelated copy of this haplolethal target gene which is immune to gRNA targeting, which are situated together at the same locus as the target gene (FIG. 5A). The transgenic construct (T) is situated on an autosome and consists of Cas9, gRNAs targeting a haplolethal gene (at the same autosomal locus as T), and a recoded version of the target gene. Potential cleavage sites on the target haplolethal gene are indicated by dashed lines and scissors, and the cleaved locus is a null form of the target gene made of what remains of the gene from the outer ends of the cleavage sites (FIG. 5A).

Figure 5B:
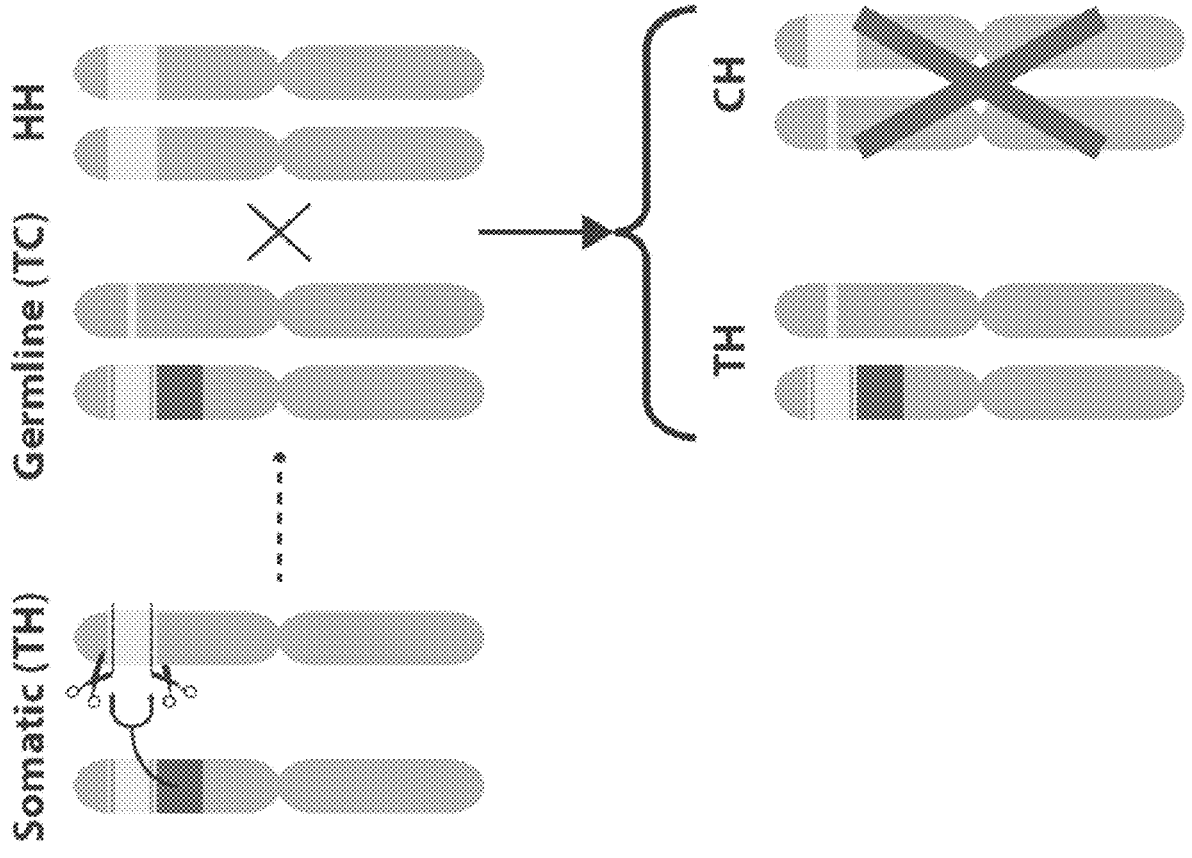

Cleavage is male specific, so in males who carry the construct (T) and a wild type copy of its target (H), the target gene is cleaved multiple times during spermatogenesis, destroying the wild type copy of the gene (C) and resulting in either T or C bearing sperm (FIG. 5B). As transgenic males mate, cleaved copies of the haplolethal gene will immediately result in the death of their carrier (both TC and CH genotypes), leaving the viable genotypes TT, TH, and HH (FIG. 5B). In heterozygotes (TH) Cas9 can find and cleave a copy of the target essential gene. The resulting cleaved locus is passed on instead of the original wildtype locus, and any offspring that receives the cleaved locus is unviable, removing either a transgene and a cleaved locus (TC) or two wild type alleles (CH) from the population (FIG. 5B). Related constructs can be implemented, as described above for the two-locus autosomal situation, in which the construct is located at a position different from that of the gene being targeted.

Figure 5C:
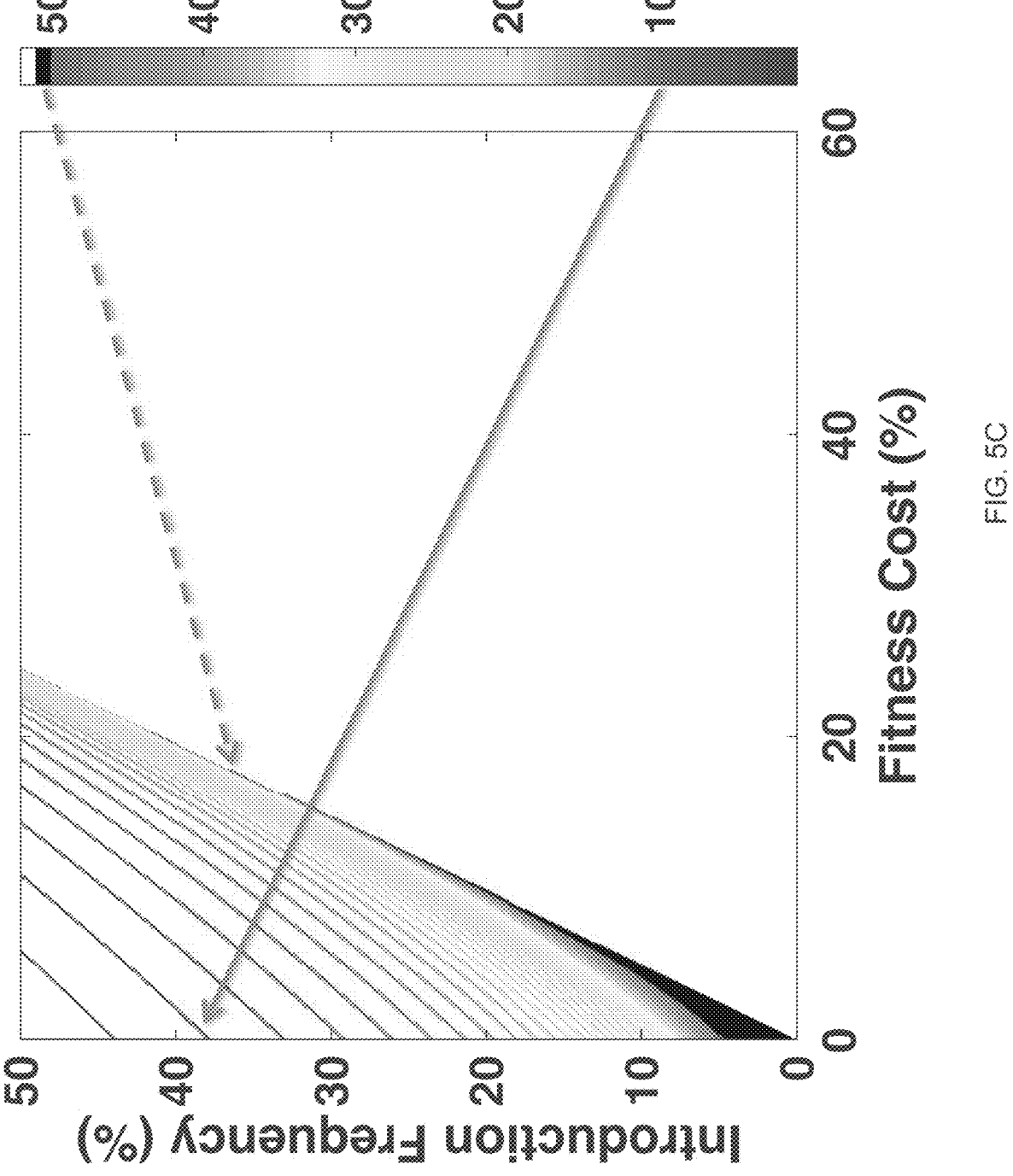

The discrete generation, deterministic population frequency model for this drive mechanism demonstrates that if Cas9 cleaves the target gene with 100% efficiency, T can drive to fixation with just a few moderate releases of TT males while bearing a fitness cost of up to approximately 60% (FIG. 5C). T can still drive population replacement when Cas9 is cleaving at non-optimal rates, but it can only tolerate correspondingly reduced fitness costs as a result (FIG. 5C). Discrete generation, deterministic population frequency modeling of cleavage mediated haplolethal drive is shown in FIG. 5C. Each data point uses a few moderate releases of transgenic mosquitoes (three releases of TT males at 50% of the population) with the specified fitness cost and Cas9 cleavage efficiency. The shade of each data point indicates the number of generations (as indicated by the bar on the right) before T bearing individuals make up >99% of the population. White indicates the inability of T to take over under the specified conditions or failure to do so within 70 generations.

The haplolethal drive is even stronger than the autosomal drive, capable of driving even with ~60% fitness costs at high cleavage efficiency. However, at reduced cleavage efficiency it withstands a smaller range of fitness costs than the 2-locus drive. Additionally, haplolethal drives rely on identifying a haploethal locus on which to base this drive mechanism as well as a pre-meiotic promoter to drive expression of either Cas9 and a post-meiotic promoter for the gRNAs, with one or both promoters also driving male specific expression. The latter two requirements are necessary for getting cleavage of the haplolethal locus in sperm without causing cleavage in the rest of the individual, thereby resulting in death of the construct-bearing individual. In some implementations Cas9 expression is limited to stages of spermatogenesis after those that require activity of the gene being targeted.

A second example of single locus ClvR targeting genes with some degree of haploinsufficiency or haplolethality is presented in FIG. 5D-G, which also illustrates the behavior of a haplosufficient locus as a point of comparison. Population genetic behavior of ClvR when targeting a haplosufficient (D, E) or haploinsufficient (F, G) essential gene. (D, E) A discrete generation, deterministic population frequency model of ClvR spread (cleavage in male and female germline; ClvR located on an autosome and the essential gene on the X; see data in Example 17) through a single panmictic population, for varying initial release ratios and fitness costs, without (D), or with (E) maternal carryover-dependent cleavage. The heatmap indicates the number of generations required for the ClvR-bearing genotype to approach fixation (i.e., >99% of the total population). (F) Heatmap showing the number of generations required for the ClvR-bearing genotype to reach fixation (<99% ClvR-bearing) for different initial release ratios and haploinsufficient fitness costs (100%=haplolethal), for a two locus autosomal version of ClvR with maternal carryover. (G) Individuals traces showing the fate of a ClvR from (F) targeting a haplolethal gene, for different release ratios. The horizontal line represents an approximation of the unstable equilibrium frequency (~31.5%; population frequencies do not change significantly over 20 generations). Population frequencies greater than equilibrium=36%, 41%, and 46%; those below=26%, 21%, and 16%. Note that the ern "Release Ratio" for all heaunaps refers to the ratio of homiozygous transgenic males compared to wild type males and females after a release has occurred (e.g., a 40% release means that 40% of the population is ClvR/ClvR male, 30% is +/+ male, and 30% is +/+female). Thus, initial release ratio also=initial population frequency. Note that for (F) and (G) ClvR itself is assumed to have no fitness cost. Such costs would further increase the minimum release ratios required for drive to occur, as in panels (D) and (E). Other examples of ClvR-mediated drive in which haploinsufficiency or haplolethality are present are found in FIGS. 31A-D.

Example 6—Maintenance of Extrachromosomal Element

Figures 6A, 6B, 6C, 6D, 6E, 6F:
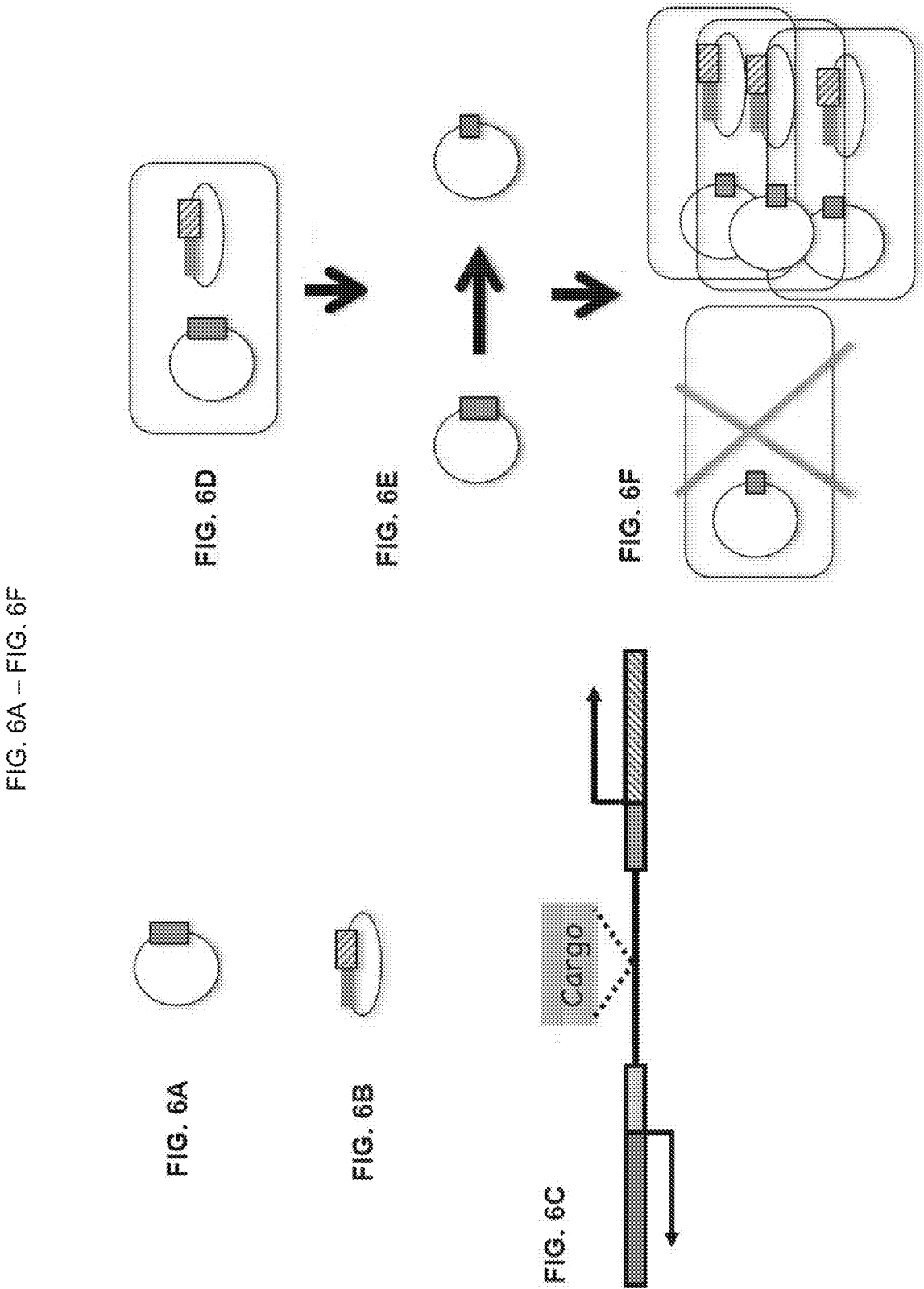
FIG. 6A-FIG. 6F show a schematic of an embodiment of maintenance of extrachromosomal element.
Figure 7:
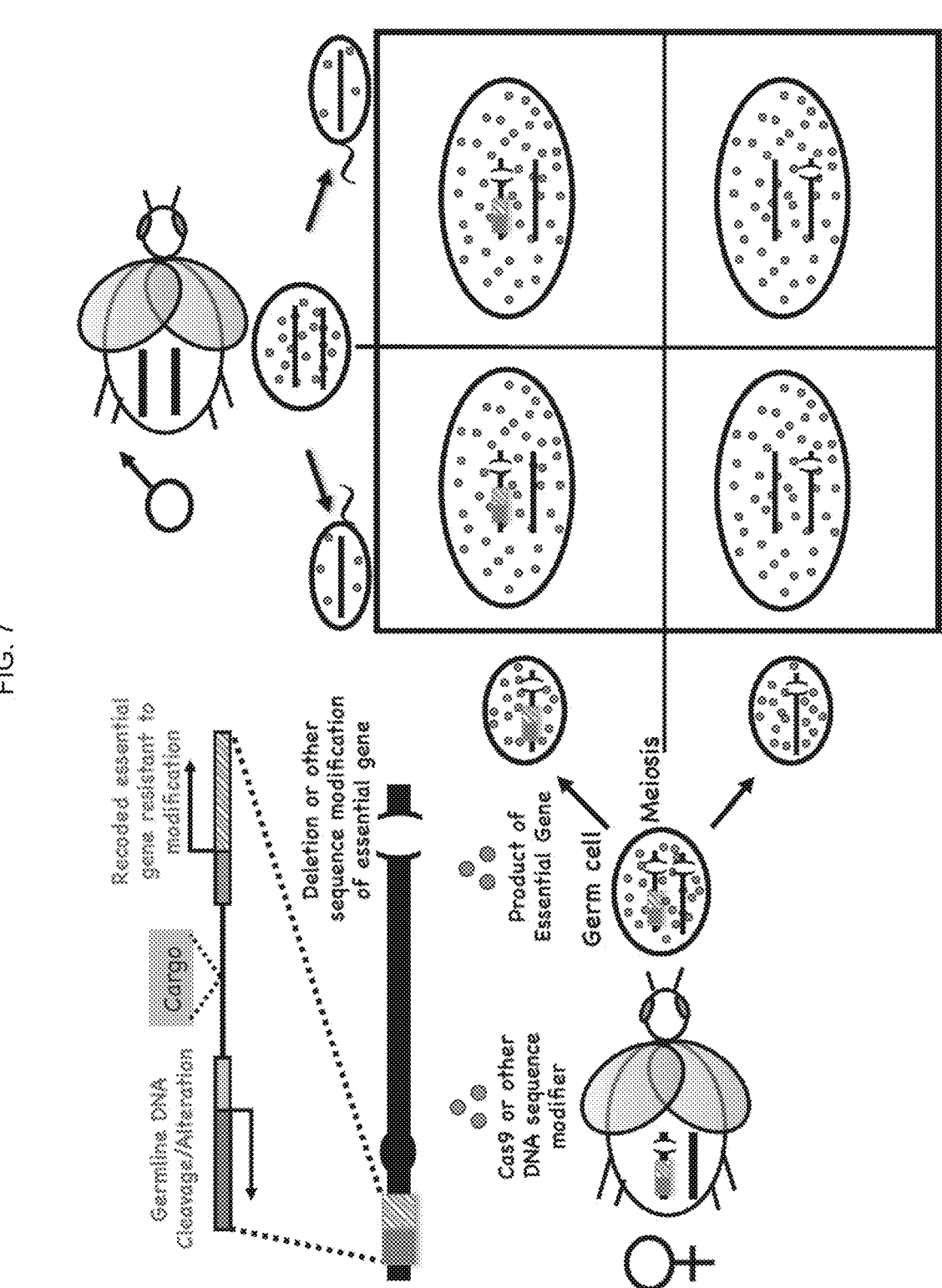
FIG. 7 shows a schematic of an embodiment the results of a cross between a female insect heterozygous for the vector with germline expression of the DNA sequence modifying enzyme and a wild type male when there is no carryover of DNA cleavage/alteration activity from germline into embryo.

FIG. 6A shows a chromosome (circle) carrying a wildtype copy of an essential gene (dark rectangle). In this example a prokaryotic chromosome carries a wildtype copy of an essential gene. FIG. 6B shows an extra-chromosomal element such as a plasmid carrying the construct (thin rectangle as nuclease and diagonal line rectangle as recoded Rescue) and any other genes (e.g., one or more cargo sequences) to be maintained in the population. An extrachromosomal element carries the vector, which carries a recoded or sequence unrelated version of the essential gene (diagonal lines) and the DNA modifying enzyme driven by a promoter (solid rectangle). FIG. 6C shows the construct, which consists of two components: (1) a site-specific DNA modifying enzyme designed to alter the sequence of an endogenous gene required for survival, proliferation, fertility, or differentiation so as to render it non-functional (left); (2) a recoded or sequence unrelated version of the essential gene resistant to cleavage, and having reduced nucleotide identity with the endogenous gene (right). Optionally, one or more cargo sequences are present (center). FIG. 6D shows the chromosome (FIG. 6A) and the extra extra-chromosomal element (FIG. 6B) in a cell and forced inheritance of the extra-chromosomal element. The endogenous copy of essential gene is altered within the cell by CleaveR to render it non-functional (FIG. 6E). However, cells that inherit CleaveR survive, proliferate, differentiate, or are fertile, whereas those that fail to inherit C fail do not survive, proliferate, differentiate, or are sterile (FIG. 6F). An expanded view of the vector shown in (FIG. 6B). Recoded essential gene (or functional equivalent that lacks significant sequence homology) transcribes to the right. DNA sequence modifying enzyme transcribes to the left. A cargo gene is located in between the two in the figure, though the actual arrangement between cargo, rescue and DNA modifying enzyme can take a number of forms. FIG. 6D shows a cell carrying the wildtype chromosome and the extrachromosomal element including the vector. FIG. 6E shows DNA modifying activity of the element results in sequence changes to the wildtype copy of essential chromosomal gene (horizontal arrow leading to a chromosome carrying a smaller version of the essential gene). FIG. 6F shows the extrachromosomal element is spontaneously lost from some cells (left). These cells die because they lack essential gene activity. Those on the right, that carry the vector and associated rescue transgene survive and proliferate.

FIG. 43 illustrates an embodiment related to Example 6 in which cells that acquire a competitor plasmid are eliminated if they end up carrying this plasmid, while losing the ClvR-bearing plasmid.

Example 7

FIG. 7 shows a schematic of an embodiment the results of a cross between organisms (in this example insects) heterozygous for the construct and a wild type organism when there is no carryover of DNA cleavage/alteration activity from germline into embryo. DNA sequence modified (parentheses) version of the essential gene is created in the female germline of heterozygotes. Both copies are cleaved, but the diploid germline cell survives because it carries one copy of the rescue transgene. Female haploid meiotic products (oocytes) survive because the essential product is provided to them from the rescue transgene. These products are inherited by progeny. All individuals inherit chromosomes carrying one sequence modified version of the essential gene. No progeny die. However, crosses between heterozygotes for the nonfunctional version of the essential gene in subsequent generations will create dead homozygotes (not shown). Note that in this example the essential locus is located on the same chromosome as the vector. This is simply for illustrative purposes as it decreases the number of genotypes that need to be shown to capture important aspects of vector behavior. As noted in the figures above, the vector can be located on any chromosome, and act to bring about sequence modifications of any essential gene, on any chromosome or extra-chromosomal element. All progeny express one or both versions of the essential gene in the example provided. Therefore, all progeny survive.

Example 8

Figure 8A:
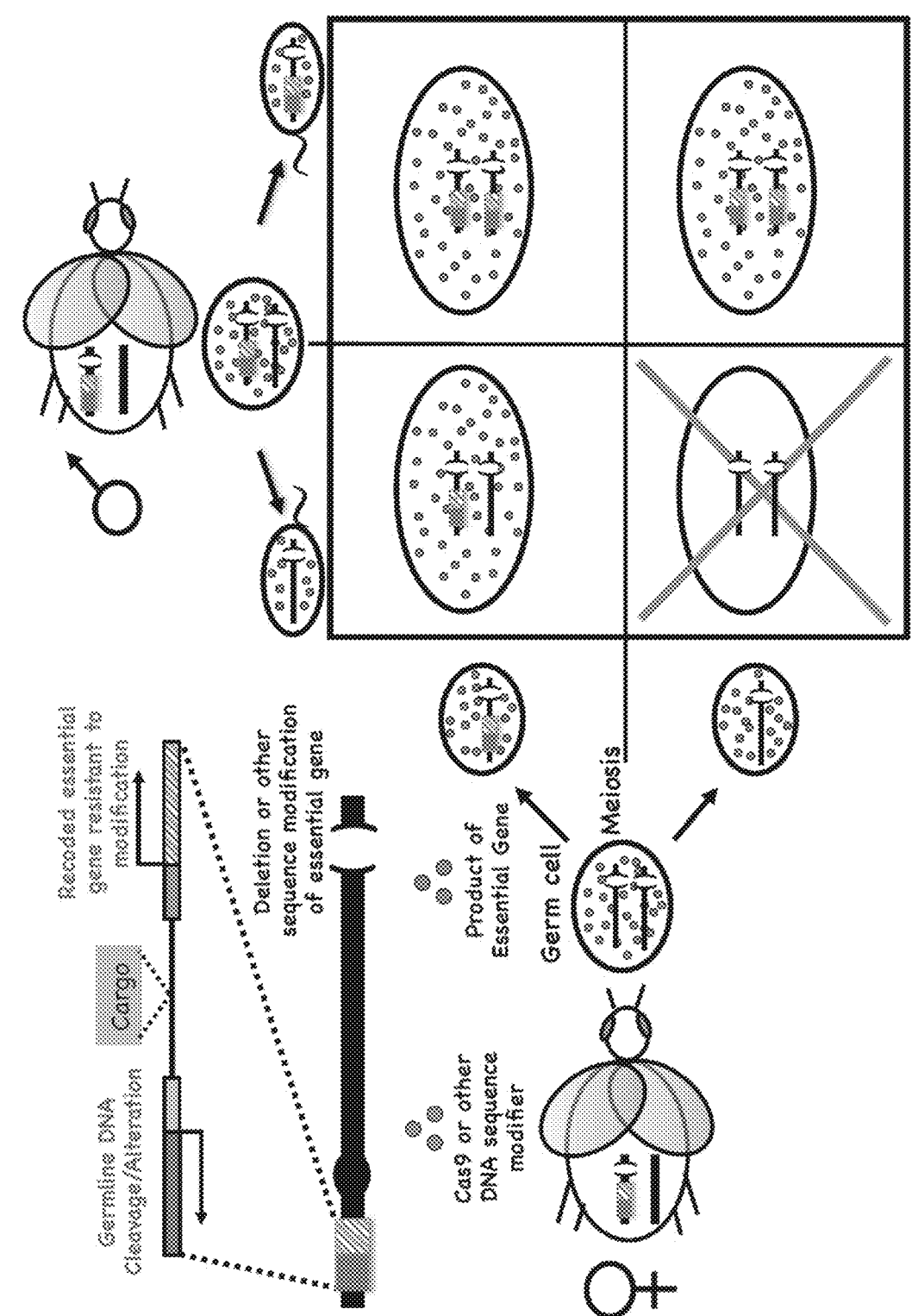
FIG. 8A shows a schematic of an embodiment the results of a cross between an insect heterozygous for the vector with germline expression of the DNA sequence modifying enzyme an a second insect heterozygous for the vector when there is no maternal transfer of DNA cleavage/alteration activity from germline into embryo. Individuals that inherit no functional copies of the essential gene die, while those that inherit at least one copy of the vector and its associated rescue transgene survive.
Figure 8B:
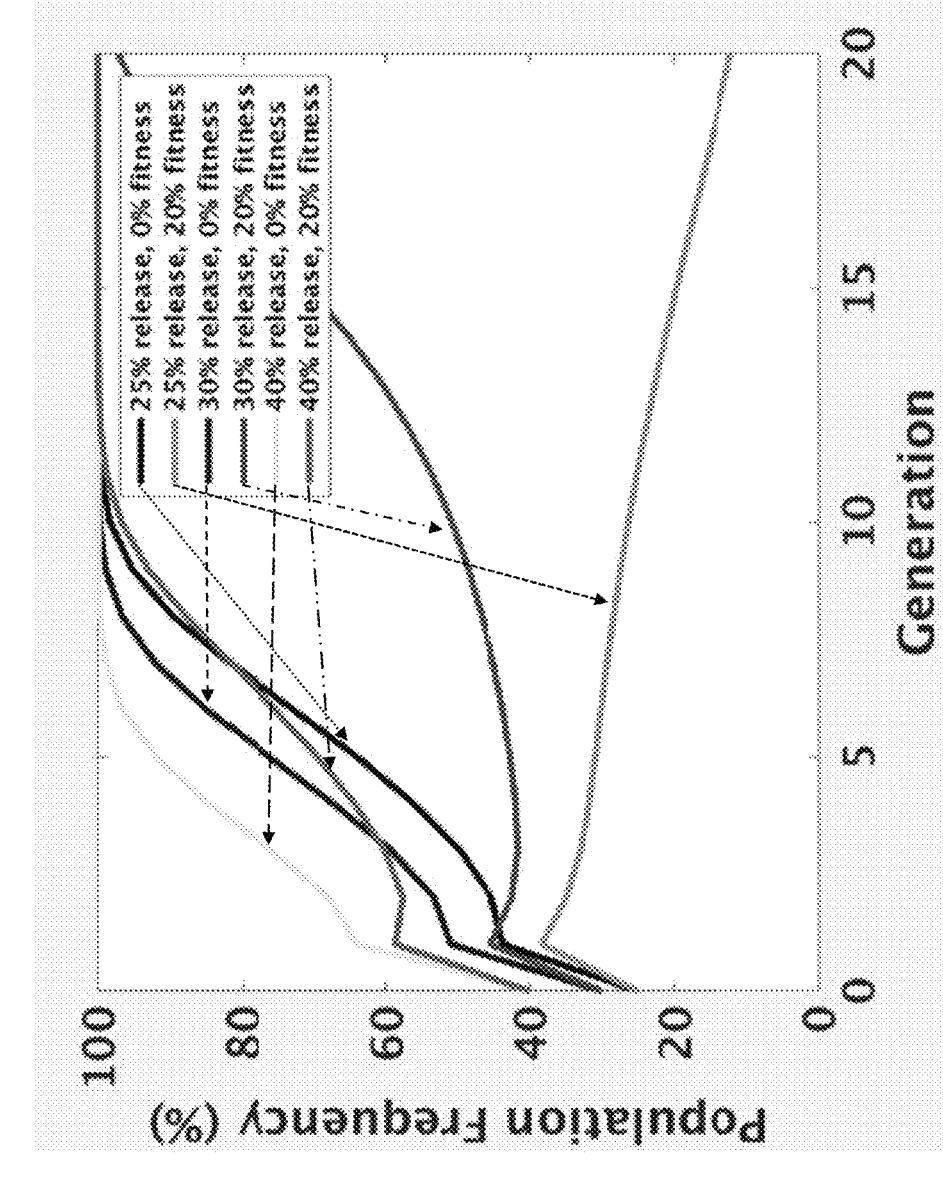
FIG. 8B shows a graph of an embodiment of vector-mediated gene drive/population replacement for an autosomal two locus scenario, with different fitness costs and introduction frequencies, and without maternal transfer of DNA cleavage/alteration activity.

FIG. 8A shows a schematic of an embodiment of the results of a cross between heterozygous organisms when there is no carryover of DNA cleavage/alteration activity from germline into embryo. Cleavage of the essential gene occurs in the parental cell resulting in survival of progeny that express the recoded protein, and death of offspring that do no inherit CleaveR (FIG. 8A). The outcome of a cross between heterozygotes is the same whether or not there is maternal carryover. Progeny that inherit the construct survive while those that do not die. FIG. 8B shows a graph of an embodiment of CleaveR gene drive for different fitness costs and introduction frequencies without maternal transfer of DNA cleavage/alteration activity.

Example 9

Figure 9B:
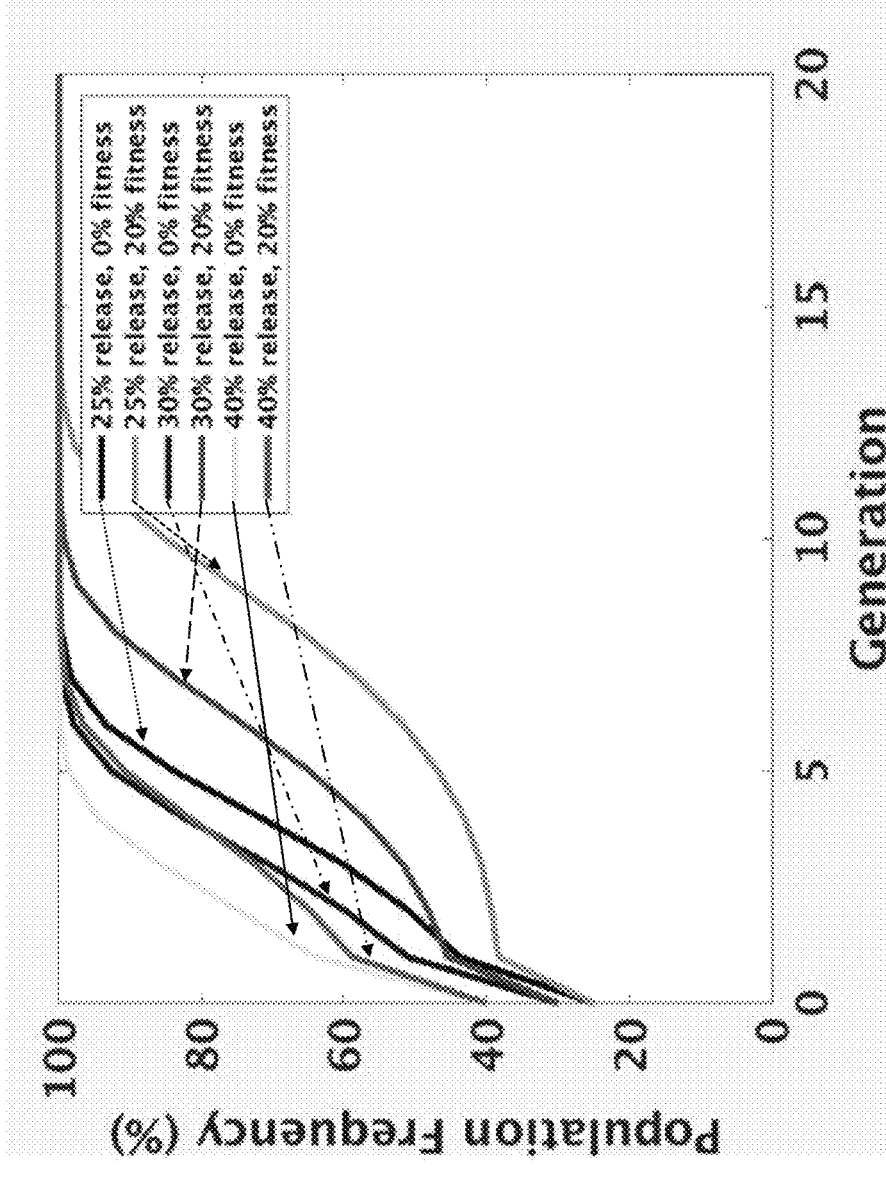
FIG. 9B shows a graph of an embodiment of vector-mediated gene drive/population replacement for different fitness costs and introduction frequencies with maternal transfer of DNA cleavage/alteration activity.

FIG. 9A shows a schematic of an embodiment the results of a cross when there is maternal transfer of DNA cleavage/alteration activity from germline into embryo. Cleavage of the essential gene occurs in the parental cell and in products of cell fusion/fertilization into which the DNA cleavage/alteration activity (or the encoding RNA(s)) is introduced during oogenesis, resulting in death of offspring that do no inherit the construct (FIG. 9A). Only progeny that express the recoded protein survive. FIG. 9B shows a graph of an embodiment of gene drive for different fitness costs and introduction frequencies with maternal transfer of DNA cleavage/alteration activity.

Example 10—Meiotic Gene Drive

FIG. 10 shows a schematic of an embodiment of a meiotic gene drive. Cleavage of the essential gene occurs in the parental cell. As a result, gametes that fail to inherit CleaveR do not survive. In such a system chromosomes that carry the vector have a selective advantage and increase in frequency. Such a system can also be used to guarantee that gametes arising from a transgenic individual always carry the trans-genes of interest (by virtue of tight genetic linkage to the construct). This ability has applications in agriculture, as it provides a method for regulating gene flow between populations of different genotypes.

Example 11—Sex Ratio Distortion

FIG. 11 shows a schematic of an embodiment of vector-mediated sex ratio distortion. A gene essential for post-meiotic sperm development is expressed on the Y chromosome as a part of the drive element. Only Y-bearing sperm, generated from diploids in which the drive element/vector has eliminated a gene required in haploid stages for sperm function, will express the product of this essential gene and be able to complete spermatogenesis/carry out fertilization. This results in sex-ratio distortion if sperm in which the gene has been inactivated fail to develop/undergo fertilization. Such a technology has many uses when the goal is to bring about population reduction or elimination by biasing the sex ratio towards males. A related approach can also be used to bias sex ratios towards males in species in which males are the homogametic sex (ZZ) and females the heterogametic sex (ZW). It can also be used for similar ends in species in which maleness is determined by a dominant allele of a male-determining locus. The primary requirement is that it be possible to eliminate and replace the activity of a gene required in haploid stages of sperm function, and that this product not be able to rescue meiotic brothers to which they may be linked by cytoplasmic bridges until late in spermatogenesis.

Example 12—Comparison of DNA Sequence Modification-Based Gene Drive with Homing-Based Gene Drive—1

Figure 12:
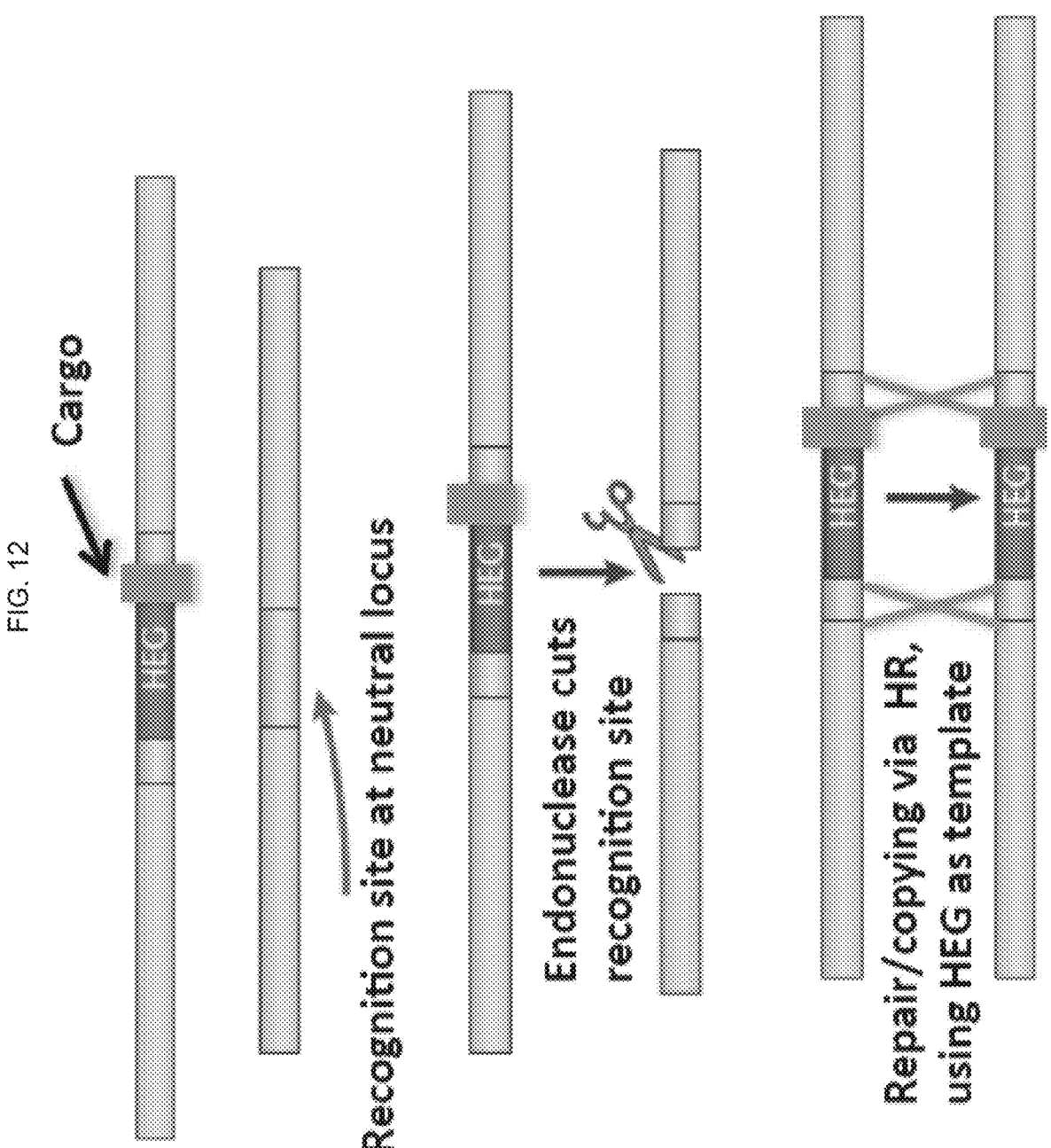
FIG. 12 shows a schematic of an embodiment of homing endonuclease gene (HEG)-based population replacement in which the cargo gene is included as a component of the HEG

FIG. 12 shows a schematic of an embodiment of a homing endonuclease-based cleavage of target gene for gene drive. The HEG cuts at a neutral locus in the wildtype chromosome, located at the same position in the genome as the HEG. The presence of the HEG disrupts the HEG cleavage site. In this example, the HEG carries a cargo gene located between the homology arms. In the middle panel, the HEG cleaves the wildtype allele. In the lower panel homologous recombination (HR) is used to repair the DNA break using the HEG-bearing chromosome as a template. Successful HR results in copying of the HEG into the cleaved chromosome. Cleavage of neutral locus by the homing nuclease results in the homing of gene drive and cargo genes into cleaved chromosome. This results in an increase in the population frequency of the HEG and its cargo transgene. However, homing to the neutral locus is required, which may be inefficient. Additionally, the cargo gene needs to be copied, which may not always occur, and development of resistance of neutral locus sequences to cleavage is very common. In contrast, with the DNA sequence modification-based drive method described herein (FIG. 8A, FIG. 9A), cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene. Additionally, there is no need for the cargo to be copied as the cargo transmitted with the chromosome. Additionally, homing is not required or utilized, and occurrence of essential genes resistant to cleavage would be rare. Additionally, some species have low rate of germline HDR, greatly if not completely hindering homing based strategies.

Example 13—Comparison of DNA Sequence Modification-Based Gene Drive with Homing-Based Gene Drive—2

Figure 13:
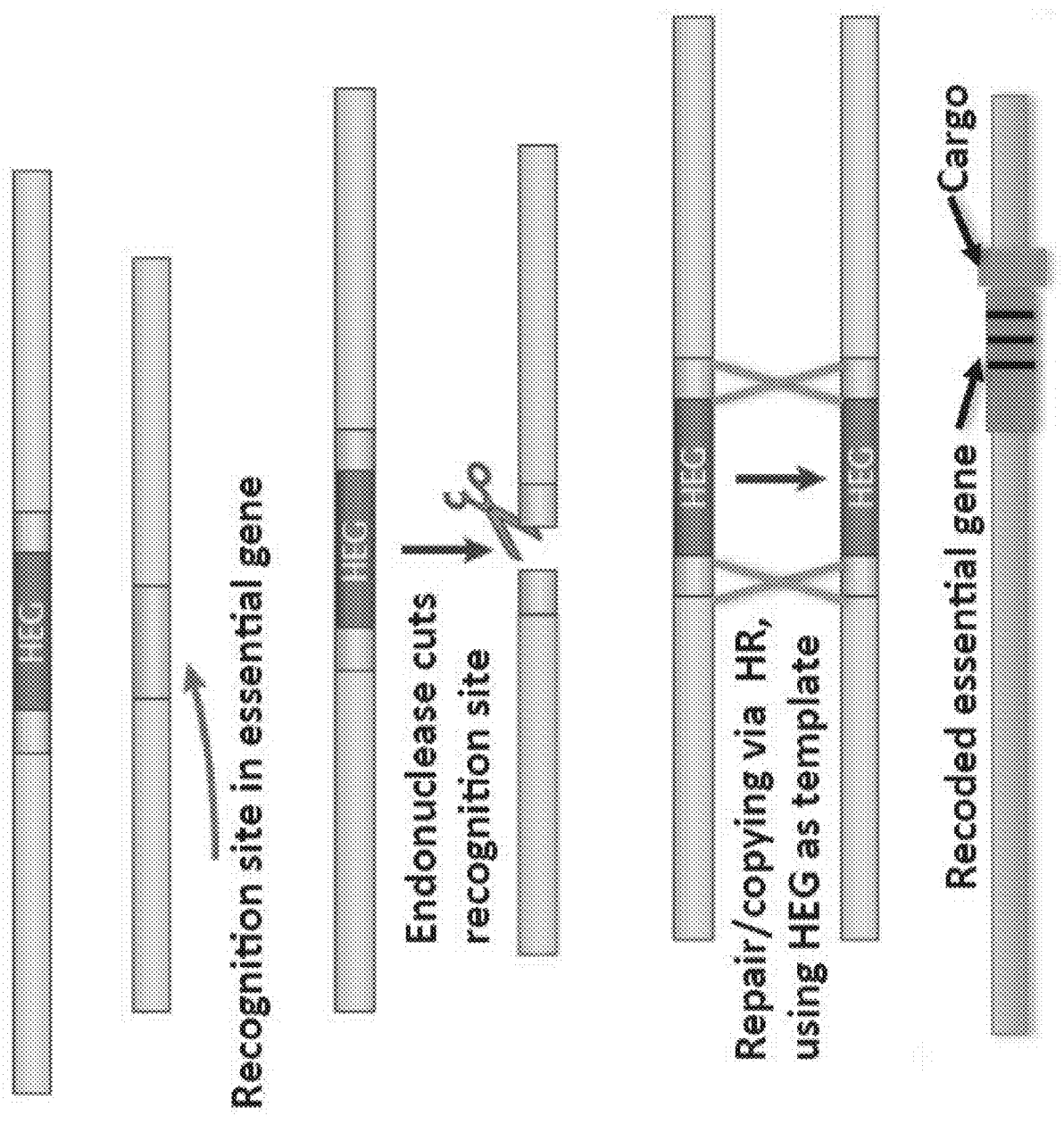
FIG. 13 shows a schematic of an embodiment of HEG-based population replacement in which the cargo is located at a different site in the genome.

FIG. 13 shows a schematic of an embodiment of a homing endonuclease-based cleavage of target gene for gene drive. The HEG cleaves an essential gene. Homing occurs into the cleaved essential gene, resulting in loss of essential gene function, and an increase in the frequency of the HEG, but only under specific conditions, since loss of both copies of an essential gene results in death or infertility. The recoded essential gene and a cargo are located elsewhere in the genome. As the frequency of the HEG increases, versions of the other chromosome that carry the recoded rescue and cargo are selected for, resulting in their spread. It is important to note that homing (which requires homologous recombination) is required for this version of population replacement to work. Cleavage alone is not sufficient as it only results in loss of essential gene function, but not an increase in HEG frequency. It is only with homing (and homologous recombination) that the frequency of the HEG increases. Progeny that inherit the chromosome with recoded essential gene and cargo survive but may experience a fitness cost in an otherwise background, which would result in their loss. Only progeny that inherit two inactive copies of the essential gene die. In contrast, with the DNA sequence modification-based drive method described herein (CleaveR; FIG. 8A, FIG. 9A, FIGS. 20A-D and FIGS. 21A-C), only cleavage is required, and cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene, which are tightly linked. The DNA sequence modification-based drive mechanism described herein does not utilize or depend on homing, only DNA sequence modification and tight linkage to a rescuing transgene.

Example 14—Comparison of DNA Sequence Modification-Based Gene Drive with *Medea*

Figure 14:
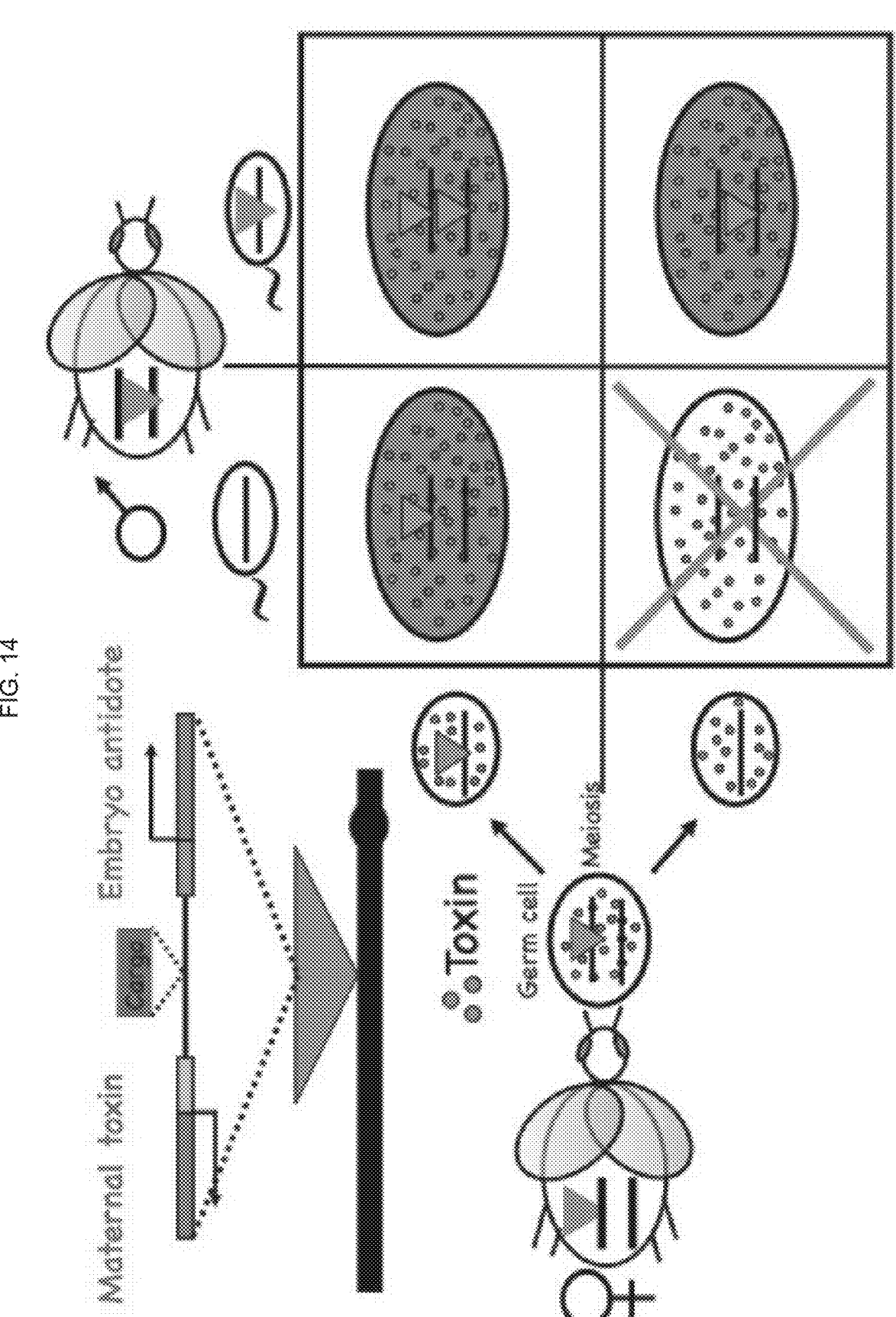
FIG. 14 shows a schematic of an embodiment of a *Medea*-based gene drive.

FIG. 14 shows a schematic of an embodiment of a *Medea*-based gene drive. In *Medea*-based gene drive a maternally deposited toxin (which may consist of maternally expressed miRNAs that result in a loss of an essential gene, as well as a protein-based toxin, (c.f. Chen et al., 2007)) has the potential to cause the death of all embryos. However, those that inherit a tightly linked antidote survive (which may include a version of the maternally expressed gene being targeted by the maternally expressed miRNAs (c.f. Chen et al., 2007)) because they turn on expression of the antidote just in time to prevent toxin action. In this drive mechanism there is no DNA sequence modification of an endogenous locus. The mechanism of action requires that a maternal (or paternal) toxin be deposited into the embryo. In the *Medea*-based system, a toxin is expressed in maternal germline resulting in the toxin being present in all oocytes/ eggs. Embryos that inherit *Medea* survive because they express an antidote in the early embryo, while those that do not inherit *Medea* die. In the *Medea*-based system, maternal expression of a toxin which can kill embryos but not oocytes is required, and rescue is achieved through early embryo expression of an antidote. In contrast, with the DNA sequence modification-based drive method described herein (CleaveR; FIG. 8A, FIG. 9A), cleavage of the essential gene results in death of progeny that lack functional copies of the essential gene, i.e., both endogenous copies are cleaved and the recoded copy of the essential gene is not inherited, and results in survival of only those progeny that inherit cargo and recoded copy of the essential gene. The DNA sequence modification-based drive mechanism described herein only requires DNA sequence modification and does not require maternal or paternal deposition of a toxin. Additionally, germline expression of a DNA modifying enzyme that targets an essential gene occurs, and rescue achieved through inheritance of a recoded version of an essential gene.

Example 15—Cleavage Mediated Drive Targeting an Essential Gene on the X-Chromosome, Proof of Concept in *Drosophila melanogaster*

Figures 15A, 15B, 15C:
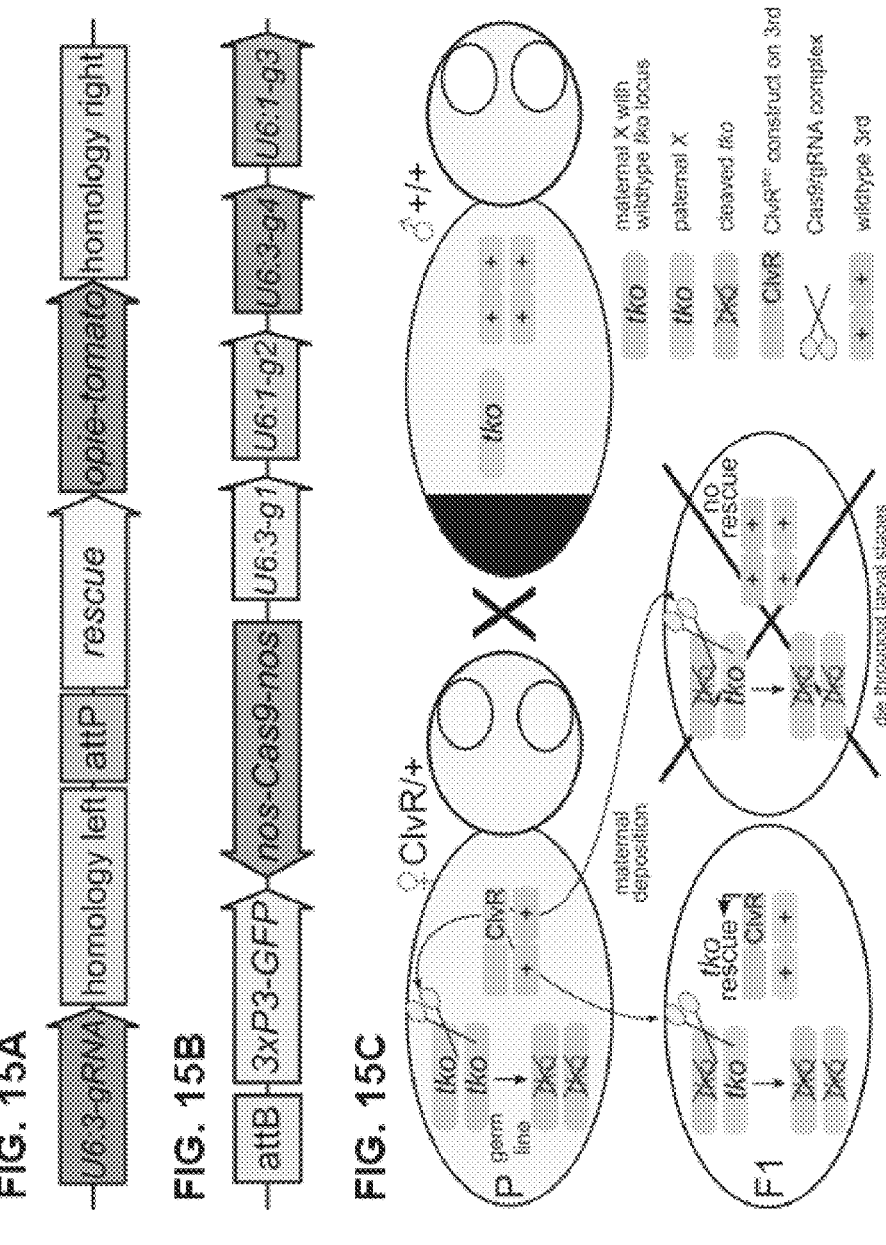
FIG. 15A-FIG. 15C show an embodiment of DNA sequence modification based gene drive (herein referred to as ClvR when a nuclease is used for DNA sequence modification) construct design and principle according to the present disclosure.

Example 15 is an embodiment of a single locus CleaveR drive system showing reduction to practice. FIG. 15A shows a schematic of an embodiment of a Construct A with a U6:3-gRNA, an attP site, the tko rescue copy from *Drosophila virilis* (Dv) and a ubiquitous opie2-td-tomato marker. Only elements between the homology arms were inserted into the germline via Cas9 mediated HR. FIG. 15B shows an embodiment of a Construct B with an attB site, a 3xP3-GFP marker, Cas9 driven by nanos regulatory elements, and a set of four U6 driven gRNAs. Construct B was integrated into the attP landing site of construct A via phiC31 integrase. FIG. 15C shows an embodiment of the principle of ClvR. Females heterozygous for the ClvR construct create cleaved tko alleles in the germline. Additionally, active Cas9/gRNA complex is deposited maternally to all embryos. Offspring without the rescue copy will die.

The cleavage mediated autosomal drive described herein (referred to as single locus CleaveR) consists of Cas9, 4 gRNAs which target an essential gene on the X-chromosome, and a recoded copy of this target gene which is immune to gRNA targeting, which are situated together on a different autosome (chromosome 3) than the target gene (FIG. 15C). FIG. 17 shows an embodiment of an alignment of the target gene (*Drosophila melanogaster* tko [second line]—Examples 15 and 16) with the recoded rescue based on *Drosophila virilis* tko. FIG. 37 shows an embodiment of an alignment of amino acid sequence of *D. virilis* tko (Dvir-Tko-aa) and the two annotated protein isoforms from *D. melanogaster* (Dm-Tko-aa-B and Dm-Tko-aa-C).

In males and females who carry at least one copy of the construct and at least one copy of the wild type target, the target gene is cleaved multiple times during gametogenesis, destroying the wild type copy of the gene and resulting in gametes bearing cleaved tko alleles (FIG. 15C). As transgenic individuals mate with wild types, cleaved copies of the essential gene will begin to accumulate in heterozygotes.

Additionally, if the CleaveR drive system is inherited through the female germline, all of the offspring will inherit Cas9 and gRNASs. Only offspring that carries the rescue encoded by CleaveR will survive (FIG. 15C). FIG. 38A- FIG. 38D show another embodiment of the ClvR construct design and principle Target Gene Selection and gRNA Design Two versions of the ClvR constructs were constructed using tko (technical knockout) on the X chromosome as the target for the ClvR system. The tko gene encodes a mitochondrial ribosome protein (Royden, Pirrotta, and January 1987). It is a recessive lethal. Benchling software suite was used to design gRNAs targeting the exonic regions of the genes at 4 sites. gRNAs were used based on on-target activity ranking (Doench et al. 2016). In addition gRNAs were selected so as to not cut in the rescue constructs (i.e., gRNAs have a mutated PAM in the rescue construct to avoid any potential off-target cleavage therein) (see below).

Cloning of ClvR Constructs and Fly Germline Transformation

All plasmids were assembled with standard molecular cloning techniques and Gibson assembly (Gibson et al. 2009). All restriction enzymes, enzymes for Gibson Assembly mastermix and Q5 polymerase used in PCRs were from NEB. Gel extraction kits and JM109 cells for cloning from Zymo Research. The gRNA cassette and Cas9 were based on pCFD3(4)-dU6:3gRNA and pnos-Cas9-nos which were a gift from Simon Bullock (Port et al. 2014) (Addgene #49410 and #62208) and modified as described previously (Oberhofer, Ivy, and Hay 2018). Construct A (FIG. 15A) was inserted into the fly germline via Cas9 mediated homologous recombination. Construct B (FIG. 15B) was integrated into an attP landing site within construct A using the phiC31 site-specific integration system.

The experiment was started with a plasmid having a dU6:3 promoter and a modified guide scaffold (Dang et al. 2015) separated by BsmBI cutsites from previous work (Oberhofer, Ivy, and Hay 2018), which was based on pCFD3-dU6:3gRNA, a gift from Simon Bullock (Addgene plasmid #49410) (Port et al. 2014). Restriction digestion was performed with BsmBI and ligated annealed oligos (PO-68E FWD+PO-68E REV) as described on flycrispr.molbio-.wisc.edu. This gRNA targets a region on the third chromosome (68E) which was chosen based on the location of an attP landing site in a widely used fly strain, zh-68E (Bischof et al. 2007). Next, the plasmid was cut with HindIII and SpeI and the following 4 fragments were assembled in a Gibson reaction (Gibson et al. 2009) to yield plasmid p68-tko-step1 (see FIG. 15A):

Two homology arms, approximately 1 kb in length up and downstream of the above gRNA target site were amplified from genomic DNA with primers P9+P10 and P15+P16; an attP site with primers P11+P12; a 4.2 kb rescue fragment with primers P13+P14. The rescue fragment was based on the tko genomic region of *Drosophila virilis*, a distant *Drosophila* species (*Drosophila* 12 Genomes Consortium et al. 2007). Additionally, 6 silent point mutations were introduced in the ORF of Dv-tko in order to avoid homology stretches >14 bp. The rescue was gene synthesized by IDT as two gBlock fragments with an additional 2 point mutations introduced in the intron to work around a synthesis complexity issue. Finally, a td-tomato marker (Shaner et al. 2004) driven by the ubiquitous opie2 promoter (Theilmann and Stewart 1992) with primers P15+P16 was used as the dominant marker.

Construct p68-tko-step1 (see FIG. 15A) was injected into a fly strain expressing Cas9 in the germline under nanos regulatory regions (Bloomington stock #54591) (Port et al. 2014). All injections were carried out by Rainbow Transgenic Flies.

Male injected G0 flies were outcrossed to w- and the progeny was scored for ubiquitous td-tomato expression. Male transformants were crossed to a TM3,Sb/TM6b,Tb balancer stock. Flies carrying the marker over TM3,Sb, were pooled and used as the injection strain for the 2nd construct following below.

For construct tko-step2 (FIG. 15B and FIG. 48), two constructs having two gRNAs each were subcloned. Construct pU6:3-U6:1-tandem (Oberhofer, Ivy, and Hay 2018) (based on (Port et al. 2014)) was digested with BsmBI and ligated back in two gRNAs encoded in the primer overhangs: P21+P22 and P23+P24.

A plasmid that had a 3xP3-GFP marker gene, an attB site as well as parts of nos-Cas9-nos flanked by gypsy insulators was digested with EcoRV and BglII. In a three fragment Gibson reaction full length nos-Cas9-nos, as well as the two gRNA cassettes from above were assembled to yield the final construct ptko-B. Cas9 was amplified with primers P25-nosCas9 FWD+P26-nos-Cas9 REV, guide cassette A with P27-guidesA FWD+P28-guidesA REV, and guide cassette B with P29-guidesB FWD+P30-guidesB REV.

Construct B was injected along with a phiC31 helper plasmid (Rainbow Transgenic Flies). Injected G0 flies were outcrossed to w- and the progeny was screened for 3xP3-GFP expression. Transgenic males were used to cross to the balancer stock TM3,Sb/TM6b,Tb as well as w[1118]. Flies carrying the GFP marker over TM3,Sb were pooled to generate the balanced stock and flies homozygous for the ClvR construct were collected in the next generation. All primers are shown in TABLE 1, and vector sequences are provided in SEQ ID NO: 39 (p68-tko-step1; FIG. 15A), SEQ ID NO: 40 (tko-step2; FIG. 15B), and SEQ ID NO: 41 (Dvir-rescue-modified; "rescue" in FIG. 15A and FIG. 17).

TABLE 1

| PRIMERS | | |
|---|---|---|
| Primer | Sequence | SEQ ID NO: |
| PO-68E FWD | gtcgTGCACAACCAGAGACTGGAG | 1 |
| PO-68E REV | aaacCTCCAGTCTCTGGTTGTGCA | 2 |
| P9-68E-hr-left FWD | cttattacgtggccaactaggtgcccaaaatgtgtgtgga | 3 |
| P10-68E-hr-left REV | GCTTCGGTGTGTCCGTCAGTgagaggttttgccgcgattt | 4 |
| P11-attP FWD | aaatcgcggcaaaacctctcACTGACGGACACACCGAAGCC | 5 |
| P12-attP REV | ccttgctgcccgcctgcagcAGTCGCGCTCGCGCGACTGA | 6 |
| P13-dv-tko FWD | TCAGTCGCGCGAGCGCGACTgctgcaggcgggcagcaagg | 7 |
| P14-dv-tko REV | gcagtgcaaaaaagttggtggggtcggacctcaagttgcatatgg | 8 |
| P15-68E-hr-right FWD | tgcaacttgaggtccgaccccaccaactttttttgcactgc | 9 |

TABLE 1-continued

PRIMERS

| Primer | Sequence | SEQ ID NO: |
|---|---|---|
| P16-68E-hr-right REV | gggcgaattgggtacaagctaggatgatgggatgctggaa | 10 |
| P21-tko-guidesA FWD | ctattttcaatttaacgtcgctgcagcgatgccattccaGTTTCa CgagctaTGTGgaaa | 11 |
| P22-tko-guidesA REV | ttcCAGCAtagctctGAAACtcgccaagggcgttgtcctgCgaagtt cacccggatatct | 12 |
| P23-tko-guidesB FWD | ctattttcaatttaacgtcgcaacattgtactgtgccgcgGTTTCag agctaTGCTGgaa | 13 |
| P24-tko-guidesB REV | ttcCAGCAtagctctGAAACatcgaaagtgcgtgctggtgCgaagttca cccggatatct | 14 |
| P25-nosCas9 FWD | GTTGTCTATACTATAAGATCTATAGGCACGGGAT AACGCT | 15 |
| P26-nos-Cas9 REV | GCAATCACAGGTGAGCAAAAAAGCTTGGATTTC ACTGGAACT | 16 |
| P27-guidesA FWD | AGTTCCAGTGAAATCCAAGCttttttgctcacctgtgattgc | 17 |
| P28-guidesA REV | aatcacaggtgagcaaaaaaaattaaccctcactaaaggga | 18 |
| P29-guidesB FWD | ccctttagtgagggttaattttttttgctcacctgtgatt | 19 |
| P30-guidesB REV | gcagcctcgagatcgatgattgccgagcacaattgtctag | 20 |
| tko-seq1 | aagcgttccaagctgcacag | 21 |
| tko-seq2 | cgcacatccatttccaattg | 22 |
| tko-seq3 | cacacacacaggtgcgttc | 23 |
| tko-seq4 | acaactagacgttggcaatcTCACACCTTCCTCTTCTTCTT | 24 |
| tko-seq5 | tcagcgggattagtgtaagt | 25 |
| tko-seq6 | catatgcaacttgaggtccg | 26 |
| s2-attB-rev | ttcgagaccgtgacctacat | 27 |
| s2-u631-seq | AGTTCCAGTGAAATCCAAGC | 28 |
| T3-seq REV | gttccctttagtgagggttaatt | 29 |
| T3-seq FWD | ATTAACCCTCACTAAAGGGA | 30 |
| CAS91F | ATGGACAAGAAGTACTCCATTG | 31 |
| CAS91R | GATCGGTATTGCCCAGAACT | 32 |
| CAS92F2 | AGCGCTAGGCTGTCCAAATC | 33 |
| CAS93F | GAGAAAATCCTCACATTTCGG | 34 |
| CAS94F2 | AGAGTGGAAAGACAATCCTGG | 35 |
| CAS95F | CTGAACGCCAAACTGATCAC | 36 |
| CAS96F | TGGACGCCACACTGATTCAT | 37 |
| CAS96R | TCACACCTTCCTCTTCTTCTT | 38 |

Example 16—ClvR Effect in Females and Males

To determine the rate of germline cleavage and carryover effect in females carrying the ClvR element, heterozygous females were crossed to w[1118] males and scored the progeny for the dominant opie2-td-tomato marker of the ClvR construct. Under normal mendelian rules only half of the progeny should carry this marker. Among the 2580 progeny from these crosses all carried the opie2-td-tomato dominant marker, showing that the system works efficiently when transmitted through females (see FIG. 9A and FIG. 16A), data in the Punnett square below each cross figure.

To determine the cleavage rate in the male germline, crosses were set up between males heterozygous for the ClvR element and females carrying a mutant copy of tko over the FM7a X-chromosome balancer (tko$^3$/FM7a/Dp(1; 2; Y)w+, BDSC_4283). Female offspring of this cross will inherit one X-chromosome from the father and one from the mother. Female offspring inheriting the mutant tko allele from the mother and not carrying the ClvR element with the rescue copy of tko will be dead, if tko was cleaved in the male germline (see FIG. 16B).

Figures 16A, 16B:
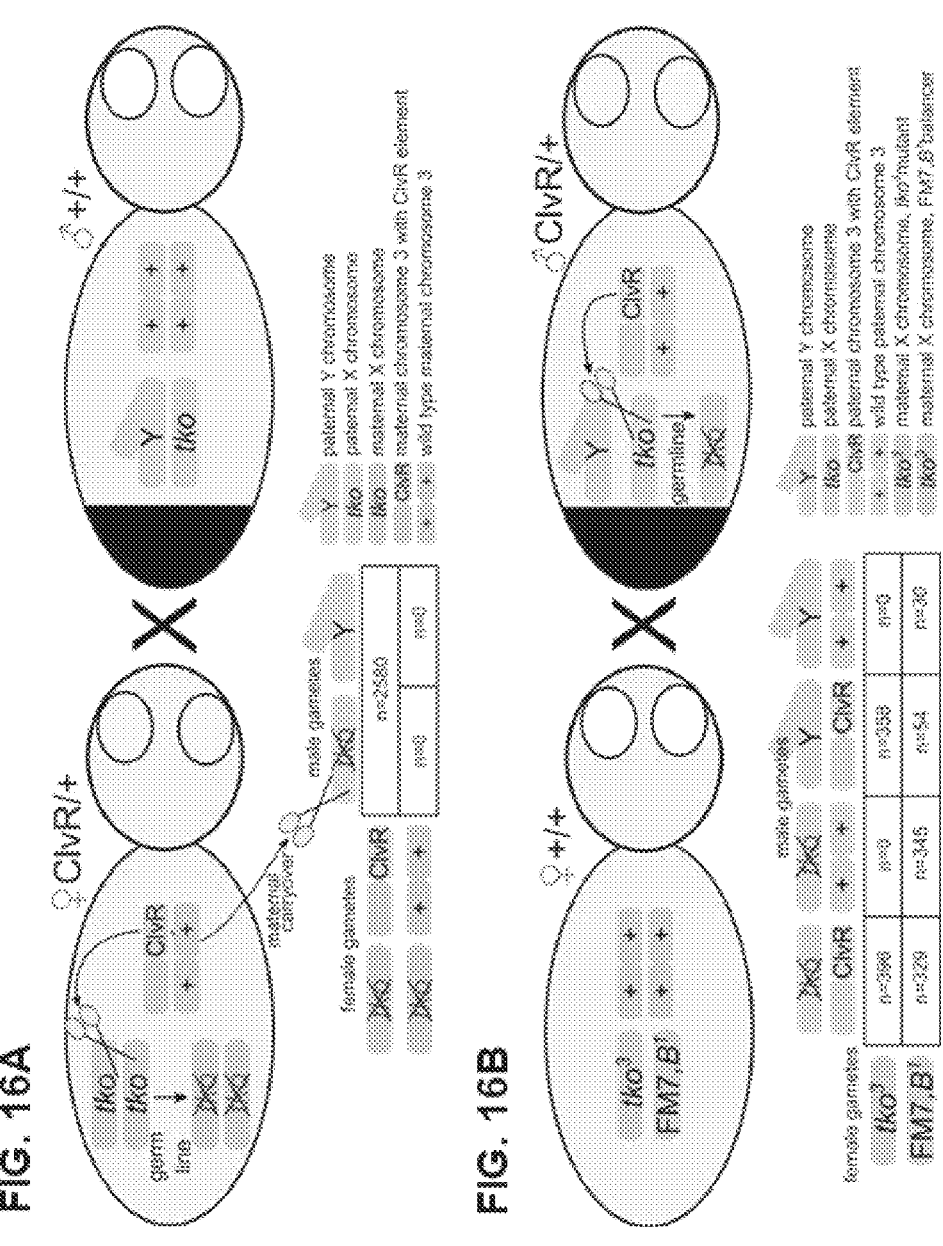
FIG. 16A-FIG. 16B show an embodiment of a determination of the effects of a CleaveR drive when transmitted through the female (FIG. 16A) or male (FIG. 16B) germline.

For FIG. 16A, B, female is shown on the left, male is shown on the right, and Cas9/gRNA complex is indicated as scissors. Top row in Panel A and B indicates the cross, lower row shows a punnett square with gametes indicated and numbers of scored progeny in the corresponding fields. Numbers showing the effect of CleaveR are indicated (FIG. 16A) Females heterozygous for the CleaveR system were crossed to wildtype males. The Cas9/gRNA complex encoded by the CleaveR element, cleaves all wildtype copies of tko in the female germline. In addition active complexes get deposited maternally into all embryos, leading to subsequent cleavage of the paternal tko allele in the zygote. Only offspring that inherited the rescue copy from the CleaveR construct were viable, showing that the CleaveR system works efficiently in the female germline and also brings about maternal carryover-dependent cleavage. In FIG. 16B, males heterozygous for the CleaveR element were crossed to a tko mutant. The only copy of widtype tko on the single male X-chromosome was cleaved in the male germline by the CleaveR system. When the cleaved tko allele was paired with the maternal mutant X-chromosome (tko3), only those animals that also inherit the rescue encoded by the CleaveR element survived, all others died. Actual data is shown in the Punnet squares below each cross. Results showed successful implementation of the DNA sequence modification-based gene drive according to the embodiments disclosed herein. FIG. 42A-FIG. 42C show another example of the effect of ClvR effect in females and males.

Example 17—ClvR Effect in Females and Males

Figure 18B:
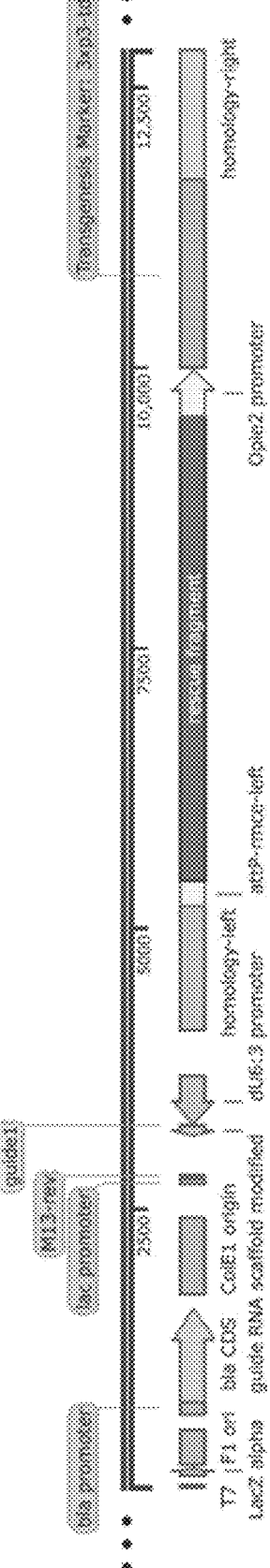
FIG. 18B shows a schematic of an embodiment of the components of the step 1 of FIG. 18A (Example 17).
Figure 18C:
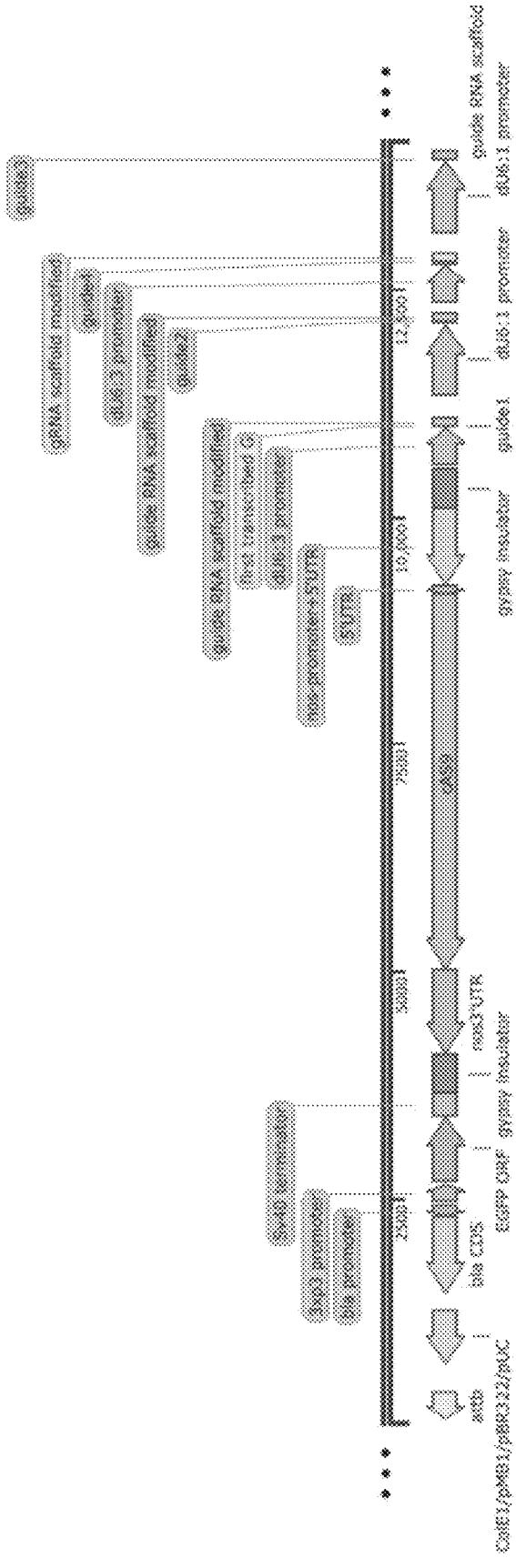
FIG. 18C shows a schematic of an embodiment of the components of the step 2 of FIG. 18A (Example 17).

FIG. 18A show a schematic of an embodiment of the components of the DNA sequence modification-based gene drive implemented in the example below, targeting the X-linked locus tko in *Drosophila*, using a third chromosome-based gene drive element. FIG. 18B (SEQ ID NO: 42) shows a schematic of an embodiment of the components of the step 1 transgenic created for the DNA sequence modification-based gene drive implemented for targeting the X-linked locus tko in *Drosophila*, using a third chromosome-based gene drive element. This construct was inserted into the *Drosophila* genome using homologous recombination, based on the left and right homology arms. FIG. 18C (SEQ ID NO: 43) shows a schematic of an embodiment of the components of the step 2 construct created for the DNA sequence modification-based gene drive implemented for targeting the X-linked locus tko in *Drosophila*, using a third chromosome-based gene drive element. This construct was inserted into the step 1 genomic region using the attb site-specific integrase target site. FIG. 19 shows an embodiment Sanger sequencing results of the gRNA1 target region of the *Drosophila* wildtype version of the tko gene and offspring: ♂ClvR$^{tko}$/+ offspring from ♀ClvR$^{tko}$/+XX ♂[1118] parents. The wildtype sequence is shown as well as products of ClvR action, which contain indels. Two flies were sequenced from 9 different single fly crosses each. All 18 analyzed flies showed indels of varying sizes at the gRNA1 target site. Results showed successful implementation of the DNA sequence modification-based gene drive according to the embodiments disclosed herein.

In some embodiments, any of the embodiments or arrangements in Examples 1-17 and Example 24 can be modified for a two vector or two locus arrangement, as described herein. See, Example 40 and FIG. 49A-49E for a specific implementation.

Example 18

ClvR selfish genetic elements can be implemented in single locus or two-locus formats. FIGS. 20A-D show schematics of embodiments of single locus ClvR (FIG. 20A), and two locus ClvR involving components located on two separate chromosomes (FIGS. 20B-D). In single locus ClvR the Rescue transgene and any associated cargo are always inherited together with components encoding the DNA sequence modifying enzyme. In contrast, in two locus ClvR, the ClvR components are distributed between two separate chromosomes. In this latter configuration they are free to segregate independently from each other during meiosis or other times when the two different genetic elements they are associated with are not co-inherited. Independent segregation gives two locus ClvR multiple unique characteristics: drive is transient, limited in space, and reversible. These points are detailed in Examples 34 and 35.

Example 19

In two locus ClvR with recombination, ClvR components are located on the same chromosome at some distance less than 50 map units away from each other. This configuration is illustrated for three different two locus ClvR configurations in FIGS. 21A-C. FIGS. 21A-C show schematics of embodiments of two locus ClvR involving components located on the same chromosome at a distance of less than 50 map units. Gene drive in this configuration will have behavior intermediate between that of single locus ClvR and two locus ClvR in which the components parts are freely recombining, on the same chromosome but separated by greater than 50 map units, or on separate chromosomes. Drive in such a system starts out similar to that of single locus ClvR, but begins to decay as recombination separates the components. Since this decay occurs more slowly than with two locus ClvR on separate chromosomes, drive remains stronger for a larger number of generations. However, ultimately, as with two locus ClvR on two different chromosomes, the frequency of the gene or genes encoding the DNA sequence modifying enzyme decrease as they find themselves in individuals lacking a functional copy of the essential gene. In consequence, ultimately, as with two locus ClvR in Example 18, ClvR with recombination is transient, limited in space, and reversible through dilution with wildtypes. These points are illustrated in a population genetic model for two locus ClvR on two different chromosomes in FIGS. 34A-F and FIGS. 35A-F and FIG. 50, Example 41.

Example 20

Separation of a functional Rescue from the Cargo can be prevented (or reduced) by locating the Cargo in an intron of the Rescue. Cargo and recoded rescue will often have minimal homology with surrounding sequences on homologous chromosomes, and thus are unlikely to recombine away from each other through traditional homologous recombination during meiosis. However, a break between the two genes followed by reciprocal end joining with the same region on the homologous chromosome could potentially separate them, though the frequency of this kind of event is unclear. Locating the ClvR cargo in an intron of the Rescue transgene (bottom panel) prevents breakage and end joining-mediated separation of a functional Rescue (the key component driven into the population by ClvR) from the Cargo. Separation could otherwise generate empty ClvR elements (ClvR$^{\Delta cargo}$, top panel), or Rescue only elements (ClvR$^{rescue}$, middle panel), the spread of which provide no beneficial function. Crossed lines indicate sites of chromosome breakage and end joining with a similar position on a homologous chromosome. Recombinant products of interest are indicated by the dotted lines. FIG. 22 shows a schematic of an embodiment of ClvR in which the Cargo transgene is located in an intron of the Rescue transgene. Similar considerations apply to two locus versions also.

Example 21

Separation of a functional Rescue from the Cargo can be prevented (or reduced) by locating the Cargo between two transgenes whose co-expression is required to produce a functional Rescue essential enzyme, such as dihydrofolate reducatse. In FIG. 23 the 5' half of DHFR is driven by its own promoter. The 3' half is driven by a strong ubiquitous promoter. The two domains are brought together to form an active enzyme through heterodimerization, mediated by specific domains at the N-terminus of each protein (boxes with diagonal lines). FIG. 23 shows a schematic of an embodiment of ClvR in which the cargo is located between two transgenes whose co-expression is required to create a functional Rescue protein. Similar considerations apply to two locus versions also.

Example 22

Separation of a functional Rescue from the Cargo can be prevented by locating the Cargo between two transgenes whose co-expression is required to produce a functional Rescue protein. Here this is achieved using a two-component transcription-based system. The gene promoter from the essential gene drives the expression of a heterologous transcriptional activator such as GAL4. The Rescue transgene contains GAL4 UAS binding sites sufficient to drive GAL4-dependent expression, upstream of an otherwise promoterless (lacking its own promoter), recoded Rescue transgene. FIG. 24 shows a schematic of an embodiment of ClvR in which the Rescue and the Cargo transgenes are arranged such that the Cargo is located between two transgenes, the presence of both of which is required for expression of a functional Rescue transgene. Similar considerations apply to two locus versions also.

Example 23

When cleavage results in a DNA break it can be repaired using multiple repair pathways, including homologous recombination. When homologous recombination is used the sequence of the repair template is important. If the repair template encodes a modified sequence that is LOF with respect to the essential gene and uncleavable (due to the sequence modification(s)), then the LOF allele is copied in place of the wildtype cleaved allele. In this way single and two locus versions of ClvR can create new LOF alleles through homologous recombination as well as through error prone pathways such as non-homologous end joining or microhomology-dependent end joining. FIG. 25 shows a schematic illustrating how ClvR can create LOF alleles using homologous recombination.

If ClvR-encoded DNA sequence modifying activity is able to move between cells in a population its relative frequency can increase as the essential gene in neighboring wildtype cells is modified to a LOF sequence. FIG. 26 shows a schematic illustrating how movement of the site-specific DNA modifying enzyme between cells can result in selection for ClvR-bearing genotypes.

Example 24

ClvR mediated drive targeting an essential gene on the second or third chromosomes, proof of concept reduction to practice in *Drosophila melanogaster.*

Figure 27:
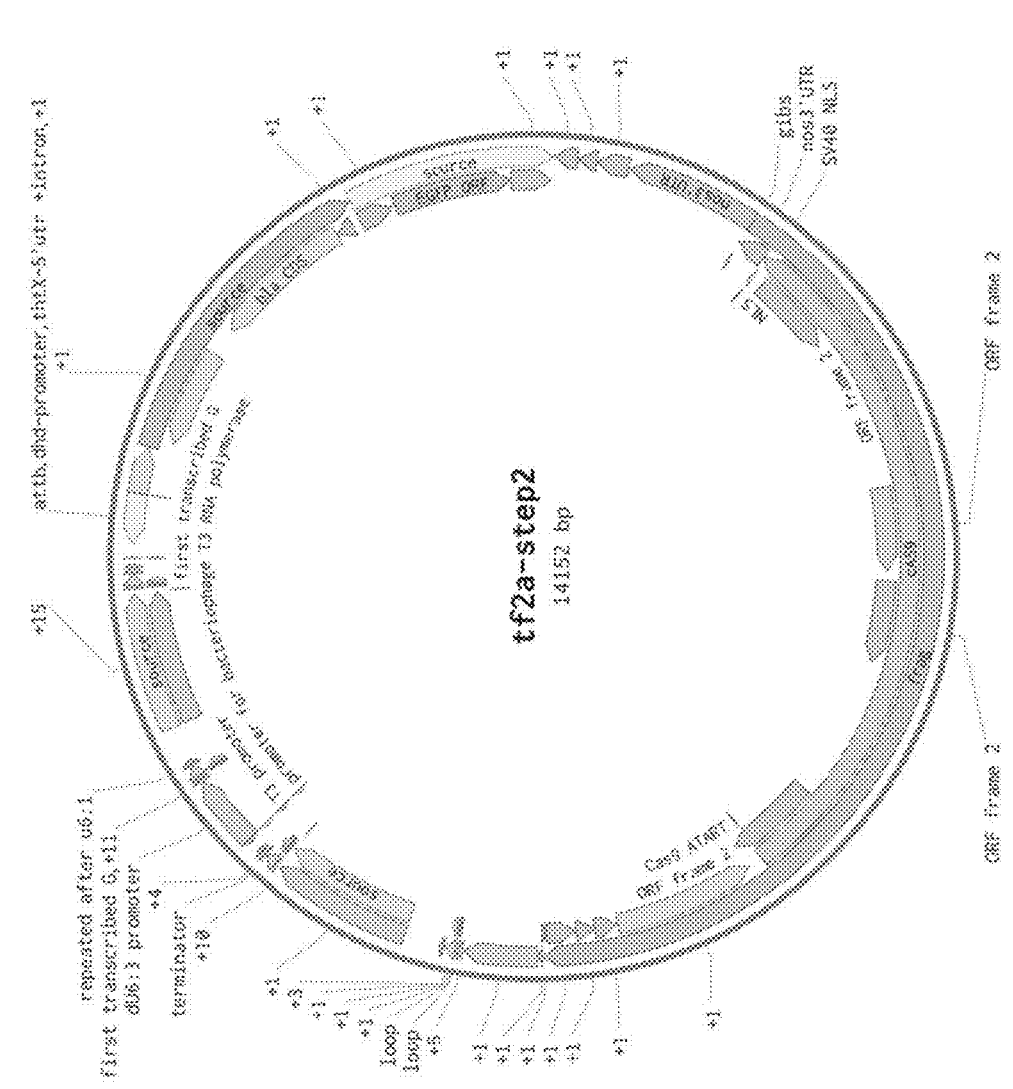
FIG. 27 shows a schematic of the second step construct for ClvR$^{tf2a}$. Sequence is listed in file labeled tf2a-step2-sequence. Sequence of step 1 *Drosophila suzukii* Rescue transgene is listed in sequence file tf2a-*suzukii-melanogaster*-alignment.
Figure 47:
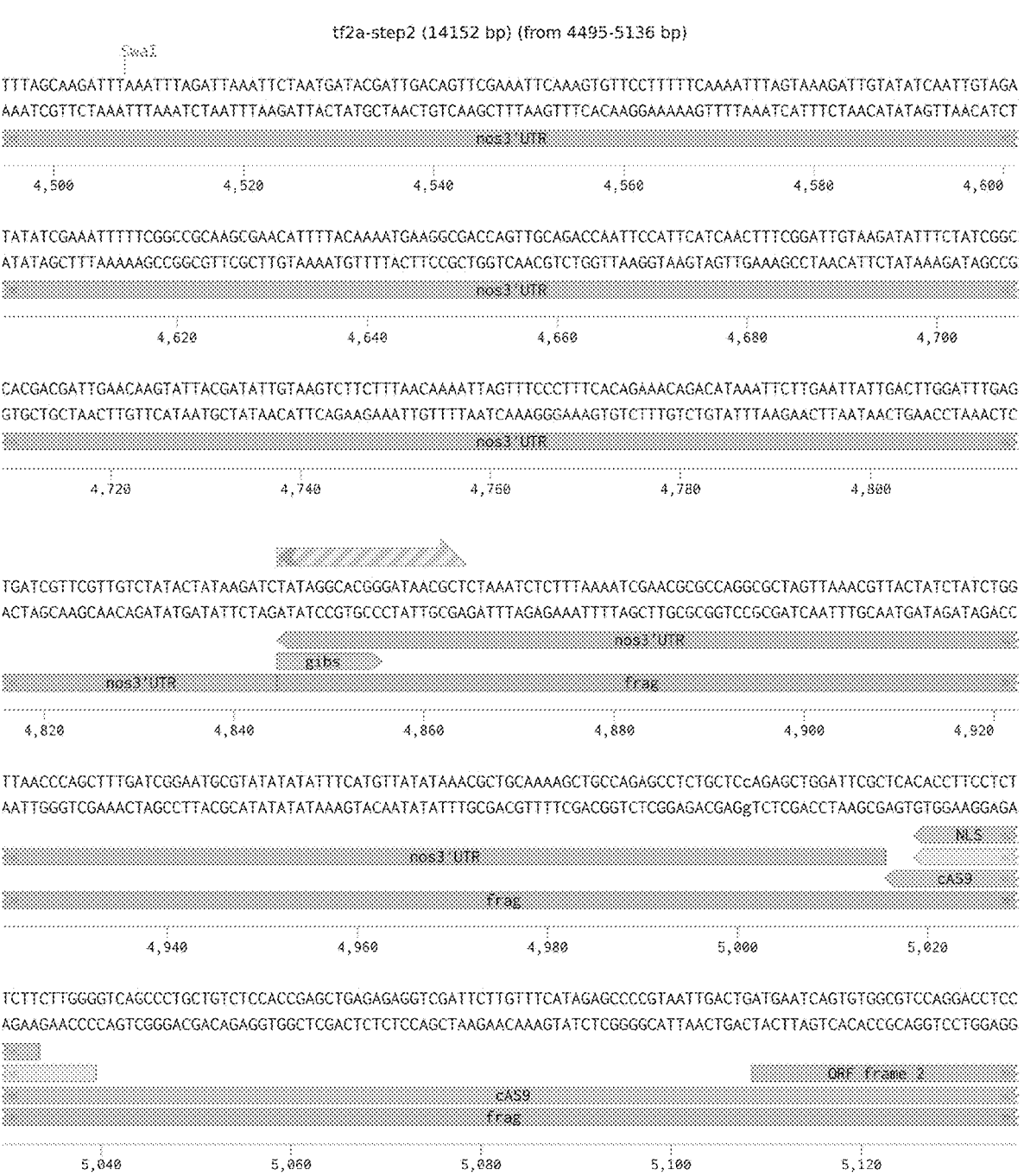
FIG. 47 depicts a sequence of some embodiments.
Figure 48:
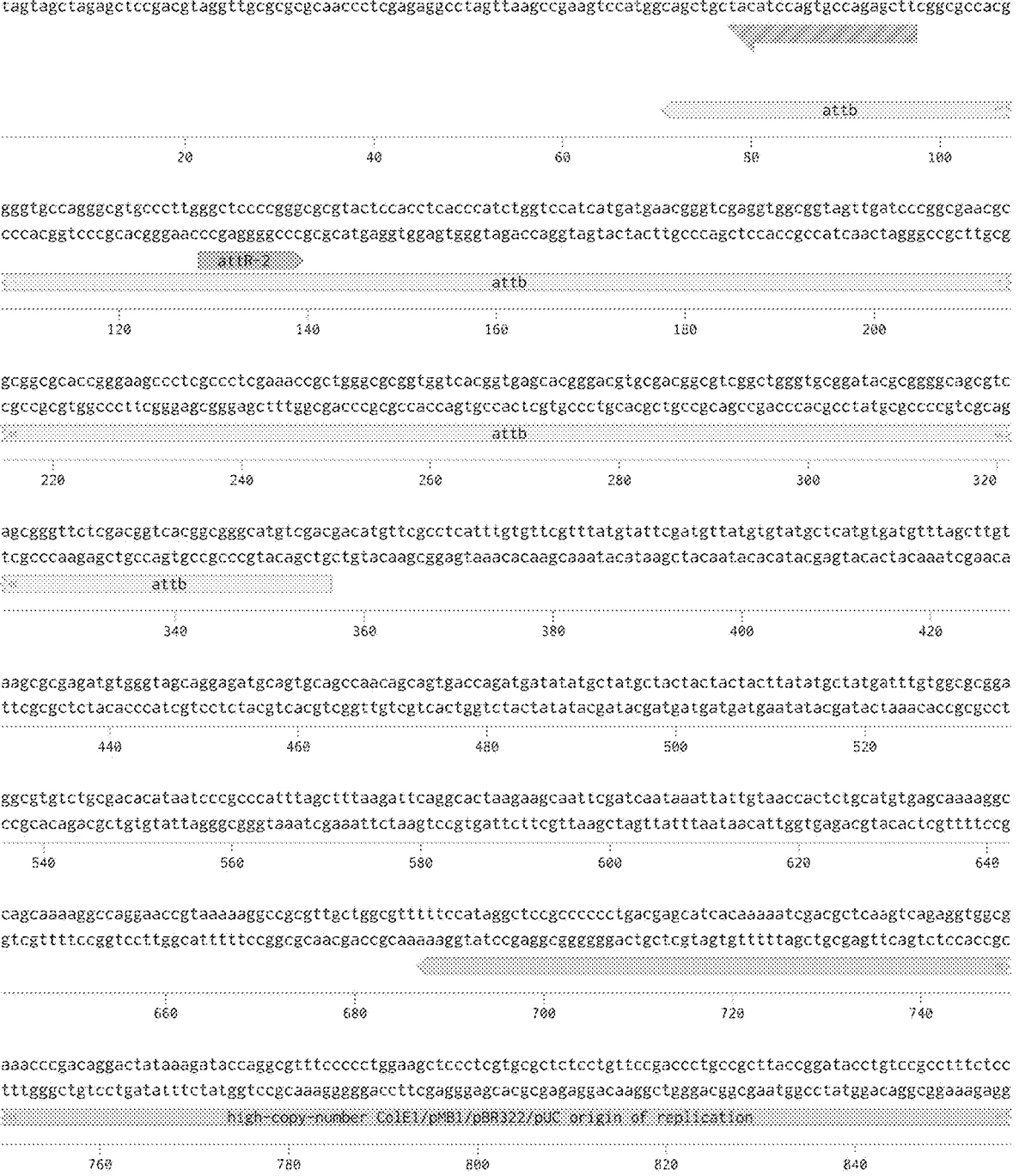
FIG. 48 depicts a sequence of some embodiments.
Figure 48:
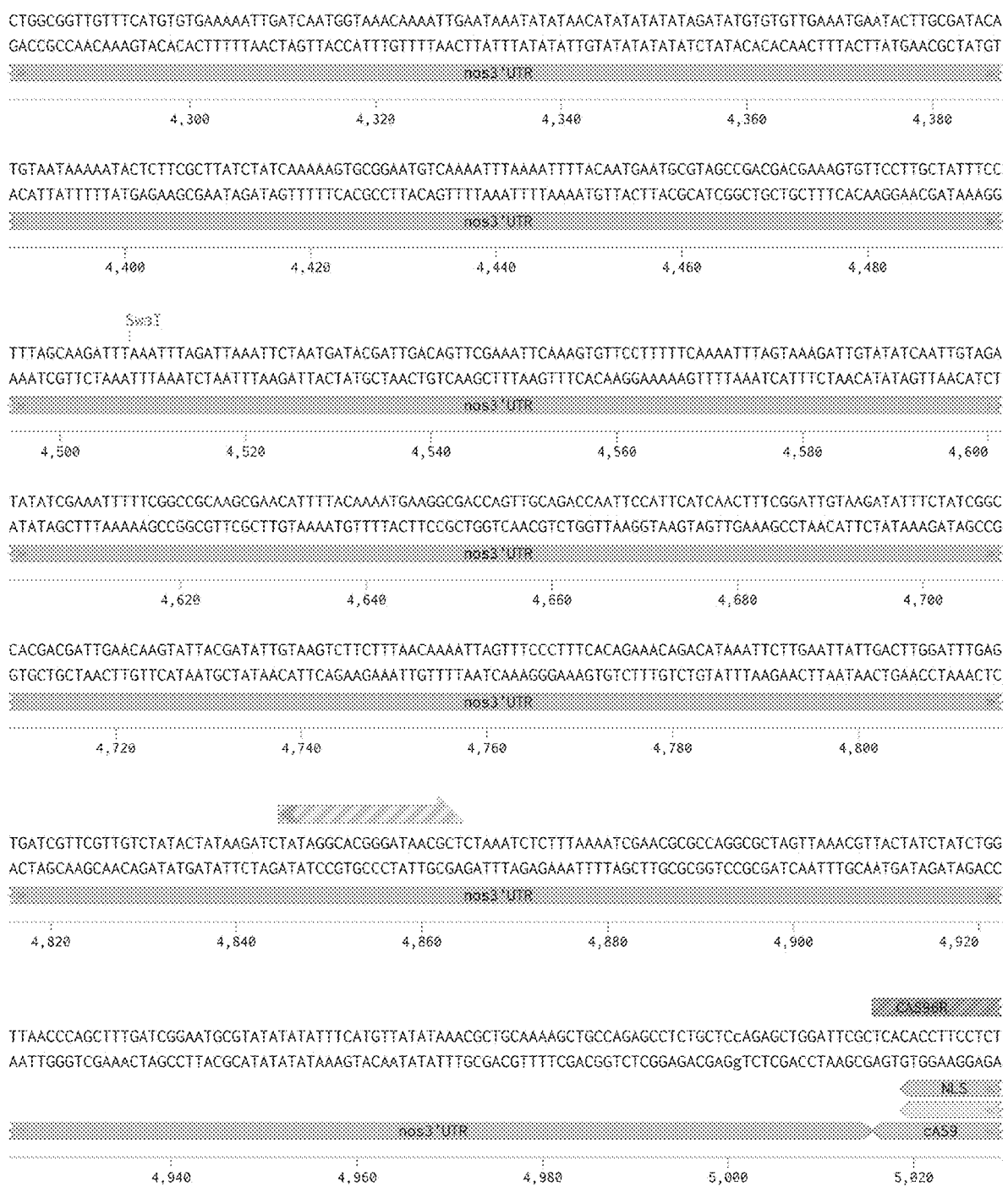
Figure 48:
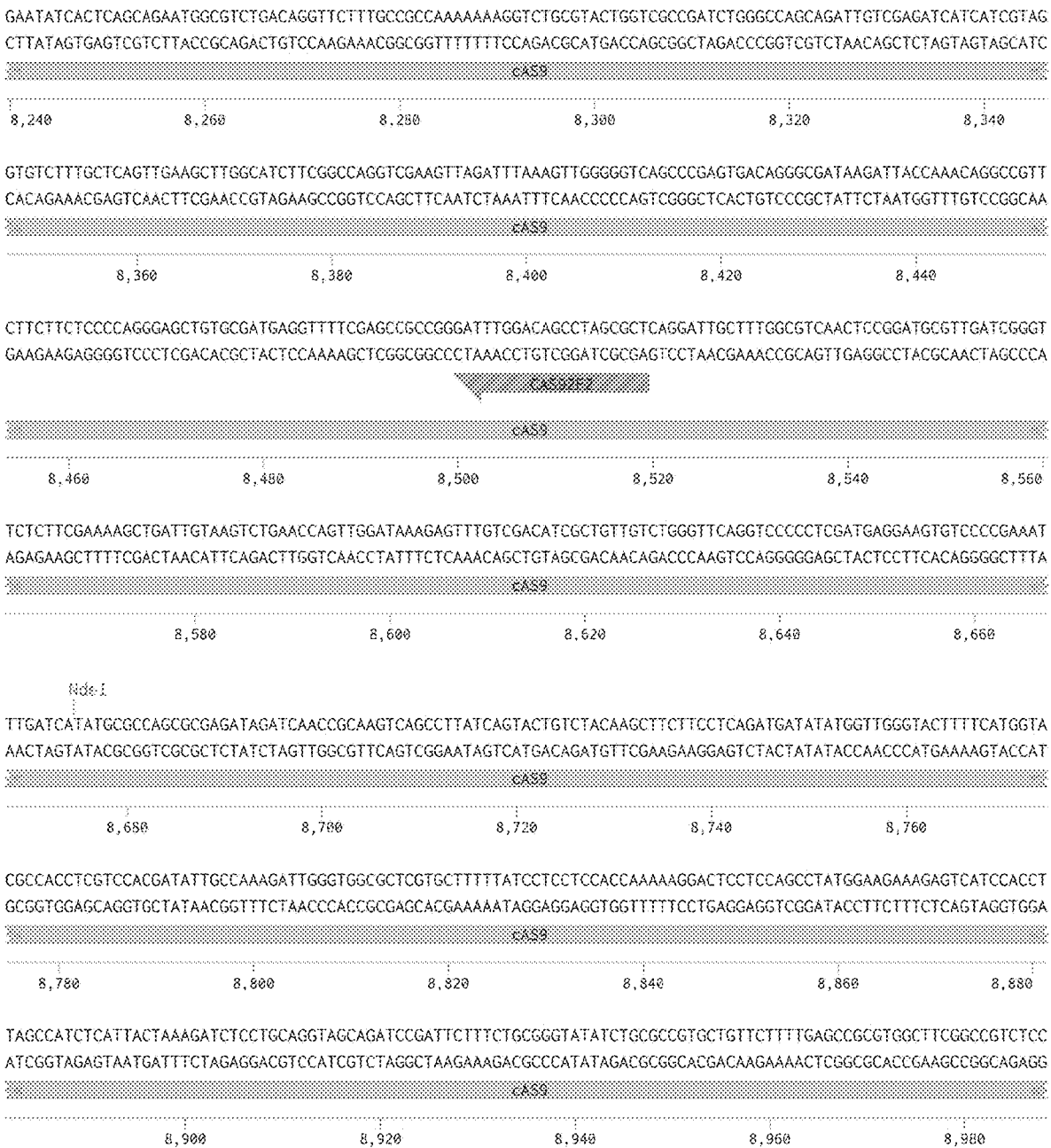
Figure 48:
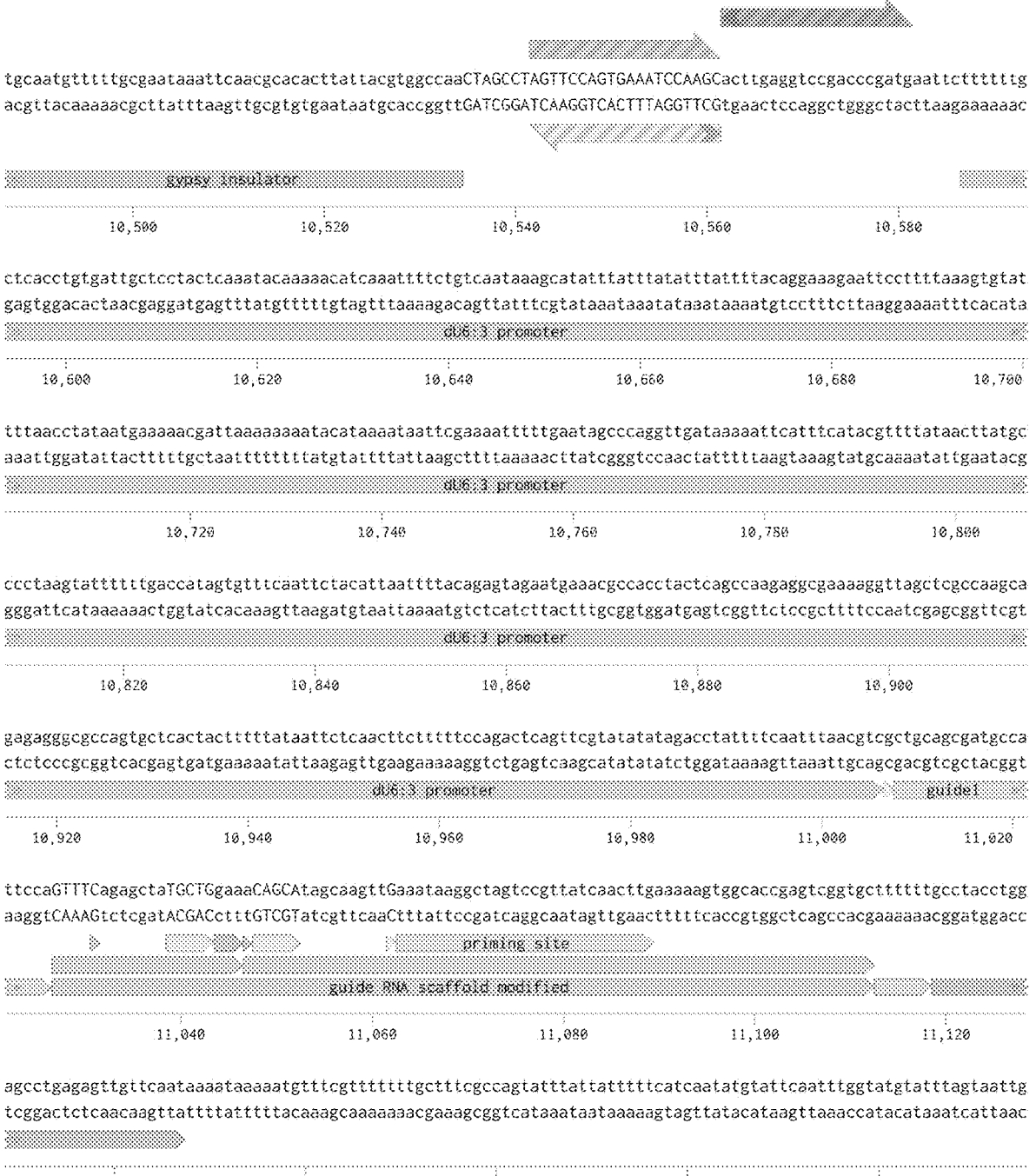

Creation of ClvR$^{Tf2a}$. The *Drosophila* gene TfIIas was chosen for targeting. A rescue version, carrying many changes from that of *Drosophila melanogaster* (as shown in FIG. 46) was introduced into the same third chromosome site as for ClvRtko. Flies carrying this construct then had introduced into the same locus a step 2 construct encoding gRNAs designed to target *Drosophila melanogaster* TfIIas, but not the recoded version (as shown in FIG. 47). This construct is shown in FIG. 27.

Figure 28:
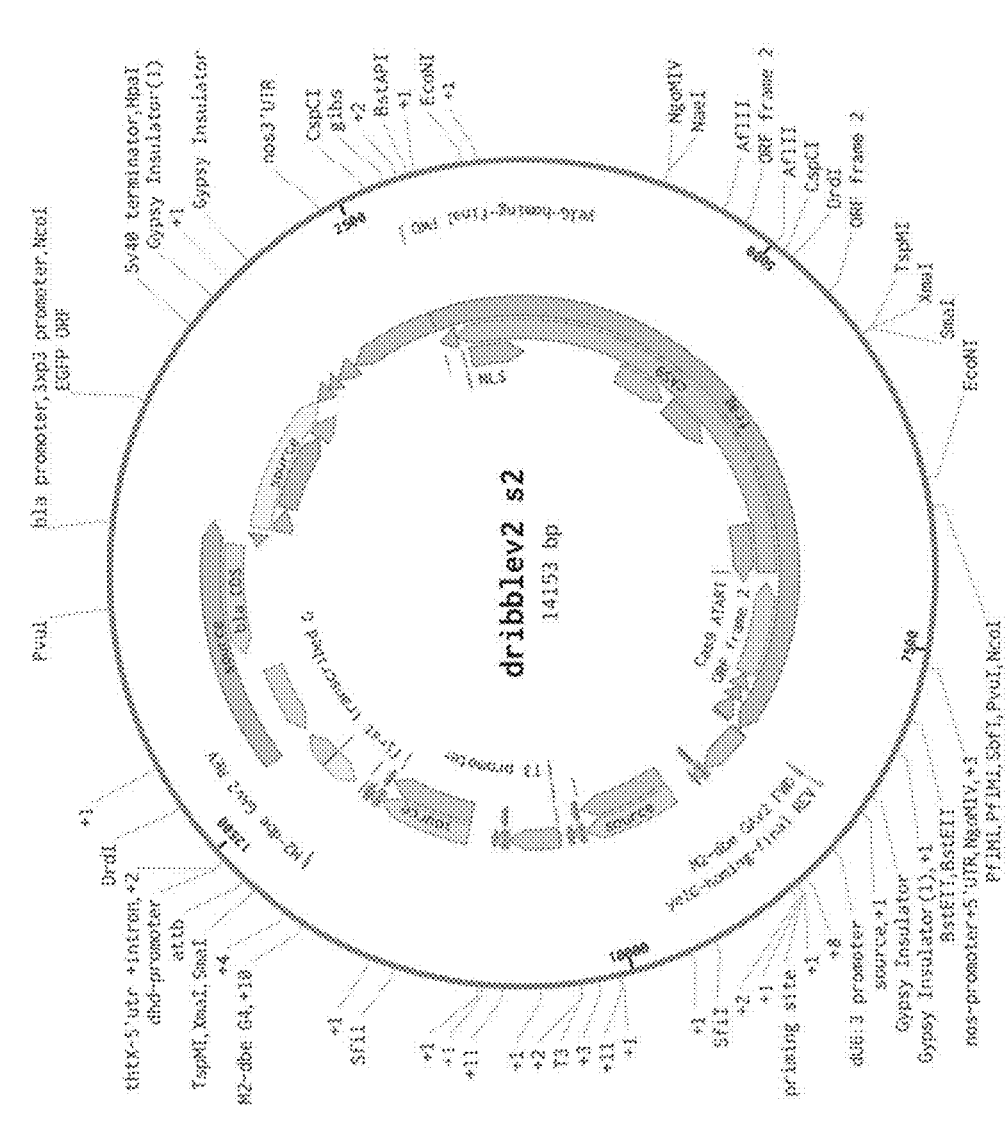
FIG. 28 shows a schematic of the second step construct for ClvR$^{dbe}$. Sequence is listed is file labeled dribble2-s2-sequence. Sequence of step 1 *Drosophila suzukii* Rescue transgene and alignment with *Drosophila melanogaster* sequence is in sequence file dribble-Dsuz-swFB-BLASTN.
Figure 44:
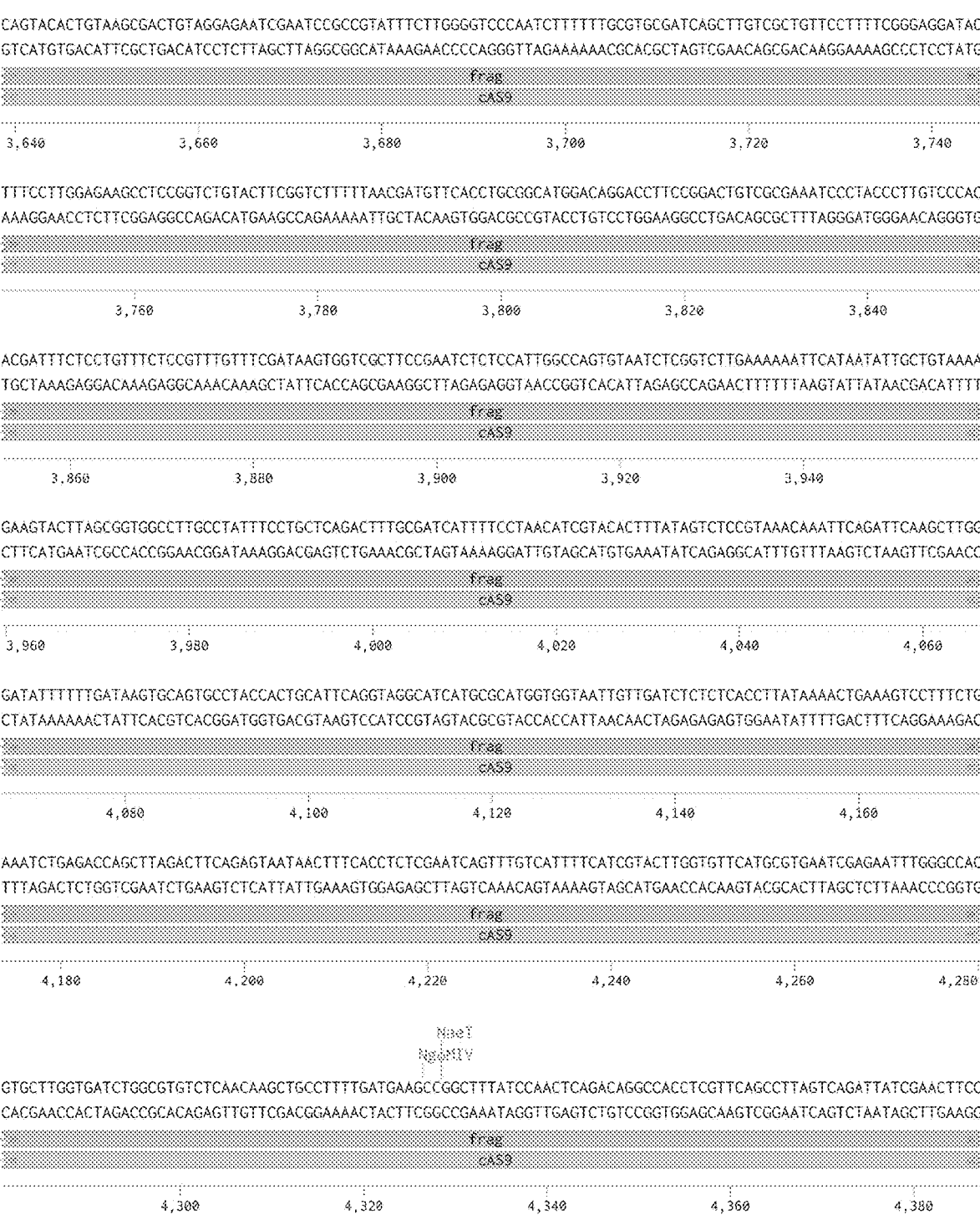
FIG. 44 depicts a sequence of some embodiments.
Figure 45:
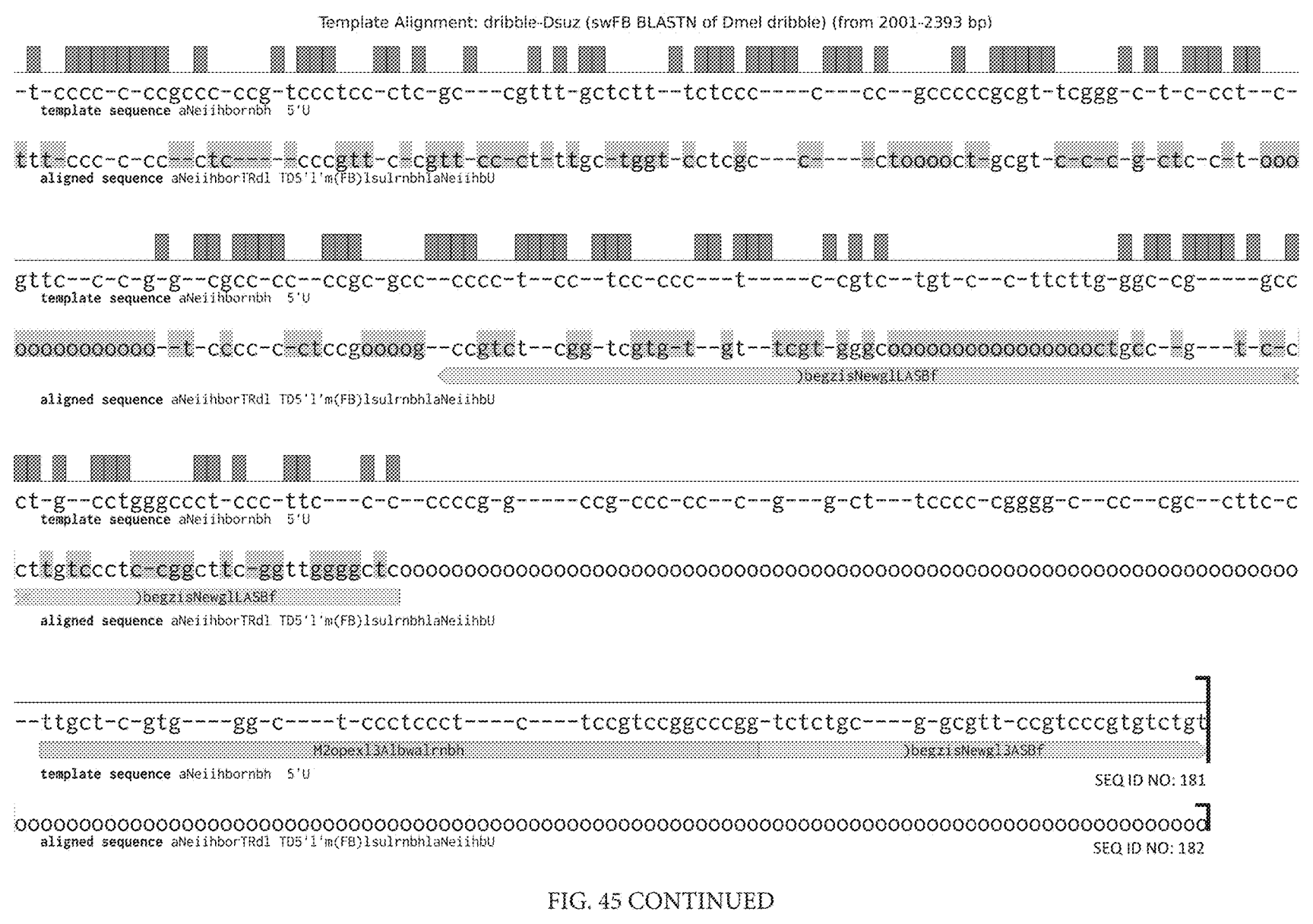

Creation of ClvR$^{dbe}$. The *Drosophila* gene dbe was chosen for targeting. A rescue version, carrying many changes from that of *Drosophila melanogaster* (as shown in FIG. 45) was introduced into the same third chromosome site as for ClvR$^{tko}$. Flies carrying this construct then had introduced into the same locus a step 2 construct encoding gRNAs designed to target *Drosophila melanogaster* dbe, but not the recoded version (as shown in FIG. 44). This construct is shown in FIG. 28.

Figures 29A, 29B, 29C, 29D:
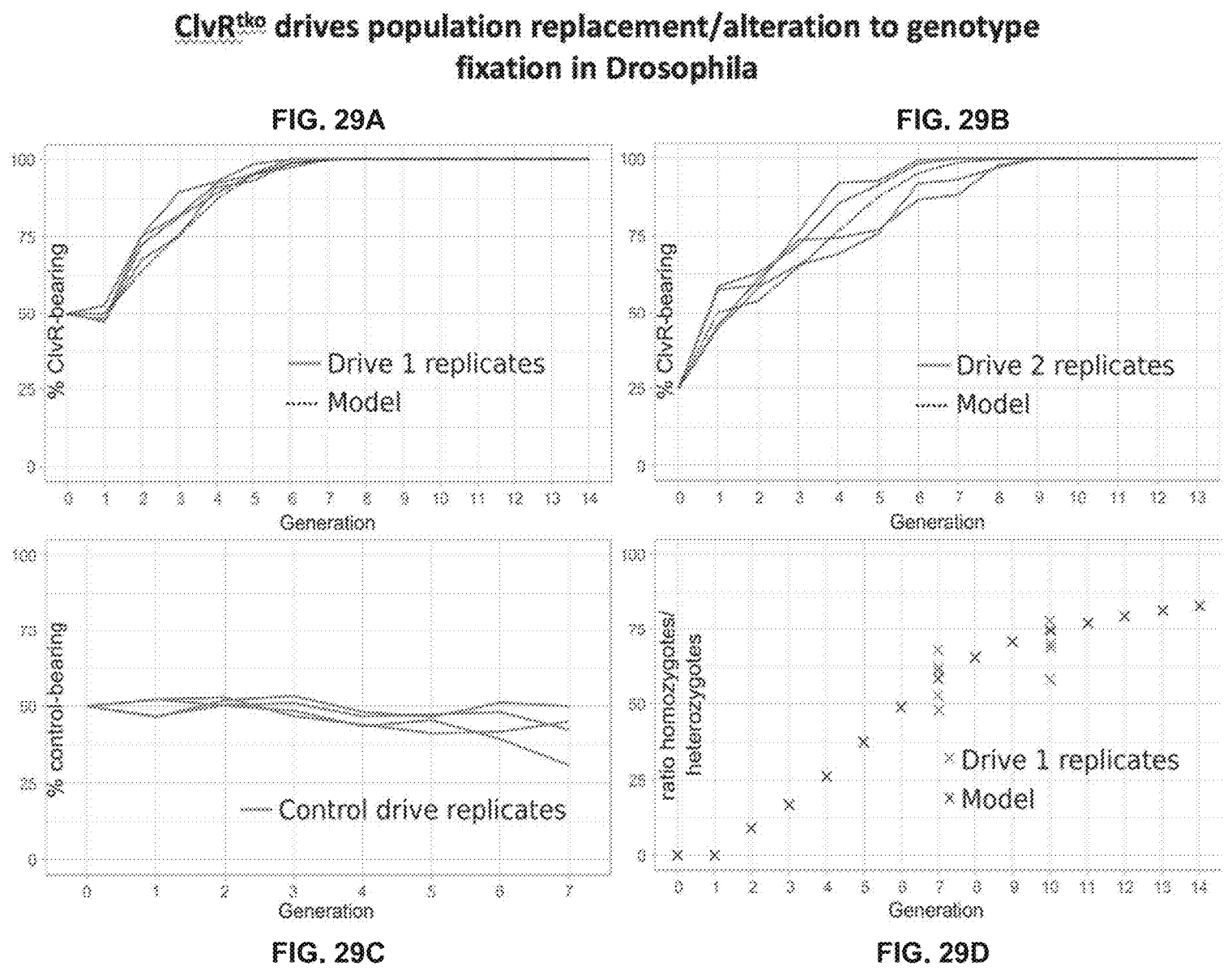

Drive of ClvR$^{tko}$ in *Drosophila.* The frequency of ClvR-bearing individuals (ClvR/+ and ClvR/ClvR) is indicated on the y-axis and the generation number on the x-axis of FIG. 29A-FIG. 29D. Drive replicates are shown in solid lines, and predicted drive behavior (Model) is shown in dotted lines. FIG. 29A shows data for Drive 1: ♂ClvR$^{tko}$/+XX ♀w$^{1118}$ as generation 0.

FIG. 29B shows data for Drive 2: ♂ClvR$^{tko}$/ClvR$^{tko}$ XX ♀w$^{1118}$ and ♂w$^{1118}$ XX ♀w$^{1118}$ at a 1:1 ratio as generation 0. FIG. 29C shows data for Control drive: ♂tkoA/+XX ♀w$^{1118}$ as generation 0. For the control drive flies carrying construct tkoA were used (see methods) that had only the rescue and the td-tomato marker, but no Cas9 and gRNAs. FIG. 29D shows data for allele frequency of ClvR$^{tko}$ in drive 1. 100 males were taken from each replicate of the drive experiment after generation 7 and generation 10, outcrossed them to w$^{1118}$ virgins, and scored the progeny for the ClvR marker. If all progeny had the ClvR marker the male parents were considered to be homozygous. Replicates coming from drive 1 are shown. The Model curve is the predicted ratio inferred from modeling of the drive with the parameters determined from TABL2 and TABLE 3, and the assumption of no fitness cost to those carrying ClvR (See, TABLE 10 for counts).

Figure 30:
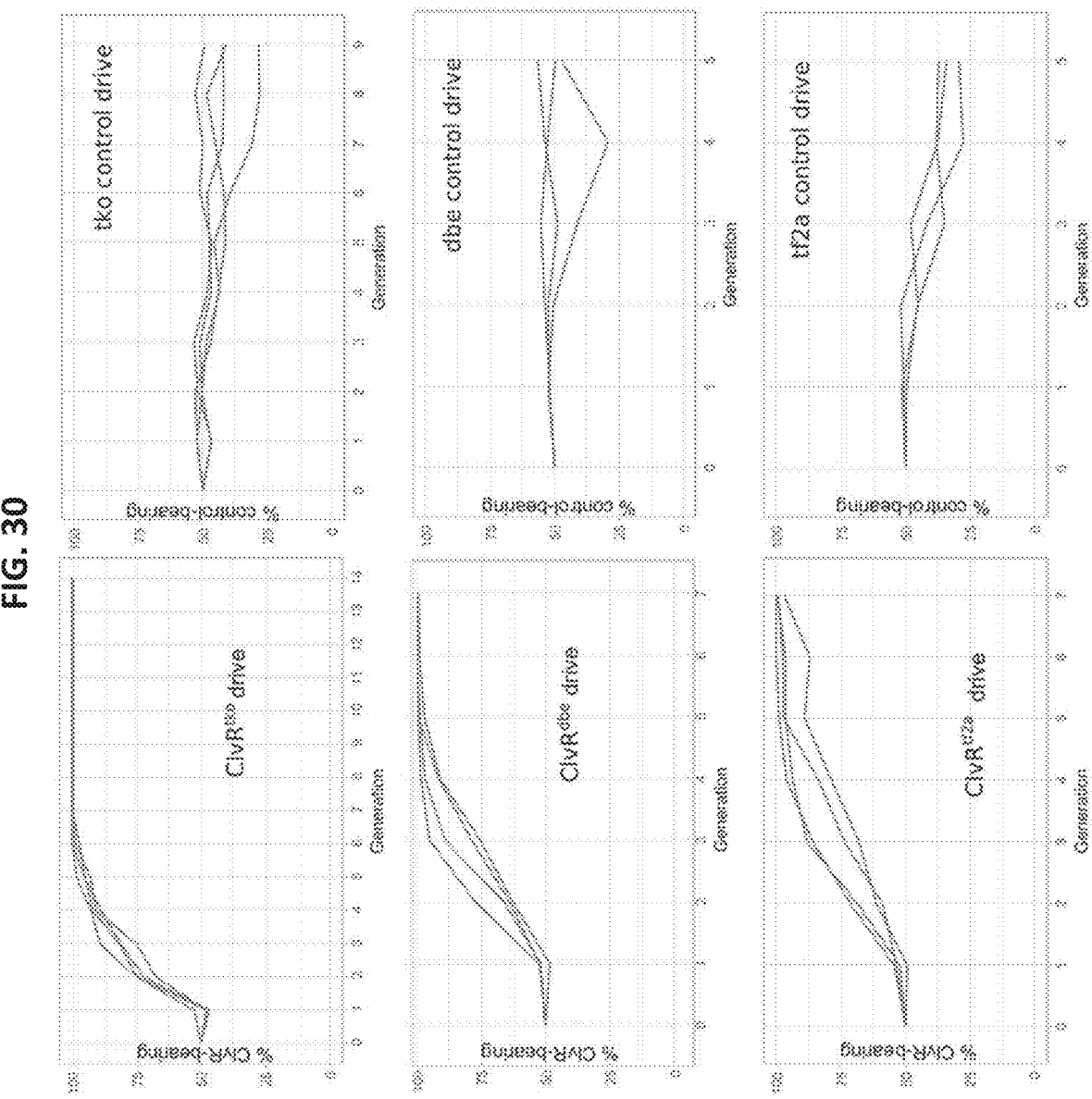
FIG. 30 shows data from example 17 (upper panels) and example 24 (middle and lower panels), illustrating drive to genotype fixation in *Drosophila* for ClvR$^{tko}$ (upper left panels), ClvR$^{tf2a}$ (lower left panels) and ClvR$^{dbe}$ (middle left panels), but not of the control constructs (right panels).

Drive of ClvR$^{tf2a}$ and ClvR$^{dbe}$ into *Drosophila*, and comparison with ClvR$^{tko}$. Drive plots are shown for all three ClvR elements and control drive experiments utilizing transgenics carrying only the step 1 construct, which carries the Rescue transgene, but lacks Cas9 or gRNAs. All gene drive constructs spread rapidly, while controls do not, demonstrating that ClvR-dependent gene drive works when targeting a variety of different genes. FIG. 30 shows data from Example 17 and Example 24 illustrating drive to genotype fixation in *Drosophila* for ClvR$^{tko}$, ClvR$^{tf2a}$ and ClvR$^{dbe}$.

Example 25

Figure 41:
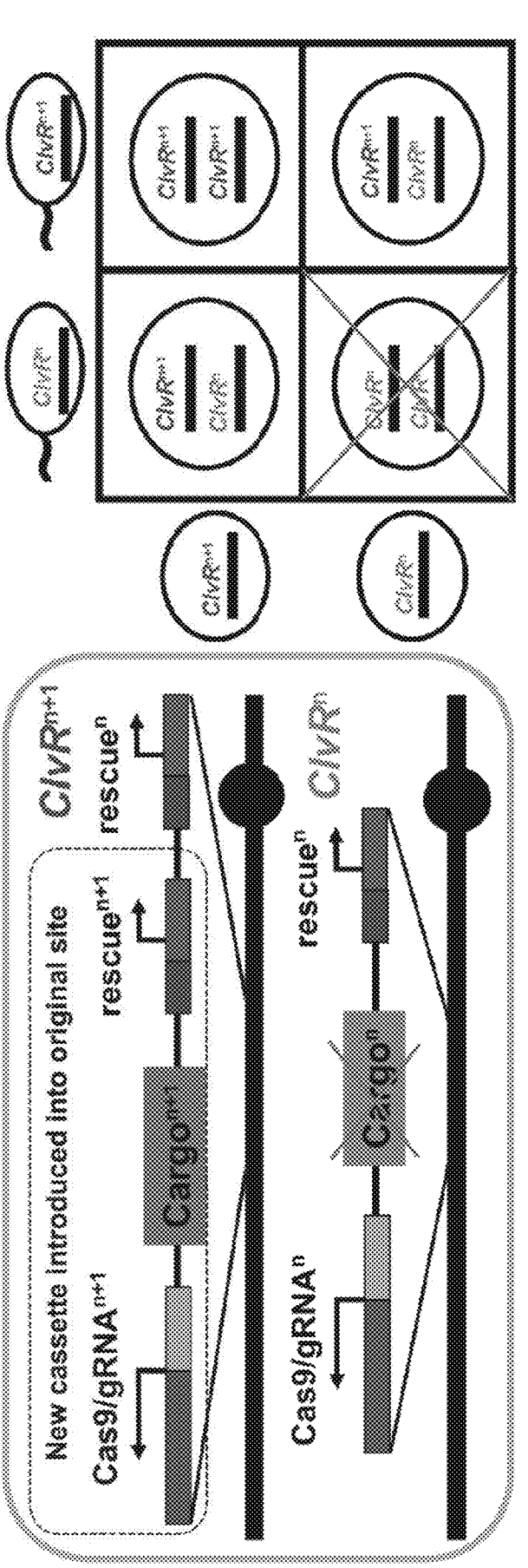
FIG. 41 shows an embodiment of removal of a first generation ClvR, coupled with replacement by a second generation ClvR element. Multiple rounds of population replacement can be carried out by locating ClvR$^{n+1}$ at the same site as ClvR$^n$, with ClvR$^{n+1}$ targeting essential gene$^{n+1}$, while also carrying the original rescuing copy of essential gene$^n$. Because progeny carrying CvR$^n$ are sensitive to loss of essential gene$^{n+1}$, only those carrying ClvR$^{n+1}$ survive, regardless of their status with respect to ClvR$^n$. The function of ClvR$^{n+1}$ can be made completely orthogonal to that of ClvR$^n$ through the use of Cas9/gRNA variants from other species that cannot load the gRNAs generated by ClvR$^n$.

For many genes loss of one copy results some fitness cost: a degree of haploinsufficiency. In extreme cases loss of one copy in a diploid can result in haplolethality, the death of heterozygotes. FIGS. 31A-D show the population genetic behavior of ClvR when targeting a haplosufficient (FIG. 31A, FIG. 31B) or haploinsufficient (FIG. 31C, FIG. 31D) essential gene (A,B) A discrete generation, deterministic population frequency model of ClvR spread (cleavage in male and female germline; ClvR located on an autosome and the essential gene on the X; see data in FIGS. 42A-C and FIGS. 29A-D) through a single panmictic population, for varying initial release ratios and fitness costs, without (FIG. 31A), or with (FIG. 31B) maternal carryover-dependent cleavage. The heatmap indicates the number of generations required for the ClvR-bearing genotype to approach fixation (i.e., >99% of the total population). (FIG. 31C) Heatmap showing the number of generations required for the ClvR-bearing genotype to reach fixation (<99% ClvR-bearing) for different initial release ratios and haploinsufficient fitness costs (100%=haplolethal), for a two locus autosomal version of ClvR with maternal carryover. (FIG. 31D) Individuals traces showing the fate of a ClvR from (FIG. 31C) targeting a haplolethal gene, for different release ratios. The horizontal line represents an approximation of the unstable equilibrium frequency (~31.5%; population frequencies do not change significantly over 20 generations). Population frequencies greater than equilibrium=36%, 41%, and 46%; those below=26%, 21%, and 16%. Note that the term "Release Ratio" for al heatmaps refers to the ratio of homozygous transgenic males compared to wild type males and females after a release has occurred (e.g. a 40% release means that 40% of the population is ClvR/ClvR male, 30% is +/+ male, and 30% is +/+ female). Thus, initial release ratio also=initial population frequency. Note that for (C) and (D) ClvR itself is assumed to have no fitness cost. Such costs would further increase the minimum release ratios required for drive to occur, as in panels (FIG. 31A) and (FIG. 31B). FIG. 31A-FIG. 31D show graphs of an embodiment of a population frequency modeling of cleavage mediated drive for genes that are haploinsufficient or haplolethal. See also, FIG. 41.

Example 26

A circuit that selects against mutation of Cas9/gRNAs to inactivity. While the spread of Cargo into a panmictic population is resistant to mutational inactivation of Cas9/gRNAs (A-C), the situation is likely to be more complicated in populations in which wildtype are continually migrating into the population. Once active Cas9-bearing ClvR has been eliminated in favor of elements carrying inactive Cas9 (B), the wildtype non-ClvR-bearing chromosome will spread since it lacks the fitness cost associated with presence of the cargo. To delay this outcome it is proposed that Cas9 activity can be made essential for Rescue function. A variant of Cas9 known as Cas9-VPR includes a domain that can activate transcription following DNA binding. Cas9-VPR can also bring about cleavage of full length target sites. Importantly, however, Cas9-VPR can also bind truncated gRNA target sites and drive transcription of a nearby gene, without cleaving these sites (Kiani, S. et al., 2015) In this way the exact same gRNAs and Cas9 are used for cleavage and transcriptional activation. The figure proposes that Cas9 expression is driven by the promoter of the essential gene. the gRNAs are expressed ubiquitously under U6 promoter control, as usual. Cas9 and gRNAs will cleave the wildtype copy of the essential gene in all tissues in which the essential gene is expressed. Cas9 and gRNAs will also drive expression of a promoterless, recoded version of the essential gene (the Rescue) in these same tissues. The system thus creates tight linkage between components required for cleavage and those required for rescue. It can fail due to point mutations in Cas9 that allow target site DNA binding and transcriptional activation but that prevent cleavage, as with dead Cas9 variants used for transcriptional regulation or visualization of specific genomic loci. These will happen, but are very specific mutations, and thus any spread of dead Cas9 within the population should be delayed. An important requirement for this approach is that the essential gene be expressed in the germline at levels sufficient to bring about Cas9-dependent germline cleavage of the wildtype essential gene. Also note that unless the essential gene is only required in the germline, Cas9 will be expressed and active in some somatic tissues. FIG. 32 shows a schematic illustrating a strategy by which Cas9, gRNAs and Rescue transgene can be implemented such that Cas9 and gRNAs are required for Rescue expression in addition to cleavage of an essential gene. See also, FIG. 41.

Example 27

Mutation of cargo genes or loss of effectiveness as a result of evolution of the host, or other species such as pathogens on which they are meant to act, requires strategies for removing an old element from the population and replacing it with a new one. Removal of a first generation ClvR, coupled with replacement by a second generation ClvR element. Multiple rounds of population replacement can be carried out by locating ClvR$^{n+1}$ at the same site as ClvR$^n$, with ClvR$^{n+1}$ targeting essential gene$^{n+1}$, while also carrying the original rescuing copy of essential gene$^n$. Because progeny carrying ClvR are sensitive to loss of essential gene$^{n+1}$, only those carrying ClvR$^{n+1}$ survive, regardless of their status with respect to ClvR$^n$. The function of ClvR$^{n+1}$ can be made completely orthogonal to that of ClvR$^n$ through the use of Cas9/gRNA variants from other species that cannot load the gRNAs generated by CvR$^n$. FIG. 33 shows schematics illustrating how second generation ClvR elements can be used to replace first generation elements when both are located at the same position in the genome.

Example 28

When ClvR components are located at two freely recombining positions in the genome, with the first locus encoding a functional DNA sequence modifying enzyme and the second locus encoding a Rescue and associated Cargo genes (two locus ClvR, version 1), gene drive is strong but transient. ClvR components are on two different chromosomes, and segregate independently at meiosis. This results in some gametes carrying the Cargo/Rescue but not Cas9/gRNA, others carrying Cas9/gRNA alone, and others carrying both transgene cassettes. The fate of these gametes in progeny (dead or alive) depends on when sequence modification occurs (in the germline alone or in somatic cells as well), and the presence or absence of the Cargo/Rescue. In short, the fates of the Cargo/Rescue and Cas9/gRNA components are dissociated because they do not always travel together through meiosis. An important implication of this behavior is that while with each two locus scenario the frequency of the Cargo/Rescue can increase in the population as compared to the non Cargo/Rescue bearing homologous chromosome (notwithstanding any limitations imposed by fitness costs associated with carrying the Cargo/Rescue cassette), the frequency of Cas9/gRNA (two locus version 1) or the Cas9/gRNA component not linked to the Cargo/Rescue (two locus version 2 and 3) will decrease over time since they sometimes find themselves in individuals who carry no functional copies of the essential gene, and are therefore dead. Since it is the presence of both Cas9 and gRNAs that leads to selection (indirectly, through the creation of LOF alleles of the essential gene) for the presence of the Cargo/Rescue, this means that in two locus ClvR the strength of drive (the ability create LOF alleles) wanes over time. Thus, two locus ClvR results in drive that is ultimately self-limiting, rather than self-sustaining, as is the case with single locus ClvR. Importantly, all the components of two locus ClvR already exist. They are exactly the same components as those used to implement ClvR$^{tko}$ and ClvRs targeting other essential genes (dribble and tf2As). It is just that the components have been rearranged in terms of their chromosomal location. FIGS. 34A-F show graphs of an embodiment of a population frequency modeling of two locus ClvR, version 1. Two locus ClvR is introduced into the wildtype population at a fixed frequency of 40%, for illustrative purposes. Cas9/gRNAs cut in the male and female germline, and in embryos that derive from Cas9/gRNA-bearing mothers, due to maternal carryover of Cas9/gRNA. (left panel) Cargo/Rescue spreads to genotype fixation for a number of fitness costs, but fails to spread when costs are higher. Fitness costs are indicated by the darkness of the line, with zero fitness cost being darkest, and 60% fitness cost being lightest. Note that 30% introduction of wildtypes at generation 200 results in loss of Rescue from the population for all fitness costs except zero, which is unlikely to exist in the wild (middle panel) Frequency of Cas9/gRNAs over time. Note that the frequency decreases rapidly whenever there is a fitness cost. In the case of no fitness cost (lightest line) the frequency does not decrease because the Cargo/Rescue has gone to allele fixation and therefore there are no individuals lacking Rescue activity. This condition is unlikely to obtain in the real world. Introduction of wildtypes results in a decrease in the frequency of the cas9/gRNA. It does not cause elimination because there is no fitness cost associated with Cas9/gRNA. It has simply been diluted by wildtypes. (right panel) Frequency of cleaved, LOF alleles of the essential gene for the conditions described in the left panel. Note that whenever ClvR spreads the frequency of the cleaved LOF allele goes to fixation. This occurs because the continuous presence of Cas9/gRNA ensures complete cleavage. Addition of wildtypes at a frequency of 30% results in loss of the cleaved allele over time when there is a fitness cost. This is because there is no cleavage (Cas9/gRNAs have already been eliminated), and therefore no creation of new LOF alleles. In addition, because there is no drive, and therefore no selection for the presence of the Rescue, which also often carries a fitness cost. Finally, with decreasing levels of Rescue, wildtype alleles of the essential gene are more fit than LOF alleles (because they allow survival in the absence of the Rescue), and therefore spread. In sum, while two locus ClvR drive is strong, it is also transient, and therefore reversible through dilution with wildtypes.

Example 29

When ClvR components are located at two freely recombining positions in the genome, with the first locus encoding a first component of the DNA sequence modifying enzyme and the second locus encoding a Rescue, associated Cargo genes and a second component of the DNA sequence modifying enzyme (two locus ClvR, versions 2 and 3), gene drive is strong but transient. FIGS. 35A-F shows graphs of an embodiment of a population frequency modeling of two locus ClvR, versions 2 and 3, with the same parameters as detailed in Example 27. Fitness costs are indicated by the darkness of the line, with zero fitness cost being darkest, and 60% fitness cost being lightest. Example 40, FIGS. 49A-E provide examples of an implementation of two locus ClvR in *Drosophila*.

Example 30

Population genetic behavior of single locus ClvR for a constant introduction frequency of 40%, different fitness costs, and periodic introduction of wildtypes beginning at generation 200. ClvR spreads for some but not all fitness cost at the 40% introduction frequency. When ClvR spreads the introduction of wildtypes at a frequency of 30% causes only transient decrease in the frequency of ClvR. These points are illustrated in FIG. 36, which shows graphs of an embodiment of a population frequency model of single locus ClvR. Fitness costs are indicated by the darkness of the line, with zero fitness cost being darkest, and 60% fitness cost being lightest.

Example 31—Genetic Behavior of ClvR$^{tko}$

Matings between heterozygous w$^{1118}$; ClvR$^{tko}$/+ males (where + indicates a third chromosome that does not carry ClvR$^{tko}$) and homozygous w$^{1118}$; +/+ females resulted in high levels of progeny viability to adulthood (95.2±2.0%), similar to those for the w$^{1118}$ strain used for transformation (95.9±2.0%). In addition, ~50% (50.1±3.0%) of the adult progeny carried ClvR$^{tko}$, as expected for Mendelian segregation and high ClvR$^{tko}$ heterozygote fitness. Matings among homozygous ClvR$^{tko}$ flies also resulted in high levels of viability to adulthood (95.1±1.7%), indicating that the presence of ClvR$^{tko}$ components (in the likely absence of functional *D. melanogaster* tko, see below) does not result in obvious fitness costs. In contrast, when heterozygous w$^{1118}$; ClvR$^{tko}$/+ females were mated with homozygous w$^{1118}$; +/+ males, 53.6±1.3% of progeny did not reach adulthood, and all surviving adults carried ClvR$^{tko}$. On the basis of these results it is inferred that the presence of ClvR$^{tko}$ in mothers results in a very high frequency (>99%) of mutational inactivation of the *D. melanogaster* tko locus in the adult female germline and in the zygote through maternal carryover-dependent cleavage of the paternal allele. In consequence, those who fail to inherit ClvR$^{tko}$ die, while those who inherit a single copy of ClvR$^{tko}$ thrive. Data are shown in TABLE 2 (Flies of the indicated cross were allowed to lay eggs in a vial for 18 hours. Afterwards, eggs were counted and allowed to develop to adulthood. Enclosed adults and were scored for genotype, with ClvR-bearing flies identified by the presence of td-tomato (tom+)) and summarized in TABLE 3 (shows the average genotype frequencies (ClvR, td-tomato and w-) and eclosion rates in % with standard deviations from 10 replicates).

TABLE 2

| SURVIVAL ASSAY | | | | | |
|---|---|---|---|---|---|
| ♂ClvR$^{tko}$/+ XX ♀w$^{1118}$ | eggs | tom+ | tom− | eclosion rate | ratio |
| | 78 | 39 | 38 | 0.987 | 0.506 |
| | 62 | 28 | 29 | 0.919 | 0.491 |
| | 38 | 17 | 20 | 0.974 | 0.459 |
| | 55 | 26 | 26 | 0.945 | 0.5 |
| | 83 | 41 | 38 | 0.952 | 0.519 |
| | 65 | 30 | 32 | 0.954 | 0.484 |
| | 22 | 11 | 10 | 0.955 | 0.524 |
| | 47 | 22 | 23 | 0.957 | 0.489 |
| | 24 | 10 | 13 | 0.958 | 0.435 |
| | 69 | 34 | 30 | 0.928 | 0.531 |
| sum | 543 | 258 | 259 | | |
| eclosion rate(SD): | 0.952 | | | SD = | 0.02 |
| ratio: | | 0.499 | 0.501 | SD = | 0.03 |
| ♀w$^{1118}$ XX ♂w$^{1118}$ | eggs | tom+ | tom− | eclosion rate | |
| | 82 | 0 | 79 | 0.963 | |
| | 69 | 0 | 67 | 0.971 | |
| | 38 | 0 | 35 | 0.921 | |
| | 16 | 0 | 16 | 1 | |
| | 68 | 0 | 65 | 0.956 | |
| | 61 | 0 | 58 | 0.951 | |
| | 53 | 0 | 51 | 0.962 | |
| | 54 | 0 | 51 | 0.944 | |
| | 93 | 0 | 90 | 0.968 | |
| | 78 | 0 | 75 | 0.962 | |
| sum | 612 | 0 | 587 | | |
| hatch rate(SD): | 0.959 | | | SD = | 0.02 |
| ratio: | | 0 | 1 | | |
| ♀ClvR$^{tko}$/+ XX ♂w$^{1118}$ | eggs | tom+ | tom− | | |
| | 38 | 17 | 0 | 0.447 | |
| | 126 | 59 | 0 | 0.468 | |
| | 46 | 22 | 0 | 0.478 | |
| | 70 | 33 | 0 | 0.471 | |
| | 52 | 25 | 0 | 0.481 | |
| | 50 | 23 | 0 | 0.46 | |
| | 53 | 24 | 0 | 0.453 | |
| | 49 | 23 | 0 | 0.469 | |
| | 61 | 27 | 0 | 0.443 | |
| | 107 | 49 | 0 | 0.458 | |
| sum | 545 | 253 | 0 | | |
| hatch rate(SD): | 0.464 | | | SD = | 0.013 |
| ratio: | | 1 | 0 | | |
| ♀ClvR$^{tko}$/ClvR$^{tko}$ XX ♂ClvR$^{tko}$/ClvR$^{tko}$ | eggs | tom+ | tom− | | |
| | 56 | 53 | 0 | 0.946 | |
| | 64 | 62 | 0 | 0.969 | |
| | 50 | 47 | 0 | 0.94 | |
| | 73 | 69 | 0 | 0.945 | |
| | 42 | 39 | 0 | 0.929 | |
| | 45 | 43 | 0 | 0.956 | |
| | 58 | 56 | 0 | 0.966 | |
| | 51 | 47 | 0 | 0.922 | |
| | 59 | 56 | 0 | 0.949 | |
| | 87 | 82 | | 0.943 | |
| sum | 388 | 369 | 0 | | |
| hatch rate(SD): | 0.951 | | | SD = | 0.017 |
| ratio: | | 1 | 0 | | |

TABLE 3

| | Cross | td-tomato+ | w- | Eclosion rate |
|---|---|---|---|---|
| | SUMMARY OF DATA IN TABLE 2 | | | |
| A | ♀$w^{1118}$ XX ♂$w^{1118}$ | 0 | 100 | 95.9 ± 2.0 |
| B | ♀$w^{1118}$ XX ♂ClvR$^{tko}$/+ | 49.9 ± 3.0 | 0.1 ± 3.0 | 95.2 ± 2 |
| C | ♀ClvR$^{tko}$/+ XX ♂$w^{1118}$ | 100 | 0 | 46.4 ± 1.3 |
| D | ♀ClvR$^{tko}$ XX ♂ClvR$^{tko}$ | 100 | 0 | 95.1 ± 1.7 |

Example 32—Crosses to Determine Rate of D. Melanogster Tko Gene Inactivation Due to Female Germline Cleavage and Maternal Carry Over-Dependent Cleavage Shown in TABLE 4 are the offspring genotype frequencies for a cross between $w^{1118}$; ClvR$^{tko}$/+ females and $w^{1118}$ males. Flies were scored as ClvR-bearing based on the presence of the td-tomato marker. Of 3736 flies scored, one did not have the td-tomato marker, resulting in a cleavage rate of 0.9997. All crosses were single fly crosses if not otherwise noted (pool=a few flies; bottle=many flies (~50)).

TABLE 4

| cross | tomato+ | tomato- | ratio | note |
|---|---|---|---|---|
| 1 | 61 | 0 | 1 | |
| 2 | 50 | 0 | 1 | |
| 3 | 63 | 0 | 1 | |
| 4 | 62 | 0 | 1 | |
| 5 | 49 | 0 | 1 | |
| 6 | 48 | 0 | 1 | |
| 7 | 50 | 0 | 1 | |
| 8 | 127 | 0 | 1 | pool |
| 9 | 55 | 0 | 1 | |
| 10 | 33 | 0 | 1 | |
| 11 | 52 | 0 | 1 | |
| 12 | 203 | 0 | 1 | pool |

TABLE 4-continued

| cross | tomato+ | tomato- | ratio | note |
|---|---|---|---|---|
| 13 | 99 | 0 | 1 | pool |
| 14 | 45 | 0 | 1 | |
| 15 | 42 | 0 | 1 | |
| 16 | 72 | 0 | 1 | |
| 17 | 53 | 0 | 1 | |
| 18 | 23 | 0 | 1 | |
| 19 | 49 | 0 | 1 | |
| 20 | 49 | 0 | 1 | |
| 21 | 38 | 0 | 1 | |
| 22 | 32 | 0 | 1 | |
| 23 | 39 | 0 | 1 | |
| 24 | 12 | 0 | 1 | |
| 25 | 46 | 0 | 1 | |
| 26 | 7 | 0 | 1 | |
| bottle 1 | 868 | 0 | 1 | bottle |
| bottle 2 | 736 | 1 | 0.9986 | bottle |
| bottle 3 | 672 | 0 | 1 | bottle |
| SUM | 3735 | 1 | 0.99973 | |

Example 33—Crosses to Determine Male Germline Cleavage Rate

Shown in TABLE 5 are the offspring genotype frequencies for crosses between ClvR$^{tko}$/+ males and tko$^3$/FM7a,B$^1$ females. Flies having the ClvR element were scored by the presence of the td-tomato marker. The tko$^3$ mutant allele is on a w+X chromosome; The X$_P$ paternal X chromosome is w− ($w^{1118}$); The ClvR$^{tko}$ element on the third chromosome is marked by the presence of td-tomato; The FM7a,B$^1$ Balancer X chromosome is identifiable by virtue of the Bar dominant eye marker (B$^1$); + refers to a wildtype third chromosome; Y refers to the Y chromosome. The male germline cleavage rate was calculated as the ratio of 8 (tko$^3$/X$_P$; +)/907 (tko$^3$/X$_P$; ClvR$^{tko}$)=0.9911. The 5 escapers from bottle 2 share a common polymorphism (FIGS. 39A-E), and thus may represent multiple isolates of the same adult male germline cleavage and repair event.

TABLE 5

| cross | ♀tko$^3$/ X$_P$;;ClvR$^{tko}$ | ♀FM7a, B$^1$/ X$_P$;;ClvR$^{tko}$ | ♀tko$^3$/ X$_P$;;+ | ♀Fm7a, B$^1$/ X$_P$;;+ | ♂tko$^3$/ Y$_P$;;ClvR$^{tko}$ | ♂FM7a, B$^1$/ Y$_P$;;ClvR$^{tko}$ | ♂tko$^3$/ Y$_p$;;+ | ♂Fm7a, B$^1$/ Y$_P$;;+ |
|---|---|---|---|---|---|---|---|---|
| 1 | 15 | 6 | 0 | 12 | 2 | 5 | 0 | 8 |
| 2 | 5 | 6 | 0 | 7 | 4 | 3 | 0 | 1 |
| 3 | 8 | 7 | 0 | 8 | 6 | 0 | 0 | 0 |
| 4 | 7 | 5 | 0 | 2 | 9 | 1 | 0 | 1 |
| 5 | 16 | 13 | 0 | 15 | 14 | 4 | 0 | 1 |
| 6 | 10 | 11 | 0 | 14 | 16 | 5 | 0 | 2 |
| 7 | 16 | 14 | 0 | 13 | 23 | 5 | 0 | 3 |
| 8 | 15 | 13 | 0 | 16 | 15 | 6 | 0 | 3 |
| 9 | 24 | 23 | 0 | 8 | 16 | 1 | 0 | 3 |
| 10 | 19 | 9 | 0 | 9 | 9 | 4 | 0 | 3 |
| 11 | 12 | 13 | 0 | 10 | 22 | 2 | 0 | 4 |
| 12 | 11 | 15 | 0 | 8 | 19 | 5 | 0 | 4 |
| 13 | 14 | 8 | 0 | 12 | 20 | 4 | 0 | 1 |
| 14 | 7 | 7 | 0 | 2 | 5 | 4 | 0 | 4 |
| 15 | 18 | 7 | 0 | 15 | 23 | 2 | 0 | 4 |
| 16 | 14 | 23 | 0 | 15 | 19 | 2 | 0 | 1 |
| 17 | 32 | 21 | 0 | 18 | 12 | 2 | 0 | 1 |
| 18 | 13 | 7 | 0 | 16 | 19 | 4 | 0 | 2 |
| 19 | 8 | 4 | 0 | 4 | 2 | 3 | 0 | 2 |
| 20 | 11 | 18 | 0 | 13 | 23 | 1 | 0 | 2 |
| 21 | 8 | 6 | 0 | 6 | 5 | 3 | 0 | 6 |
| 22 | 27 | 19 | 0 | 13 | 16 | 1 | 0 | 2 |
| 23 | 17 | 6 | 0 | 15 | 11 | 1 | 0 | 4 |
| 24 | 14 | 17 | 0 | 19 | 17 | 6 | 0 | 1 |
| 25 | 11 | 8 | 0 | 3 | 8 | 3 | 0 | 4 |
| 26 | 11 | 10 | 0 | 8 | 11 | 1 | 0 | 0 |
| 27 | 14 | 14 | 0 | 13 | 15 | 1 | 0 | 4 |
| 28 | 18 | 18 | 0 | 14 | 18 | 1 | 0 | 3 |
| 29 | 19 | 18 | 0 | 10 | 27 | 0 | 0 | 2 |

TABLE 5-continued

| cross | ♀tko³/ $X_P$;;ClvR$^{tko}$ | ♀FM7a, B¹/ $X_P$;;ClvR$^{tko}$ | ♀tko³/ $X_P$;;+ | ♀Fm7a, B¹/ $X_P$;;+ | ♂tko³/ $Y_P$;;ClvR$^{tko}$ | ♂FM7a, B¹/ $Y_P$;;ClvR$^{tko}$ | ♂tko³/ $Y_P$;;+ | ♂Fm7a, B¹/ $Y_P$;;+ |
|---|---|---|---|---|---|---|---|---|
| 30 | 16 | 17 | 0 | 11 | 23 | 6 | 0 | 3 |
| 31 | 16 | 17 | 0 | 13 | 12 | 0 | 0 | 1 |
| 32 | 18 | 13 | 0 | 16 | 17 | 0 | 0 | 2 |
| 33 | 15 | 13 | 0 | 13 | 22 | 3 | 0 | 2 |
| 34 | 15 | 17 | 0 | 11 | 15 | 4 | 0 | 4 |
| 35 | 11 | 11 | 0 | 11 | 13 | 1 | 0 | 3 |
| bottle1 | 219 | 165 | 3 | 200 | 216 | 21 | 0 | 11 |
| bottle2 | 183 | 169 | 5 | 154 | 156 | 33 | 0 | 19 |
| sum | 907 | 768 | 8 | 747 | 880 | 148 | 0 | 121 |
| total flies counted | 3579 | | | | | | | |

Example 34—Analysis of Escapers

Shown in TABLE 6 are the alterations in the gRNA target sites of escaper flies. Flies are numbered based on the cross they were coming from (escF1 from bottle 2 of female ClvR$^{tko}$/+ mothers; escM1A-escM8B from male ClvR$^{tko}$/+ fathers. See, FIGS. 42A-C for mating scheme to isolate the escaper X-chromosome). '+' indicates an unaltered target site, numbers indicate the size of the deletion. The last two columns show the number of progeny from an outcross of the escaper males to ClvR$^{tko}$/+ females, and the fraction carrying the ClvR marker td-tomato (tom+) or lacking it (tom−). The two males escM3A and esc M3B gave a mixed sequencing signal, which could not be aligned unambiguously (ND, not determined). All escapers were still sensitive to ClvR drive, as shown by the results of the outcross to ClvR$^{tko}$/+ females, which resulted in a progeny population in which all individuals carried ClvR$^{tko}$ (tom+), indicating that the D. melanogaster tko locus had been disrupted in all non-ClvR$^{tko}$-bearing individuals.

TABLE 6

| escaper | g1 | g2 | g3 | g4 | tom+ | tom− |
|---|---|---|---|---|---|---|
| escF1 | + | + | + | + | 62 | 0 |
| escM1A | 3 | + | + | + | 31 | 0 |
| escM1B | 3 | + | + | + | 65 | 0 |
| escM2A | 3 | + | + | + | 66 | 0 |
| escM2B | 3 | + | + | + | 62 | 0 |
| escM3A | ND | ND | ND | ND | 45 | 0 |
| escM3B | ND | ND | ND | ND | 37 | 0 |
| escM4A | 3 | + | + | + | 34 | 0 |
| escM4B | 3 | + | + | + | 48 | 0 |
| escM5A | 3 | + | + | + | 79 | 0 |
| escM5B | 3 | + | + | + | 87 | 0 |
| escM6A | 3 | + | + | + | 50 | 0 |
| escM6B | 3 | + | + | + | 68 | 0 |
| escM7A | 3 | + | + | + | 62 | 0 |
| escM7B | 3 | + | + | + | 57 | 0 |
| escM8A | 3 | + | + | + | 73 | 0 |
| escM8B | 3 | + | + | + | 85 | 0 |

Example 35—ClvR$^{tko}$ Genotype Frequencies During Introgression into 5 Different GDL Genetic Backgrounds ClvR$^{tko}$/+ females were mated each generation with GDL males. Labels of GDL lines from (35, 52) are given in the column headers. Progeny were counted and their genotypes were scored with respect to the presence of the ClvR td-tomato marker. After each generation 30 virgins were collected and backcrossed to wildtype males of the corresponding GDL stock. Shown are the numbers of scored flies with the ClvR marker td-tomato. Flies without the marker are indicated in brackets. Maternal germline and carryover-dependent mutation of the D. melanogaster tko locus was efficient since progeny lacking ClvR$^{tko}$ were not observed, 0/7882. Data are shown in TABLE 7

TABLE 7

| Generation | B12 | I02 | N23 | T01 | ZW140 |
|---|---|---|---|---|---|
| 1 | 103(0) | 73(0) | 84(0) | 90(0) | 85(0) |
| 2 | 184(0) | 206(0) | 217(0) | 212(0) | 194(0) |
| 3 | 272(0) | 221(0) | 259(0) | 211(0) | 236(0) |
| 4 | 304(0) | 447(0) | 316(0) | 350(0) | 253(0) |
| 5 | 342(0) | 228(0) | 297(0) | 206(0) | 249(0) |
| 6 | 540(0) | 406(0) | 453(0) | 429(0) | 415(0) |
| SUM | 1745 | 1581 | 1626 | 1498 | 1432 |
| Total flies scored | 7882 | | | | |

Example 36—Sequence Polymorphisms in the Tko gRNA Target Sites Used in this Study, in Drosophila Strains from the 1000 Fly Genomes Project Shown in TABLE 8 are pre-existing polymorphisms (SNP) in these strains, with the location and type of the SNP in the corresponding gRNA target site. The last column gives the number of gRNA target sites used in this work that are not altered in each strain. The gRNA2 target site was polymorphic in about half of the 1000 fly genomes, and was also present at some frequency in the lab strain used in the experiments, w$^{1118}$. With this data available it should be possible to select more conserved target sites, e.g. acagccttcagcttaacgccGGG (conserved in all), and gtgctggtgcgcctctccacCGG (SNP in one strain), though it remains to be determined if gRNAs corresponding to these sequences are highly active (see the results in the main text with gRNA3).

TABLE 8

| strain | gRNA1 | gRNA2 | gRNA3 | gRNA4 | Functional gRNAs |
|--------|-------|-------|-------|-------|------------------|
| US103 | + | G --> A (bp10) | + | C --> A (bp13) | 2 |
| GU6 | + | + | + | T --> C (bp10) | 3 |
| KR39 | + | A --> G (bp7) | + | C --> A (bp13) | 2 |
| RAL149 | + | + | + | C --> A (bp13) | 3 |
| RAL808 | + | G --> A (bp10) | + | C --> A (bp13) | 2 |
| SP188 | + | A --> G (bp7) | + | C --> A (bp13) | 2 |
| ZI420 | + | G --> A (bp10) | + | C --> A (bp13) | 2 |
| ZI508 | + | + | + | C --> A (bp13) | 3 |
| CO10N | C --> T (bp8) | + | + | + | 3 |
| ZI251N | C --> T (bp8) | G --> A (bp10) | + | + | 2 |

Example 37—Molecular Analysis of ClvR Induced Mutations at the Target Locus

Shown in TABLE 9A are the type of cleavage events observed at the different gRNA target sites (g1-g4) in male progeny of ClvR$^{tko}$/+ mothers (from FIG. 3B). Unaltered target sites are indicated as '+', polymorphisms predicted to render the target site resistant to cleavage are indicated by 'SNP', and gRNA target site mutations likely to result in LOF as 'indel'. Shown in TABLE 9B, as with TABLE 9A, but with males coming from a homozygous ClvR$^{tko}$ stock inbred for 3 generations. Note how mutations accumulate over multiple generations.

TABLE 9A

| fly | g1 | g2 | g3 | g4 |
|-----|-----|-----|-----|-----|
| 1.1 | indel | + | + | indel |
| 1.2 | indel | SNP | + | indel |
| 2.1 | indel | SNP | + | + |
| 2.2 | indel | SNP | + | + |
| 3.1 | indel | + | + | + |
| 3.2 | indel | SNP | + | + |
| 4.1 | indel | + | + | indel |
| 4.2 | indel | indel | + | indel |
| 5.1 | indel | indel | + | indel |
| 5.2 | indel | indel | + | + |
| 6.1 | indel | + | + | + |
| 6.2 | indel | + | + | + |
| 7.1 | indel | + | + | + |
| 7.2 | indel | + | + | + |
| 8.1 | indel | + | + | indel |
| 8.2 | indel | + | + | indel |
| 9.1 | indel | + | + | indel |
| 9.2 | indel | + | + | indel |

TABLE 9B

| fly | g1 | g2 | g3 | g4 |
|-----|-----|-----|-----|-----|
| 1 | indel | SNP | + | indel |
| 2 | indel | indel | + | indel |
| 3 | indel | SNP | + | indel |
| 4 | indel | indel | + | indel |
| 5 | indel | SNP | + | indel |
| 6 | indel | indel | + | indel |
| 7 | indel | + | + | indel |
| 8 | indel | SNP | + | indel |
| 9 | indel | SNP | + | indel |
| 10 | indel | SNP | indel | indel |
| 11 | indel | indel | + | indel |
| 12 | indel | indel | + | indel |

Example 38—Allele Frequency of ClvR$^{tko}$ in Drive Experiment 1. Shown are Male Outcrosses Taken from the Drive Experiment to w$^{1118}$ Virgins Shown in TABLE 10 are male outcrosses taken from the drive experiment to w$^{1118}$ virgins. A male was considered to be homozygous if all progeny had the ClvR td-tomato marker and heterozygous if not. Note that not all of the 100 set up outcrosses produced offspring (sum of scored crosses ranged from 92-96). Data shown here was used to plot FIG. 29D.

TABLE 10

| replicate | generation | ratio (%) | sum | homozygous | heterozygous |
|-----------|-----------|-----------|-----|------------|--------------|
| A | 7 | 47.87 | 94 | 45 | 49 |
| B | 7 | 52.69 | 93 | 49 | 44 |
| C | 7 | 67.71 | 96 | 65 | 31 |
| D | 7 | 61.96 | 92 | 57 | 35 |
| E | 7 | 60.87 | 92 | 56 | 36 |
| A | 10 | 57.89 | 95 | 55 | 40 |
| B | 10 | 68.48 | 92 | 63 | 29 |
| C | 10 | 77.89 | 95 | 74 | 21 |
| D | 10 | 69.79 | 96 | 67 | 29 |
| E | 10 | 75 | 96 | 72 | 24 |
| M | 0 | 0 | | | |
| M | 1 | 0 | | | |
| M | 2 | 9.08 | | | |
| M | 3 | 16.79 | | | |
| M | 4 | 26.12 | | | |
| M | 5 | 37.43 | | | |
| M | 6 | 48.81 | | | |
| M | 7 | 58.29 | | | |
| M | 8 | 65.32 | | | |
| M | 9 | 70.42 | | | |
| M | 10 | 74.23 | | | |
| M | 11 | 77.17 | | | |

Example 39—Molecular Nature of *D. melanogaster* Tko Mutations Created Following Exposure to ClvR$^{tko}$ To analyze the mutations in *D. melanogaster* tko created by ClvR$^{tko}$, 2 ClvR$^{tko}$-bearing male progeny were selected from each of 9 individual single crosses (18 total flies) between heterozygous ClvR$^{tko}$ females and w$^{1118}$ males (from FIG. 3B). Sequencing results from the region of the *D. melanogaster* tko locus spanning the gRNA-binding sites are summarized in TABLE 9A (FIGS. 40A and 40B). The gRNA1 target site contained indels of varying size in all 18 individuals. The gRNA2 target site contained a likely pre-existing polymorphism in 4 individuals (also observed in roughly half of the 1000 fly genome project strains (Lack J. B., et al., 2016)), and a 2 bp deletion in 3. The gRNA3 target site was unaltered in all individuals, and the gRNA4 target contained indels in 9 individuals. Somewhat surprisingly, larger deletions between target sites were not observed. This raises the possibility, suggested by others (Farasat, I. et al., 2016), that close juxtaposition of multiple target sites—in the present case four target sites within the 250 bp region constituting the tko open reading frame—limits Cas9's ability to simultaneously interact with and/or cleave multiple nearby target sites as a consequence of Cas9-dependent DNA supercoiling.

One implication of such a model is that mutations should accumulate at additional target sites over time, as the target sites first cleaved by Cas9 are rendered non-functional for further Cas9 binding due to mutation within the gRNA target site. To explore this possibility, and the general question of whether all gRNA target sites can be cleaved, the *melanogaster* tko locus was sequenced from a homozygous ClvR$^{tko}$ stock that had been inbred for three generations (TABLE 9B; FIG. 40C and FIG. 40D). Among the twelve analyzed males, all twelve had mutations at the gRNA1 target site. The gRNA2 target site was mutated in five, unaltered in one individual, and carried the suspected common polymorphism in the remaining six. The gRNA3 target site was mutated in one fly, and the gRNA4 target site was mutated in all twelve flies. Thus, all sites can be cleaved, though cleavage efficiencies differ (from 100% for gRNA1 in generation 1 to 8% for gRNA3 after 3 generations). Many of these mutations presumably arise initially from error-prone repair by non-homologous end joining or microhomology-mediated end joining pathways. However, it is noted that ClvR may also utilize HR and homing to create new LOF alleles when the ClvR-bearing individuals introduced into the wild population carry (as the above results indicate they will) uncleavable LOF indels in the essential gene. Thus, if ClvR-bearing individuals carrying LOF indels in the essential gene mate with wildtype, ClvR-bearing progeny will be heterozygous for chromosomes that carry the LOF indels and the wildtype version of the essential gene. In the germline of these individuals, the LOF indel-bearing chromosome (which are uncleavable) could serve as a template for HR-dependent repair of cleaved wildtype alleles, converting them to the LOF sequence.

Example 40

The example presents an implementation of a two locus ClvR wherein the Rescue, Cargo and gRNAs are located on the third chromosome, Cas9 is located on the second chromosome, and the locus being targeted by Cas9 and gRNAs for cleavage is the tko locus, located on the X chromosome. This is version 3, illustrated in FIG. 20D, and as modeled in FIGS. 35A-35F.

In this example the construct for the "Cleaver" element consisted of Cas9 under the control of nanos regulatory elements (promoter and UTRs), a 3×P3-td-tomato dominant marker gene, and an attB site to facilitate site-specific integration into the fly genome. This construct along with a phiC31 integrase helper plasmid was injected into a fly stock that had an attP site at 59D3 on chromosome 2. Successful integration of Cas9 into the second chromosome was identified by the expression of tdTomato in the eyes of the flies.

The "Rescue" element of two-locus ClvR (Cargo, Rescue and gRNAs) was created by modifying the single-locus version of ClvR$^{tko}$ from Oberhofer et al., 2019. This was achieved by injecting Cas9/gRNA RNP-complexes into ClvR$^{tko}$ flies. The Cas9/gRNA RNP-complexes targeted the Cas9 reading frame of ClvR$^{tko}$ to create mutations within and abolish Cas9 function at that site. Flies carrying both the second and third chromosome constructs, which are illustrated in FIG. 49A, were made doubly homozygous and kept as a stock.

In the gene drive experiment, males homozygous for the second and third chromosome constructs were mated with wildtype females. At the same time wildtype males were mated with wildtype females. Mated females at a ratio of 2:1 (mated with transgenic: mated with wildtype) were then introduced into four bottles and allowed to lay eggs for several days. Adults were then removed and progeny allowed to develop to adulthood. After three days of mating among this adult population, adults were scored for the presence or absence of markers that identify the transgene-bearing third chromosome and the transgene-bearing second chromosome, using a fluorescence microscope. Adults were then transferred to fresh bottles for three days, removed and the process repeated for a number of generations.

Figure 49B:
FIG. 49B shows an embodiment of population dynamics of components of a two locus ClvR system in *Drosophila*, in four replicates. Version 3, as illustrated in FIG. 20D, is implemented. Rescue, gRNAs and Cargo are present on the third chromosome. Cas9 is on the second chromosome, and the target locus, tko, is on the X. Rescue and Cargo are found in two different populations of individuals, as is Cas9. See example X.
Figure 49C:
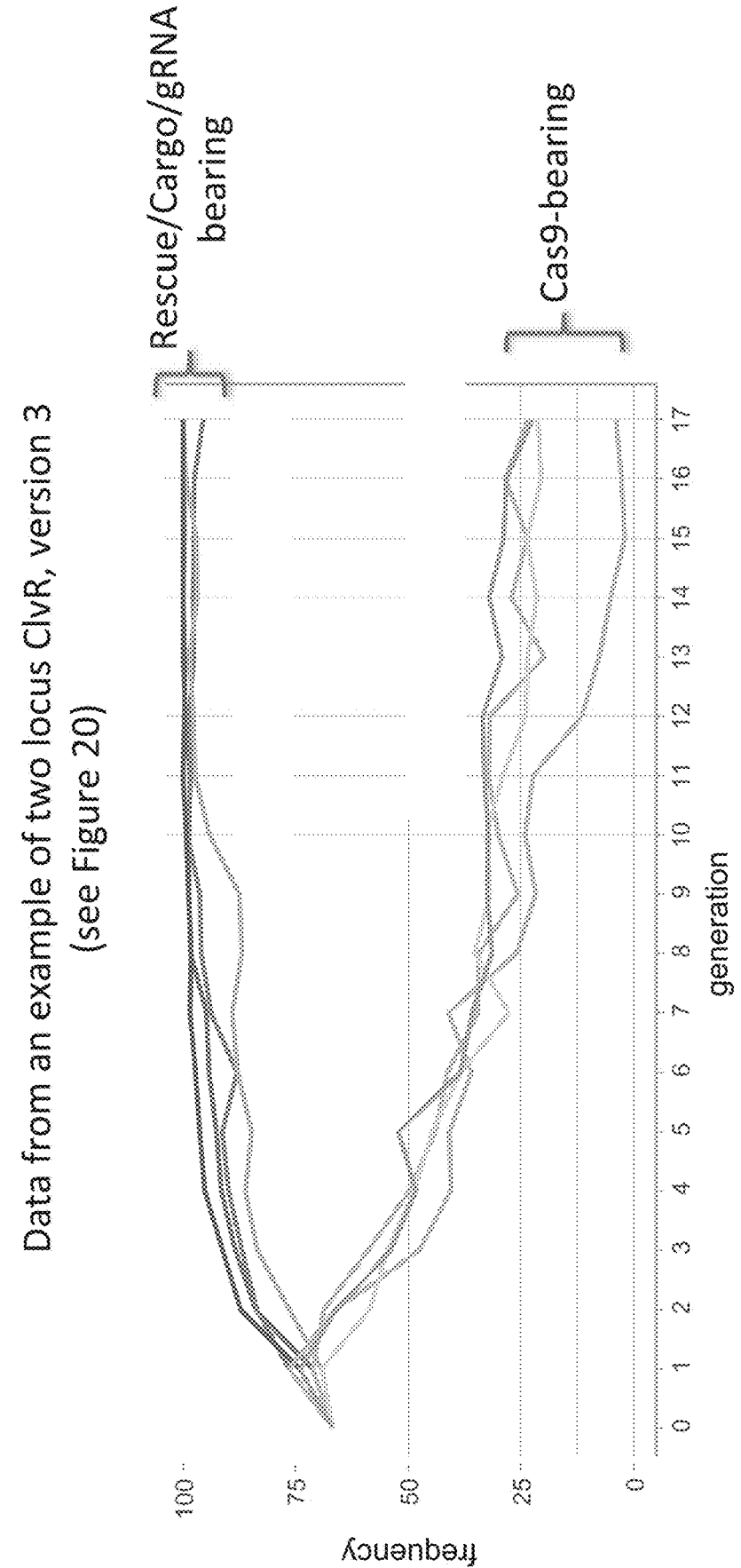
FIG. 49C shows an embodiment of population dynamics of components of a two-locus ClvR system in *Drosophila*, in four replicates. Version 3, as illustrated in FIG. 20D, is implemented. Rescue, gRNAs and Cargo are present on the third chromosome. Cas9 is on the second chromosome, and the target locus, tko, is on the X. Rescue and Cargo are ultimately found in almost all individuals in the population. In contrast, the frequency of Cas9-bearing individuals decreases over time.
Figure 49D:
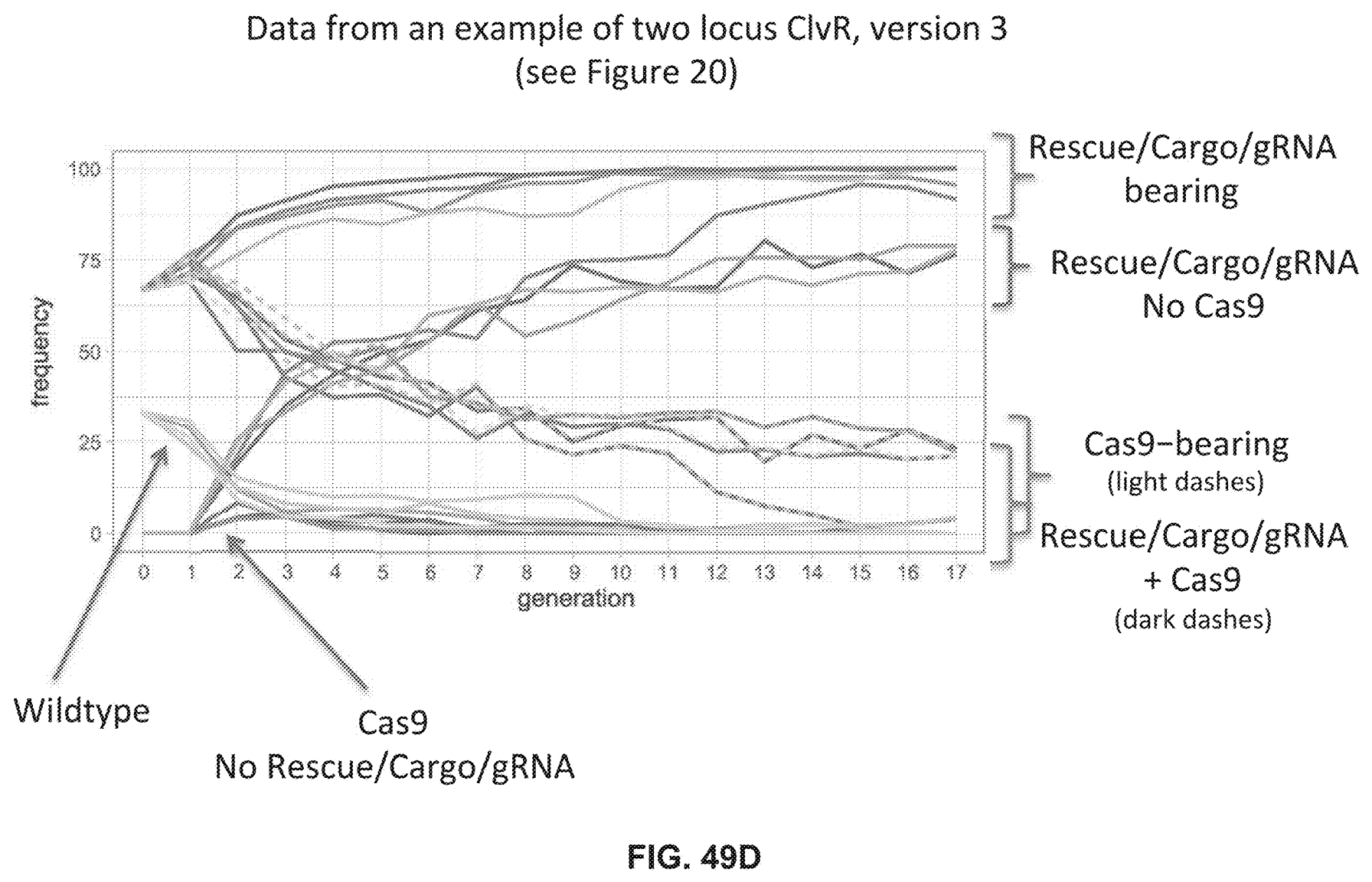
Figure 49E:
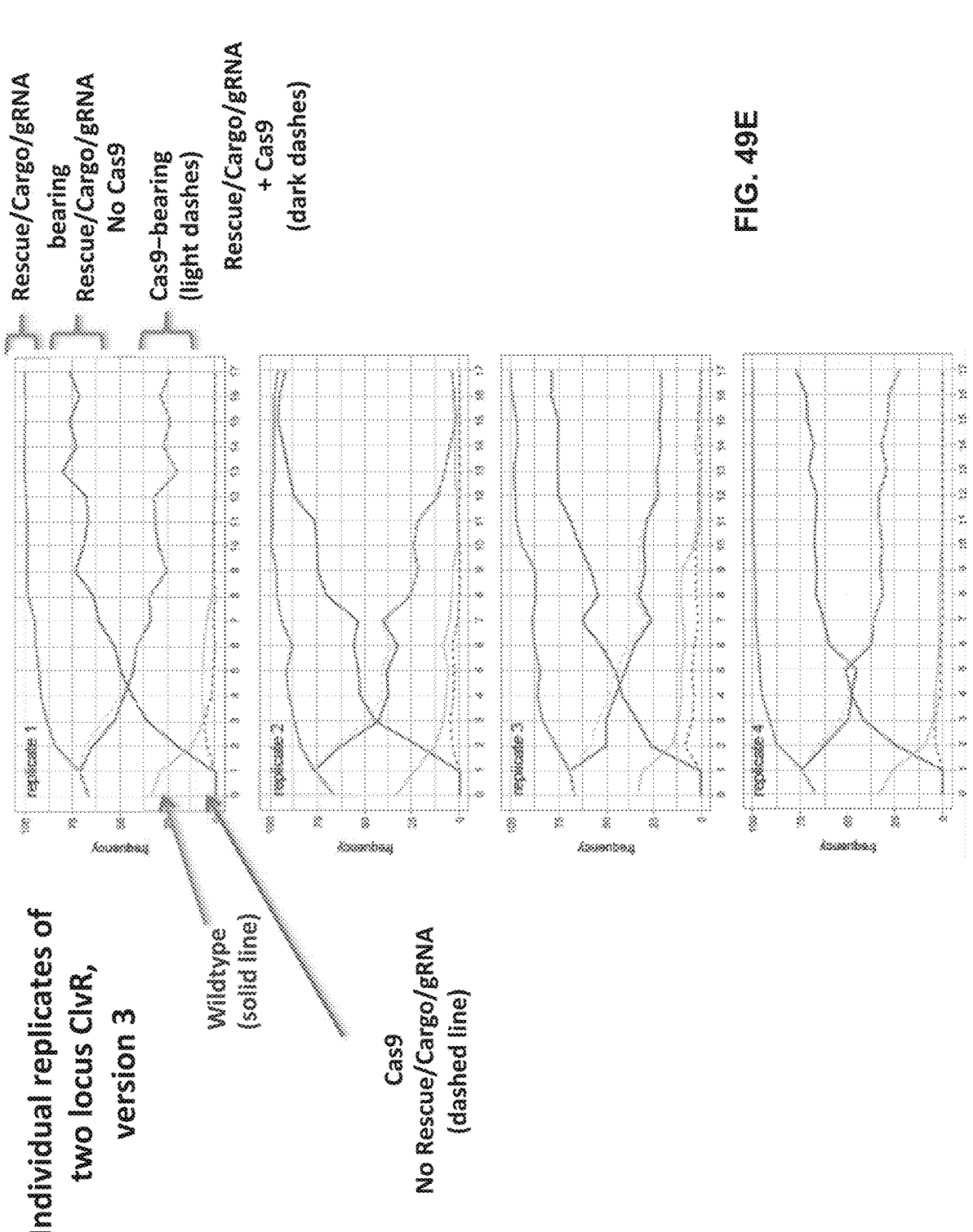
FIG. 49E shows an embodiment of individual replicates of the four drive experiments illustrated in FIGS. 49B-49D.

Counts of the proportion of individuals carrying the two transgenic components (Cas9 and/or Rescue+ Cargo) were plotted for each generation for the four replicates, and are summarized in FIGS. 49B-49D. FIG. 49B and FIG. 49C present a subset of the different transgene-bearing and non-transgene-bearing genotypes observed over time, for ease of visualization. FIG. 49D presents all combinations of transgene-bearing and non-transgene-bearing genotypes. Note that the frequency of Rescue+ Cargo+gRNA-bearing genotypes increases over time for all replicates, while the frequency of Cas9-bearing genotypes decreases. Whenever Cas9 and Rescue+ Cargo+gRNA are found in the same individual, cleavage at the tko locus occurs. Progeny that inherit the Rescue+ Cargo+gRNAs always survive because they carry at least one copy of the Rescue transgene. In contrast, those who inherit Cas9 but not the Rescue transgene may die if the transgene is in an individual that lack a functional copy of tko, resulting in a decrease in Cas9 frequency in the population over the generations.

Example 41

This example shows, using modeling, the effects of linkage between two components of the two locus ClvR system. When both components of the system are at the same locus they always travel together and have a recombination distance of 0 with respect to each other (0 m.u.=map units) (FIG. 50). In this scenario whenever the Rescue-bearing construct spreads so does Cas9. In contrast, as the distance between these two constructs increases Cas9 starts to find itself in individuals who have no functional copies of the essential gene, which results in a decrease in its population frequency over time.

An interesting case is presented by the example of a 12.5% recombination distance (m.u.=map units). As shown in FIG. 50, the frequency of the Rescue-bearing construct goes to 100%, as does the frequency of the cleaved target sequence in the essential gene. These events occur because Cas9 is found together with Rescue+ Cargo+gRNAs a relatively high frequency of the time as compared with the situation in which Cas9 freely recombines with the other locus (50+% recombination). Thus, by about generation 25 all endogenous versions of the essential gene have been cleaved and the population is now dependent on (addicted to) the presence of the rescue transgene. Importantly, however, the frequency of Cas9 has decreased significantly. This means that while the population is locked into a Rescue-bearing state, its ability to engage in further drive into new space is limited, as is its ability to drive in the face of new introductions of wildtype. For any given introduction frequency the frequency of Cas9 is higher with linkage than without because Cas9 more often finds itself in Rescue-bearing individuals, and therefore survives the loss through cleavage of the endogenous copy of the essential gene. In contrast, as the distance between Cas9 and the Rescue-bearing construct increases the probability that Cas9 will find itself in individuals lacking any functional copies of the essential gene rises, resulting in its loss from the population.

For example, for the 12.5% recombination distance illustrated in FIG. 50 an implication is that while the Rescue-bearing construct has gone to 100%, the frequency of Cas9 does decrease significantly. This means that if more wild-types were added to the population the level of drive would be decreased, as illustrated in FIGS. 34 and 35 for the case of unlinked loci, albeit more slowly. This can be useful if migration continually brings in some level of wildtype individuals. It can also be useful as a way of bringing about reversibility, through dilution with wildtypes. Linkage will often demand that more wildtypes be added than in the case of no linkage.

Linkage is also important in terms of thinking about the ability of ClvR to spread beyond a target area. In short, by titrating the degree of linkage between the two locus components one can titrate the extent of ClvR spread in space. This can be appreciated by considering first the case of completely linked loci, single locus ClvR. In this case drive is always present. However, when different degrees of linkage are present the two components of the system dissociate from each other specific kinetics. The important point is that regardless of the degree of linkage, as two locus ClvR spreads in space, drive will decrease as Cas9 segregates away from the Rescue-bearing components. It will segregate slowly when recombination distances are low (12.5 m.u.), and more rapidly when recombination distances are higher. In any case other than complete linkage, segregation of Cas9 from Rescue-bearing constructs will ultimately result in loss of drive. In this way any degree of linkage makes two locus ClvR ultimately a self-limiting drive system with respect to spread in space. Two locus Clvr can spread to genotype fixation in a constrained area in which all the wildtype copies of the essential gene have been lost (genetic addiction) (as in FIG. 50, 12.5% recombination). But, when spread in space is not constrained, the ultimate loss of Cas9 through segregation and loss in dead individuals who lack functional copies of the essential gene results in loss of drive potential.

REFERENCES

WHO World Malaria Report 2014. WHO at <who.int/malaria/publications/world_malaria_report_2014/en/>

Alphey, L. Genetic Control of Mosquitoes. Annu. Rev. Entomol. 59, 205-224 (2014).

Resnik, D. B. Ethical Issues in Field Trials of Genetically Modified Disease-Resistant Mosquitoes. Dev. World Bioeth. 14, 37-46 (2014).

Malavasi, A. Project *Aedes* transgenic population control in Juazeiro and Jacobina Bahia, Brazil. BMC Proc. 8, O11 (2014).

Popovici, J. et al. Assessing key safety concerns of a *Wolbachia*-based strategy to control dengue transmission by *Aedes* mosquitoes. Mem. Inst. Oswaldo Cruz 105, 957-964 (2010).

Walker, T. et al. The wMel *Wolbachia* strain blocks dengue and invades caged *Aedes aegypti* populations. Nature 476, 450-453 (2011).

Hoffmann, A. A. et al. Successful establishment of *Wolbachia* in *Aedes* populations to suppress dengue transmission. Nature 476, 454-457 (2011).

Sebrovskii, A. S. A New Possible Method of Pest Control. Zool Zh 19, 618-630 (1940).

Curtis, C. F. Possible Use of Translocations to fix Desirable Genes in Insect Pest Populations. Nature 218, 368-369 (1968).

Gould, F. & Schliekelman, P. POPULATION GENETICS OF AUTOCIDAL CONTROL AND STRAIN REPLACEMENT. Annu. Rev. Entomol. 49, 193-217 (2004).

Sinkins, S. P. & Gould, F. Gene drive systems for insect disease vectors. Nat. Rev. Genet. 7, 427-435 (2006).

Chen, C.-H. et al. A Synthetic Maternal-Effect Selfish Genetic Element Drives Population Replacement in *Drosophila*. Science 316, 597-600 (2007).

Gould, F., Huang, Y., Legros, M. & Lloyd, A. L. A Killer-Rescue system for self-limiting gene drive of anti-pathogen constructs. Proc. R. Soc. B Biol. Sci. 275, 2823-2829 (2008).

Marshall, J. M. & Hay, B. A. GENERAL PRINCIPLES OF SINGLE-CONSTRUCT CHROMOSOMAL GENE DRIVE: SINGLE-CONSTRUCT GENE DRIVE. Evolution 66, 2150-2166 (2012).

Marshall, J. M. The Impact of Dissociation on Transposon-Mediated Disease Control Strategies. Genetics 178, 1673-1682 (2008).

Davis, S., Bax, N. & Grewe, P. Engineered Underdominance Allows Efficient and Economical Introgression of Traits into Pest Populations. j. Theor. Biol. 212, 83-98 (2001).

Magori, K. Genetically Engineered Underdominance for Manipulation of Pest Populations: A Deterministic Model. Genetics 172, 2613-2620 (2005).

Brelsfoard, C. L. & Dobson, S. L. *Wolbachia*-based strategies to control insect pests and disease vectors. Asia Pac j Mol Biol Biotechnol 17, 55-63 (2009).

Huang, Y., Magori, K., Lloyd, A. L. & Gould, F. INTRODUCING DESIRABLE TRANSGENES INTO INSECT POPULATIONS USING Y-LINKED MEIOTIC DRIVE?A THEORETICAL ASSESSMENT. Evolution 61, 717-726 (2007).

Lyttle, T. W. Experimental population genetics of meiotic drive systems I. Pseudo-Y chromosomal drive as a means of eliminating cage populations of *Drosophila melanogaster*. Genetics 86, 413-445 (1977).

Magnusson, K. et al. Demasculinization of the *Anopheles gambiae*×chromosome. BMC Evol. Biol. 12, 69 (2012).

Simoni, A. et al. Development of synthetic selfish elements based on modular nucleases in *Drosophila melanogaster*. Nucleic Acids Res. 42, 7461-7472 (2014).

Burt, A. & Koufopanou, V. Homing endonuclease genes: the rise and fall and rise again of a selfish element. Curr. Opin. Genet. Dev. 14, 609-615 (2004).

Gimble, F. S. Invasion of a multitude of genetic niches by mobile endonuclease genes. FEMS Microbiol. Lett. 185, 99-107 (2000).

Galizi, R. et al. A synthetic sex ratio distortion system for the control of the human malaria mosquito. Nat. Commun. 5, (2014).

Akbari, O. S. et al. A Synthetic Gene Drive System for Local, Reversible Modification and Suppression of Insect Populations. Curr. Biol. 23, 671-677 (2013).

Akbari, O. S. et al. Novel Synthetic *Medea* Selfish Genetic Elements Drive Population Replacement in *Drosophila*; a Theoretical Exploration of *Medea*—Dependent Population Suppression. ACS Synth. Biol. 3, 915-928 (2014).

Esvelt, K. M., Smidler, A. L., Catteruccia, F. & Church, G. M. Concerning RNA-guided gene drives for the alteration of wild populations. eLife e03401 (2014). doi:10.7554/eLife.03401

Isaacs, A. T. et al. Engineered Resistance to *Plasmodium falciparum* Development in Transgenic *Anopheles stephensi*. PLOS Pathog. 7, e1002017 (2011).

Hollingdale, M. R., Nardin, E. H., Tharavanij, S., Schwartz, A. L. & Nussenzweig, R. S. Inhibition of entry of *Plasmodium falciparum* and *P. vivax* sporozoites into cultured cells; an in vitro assay of protective antibodies. J. Immunol. 132, 909-913 (1984).

Li, F., Patra, K. P. & Vinetz, J. M. An Anti-Chitinase Malaria Transmission-Blocking Single-Chain Antibody as an Effector Molecule for Creating a *Plasmodium falciparum*-Refractory Mosquito. J. Infect. Dis. 192, 878-887 (2005).

Yen, P.-S., James, A., Li, J.-C., Chen, C.-H. & Failloux, A.-B. Synthetic miRNAs induce dual arboviral-resistance phenotypes in the vector mosquito *Aedes aegypti*. Commun. Biol. 1, 11 (2018).

Franz, A. W. E. et al. Engineering RNA interference-based resistance to dengue virus type 2 in genetically modified *Aedes aegypti*. Proc. Natl. Acad. Sci. 103, 4198-4203 (2006).

Mathur, G. et al. Transgene-mediated suppression of dengue viruses in the salivary glands of the yellow fever mosquito, *Aedes aegypti*. Insect Mol. Biol. 19, 753-763 (2010).

Travanty, E. A. et al. Using RNA interference to develop dengue virus resistance in genetically modified *Aedes aegypti*. Insect Biochem. Mol. Biol. 34, 607-613 (2004).

Castillo, J. A. et al. Complex interaction between dengue virus replication and expression of miRNA-133a. BMC Infect. Dis. 16, (2016).

Shmakov, S. et al. Discovery and Functional Characterization of Diverse Class 2 CRISPR-Cas Systems. Mol. Cell 60, 385-397 (2015).

Koonin, E. V., Makarova, K. S. & Zhang, F. Diversity, classification and evolution of CRISPR-Cas systems. Curr. Opin. Microbiol. 37, 67-78 (2017).

Shmakov, S. et al. Diversity and evolution of class 2 CRISPR-Cas systems. Nat. Rev. Microbiol. 15, 169-182 (2017).

Koonin, E. V., Makarova, K. S. & Wolf, Y. I. Evolutionary Genomics of Defense Systems in Archaea and Bacteria. Annu. Rev. Microbiol. 71, 233-261 (2017).

Bischof, Johannes, Robert K. Maeda, Monika Hediger, Frangois Karch, and Konrad Basler. 2007. "An Optimized Transgenesis System for *Drosophila* Using Germ-Line-Specific phiC31 Integrases." Proceedings of the National Academy of Sciences of the United States of America 104 (9): 3312-17.

Dang, Ying, Gengxiang Jia, Jennie Choi, Hongming Ma, Edgar Anaya, Chunting Ye, Premlata Shankar, and Haoquan Wu. 2015. "Optimizing sgRNA Structure to Improve CRISPR-Cas9 Knockout Efficiency." Genome Biology 16 (December): 280.

Doench, John G., Nicolo Fusi, Meagan Sullender, Mudra Hegde, Emma W. Vaimberg, Katherine F. Donovan, Ian Smith, et al. 2016. "Optimized sgRNA Design to Maximize Activity and Minimize off-Target Effects of CRISPR-Cas9." Nature Biotechnology 34 (2): 184-91.

*Drosophila* 12 Genomes Consortium, Andrew G. Clark, Michael B. Eisen, Douglas R. Smith, Casey M. Bergman, Brian Oliver, Therese A. Markow, et al. 2007. "Evolution of Genes and Genomes on the *Drosophila* Phylogeny." Nature 450 (7167): 203-18.

Gibson, Daniel G., Lei Young, Ray-Yuan Chuang, J. Craig Venter, Clyde A. Hutchison, and Hamilton O. Smith. 2009. "Enzymatic Assembly of DNA Molecules up to Several Hundred Kilobases." Nature Methods 6 (5): 343-45.

Kiani S, et al. (2015) Cas9 gRNA engineering for genome editing, activation and repression. Nat Methods 12(11): 1051-1054.

Oberhofer, Georg, Tobin Ivy, and Bruce A. Hay. 2018. "Behavior of Homing Endonuclease Gene Drives Targeting Genes Required for Viability or Female Fertility with Multiplexed Guide RNAs." bioRxiv.

Port, Fillip, Hui-Min Chen, Tzumin Lee, and Simon L. Bullock. 2014. "Optimized CRISPR/Cas Tools for Efficient Germline and Somatic Genome Engineering in *Drosophila*." Proceedings of the National Academy of Sciences of the United States of America 111 (29): E2967-76.

Royden, C. S., V. Pirrotta, and L. Y. January 1987. "The Tko Locus, Site of a Behavioral Mutation in D. *Melanogaster*, Codes for a Protein Homologous to Prokaryotic Ribosomal Protein S12." Cell 51 (2): 165-73.

Shaner, Nathan C., Robert E. Campbell, Paul A. Steinbach, Ben N. G. Giepmans, Amy E. Palmer, and Roger Y. Tsien. 2004. "Improved Monomeric Red, Orange and Yellow Fluorescent Proteins Derived from Discosoma Sp. Red Fluorescent Protein." Nature Biotechnology 22 (12): 1567-72.

Theilmann, D. A., and S. Stewart. 1992. "Molecular Analysis of the Trans-Activating IE-2 Gene of *Orgyia Pseudotsugata* Multicapsid Nuclear Polyhedrosis Virus." Virology 187 (1): 84-96.

Akbari, Omar S., Chun-Hong Chen, John M. Marshall, Haixia Huang, Igor Antoshechkin, and Bruce A. Hay. 2012. "Novel Synthetic Medea Selfish Genetic Elements Drive Population Replacement in *Drosophila*; a Theoretical Exploration of Medea-Dependent Population Suppression." *ACS Synthetic Biology*, December.

Akbari, Omar S., Kelly D. Matzen, John M. Marshall, Haixia Huang, Catherine M. Ward, and Bruce A. Hay. 2013. "A Synthetic Gene Drive System for Local, Reversible Modification and Suppression of Insect Populations." Current Biology: CB 23 (8): 671-77.

Altrock, P. M., A. Traulsen, and F. A. Reed. 2011. "Stability Properties of Underdominance in Finite Subdivided Populations." PLoS Computational Biology 7 (11): e1002260.

Altrock, P. M., A. Traulsen, R. G. Reeves, and F. A. Reed. 2010. "Using Underdominance to Bi-Stably Transform Local Populations." Journal of Theoretical Biology 267 (1): 62-75.

Beaghton, A., P. J. Beaghton, and A. Burt. 2016. "Gene Drive through a Landscape: Reaction-Diffusion Models of Population Suppression and Elimination by a Sex Ratio Distorter." Theoretical Population Biology 108 (April): 51-69.

Beaghton, A., A. Hammond, T. Nolan, A. Crisanti, H. C. Godfray, and A. Burt. 2017. "Requirements for Driving Antipathogen Effector Genes into Populations of Disease Vectors by Homing." Genetics 205 (4): 1587-96.

Ben-David, E., A. Burga, and L. Kruglyak. 2017. "A Maternal-Effect Selfish Genetic Element in *Caenorhabditis Elegans*." Science 356 (6342): 1051-55.

Braig, H. R., and G. Yan. 2001. "The Spread of Genetic Constructs in Natural Insect Populations." In Genetically Engineered Organisms: Assessing Environmental and Human Health Effects, edited by D. K. Letourneau and B. E. Burrows, 251-314. CRC Press.

Buchman, A. B., T. Ivy, J. M. Marshall, O. S. Akbari, and B. A. Hay. 2018. "Engineered Reciprocal Chromosome Translocations Drive High Threshold, Reversible Population Replacement in *Drosophila.*" *ACS Synthetic Biology.*

Burt, A. 2003. "Site-Specific Selfish Genes as Tools for the Control and Genetic Engineering of Natural Populations." Proceedings. Biological Sciences/The Royal Society270 (1518): 921-28.

Burt, A., and R. Trivers. 1998. "Genetic Conflicts in Genomic Imprinting." Proceedings. Biological Sciences/ The Royal Society265 (1413): 2393-97.

Champer, J., R. Reeves, S. Y. Oh, C. Liu, J. Liu, A. G. Clark, and P. W. Messer. 2017. "Novel CRISPR/Cas9 Gene Drive Constructs Reveal Insights into Mechanisms of Resistance Allele Formation and Drive Efficiency in Genetically Diverse Populations." PLoS Genetics13 (7): e1006796.

Chan, Yuk-Sang, David S. Huen, Ruth Glauert, Eleanor Whiteway, and Steven Russell. 2013. "Optimising Homing Endonuclease Gene Drive Performance in a Semi-Refractory Species: The *Drosophila Melanogaster* Experience." PloS One8 (1): e54130.Chan, Yuk-Sang, Daniel A. Naujoks, David S. Huen, and Steven Russell. 2011. "Insect Population Control by Homing Endonuclease-Based Gene Drive: An Evaluation in *Drosophila Melanogaster.*" Genetics188 (1): 33-44.

Chen, C. H., H. Huang, C. M. Ward, J. T. Su, L. V. Schaeffer, M. Guo, and B. A. Hay. 2007. "A Synthetic Maternal-Effect Selfish Genetic Element Drives Population Replacement in *Drosophila.*" Science316 (5824): 597-600.

Davis, Stephen, Nicholas Bax, and Peter Grewe. 2001. "Engineered Underdominance Allows Efficient and Economical Introgression of Traits into Pest Populations." Journal of Theoretical Biology212 (1): 83-98.

Farasat I, Salis H M (2016) A Biophysical Model of CRISPR/Cas9 Activity for Rational Design of Genome Editing and Gene Regulation. PLoS Comput Biol12(1): e1004724.

Galizi, R., L. A. Doyle, M. Menichelli, F. Bernardini, A. Deredec, A. Burt, B. L. Stoddard, N. Windbichler, and A. Crisanti. 2014. "A Synthetic Sex Ratio Distortion System for the Control of the Human Malaria Mosquito." Nature Communications5: 3977.

Galizi, R., A. Hammond, K. Kyrou, C. Taxiarchi, F. Bernardini, S. M. O'Loughlin, P. A. Papathanos, T. Nolan, N. Windbichler, and A. Crisanti. 2016. "A CRISPR-Cas9 Sex-Ratio Distortion System for Genetic Control." Scientific Reports6: 31139.Gantz, V. M., and E. Bier. 2015. "The Mutagenic Chain Reaction: A Method for Converting Heterozygous to Homozygous Mutations." Science348 (6233): 442-44.

Gantz, V. M., N. Jasinskiene, O. Tatarenkova, A. Fazekas, V. M. Macias, E. Bier, and A. A. James. 2015. "Highly Efficient Cas9-Mediated Gene Drive for Population Modification of the Malaria Vector Mosquito *Anopheles Stephensi.*" Proceedings of the National Academy of Sciences of the United States of America112 (49): E6736-43.

Godfray, H. C. J., A. North, and A. Burt. 2017. "How Driving Endonuclease Genes Can Be Used to Combat Pests and Disease Vectors." BMC Biology5 (1): 81.

Gokhale, Chaitanya S., Richard Guy Reeves, and Floyd A. Reed. 2014. "Dynamics of a Combined *Medea*-Under-dominant Population Transformation System." BMC Evolutionary Biology14: 98.

Gould, Fred, and Paul Schliekelman. 2004. "Population Genetics of Autocidal Control and Strain Replacement." Annual Review of Entomology 49: 193-217.

Hammond, A., R. Galizi, K. Kyrou, A. Simoni, C. Siniscalchi, D. Katsanos, M. Gribble, et al. 2016. "A CRISPR-Cas9 Gene Drive System Targeting Female Reproduction in the Malaria Mosquito Vector *Anopheles Gambiae.*" Nature Biotechnology 34 (1): 78-83.

Hay, Bruce A., Chun-Hong Chen, Catherine M. Ward, Haixia Huang, Jessica T. Su, and Ming Guo. 2010. "Engineering the Genomes of Wild Insect Populations: Challenges, and Opportunities Provided by Synthetic *Medea* Selfish Genetic Elements." Journal of Insect Physiology 56 (10): 1402-13.

Hu, W., Z. D. Jiang, F. Suo, J. X. Zheng, W. Z. He, and L. L. Du. 2017. "A Large Gene Family in Fission Yeast Encodes Spore Killers That Subvert Mendel's Law." *eLife* 6.

Lack J B, Lange J D, Tang A D, Corbett-Detig R B, Pool J E (2016) A Thousand Fly Genomes: An Expanded *Drosophila* Genome Nexus. Mol Biol Evol 33(12):3308-3313.

Marshall, J. M. 2009. "The Effect of Gene Drive on Containment of Transgenic Mosquitoes." Journal of Theoretical Biology258 (2): 250-65.

Marshall, J. M., and B. A. Hay. 2011. "Inverse *Medea* as a Novel Gene Drive System for Local Population Replacement: A Theoretical Analysis." The Journal of Heredity 102 (3): 336-41.

——. 2012. "Confinement of Gene Drive Systems to Local Populations: A Comparative Analysis." Journal of Theoretical Biology294: 153-71.

Marshall, John M., and Bruce A. Hay. 2012a. "Confinement of Gene Drive Systems to Local Popu . . . [J Theor Biol. 2012]—PubMed—NCBI." Journal of Theoretical Biology294 (February): 153-71.

——. 2012b. "General Principles of Single-Construct Chromosomal . . . [Evolution. 2012]—PubMed—NCBI." Evolution; International Journal of Organic Evolution 66 (7): 2150-66.

Marshall, John M., Geoffrey W. Pittman, Anna B. Buchman, and Bruce A. Hay. 2011. "Semele: A Killer-Male, Rescue-Female System for Suppression and Replacement of Insect Disease Vector Populations." Genetics187 (2): 535-51.

Nuckolls, N. L., M. A. Bravo Nunez, M. T. Eickbush, J. M. Young, J. J. Lange, J. S. Yu, G. R. Smith, S. L. Jaspersen, H. S. Malik, and S. E. Zanders. 2017. "Wtf Genes Are Prolific Dual Poison-Antidote Meiotic Drivers." *eLife*-6.

Preston, Christine R., Carlos C. Flores, and William R. Engels. 2006. "Differential Usage of Alternative Pathways of Double-Strand Break Repair in *Drosophila.*" Genetics172 (2): 1055-68.

Reeves, R. G., J. Bryk, P. M. Altrock, J. A. Denton, and F. A. Reed. 2014. "First Steps towards Underdominant Genetic Transformation of Insect Populations." PloS One9 (5): e97557.

Seidel, H. S., M. Ailion, J. Li, A. van Oudenaarden, M. V. Rockman, and L. Kruglyak. 2011. "A Novel Sperm-Delivered Toxin Causes Late-Stage Embryo Lethality and Transmission Ratio Distortion in C. *Elegans.*" PLoS Biology9 (7): e1001115.

Simoni, A., C. Siniscalchi, Y. S. Chan, D. S. Huen, S. Russell, N. Windbichler, and A. Crisanti. 2014. "Development of Synthetic Selfish Elements Based on Modular Nucleases in *Drosophila Melanogaster*." Nucleic Acids Research 42 (11): 7461-72.

Wade, M. J., and R. W. Beeman. 1994. "The Population Dynamics of Maternal-Effect Selfish Genes." Genetics138 (4): 1309-14.

Ward, Catherine M., Jessica T. Su, Yunxin Huang, Alun L. Lloyd, Fred Gould, and Bruce A. Hay. 2011. *"Medea* Selfish Genetic Elements as Tools for Altering Traits of Wild Populations: A Theoretical Analysis." Evolution; International Journal of Organic Evolution 65 (4): 1149-62.

Windbichler, Nikolai, Philippos Aris Papathanos, Flaminia Catteruccia, Hilary Ranson, Austin Burt, and Andrea Crisanti. 2007. "Homing Endonuclease Mediated Gene Targeting in *Anopheles Gambiae* Cells and Embryos." Nucleic Acids Research 35 (17): 5922-33.

Windbichler, N., M. Menichelli, P. A. Papathanos, S. B. Thyme, H. Li, U. Y. Ulge, B. T. Hovde, et al. 2011. "A Synthetic Homing Endonuclease-Based Gene Drive System in the Human Malaria Mosquito." Nature 473 (7346): 212-15.

Windbichler, N., P. A. Papathanos, and A. Crisanti. 2008. "Targeting the X Chromosome during Spermatogenesis Induces Y Chromosome Transmission Ratio Distortion and Early Dominant Embryo Lethality in *Anopheles Gambiae*." PLoS Genetics4 (12): e1000291. Sun, N., and H. Zhao. 2014. "A Single-Chain TALEN Architecture for Genome Engineering." Molecular bioSystems 10 (3): 446-53.

---

What is claimed is:

1. A composition comprising two vectors:

a first vector comprising:

a first sequence encoding a first component of a DNA sequence modifying complex, wherein the first component of the DNA sequence modifying complex is a nuclease, wherein the nuclease is Cas9 nuclease;

a second sequence encoding a second component of the DNA sequence modifying complex, wherein the second component of the DNA sequence modifying complex is a guide RNA, wherein the guide RNA enables the Cas9 nuclease to target specific sequences within the essential gene;

a first promoter operably linked to the first sequence encoding the first component of the DNA sequence modifying complex, wherein the first promoter comprises at least one of a germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, a viral promoter or prokaryotic promoter; and a second promoter operably linked to the second sequence encoding the second component of the DNA sequence modifying complex, wherein the second promoter comprises at least one of a germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, a viral promoter or prokaryotic promoter;

wherein the DNA sequence modifying complex is configured to induce one or more sequence modifications in an endogenous copy of an essential gene;

a second vector comprising:

a rescue transgene sequence, wherein the rescue transgene is either a recoded copy of the essential gene or is a gene of unrelated sequence, wherein the rescue transgene encodes a protein that is functionally equivalent to a protein encoded by the essential gene; and a rescue transgene promoter operably linked to the rescue transgene sequence, wherein the rescue transgene promoter comprises at least one of a endogenous promoter for the essential gene, germline promoter, a male specific germline promoter, a female specific germline promoter, a cell-type specific promoter, a tissue-specific promoter, a ubiquitous promoter, a promoter activated at a specific stage of mitosis, a promoter activated at a specific stage of meiosis, a viral promoter or prokaryotic promoter, wherein the composition comprising two vectors is configured for reversibly modifying a population of organisms.

2. The composition of claim 1, wherein the nuclease cleaves and generates one or more double strand breaks in the endogenous copy of the essential gene.

3. The composition of claim 2, wherein the one or more double strand breaks are repaired to create an altered sequence of the essential gene.

4. The composition of claim 1, wherein the DNA sequence modifying complex does not modify the rescue transgene.

5. The composition of claim 1, wherein the composition comprising two vectors further comprises one or more cargo sequences.

6. The composition of claim 5, wherein the one or more cargo sequences comprise a one or more foreign gene sequences, or one or more alleles of an endogenous chromosomal or extra-chromosomal gene to which one of the vectors has been linked through nearby, or internal to the gene, insertion on the chromosome or extra-chromosomal element that carries the endogenous allele of interest.

7. A method of reversibly modifying a population, the method comprising:

obtaining a wild type organism, positioning the two vectors of claim 1 in the wild type organism generating an altered organism by inducing one or more sequence modifications in an essential gene by a DNA sequence modifying complex that result in a defect in survival, growth control, fertility, or differentiation in one or more cells in the organism, and rescuing the defect in survival, growth control, fertility, or differentiation by a rescue transgene in the composition comprising two vectors, introducing the altered organism in an environment wherein an increase in a frequency of the altered organism is desired relative to a frequency of the wild type organism in a population;

replacing the wild type organism with the altered organism in the population in the environment, thereby obtaining a modified population reintroducing the wild type organism in an environment wherein an increase in the frequency of the wild type organism is desired relative to the frequency of the altered organism in the modified population;

replacing the altered organism with the wild type organism in the modified population in the environment, thereby reversibly modifying the population.

8. The method of claim 7, wherein the one or more cells comprise somatic cells, germline cells, gametes, or a combination thereof.

9. The method of claim 7, wherein the reversible modification of the population occurs at a rapid rate, high frequency, or both.

10. The method of claim 9, wherein the rapid rate is defined as replacement of at least 90% of the wild type organism by the altered organism or vice versa in the population after at most 100 generations.

11. The method of claim 9, wherein the high frequency is defined as replacement of at least 90% of the wild type organism by the altered organism or vice versa after 100 generations in the population.

* * * * *

```
                              SEQUENCE LISTING

Sequence total quantity: 43
SEQ ID NO: 1            moltype = DNA  length = 24
FEATURE                Location/Qualifiers
misc_feature           1..24
                       note = P0-68E FWD
source                 1..24
                       mol_type = other DNA
                       organism = synthetic construct
SEQUENCE: 1
gtcgtgcaca accagagact ggag                                       24

SEQ ID NO: 2            moltype = DNA  length = 24
FEATURE                Location/Qualifiers
misc_feature           1..24
                       note = P0-68E REV
source                 1..24
                       mol_type = other DNA
                       organism = synthetic construct
SEQUENCE: 2
aaacctccag tctctggttg tgca                                       24

SEQ ID NO: 3            moltype = DNA  length = 40
FEATURE                Location/Qualifiers
misc_feature           1..40
                       note = P9-68E-hr-left FWD
source                 1..40
                       mol_type = other DNA
                       organism = synthetic construct
SEQUENCE: 3
cttattacgt ggccaactag gtgcccaaaa tgtgtgtgga                       40

SEQ ID NO: 4            moltype = DNA  length = 40
FEATURE                Location/Qualifiers
misc_feature           1..40
                       note = P10-68E-hr-left REV
source                 1..40
                       mol_type = other DNA
                       organism = synthetic construct
SEQUENCE: 4
gcttcggtgt gtccgtcagt gagaggtttt gccgcgattt                       40

SEQ ID NO: 5            moltype = DNA  length = 41
FEATURE                Location/Qualifiers
misc_feature           1..41
                       note = P11-attP FWD
source                 1..41
                       mol_type = other DNA
                       organism = synthetic construct
SEQUENCE: 5
aaatcgcggc aaaacctctc actgacggac acaccgaagc c                     41

SEQ ID NO: 6            moltype = DNA  length = 40
FEATURE                Location/Qualifiers
misc_feature           1..40
                       note = P12-attP REV
source                 1..40
                       mol_type = other DNA
                       organism = synthetic construct
```

-continued

```
SEQUENCE: 6
ccttgctgcc cgcctgcagc agtcgcgctc gcgcgactga                             40

SEQ ID NO: 7              moltype = DNA   length = 40
FEATURE                  Location/Qualifiers
misc_feature             1..40
                         note = P13-dv-tko FWD
source                   1..40
                         mol_type = other DNA
                         organism = synthetic construct
SEQUENCE: 7
tcagtcgcgc gagcgcgact gctgcaggcg ggcagcaagg                             40

SEQ ID NO: 8              moltype = DNA   length = 45
FEATURE                  Location/Qualifiers
misc_feature             1..45
                         note = P14-dv-tko REV
source                   1..45
                         mol_type = other DNA
                         organism = synthetic construct
SEQUENCE: 8
gcagtgcaaa aaagttggtg gggtcggacc tcaagttgca tatgg                       45

SEQ ID NO: 9              moltype = DNA   length = 40
FEATURE                  Location/Qualifiers
misc_feature             1..40
                         note = P15-68E-hr-right FWD
source                   1..40
                         mol_type = other DNA
                         organism = synthetic construct
SEQUENCE: 9
tgcaacttga ggtccgaccc caccaacttt tttgcactgc                             40

SEQ ID NO: 10             moltype = DNA   length = 40
FEATURE                  Location/Qualifiers
misc_feature             1..40
                         note = P16-68E-hr-right REV
source                   1..40
                         mol_type = other DNA
                         organism = synthetic construct
SEQUENCE: 10
gggcgaattg ggtacaagct aggatgatgg gatgctggaa                             40

SEQ ID NO: 11             moltype = DNA   length = 60
FEATURE                  Location/Qualifiers
misc_feature             1..60
                         note = P21-tko-guidesA FWD
source                   1..60
                         mol_type = other DNA
                         organism = synthetic construct
SEQUENCE: 11
ctattttcaa tttaacgtcg ctgcagcgat gccattccag tttcagagct atgctggaaa    60

SEQ ID NO: 12             moltype = DNA   length = 60
FEATURE                  Location/Qualifiers
misc_feature             1..60
                         note = P22-tko-guidesA REV
source                   1..60
                         mol_type = other DNA
                         organism = synthetic construct
SEQUENCE: 12
ttccagcata gctctgaaac tcgccaaggg cgttgtcctg cgaagttcac ccggatatct    60

SEQ ID NO: 13             moltype = DNA   length = 60
FEATURE                  Location/Qualifiers
misc_feature             1..60
                         note = P23-tko-guidesB FWD
source                   1..60
                         mol_type = other DNA
                         organism = synthetic construct
SEQUENCE: 13
ctattttcaa tttaacgtcg caacattgta ctgtgccgcg gtttcagagc tatgctggaa    60

SEQ ID NO: 14             moltype = DNA   length = 60
FEATURE                  Location/Qualifiers
misc_feature             1..60
                         note = P24-tko-guidesB REV
source                   1..60
                         mol_type = other DNA
```

-continued

```
                        organism = synthetic construct
SEQUENCE: 14
ttccagcata gctctgaaac atcgaaagtg cgtgctggtg cgaagttcac ccggatatct   60

SEQ ID NO: 15          moltype = DNA   length = 40
FEATURE                Location/Qualifiers
misc_feature           1..40
                       note = P25-nosCas9 FWD
source                 1..40
                       mol_type = other DNA
                       organism = synthetic construct
SEQUENCE: 15
gttgtctata ctataagatc tataggcacg ggataacgct                          40

SEQ ID NO: 16          moltype = DNA   length = 42
FEATURE                Location/Qualifiers
misc_feature           1..42
                       note = P26-nos-Cas9 REV
source                 1..42
                       mol_type = other DNA
                       organism = synthetic construct
SEQUENCE: 16
gcaatcacag gtgagcaaaa aagcttggat ttcactggaa ct                       42

SEQ ID NO: 17          moltype = DNA   length = 42
FEATURE                Location/Qualifiers
misc_feature           1..42
                       note = P27-guidesA FWD
source                 1..42
                       mol_type = other DNA
                       organism = synthetic construct
SEQUENCE: 17
agttccagtg aaatccaagc ttttttgctc acctgtgatt gc                       42

SEQ ID NO: 18          moltype = DNA   length = 41
FEATURE                Location/Qualifiers
misc_feature           1..41
                       note = P28-guidesA REV
source                 1..41
                       mol_type = other DNA
                       organism = synthetic construct
SEQUENCE: 18
aatcacaggt gagcaaaaaa aattaaccct cactaaaggg a                        41

SEQ ID NO: 19          moltype = DNA   length = 40
FEATURE                Location/Qualifiers
misc_feature           1..40
                       note = P29-guidesB FWD
source                 1..40
                       mol_type = other DNA
                       organism = synthetic construct
SEQUENCE: 19
ccctttagtg agggttaatt ttttttgctc acctgtgatt                          40

SEQ ID NO: 20          moltype = DNA   length = 40
FEATURE                Location/Qualifiers
misc_feature           1..40
                       note = P30-guidesB REV
source                 1..40
                       mol_type = other DNA
                       organism = synthetic construct
SEQUENCE: 20
gcagcctcga gatcgatgat tgccgagcac aattgtctag                          40

SEQ ID NO: 21          moltype = DNA   length = 20
FEATURE                Location/Qualifiers
misc_feature           1..20
                       note = tko-seq1
source                 1..20
                       mol_type = other DNA
                       organism = synthetic construct
SEQUENCE: 21
aagcgttcca agctgcacag                                                20

SEQ ID NO: 22          moltype = DNA   length = 20
FEATURE                Location/Qualifiers
misc_feature           1..20
                       note = tko-seq2
source                 1..20
```

-continued

```
                             mol_type = other DNA
                             organism = synthetic construct
SEQUENCE: 22
cgcacatcca tttccaattg                                              20

SEQ ID NO: 23          moltype = DNA   length = 19
FEATURE                Location/Qualifiers
misc_feature           1..19
                       note = tko-seq3
source                 1..19
                       mol_type = other DNA
                       organism = synthetic construct
SEQUENCE: 23
cacacacaca ggtgcgttc                                               19

SEQ ID NO: 24          moltype = DNA   length = 41
FEATURE                Location/Qualifiers
misc_feature           1..41
                       note = tko-seq4
source                 1..41
                       mol_type = other DNA
                       organism = synthetic construct
SEQUENCE: 24
acaactagac gttggcaatc tcacaccttc ctcttcttct t                      41

SEQ ID NO: 25          moltype = DNA   length = 20
FEATURE                Location/Qualifiers
misc_feature           1..20
                       note = tko-seq5
source                 1..20
                       mol_type = other DNA
                       organism = synthetic construct
SEQUENCE: 25
tcagcgggat tagtgtaagt                                              20

SEQ ID NO: 26          moltype = DNA   length = 20
FEATURE                Location/Qualifiers
misc_feature           1..20
                       note = tko-seq6
source                 1..20
                       mol_type = other DNA
                       organism = synthetic construct
SEQUENCE: 26
catatgcaac ttgaggtccg                                              20

SEQ ID NO: 27          moltype = DNA   length = 20
FEATURE                Location/Qualifiers
misc_feature           1..20
                       note = s2-attB-rev
source                 1..20
                       mol_type = other DNA
                       organism = synthetic construct
SEQUENCE: 27
ttcgagaccg tgacctacat                                              20

SEQ ID NO: 28          moltype = DNA   length = 20
FEATURE                Location/Qualifiers
misc_feature           1..20
                       note = s2-u631-seq
source                 1..20
                       mol_type = other DNA
                       organism = synthetic construct
SEQUENCE: 28
agttccagtg aaatccaagc                                              20

SEQ ID NO: 29          moltype = DNA   length = 23
FEATURE                Location/Qualifiers
misc_feature           1..23
                       note = T3-seq REV
source                 1..23
                       mol_type = other DNA
                       organism = synthetic construct
SEQUENCE: 29
gttcccttta gtgagggtta att                                          23

SEQ ID NO: 30          moltype = DNA   length = 20
FEATURE                Location/Qualifiers
misc_feature           1..20
                       note = T3-seq FWD
```

-continued

```
source                    1..20
                          mol_type = other DNA
                          organism = synthetic construct
SEQUENCE: 30
attaaccctc actaaaggga                                            20

SEQ ID NO: 31             moltype = DNA   length = 22
FEATURE                   Location/Qualifiers
misc_feature              1..22
                          note = CAS91F
source                    1..22
                          mol_type = other DNA
                          organism = synthetic construct
SEQUENCE: 31
atggacaaga agtactccat tg                                         22

SEQ ID NO: 32             moltype = DNA   length = 20
FEATURE                   Location/Qualifiers
misc_feature              1..20
                          note = CAS91R
source                    1..20
                          mol_type = other DNA
                          organism = synthetic construct
SEQUENCE: 32
gatcggtatt gcccagaact                                            20

SEQ ID NO: 33             moltype = DNA   length = 20
FEATURE                   Location/Qualifiers
misc_feature              1..20
                          note = CAS92F2
source                    1..20
                          mol_type = other DNA
                          organism = synthetic construct
SEQUENCE: 33
agcgctaggc tgtccaaatc                                            20

SEQ ID NO: 34             moltype = DNA   length = 21
FEATURE                   Location/Qualifiers
misc_feature              1..21
                          note = CAS93F
source                    1..21
                          mol_type = other DNA
                          organism = synthetic construct
SEQUENCE: 34
gagaaaatcc tcacatttcg g                                          21

SEQ ID NO: 35             moltype = DNA   length = 21
FEATURE                   Location/Qualifiers
misc_feature              1..21
                          note = CAS94F2
source                    1..21
                          mol_type = other DNA
                          organism = synthetic construct
SEQUENCE: 35
agagtggaaa gacaatcctg g                                          21

SEQ ID NO: 36             moltype = DNA   length = 20
FEATURE                   Location/Qualifiers
misc_feature              1..20
                          note = CAS95F
source                    1..20
                          mol_type = other DNA
                          organism = synthetic construct
SEQUENCE: 36
ctgaacgcca aactgatcac                                            20

SEQ ID NO: 37             moltype = DNA   length = 20
FEATURE                   Location/Qualifiers
misc_feature              1..20
                          note = CAS96F
source                    1..20
                          mol_type = other DNA
                          organism = synthetic construct
SEQUENCE: 37
tggacgccac actgattcat                                            20

SEQ ID NO: 38             moltype = DNA   length = 21
FEATURE                   Location/Qualifiers
misc_feature              1..21
```

```
                        note = CAS96R
source                  1..21
                        mol_type = other DNA
                        organism = synthetic construct
SEQUENCE: 38
tcacaccttc ctcttcttct t                                                    21

SEQ ID NO: 39           moltype = DNA   length = 12817
FEATURE                 Location/Qualifiers
misc_feature            1..12817
                        note = p68-tko-step1
source                  1..12817
                        mol_type = other DNA
                        organism = synthetic construct
SEQUENCE: 39
agcttgtacc caattcgccc tatagtgagt cgtattacaa ttcactggcc gtcgttttac    60
aacgtcgtga ctgggaaaac cctggcgtta cccaacttaa tcgccttgca gcacatcccc   120
ctttcgccag ctggcgtaat agcgaagagg cccgcaccga tcgcccttcc caacagttgc   180
gcagcctgaa tggcgaatgg gacgcgccct gtagcggcgc attaagcgcg gcgggtgtgg   240
tggttacgcg cagcgtgacc gctacacttg ccagcgccct agcgcccgct cctttcgctt   300
tcttcccttc ctttctcgcc acgttcgccg gctttccccg tcaagctcta aatcgggggc   360
tccctttagg gttccgattt agtgctttac ggcacctcga ccccaaaaaa cttgattagg   420
gtgatggttc acgtagtggg ccatcgccct gatagacggt ttttcgccct ttgacgttgg   480
agtccacgtt ctttaatagt ggactcttgt tccaaactgg aacaacactc aaccctatct   540
cggtctattc ttttgattta taaggaattt tgccgatttc ggcctattgg ttaaaaaatg   600
agctgattta acaaaaattt aacgcgaatt ttaacaaaat attaacgctt acaatttagg   660
tggcactttt cggggaaatg tgcgcggaac ccctatttgt ttatttttct aaatacattc   720
aaatatgtat ccgctcatga cacaataacc ctgataaatg cttcaataat attgaaaaag   780
gaagagtatg agtattcaac atttccgtgt cgcccttatt cccttttttg cggcattttg   840
ccttcctgtt tttgctcacc cagaaacgct ggtgaaagta aaagatgctg aagatcagtt   900
gggtgcacga gtgggttaca tcgaactgga tctcaacagc ggtaagatcc ttgagagttt   960
tcgccccgaa gaacgttttc caatgatgag cacttttaaa gttctgctat gtggcgcggt  1020
attatcccgt attgacgccg ggcaagagca actcggtcgc cgcatacact attctcagaa  1080
tgacttggtt gagtactcac cagtcacaga aaagcatctt acggatggca tgacagtaag  1140
agaattatgc agtgctgcca taaccatgag tgataacact gcggccaact tacttctgac  1200
aacgatcgga ggaccgaagg agctaaccgc ttttttgcac aacatggggg atcatgtaac  1260
tcgccttgat cgttgggaac cggagctgaa tgaagccata ccaaacgacg agcgtgacac  1320
cacgatgcct gtagcaatgg caacaacgtt gcgcaaacta ttaactggcg aactacttac  1380
tctagcttcc cggcaacaat taatagactg gatggaggcg gataaagttg caggaccact  1440
tctgcgctcg gcccttccgg ctggctggtt tattgctgat aaatctggag ccggtgagcg  1500
tgggtctcgc ggtatcattg cagcactggg gccagatggt aagccctccc gtatcgtagt  1560
tatctacacg acggggagtc aggcaactat ggatgaacga aatagacaga tcgctgagat  1620
aggtgcctca ctgattaagc attggtaact gtcagaccaa gtttactcat atatacttta  1680
gattgattta aaacttcatt tttaatttaa aaggatctag gtgaagatcc tttttgataa  1740
tctcatgacc aaaatccctt aacgtgagtt ttcgttccac tgagcgtcag accccgtaga  1800
aaagatcaaa ggatcttctt gagatccttt ttttctgcgc gtaatctgct gcttgcaaac  1860
aaaaaaacca ccgctaccag cggtggtttg tttgccggat caagagctac caactctttt  1920
tccgaaggta actggcttca gcagagcgca gataccaaat actgtccttc tagtgtagcc  1980
gtagttaggc caccacttca agaactctgt agcaccgcct acatacctcg ctctgctaat  2040
cctgttacca gtggctgctg ccagtggcga taagtcgtgt cttaccgggt tggactcaag  2100
acgatagtta ccggataagg cgcagcggtc gggctgaacg gggggttcgt gcacacagcc  2160
cagcttggag cgaacgacct acaccgaact gagatatcta cagcgtgagc tatgagaaag  2220
cgccacgctt cccgaaggga gaaaggcgga caggtatccg gtaagcggca gggtcggaac  2280
aggagagcgc acgagggagc ttccaggggg aaacgcctgg tatctttata gtcctgtcgg  2340
gtttcgccac ctctgacttg agcgtcgatt tttgtgatgc tcgtcagggg ggcggagcct  2400
atggaaaaac gccagcaacg cggcctttttt acggttcctg gccttttgct ggccttttgc  2460
tcacatgttc tttcctgcgt tatcccctga ttctgtggat aaccgtatta ccgcctttga  2520
gtgagctgat accgctcgcc gcagccgaac gaccgagcgc agcgagtcag tgagcgagga  2580
agcggaagag cgcccaatac gcaaaccgcc tctccccgcg cgttggccga ttcattaatg  2640
cagctggcac gacaggtttc ccgactggaa agcgggcagt gagcgcaacg caattaatgt  2700
gagttagctc actcattagg caccccaggc tttacacttt atgcttccgg ctcgtatgtt  2760
gtgtggaatt gtgagcggat aacaatttca cacaggaaac agctatgacc atgattacgc  2820
caagcgcgca attaaccctc actaaaggga acaaaagctg gagctcctgc aggttgttgg  2880
ttggcacacc acaaatatac tgttgccgag cacaattgat tagaatgcat acgcattaag  2940
cgaacattaa aaagatgtga aaacataact attatgtcta aataaacaca cgtcagatgt  3000
atgtacgtca acgaaaacc attgtctata tattacaatt actaaataca taccaaattg  3060
aatacatatt gatgaaaaat aataaatact ggcgaaagca aaaaaacgaa acatttttat  3120
tttattgaac aactctcagg ctccaggtag gcaaaaaagc accgactcgg tgccacttttt  3180
tcaagttgat aacggactag ccttatttca acttgcatg ctgtttccag catagctctg  3240
aaacctccag tctctggttg tgcacgacgt taaattgaaa ataggtctat atatacgaac  3300
tgagtctgga aaaagaagtt gagaattata aaaagtagtg agcactggcg ccctctctgc  3360
ttggcgagct aaccttttcg cctcttggct gagtaggtgg cgtttcattc tactctgtaa  3420
aattaatgta gaattgaaac actatggtca aaaaatactt aggggcataa gttataaaac  3480
gtatgaaatg aacttttatc aacctgggct attcaaaaat tttcgaatta ttttatgtat  3540
tttttttaat cgtttttcat tataggttaa aatacacttt aaaaggaatt ctttcctgta  3600
aaataaaatat aaataaatat gctttattga cagaaaattt gatgtttttg tatttgagta  3660
ggagcaatca caggtgagca aaaaagaatt catcaattga tcggctaaat ggtatggcaa  3720
gaaaaggtat gcaatataat aatctttat tgggtatgca acgaaaattt gtttcgtcaa  3780
cgtatgcaat attcttttat aaaagagggt atgcaatgta ttttattaaa aacgggtatg  3840
```

-continued

```
caatataata atcttttatt gggtatgcaa cgaaaatttg tttcgtcaaa gtatgcaata 3900
tttttttatta aaagagggta tgcaatgtat tttattaaaa acgggtatgc aataaaaaat 3960
tatttggttt ctctaaaaag tatgcagcac ttattttttg ataaggtatg caacaaaatt 4020
ttactttgcc gaaaatatgc aatgtttttg cgaataaatt caacgcacac ttattacgtg 4080
gccaactagg tgcccaaaat gtgtgtggac tacgaaattt tccaaattta agatgctatc 4140
tttaaaccaa tgaaatatgg ttcgtatact atgaatttc aattaggcga acatcaatga 4200
ttcccccccc agaaaccga catagcagag cacacgagca ggcgcaaatt gagaaaccca 4260
tccgcgtgaa gtcggttaat ttgcccatct tcttctggac gcgttcgtgc acccgctgct 4320
catccggcgg agtattgtac cattgtgtac ggccgtagtc cgtgtgcctt cgttttggcg 4380
ttcatgcatg agcagcccaa ttccttgctg ccccattcgg ttacattgca cagtggacac 4440
aaaagctagt tttgtagtca aagtacgaa ttcacaaatt atataaactg atatagttca 4500
tagatagtat aaactgatac caagtaacag atacacattt aaataggtaa actgtgtctg 4560
tgatcaaact gtttcttttc gtgtcgaaga atcaattaaa aatgattgaa tcattatatt 4620
tatttccgtt aaaagctgtg caggctgttc aaaatgtttt aatgaaaaaa tacgaatttt 4680
tagactgtct gaatcacagt gtgctcgctt acatttccgc tttcctcttt tggcaactcg 4740
atgtcgcctt tggggctctt ttggagaccg gaaaaaggca acattttcta ttcgattctt 4800
tttgccaatt gcccgagact gtgtcctgtc ggcatatgac gaatacgtaa cgtacgtgac 4860
ggcgacgtta ctcatacgca ccgtgggtag ctgcagacat ctcagcaccc acgttcgcga 4920
attattttga attcgactcc ctgggcgata tttgtttttc gcttttgcat attttgcggg 4980
caatttgggt aaaaggattt ccgcactctg cgacgccgtc ttcagtttgc ggctttcgtt 5040
tttttcctag tagttcggca cacatttttcc tcgccgcttc ggcaaatcgc tcacgtaaaa 5100
tatgcatgcg tttccttggc ggttttgcgc tctcaagtgc ctgcaattca attacatttc 5160
gattgatttt catgtttggc cccaaatcgc ggcaaaacct ctcactgacg gacacaccga 5220
agccccggcg gcaaccctca gcggatgccc cggggcttca cgttttccca ggtcagaagc 5280
ggttttcggg agtagtgccc caactggggt aacctttgag ttctctcagt tgggggcgta 5340
gggtcgccga catgacacaa ggggttgtga ccggggtgga cacgtacgcg ggtgcttacg 5400
accgtcagtc gcgcgagcgc gactgctgca ggcgggcagc aaggcgtccc atccgcatta 5460
cgtgcccagc tatttgccag ctatgcccga tcctcatgcc tatattcgaa cgcccacgca 5520
caagcagccc gtaaccgaat acgaggcaat aagggaaaag gcagccagtc agaagcgtga 5580
cgttgagaag gcgctgacca aatttctgtg caaaacaaca gaaacaaaca atctctttcc 5640
caccgaggac aacatgtttc cgtgtaagta agcgctgcga ttaatggttc ttggttcttt 5700
attcaaatgt ttcgacttct ttttctgaat gcaacagtaa tcgcctgtaa gcccgccttt 5760
ccggcgtatg cagctgcctt gaatcccaca gatcaggtat ttgacttcga ggagctggag 5820
taccactact tggtggccaa tcgtacggaa gatgtgccca gtaaaggtag gtccaaattg 5880
tacacaatag atattccaat gaacacaggc tctactttca tttgcagagg agggcgagga 5940
gggtgacagt gagaatgagg aactggatgg cgacaagtcc aaggaggaga agcccgagct 6000
ggagatcaag cccaattcaa caacaaataa agctatttta gagaatccca atatagacaa 6060
tccctacttg cgtgccgcta cactgccaaa gcgttccaag ctgcacagtg agtgcactac 6120
accacgcatg gtgccctcac gaagtataca ctcggcttca cccacgacac cgacgccctc 6180
aactctagag ataaccaaaa gtagtgctta gttataatta taaatagatg cattgtaatt 6240
gtgtatagtt ttttaaaaaa aaaatattgg ataaacaaac tcttttcttc ttatcgatag 6300
ttcgtgcttt tgcttaaaat ggtgtgcgat ggcagcgctg cggcaacaaa cagctgtttc 6360
gatataaaag tacattttac ttatcgatag ctcgtgctat tgcataaaat gatgttaggt 6420
ggcaacgctg cggcaacaat cagctgttta ccaggccgca gcaacgttac agtgcatttt 6480
acatttttacc aagttgaatt aataaaaattg ctttttaaaa gtgtttacta aattaaaaag 6540
ccaacaaatt gttgttgttt tcgttgctta caagcggctg ctgtacataa attatacata 6600
ttagcgtaa acgtgctcaa catgaatttc ctgcgccaaa cattcaacgt tacgaaacaa 6660
ttgacggcac aaggtaagtt ttaacaaaaa tccctatttta aaacattgcg ttgcggctat 6720
ttattcaact tcgagtcccg tgttctatat acatacgcgc ccacgcgcct aattgccaac 6780
catgtgaggc agccggtagc cgcttgcgca catccatttc caattggtga ctgtgcgcat 6840
tttgtgttta tccaaggatc ctgcgttcca ttgtgtgcac acaatgattt gtattgtcag 6900
ttgtttgcct gcgatctcaa ctctttaca tgggcgcgtg gccggcttgc gagcctgtcg 6960
cccgtctgcc agttctctag ttgtcgtcgt accccccttc cccctgccca gcccttatc 7020
gtgtgtctag tctgtgaata tttttataag cattttctca tgtgtgtttc ctgtttgtgt 7080
gttttaatgt gtcctcaaaa tgttcacgg agcctacaaa gtgtgtattg agaatatata 7140
tatatatata tagtccatct gtccatcttg gatatttgtc attggaacgg gcgagcgaaa 7200
aaagggtttg tcaatgaaaa acttatcatt ttcattatgt gcaacattta ctaaccaaat 7260
ctattcaata cataggttgg acaaacttgc cttctgttct tcgagataac ttcagcaaag 7320
tctgccaatg cgatctgaag tccattcaat ttttggccta gcaaaaaacg cattcgtttt 7380
tctgcttgtt ttaattaaaa ttcacaacaa aatccgcata acatgaggcc caccctcaac 7440
aataggaatt tgcatgacat gcacacaata aggaaaaaac aacacaagaa aaaaaaatta 7500
tgagaaaagg acacacacac acacacaggt gcgttcggat cgcggcagac aatgcacgga 7560
gctgtgattg gcatagttct tgctgtgcgc ctgctcccat tgtaagcgat tgtccagcgt 7620
tatggtaatt attacctgtg tgtacgtgtg tgtgtgttgg tgtggcattt aattaaaaat 7680
tgttgtcgtt tgcgattttg gctgcagtac agtcgagtcc agtcgggagt ccagctgaac 7740
agaaatctga gcatcagaca gtcaaccccc gtgcatggct aaaggttctc aatgcttaaa 7800
aggcttgaga actgcagttg ccgctgaccc acagccgcgt catttggctg caattatttg 7860
tgaaaataac cttatatatg catgatatgt ggatggatat ggatggatat atggatgtgc 7920
gcagcataac aattattttg cgattttcac agagattagc cacaacaaaa gcgcaatggc 7980
cattgttgct tgggcatttg gaactggcca actgtttctg accctttgt catgttgtgt 8040
ccgttctctc gtttgtgtca aatgttttta gccgctcgct gcggctgcgc tcacacatgc 8100
ggcagcagct accatataca atttatatac caatatatgt acacatattt aattggtaca 8160
gttgtgtcca cttgcattgt atgtgtacac ttaacgcact cttgcaattc cggacaagtc 8220
aagaggagac aactagacgt tggcaatcgg aaattggaag cctacagaa acactgcgtt 8280
tataacttgt tctcagctgt ttctctctct catcttgatt acattgcagc gctgcagagc 8340
aattatttgt gtgccgcatt gcgcggcatg gcatcgttga atcaaatgca tcgcactggg 8400
ccgcatataa agaagcgtcc gccacgtcag cccctggacg gtaaaccgtt tgccaaggga 8460
gtggtgctca agacactgat caagaagcca aagaaaccaa actcggcgaa tcgtaaatgc 8520
gcgctggtgc gcttatccac gggaaaggag atggtcgcct atatacccgg cattggacat 8580
```

```
aatctgcagg agcataatat tgtactgtgt cgcgtcggac gactgcagga tgtgcccggc   8640
gtcaagctga aggcggtgcg cggtgtctac gatctggcgc acgttatcaa gaagggccaa   8700
tgacaaccaa ctaccatgta attctcttcc ataaaaaaac aaaaaaaaaa taagaaaaga   8760
aaacaagcca aatctttgag tactctgcta ttcttgtgca gcatatatta ttatgatttt   8820
tttaatggaa aattatgcag ctcagcggga ttagtgtaag tagccaacac acaacaagtg   8880
agctctggcc tcgcctcatc ccaacttgtc ttgccgtaat cttaagtcaa caggccaaat   8940
tgcgagccaa acaattggcc agtgttgcca acgacgctgc cgaaaaagga gctaaatccc   9000
attggaaaat agctaaaaaa tagccagagc atgaattgga cgactgaaga cagctgaaat   9060
tggccagaat ttggccagaa tatagctgat atcgcaacac tgcacatttg ttgcccactc   9120
gaaatatgat tttaacggca tttttacgct ttagcaggca aatccctttt tgaagaaacg   9180
gcccgtcttt acttttttaac agaatttgct tgcacaaatt ttatgccaaa taatcgttaa   9240
gcgaaatggg cgtcgacagg ccacgccaca ttttcacagt acgcagagcc tcgccacgcc   9300
tttgcaacag gatacaacaa attttgaata ggcaccgacc aggttgtcgt gcatctgggc   9360
tgaacgataa catctgtatt aaatcaatcc catattcaag cttccaaagg atttcggcaa   9420
catgccaatt ccgctattaa tctttcgggt tatcctgaat atctgggtag tcctaggtgt   9480
ggagctggtg tcgcttatgg cagagcagct gaatgctaac atatacgagc ataaaaagtt   9540
tcatcaggaa tccatatgca acttgaggtc cgaccccacc aacttttttg cactgcaaaa   9600
aaacacgctt ttgcacgcgg gcccatacat agtacaaact ctacgtttcg tagactattt   9660
tacataaata gtctacaccg ttgtatacgc tccaaataca ctaccacaca ttgaaccttt   9720
ttgcagtgca aaaaagtacg tgtcggcagt cacgtaggcc ggccttatcg ggtcgcgtcc   9780
tgtcacgtac gaatcacatt atcggaccgg acgagtgttg tcttatcgtg acaggacgcc   9840
agcttcctgt gttgctaacc gcagccggac gcaactcctt atcggaacag gacgcgcctc   9900
catatcagcc gcgcgttatc tcatgcgcgt gaccggacac gaggcgcccg tcccgcttat   9960
cgcgcctata aatacagccc gcaacgatct ggtaaacaca gttgaacaga tggtgagcaa  10020
gggcgaggag gtcatcaaag agttcatgcg cttcaaggtg cgcatggagg gctccatgaa  10080
cggccacgag ttcgagatcg aggcgagggg cgagggccgc cctacgaagg gcaccagac  10140
cgccaagctg aaggtgacca agggcggcccc cctgcccttc gcctgggaca tcctgtcccc  10200
ccagttcatg tacggctcca aggcgtacgt gaagcacccc gccgacatcc ccgattacaa  10260
gaagctgtcc ttccccgagg gcttcaagtg ggagcgcgtg atgaacttcg aggacggcgg  10320
tctggtgacc gtgacccagg actcctccct gcaggacgac acgctgatct acaaggtgaa  10380
gatgcgcggc accaacttcc ccccgacgg ccccgtaatg cagaagaaga ccatgggctg  10440
ggaggcctcc accgagcgcc tgtaccccg cgacggcgtg ctgaagggcg agatccacca  10500
ggccctgaag ctgaaggacg gcggccacta cctggtggag ttcaagacca tctacatggc  10560
caagaagccc gtgcaactgc ccggctacta ctacgtggac gccaagctgg acatcaacctc  10620
ccacaacgag gactacacca tcgtggaaca gtacgagcgc tccgagggcc gccaccacct  10680
gttcctgggg catggcaccg gcagcaccgg cagcggcagc tccggcaccg cctcctccga  10740
ggacaacaac atggccgtta tcaaggaatt tatgcgcttc aaagttagga tggagggatc  10800
catgaacgga catgagttcg agatcgaggg agaggcgag ggacgcccgt atgaaggcac  10860
acaaacgacc aaactcaagg tcaccaaggg cggaccactg cccttcgcct gggatatcct  10920
gagtccccag tttatgtacg gcagcaaggc ctacgttaag caccccgctg acataccgga  10980
ctacaaaaag ctgtcctttc cggaaggctt caagtgggag cgcgtgatga atttcgaaga  11040
cggaggactg gtcactgtga cccaagatag cagtttgcag gacggtacac tgatctataa  11100
ggttaaaatg cgcggccacta actttccgcc agatggccca gtgatgcaga agaagaccat  11160
gggtgggggag gcatccaccg aacgtctgta ccctcgagac ggagtgctca agggcgagat  11220
ccatcaggcc ctcaaactga aagatggtgg tcactacctg gtcgaattta gaccatttta  11280
catggccaag aagccggttc agctgccccgg atattattat gtggatacga aactggatat  11340
aacttcgcat aacgaagact acaccattgt cgagcagtat gagcgcagcg aaggccgaca  11400
tcacctgttc ctctacggca tggacgagct gtacaagtag gcggccgcga ctctagatca  11460
taatcagcca taccacattt gtagaggttt tacttgcttt aaaaaacctc ccacacctcc  11520
ccctgaacct gaaacataaa atgaatgcaa ttgttgttgt taacttgttt attgcagctt  11580
ataatggtta caaataaagc aatagcatca caaatttcac aaataaagca tttttttcac  11640
tgcattctag ttgtggtttg tccaaactca tcaatgtatc ttaaagcttc agtctctggt  11700
tgtgcatgga gcgtggtttt ggggcgattc acgagcgtga accgatattt tccatacgtc  11760
atgtttgcct tgctttacac tccaggaaac ctcatccgtt taatttagcc ggaagtgttg  11820
caatagatgc cacatcacaa tcgacttaat aattttttta ggagcaagtt ttaatggaaa  11880
cagtttctga taaataaata tacatatcaa cttagtacaa gaatatccag ctgaaagaat  11940
ggtatatata tatatatata tacttgtgtt tgtttctatg acagtttctt cacagctttc  12000
gattttctta tggcacatcg cgcgacagtt gaaatgaaaa actgaaatca gtgaaacccc  12060
gaaaaactg aaaaagccac ggaaattgta cagatacaca gatacgcaga tacaccagca  12120
aatgtacaaa aaggtctata tacatatata tgtagctact cacttatgtt gtccttcgca  12180
gattgctccc tttaagcaaa taaaaaaaag ttggctccac gccgaaaaga aataaaatta  12240
aatggagaat cgcaaatcca tagtgagcca aaggcaaatc tataaaagaa atgaaacgaa  12300
attcattcat tttcgttttc gagttcgaat atttaagtta tatatataaa cgcagtattt  12360
atccatgtaa tcgaaccaca aaagcccaat gagaaaaccc tacattttat gctgagcatc  12420
acaaaatgcc tttcctttca catgaattta tgtattttaa tcaatttccc tcgctgtggc  12480
agttaaatat cctaaatttg tccaacgaaa ttgatgcttc aattattcga atgacgacgt  12540
ttaatggct ttcgaggaat aaaagcaaaa attcacaaga aaaacgcctc tgcatccatg  12600
ctcattatcg gaatcaatta aaatttcaca tgtatcgtta gcatggccat gtcagcaaat  12660
ccacgggatt cggctagagt cctccaaaat acgcccacgg gacccataca ccttcgaaat  12720
gatccaacat caatccctat ccaaatgtat acttagatat gtacatacct tgtcttttct  12780
tggtcggcga atggggggttc cagcatccca tcatcct              12817
```

SEQ ID NO: 40          moltype = DNA   length = 14148
FEATURE                Location/Qualifiers
misc_feature           1..14148
                       note = tko-step2
source                 1..14148
                       mol_type = other DNA
                       organism = synthetic construct

```
SEQUENCE: 40
atcatcgatc tcgaggctgc atccaacgcg cgcgttggga gctctccgga tcaattcggc   60
ttcaggtacc gtcgacgatg taggtcacgg tctcgaagcc gcggtgcggg tgccagggcg  120
tgcccttggg ctccccgggc gcgtactcca cctcacccat ctggtccatc atgatgaacg  180
ggtcgaggtg gcggtagttg atcccggcga acgcgcggcg caccgggaag ccctcgccct  240
cgaaaccgct gggcgcggtg gtcacggtga gcacgggacg tgcgacggcg tcggctgggt  300
gcggatacgc ggggcagcgt cagcgggttc tcgacggtca cggcgggcat gtcgacgaca  360
tgttcgcctc atttgtgttc gtttatgtat tcgatgttat gtgtatgctc atgtgatgtt  420
tagcttgtaa gcgcgagatg tgggtagcag gagatgcagt gcagccaaca gcagtgacca  480
gatgatatat gctatgctac tactactact tatatgctat gatttgtggc gcggaggcgt  540
gtctgcgaca cataatcccg cccatttagc tttaagattc aggcactaag aagcaattcg  600
atcaataaat tattgtaacc actctgcatg tgagcaaaag gccagcaaaa ggccaggaac  660
cgtaaaaagg ccgcgttgct ggcgtttttc cataggctcc gcccccctga cgagcatcac  720
aaaaatcgac gctcaagtca gaggtggcga aacccgacag gactataaag ataccaggcg  780
tttccccctg gaagctccct cgtgcgctct cctgttccga ccctgccgct taccggatac  840
ctgtccgcct ttctcccttc gggaagcgtg gcgctttctc atagctcacg ctgtaggtat  900
ctcagttcgg tgtaggtcgt tcgctccaag ctgggctgtg tgcacgaacc ccccgttcag  960
cccgaccgct gcgccttatc cggtaactat cgtcttgagt ccaacccggt aagacacgac 1020
ttatcgccac tggcagcagc cactggtaac aggattagca gagcgaggta tgtaggcggt 1080
gctacagagt tcttgaagtg gtggcctaac tacggctaca ctagaagaac agtatttggt 1140
atctgcgctc tgctgaagcc agttaccttc ggaaaaagag ttggtagctc ttgatccggc 1200
aaacaaacca ccgctggtag cggtggtttt tttgtttgca agcagcagat tacgcgcaga 1260
aaaaaaggat ctcaagaaga tcctttgatc ttttctacgg ggtctgacgc tcagtggaac 1320
gaaaactcac gttaagggat tttggtcatg agattatcaa aaaggatctt cacctagatc 1380
cttttaaatt aaaaatgaag ttttaaatca atctaaagta tatatgagta aacttggtct 1440
gacagttacc aatgcttaat cagtgaggca cctatctcag cgatctgtct atttcgttca 1500
tccatagttg cctgactccc cgtcgtgtag ataactacga tacggagggg cttaccatct 1560
ggccccagtg ctgcaatgat accgcgagac ccacgctcac cggctccaga tttatcagca 1620
ataaaccagc cagccggaag ggccgagcgc agaagtggtc ctgcaacttt atccgcctcc 1680
atccagtcta ttaattgttg ccgggaagct agagtaagta gttcgccagt taatagtttg 1740
cgcaacgttg ttgccattgc tacaggcatc gtggtgtcac gctcgtcgtt tggtatggct 1800
tcattcagct ccggttccca acgatcaagc gagttacat gatcccccat gttgtgcaaa 1860
aaagcggtta gctccttcgg tcctccgatc gttgtcagaa gtaagttggc cgcagtgtta 1920
tcactcatgg ttatggcagc actgcataat tctcttactg tcatgccatc cgtaagatgc 1980
ttttctgtga ctggtgagta ctcaaccaag tcattctgag aatagtgtat gcggcgaccg 2040
agttgctctt gcccggcgtc aatacggat aataccgcgc cacatagcag aactttaaaa 2100
gtgctcatca ttggaaaacg ttcttcgggg cgaaaactct caaggatctt accgctgttg 2160
agatccagtt cgatgtaacc cactcgtgca cccaactgat cttcagcatc ttttactttc 2220
accagcgttt ctgggtgagc aaaaacagga aggcaaaatg ccgcaaaaaa gggaataagg 2280
gcgacacgga aatgttgaat actcatactc ttcctttttc aatattattg aagcatttat 2340
cagggttatt gtctcatgag cggatacata tttgaatgta tttagaaaaa taaacaaata 2400
ggggttccgc gcacatttcc ccgaaaagtg ccacctgacg tcgacggatc gggagatcgg 2460
cgcgggactt aattcaatta gagactaatt caattagagc taattcaatt agatccaag 2520
cttatcgatt tcgaaccctc gaccgccgga gtataaatag aggcgcttcg tctacggagc 2580
gacaattcaa ttcaaacaag caaagtgaac acgtcgctaa gcgaaagcta agcaaataaa 2640
caagcgcagc tgaacaagct aaacaatcgg ctcgagaccg gtcgccacca tggtgagcaa 2700
gggcgaggag ctgttcaccg gggtggtgcc catcctggtc gagctggacg gcgacgtaaa 2760
cggccacaag ttcagcgtgt ccggcgaggg cgagggcgat gccacctacg gcaagctgac 2820
cctgaagttc atctgcacca ccggcaagct gcccgtgccc tggcccaccc tcgtgaccac 2880
cctgacctac ggcgtgcagt gcttcagccg ctaccccgac cacatgaagc agcacgactt 2940
cttcaagtcc gccatgcccg aaggctacgt ccaggagcgc accatcttct tcaaggacga 3000
cggcaactac aagacccgcg ccgaggtgaa gttcgagggc gacaccctgg tgaaccgcat 3060
cgagctgaag ggcatcgact tcaaggagga cggcaacatc ctggggcaca gctggagta 3120
caactacaac agccacaacg tctatatcat ggccgacaag cagaagaacg gcatcaaggt 3180
gaacttcaag atccgccaca acatcgagga cggcagcgtg cagctcgccg accactacca 3240
gcagaacacc cccatcggcg acggccccgt gctgctgccc gacaaccact acctgagcac 3300
ccagtccgcc ctgagcaaag accccaacga gaagcgcgat cacatggtcc tgctggagtt 3360
cgtgaccgcc gccgggatca ctctcggcat ggacgagctg tacaagtaaa gcggccgcga 3420
ctctagatca taatcagcca taccacattt gtagaggttt tacttgcttt aaaaaacctc 3480
ccacacctcc ccctgaacct gaaacataaa atgaatgcaa ttgttgttgt taacttgttt 3540
attgcagctt ataatggtta caaataaagc aatagcatca caaatttcac aaataaagca 3600
tttttttcac tgcattctag ttgtggtttg tccaaactca tcaatgtatc ttagttgttg 3660
gttggcacac cacaaatata ctgttgccga gcacaattga tcggctaaat ggtatggcaa 3720
gaaaaggtat gcaatataat aatctttat tgggtatgca acgaaaattt gtttcgtcaa 3780
cgtatgcaat attctttatt aaaagagggt atgcaatgca ttttattaaa aacgggtatg 3840
caatataata atctttatt gggtatgcaa cgaaaatttg tttcgtcaaa gtatgcaata 3900
tttttttatta aaagagggta tgcaatgtat tttattaaaa acgggtatgc aataaaaaat 3960
tatttggttt ctctaaaaag tatgcagcac ttattttttg ataaggtatg caacaaaatt 4020
ttactttgcc gaaaatatgc aatgtttttg cgaataaatt caacgcacac ttattacgtg 4080
gccaacgcgc ctagtggatc cttcctggcc cttttcgaga aacgccgcga gggcgaaaag 4140
gattagttgt ttcaaacgca agaaggacat ttgtttcctt aaattgtaac catttcttta 4200
tttggcactc gagccattga attttcatt ttcagaatat gtgtacacat tttttaaaaa 4260
aataaaaaaa ttatataatg ctggcggttg tttcatgtgt gaaaaattga tcaatggtaa 4320
acaaaattga ataaatatat aacatatata tatgtatgaa tgaatacttg 4380
cgatacatgt aataaaaaata ctcttcgctt atctatcaaa aagtgcggaa tgtcaaaatt 4440
taaaatttta caatgaatgc gtagccgacg acgaaagtgt tccttgctat ttcctttagc 4500
aagatttaaa tttagattaa attctaatga tacgattgac agttcgaaat tcaaagtgtt 4560
cctttttcaa aatttagtaa agattgtata tcaattgtag atatatcgaa attttttcggc 4620
cgcaagcgaa cattttacaa aatgaaggcg accagttgca gaccaattcc attcatcaac 4680
```

-continued

```
tttcggattg taagatattt ctatcggcca cgacgattga acaagtatta cgatattgta  4740
agtcttcttt aacaaaatta gtttcccttt cacagaaaca gacataaatt cttgaattat  4800
tgacttggat ttgagtgatc gttcgttgtc tatactataa gatctatagg cacgggataa  4860
cgctctaaat ctctttaaaa tcgaacgcgc caggcgctag ttaaacgtta ctatctatct  4920
ggttaaccca gctttgatcg gaatgcgtat atatatttca tgttatataa acgctgcaaa  4980
agctgccaga gcctctgctc cagagctgga ttcgctcaca ccttcctctt cttcttgggg  5040
tcagccctgc tgtctccacc gagctgagag aggtcgattc ttgtttcata gagccccgta  5100
attgactgat gaatcagtgt ggcgtccagg acctcctttg tagaggtgta ccgctttctg  5160
tctatggtgg tgtcgaagta cttgaaggct gcaggcgcgc ccaagttggt cagagtaaac  5220
aagtggataa tgttttctgc ctgctccctg atgggcttat ccctgtgctt attgtaagca  5280
gaaagcacct tatcgaggtt agcgtcggcg aggatcactc ttttggagaa ttcgcttatt  5340
tgctcgatga tctcatcaag gtagtgtttg tgttgttcca cgaacagctg cttctgctca  5400
ttatcttcgg gagacccttt gagcttttca tagtggctgg ccagatacaa gaaattaacg  5460
tatttagagg gcagtgccag ctcgttacct ttctgcagct cgcccgcact agcgagcatt  5520
cgtttccggc cgtttttcaag ctcaaagaga gagtacttgg gaagcttaat gatgaggtct  5580
tttttgacct ctttatatcc tttcgcctcg agaaagtcga tggggttttt ttcgaagctt  5640
gatcgctcca tgattgtgat gcccagcagt tccttgacgc ttttgagttt tttagacttc  5700
cctttctcca ctttggccac aaccagtaca ctgtaagcga ctgtaggaga atcgaatccg  5760
ccgtatttct tggggtccca atcttttttg cgtgcgatca gcttgtcgct gttccttttc  5820
gggaggatac tttccttgga gaagcctccg gtctgtactt cggtcttttt aacgatgttc  5880
acctgcggca tggacaggac cttccggact gtcgcgaaat ccctacccct gtcccacacg  5940
atttctcctg tttctccgtt tgtttcgata agtggtcgct tccgaatctc tccattggcc  6000
agtgtaatct cggtcttgaa aaaattcata atattgctgt aaaagaagta cttagcggtg  6060
gccttgccta tttcctgctc agactttgcg atcattttcc taacatcgta cactttatag  6120
tctccgtaaa caaattcaga ttcaagcttg ggatattttt tgataagtgc agtgcctacc  6180
actgcattca ggtaggcatc atgcgcatgg tggtaattgt tgatctctct caccttataa  6240
aactgaaagt cctttctgaa atctgagacc agcttagact tcagagtaat aactttcacc  6300
tctcgaatca gtttgtcatt ttcatcgtac ttggtgttca tgcgtgaatc gagaatttgg  6360
gccacgtgct tggtgatctg gcgtgtctca acaagctgcc ttttgatgaa gccggcttta  6420
tccaactcag acaggccacc tcgttcagcc ttagtcagat tatcgaactt ccgttgtgtg  6480
atcagtttgg cgttcagcag ctgccgccaa taatttttca tttttcttgac aacttcttct  6540
gaggggacgt tatcactctt ccctctattt ttatcggatc ttgtcaacac tttattatca  6600
atagaatcat ctttgagaaa agactggggc acgatatgat ccacgtcgta gtcggagagc  6660
cgattgatgt ccagttcctg atccacgtac atgtccctgc cgttctgcag gtagtacagg  6720
tagagcttct cattctgaag ctgggtgttt tcaactgggt gttccttaag gatttgggac  6780
cccagttctt ttataccctc ttcaatcctc ttcatccttt ccctactgtt cttctgtccc  6840
ttctgggtag tttggttctc tcgggccatc tcgataacga tattctcggg cttatgcctt  6900
cccattactt tgacgagttc atccacgacc ttaacggtct gcagtattcc ctttttgata  6960
gctgggctac ctgcaagatt agcgatgtgc tcgtgaagac tgtcccctg gccagaaact  7020
tgtgcttttct ggatgtcctc cttaaaggtg agagagtcat catggatcaa ctgcatgaag  7080
ttccggttgg caaatccatc ggacttaaga aaatccagga ttgtctttcc actctgcttg  7140
tctcggatcc cattgatcag ttttcttgac agccgcccccc atcctgtata tcggcgcctc  7200
ttgagctgtt tcatgacttt tcgtcgaag agatgagcgt aagttttcaa gcgttcttca  7260
atcatctccc tatcttcaaa caacgtaagg gtgaggacaa tgtcctcaag aatgtcctcg  7320
ttctcctcat tgtccaggaa gtccttgtct ttaatgattt tcaggagatc gtgatacgtt  7380
cccagggatg cgttgaagcg atcctccact ccgctgattt caacagagtc gaaacattca  7440
atcttttttga aatagtcttc tttgagctgt ttcacggtaa ctttccggtt cgtcttgaag  7500
aggaggtcca cgatagcttt cttctgctct ccagacagga atgctggctt tctcatccct  7560
tctgtgacgt atttgacctt ggtgagctcg ttataaactg tgaagtactc gtacagcaga  7620
gagtgtttag gaagcacctt ttcgttaggc agattttttat caaagttagt catcctttcg  7680
atgaaggact gggcagaggc ccccttatcc acgacttcct cgaagttcca ggagttgatg  7740
gtctcttctg atttgcgagt catccacgcg aatctggaat ttccccgggc gaggggggcct  7800
acatagtagg gtatccgaaa tgtgaggatt ttctcaatct tttccctgtt atctttcaaa  7860
aaggggtaga aatcctcttg ccgcctgagg atagcgtgca gttcgcccag gtgaatctgg  7920
tggggatgc ttccattgtc gaaagtgcgc tgtttgcgca acagatcttc tctgttaagc  7980
tttaccagca gctcctcggt gccgtccatt ttttccaaga tgggcttaat aaatttgtaa  8040
aattcctcct ggcttgctcc gccgtcaatg tatccggcgt agccatttt agactgatcg  8100
aagaaaattt ccttgtactt ctcaggcagt tgctgtctga caagggcctt cagcaaagtc  8160
aagtcttggt ggtgctcatc atagcgcttg atcatactag cgctcagcgg agctttggtg  8220
atctccgtgt tcactcgcag aatatcactc agcagaatgg cgtctgacag gttctttgcc  8280
gccaaaaaaa ggtctgcgta ctggtcgccg atctgggcca gcagattgtc gagatcatca  8340
tcgtaggtgt cttttgctcag ttgaagcttg gcatcttcgg ccaggtcgaa gttagattta  8400
aagttggggg tcagcccgag tgacaggcg ataagattac caaacaggcc gttcttcttc  8460
tccccaggga gctgtgcgat gaggtttcg agccgccggg atttggacag cctagcgctc  8520
aggattgctt tggcgtcaac tccggatgcg ttgatcgggt tctcttcgaa aagctgcattg  8580
taagtctgaa ccagttggat aaaagagttt tcgacatcgc tgttgtctgg gttcaggtcc  8640
ccctcgatga ggaagtgtcc ccgaaatttg atcatatgcg ccagcgcgag atagatcaac  8700
cgcaagtcag cctatcagt actgtctaca agcttcttcc tcagatgata tatggttggg  8760
tacttttcat ggtacgccac ctcgtccacg atattgccaa agattgggtg gcgctcgtgc  8820
ttttttatcct cctccaccaa aaaggactcc tccagcctat ggaagaaaga gtcatccacc  8880
ttagccatct cattactaaa gatctcctgc aggtagcaga tccgattctt tctgcgggta  8940
tatctgcgcc gtgctgttct tttgagccgc gtggcttcgg ccgtctcccc ggagtcgaac  9000
aggaggggcgc caatgaggtt cttctttatg ctgtggcgat cggtattgcc cagaactttg  9060
aattttttgc tcggcaccttt gtactcgtcc gtaatgacgg cccagccgac gctgttttgga  9120
ccgatatcga gcccaatgga gtacttcttg tccatggcga aaatccgggt cgaaagttac  9180
ggttatcgcg cactctactt tccacaaatc ctcacccaaa aaccaagcac agtttattca  9240
actgaagtat tcgcgatact tctttatcta ataataatgt acatgtaact aaaactcgctt  9300
ttgggttaaa atcgtgacgc agaggcaaaa aaaatcgtat gtcccttaga caacttgaaa  9360
caactgcgaa gcgtacggca attccaggaa ttttgtggta aagctacgcg ccaactaacg  9420
```

-continued

```
gttcttgctt agaggtggaa taatgtagtt ttccagcgat aataaatata tcgatatttt    9480
tagtaaaatt gaaaaggtaa acttaatttt agaaaataat ttataagaaa tttaatagta    9540
tgcaaaataa tttttacttg ctaagaatat gtgccactaa ttaaaagctg gacaccgcgc    9600
aatgaaaat agtactacaa cacagcaaca aagcctgagt tatcaacaaa aaaatacgaa     9660
aacatctccc aaaactaagc acccacacgc gccactcgcc gtcacaacac aatcactgca    9720
caccaccatt cgaatttcgc gcactgtgac aacatcacat gatatcggcg cggcaacatc    9780
ggattaccga caaaacgaac tatcgcacga gccaccgccg gcgaagagcg ctcgttttgc    9840
aacaccggcg cgcgctgaac gaagagaaca gctgactgct tgatacgtgc gtgtttcgcg    9900
gcaggaatta cataaagttt agagcctctg acgccagacc ccccgaacat tcgctccgat    9960
caaactacct gcgaacggtc acctaatccc caccatgcat ggtaggttac ctctgatccc    10020
ggtcatcact ggcgttcgct cacatccgtc cttacatgtg catatttcga ggttaaaacg    10080
gtcgaagctt ggatccgcta gcgttgttgg ttggcacacc acaaatatac tgttgccgag    10140
cacaattgat cggctaaatg gtatggcaag aaaaggtatg caatataata atctttatt     10200
gggtatgcaa cgaaaatttg tttcgtcaac gtatgcaata ttctttatta aaagagggta    10260
tgcaatgtat tttattaaaa acgggtatgc aatataataa tctttattg ggtatgcaac     10320
gaaaatttgt ttcgtcaaag tatgcaatat ttttattaa aagagggtat gcaatgtatt     10380
ttattaaaaa cgggtatgca ataaaaaatt atttggtttc tctaaaaagt atgcagcact    10440
tattttttga taaggtatgc aacaaaattt tactttgccg aaaatatgca atgttttgc     10500
gaataaattc aacgcacact tattacgtgg ccaactagcc tagttccagt gaaatccaag    10560
cacttgaggt ccgacccgat gaattctttt ttgctcacct gtgattgctc ctactcaaat    10620
acaaaaacat caaattttct gtcaataaag catatttatt tatatttatt ttacaggaaa    10680
gaattccttt taaagtgtat tttaacctat aatgaaaaac gattaaaaaa aatacataaa    10740
ataattcgaa aatttttgaa tagcccaggt tgataaaaat tcatttcata cgttttataa    10800
cttatgcccc taagtatttt ttgaccatag tgtttcaatt ctacattaat tttacagagt    10860
agaatgaaac gccacctact cagccaagag gcgaaaaggt tagctcgcca agcagagagg    10920
gcgccagtgc tcactacttt ttataattct caacttcatt ttccagactc agttcgtata    10980
tatagaccta tttttcaattt aacgtcgctg cagcgatgcc attccagttt cagagctatg    11040
ctggaaacag catagcaagt tgaaataagg ctagtccgtt atcaacttga aaaagtggca    11100
ccgagtcggt gctttttgc ctacctggag cctgagagtt gttcaataaa ataaaaatgt      11160
ttcgtttttt tgctttcgcc agtatttatt attttcatc aatatgtatt caatttggta     11220
tgtatttagt aattgtaata tatagacaat ggttttccgt tgacgtacat acatctgacg    11280
tgtgtttatt tagacataat agttatgttt tcacatcttt ttaatgttcg cttaatgcgt    11340
atgcattcta gattttcaac gtcctcgata gtatagtggt tagtatcccc gcctgtcacg    11400
cgggagaccg gggttcaatt ccccgtcggg gagaatctgt gattctttt tttttctttt     11460
tactttgtta tataaacaat ttttgtttta attgaatcta atttgccatt gcttttagga    11520
atctcaggca tccagcaagc gtttgtccgc cgaatcgccc atcagtgaag aagatcctgt    11580
ggcggctacg aaaatctccc cggccatgtc ggcctccacc tccagcgaaa aacccatcag    11640
cgagctggcc acctctgtgc tgacccaccg cttttccagac tccacctcct cacccggcga   11700
acatggcctt ggacgaatgc agttgtcgat ccgctacagc gcccagcgtc aaaaactaga    11760
cgtgaccata cacaaaatcc agaagatacc acttcgcgat cccagcaata tccccgatcc    11820
gtatgttaag ctgtatctgt tgcctggacg caccaaggag tcgaaacgca agacgagcgt    11880
gatcaaggac aactgcaacc ccgtctacga tgcatccttt gagtacctga tttccattgc    11940
cgaactcagg cagacggaac tggaggtgac ggtgtgtcgc caaaagggat tcctatccgg    12000
cggtagtccc atcattggca tggtaggtac ccgaaagcaa ccccttagtt acagacacag    12060
cgcgtacgtc cttcgcatcc ttatgattcc caagtacata ttctgcaaga gtacagtata    12120
tataggaaag atatccgggt gaacttcgca ggacaacgcc cttggcgagt ttcagagcta    12180
tgctggaaac agcatagcaa gttgaaataa ggctagtccg ttatcaactt gaaaaagtgg    12240
caccgagtcg gtgctttttt gcctacctgg agcctgagag ttgttcaatc tagacaattg    12300
tgctcggcaa cagtatattt gtggtgtgcc aaccaacaac ctgcaggagc tccagctttt    12360
gttccctta gtgagggtta attttttttg ctcacctgtg attgctccta ctcaaataca     12420
aaaacatcaa atttttctgtc aataaagcat atttattat attttatt ttacaggaaa      12480
ttcctttaaa agtgtatttt aacctataat gaaaaacgat taaaaaaaat acataaaata    12540
attcgaaaat ttttgaatag cccaggttga taaaaattca tttcatacgt tttataactt    12600
atgcccctaa gtatttttg accatagtgt ttcaattcta cattaatttt acagagtaga     12660
atgaaacgcc acctactcag ccaagaggcg aaaaggttag ctcgccaagc agagagggcg    12720
ccagtgctca ctacttttta taattctcaa cttctttttc cagactcagt tcgtatatat    12780
agacctattt tcaatttaac gtcgcaacat tgtactgtgc cgcggtttca gagctatgct    12840
ggaaacagca tagcaagttg aaataaggct agtccgttat caacttgaaa aagtggcacc    12900
gagtcggtgc tttttttgcct acctggagcc tgagagtttg tcaataaaat aaaaatgttt    12960
cgttttttg cttctgccag tatttattat ttttcatcaa tatgtattca atttggtatg     13020
tatttagtaa ttgtaatata tagacaatgg ttttccgttg acgtacatac atctgacgtg    13080
tgtttattta gacataatag ttatgttttt acatctttt aatgttcgct taatgcgtat     13140
gcattctaga ttttcaacgt cctcgatagt atagtggtta gtatccccgc ctgtcacgcg    13200
ggagaccggg gttcaattcc ccgtcgggga gaatctgtga ttctttttt tttctttta     13260
ctttgttata taaacaattt ttgtttaat tgaatctaat ttgccattgc ttttaggaat     13320
ctcaggcatc cagcaagcgt ttgtccgccg aatcgcccat cagtgaagaa gatcctgtgg    13380
cggctacgaa aatctccccg gccatgtcgg cctccacctc cagcgaaaaa cccatcagcg    13440
agctggccac ctctgtgctg acccaccgct tttccagact cacctcctc cccggcgaac      13500
atggccttgg acgaatgcag ttgtcgatcc gctacagcgc ccagcgtcaa aaactagacg    13560
tgaccataca caaatccag aagataccac ttcgcgatcc cagcaatatc cccgatccgt      13620
atgttaagct gtatctgttg cctggacgca ccaaggagtc gaaacgcaag acgagcgtga    13680
tcaaggacaa ctgcaacccc gtctacgatg catcctttga gtacctgatt tccattgccg    13740
aactcaggca gacggaactg gaggtgacgg tgtgcaccca aaagggattc ctatccggcg    13800
gtagtcccat cattggcatg gtaggtaccc gaaagcaacc cttagttac agacacagcg     13860
cgtacgtcct tcgcatcctt atgattccca agtacatatt ctgcaagagt acagtatata    13920
taggaaagat atccgggtga acttcgcacc agcacgcact ttcgatgttt cagagctatg    13980
ctggaaacag catagcaagt tgaaataagg ctagtccgtt atcaacttga aaaagtggca    14040
ccgagtcggt gctttttgc ctacctggag cctgagagtt gttcaatcta gacaattgtg      14100
ctcggcaaca gtatatttgt ggtgtgccgt accgggccaa ttcgagct                 14148
```

-continued

```
SEQ ID NO: 41            moltype = DNA   length = 4152
FEATURE                  Location/Qualifiers
misc_feature             1..4152
                         note = Dvir-rescue-modified
source                   1..4152
                         mol_type = other DNA
                         organism = synthetic construct
SEQUENCE: 41
gctgcaggcg ggcagcaagg cgtcccatcc gcattacgtg cccagctatt tgccagctat  60
gcccgatcct catgcctata ttcgaacgcc cacgcacaag cagcccgtaa ccgaatacga  120
ggcaataagg gaaaaggcag ccagtcagaa gcgtgacgtt gagaaggcgc tgaccaaatt  180
tctgtgcaaa acaacagaaa caaacaatct ctttcccacc gaggacaaca tgtttccgtg  240
taagtaagcg ctgcgattaa tggttcttgg ttctttattc aaatgtttcg acttcttttt  300
ctgaatgcaa cagtaatcgc ctgtaagccc gcctttccgg cgtatgcagc tgccttgaat  360
cccacagatc aggtatttga cttcgaggag ctggagtacc actacttggt ggccaatcgt  420
acggaagatg tgcccagtaa aggtaggtcc aaattgtaca caatagatat tccaatgaac  480
acaggctcta ctttcatttg cagaggaggg cgaggagggt gacagtgaga atgaggaact  540
ggatggcgac aagtccaagg aggagaagcc cgagctggag atcaagccca attcaacaac  600
aaataaagct attttagaga atcccaatat agacaatccc tacttgcgtg ccgctacact  660
gccaaagcgt tccaagctgc acagtgagtg cactacacca cgcatggtgc cctcacgaag  720
tatacactcg gcttcaccca cgacaccgac gccctcaact ctagagataa ccaaaagtag  780
tgcttagtta taattataaa tagatgcatt gtaattgtgt atagtttttt aaaaaaaaaa  840
tattggataa acaaactctt ttcttcttat cgatagttcg tgcttttgct taaaatggtg  900
tgcgatggca gcgctgcggc aacaaacagc tgtttcgata taaaagtaca ttttacttat  960
cgatagctcg tgctattgca taaaatgatg ttaggtggca acgctgcggc aacaatcagc  1020
tgtttaccag gccgcagcaa cgttacagtg cattttacat tttaccaagt tgaattaata  1080
aaaattgcttt ttaaaagtgt ttactaaatt aaaaagccaa caaattgttg ttgttttcgt  1140
tgcttacaag cggctgctgt acataaatta tacatattag cgctaaacgt gctcaacatg  1200
aatttcctgc gccaaacatt caacgttacg aaacaattga ggcgcacaagg taagttttaa  1260
caaaaatccc tatttaaaac attgcgttgc ggctatttat tcaacttcga gtcccgtgtt  1320
ctatatacat acgcgcccac gcgcctaatt gccaaccatg tgaggcagcc ggtagccgct  1380
tgcgcacatc catttccaat tggtgactgt gcgcatttttg tgtttatcca aggatcctgc  1440
gttccattgt gtgcacacaa tgatttgtat tgtctgttgt ttgcctgcga tctcaactct  1500
tttacatggg cgcgtggccg gcttgcgagc ctgtcgcccg tctgccagtt ctctagttgt  1560
cgtcgtaccc cccttccccc tgcccagccc cttatcgtgt gtctagtctg tgaatatttt  1620
tataagcatt ttctcatgtg tgtttcctgt ttgtgtgtt taatgtgtcc tcaaaactgt  1680
tcacggagcc tacaaagtgt gtattgagaa tatatatata tatatatagt ccatctgtcc  1740
atcttggata tttgtcattg gaacgggcga gcgaaaaaag ggtttgtcaa tgaaaaactt  1800
atcattttca ttatgtgcaa catttactaa ccaaatctat tcaatacata ggttggacaa  1860
acttgccttc tgttcttcga gataacttca gcaaagtctg ccaatgcgat ctgaagtcca  1920
ttcaattttt ggcctagcaa aaaacgcatt cgttttcttg cttgtttttaa ttaaaaattca  1980
caacaaaatc cgcataacat gaggcccacc ctcaacaata ggaatttgca tgacatgcac  2040
acaataagga aaaacaaca caagaaaaa aaattatgag aaaaggacac acacacacac  2100
acaggtgcgt tcggatcgcg gcagacaatg cacggagctg tgattggcat agttcttgct  2160
gtgcgcctgc tcccattgta agcgattgtc cagcgttatg gtaattatta cctgtgtgta  2220
cgtgtgtgtg tgtgtgtgtg gcatttaatt aaaaattgtt gtcgtttgcg attttggctg  2280
cagtacagtc gagtccagtc gggagtccag ctgaacagaa atctgagcat cagacagtca  2340
acccccgtgc atggctaaag gttctcaatg cttaaaaggc ttgagaactg cagttgccgc  2400
tgacccacag ccgcgtcatt tggctgcaat tatttgtgaa aataaccttaa tatatgcatg  2460
atatgtggat ggatatggat ggatatatgg atgtgcgcag cataacaatt attttgcagt  2520
tttcacagag attagccaca acaaaaggcg aatggccatt gttgcttggg catttggaac  2580
tggccaactg tttctgaccc tttttgtcatg ttgtgtccgt tctctcgttt gtgtcaaatg  2640
tttttagccg ctcgctgcgg ctgcgctcac acatgcggca gcagctacca tatacaattt  2700
atataccaat atatgtacac atatttaatt ggtacagttg tgtccacttg cattgtatgt  2760
gtacacttaa cgcactcttg caattccgga caagtcaaga ggagacaact agacgttggc  2820
aatcggaaat tggaagcctt acagaaacac tgcgtttata acttgttctc agctgtttct  2880
ctctctcatc ttgattacat tgcagcgctg cagagcaatt atttgtgtgc cgcattgcgc  2940
ggcatggcat cgttgaatca aatgcatcgc actgggccgc atataaagaa gcgtccgcca  3000
cgtcagcccc tggacggtaa accgtttgcc aagggagtgg tgctcaagac actgatcaag  3060
aagccaaaga aaccaaactc ggcgaatcgt aaatgcgcgc tggtgcgctt atccacggga  3120
aaggagatgg tcgcctatat acccggcatt ggacataatc tgcaggagca taatattgta  3180
ctgtgtcgcg tcggacgact gcaggatgtg cccggcgtca agctgaaggc ggtgcgcggt  3240
gtctacgatc tggcgcacgt tatcaagaag ggccaatgac aaccaactac catgtaattc  3300
tcttccataa aaaaacaaaa aaaaaataag aaaagaaaac aagccaaatc tttgagtact  3360
ctgctattct tgtgcagcat atattattat gattttttta atggaaaatt atgcagctca  3420
gcgggattag tgtaagtagc caacacacaa caagtgagct ctggcctcgc ctcatcccaa  3480
cttgtcttgc cgtaatctta agtcaacagg ccaaattgcg agccaaacaa ttggccagtg  3540
ttgccaacga cgctgccgaa aaaggagcta aatcccattg gaaaatagct aaaaaatagc  3600
cagagcatga attggacgac tgaagacagc tgaaattggc cagaatttgg ccagaatata  3660
gctgatatcg caacactgca catttgttgc ccactcgaaa tatgatttta acggcatttt  3720
tacgctttag caggcaaatc cctttttgaa gaaacggccc gtctttactt tttaacgaaa  3780
tttgcttgca caaattttat gccaaataat cgttaagcga aatgggcgtc gacaggccac  3840
gccacatttt cacagtcagc agagcctcgc cacgcctttg caacaggata caacaaattt  3900
tgaataggca ccgaccaggt tgtcgtgcat ctgggctgaa cgataacatc tgtattaaat  3960
caatcccata ttcaagcttc caaaggattt cggcaacatg ccaattccgc tattaatctt  4020
tcgggttatc ctgaatatct gggtagtcct aggtgtggag ctggtgtcgc ttatggcaga  4080
gcagctgaat gctaacatat acgagcataa aaagtttcat caggaatcca tatgcaactt  4140
gaggtccgac cc                                                      4152
```

-continued

```
SEQ ID NO: 42            moltype = DNA  length = 12817
FEATURE                  Location/Qualifiers
misc_feature             1..12817
                         note = tko-step1-genbank
source                   1..12817
                         mol_type = other DNA
                         organism = synthetic construct
SEQUENCE: 42
agcttgtacc caattcgccc tatagtgagt cgtattacaa ttcactggcc gtcgttttac   60
aacgtcgtga ctgggaaaac cctggcgtta cccaacttaa tcgccttgca gcacatcccc  120
ctttcgccag ctggcgtaat agcgaagagg cccgcaccga tcgcccttcc caacagttgc  180
gcagcctgaa tggcgaatgg gacgcgccct gtagcggcgc attaagcgcg gcgggtgtgg  240
tggttacgcg cagcgtgacc gctacacttg ccagcgccct agcgcccgct cctttcgctt  300
tcttcccttc ctttctcgcc acgttcgccg gctttccccg tcaagctcta aatcgggggc  360
tccctttagg gttccgattt agtgctttac ggcacctcga ccccaaaaaa cttgattagg  420
gtgatggttc acgtagtggg ccatcgccct gatagacggt ttttcgccct ttgacgttgg  480
agtccacgtt ctttaatagt ggactcttgt tccaaactgg aacaacactc aaccctatct  540
cggtctattc ttttgattta taagggattt tgccgatttc ggcctattgg ttaaaaaatg  600
agctgattta acaaaaattt aacgcgaatt ttaacaaaat attaacgctt acaatttagg  660
tggcactttt cggggaaatg tgcgcggaac ccctatttgt ttatttttct aaatacattc  720
aaatatgtat ccgctcatga caataaccc ctgataaatg cttcaataat attgaaaaag  780
gaagagtatg agtattcaac atttccgtgt cgcccttatt cccttttttg cggcattttg  840
ccttcctgtt tttgctcacc cagaaacgct ggtgaaagta aaagatgctg aagatcagtt  900
gggtgcacga gtgggttaca tcgaactgga tctcaacagc ggtaagatcc ttgagagttt  960
tcgccccgaa gaacgttttc caatgatgag cacttttaaa gttctgctat gtggcgcggt 1020
attatcccgt attgacgccg ggcaagagca actcggtcgc cgcatacact attctcagaa 1080
tgacttggtt gagtactcac cagtcacaga aaagcatctt acggatggca tgacagtaag 1140
agaattatgc agtgctgcca taaccatgag tgataacact gcggccaact tacttctgac 1200
aacgatcgga ggaccgaagg agctaaccgc tttttgcac aacatggggg atcatgtaac 1260
tcgccttgat cgttgggaac cggagctgaa tgaagccata ccaaacgacg agcgtgacac 1320
cacgatgcct gtagcaatgg caacaacgtt gcgcaaacta ttaactggcg aactacttac 1380
tctagcttcc cggcaacaat taatagactg gatggaggcg gataaagttg caggaccact 1440
tctgcgctcg gcccttccgg ctggctggtt tattgctgat aaatctggag ccggtgagcg 1500
tgggtctcgc ggtatcattg cagcactggg gccagatggt aagccctccc gtatcgtagt 1560
tatctacacg acggggagtc aggcaactat ggatgaacga aatagacaga tcgctgagat 1620
aggtgcctca ctgattaagc attggtaact gtcagaccaa gtttactcat atatacttta 1680
gattgattta aaacttcatt tttaatttaa aaggatctag gtgaagatcc tttttgataa 1740
tctcatgacc aaaatccctt aacgtgagtt ttcgttccac tgagcgtcag accccgtaga 1800
aaagatcaaa ggatcttctt gagatccttt ttttctgcgc gtaatctgct gcttgcaaac 1860
aaaaaaacca ccgctaccag cggtggtttg tttgccggat caagagctac caactctttt 1920
tccgaaggta actggcttca gcagagcgca gataccaaat actgtccttc tagtgtagcc 1980
gtagttaggc caccacttca agaactctgt agcaccgcct acatacctcg ctctgctaat 2040
cctgttacca gtggctgctg ccagtggcga taagtcgtgt cttaccgggt tggactcaag 2100
acgatagtta ccggataagg cgcagcggtc gggctgaacg gggggttcgt gcacacagcc 2160
cagcttggag cgaacgacct acaccgaact gagataccta cagcgtgagc tatgagaaag 2220
cgccacgctt cccgaaggga gaaaggcgga caggtatccg gtaagcggca gggtcggaac 2280
aggagagcgc acgagggagc ttccaggggg aaacgcctgg tatctttata gtcctgtcgg 2340
gtttcgccac ctctgacttg agcgtcgatt tttgtgatgc tcgtcagggg ggcggagcct 2400
atggaaaaac gccagcaacg cggccttttt acggttcctg gccttttgct ggccttttgc 2460
tcacatgttc tttcctgcgt tatcccctga ttctgtggat aaccgtatta ccgcctttga 2520
gtgagctgat accgctcgcc gcagccgaac gaccgagcgc agcgagtcag tgagcgagga 2580
agcggaagag cgcccaatac gcaaaccgcc tctccccgcg cgttggccga ttcattaatg 2640
cagctggcac gacaggtttc ccgactggaa agcgggcagt gagcgcaacg caattaatgt 2700
gagttagctc actcattagg caccccaggc tttacacttt atgcttccgg ctcgtatgtt 2760
gtgtggaatt gtgagcggat aacaatttca cacaggaaac agctatgacc atgattacgc 2820
caagcgcgca attaaccctc actaaaggga acaaaagctg gagctcctgc aggttgttgg 2880
ttggcacacc acaaatatac tgttgccgag cacaattgtc tagaatgcat acgcattaag 2940
cgaacattaa aaagatgtga aaacataact attatgtcta aataaacaca cgtcagatgt 3000
atgtacgtca acggaaaacc attgtctata tattacaatt actaaataca taccaaattg 3060
aatacatatt gatgaaaaat aataaatact ggcgaaagca aaaaaacgaa acatttttat 3120
tttattgaac aactctcagg ctccaggtag gcaaaaaagc accgactcgg tgccactttt 3180
tcaagttgat aacggactag ccttatttca acttgctatg ctgttccag catagctctg 3240
aaacctccag tctctggttg tgcacgacgt taaattgaaa ataggtctat atatacgaac 3300
tgagtctgga aaagaagtt gagaattata aaaagtagtg agcactgcg ccctctctg 3360
ttggcgagct aaccttttcg cctcttggct gagtaggtgg cgtttcattc tactctgtaa 3420
aattaatgta gaattgaaac actatggtca aaaaatactt aggggcataa gttataaaac 3480
gtatgaaatg aatttttatc aacctgggct attcaaaaat tttcgaatta ttttatgtat 3540
ttttttaat cgtttttcat tataggttaa aatacacttt aaaaggaatt cttcctgta 3600
aaataaatat aaataaatat gctttattga cagaaaattt gatgtttttg tatttgagta 3660
ggagcaatca caggtgagca aaaaagaatt catcaattga tcggctaaat ggtatggcaa 3720
gaaaaggtat gcaatataat aatctttat tgggtatgca acgaaaattt gtttcgtcaa 3780
cgtatgcaat attctttatt aaaagagggt atgcaatgta ttttattaaa aacgggtatg 3840
caatataata atcttttatt gggtatgcaa cgaaaattg tttcgtcaaa gtatgcaata 3900
tttttttatta aaagagggta tgcaatgtat tttattaaaa acgggtatgc aataaaaaat 3960
tatttggttt ctctaaaaag tatgcagcac ttatttttg ataaggtatg caacaaaatt 4020
ttactttgcc gaaaatatgc aatgtttttg cgaataaatt caacgcacac ttattacgtg 4080
gccaactagg tgcccaaaat gtgtgtggac tacgaaattt tccaaattta agatgctatc 4140
tttaaaccaa tgaaatatgg ttcgtatact atgaattttc aattaggcga acatcaatga 4200
```

-continued

```
ttcccccccc agaaaaccga catagcagag cacacgagca ggcgcaaatt gagaaaccca 4260
tccgcgtgaa gtcggttaat ttgcccatct tcttctggac gcgttcgtgc accgcctgct 4320
catccggcgg agtattgtac cattgtgtac ggccgtagtc cgtgtgcctt cgttttggcg 4380
ttcatgcatg agcagcccaa ttccttgctg ccccattcgg ttacattgca cagtggacac 4440
aaaagctagt tttgtagtca aagtacagaa ttcacaaatt atataaactg atatagttca 4500
tagatagtat aaactgatac caagtaacag atacacattt aaataggtaa actgtgtctg 4560
tgatcaaact gtttcttttc gtgtcgaaga atcaattaaa aatgattgaa tcattatatt 4620
tatttccgtt aaaagctgtg caggctgttc aaaatgtttt aatgaaaaaa tacgaatttt 4680
tagactgtct gaatcacagt gtgctcgctt acatttccgc tttcctcttt tggcaactcg 4740
atgtcgcctt tggggctctt ttggagaccg gaaaaaggca acattttcta ttcgattctt 4800
tttgccaatt gcccgagact gtgtcctgtc ggcatatgac gaatacgtaa cgtacgtgac 4860
ggcgacgtta ctcatacgca ccgtgggtag ctgcagacat ctcagcaccc acgttcgcga 4920
attattttga attcgactcc ctgggcgata tttgtttttc gcttttgcat attttgcggg 4980
caatttgggt aaaaggattt ccgcactctg cgacgccgtc ttcagtttgc ggctttcgtt 5040
tttttcctag tagttcggca cacatttccc tcgccgcttc ggcaaatcgc tcacgtaaaa 5100
tatgcatgcg tttccttggc ggttttgcgc tctcaagtgc ctgcaattca attacatttc 5160
gattgatttt catgtttggc cccaaatcgc ggcaaaacct ctcactgacg gacacaccga 5220
agccccggcg gcaaccctca gcggatgccc cggggcttca cgttttccca ggtcagaagc 5280
ggttttcggg agtagtgccc caactgggggt aaccctttgag ttctctcagt tgggggcgta 5340
gggtcgccga catgacacaa ggggttgtga ccggggtgga cacgtacgcg ggtgcttacg 5400
accgtcagtc gcgcgagcgc gactgctgca ggcgggcagc aaggcgtccc atccgcatta 5460
cgtgcccagc tatttgccag ctatgcccga tcctcatgcc tatattcgaa cgccccacgca 5520
caagcagccc gtaaccgaat acgaggcaat aagggaaaag gcagccagtc agaagcgtga 5580
cgttgagaag gcgctgacca aatttctgtg caaaacaaca gaaacaaaca atctctttcc 5640
caccgaggac aacatgtttc cgtgtaagta agcgctgcga ttaatggttc ttggttcttt 5700
attcaaatgt ttcgacttct ttttctgaat gcaacagtaa tgcctgtaa gcccgccttt 5760
ccggcgtatg cagctgcctt gaatcccaca gatcaggtat ttgacttcga ggagctggag 5820
taccactact tggtggccaa tcgtacggaa gatgtgccca gtaaaggtag gtccaaattg 5880
tacacaatag atattccaat gaacacaggc tctactttca tttgcagagg agggcgagga 5940
gggtgacagt gagaatgagg aactggatgg cgacaagtcc aaggaggaga agcccgagct 6000
ggagatcaag cccaattcaa caacaaataa agctatttta gagaatccca atatagacaa 6060
tccctacttg cgtgccgcta cactgccaaa gcgttccaag ctgcacagtg agtgcactac 6120
accacgcatg gtgccctcac gaagtataca ctcggcttca cccacgacac cgacgccctc 6180
aactctagag ataaccaaaa gtagtgctta gttataatta taaatagatg cattgtaatt 6240
gtgtatagtt ttttaaaaaa aaaatattgg ataaacaaac tctttcttc ttatcgatag 6300
ttcgtgcttt tgcttaaaat ggtgtgcgat ggcagcgctg cggcaacaaa cagctgtttc 6360
gatataaaag tacattttac ttatcgatag ctcgtgctat tgcataaaat gatgttaggt 6420
ggcaacgctg cggcaacaat cagctgttta ccaggccgca gcaacgttac agtgcatttt 6480
acattttacc aagttgaatt aataaaattg ctttttaaaa gtgtttacta aattaaaaag 6540
ccaacaaatt gttgttgttt tcgttgctta caagcggctg ctgtacataa attatacata 6600
ttagcgctaa acgtgctcaa catgaatttc ctgcgccaaa cattcaacgt tacgaaacaa 6660
ttgacggcac aaggtaagtt ttaacaaaaa tccctatttta aaacattgcg ttgcggctat 6720
ttattcaact tcgagtcccg tgttctatat acatacgcgc cacgcgcct aattgccaac 6780
catgtgaggc agccggtagc cgcttgcgca catccatttc caattggtga ctgtgcgcat 6840
tttgtgttta tccaaggatc ctgcgttcca ttgtgtgcac acaatgattt gtattgtctg 6900
ttgtttgcct gcgatctcaa ctcttttaca tgggcgcgtg gccggcttgc gagcctgtcg 6960
cccgtctgcc agttctctag ttgtcgtcgt acccccccttc ccctgccca gccccttatc 7020
gtgtgtctag tctgtgaata tttttataag cattttctca tgtgtgtttc ctgtttgtgt 7080
gttttaatgt gtcctcaaaa ctgttcacgg agcctacaaa gtgtgtattg agaatatata 7140
tatatatata tagtccatct gtccatcttg gatatttgtc attggaacgg gcgagcgaaa 7200
aaagggtttg tcaatgaaaa acttatcatt ttcattatgt gcaacattta ctaaccaaat 7260
ctattcaata cataggttgg acaaacttgc cttctgttct tcgagataac ttcagcaaag 7320
tctgccaatg cgatctgaag tccattcaat ttttggccta gcaaaaaacg cattcgtttt 7380
tctgcttgtt ttaattaaaa ttcacaacaa aatccgcata acatgaggcc caccctcaac 7440
aataggaatt tgcatgacat gcacacaata aggaaaaaac aacacaagaa aaaaaaatta 7500
tgagaaaagg acacacacac acacacaggt gcgttcggat cgcggcagac aatgcacgga 7560
gctgtgattg gcatagttct tgctgtgcgc ctgctcccat tgtaagcgat tgtccagcgt 7620
tatggtaatt attacctgtg tgtacgtgtg tgtgtgtgtg tgtggcattt aattaaaaat 7680
tgttgtcgtt tgcgattttg gctgcagtac agtcgagtcc agtcgggagt ccagctgaac 7740
agaaatctga gcatcagaca gtcaacccc gtgcatggct aaaggttctc aatgcttaaa 7800
aggcttgaga actgcagttg ccgctgaccc acagccgcgt catttggctg caattatttg 7860
tgaaaataac cttatatatg catgatatgt ggatggatat ggatggatat atggatgtgc 7920
gcagcataac aattattttg cgattttcac agagattagc cacaacaaaa ggcgaatggc 7980
cattgttgct tgggcatttg gaactggcca actgtttctg accctttgt catgttgtgt 8040
ccgttctctc gtttgtgtca aatgtttta gccgctcgct gcggctgcgc tcacacatgc 8100
ggcagcagct accatataca atttatatac caatatatgt acacatattt aattggtaca 8160
gttgtgtcca cttgcattgt atgtgtacac ttaacgcact cttgcaattc cggacaagtc 8220
aagaggagac aactagacgt tggcaatcgg aaattggaag ccttacagaa acactgcgtt 8280
tataacttgt tctcagctgt ttctctctct catcttgatt acattgcagc gctgcagagc 8340
aattatttgt gtgccgcatt gcgcggcatg gcatcgttga atcaaatgca tcgcactggg 8400
ccgcatataa agaagcgtcc gccacgtcag cccctggacg gtaaaccgtt tgccaaggga 8460
gtggtgctca agacactgat caagaagcca aagaaaccaa actcggcgaa tcgtaaatgc 8520
gcgctggtgc gcttatccac gggaaaggag atggtcgcct atatacccgg cattggacat 8580
aatctgcagg agcataatat tgtactgtgt cgcgtcggag gactgcagga tgtgcccggc 8640
gtcaagctga aggcggtgcg cggtgtctac gatctggcgc acgttatcaa gaagggccaa 8700
tgacaaccaa ctaccatgta attctcttcc ataaaaaaac aaaaaaaaaa taagaaaaga 8760
aaacaagcca aatctttgag tactctgcta ttcttgtgca gcatatatta ttatgatttt 8820
tttaatggaa aattatgcag ctcagcggga ttagtgtaag tagccaacac acaacaagtg 8880
agctctggcc tcgcctcatc ccaacttgtc ttgccgtaat cttaagtcaa caggccaaat 8940
```

-continued

```
tgcgagccaa acaattggcc agtgttgcca acgacgctgc cgaaaaagga gctaaatccc    9000
attggaaaat agctaaaaaa tagccagagc atgaattgga cgactgaaga cagctgaaat    9060
tggccagaat ttggccagaa tatagctgat atcgcaacac tgcacatttg ttgcccactc    9120
gaaatatgat tttaacggca tttttacgct ttagcaggca aatccctttt tgaagaaacg    9180
gcccgtcttt acttttttaac agaatttgct tgcacaaatt ttatgccaaa taatcgttaa    9240
gcgaaatggg cgtcgacagg ccacgccaca ttttcacagt acgcagagcc tcgccacgcc    9300
tttgcaacag gatacaacaa attttgaata ggcaccgacc aggttgtcgt gcatctgggc    9360
tgaacgataa catctgtatt aaatcaatcc catattcaag cttccaaagg atttcggcaa    9420
catgccaatt ccgctattaa tctttcgggt tatcctgaat atctgggtag tcctaggtgt    9480
ggagctggtg tcgcttatgg cagagcagct gaatgctaac atatacgagc ataaaaagtt    9540
tcatcaggaa tccatatgca acttgaggtc cgacccacc aacttttttg cactgcaaaa    9600
aaacacgctt ttgcacgcgg gcccatacat agtacaaact ctacgtttcg tagactattt    9660
tacatataaa gtctacaccg ttgtatacgc tccaaataca ctaccacaca ttgaacctt    9720
ttgcagtgca aaaaagtacg tgtcggcagt cacgtaggcc ggccttatcg ggtcgcgtcc    9780
tgtcacgtac gaatcacatt atcggaccgg acgagtgttg tcttatcgtg acaggacgcc    9840
agcttcctgt gttgctaacc gcagccgac gcaactcctt atcggaacag gacgcgcctc    9900
catatcagcc gcgcgttatc tcatgcgcgt gaccggacac gaggcgcccg tcccgcttat    9960
cgcgcctata aatacagccc gcaacgatct ggtaaacaca gttgaacaga tggtgagcaa    10020
gggcgaggag gtcatcaaag agttcatgcg cttcaaggtg cgcatggagg gctccatgaa    10080
cggccacgag ttcgagatcg agggcgaggg cgagggccgc ccctacgagg gcacccagac    10140
cgccaagctg aaggtgacca agggcggccc cctgcccttc gcctgggaca tcctgtcccc    10200
ccagttcatg tacggctcca aggcgtacgt gaagcacccc gccgacatcc ccgattacaa    10260
gaagctgtcc ttccccgagg gcttcaagtg ggagcgcgtg atgaacttcg aggacggcgg    10320
tctggtgacc gtgacccagg actcctccct gcaggacggc acgctgatct acaaggtgaa    10380
gatgcgcggc accaacttcc cccccgacgg ccccgtaatg cagaagaaga ccatgggctg    10440
ggaggcctcc accgagcgcc tgtaccccg cgacggcgtg ctgaagggcg agatccacca    10500
ggccctgaag ctgaaggacg gcggccacta cctggtggag ttcaagacca tctacatggc    10560
caagaagccc gtgcaactgc ccggctacta ctacgtggac accaagctgg acatccactc    10620
ccacaacgag gactacacca tcgtggaaca gtacgagcgc tccgagggcc gccaccacct    10680
gttcctgggg catggcaccg gcagcaccgg cagcggcagc tccggcaccg cctcctccga    10740
ggacaacaac atggccgtta tcaaggaatt tatgcgcttc aaagttagga tggagggatc    10800
catgaacgga catgagttcg agatcgaggg agagggcgag ggacgcccgt atgaaggcac    10860
acaaacagcc aaactcaagg tcaccaaggg cggaccactg cccttcgcct gggatatcct    10920
gagtcccag tttatgtacg gcagcaaggc ctacgttaag caccccgctg acataccgga    10980
ctacaaaaag ctgtcctttc cggaaggctt caagtgggag cgcgtgatga tttcgaaga    11040
cggaggactg gtcactgtga cccaagatag cagtttgcag gacggtacac tgatctataa    11100
ggttaaaatg cgcggcacta actttccgcc agatggccca gtgatgcaga agaagaccat    11160
gggttgggag gcatccaccg aacgtctgta ccctcgagac ggagtgctca agggcgagat    11220
ccatcaggcc ctcaaactga aagatggtgg tcactacctg gtcgaattta gaccattta    11280
catggccaag aagccggttc agctgcccg atattattat gtggatacga aactggatat    11340
aacttcgcat aacgaagact acaccattgt cgagcagtat gagcgcagcg aaggccgaca    11400
tcacctgttc ctctacggca tggacgagct gtacaagtag gcggccgcga ctctagatca    11460
taatcagcca taccacattt gtagaggttt tacttgcttt aaaaaacctc ccacacctcc    11520
ccctgaacct gaaacataaa atgaatgcaa ttgttgttgt taacttgttt attgcagctt    11580
ataatggtta caaataaagc aatagcatca caaatttcac aaataaagca ttttttttcac    11640
tgcattctag ttgtggtttg tccaaactca tcaatgtatc ttaaagcttc agtctctggt    11700
tgtgcatgga gcgtgttttt ggggcgattt acgagcgtga accgatattt tccatacgtc    11760
atgtttgcct tgctttacac tccaggaaac ctcatccgtt taatttagcc ggaagtgttg    11820
caatagatgc cacatcacaa tcgacttaat aatttttta ggagcaagtt ttaatggaaa    11880
cagtttctga taaataaaata tacatatcaa cttagtacaa gaatatccag ctgaaagaat    11940
ggtatatata tacttgtgtt tgtttctatg acagtttctt cacagcttc cacctcggc    12000
gatttctta tggcacatcg cgcgacagtt gaaatgaaaa actgaaatca gtgaaacccc    12060
gaaaaactg aaaaagccac ggaaattgta cagatacaca gatacgcaga tacaccagca    12120
aatgtacaaa aaggtctata tacatatata tgtagctact cacttatgtt gtccttcgca    12180
gattgctccc tttaagcaaa taaaaaaaag ttggctccac gccgaaaaga aataaaatta    12240
aatggagaat cgcaaatcca tagtgagcca aaggcaaatc tataaaagaa atgaaacgaa    12300
attcattcat tttcgttttc gagttcgaat atttaagtta tatataaaa cgcagtattt    12360
atccatgtaa tcgaaccaca aaagcccaat gagaaaaccc tacatttat gctgagcatc    12420
acaaaatgcc tttcctttca catgaattta tgtattttaa tcaattccc tcgctgtggc    12480
agttaaatat cctaaatttg tccaacgaaa ttgatgcttc aattattcga atgacgacgt    12540
ttaatgggct ttcgaggaat aaaagcaaaa attcacaaga aaaacgcctc tgcatccatg    12600
ctcattatcg gaatcaatta aaatttcaca tgtatcgtta gcatggccat gtcagcaaat    12660
ccacgggatt cggctagagt cctccaaaat acgcccacgg gacccataca ccttcgaaat    12720
gatccaacat caatccctat ccaaatgtat acttagatat gtacatacct tgtcttttct    12780
tggtcgccga atggggggttc cagcatccca tcatcct                            12817
```

```
SEQ ID NO: 43            moltype = DNA  length = 14148
FEATURE                  Location/Qualifiers
misc_feature            1..14148
                        note = tko-step2-genbank
source                  1..14148
                        mol_type = other DNA
                        organism = synthetic construct
SEQUENCE: 43
atcatcgatc tcgaggctgc atccaacgcg cgcgttggga gctctccgga tcaattcggc    60
ttcaggtacc gtcgacgatg taggtcacgg tctcgaagcc gcggtgcggg tgccagggcg    120
tgcccttggg ctccccgggc gcgtactcca cctcacccat ctggtccatc atgatgaacg    180
ggtcgaggtg gcggtagttg atcccggcga acgcgcggcg caccgggaag ccctcgccct    240
cgaaaccgct gggcgcggtg gtcacggtga gcacgggacg tgcgacggcg tcggctgggt    300
```

-continued

```
gcggatacgc ggggcagcgt cagcgggttc tcgacggtca cggcgggcat gtcgacgaca   360
tgttcgcctc atttgtgttc gtttatgtat tcgatgttat gtgtatgctc atgtgatgtt   420
tagcttgtaa gcgcgagatg tgggtagcag gagatgcagt gcagccaaca gcagtgacca   480
gatgatatat gctatgctac tactactact tatatgctat gatttgtggc gcggaggcgt   540
gtctgcgaca cataatcccg cccatttagc tttaagattc aggcactaag aagcaattcg   600
atcaataaat tattgtaacc actctgcatg tgagcaaaag gccagcaaaa ggccaggaac   660
cgtaaaaagg ccgcgttgct ggcgtttttc cataggctcc gcccccctga cgagcatcac   720
aaaaatcgac gctcaagtca gaggtggcga aacccgacag gactataaag ataccaggcg   780
tttcccctg gaagctccct cgtgcgctct cctgttccga ccctgccgct taccggatac   840
ctgtccgcct ttctcccttc gggaagcgtg gcgctttctc atagctcacg ctgtaggtat   900
ctcagttcgg tgtaggtcgt tcgctccaag ctgggctgtg tgcacgaacc ccccgttcag   960
cccgaccgct gcgccttatc cggtaactat cgtcttgagt ccaacccggt aagacacgac  1020
ttatcgccac tggcagcagc cactggtaac aggattagca gagcgaggta tgtaggcggt  1080
gctacagagt tcttgaagtg gtggcctaac tacggctaca ctagaagaac agtatttggt  1140
atctgcgctc tgctgaagcc agttaccttc ggaaaaagag ttggtagctc ttgatccggc  1200
aaacaaacca ccgctggtag cggtggtttt tttgtttgca agcagcagat tacgcgcaga  1260
aaaaaaggat ctcaagaaga tcctttgatc ttttctacgg ggtctgacgc tcagtggaac  1320
gaaaactcac gttaagggat tttggtcatg agattatcaa aaaggatctt cacctagatc  1380
cttttaaatt aaaaatgaag ttttaaatca atctaaagta tatatgagta aacttggtct  1440
gacagttacc aatgcttaat cagtgaggca cctatctcag cgatctgtct atttcgttca  1500
tccatagttg cctgactccc cgtcgtgtag ataactacga tacgggaggg cttaccatct  1560
ggccccagtg ctgcaatgat accgcgagac ccacgctcac cggctccaga tttatcagca  1620
ataaaccagc cagccggaag ggccgagcgc agaagtggtc ctgcaacttt atccgcctcc  1680
atccagtcta ttaattgttg ccgggaagct agagtaagta gttcgccagt taatagtttg  1740
cgcaacgttg ttgccattgc tacaggcatc gtggtgtcac gctcgtcgtt tggtatggct  1800
tcattcagct ccggttccca acgatcaagg cgagttacat gatcccccat gttgtgcaaa  1860
aaagcggtta gctccttcgg tcctccgatc gttgtcagaa gtaagttggc cgcagtgtta  1920
tcactcatgg ttatggcagc actgcataat tctcttactg tcatgccatc cgtaagatgc  1980
ttttctgtga ctggtgagta ctcaaccaag tcattctgag aatagtgtat gcggcgaccg  2040
agttgctctt gcccggcgtc aatacggat aataccgcgc cacatagcag aactttaaaa  2100
gtgctcatca ttggaaaacg ttcttcgggg cgaaaactct caaggatctt accgctgttg  2160
agatccagtt cgatgtaacc cactcgtgca cccaactgat cttcagcatc ttttactttc  2220
accagcgttt ctgggtgagc aaaaacagga aggcaaaatg ccgcaaaaaa gggaataagg  2280
gcgacacgga aatgttgaat actcatactc ttcctttttc aatattattg aagcatttat  2340
cagggttatt gtctcatgag cggatacata tttgaatgta tttagaaaaa taaacaaata  2400
ggggttccgc gcacatttcc ccgaaaagtg ccacctgacg tcgacggatc gggagatcgg  2460
cgcgggatcc aattcaatta gagactaatt caattagagc taattcaatt aggatccaag  2520
cttatcgatt tcgaaccctc gaccgccgga gtataaaatg aggcgcttcg tctacggagc  2580
gacaattcaa ttcaaacaag caaagtgaac acgtcgctaa gcgaaagcta agcaaataaa  2640
caagcgcagc tgaacaagct aaacaatcgg ctcgagaccg gtcgccacca tggtgagcaa  2700
gggcgaggag ctgttcaccg gggtggtgcc catcctggtc gagctggacg gcgacgtaaa  2760
cggccacaag ttcagcgtgt ccggcgaggg cgagggcgat gccacctacg gcaagctgac  2820
cctgaagttc atctgcacca ccggcaagct gcccgtgccc tggcccaccc tcgtgaccac  2880
cctgacctac ggcgtgcagt gcttcagccg ctaccccgac cacatgaagc agcacgactt  2940
cttcaagtcc gccatgcccg aaggctacgt ccaggagcgc accatcttct tcaaggacga  3000
cggcaactac aagacccgcg ccgaggtgaa gttcgagggc gacaccctgg tgaaccgcat  3060
cgagctgaag ggcatcgact tcaaggagga cggcaacatc ctggggcaca agctggagta  3120
caactacaac agccacaacg tctatatcat ggccgacaag cagaagaacg gcatcaaggt  3180
gaacttcaag atccgccaca acatcgagga cggcagcgtg cagctcgccg accactacca  3240
gcagaacacc cccatcggcg acggccccgt gctgctgccc gacaaccact acctgagcac  3300
ccagtccgcc ctgagcaaag accccaacga gaagcgcgat cacatggtcc tgctggagtt  3360
cgtgaccgcc gccgggatca ctctcggcat ggacgagctg tacaagtaaa gcggccgcga  3420
ctctagatca taatcagcca taccacattt gtagaggttt tacttgcttt aaaaaacctc  3480
ccacacctcc ccctgaacct gaaacataaa atgaatgcaa ttgttgttgt taacttgttt  3540
attgcagctt ataatggtta caaataaagc aatagcatca caaatttcac aaataaagca  3600
ttttttttcac tgcattctag ttgtggtttg tccaaactca tcaatgtatc ttagttgttg  3660
gttggcacac cacaaatata ctgttgccga gcacaattga tcggctaaat ggtatggcaa  3720
gaaaaggtat gcaatataat aatcttttat tgggtatgca acgaaaattt gtttcgtcaa  3780
cgtatgcaat attctttatt aaaagagggt atgcaatgta ttttattaaa aacgggtatg  3840
caatataata atcttttatt gggtatgcaa cgaaaatttg tttcgtcaaa gtatgcaata  3900
ttttttatta aaagagggta tgcaatgtat tttattaaaa acgggtatgc aataaaaaat  3960
tatttggttt ctctaaaaag tatgcagcac ttattttttg ataaggtatg caacaaaatt  4020
ttactttgcc gaaaatatgc aatgttttg cgaataaatt caacgcacac ttattacgtg  4080
gccaacgcgc ctagtggatc cttcctggcc tttttcgaga aacgccgcga gggcgaaaag  4140
gattagttgt ttcaaacgca agaaggacat ttgtttcctt aaattgtaac catttcttta  4200
tttggcactc gagccattga atttttcatt ttcagaatat gtgtacacat tttttaaaaa  4260
aataaaaaaa ttatataatg ctggcggttg tttcatgtgt gaaaaattga tcaatggtaa  4320
acaaaattga ataaatatat aacatatata tatagatatg tgtgttgaa tgaatacttg  4380
cgatacatgt aataaaaaata ctcttcgctt atctatcaaa aagtgcggaa tgtcaaaatt  4440
taaaatttta caatgaatgc gtagccgacg acgaaagtgt tccttgctat ttcctttagc  4500
aagatttaaa tttagattaa attctaatga tacgattgac agttcgaaat tcaaagtgtt  4560
ccttttcaa aatttagtaa agattgtata tcaattgtag atatatcgaa attttttcggc  4620
cgcaagcgaa cattttacaa aatgaaggcg accagttgca gaccaattcc attcatcaac  4680
tttcggattg taagatattt ctatcggcca cgacgattga acaagtatta cgatattgta  4740
agtcttcttt aacaaaatta gtttcccttt cacagaaaca gacataaatt cttgaattat  4800
tgacttggat ttgagtgatc gttcgttgtc tatactataa gatctatagg cacgggataa  4860
cgctctaaat ctctttaaaa tcgaacgcgc caggcgctag ttaaacgtta ctatctatct  4920
ggttaaccca gctttgatcg gaatgcgtat atatatttca tgttatataa acgctgcaaa  4980
agctgccaga gcctctgctc cagagctgga ttcgctcaca ccttcctctt cttcttgggg  5040
```

-continued

```
tcagccctgc tgtctccacc gagctgagag aggtcgattc ttgtttcata gagccccgta  5100
attgactgat gaatcagtgt ggcgtccagg acctcctttg tagaggtgta ccgctttctg  5160
tctatggtgg tgtcgaagta cttgaaggct gcaggcgcgc ccaagttggt cagagtaaac  5220
aagtggataa tgttttctgc ctgctccctg atgggcttat ccctgtgctt attgtaagca  5280
gaaagcacct tatcgaggtt agcgtcggcg aggatcactc ttttggagaa ttcgcttatt  5340
tgctcgatga tctcatcaag gtagtgtttg tgttgttcca cgaacagctg cttctgctca  5400
ttatcttcgg gagacccttt gagcttttca tagtggctgg ccagatacaa gaaattaacg  5460
tatttagagg gcagtgccag ctcgttacct ttctgcagct cgcccgcact agcgagcatt  5520
cgtttccggc cgttttcaag ctcaaagaga gagtacttgg gaagcttaat gatgaggtct  5580
tttttgacct ctttatatcc tttcgcctcg agaaagtcga tggggttttt ttcgaagctt  5640
gatcgctcca tgattgtgat gcccagcagt tccttgacgc ttttgagttt tttagacttc  5700
cctttctcca ctttggccac aaccagtaca ctgtaagcga ctgtaggaga atcgaatccg  5760
ccgtatttct tggggtccca atctttttg cgtgcgatca gcttgtcgct gttccttttc  5820
gggaggatac tttccttgga gaagcctccg gtctgtactt cggtctttt aacgatgttc  5880
acctgcggca tggacaggac cttccggact gtcgcgaaat ccctaccctt gtcccacacg  5940
atttctcctg tttctccgtt tgtttcgata agtggtcgct tccgaatctc tccattggcc  6000
agtgtaatct cggtcttgaa aaaattcata atattgctgt aaaagaagta cttagcggtg  6060
gccttgccta tttcctgctc cgactttgcg atcattttcc taacatcgta cacttttatag  6120
tctccgtaaa caaattcaga ttcaagcttg ggatatttt tgataagtgc agtgcctacc  6180
actgcattca ggtaggcatc atgcgcatgg tggtaattgt tgatctctct caccttataa  6240
aactgaaagt cctttctgaa atctgagacc agcttagact tcagagtaat aactttcacc  6300
tctcgaatca gtttgtcatt ttcatcgtac ttggtgttca tgcgtgaatc gagaatttgg  6360
gccacgtgct tggtgatctg gcgtgtctca acaagctgcc ttttgatgaa gccggcttta  6420
tccaactcag acaggccacc tcgttcagcc ttagtcagat tatcgaactt ccgttgtgtg  6480
atcagtttgg cgttcagcag ctgccgccaa taattttca ttttcttgac aacttcttct  6540
gaggggacgt tatcactctt ccctctattt ttatcggatc ttgtcaacac tttattatca  6600
atagaatcat ctttgagaaa agactggggc acgatatgat ccacgtcgta gtcggagagc  6660
cgattgatgt ccagttcctg atccacgtac atgtccctgc cgttctgcag gtagtacagg  6720
tagagcttct cattctgaag ctgggtgttt tcaactgggt gttccttaag gatttgggac  6780
cccagttctt ttataccctc ttcaatcctc ttcatccttt ccctactgtt cttctgtccc  6840
ttctgggtag tttggttctc tcgggccatc tcgataacga tattctcggg cttatgcctt  6900
cccattactt tgacgagttc atccacgacc ttaacggtct gcagtattcc ctttttgata  6960
gctgggctac ctgcaagatt agcgatgtgc tcgtgaagac tgtcccctg gccagaaact  7020
tgtgctttct ggatgtcctc cttaaaggtg agagagtcat catggatcaa ctgcatgaag  7080
ttccggttgg caaatccatc ggacttaaga aaatccagga ttgtctttcc actctgcttg  7140
tctcggatcc cattgatcag ttttcttgac agccgccccc atcctgtata tcggcgcctc  7200
ttgagctgtt tcatgacttt gtcgtcgaag agatgagcgt aagttttcaa gcgttcttca  7260
atcatctccc tatcttcaaa caacgtaagg gtgaggacaa tgtcctcaag aatgtcctcg  7320
ttctcctcat tgtccaggaa gtccttgtct ttaatgattt tcaggagatc gtgatacgtt  7380
cccagggatg cgttgaagcg atcctccact ccgctgattt caacagagtc gaaacattca  7440
atcttttga aatagtcttc tttgagctgt ttcacggtaa ctttccggtt cgtcttgaag  7500
aggaggtcca cgatagcttt cttctgctct ccagacagga atgctggctt tctcatccct  7560
tctgtgacgt atttgacctt ggtgagctcg ttataaactg tgaagtactc gtacagcaga  7620
gagtgtttag gaagcacctt ttcgttaggc agattttat caaagttagt catccttcg  7680
atgaaggact gggcagaggc ccccttatcc acgacttcct cgaagttcca gggagtgatg  7740
gtctcttctg atttgcgagt catccacgcg aatctggaat ttccccgggc gaggggcct  7800
acatagtagg gtatccgaaa tgtgaggatt ttctcaatct tttccctgtt atctttcaaa  7860
aaggggtaga aatcctcttg ccgcctgagg atagcgtgca gttcgcccag gtgaatctgg  7920
tggggatgc ttccattgtc gaaagtgcgc tgtttgcgca acagatcttc tctgttaagc  7980
tttaccagca gctcctcggt gccgtccatt ttttccaaga tgggcttaat aaatttgtaa  8040
aattcctcct ggcttgctcc ggtcgtcaatg tatccggcgt agccattttt agactgatcg  8100
aagaaaattt ccttgtactt ctcaggcagt tgctgtctga caagggcctt cagcaaagtc  8160
aagtcttggt ggtgctcatc atagcgcttg atcatactag cgctcagcgg agctttggtg  8220
atctccgtgt tcactcgcag aatatcactc agcagaatgg cgtctgacag gttctttgcc  8280
gccaaaaaa ggtctgcgta ctggtcgccg atctgggcca gcagattgtc gagatcatca  8340
tcgtaggtgt ctttgctcag ttgaagcttg gcatcttcgg ccaggtcgaa gttagattta  8400
aagttggggg tcagcccgag tgacagggcg ataagattac caaacaggcc gttcttcttc  8460
tccccaggga gctgtgcgat gaggttttcg agccgccggg atttggacag cctagcgctc  8520
aggattgctt tggcgtcaac tccggatgcg ttgatcgggt tctcttcgaa aagctgattg  8580
taagtctgaa ccagttggat aaagagtttg tcgacatcgc tgttgtctgg gttcaggtcc  8640
ccctcgatga ggaagtgtcc ccgaaatttg atcatatgcg ccagcgcgag atagatcaac  8700
cgcaagtcag ccttatcagt actgtctaca agcttcttcc tcagtgata tatggttggg  8760
tacttttcat ggtacgccac ctcgtccacg atattgccaa agattgggtg gcgctcgtgc  8820
tttttatcct cctccaccaa aaaggaactcc tccagcctat ggaagaaaga gtcgatatttt  8880
ttagccatct cattactaaa gatctcctgc aggtagcaga tccgattctt tctgcgggta  8940
tatctgcgcc gtgctgttct tttgagccgc gtggcttcgg ccgtctcccc ggagtcgaac  9000
aggagggcgc caatgaggtt cttctttatg ctgtggcgat cggtattgcc cagaactttg  9060
aattttttgc tcggcacctt gtactcgtcc gtaatgacgg cccagccgac gctgtttgtg  9120
ccgatatcga gcccaatgga gtacttcttg tccatggcga aaatccgggt cgaaagttac  9180
ggttatcgcg cactctactt tccacaaatc ctcacccaaa aaccaagcac agtttattca  9240
actgaagtat tcgcgatact tctttatcta ataataatgt acatgtaact aaactcgctt  9300
ttgggttaaa atcgtgacgc agaggcaaaa aaaatcgtat gtcccttaga caacttgaaa  9360
caactgcgaa gcgtacggca attccaggaa ttttgtggta aagctacgcg ccaactaacg  9420
gttcttgctt agaggtggaa taatgtagtt ttccagcgat aataaatata tcgatatttt  9480
tagtaaaatt gaaaaggtaa acttaatttt agaaaataat ttataagaaa tttaatagta  9540
tgcaaaataa ttttttacttg ctaagaatat gtgccactaa ttaaaagctg acaccgcgc  9600
aatggaaaat agtactacaa cacagcaaca aagcctgagt tatcaacaaa aaaatacgaa  9660
aacatctccc aaaactaagc acccacacg gccactcgcc gtcacaacac aatcactgca  9720
caccaccatt cgaatttcgc gcactgtgac aacatcacat gatatcggcg cggcaacatc  9780
```

-continued

```
ggattaccga caaaacgaac tatcgcacga gccaccgccg gcgaagagcg ctcgttttgc    9840
aacaccggcg cgcgctgaac gaagagaaca gctgactgct tgatacgtgc gtgtttcgcg    9900
gcaggaatta cataaagttt agagcctctg acgccagacc ccccgaacat tcgctccgat    9960
caaactacct gcgaacggtc acctaatccc caccatgcat ggtaggttac ctctgatccc    10020
ggtcatcact ggcgttcgct cacatccgtc cttacatgtg catatttcga ggttaaaacg    10080
gtcgaagctt ggatccgcta gcgttgttgg ttggcacacc acaaatatac tgttgccgag    10140
cacaattgat cggctaaatg gtatggcaag aaaaggtatg caatataata atctttatt     10200
gggtatgcaa cgaaaatttg tttcgtcaac gtatgcaata ttctttatta aaagagggta    10260
tgcaatgtat tttattaaaa acgggtatgc aatataataa tctttattg ggtatgcaac     10320
gaaaatttgt ttcgtcaaag tatgcaatat tttttattaa aagagggtat gcaatgtatt    10380
ttattaaaaa cgggtatgca ataaaaaatt atttggtttc tctaaaaagt atgcagcact    10440
tattttttga taaggtatgc aacaaaattt tactttgccg aaaatatgca atgttttgc     10500
gaataaattc aacgcacact tattacgtgg ccaactagcc tagttccagt gaaatccaag    10560
cacttgaggt ccgacccgat gaattctttt ttgctcacct gtgattgctc ctactcaaat    10620
acaaaaacat caaattttct gtcaataaag catatttatt tatatttatt ttacaggaaa    10680
gaattccttt taaagtgtat tttaacctat aatgaaaaac gattaaaaaa aatacataaa    10740
ataattcgaa aatttttgaa tagcccaggt tgataaaaat tcatttcata cgtttttataa   10800
cttatgcccc taagtatttt ttgaccatag tgtttcaatt ctacattaat tttacagagt    10860
agaatgaaac gccacctact cagccaagag gcgaaaaggt tagctcgcca agcagagagg     10920
gcgccagtgc tcactacttt ttataattct caacttcttt ttccagactc agttcgtata    10980
tatagaccta ttttcaattt aacgtcgctg cagccgatgcc attccagttt cagagctatg    11040
ctggaaacag catagcaagt tgaaataagg ctagtccgtt atcaacttga aaaagtggca    11100
ccgagtcggt gctttttgc ctacctggag cctgagagtt gttcaataaa ataaaaatgt      11160
ttcgtttttt tgctttcgcc agtatttatt attttttcatc aatatgtatt caatttggta   11220
tgtatttagt aattgtaata tatagacaat ggttttccgt tgacgtacat acatctgacg    11280
tgtgtttatt tagacataat agttatgttt tcacatcttt ttaatgttcg cttaatgcgt    11340
atgcattcta gatttttcaac gtcctcgata gtatagtggt tagtatcccc gcctgtcacg    11400
cgggagaccg gggttcaatt ccccgtcggg gagaatctgt gattcttttt tttttttctt     11460
tactttgtta tataaacaat ttttgttta attgaatcta atttgccatt gcttttagga     11520
atctcaggca tccagcaagc gtttgtccgc cgaatcgccc atcagtgaag aagatcctgt    11580
ggcggctacg aaaatctccc cggccatgtc ggcctccacc tccagcgaaa aacccatcag    11640
cgagctggcc acctctgtgc tgacccaccg ctttccgcagac tccacctcct caccccggcga   11700
acatggcctt ggacgaatgc agttgtcgat ccgctacagc gcccagcgtc aaaaactaga     11760
cgtgaccata cacaaaatcc agaagatacc acttcgcgat cccagcaata tccccgatcc     11820
gtatgttaag ctgtatctgt tgcctggacg caccaaggag tcgaaacgca agacgagcgt    11880
gatcaaggac aactgcaacc ccgtctacga tgcatccttt gagtacctga tttccattgc    11940
cgaactcagg cagacggaac tggaggtgac ggtgtgcacc caaaagggat tcctatccgg    12000
cggtagtccc atcattggca tggtaggtac ccgaaagcaa cccccttagtt acagacacag    12060
cgcgtacgtc cttcgcatcc ttatgattcc caagtacata ttctgcaaga gtacagtata    12120
tataggaaag atatccgggt gaacttcgca ggacaacgcc cttggcgagt ttcagagcta    12180
tgctggaaac agcatagcaa gttgaaataa ggctagtccg ttatcaactt gaaaaagtgg    12240
caccgagtcg gtgcttttt gcctacctgg agcctgagag ttgttcaatc tagacaattg     12300
tgctcggcaa cagtatattt gtggtgtgcc aaccaacaac ctgcaggagc tccagcttt     12360
gttcccttta gtgagggtta attttttttg ctcacctgtg attgctccta ctcaaataca    12420
aaaacatcaa attttctgtc aataaagcat atttatttat atttatttta caggaaagaa    12480
ttcctttaa agtgtatttt aacctataat gaaaaacgat taaaaaaat acataaaata      12540
attcgaaaat ttttgaatag cccaggttga taaaaattca tttcatacgt tttataactt    12600
atgcccctaa gtatttttg accatagtgt ttcaattcta cattaatttt acagagtaga     12660
atgaaacgcc acctactcag ccaagaggcg aaaaggttag ctcgccaagc agagagggcg     12720
ccagtgctca ctactttta taattctcaa cttcttttc cagactcagt tcgtatatat      12780
agacctattt tcaatttaac gtcgcaacat tgtactgtgc cgcggtttca gagctatgct    12840
ggaaacagca tagcaagttg aaataaggct agtccgttat caacttgaaa aagtggcacc    12900
gagtcggtgc tttttgcct acctggagcc tgagagttgt tcaatataat aaaaatgttt     12960
cgttttttg ctttcgccag tatttattat tttttcatca tatgtattca atttggtatg    13020
tatttagtaa ttgtaatata tagacaatgg ttttccgttg acgtacatac atctgacgtg    13080
tgtttattta gacataatag ttatgttttc acatcttttt aatgttcgct taatgcgtat    13140
gcattctaga ttttcaacgt cctcgatagt atagtggtta gtatcccgc ctgtcacgcg     13200
ggagaccggg ttcaattcc cgtcgggga gaatctgtga ttcttttttt ttctttta       13260
ctttgttata aacaattt tgtttttaat tgaatctaat ttgccattgc ttttaggaat      13320
ctcaggcatc cagcaagcgt ttgtccgccg aatcgcccat cagtgaagaa gatcctgtgg    13380
cggctacgaa aatctccccg gccatgtcgg cctccacctc cagcgaaaaa cccatcagcg    13440
agctggccac ctctgtgctg acccaccgct ttccagactc cacctcctca cccggcgaac    13500
atggccttgg acgaatgcag ttgtcgatcc gctacagcgc ccagcgtcaa aaactagacg    13560
tgaccataca caaatccag aagataccac ttcgcgatcc cagcaatatc cccgatccg      13620
atgttaagct gtatctgttg cctggacgca ccaaggagtc gaaacgcaag acgagcgtga    13680
tcaaggacaa ctgcaacccc gtctacgatg catcctttga gtacctgatt tccattgccg    13740
aactcaggca gacggaactg gaggtgacgg tgtgcaccca aaagggattc ctatccggcg    13800
gtagtcccat cattggcatg gtaggtaccc gaaagcaacc ccttagttac agacacagcg    13860
cgtacgtcct tcgcatcctt atgattccca agtacatatt ctgcaagagt acagtatata    13920
taggaaagat atccgggtga acttcgcacc agcacgcact ttcgatgttt cagagctatg    13980
ctggaaacag catagcaagt tgaaataagg ctagtccgtt atcaacttga aaaagtggca    14040
ccgagtcggt gctttttgc ctacctggag cctgagagtt gttcaatcta gacaattgtg     14100
ctcggcaaca gtatatttgt ggtgtgccgt accgggccaa ttcgagct                 14148
```